(12) United States Patent
Ge et al.

(10) Patent No.: US 10,017,492 B2
(45) Date of Patent: Jul. 10, 2018

(54) ISOINDOLINE DERIVATIVE, INTERMEDIATE, PREPARATION METHOD, PHARMACEUTICAL COMPOSITION AND USE THEREOF

(71) Applicant: KANGPU BIOPHARMACEUTICALS, LTD., Shanghai (CN)

(72) Inventors: Chuansheng Ge, Shanghai (CN); Wen-Cherng Lee, Shanghai (CN); Baisong Liao, Shanghai (CN); Lei Zhang, Shanghai (CN)

(73) Assignee: KANGPU BIOPHARMACEUTICALS, LTD., Shanghai (CN)

( * ) Notice: Subject to any disclaimer, the term of this patent is extended or adjusted under 35 U.S.C. 154(b) by 0 days.

(21) Appl. No.: 15/523,651

(22) PCT Filed: Aug. 27, 2015

(86) PCT No.: PCT/CN2015/088312
§ 371 (c)(1),
(2) Date: May 1, 2017

(87) PCT Pub. No.: WO2016/065980
PCT Pub. Date: May 6, 2016

(65) Prior Publication Data
US 2017/0313676 A1 Nov. 2, 2017

(30) Foreign Application Priority Data

Oct. 30, 2014 (CN) .......... 2014 1 0605148
Nov. 11, 2014 (CN) .......... 2014 1 0632870

(51) Int. Cl.
| | |
|---|---|
| *C07D 401/04* | (2006.01) |
| *C07D 401/14* | (2006.01) |
| *A61K 31/45* | (2006.01) |
| *A61K 45/06* | (2006.01) |
| *A61K 31/5377* | (2006.01) |
| *A61K 31/496* | (2006.01) |
| *C07B 59/00* | (2006.01) |

(52) U.S. Cl.
CPC ............ *C07D 401/04* (2013.01); *A61K 31/45* (2013.01); *A61K 31/496* (2013.01); *A61K 31/5377* (2013.01); *A61K 45/06* (2013.01); *C07B 59/002* (2013.01); *C07D 401/14* (2013.01); *C07B 2200/05* (2013.01)

(58) Field of Classification Search
CPC ... C07D 413/14; C07D 401/14; C07D 417/14
See application file for complete search history.

(56) References Cited

U.S. PATENT DOCUMENTS

| 4,678,500 | A | 7/1987 | Hay et al. | |
|---|---|---|---|---|
| 7,863,451 | B2 * | 1/2011 | Muller ................. | C07D 401/04 546/201 |
| 8,841,325 | B2 * | 9/2014 | Brosseau ........... | G01N 33/5011 514/315 |
| 2007/0255076 | A1 | 11/2007 | Ito et al. | |

| 2009/0069379 | A1 | 3/2009 | Czarnik | |
|---|---|---|---|---|
| 2010/0204227 | A1 | 8/2010 | Muller et al. | |
| 2011/0196150 | A1* | 8/2011 | Man ..................... | C07D 401/04 540/544 |
| 2012/0053159 | A1 | 3/2012 | Muller et al. | |
| 2013/0143922 | A1 | 6/2013 | Greig et al. | |

FOREIGN PATENT DOCUMENTS

| CN | 105566290 A | 5/2016 |
|---|---|---|
| WO | 9420085 A1 | 9/1994 |
| WO | 98/03502 | 1/1998 |
| WO | 98/03502 A1 | 1/1998 |
| WO | 9854170 A1 | 12/1998 |
| WO | 02/059106 A1 | 8/2002 |
| WO | 2002/059106 A1 | 8/2002 |
| WO | 02/094180 A2 | 11/2002 |
| WO | 2003014315 A2 | 2/2003 |
| WO | 2005028436 A2 | 3/2005 |
| WO | 2006018182 A1 | 2/2006 |
| WO | 2006028964 A1 | 3/2006 |
| WO | 2010/053732 A1 | 5/2010 |
| WO | 2010056344 A1 | 5/2010 |
| WO | 2010139266 A1 | 12/2010 |
| WO | 2011/100380 A1 | 8/2011 |
| WO | 2011160042 A2 | 12/2011 |
| WO | 2012015986 A2 | 2/2012 |
| WO | 2012068512 A1 | 5/2012 |
| WO | 2012/079022 A1 | 6/2012 |
| WO | 2014116573 A1 | 7/2014 |
| WO | 2014180882 A2 | 11/2014 |

OTHER PUBLICATIONS

Wolff, Manfred E., Burger's Medicinal Chemistry and Drug Discovery, Fifth Ed., vol. 1: Principles and Practice, John Wiley & Sons, 1995, 975.*

(Continued)

*Primary Examiner* — Erich A Leeser
(74) *Attorney, Agent, or Firm* — Finnegan, Henderson, Farabow, Garrett & Dunner, LLP

(57) ABSTRACT

Provided are an isoindoline derivative, intermediate, preparation method, pharmaceutical composition and use thereof. The isoindoline derivative and the pharmaceutical composition thereof can regulate the production or activity of immunological cytokines, thus effectively treating cancer and inflammatory disease.

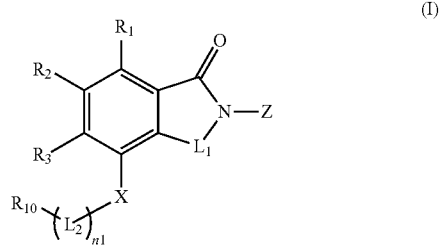

(I)

23 Claims, No Drawings

(56) References Cited

OTHER PUBLICATIONS

Banker, Gilbert S. et al., Modem Pharmaceutics, Marcel Dekker, New York, 1996.*

West, Anthony R., Solid State Chemistry and Its Applications, Wiley, New York, 1988, 358.*

Gautam Sethi et al., "TNF: A master switch for inflammation to cancer", Bioscience, pp. 5904-5107, 2008.

Harald Wajant et al., "The Role of TNF in Cancer", Springer, pp. 1-15, 2009.

Shui-Tein Chen et al., "Facile Preparation of Optically Pure [α-2H]-~α-Amino Acids", Biotechnology Letters, pp. 269-274, 1992.

Nick J. Manesis et al., "Synthesis of an Isotopically Labeled Dilactam-Bridged Tetrapeptide", American Chemical Society, pp. 5342-5349, 1987.

Martin Stogniew et al., "Synthesis of Deuterium Enriched L-Glutamine and 4-Aminobutanamide From Pyridazinones", Journal of Labelled Compounds and Radiopharmaceuticals, 897-903, 1980.

A.T.Blomquist et al., "Deuterated Amino Acids. 111. Synthesis of DL-Aspartic-2,3,3-d3 Acid, ~-Glutamic-2,3,3,4,4-dA~cid, L-Asparagine-2,3,3-d3, and ~-Glutamine-2,3,3,4,4-d51,2a", Deuterated Amino Acids. III., 4121-4127, 1966.

Submitted by Björn C. Söderberg et al., "Synthesis of Indoles by Palladium-Catalyzed Reductive N-Heteroannulation of 2-Nitrostyrenes: Methyl Indole-4-Carboxylate [(1H-Indole-4-carboxylic acid, methyl ester)]", Organic Syntheses, 75-84, 2003.

George W. Muller et al., "Amino-Substituted Thalidomide Analogs: Potent Inhibitors of TNF-ct Production", Bioorganic & Medicinal Chemistry Letters 9, 1625-1630, 1999.

Jarkko Rautio et al., "Prodrugs: design and clinical applications", nature reviews, 255-270, 2008.

Stella et al., Prodrugs Challenges and Rewards, 2007.

P.Heinrich Stahl et al., Handbook of Pharmaceutical Salts Properties, Selection, and Use, 2002.

Nov. 13, 2015 International Search Report issued in International Patent Application No. PCT/CN2015/088312.

Nov. 13, 2015 Written Opinion of the International Searching Authority issued in International Patent Application No. PCT/CN2015/088312.

Mar. 2, 2017 International Preliminary Report on Patentability issued in International Patent Application No. PCT/CN2015/088312.

* cited by examiner

ISOINDOLINE DERIVATIVE, INTERMEDIATE, PREPARATION METHOD, PHARMACEUTICAL COMPOSITION AND USE THEREOF

The application claims priorities of Chinese Patent Application CN201410605148.8 filed on Oct. 30, 2014 and Chinese Patent Application CN201410632870.0 filed on Nov. 11, 2014, the contents of which are incorporated herein by reference in their entireties.

FIELD OF INVENTION

The present invention relates to an isoindoline derivative, intermediate, preparation method, pharmaceutical composition and use thereof.

PRIOR ARTS

Tumor necrosis factor-α (TNF-α) is a kind of proinflammatory cytokine, which plays an important role in immune homeostasis, inflammation, and host defense. TNF-α has been proved to be one of the major mediators of inflammation. TNF-α can also be produced by tumors, and can play a role in promoting the formation of tumors, also can cause the programmed cell death of tumors. In addition, TNF-α also affects the processes such as apoptosis, necrosis, angiogenesis, immune cell activation, differentiation and cell migration, all these processes play an important role in tumorigenesis and tumor progression.

Uncontrolled activity of TNF-α or overproduction of TNF-α is related to the pathology of various diseases, including but not limited to cancers, such as, colon, rectum, prostate, breast, brain and colon cancer; and inflammatory diseases, especially cancer-associated inflammation. The dysregulation of TNF-α can also lead to autoimmune diseases, toxic shock syndrome, cachexia, arthritis, psoriasis, HIV infection and AIDS, neurological diseases and central nervous system diseases, sepsis, congestive heart failure, allograft rejection and virus infections. Thus, reducing the level of TNF-α, or regulating the activity of TNF-α is a promising strategy in treating many immunological, inflammatory and malignant diseases (e.g., cancers and inflammation). Such as, Sethi et al. *Front. Biosci.* (2008) 13, 5094-5107 和 *Results Prob. Cell Differ.* (2009) 49, 1-15.

Lenalidomide (3-(4-amino-1,3-dihydro-1-oxo-2H-isoindole-2-yl)-piperidine-2,6-dione) is a small molecule immune regulator, it has been proved that it can inhibit the secretion of TNF-α and other proinflammatory cytokines, and increase the secretion of anti-inflammatory cytokines. Lenalidomide was approved for treating multiple myeloma (in 2006), myelodysplastic syndrome (in 2005) and mantle cell lymphoma (in 2013). In addition, in clinical trials, Lenalidomide alone or in combination with other therapeutic agents, can treat non-Hodgkin's lymphoma, papillary and follicular thyroid carcinoma, prostate cancer, chronic lymphocytic leukemia, amyloidosis, I type complex regional pain syndrome, malignant melanoma, nerve root disease, myelofibrosis, glioblastoma, gliosarcoma, malignant glioma, myeloid leukemia, refractory plasmacytoma, chronic myelomonocytic leukemia, follicular lymphoma, ciliary body and chronic melanoma, iridic melanoma, recurrent interocular melanoma, extraocular spreading melanoma, solid tumor, T cell lymphoma, erythroid lymphoma, monoblastic and monocytic leukemia; myeloid leukemia and brain tumors, meningioma, spinal tumor, thyroid cancer, mantle cell lymphoma, non-small cell lung cancer, ovarian cancer, renal cell carcinoma, myelofibrosis, Burkitt's lymphoma, Hodgkin lymphoma, large cell lymphoma and macroglobulinemia (see WO 2012/015986).

However, Lenalidomide has many side effects. In fact, Lenalidomide's prescription information clearly recites that the drug has a risk of myelosuppression, deep vein thrombosis, pulmonary embolism and teratogenesis. During the clinical trials, a majority of patient taking Lenalidomide needs a reduction of dose due to the hematologic toxicity. Therefore, although Lenalidomide is of useful activity, its potency is limited by the significant occurrence of side effects. Therefore, Lenalidomide derivatives being of improved structures are urgently desired to optimize its performance in the field.

CONTENT OF THE PRESENT INVENTION

The present invention provides an isoindoline derivative, intermediate, preparation method, pharmaceutical composition and use thereof. The isoindoline derivative of the present invention can regulate the production or activity of cytokines (e.g. TNF-α) so as to effectively treat cancers and inflammatory diseases.

The present invention provides an isoindoline derivative represented by general formula (I), a pharmaceutically acceptable salt, a solvate, a polymorph, a stereoisomer, a isotopic compound, a metabolite or a prodrug thereof;

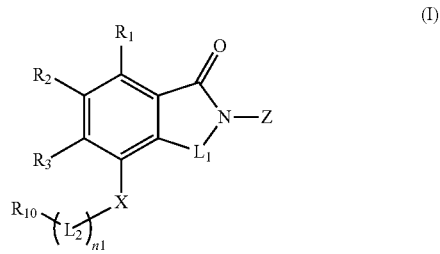

in the general formula (I), n1 is selected from 0 or 1;
Z is

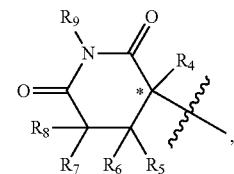

wherein, the carbon atom labelled by * is an asymmetric center;
each of $R_1$, $R_3$, $R_4$, $R_5$, $R_6$, $R_7$, $R_8$ and $R_9$ is independently selected from H or D;
$R_2$ is selected from H, D or a halogen;
each of $L_1$ and $L_2$ is independently selected from $CD_2$, CHD or $CH_2$;
X is selected from NH, ND or O;
$R_{10}$ is H, D or

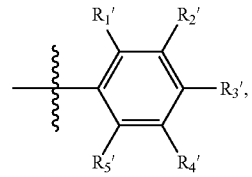

wherein, each of $R_1'$, $R_2'$, $R_3'$, $R_4'$ and $R_5'$ is independently selected from H, D, a halogen, a cyano, a hydroxyl,

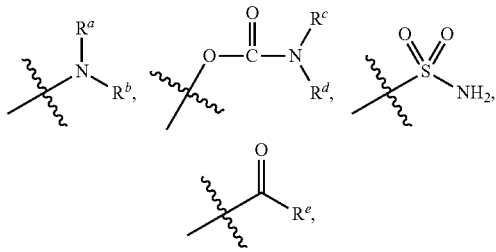

substituted or unsubstituted $(C_1\text{-}C_{12})$alkyl, a substituted or unsubstituted $(C_1\text{-}C_{12})$alkoxy, a $(C_2\text{~}C_{20})$heterocycloalkyl or a deuterated $(C_2\text{~}C_{20})$heterocycloalkyl; wherein, each of $R^a$ and $R^b$ is independently H, a $(C_1\text{-}C_{12})$alkyl or a $(C_1\text{-}C_{12})$alkylacyl; each of $R^c$ and $R^d$ is independently H or a $(C_1\text{-}C_{12})$alkyl; $R^e$ is

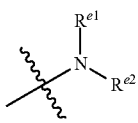

or a $(C_2\text{~}C_{20})$heterocycloalkyl; each of $R^{e1}$ and $R^{e2}$ is independently H or a $(C_1\text{-}C_{12})$alkyl;

the substituent contained in the substituted $(C_1\text{-}C_{12})$ alkoxy is selected from the group consisting of D, a halogen, a hydroxyl, a $(C_1\text{-}C_{12})$alkoxy, a $(C_2\text{~}C_{20})$heterocycloalkyl, a $(C_2\text{~}C_{20})$heterocycloalkyl substituted with a $(C_1\text{-}C_{12})$alkyl,

wherein each of $R^f$ and $R^g$ is independently H or a $(C_1\text{-}C_{12})$ alkyl; $R^h$ is a $(C_2\text{~}C_{20})$heterocycloalkyl;

the substituent contained in the substituted $(C_1\text{-}C_{12})$alkyl is selected from the group consisting of D, a $(C_2\text{~}C_{20})$ heterocycloalkyl, a deuterated $(C_2\text{~}C_{20})$heterocycloalkyl, a $(C_2\text{~}C_{20})$heterocycloalkyl substituted with a $(C_1\text{-}C_{12})$alkyl and a $(C_2\text{~}C_{20})$heterocycloalkyl substituted with a deuterated $(C_1\text{-}C_{12})$alkyl;

when more than one substituents are contained in the substituted $(C_1\text{-}C_{12})$alkoxy or the substituted $(C_1\text{-}C_{12})$ alkoxy, the substituents are the same or different;

in each of the groups mentioned above, the heteroatom of the $(C_2\text{~}C_{20})$heterocycloalkyl contained in the $(C_2\text{~}C_{20})$ heterocycloalkyl, the deuterated $(C_2\text{~}C_{20})$heterocycloalkyl, the $(C_2\text{~}C_{20})$heterocycloalkyl substituted with a $(C_1\text{-}C_{12})$ alkyl or the $(C_2\text{~}C_{20})$heterocycloalkyl substituted with a deuterated $(C_1\text{-}C_{12})$alkyl is selected from the group consisting of O, N and S;

provided that in the general formula (I), when n1 is 0, $R_1$, $R_3$ and $R_{10}$ are H or D, X is NH or ND, $R_2$ is a halogen;

provided that in the general formula (I), when n1 is 1, X is O and $R_2$ is H or D, $R_{10}$ is

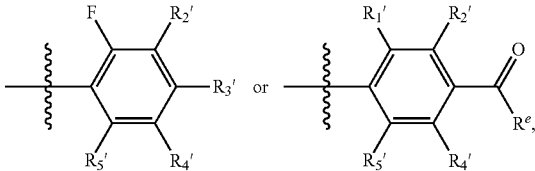

when $R_{10}$ is

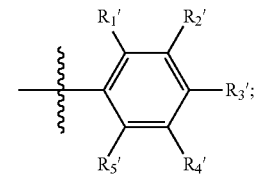

$R^e$ is a $(C_2\text{-}C_{20})$heterocycloalkyl;

provided that in the general formula (I), when n1 is 1 and X is NH, $R_{10}$ is

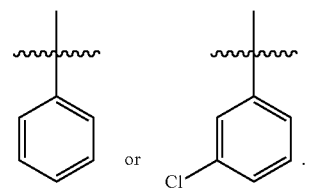

provided that in the general formula (I) and Z, when n1 is 1, X is NH, $R_1$ to $R_9$ are H and both of $L_1$ and $L_2$ are $CH_2$, $R_{10}$ is not

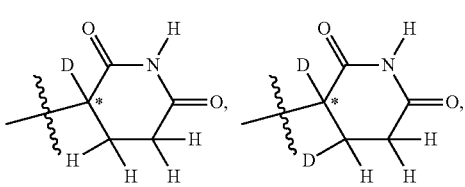

Preferably, in the general formula (I), the asymmetric center refers to an achiral carbon, a (S) configuration carbon, an enriched (S) configuration carbon, a (R) configuration carbon, an enriched (R) configuration carbon or a racemate.

In the general formula (I), Z is preferably selected from the group consisting of -continued

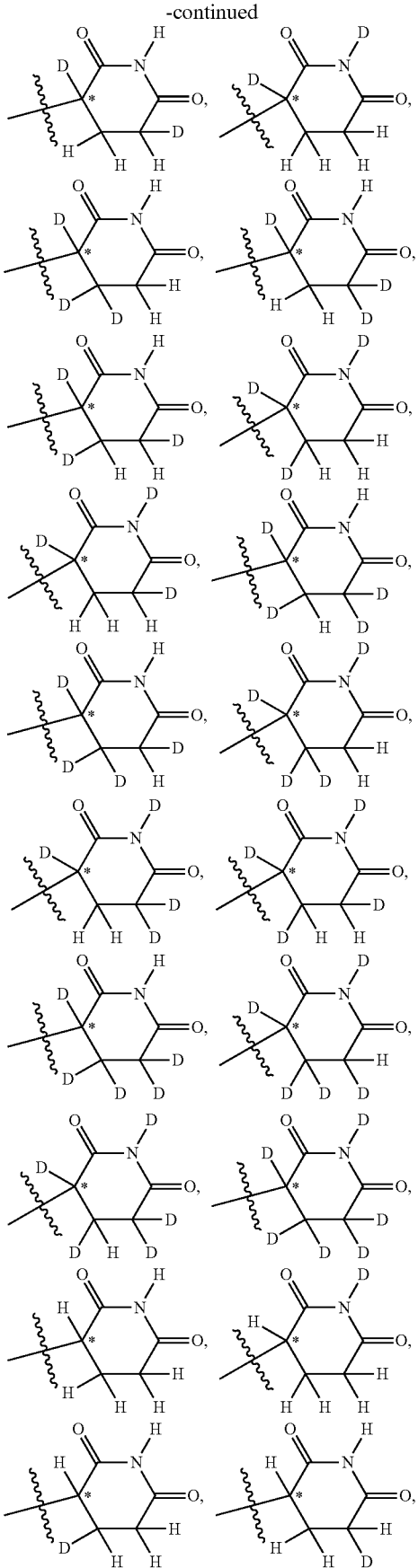

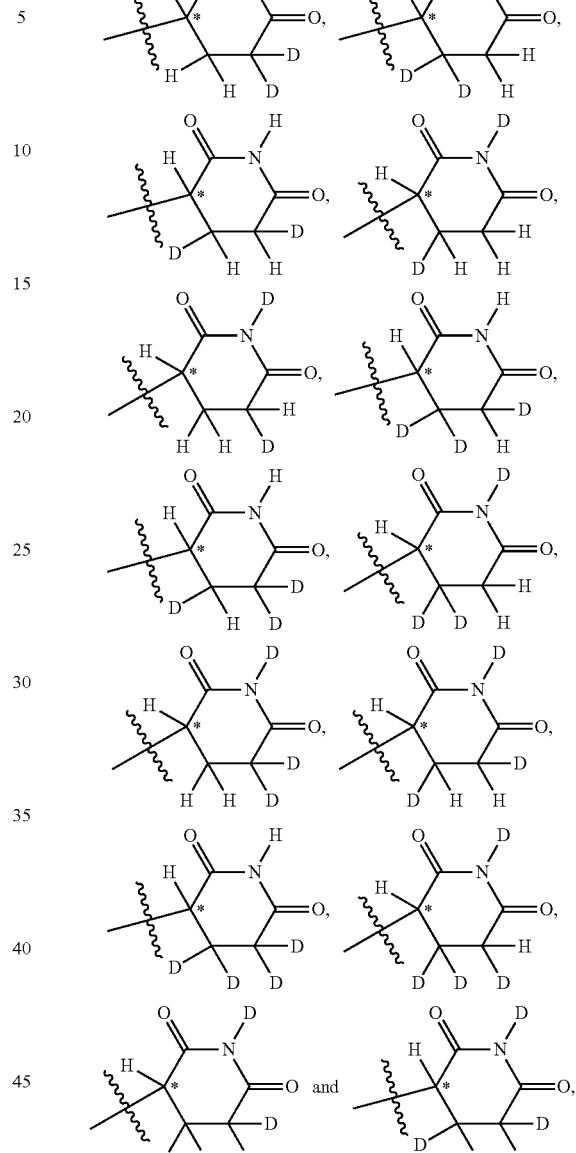

wherein, * is defined as above.

In each of the groups mentioned above, the $(C_2 \sim C_{20})$ heterocycloalkyl contained in the $(C_2 \sim C_{20})$ heterocycloalkyl, the deuterated $(C_2 \sim C_{20})$ heterocycloalkyl, the $(C_2 \sim C_{20})$ heterocycloalkyl substituted with a $(C_1 - C_{12})$ alkyl or the $(C_2 \sim C_{20})$ heterocycloalkyl substituted with a deuterated $(C_1 - C_{12})$ alkyl is preferably a $(C_2 - C_6)$ heterocycloalkyl containing 1 or 2 heteroatom(s) selected from N or O. The $(C_2 - C_6)$ heterocycloalkyl is preferably pyrrolidine

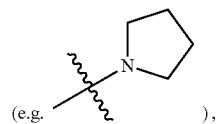

(e.g. ), morpholinyl

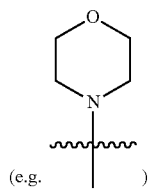 [SMILES: *N1CCOCC1]

(e.g. )

or piperazinyl

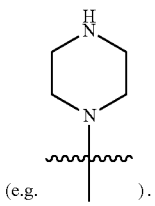

(e.g. ).

The $(C_1-C_{12})$alkyl contained in the $(C_2\sim C_{20})$heterocycloalkyl substituted with a $(C_1-C_{12})$alkyl or the $(C_2\sim C_{20})$heterocycloalkyl substituted with a deuterated $(C_1-C_{12})$alkyl is preferably a $(C_1-C_4)$alkyl. The $(C_1-C_4)$alkyl is preferably a methyl, an ethyl, a propyl, an isopropyl, a n-butyl, an isobutyl, or a tert-butyl. The deuterated $(C_2\sim C_{20})$heterocycloalkyl is preferably

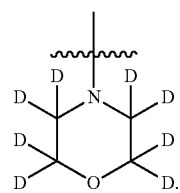

The $(C_2\sim C_{20})$heterocycloalkyl substituted with a $(C_1-C_{12})$alkyl is preferably

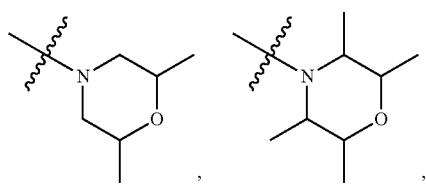

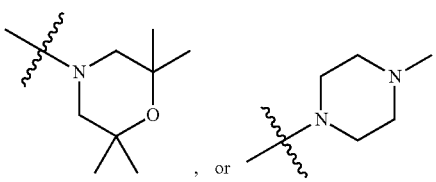

, or .

The $(C_2\sim C_{20})$heterocycloalkyl substituted with a deuterated $(C_1-C_{12})$alkyl is preferably

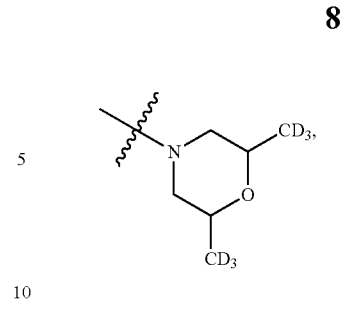

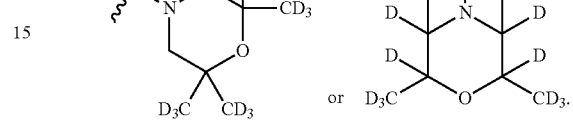

In the general formula (I), when $R_{10}$ is

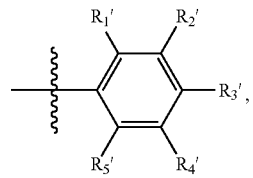

each of $R_1'$, $R_2'$, $R_3'$, $R_4'$ and $R_5'$ is independently selected from

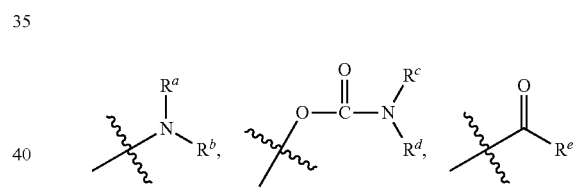

or a substituted $(C_1-C_{12})$alkoxy, each of $R^a$ and $R^b$ is independently a $(C_1-C_{12})$alkyl or a $(C_1-C_{12})$alkylacyl, each of $R^c$ and $R^d$ is independently a $(C_1-C_{12})$alkyl

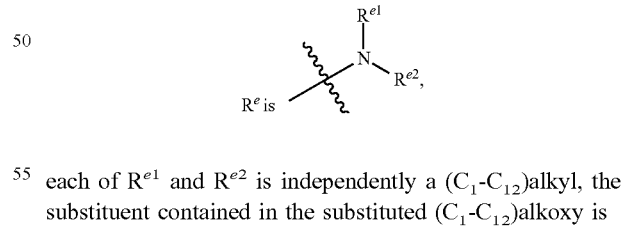

$R^e$ is each of $R^{e1}$ and $R^{e2}$ is independently a $(C_1-C_{12})$alkyl, the substituent contained in the substituted $(C_1-C_{12})$alkoxy is and each of $R^f$ and $R^g$ is independently a $(C_1-C_{12})$alkyl, the structure of the $(C_1-C_{12})$alkylacyl is

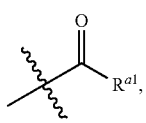

is $(C_1-C_{12})$alkyl; in the definitions of $R^a$, $R^b$, $R^{a1}$, $R^c$, $R^d$, $R^{e1}$, $R^{e2}$, $R^f$ and $R^g$, the $(C_1-C_{12})$alkyl is preferably a $(C_1-C_4)$alkyl. The $(C_1-C_4)$alkyl is preferably a methyl, an ethyl, a propyl, an isopropyl, a n-butyl, an isobutyl or a tert-butyl.

In the general formula (I), when $R_{10}$ is

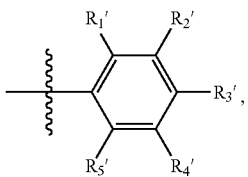

each of $R_1'$, $R_2'$, $R_3'$, $R_4'$ and $R_5'$ is independently selected from a substituted $(C_1-C_{12})$alkoxy and the substituent contained in the substituted $(C_1-C_{12})$alkoxy is selected from a $(C_1-C_{12})$alkoxy, the $(C_1-C_{12})$alkoxy is preferably a $(C_1-C_4)$alkoxy. The $(C_1-C_4)$alkoxy is preferably a methoxy, an ethoxy, a propoxy, an isopropoxy, a n-butoxy, an isobutoxy, or a tert-butoxy.

In the general formula (I), when $R_{10}$ is

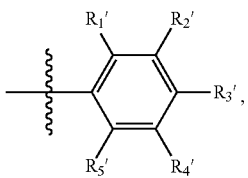

each of $R_1'$, $R_2'$, $R_3'$, $R_4'$ and $R_5'$ is independently selected from a substituted $(C_1-C_{12})$alkoxy and the substituent contained in the substituted $(C_1-C_{12})$alkoxy is selected from

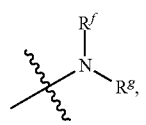

the

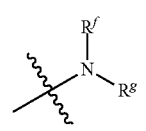

is preferably

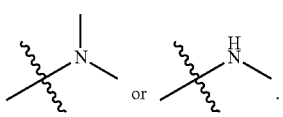

In the general formula (I), when $R_{10}$

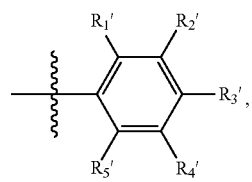

each of $R_1'$, $R_2'$, $R_3'$, $R_4'$ and $R_5'$ is independently selected from a substituted $(C_1-C_{12})$alkoxy and the substituent contained in the substituted $(C_1-C_{12})$alkoxy is selected from

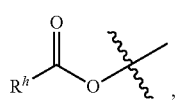

the

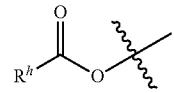

is preferably

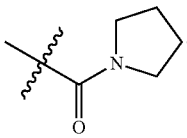

In the general formula (I), when $R_{10}$ is

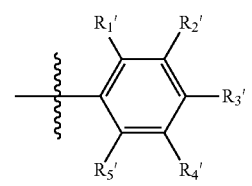

and each of $R_1'$, $R_2'$, $R_3'$, $R_4'$ and $R_5'$ is independently selected from a halogen, the halogen is preferably F, Cl, Br or I.

In the general formula (I), when $R_{10}$ is

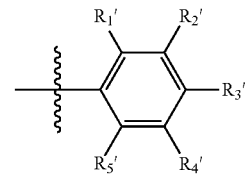

and each of $R_1'$, $R_2'$, $R_3'$, $R_4'$ and $R_5'$ is independently selected from a substituted or unsubstituted $(C_1-C_{12})$alkyl, the substituted or unsubstituted $(C_1-C_{12})$alkyl is preferably a substituted or unsubstituted $(C_1-C_4)$alkyl. The substituted or unsubstituted $(C_1-C_4)$alkyl is preferably a substituted or unsubstituted methyl, a substituted or unsubstituted ethyl, a substituted or unsubstituted n-propyl, a substituted or unsubstituted isopropyl, a substituted or unsubstituted n-butyl, a substituted or unsubstituted isobutyl, or a substituted or unsubstituted tert-butyl. The substituted $(C_1-C_{12})$alkyl is preferably

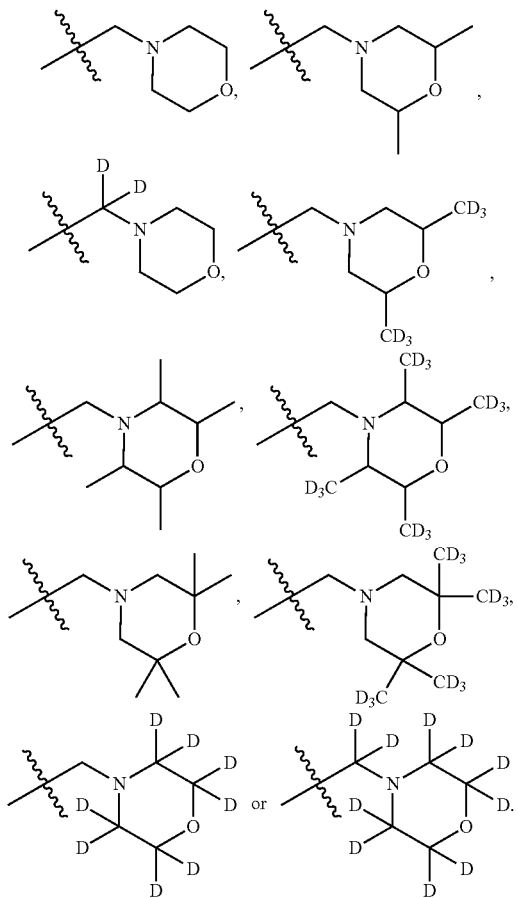

In the general formula (I), when $R_{10}$ is

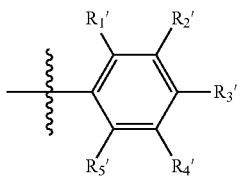

and each of $R_1'$, $R_2'$, $R_3'$, $R_4'$ and $R_5'$ is independently selected from a substituted or unsubstituted $(C_1-C_{12})$alkoxy, the substituted or unsubstituted $(C_1-C_{12})$alkoxy is preferably a substituted or unsubstituted $(C_1-C_4)$alkoxy. The substituted or unsubstituted $(C_1-C_4)$alkoxy is preferably a substituted or unsubstituted methoxy, a substituted or unsubstituted ethoxy, a substituted or unsubstituted n-propoxy, a substituted or unsubstituted n-butoxy. a substituted or unsubstituted isobutoxy, or a substituted or unsubstituted tert-butoxy. The substituted $(C_1-C_{12})$alkoxy is preferably

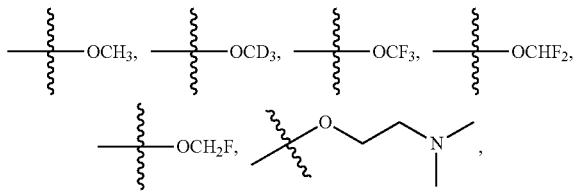

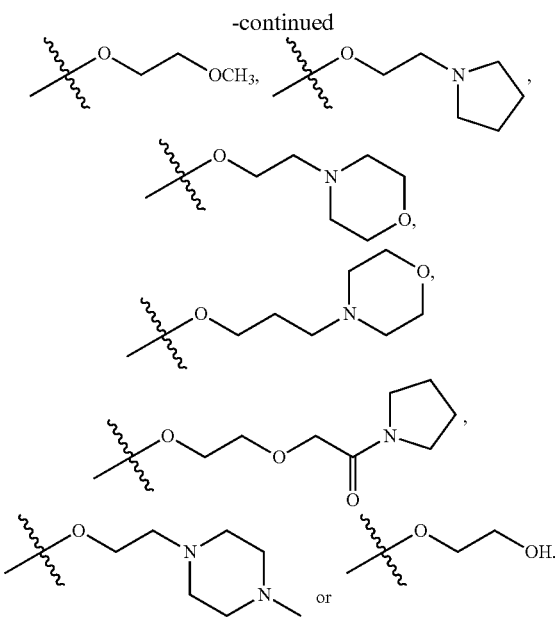

In the general formula (I), when $R_{10}$ is

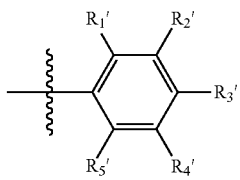

and each of $R_1'$, $R_2'$, $R_3'$, $R_4'$ and $R_5'$ is independently selected from

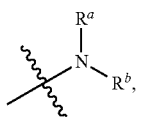

the

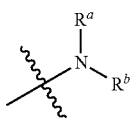

is preferably

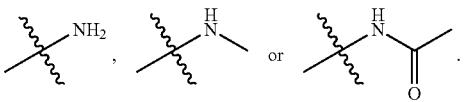

In the general formula (I), when $R_{10}$ is

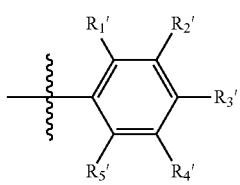

and each of $R_1'$, $R_2'$, $R_3'$, $R_4'$ and $R_5'$ is independently selected from

[structure: -O-C(=O)-N($R^c$)($R^d$)]

the

[structure: -O-C(=O)-N($R^c$)($R^d$)]

is preferably

[structures: -O-C(=O)-N(CH3)- or -O-C(=O)-NH-]

In the general formula (I), when $R_{10}$ is

[structure: phenyl with $R_1'$, $R_2'$, $R_3'$, $R_4'$, $R_5'$]

and each of $R_1'$, $R_2'$, $R_3'$, $R_4'$ and $R_5'$ is independently selected from

[structure: -C(=O)-$R^e$]

the

[structure: -C(=O)-$R^e$]

is preferably

[structures: -C(=O)-morpholine, -C(=O)-NH2, or -C(=O)-NH-CH3]

In the general formula (I), the

[structure: phenyl with $R_1'$, $R_2'$, $R_3'$, $R_4'$, $R_5'$]

is preferably

[structures: various fluorinated methoxy/ethoxy substituted phenyl groups including F with OMe, F with OCF3, F with OCHF2, F with OCH2F, F with OEt, and dimethylphenyl]

-continued
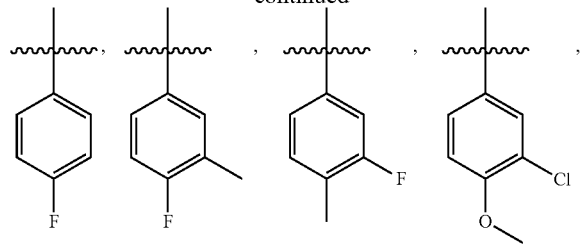 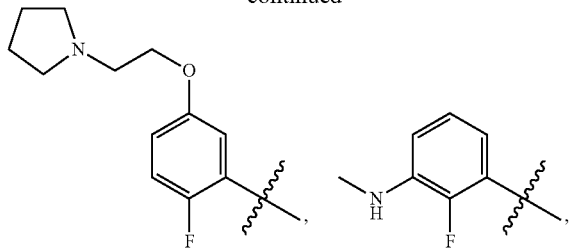
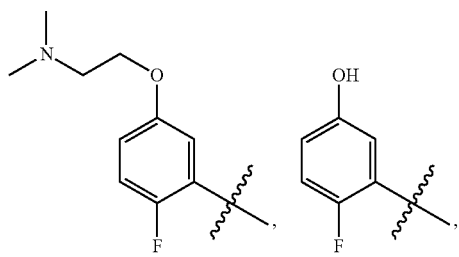 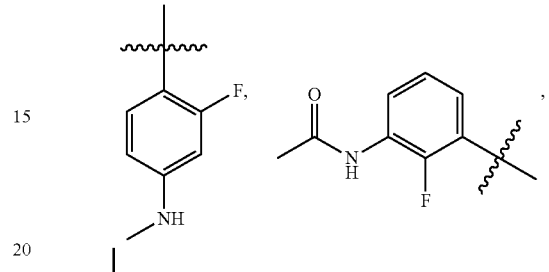
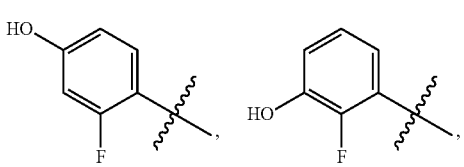 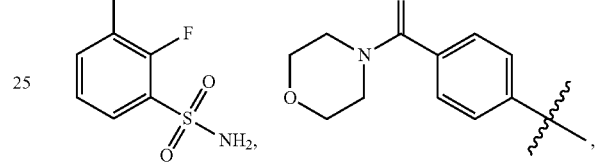
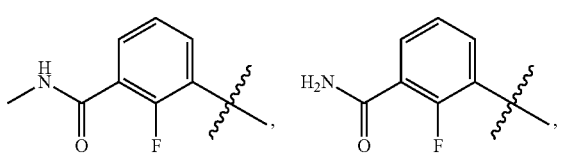 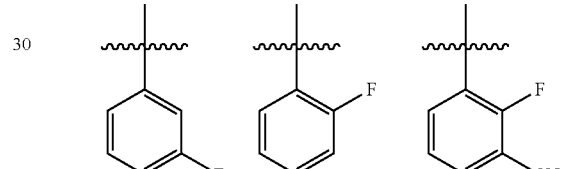
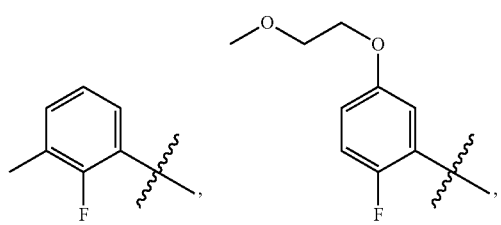 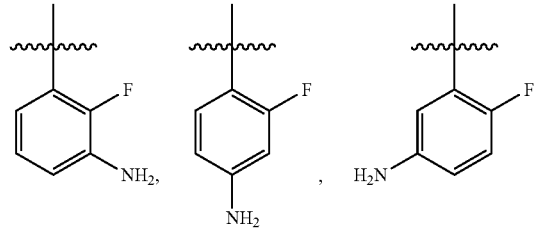
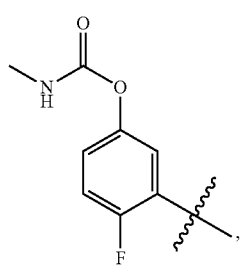 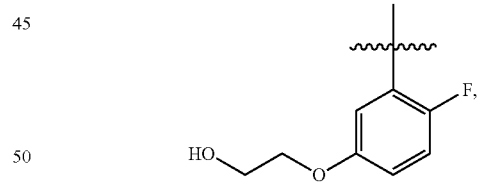
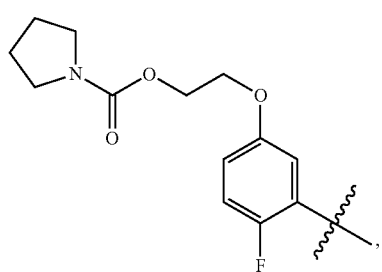 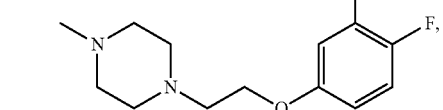
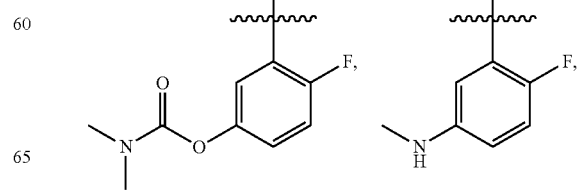

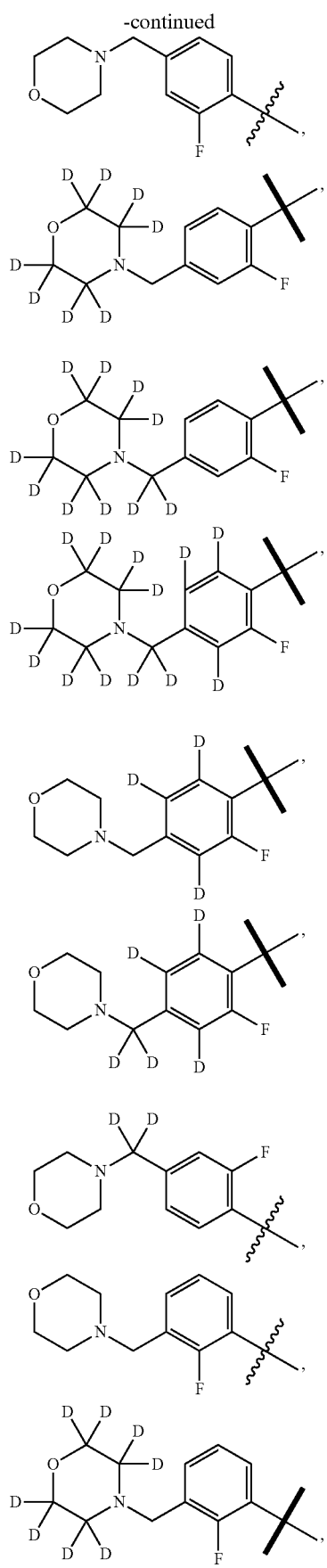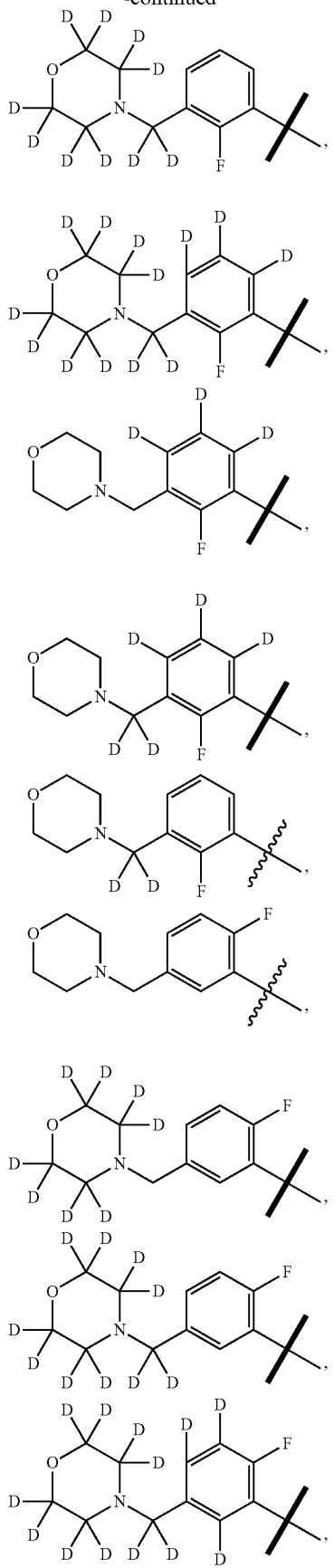

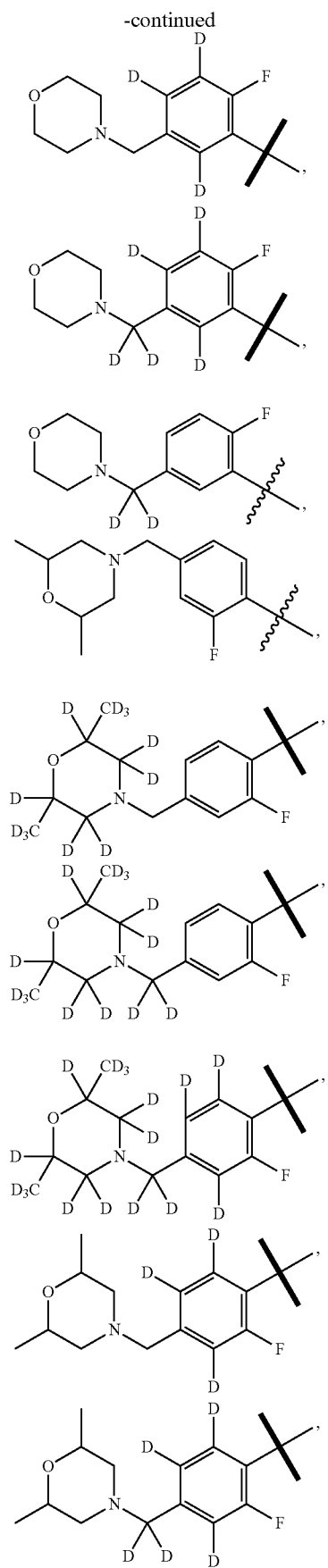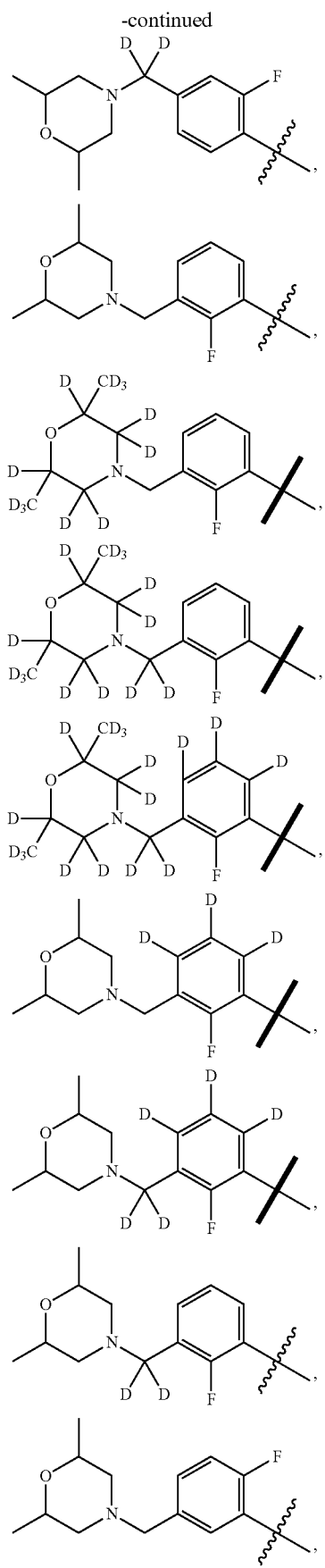

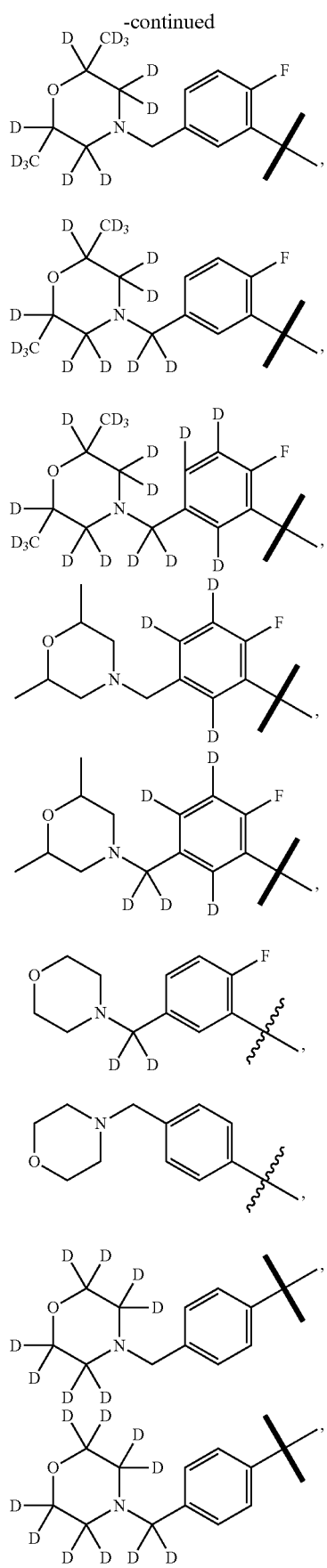
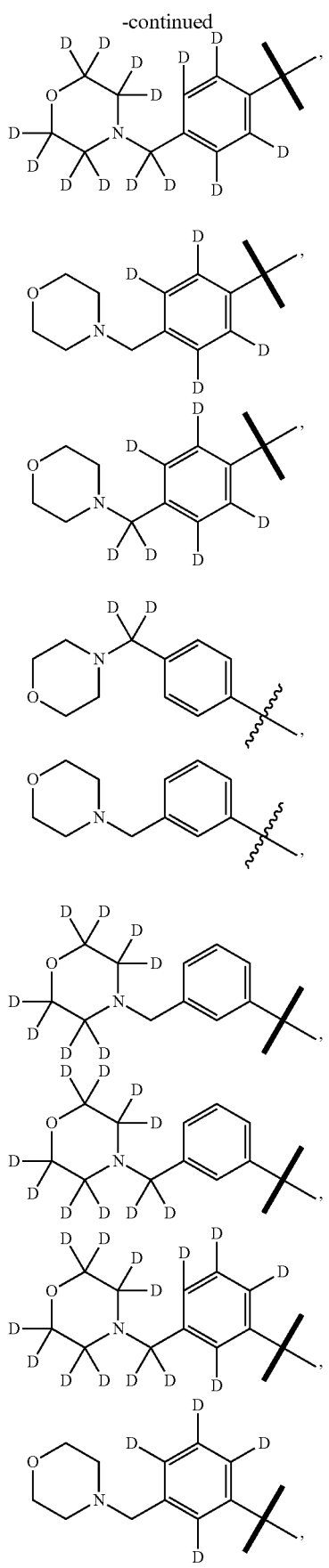

-continued
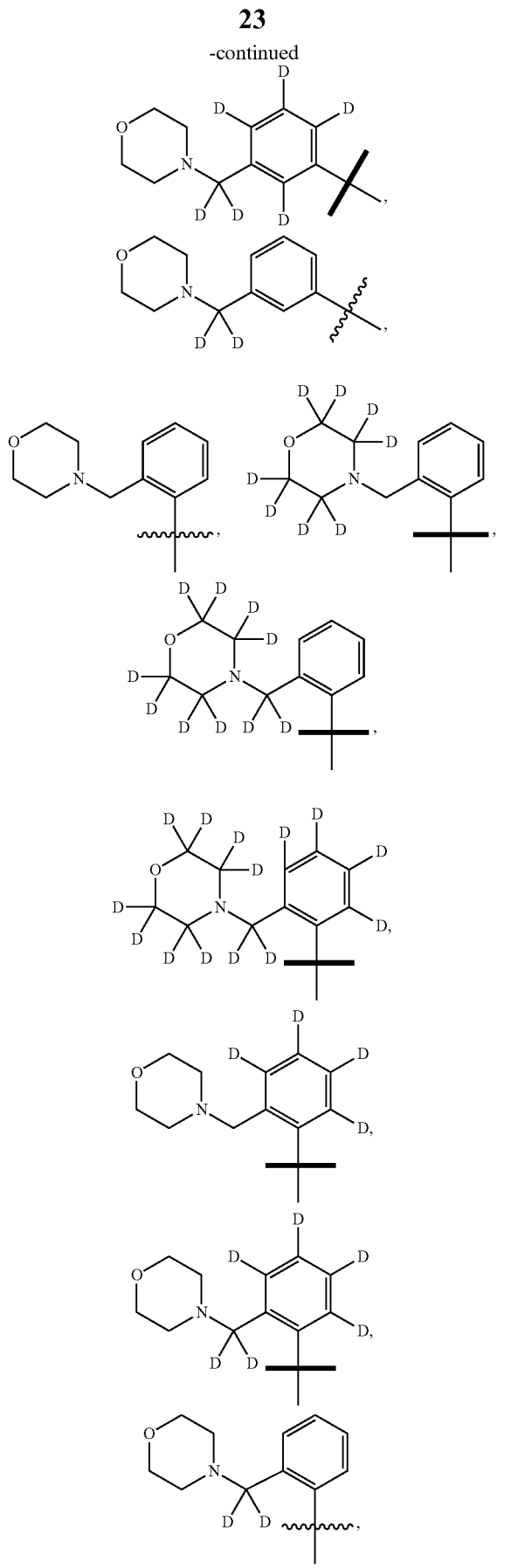
-continued
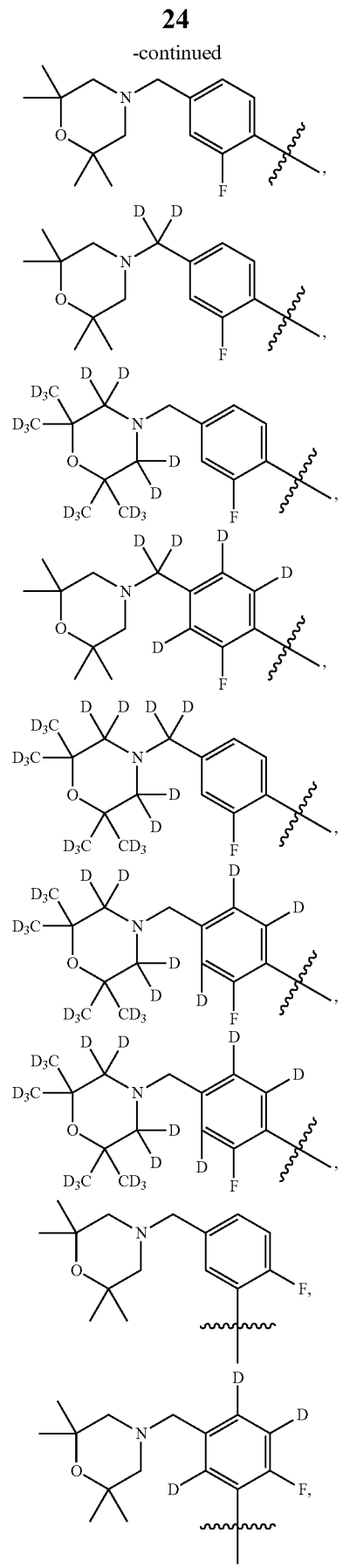

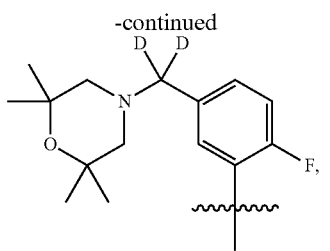
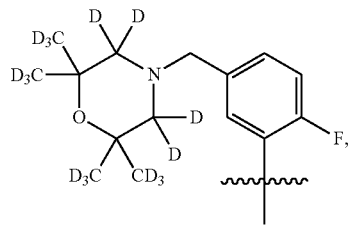
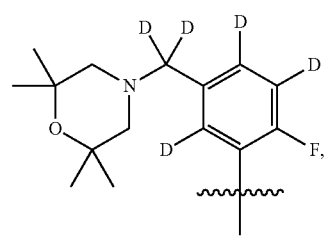
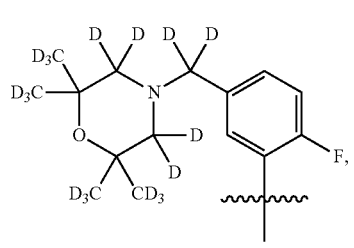
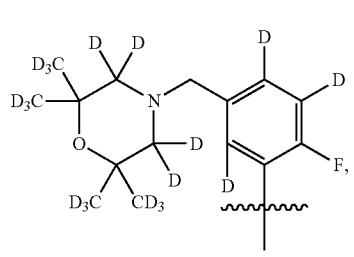
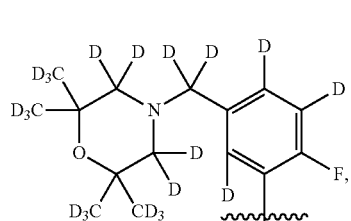
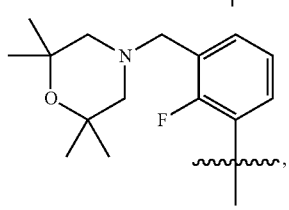
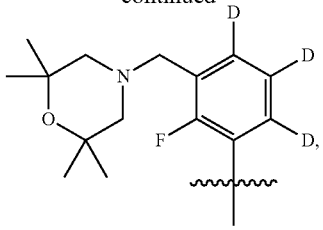
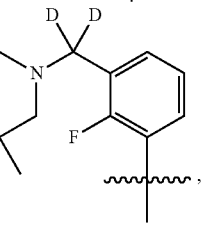
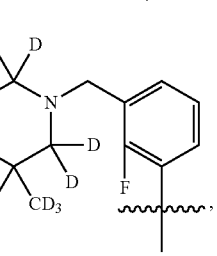
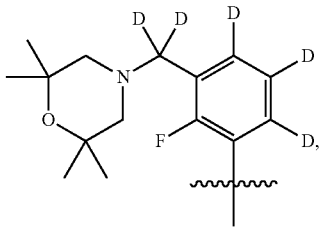
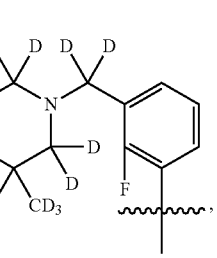
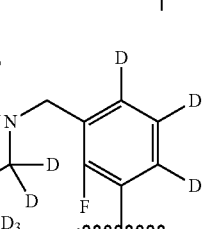
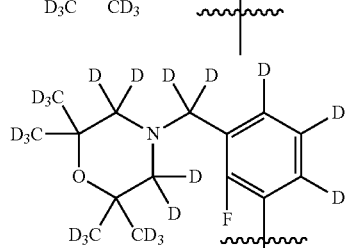
In the general formula (I), preferably, when n1 is 1, $R_2$ is H or D.

In the general formula (I), preferably, when n1 is 1 and $R_2$ is H or D, $R_{10}$ is

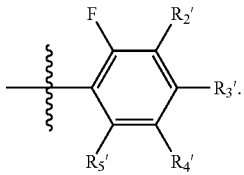

Preferably, in the definition of $R_{10}$, $R_5'$ is selected from H or D, one of $R_2'$, $R_3'$ and $R_4'$ is selected from a halogen, a cyano, a hydroxyl,

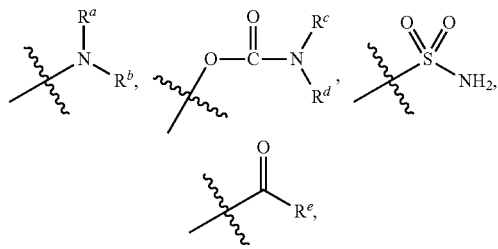

a substituted or unsubstituted $(C_1\text{-}C_{12})$alkyl, a substituted or unsubstituted $(C_1\text{-}C_{12})$alkoxy, a $(C_2\text{~}C_{20})$heterocycloalkyl or a deuterated $(C_2\text{~}C_{20})$heterocycloalkyl, the others are selected from H or D; in the above case, when $R_2'$, $R_4'$ and $R_5'$ are selected from H or D, $R_3'$ is selected from a halogen, a cyano,

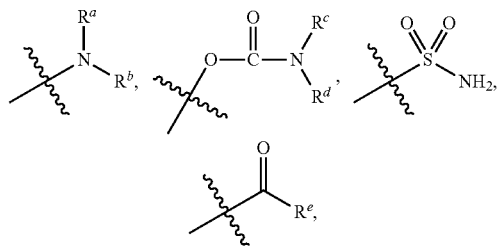

a substituted or unsubstituted $(C_1\text{-}C_{12})$alkyl, a substituted or unsubstituted $(C_1\text{-}C_{12})$alkoxy, a $(C_2\text{~}C_{20})$heterocycloalkyl or a deuterated $(C_2\text{~}C_{20})$heterocycloalkyl.

In the general formula (I), when n1 is 1, $R_2$ is H or D, X is NH or ND and $R_{10}$ is

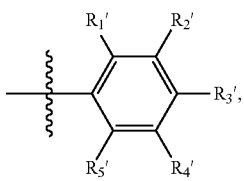

preferably, $R_1'$, $R_4'$ and $R_5'$ are H, $R_2'$ is selected from a halogen or a substituted or unsubstituted $(C_1\text{-}C_{12})$alkyl; $R_3'$ is selected from a halogen, a substituted or unsubstituted $(C_1\text{-}C_{12})$alkyl or a substituted or unsubstituted $(C_1\text{-}C_{12})$ alkoxy.

In the general formula (I), preferably, when n1 is 1, $R_2$ is a halogen and $R_{10}$ is

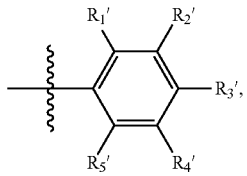

$R_1'$ or $R_5'$ is rather than a halogen. Preferably, the general formula (I) is selected from the group consisting of

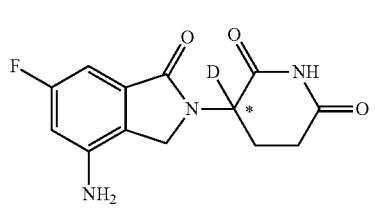
I-01

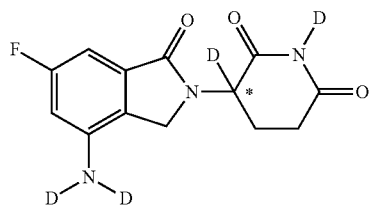
I-02

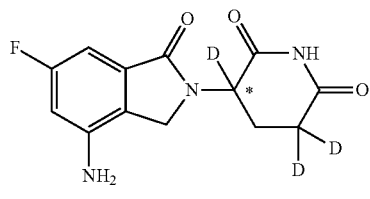
I-03

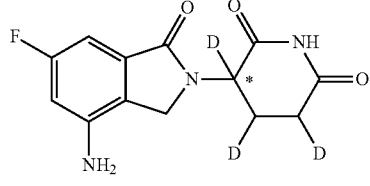
I-04

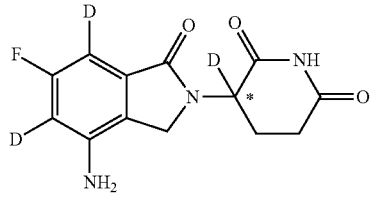
I-05

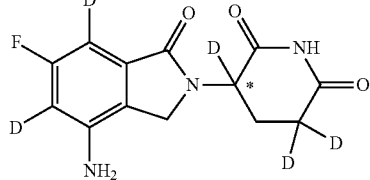
I-06

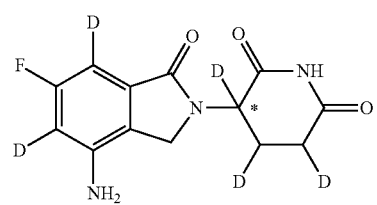 I-07
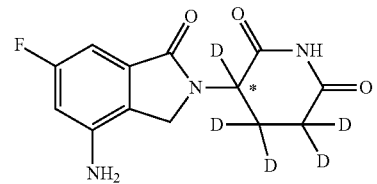 I-08
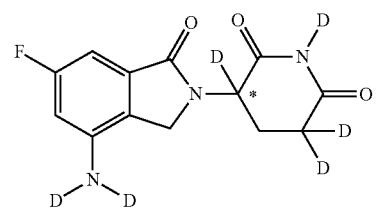 I-09
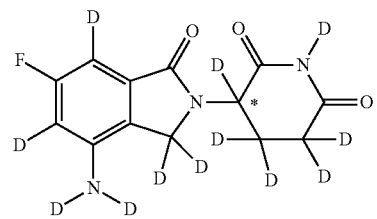 I-10
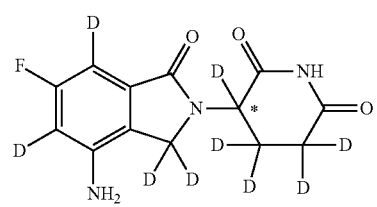 I-11
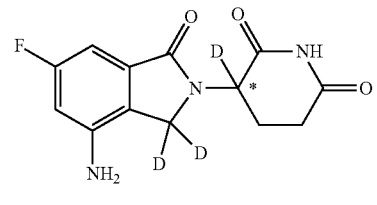 I-12
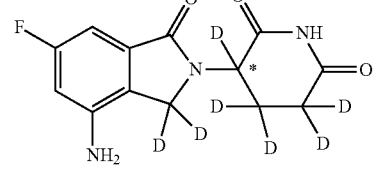 I-13
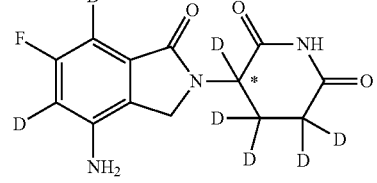 I-14
 I-15
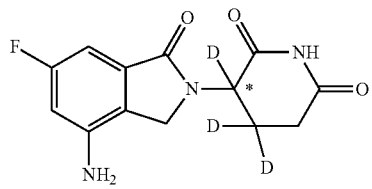 I-16
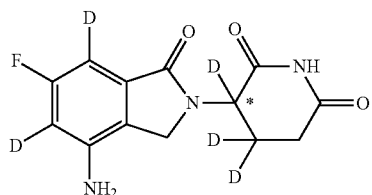 I-17
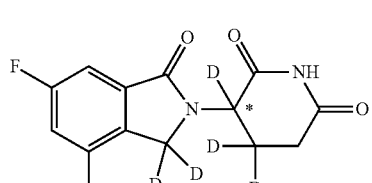 I-18
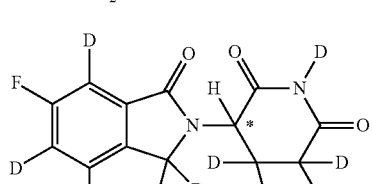 I-19
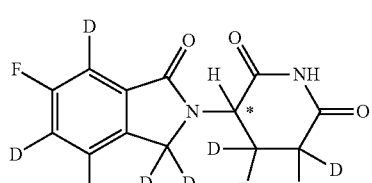 I-20
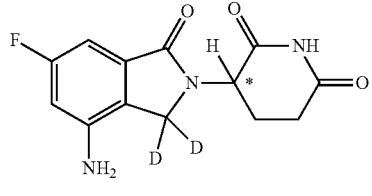 I-21
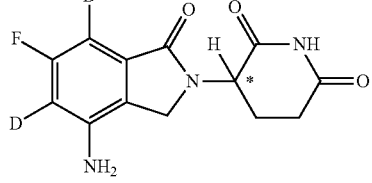 I-22

-continued

| I-39 | I-47 |
| I-40 | I-48 |
| I-41 | I-49 |
| I-42 | I-50 |
| I-43 | I-51 |
| I-44 | I-52 |
| I-45 | I-53 |
| I-46 | I-54 |

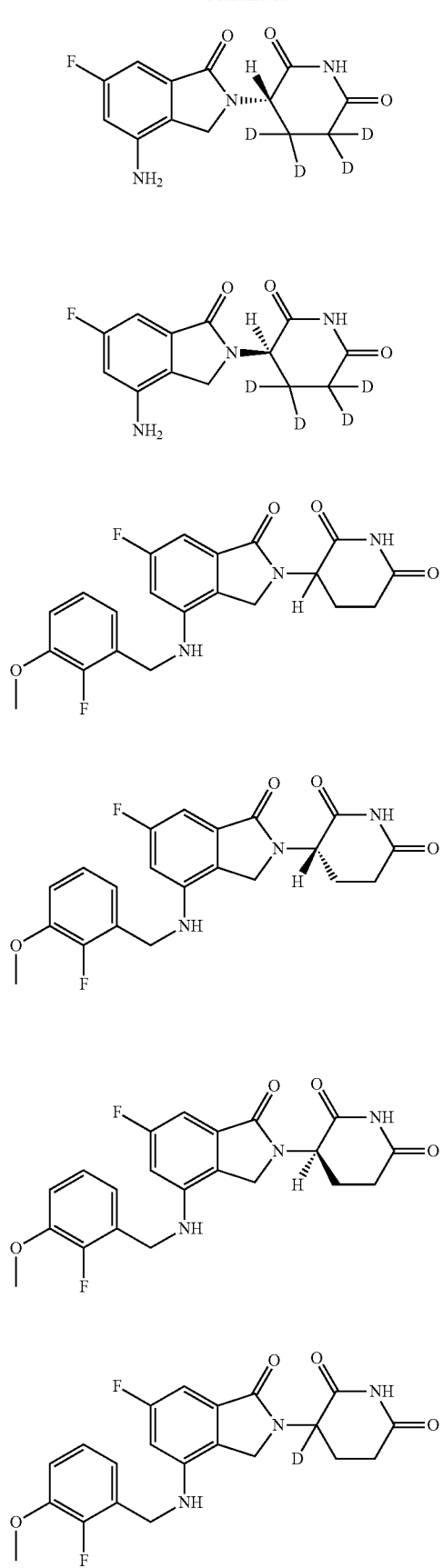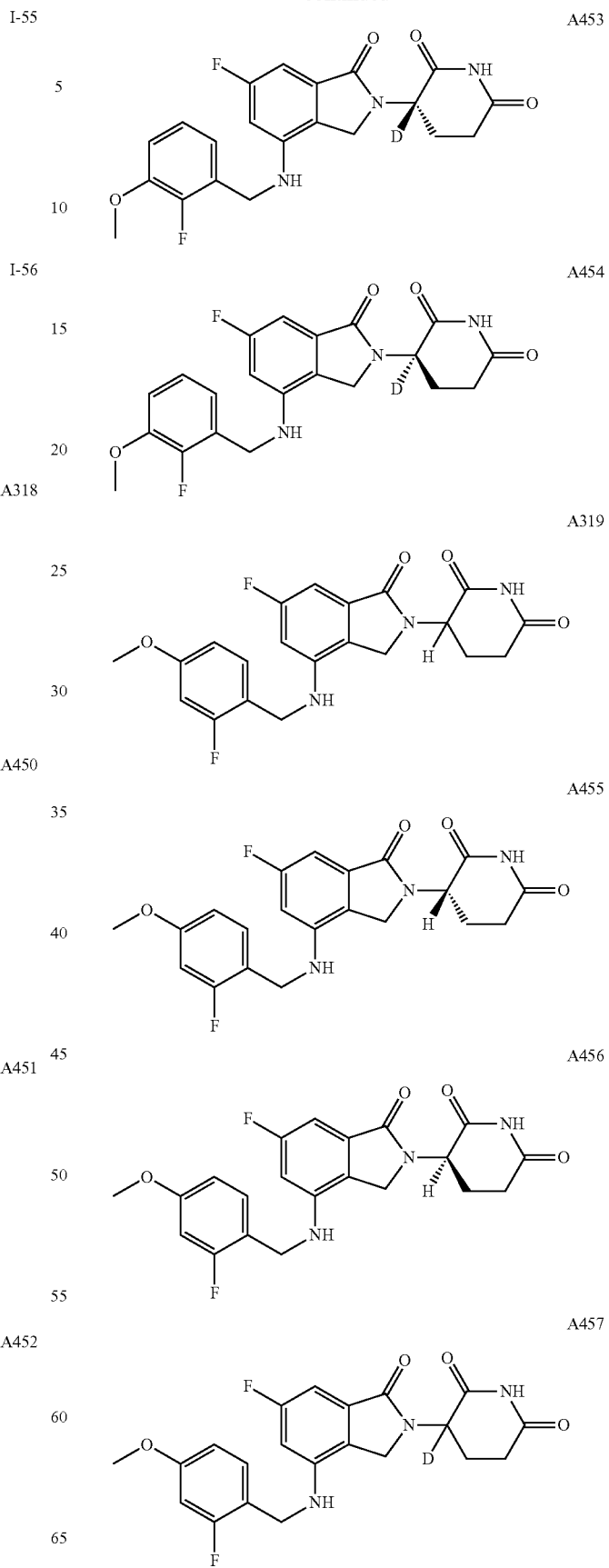

A458
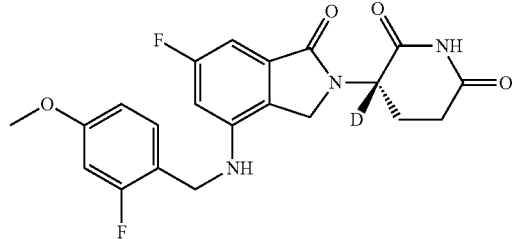
A463
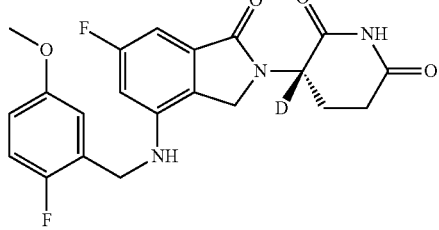
A459
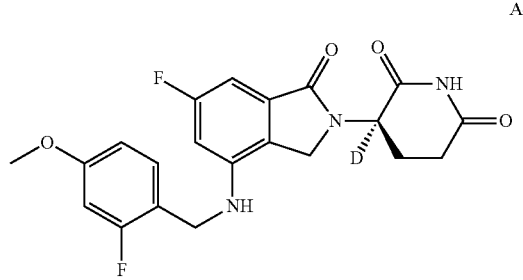
A464
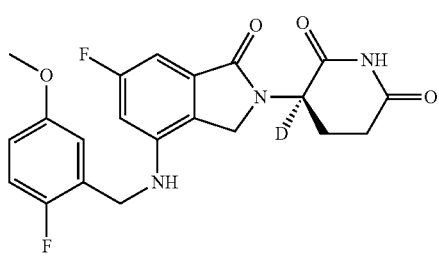
A320
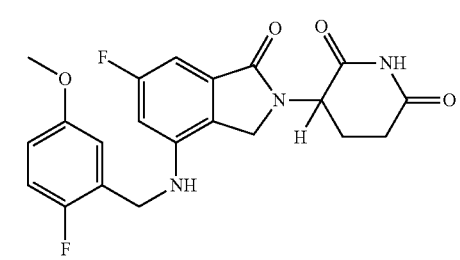
A196
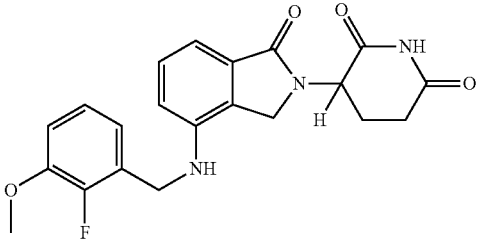
A460
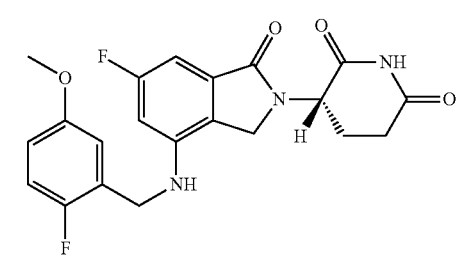
A465
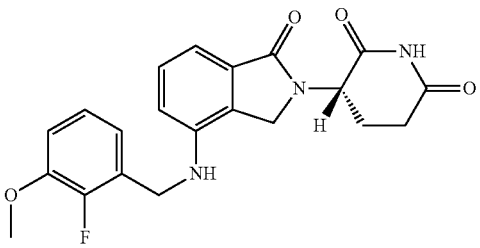
A461
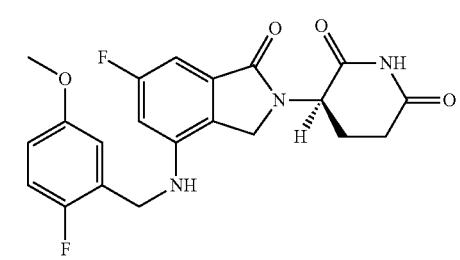
A466
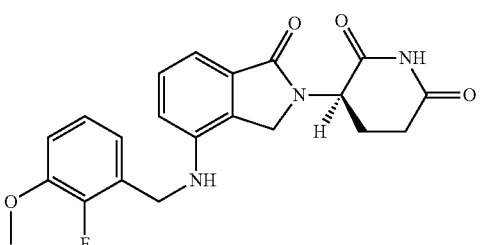
A462
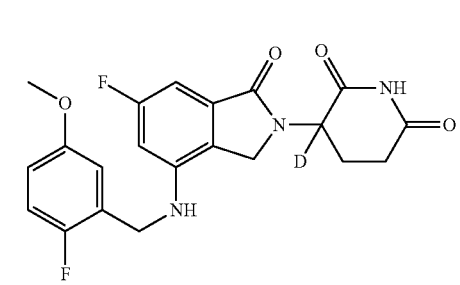
A467
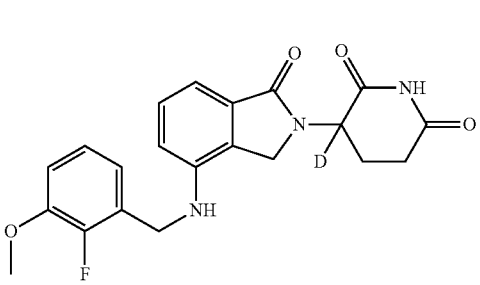

A357 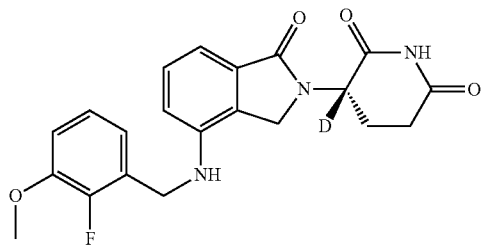
A468 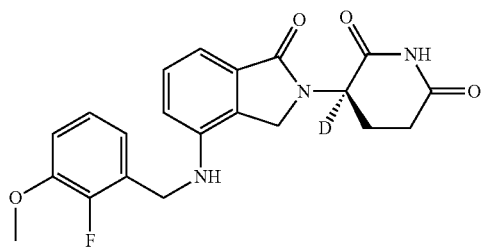
A197 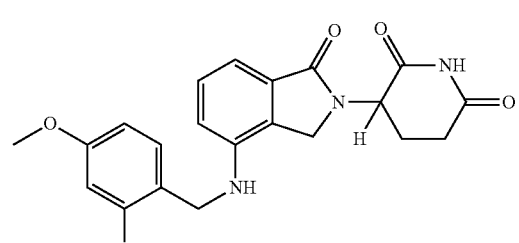
A469
A470
A340
A356 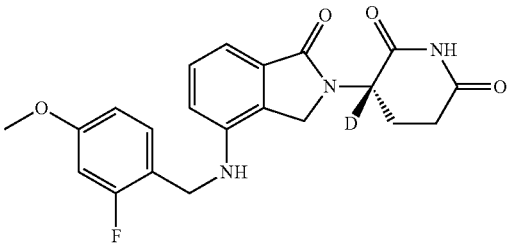
A471 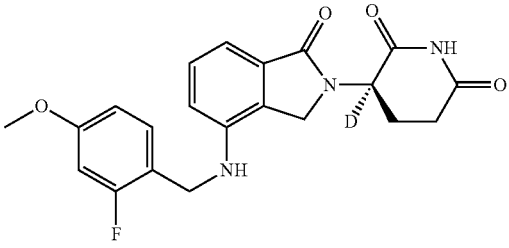
A195 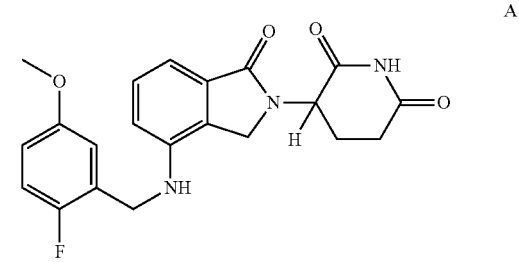
A472 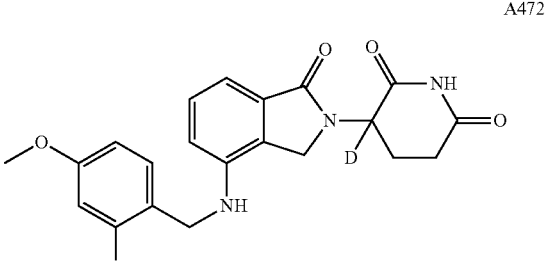
A341 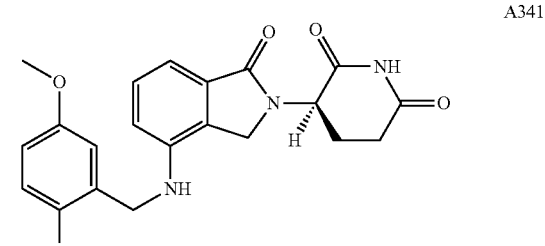
A473 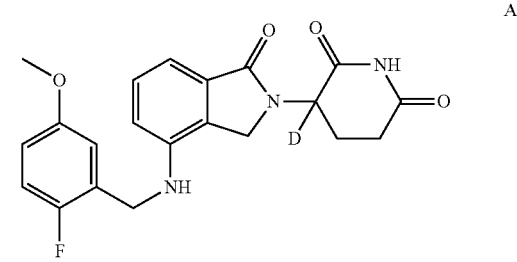

A343
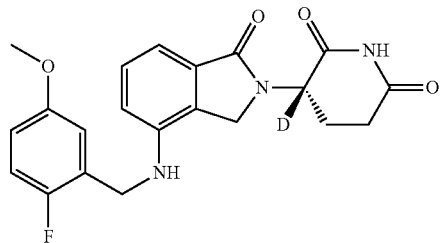
A342
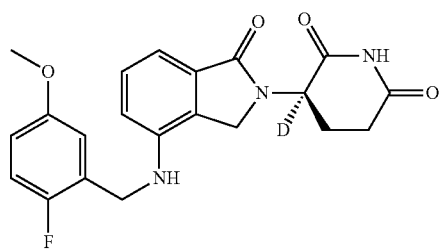
A327
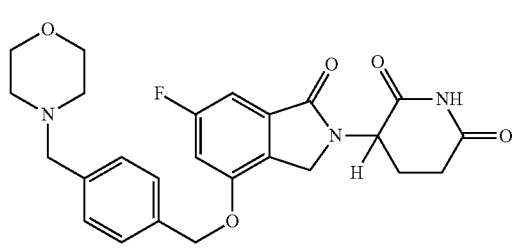
A474
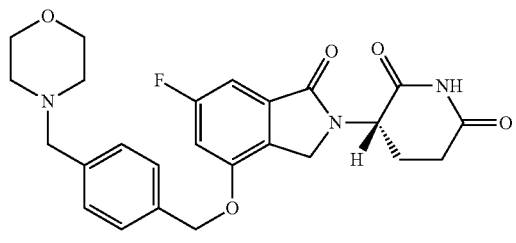
A475
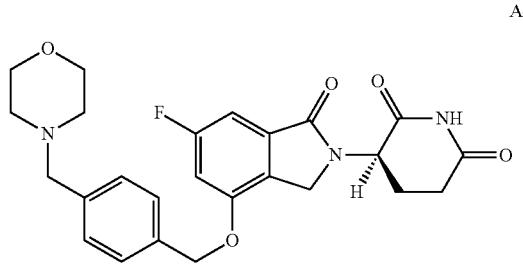
A476
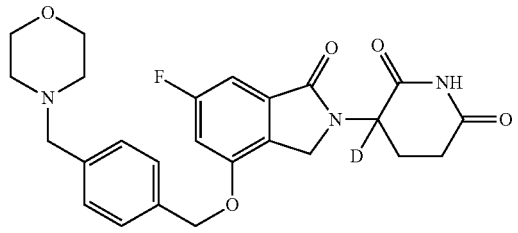
A477
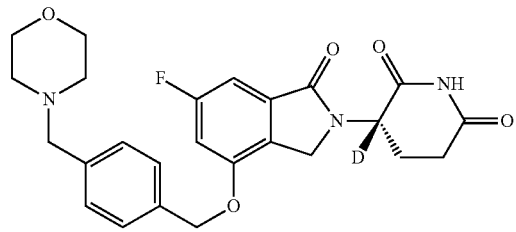
A478
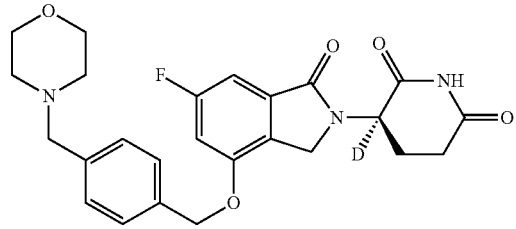
A331
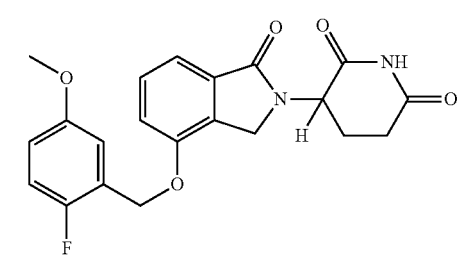
A484
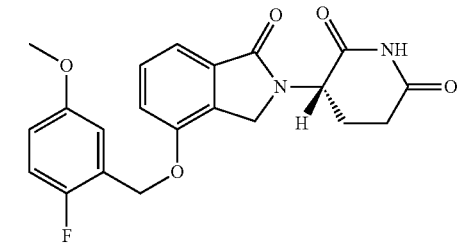
A485
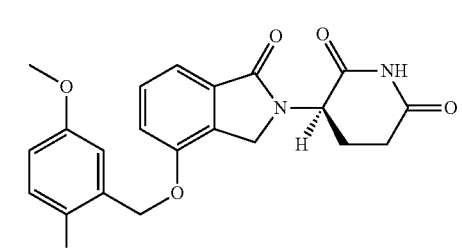
A486
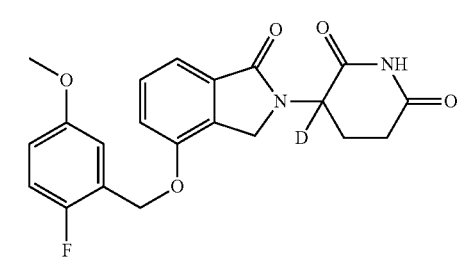

A379
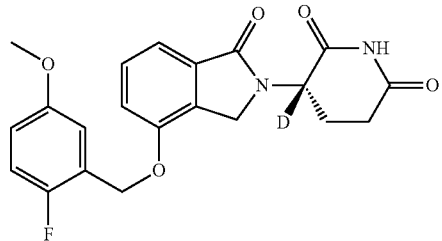
A487
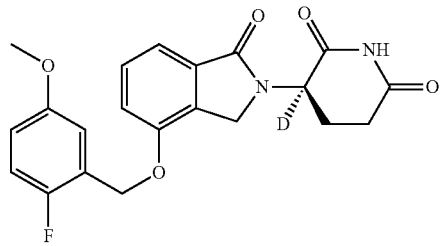
A329
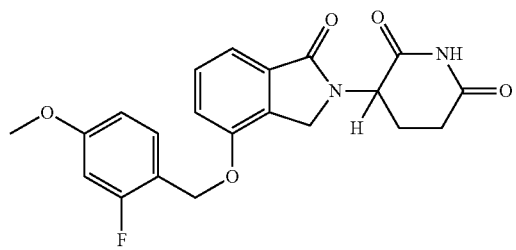
A488
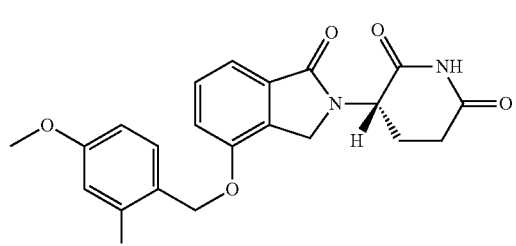
A489
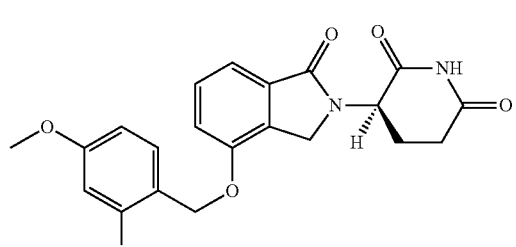
A490
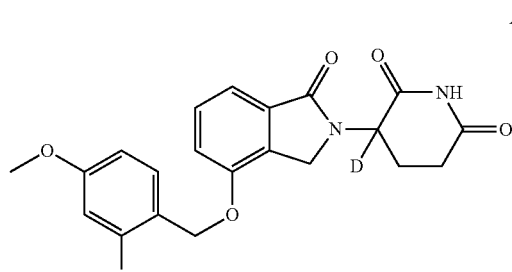
A393
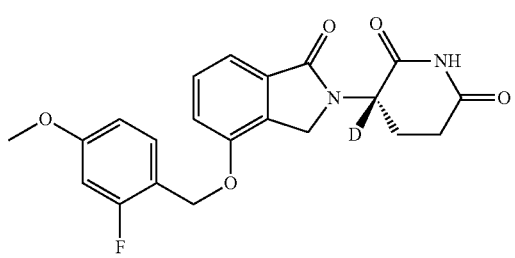
A392
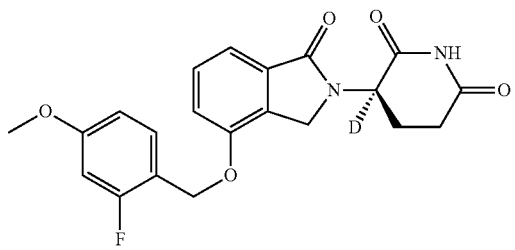
A334
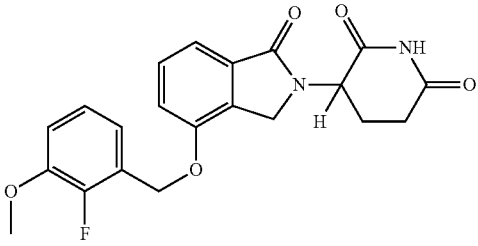
A491
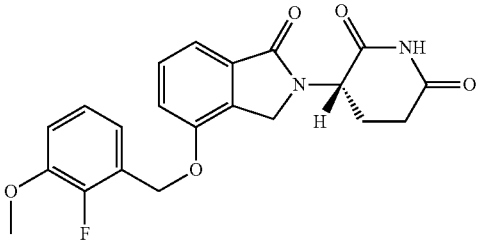
A492
A493
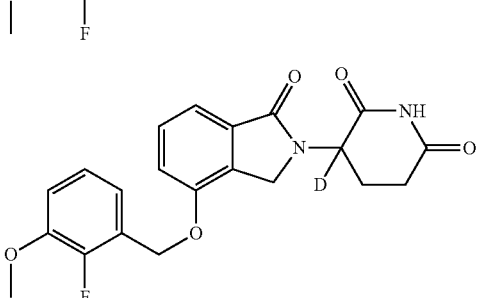

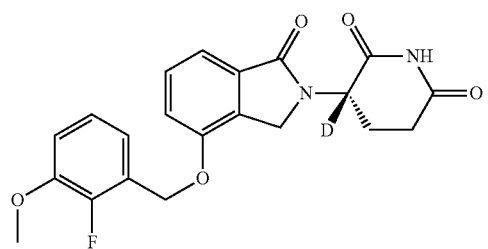 A380
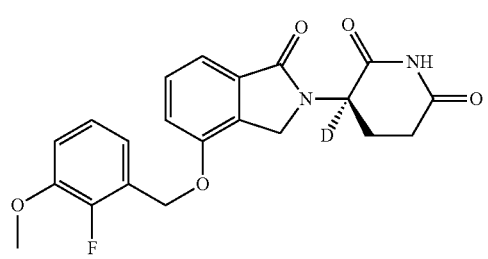 A494
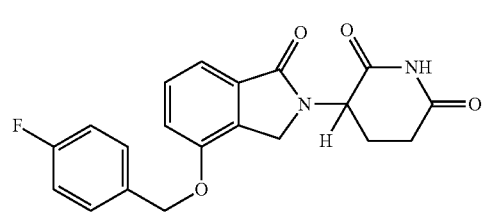 A333
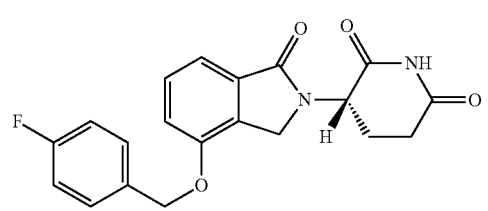 A495
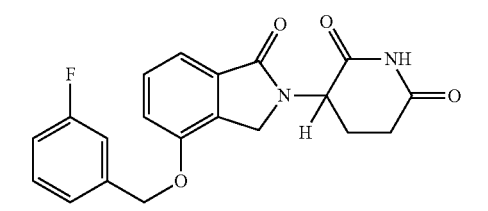 A332
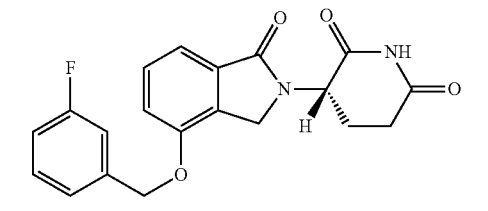 A500
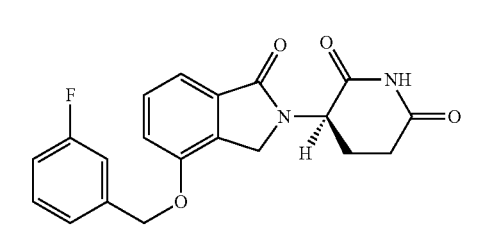 A501
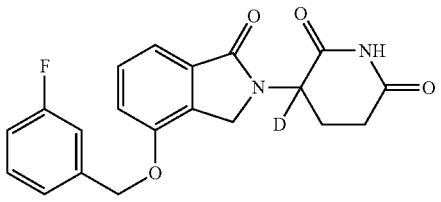 A502
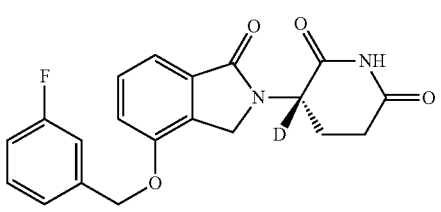 A503
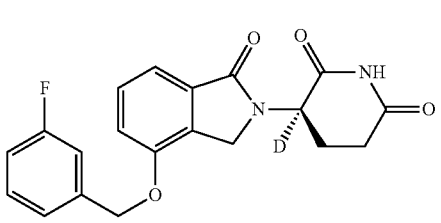 A504
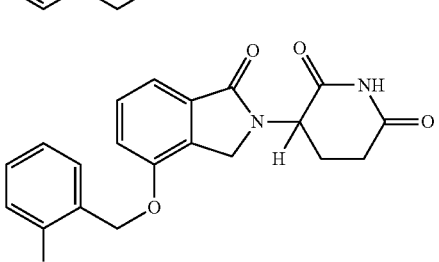 A336
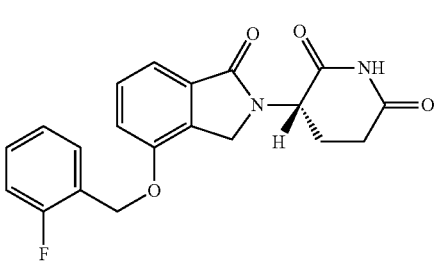 A505
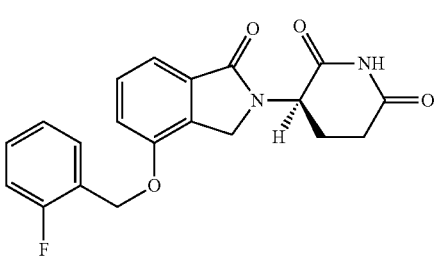 A506
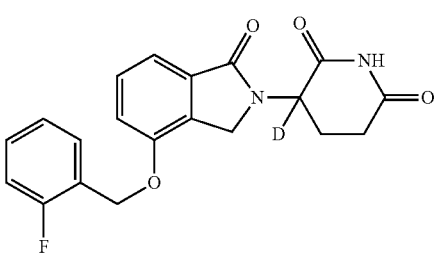 A507

A508 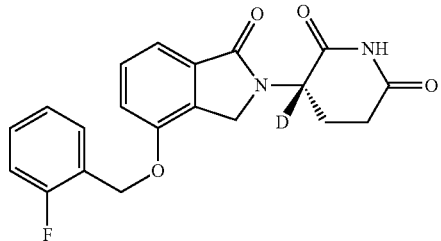
A509 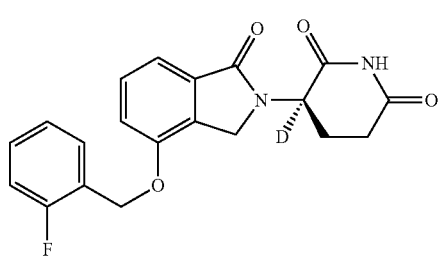
A346 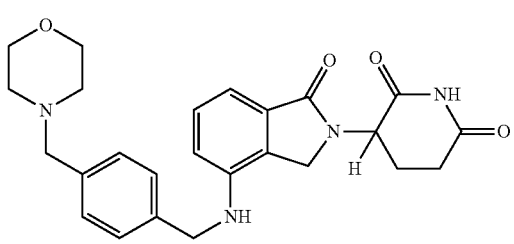
A510 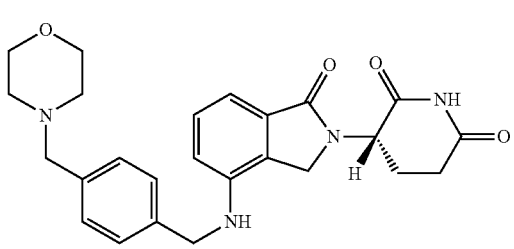
A511 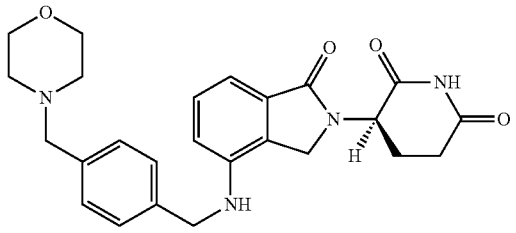
A512 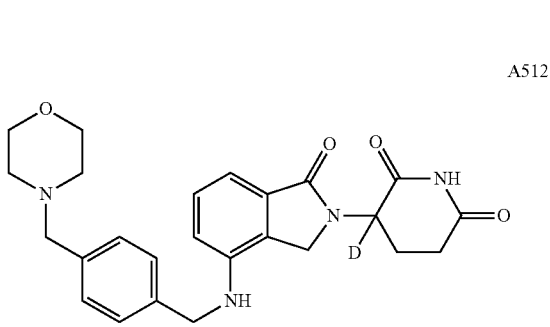
A373 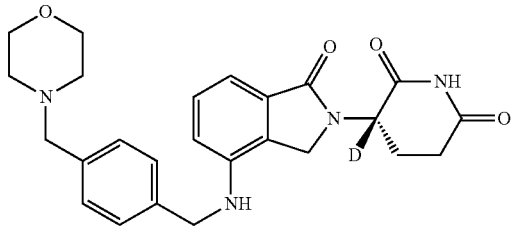
A513 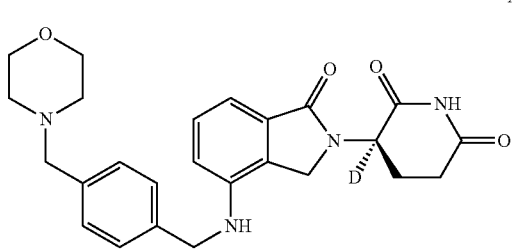
A352 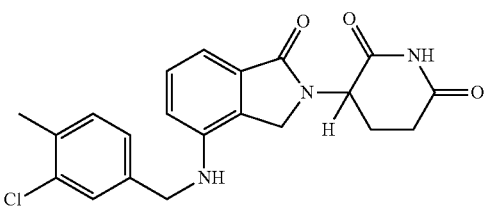
A529 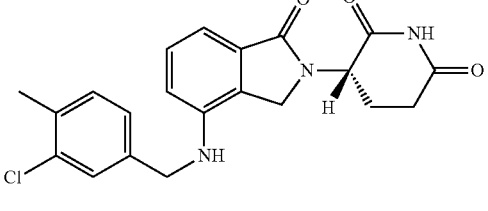
A530 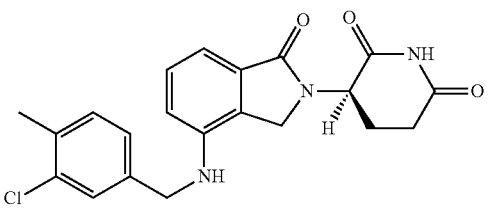
A531 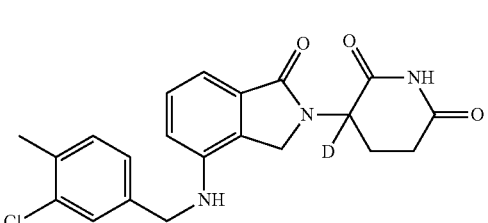
A532 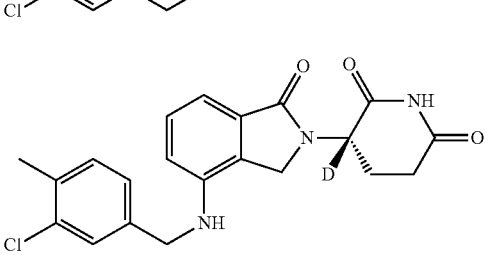

A533 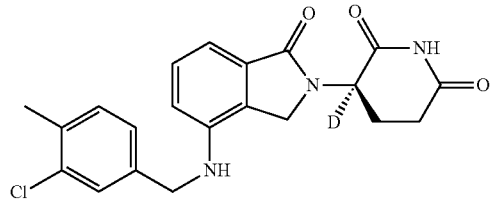
A353 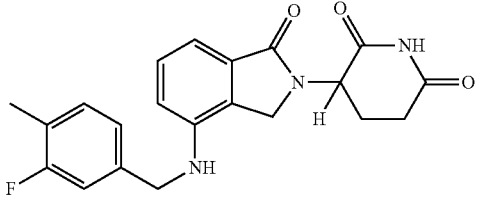
A350 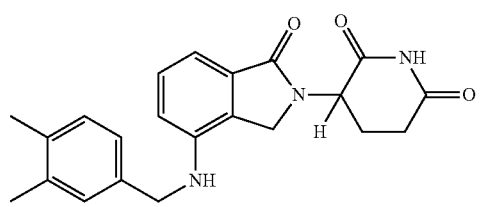
A549 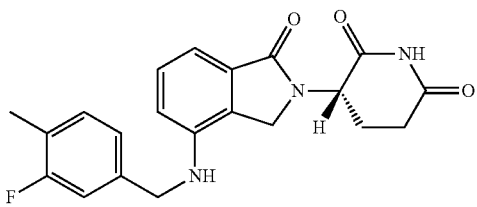
A539 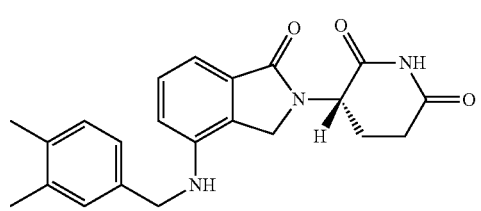
A550 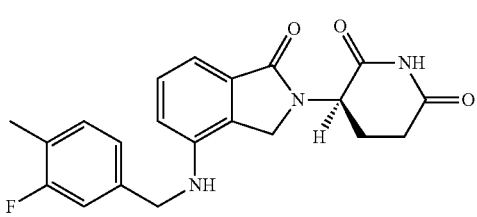
A540 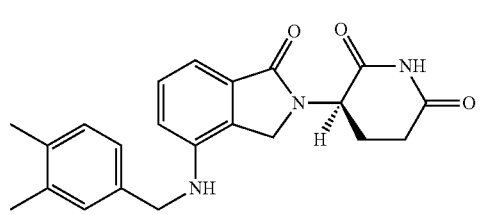
A551 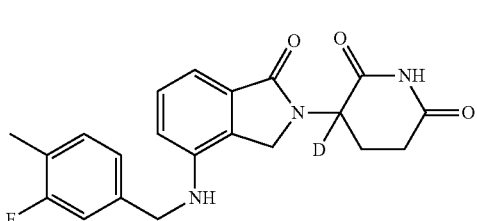
A541 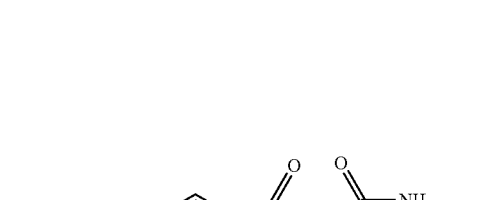
A552 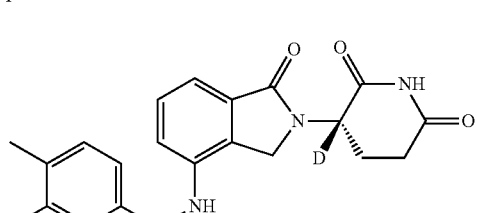
A542 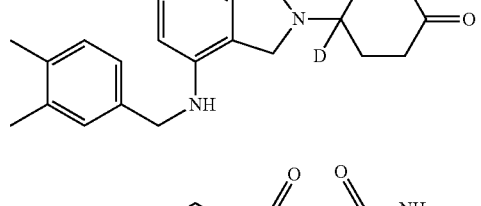
A553 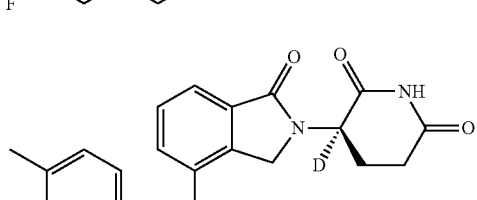
A543 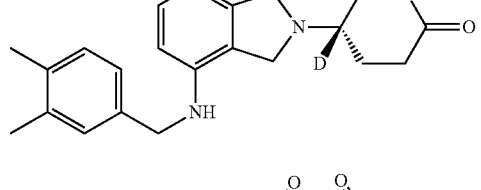
A349 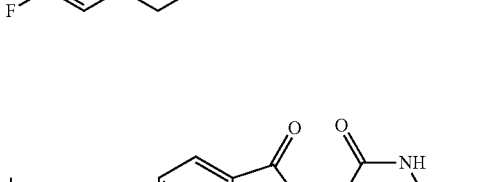
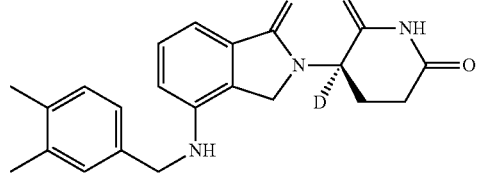

A554
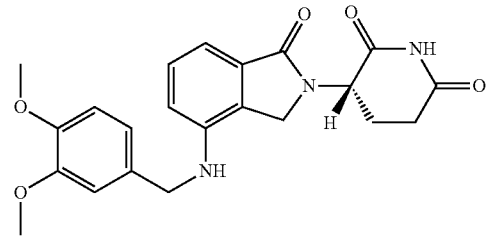
A555
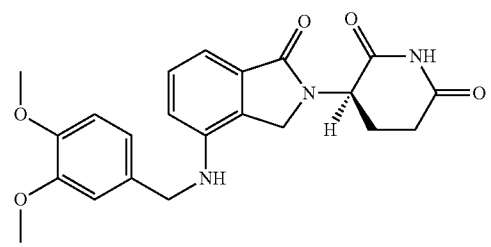
A556
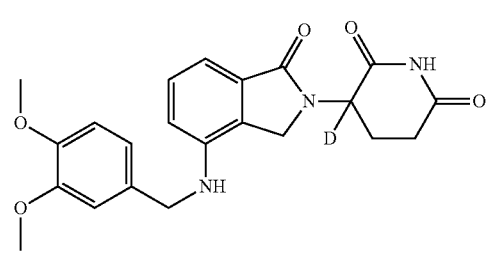
A557
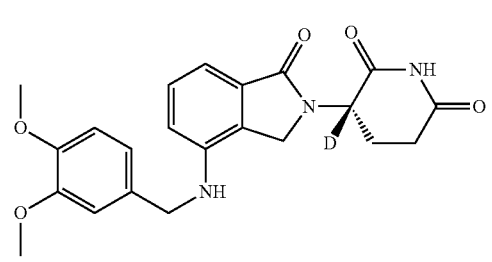
A558
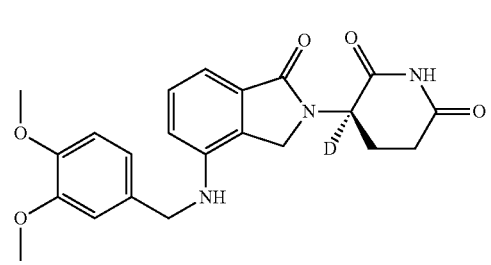
A354
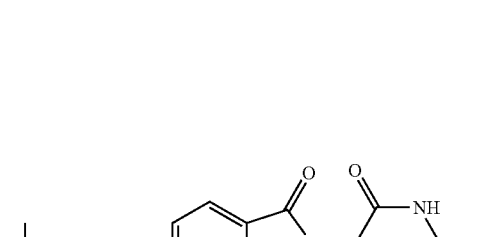
A559
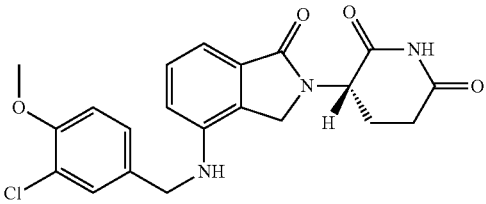
A560
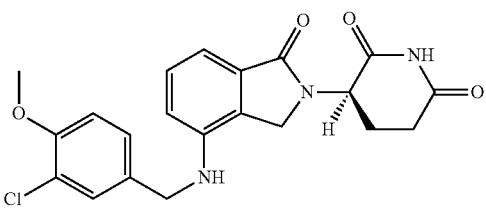
A561
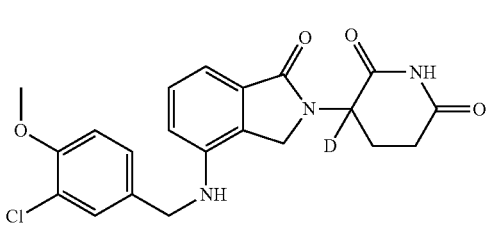
A562
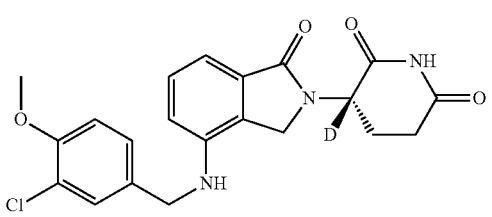
A563
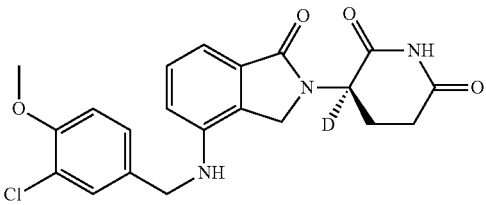
A355
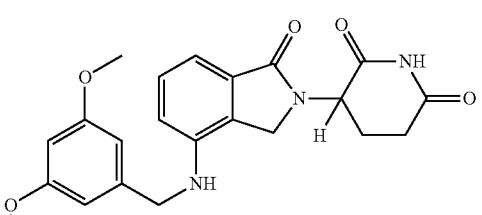
A564
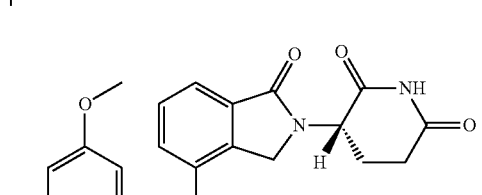

A565 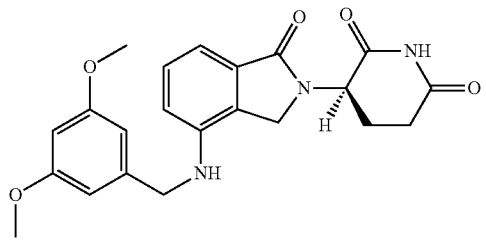
A566 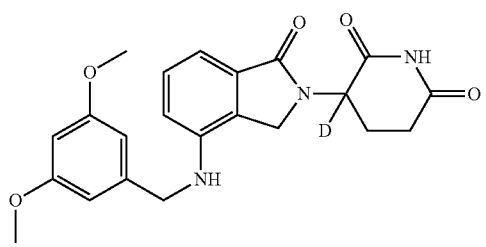
A567 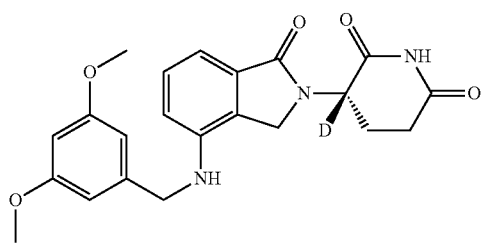
A568 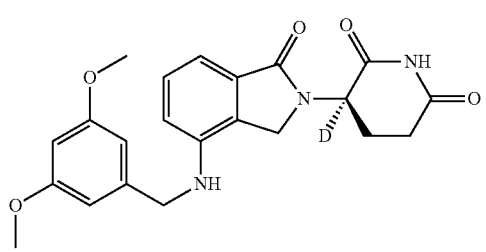
A351 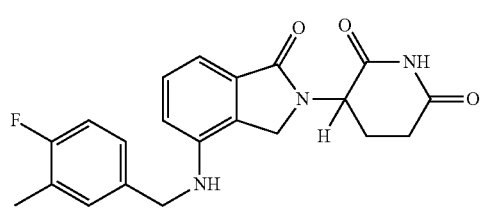
A569 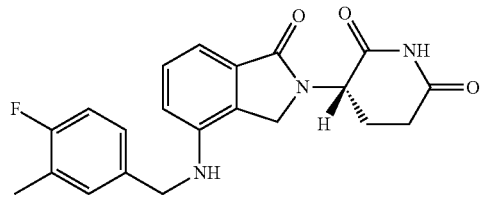
A570 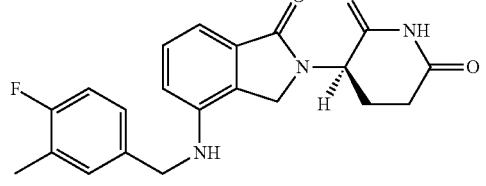
A571 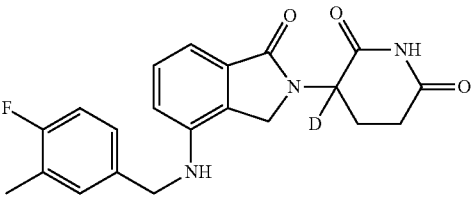
A572 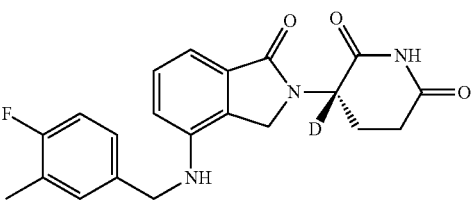
A573 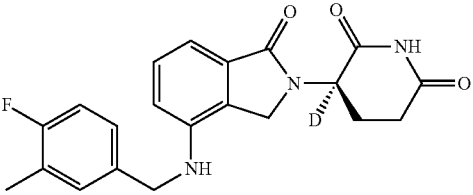
A359 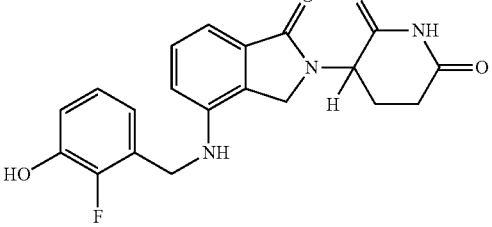
A574 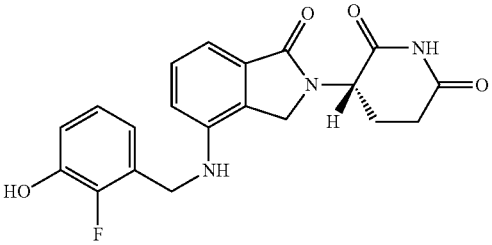
A575 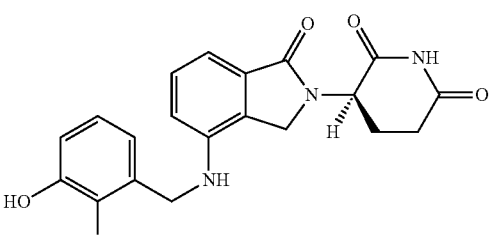
A576 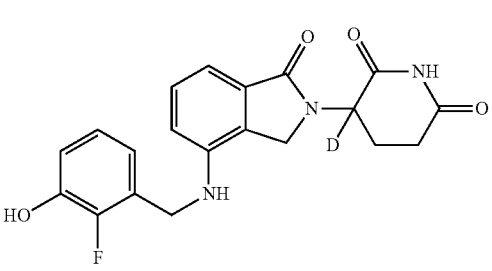

A577 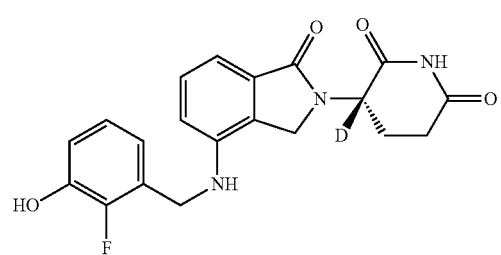
A578 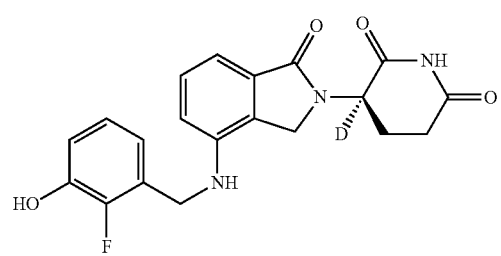
A360 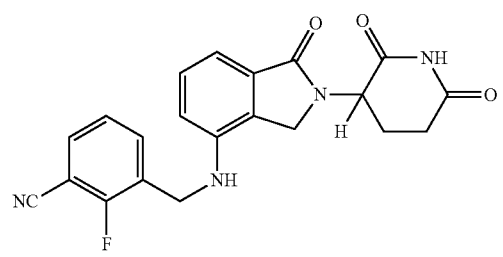
A579 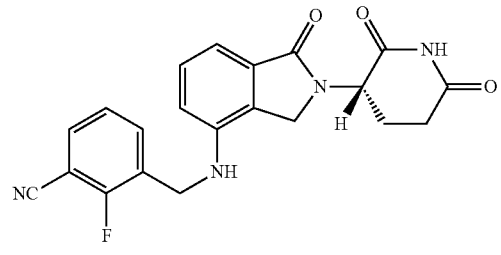
A580 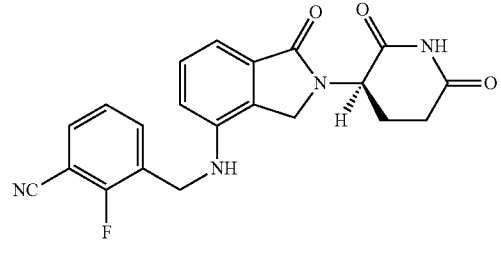
A581 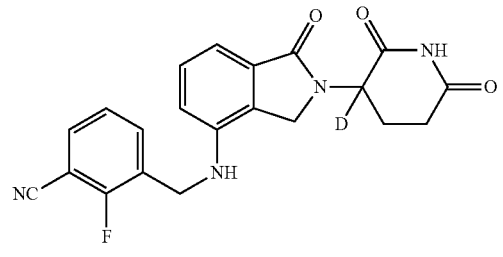
A582 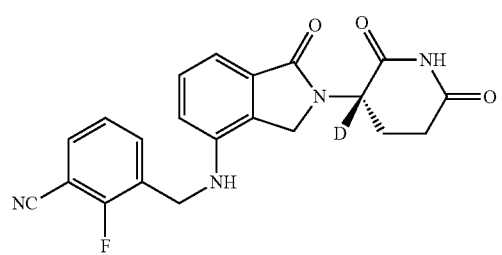
A583 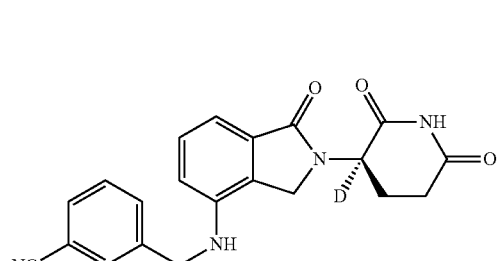
A367 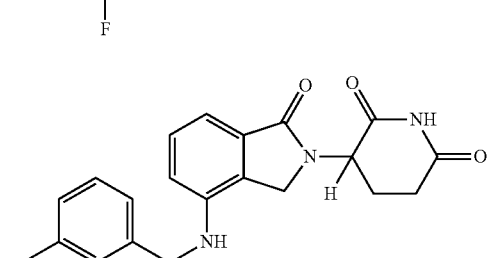
A584 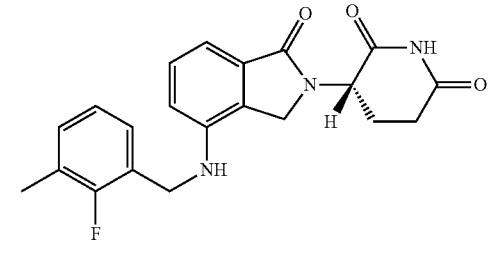
A585 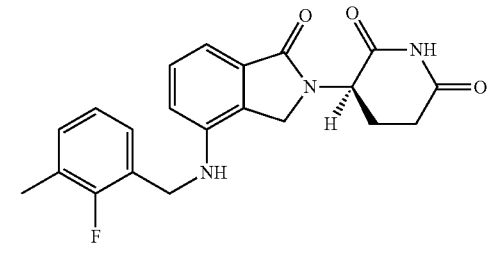
A586 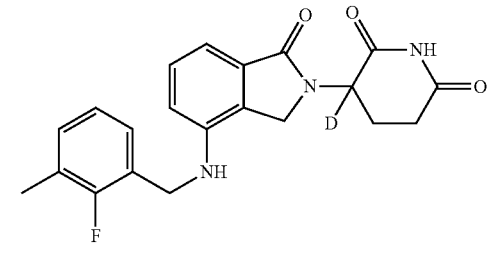

A587 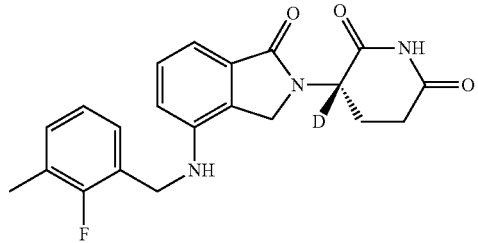
A588 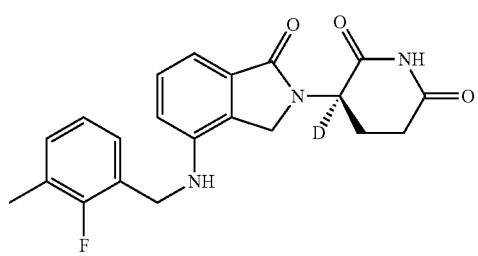
A361 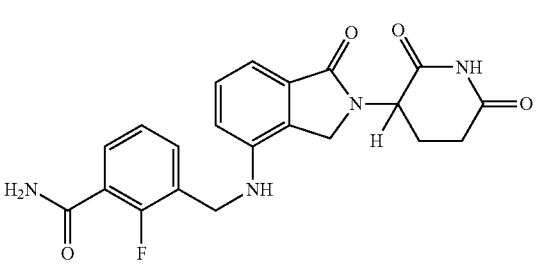
A589 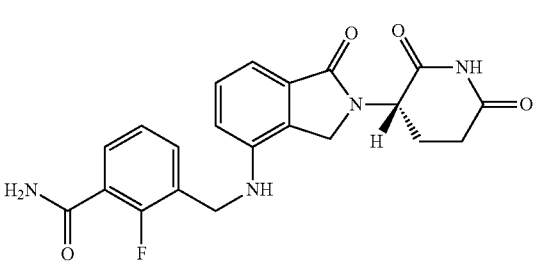
A590 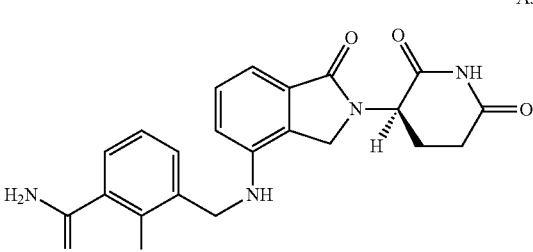
A591 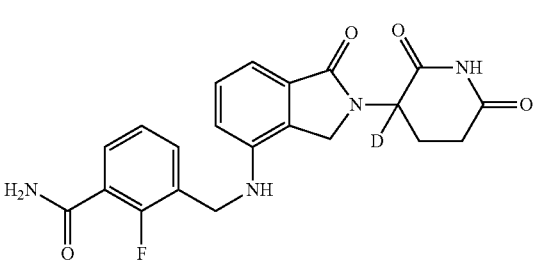
A592 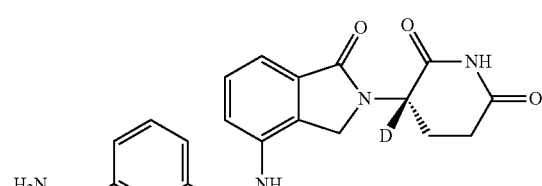
A593 
A362 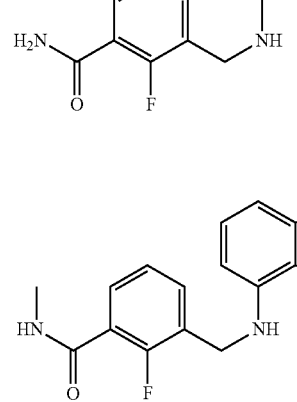
A594 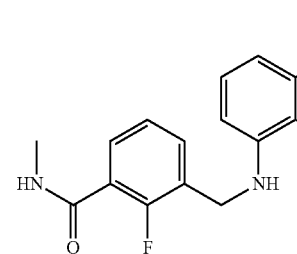
A595 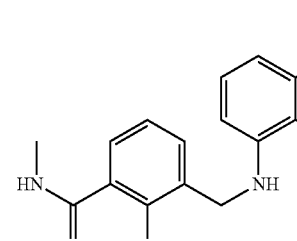
A596

A597
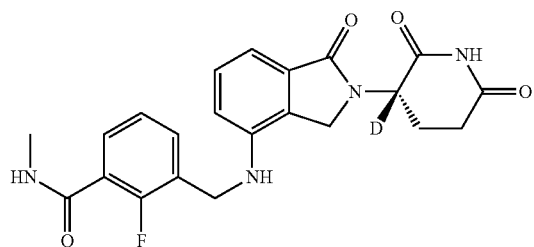
A601
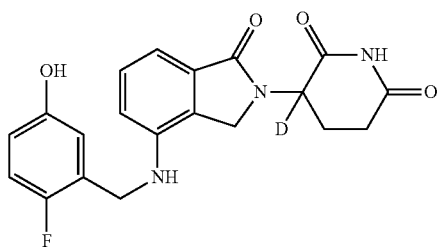
A598
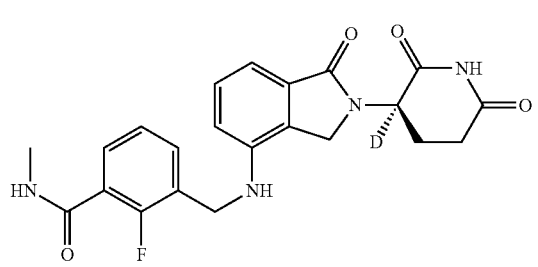
A602
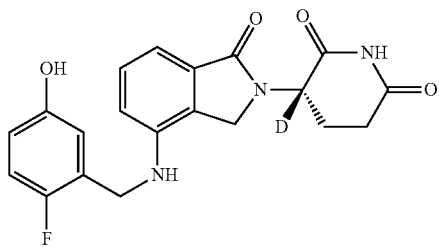
A364
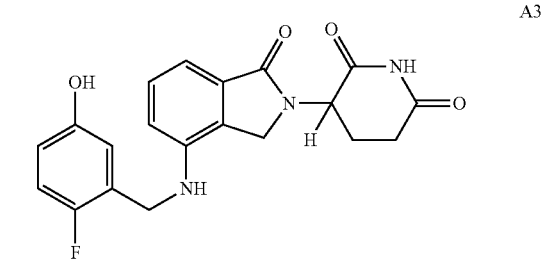
A603
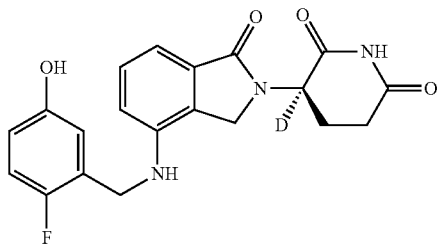
A599
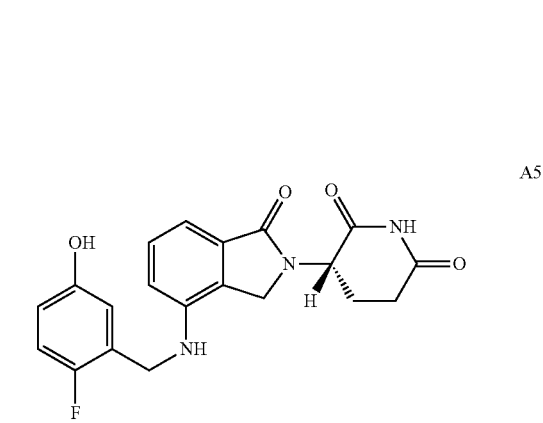
A615
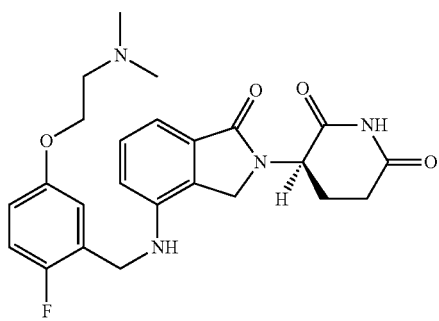
A600
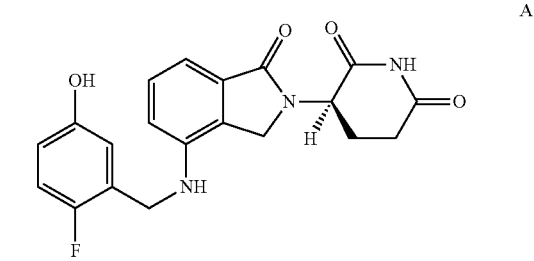
A616
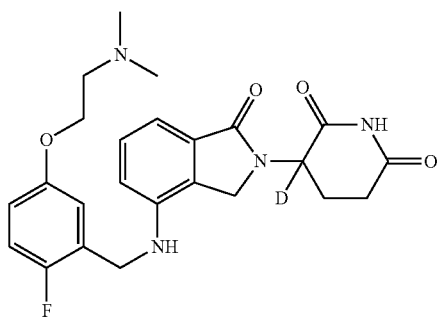

A617
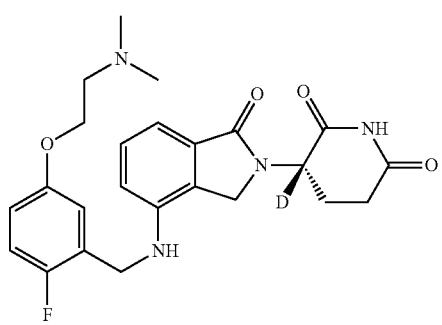
A618
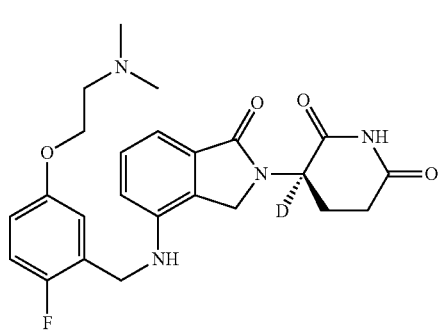
A370
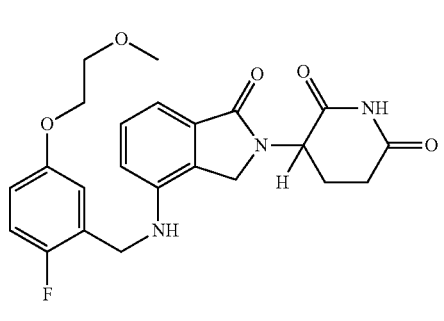
A619
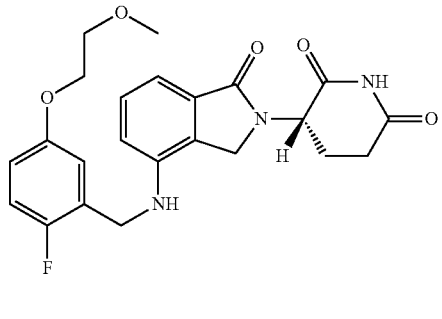
A620
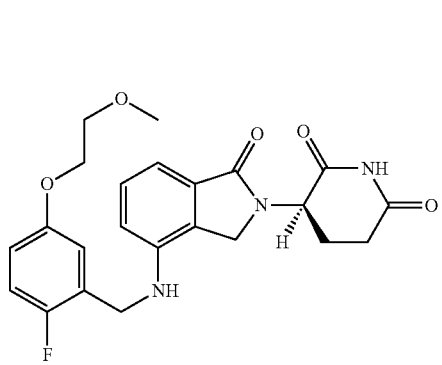
A621
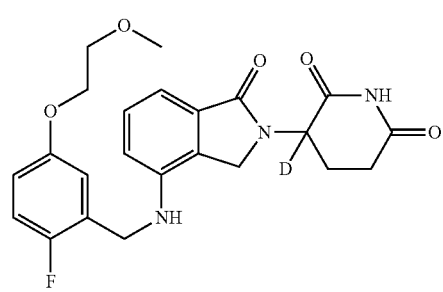
A622
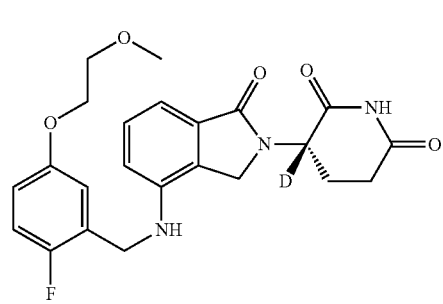
A623
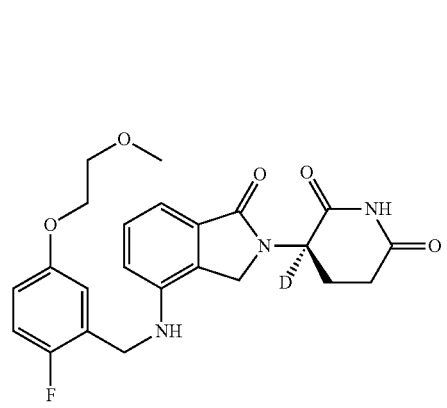
A376
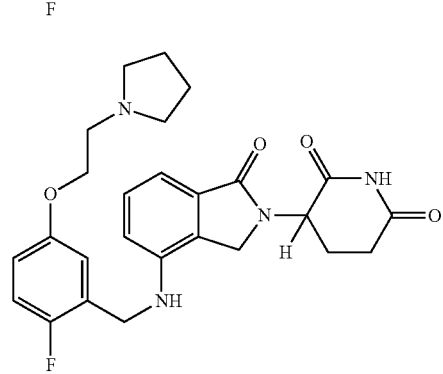
A624
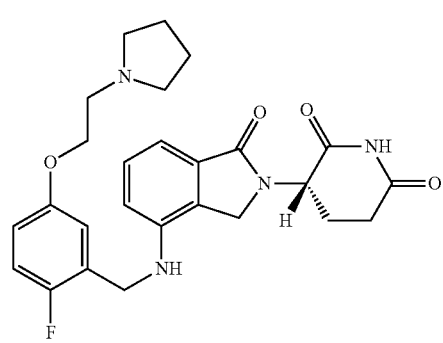

A625 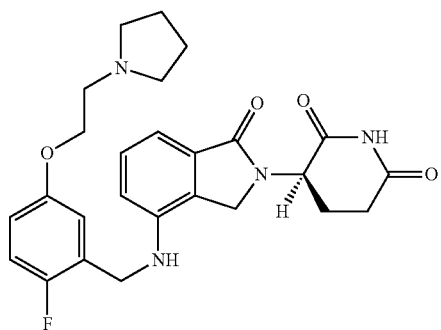
A626 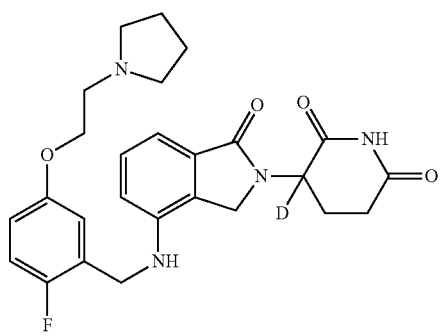
A627 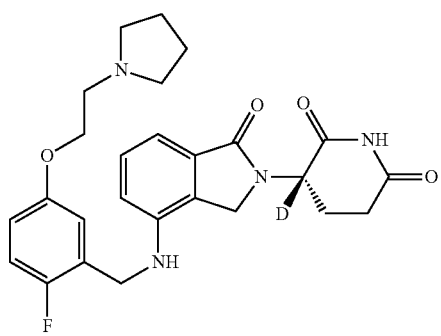
A628 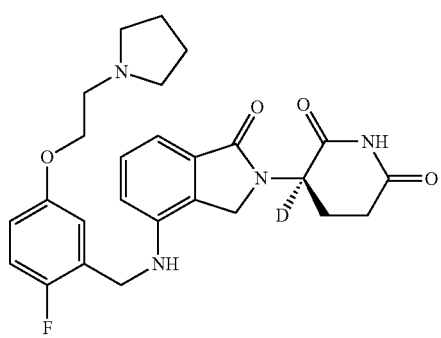
A368 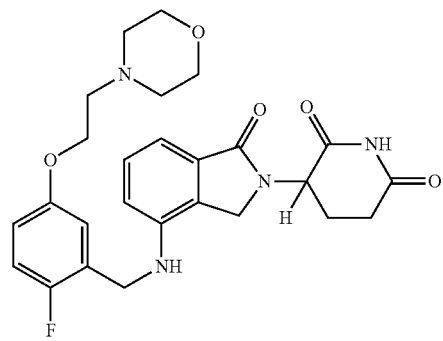
A629 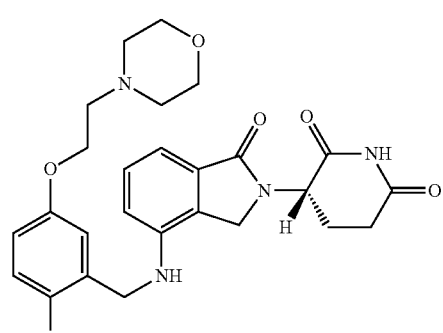
A630 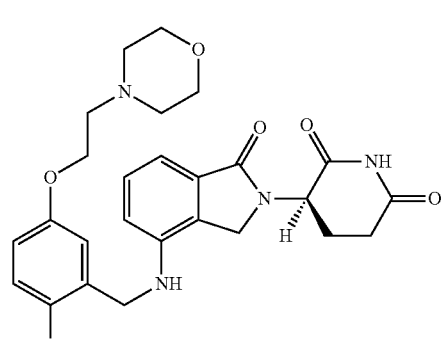
A631 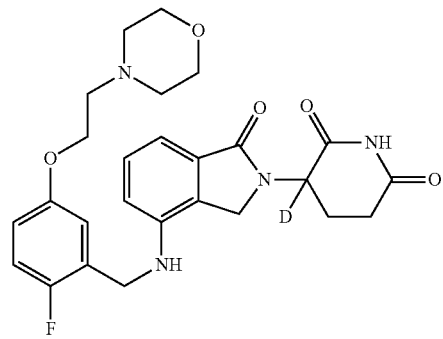

A632
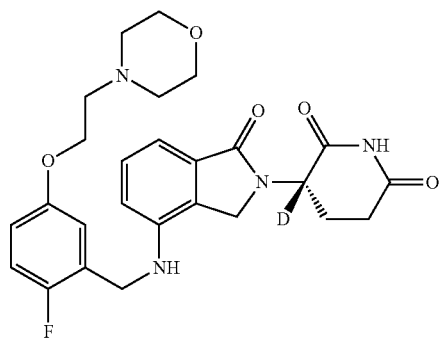
A633
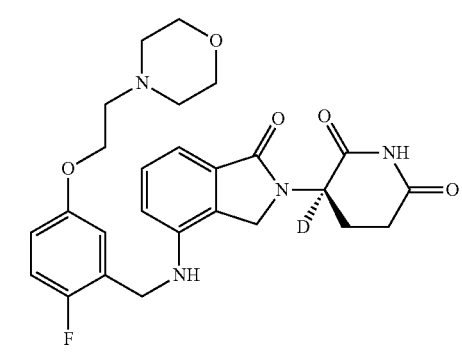
A369
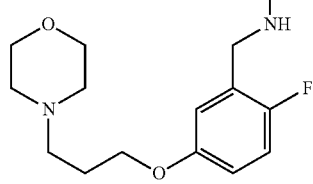
A634
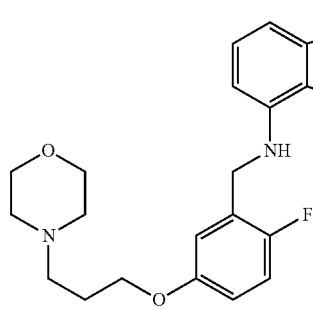
A635
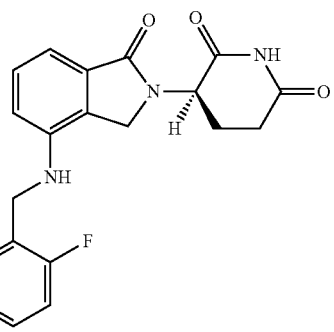
A636
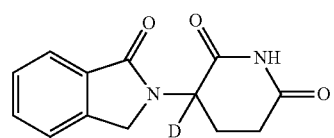
A637
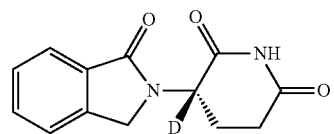
A638
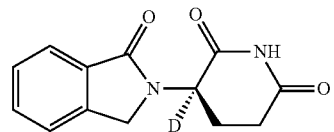

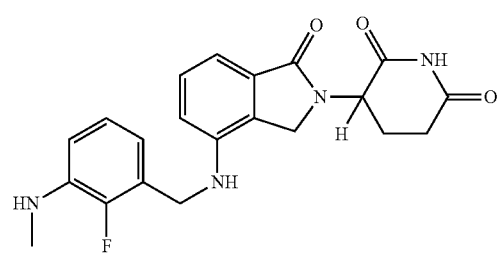
A372
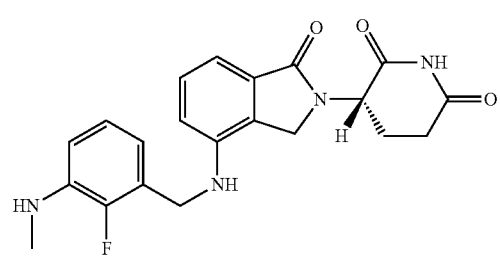
A639
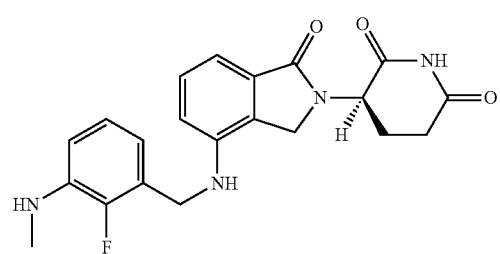
A640
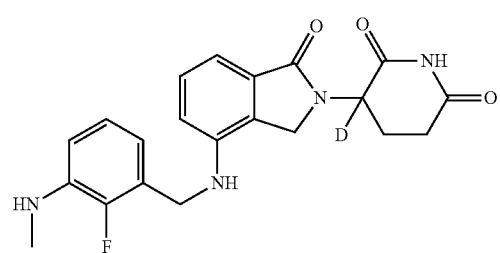
A641
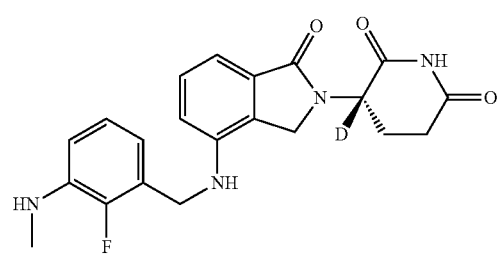
A642
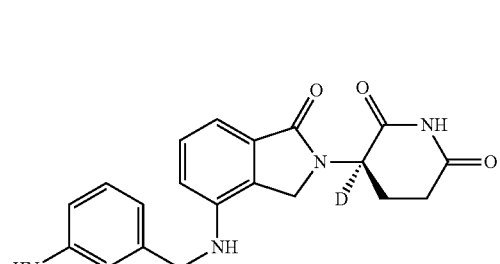
A643
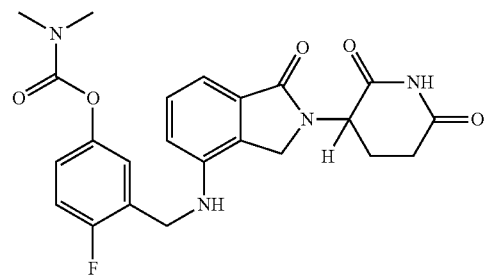
A378
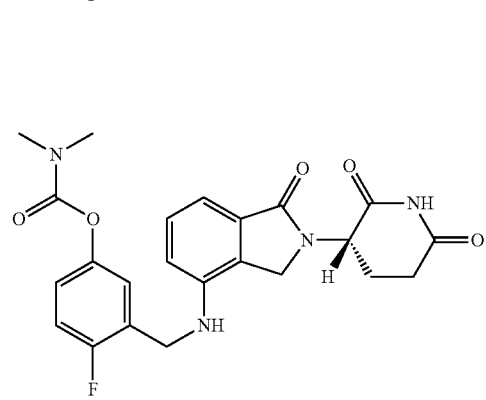
A644
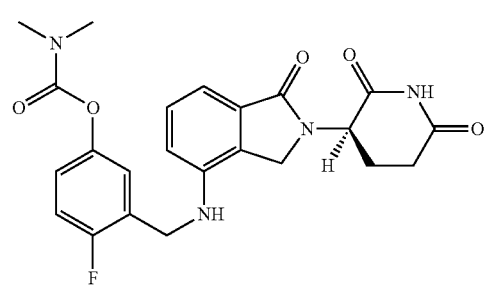
A645
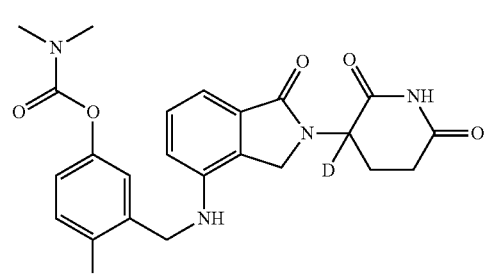
A646
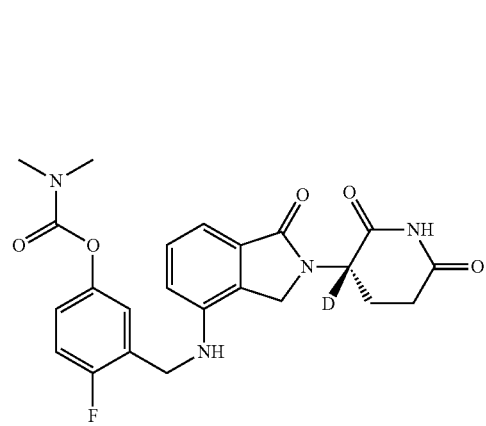
A647

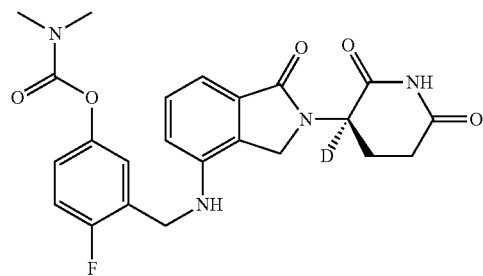
A648
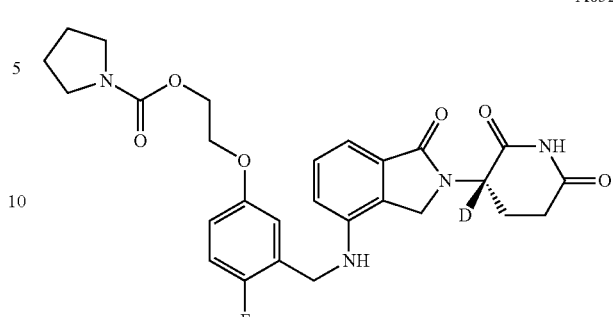
A374
A652
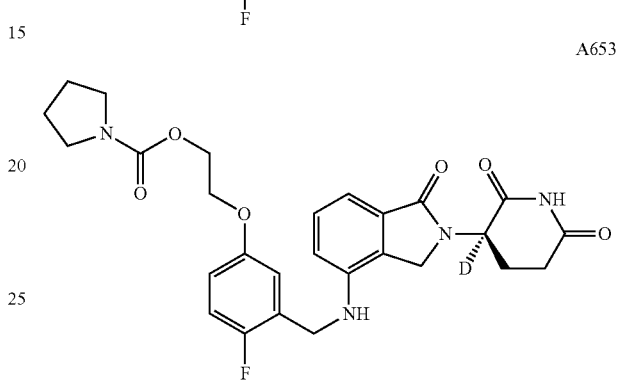
A649
A653
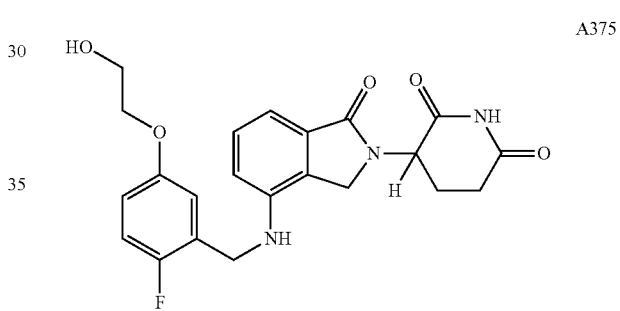
A650
A375
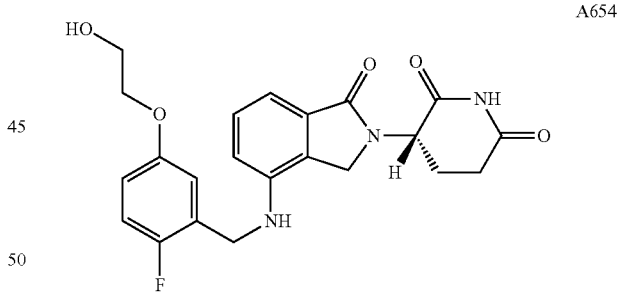
A651
A654
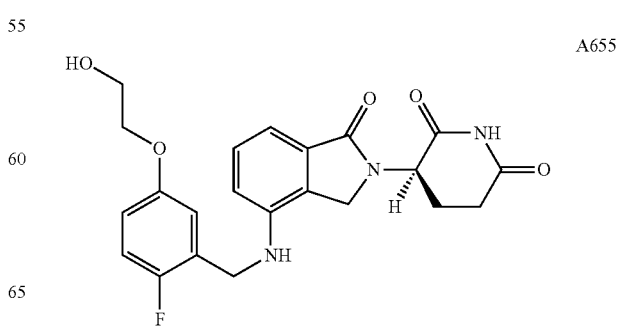
A655

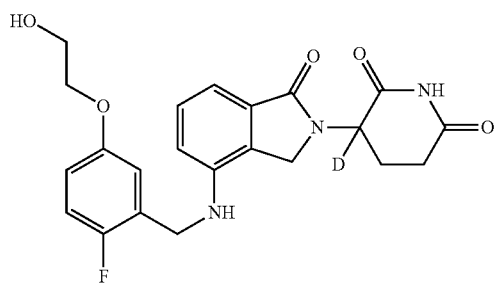
A656
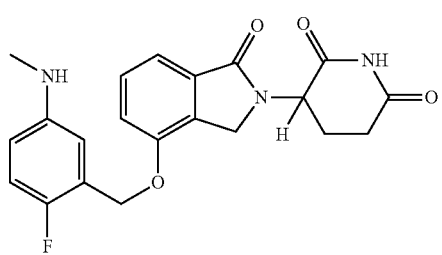
A390
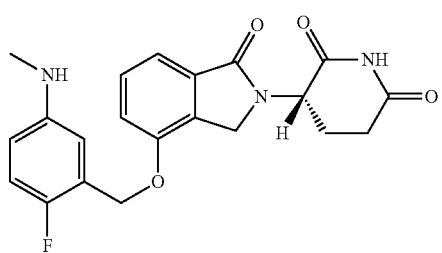
A657
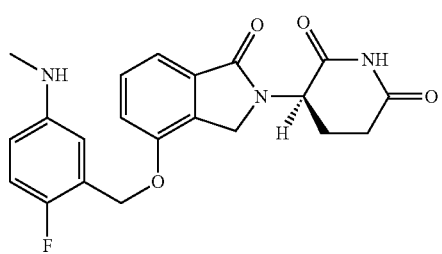
A658
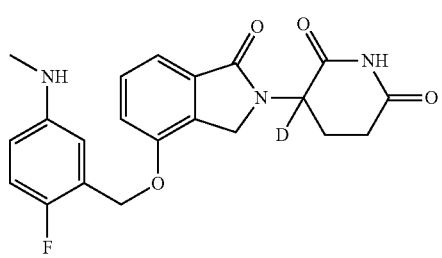
A659
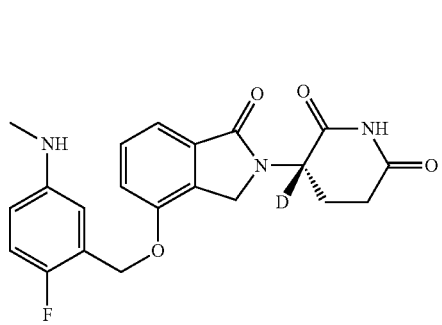
A660
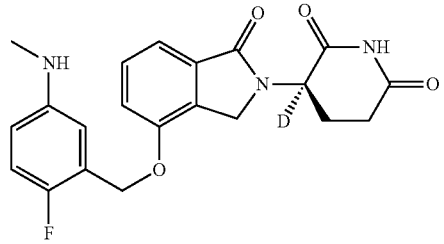
A661
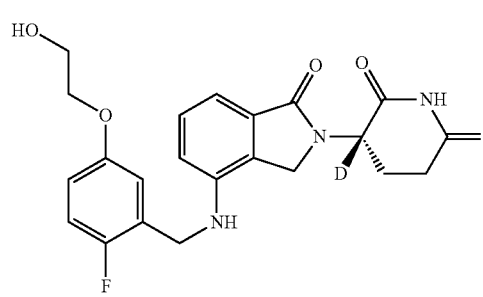
A662
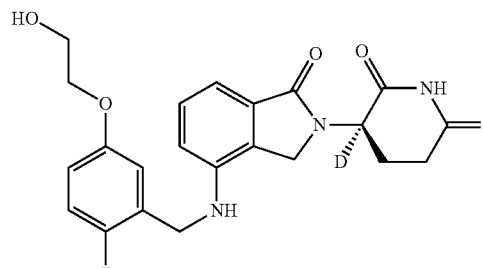
A663
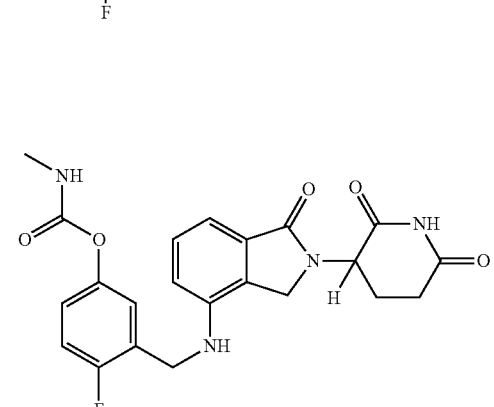
A371
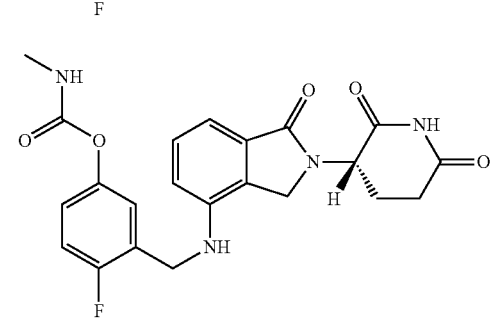
A664

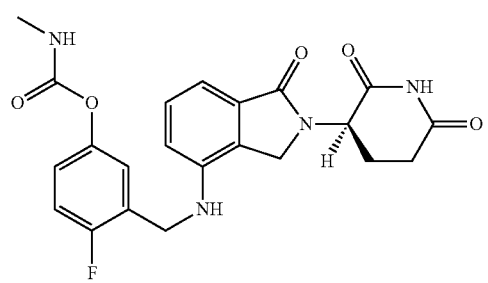
A665
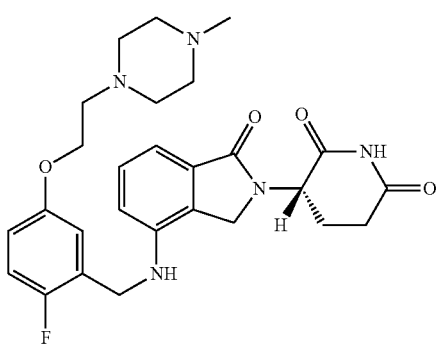
A669
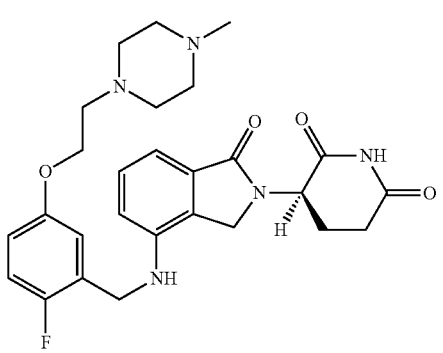
A670
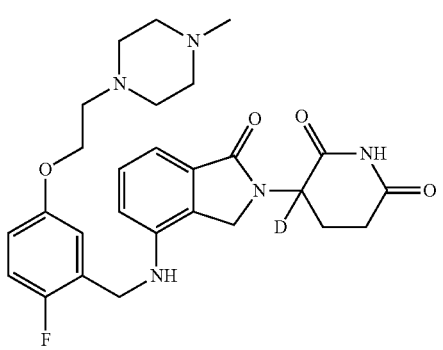
A671
A666
A667
A668
A377
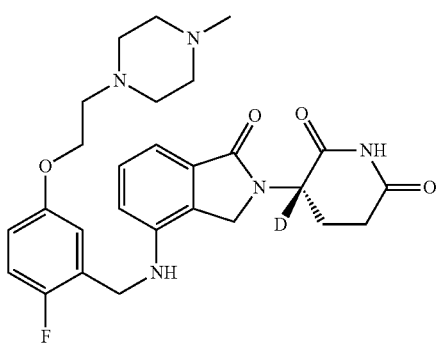
A672

A673
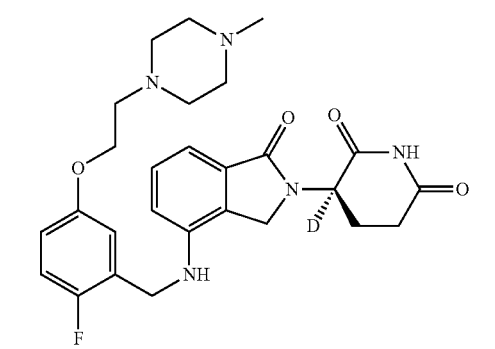
A385
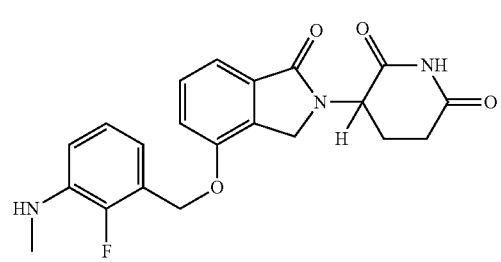
A674
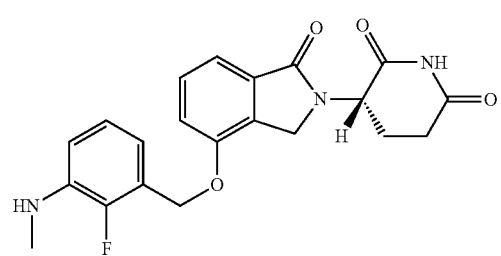
A675
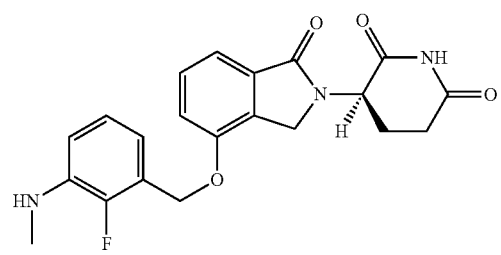
A676
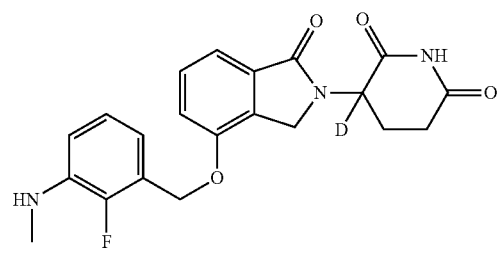
A677
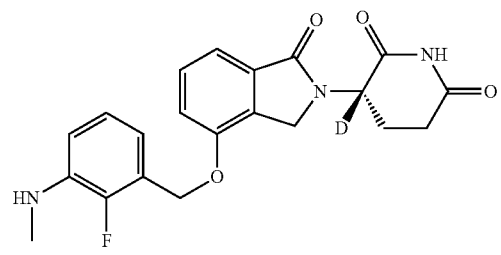
A678
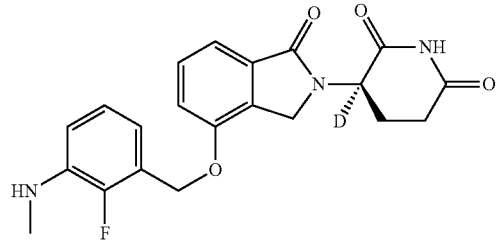
A394
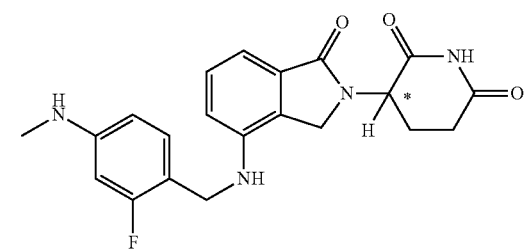
A679
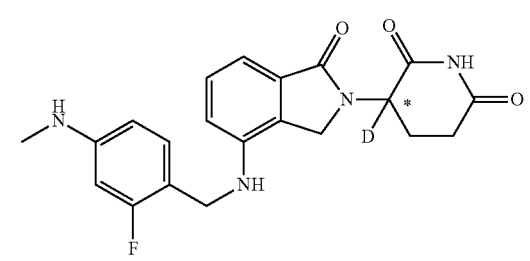
A387
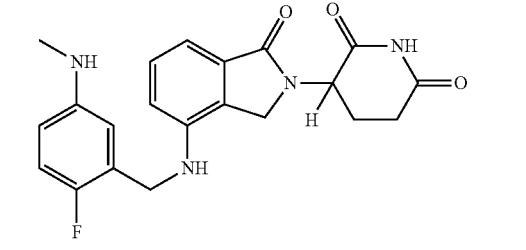
A680
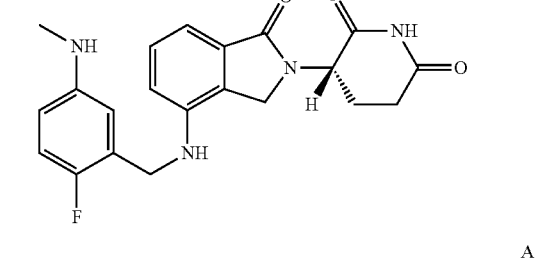
A681
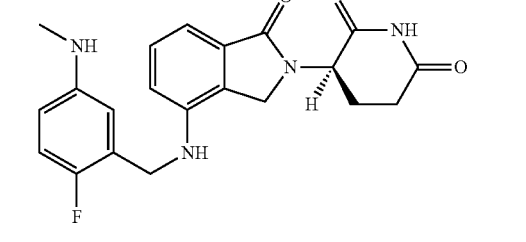

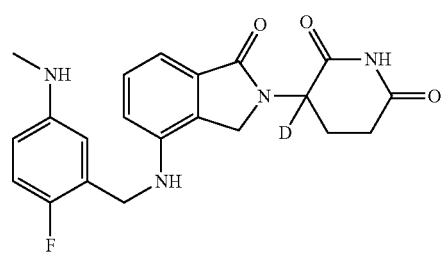
A682
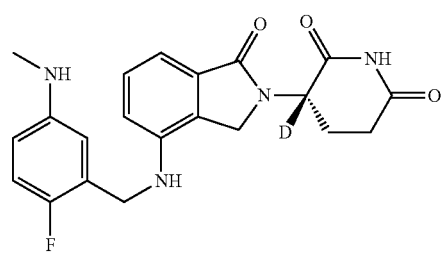
A683
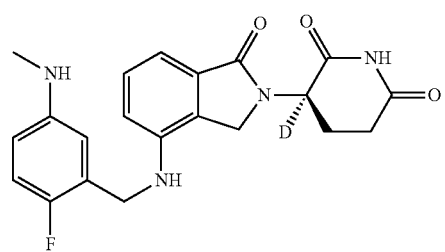
A684
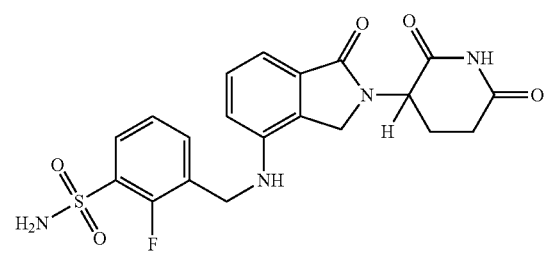
A389

A685
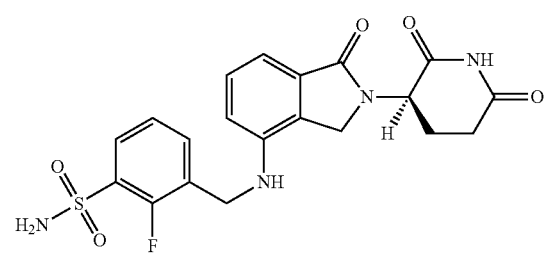
A686
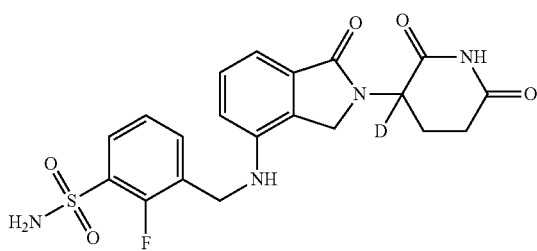
A687
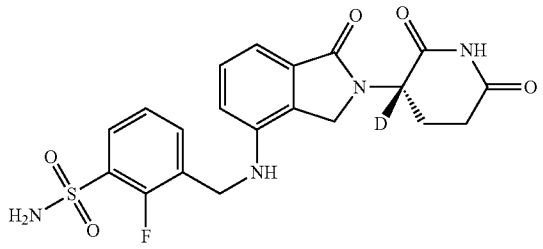
A688
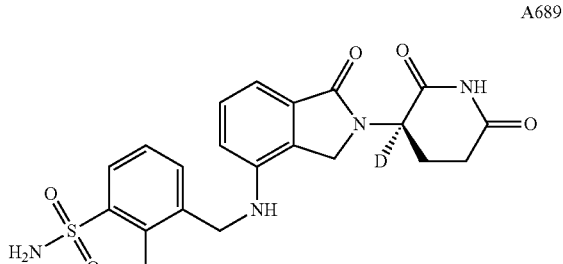
A689
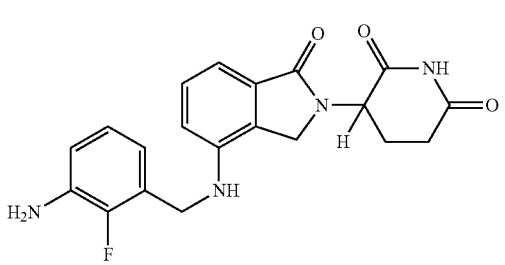
A384
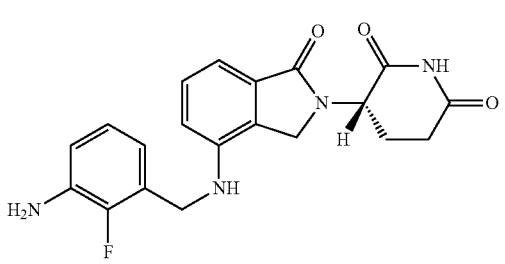
A690
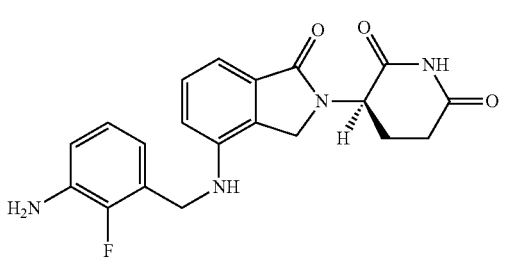
A691

A692
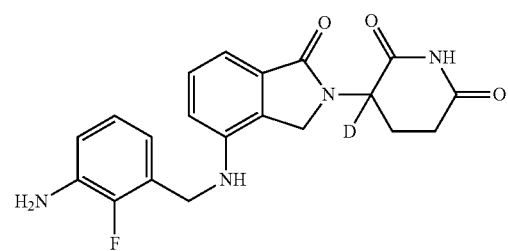
A693
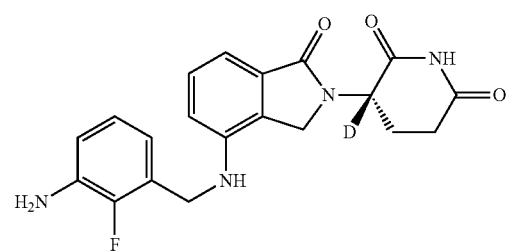
A694
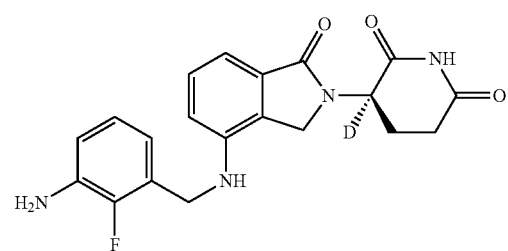
A388
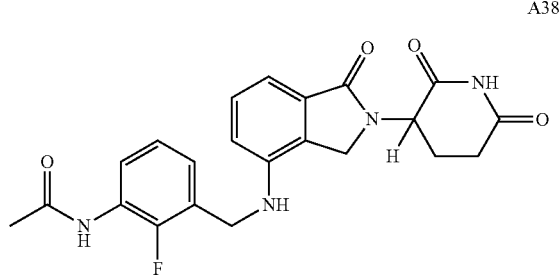
A695
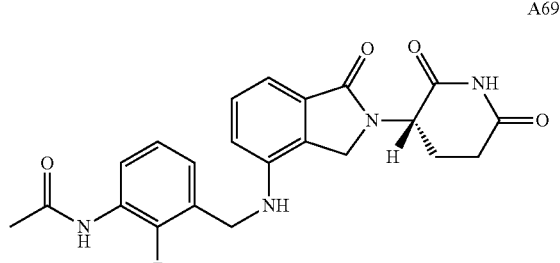
A696
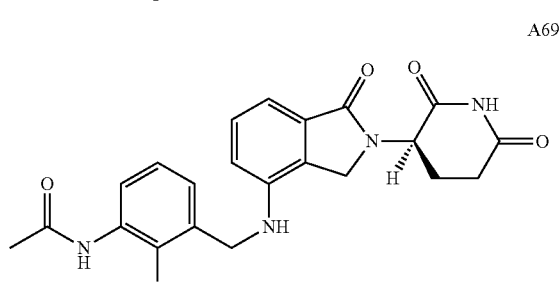
A697
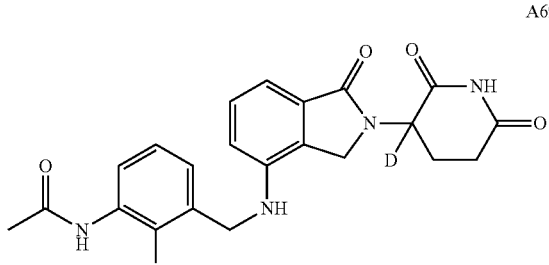
A698
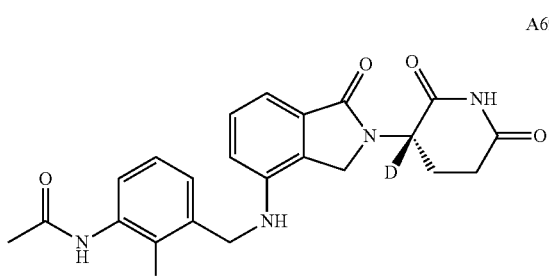
A699
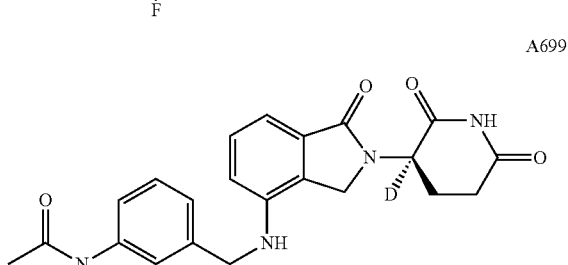
A397
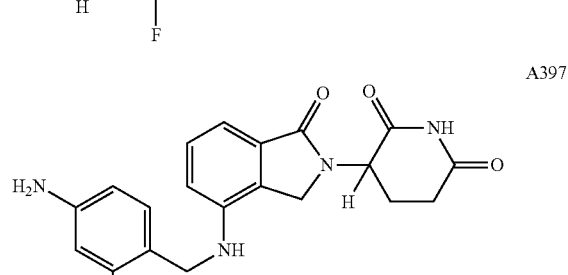
A700
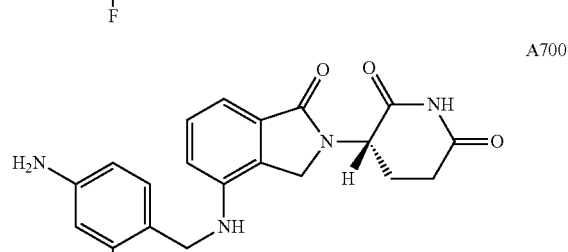
A701
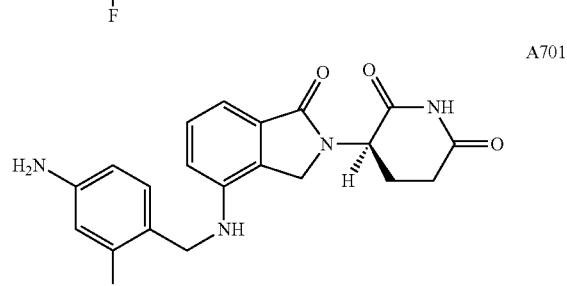

A702 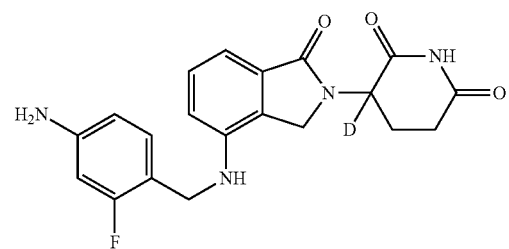
A703 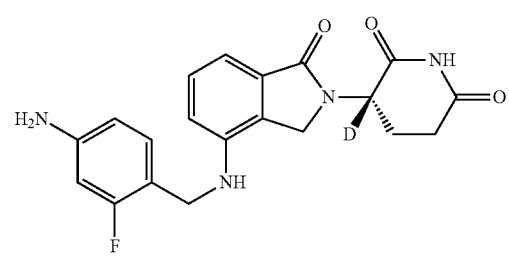
A704 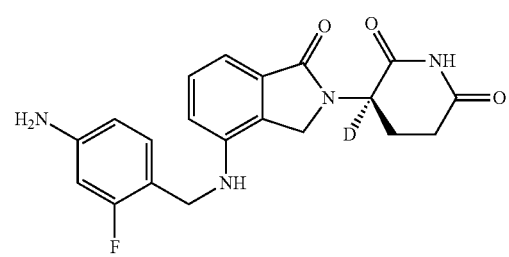
A391 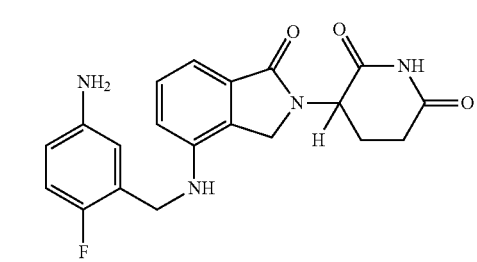
A705 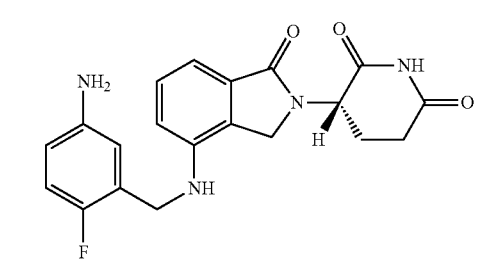
A706 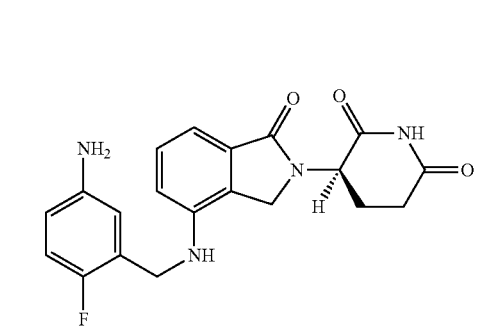
A707 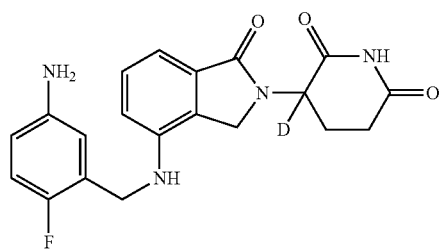
A708 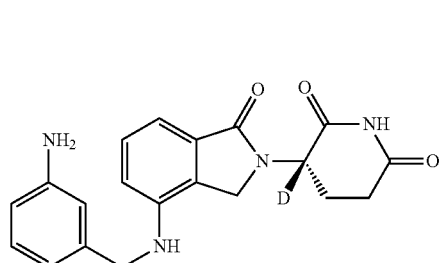
A709 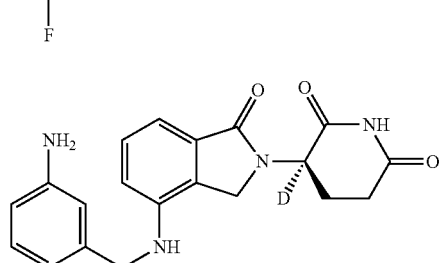
A396 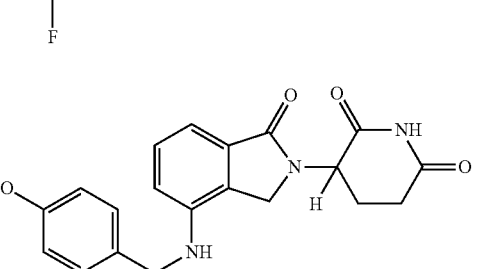
A710 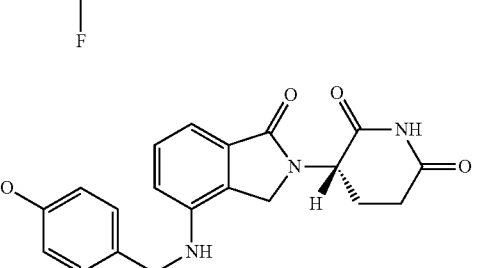
A711 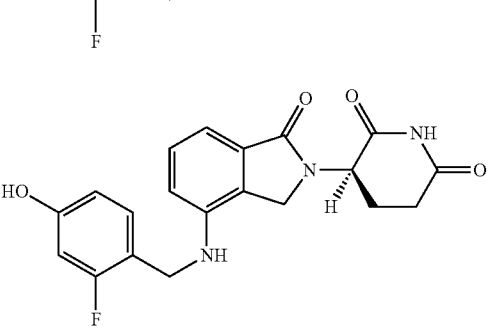

A712
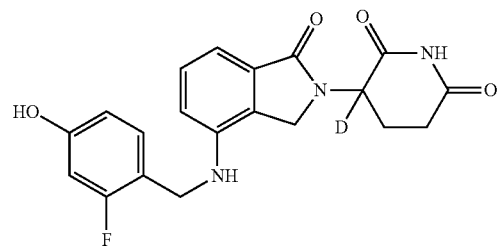
A713
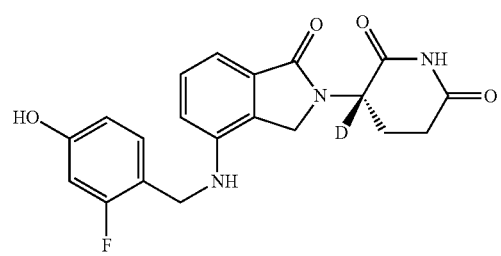
A714
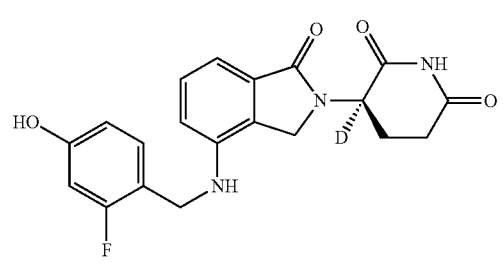
A405
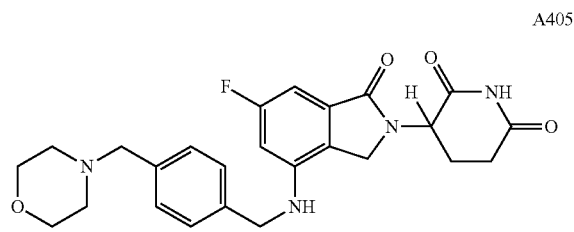
A715
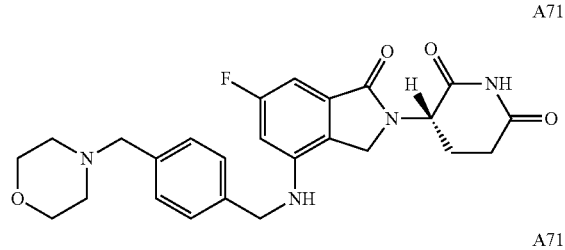
A716

A717
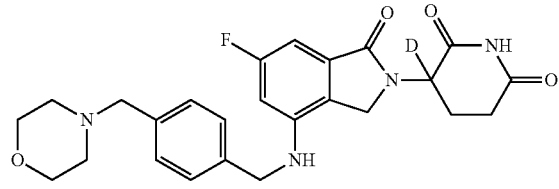
A718
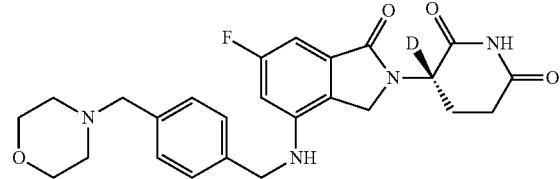
A719
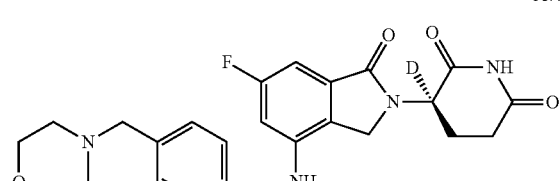
A407
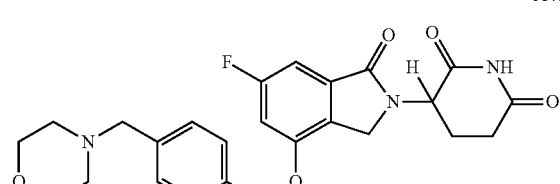
A720
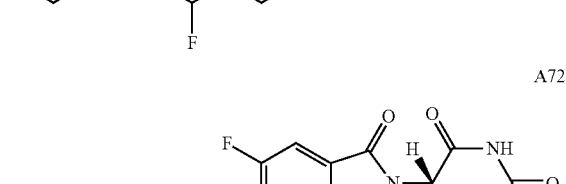
A721
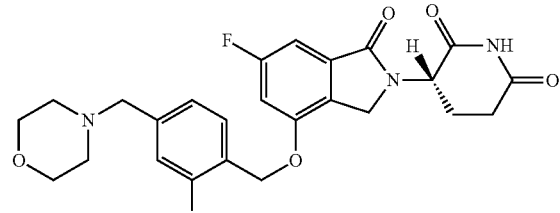
A722
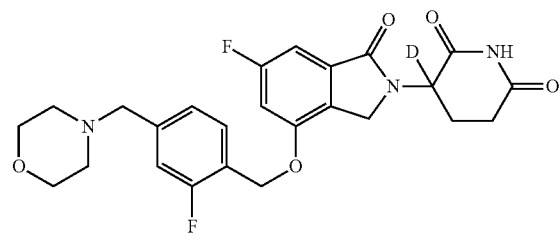

A723
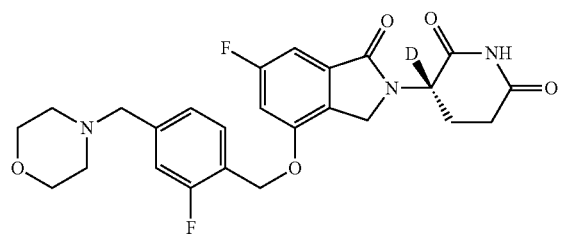
A724
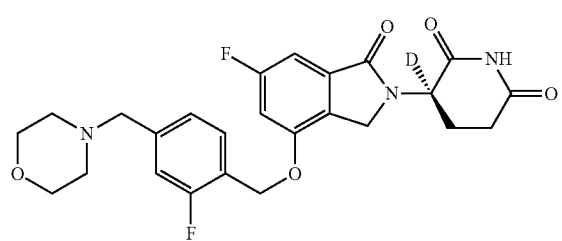
A725
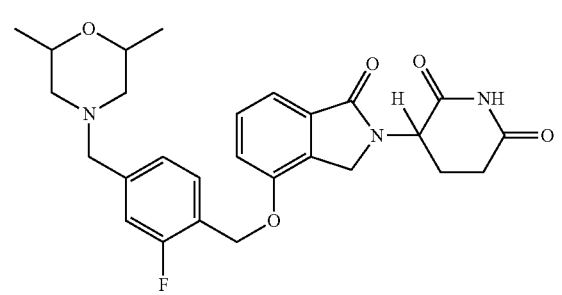
A726
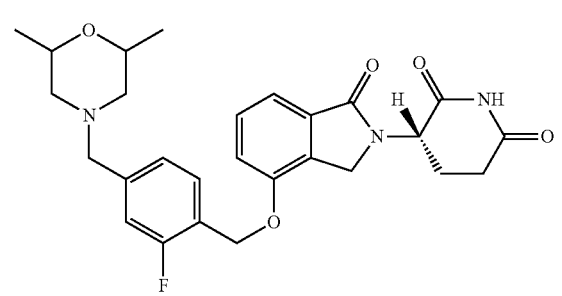
A727
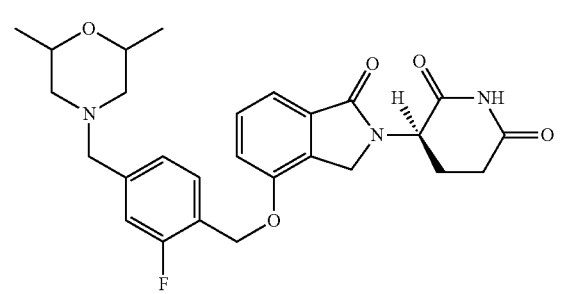
A427
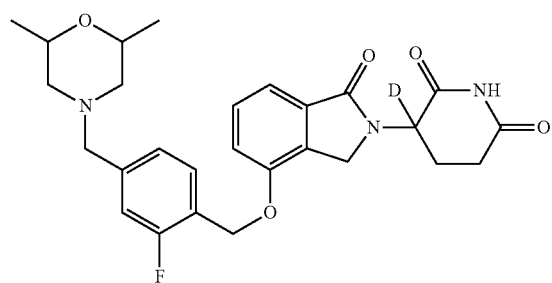
A728
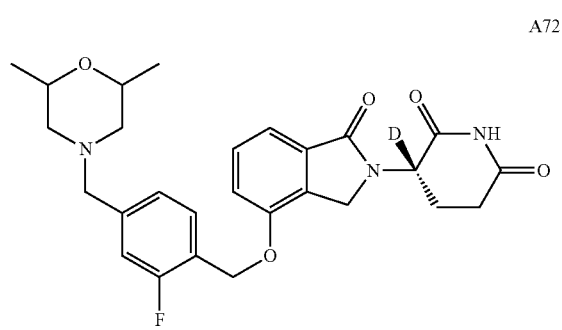
A729
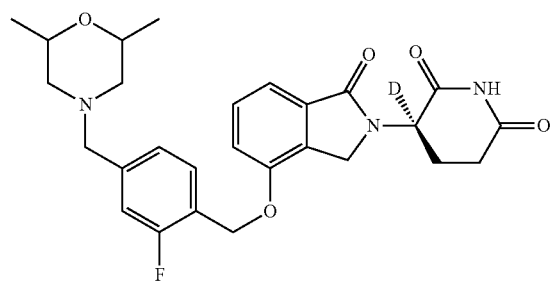
A730
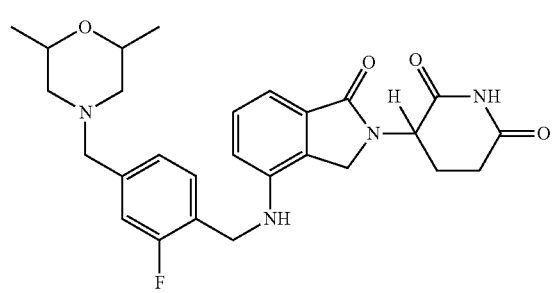
A731
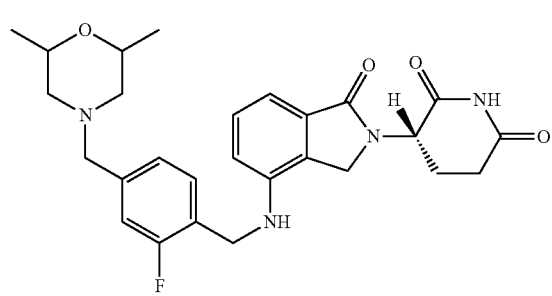

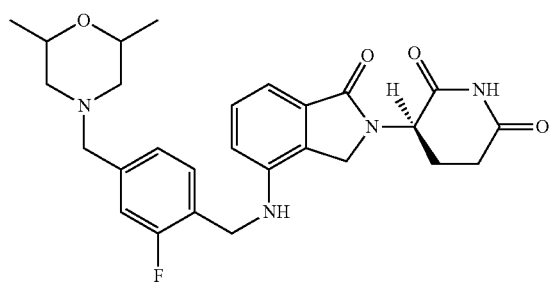
A732
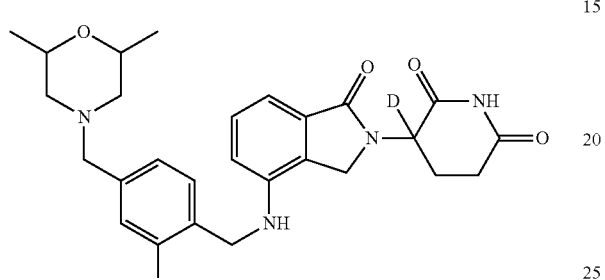
A428
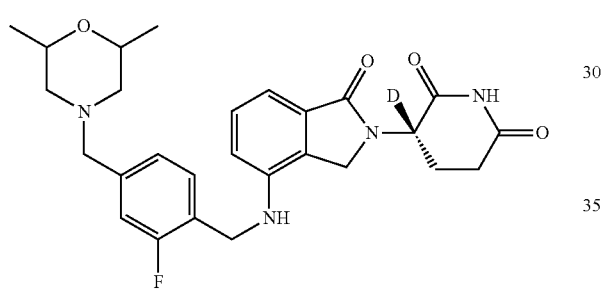
A733
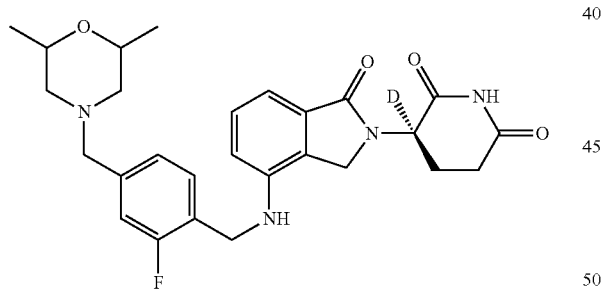
A734
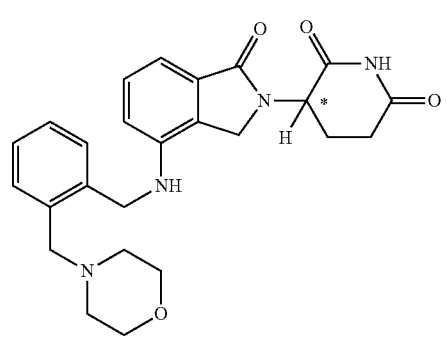
A735
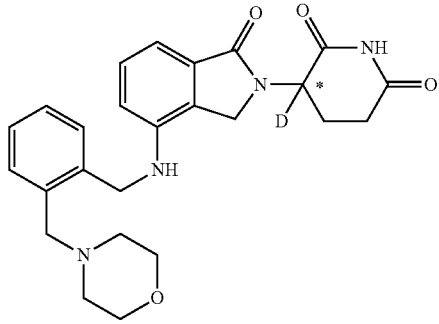
A736
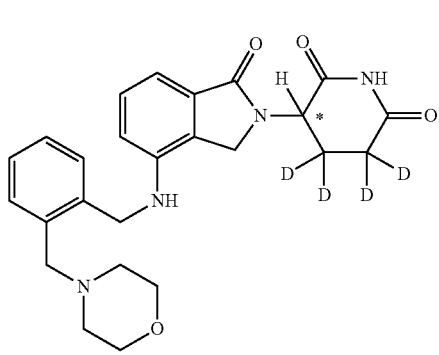
A737
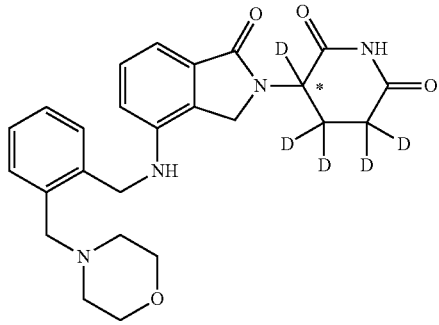
A738
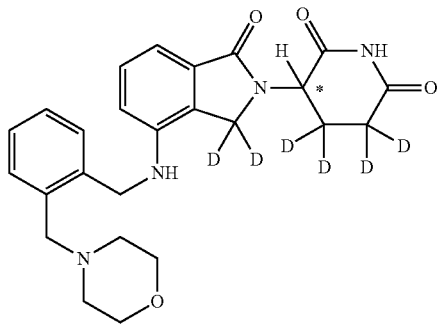
A739

A740
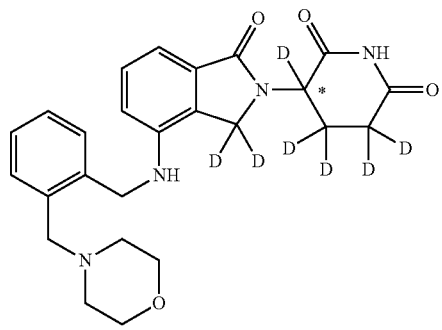
A741
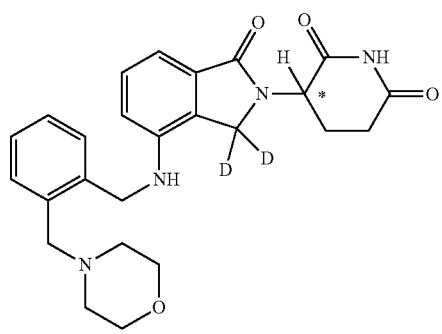
A742
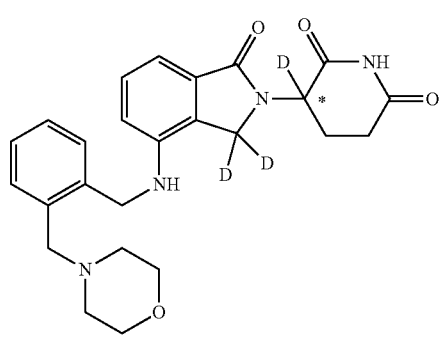
A743
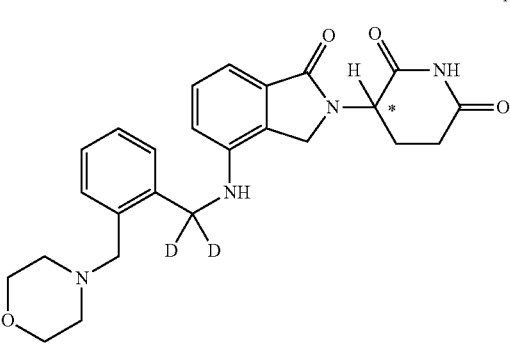
A744
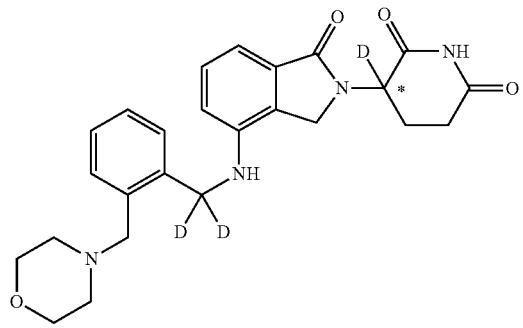
A745
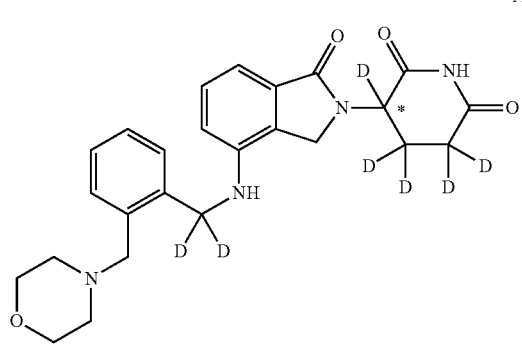
A746
A747
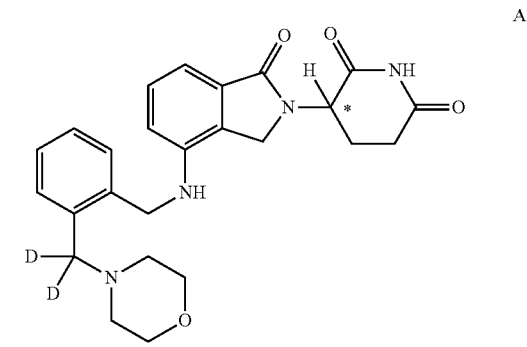

91
-continued
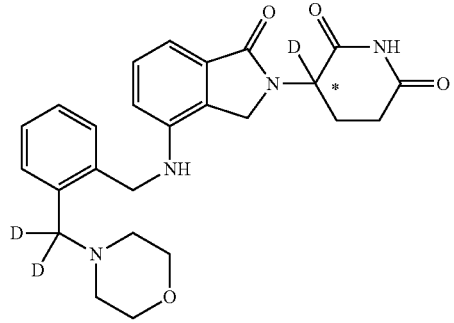
A748
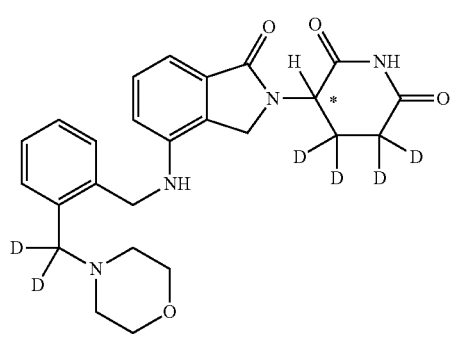
A749
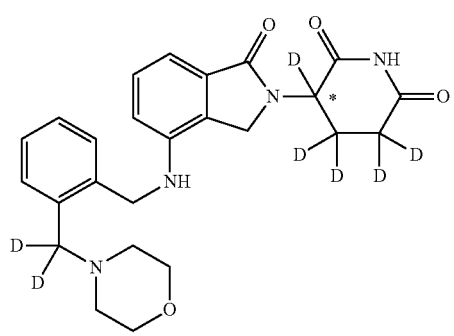
A750
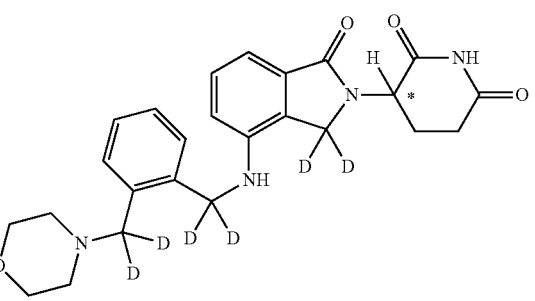
A751
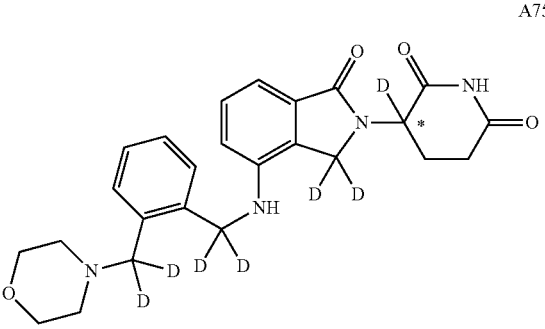
A752
92
-continued
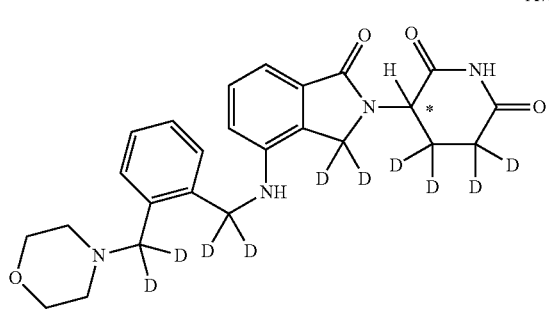
A753
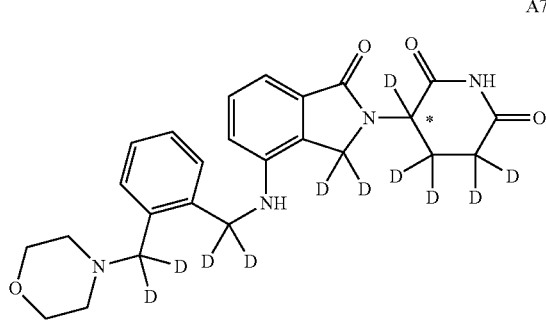
A754
A755
A756

93
-continued
A757
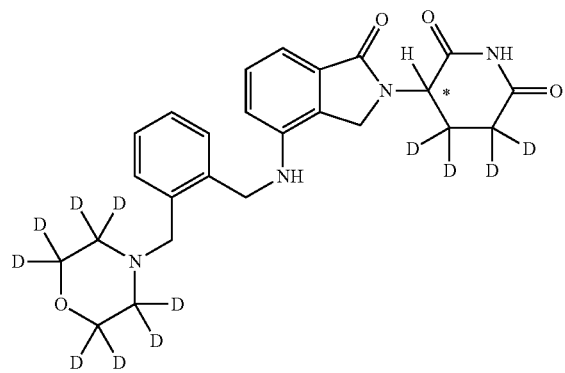
A758
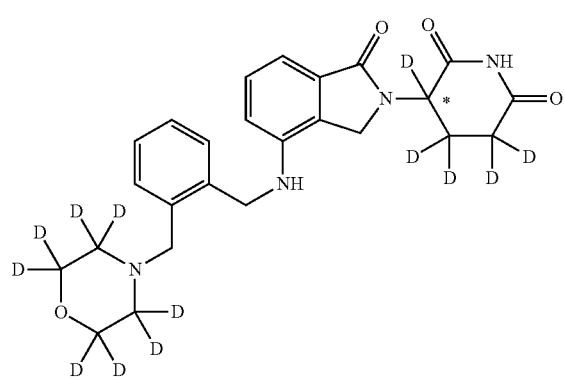
A759
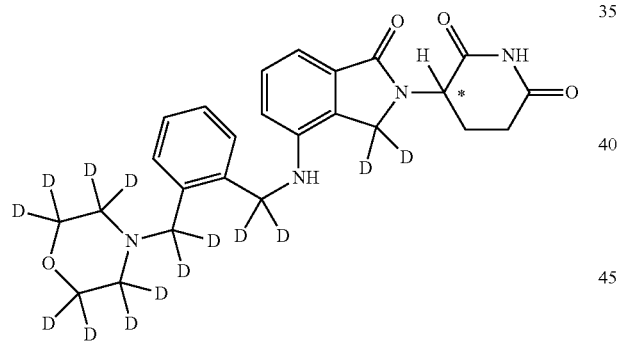
A760
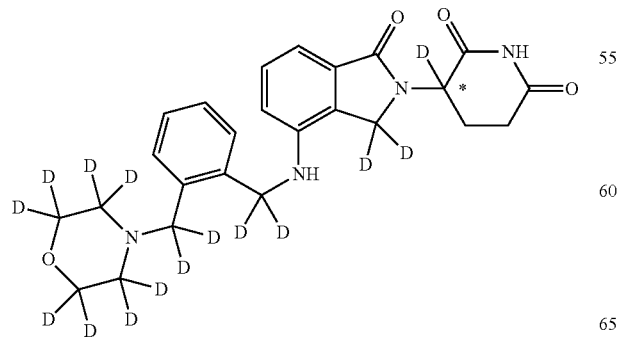
94
-continued
A761
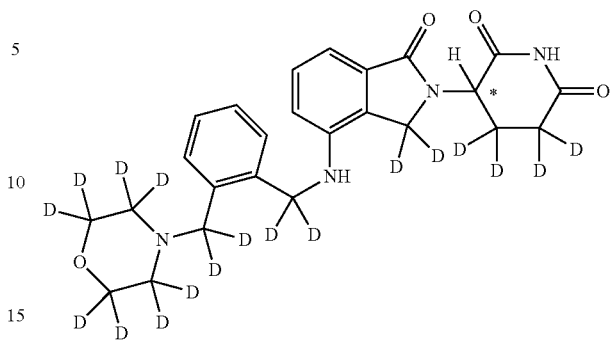
A762
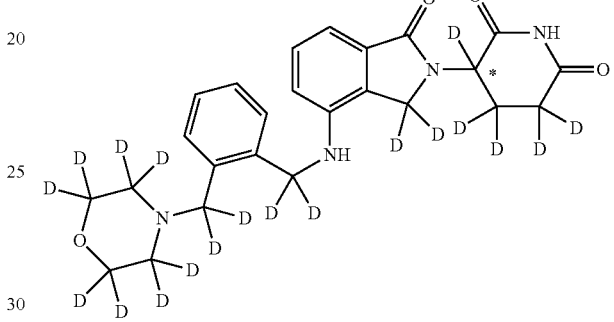
A763
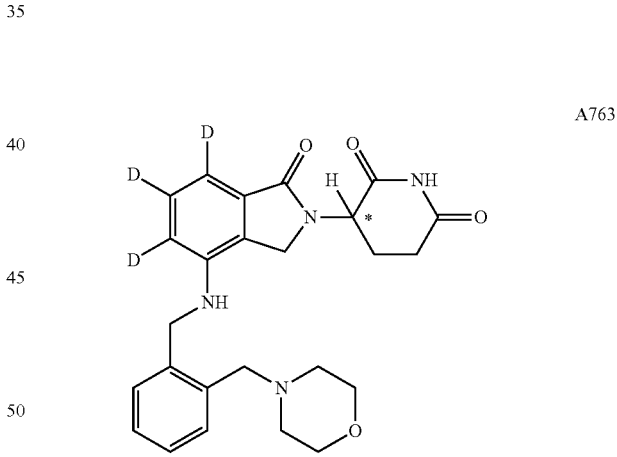
A764
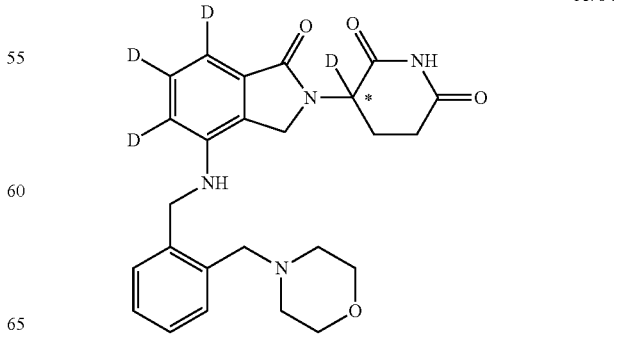

A765
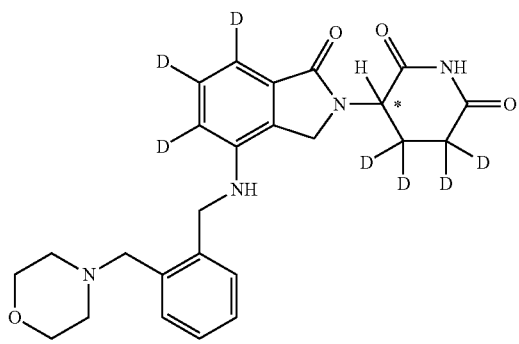
A766
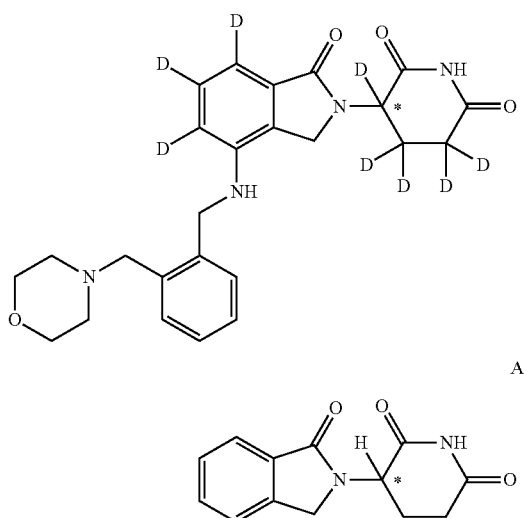
A767
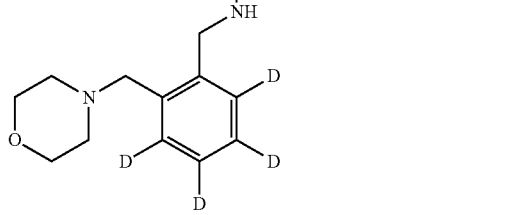
A768
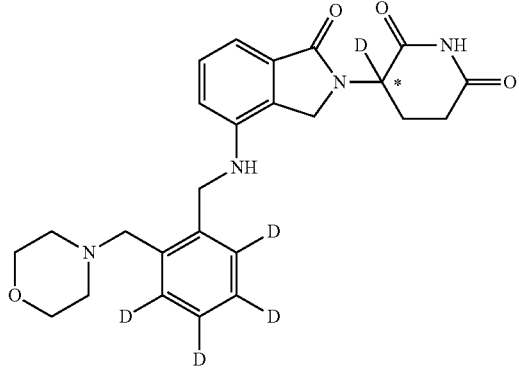
A769
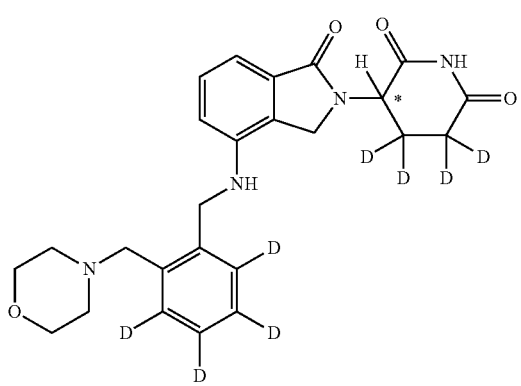
A770
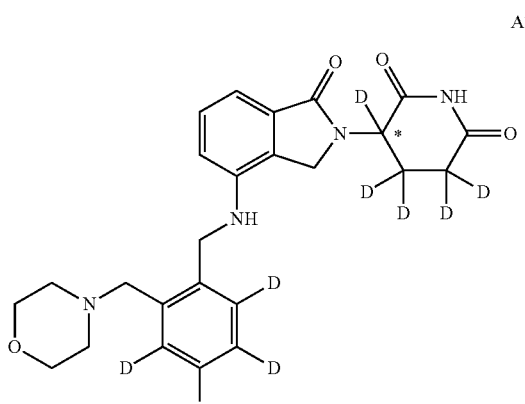
A771
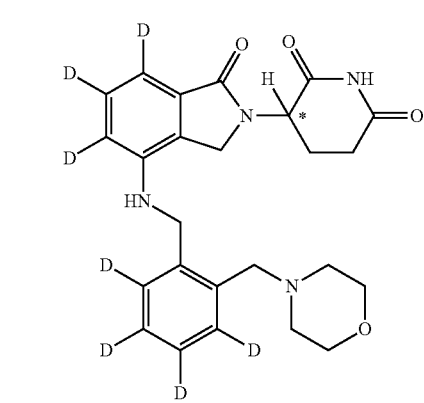
A772
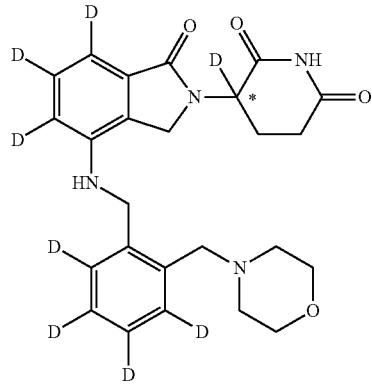

A773
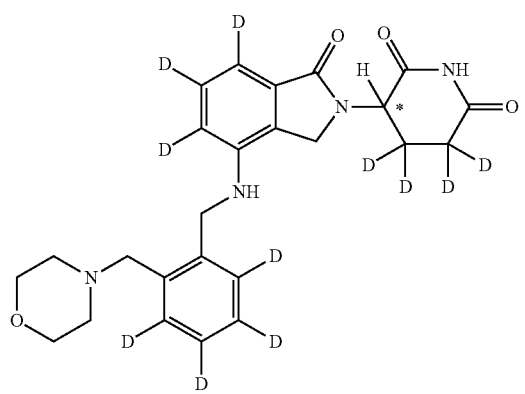
A774
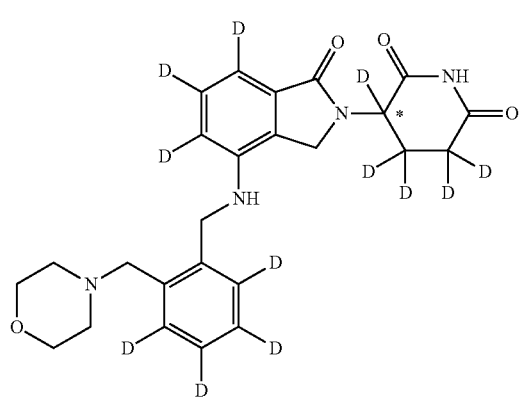
A775
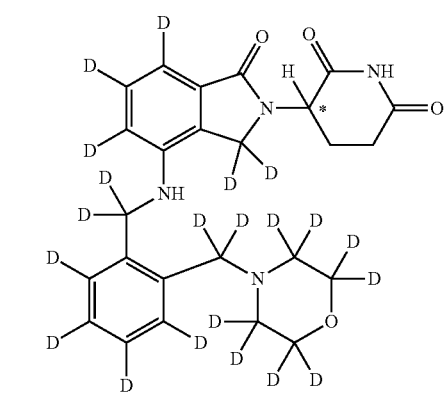
A776
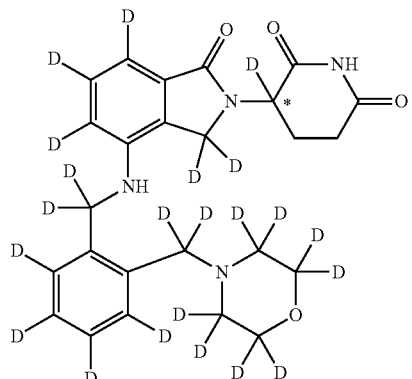
A777
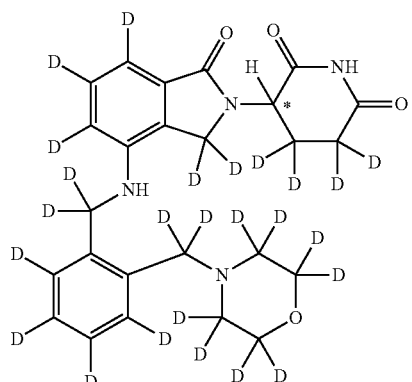
A778
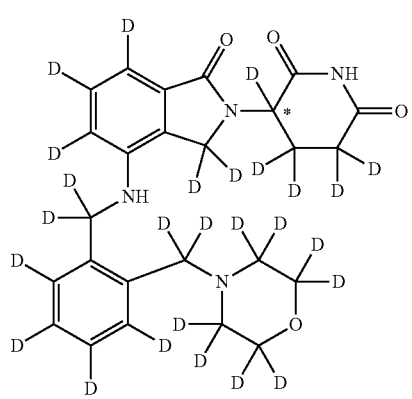
A779
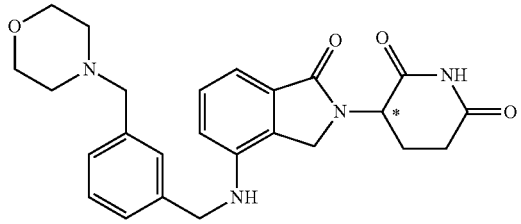

A780
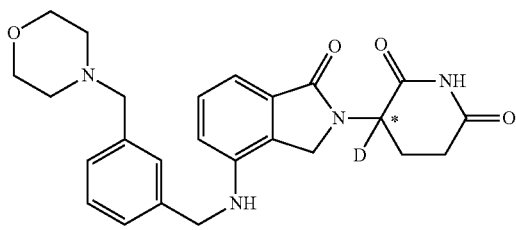
A781
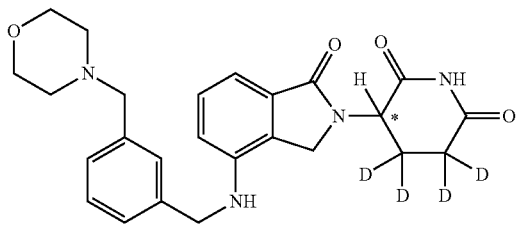
A782
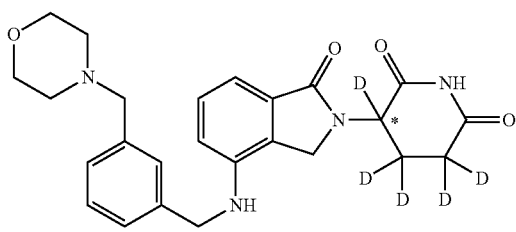
A783
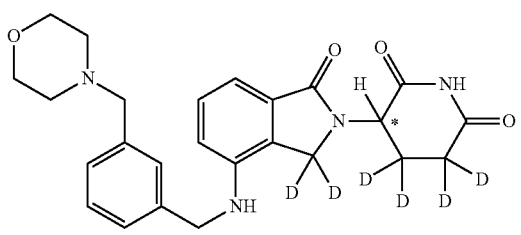
A784
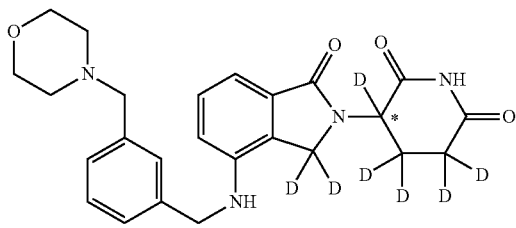
A785
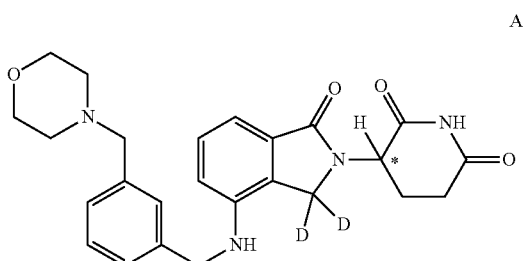
A786
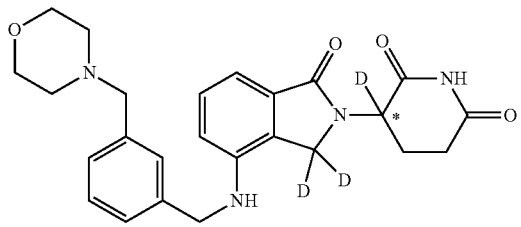
A787
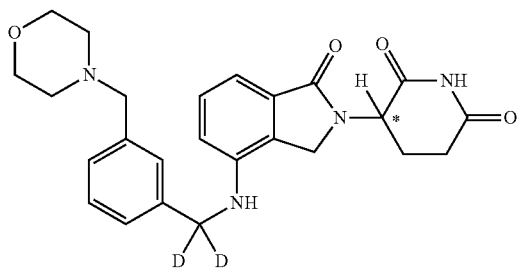
A788
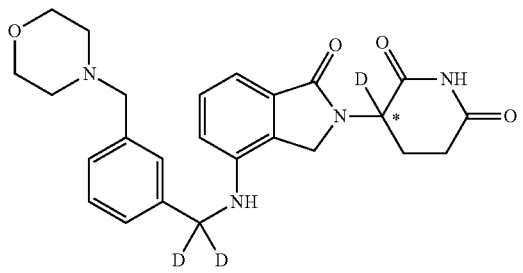
A789
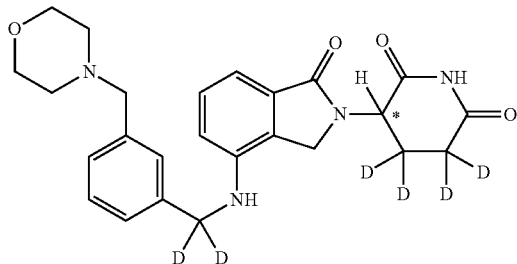
A790
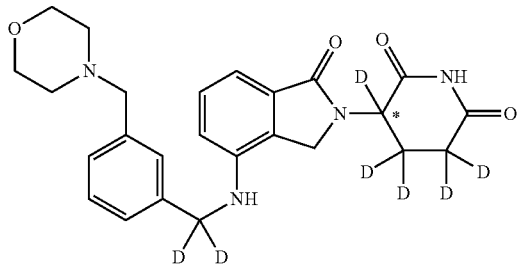

A791
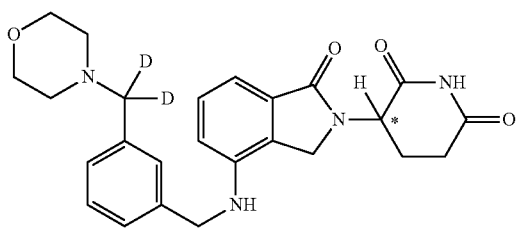
A792
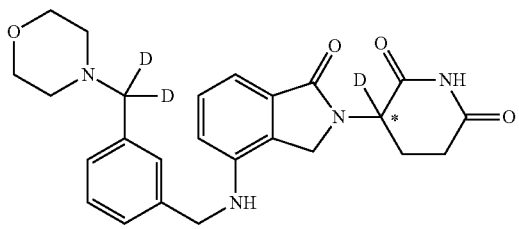
A793
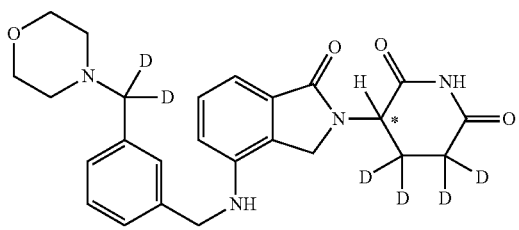
A794
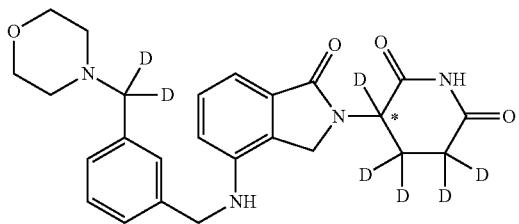
A795
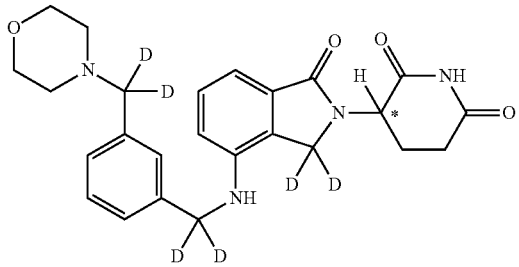
A796
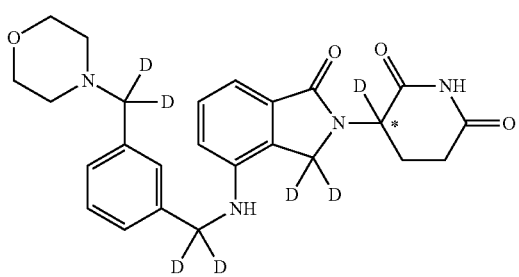
A797
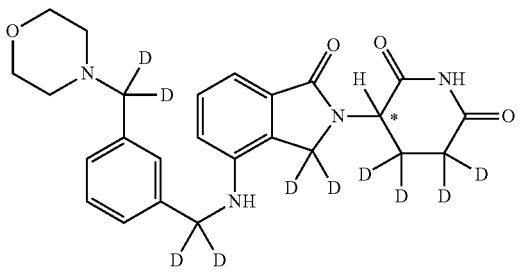
A798
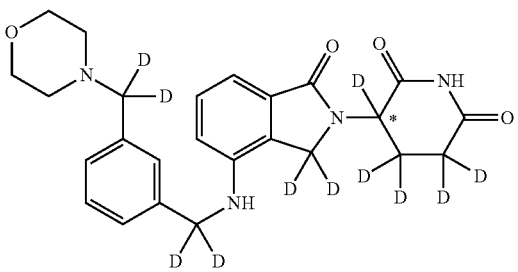
A799
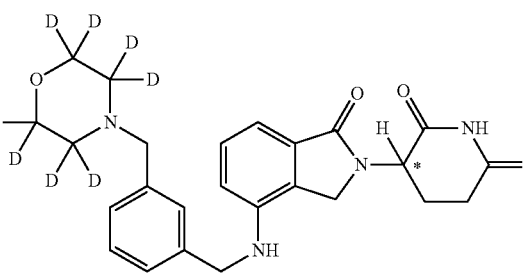
A800
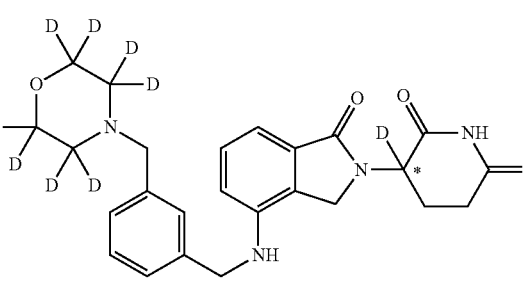
A801
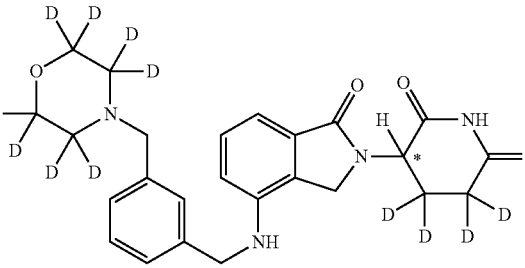

103
-continued

104
-continued

A813
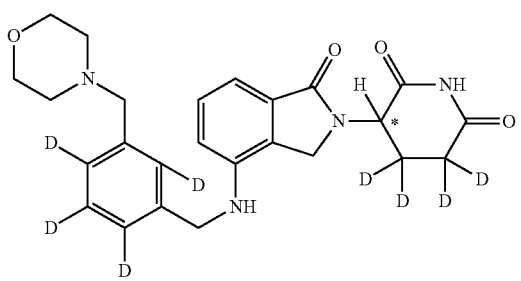
A814
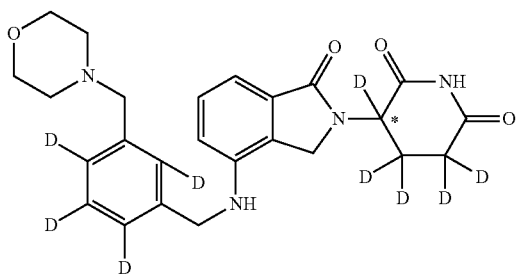
A815
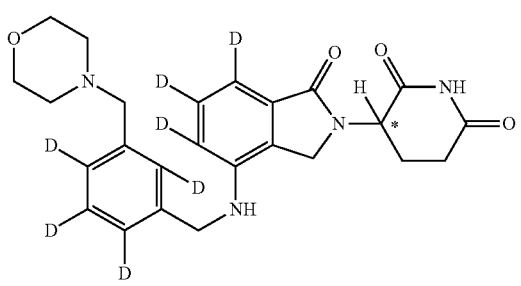
A816
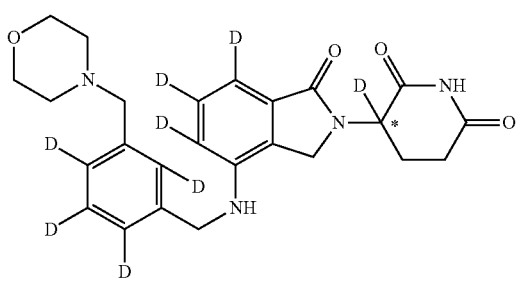
A817
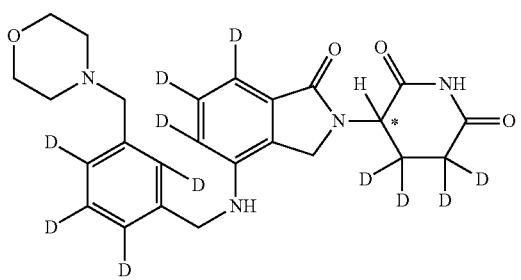
A818
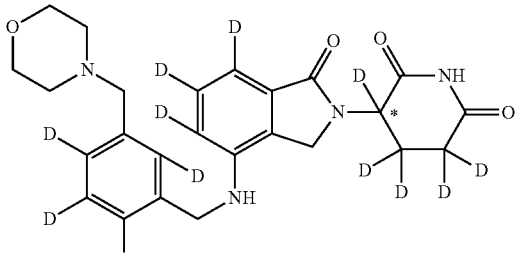
A819
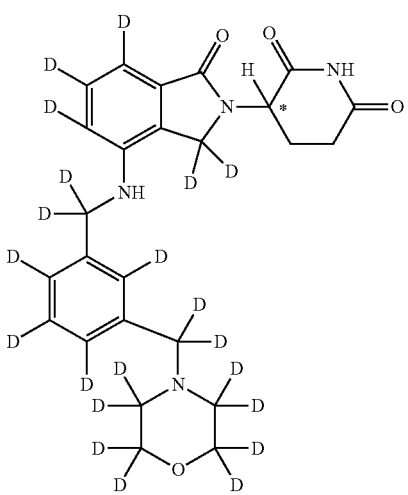
A820
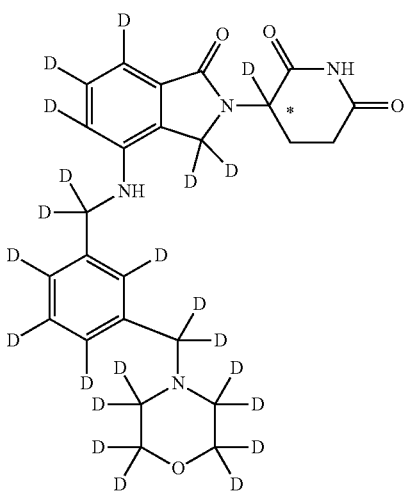
A821
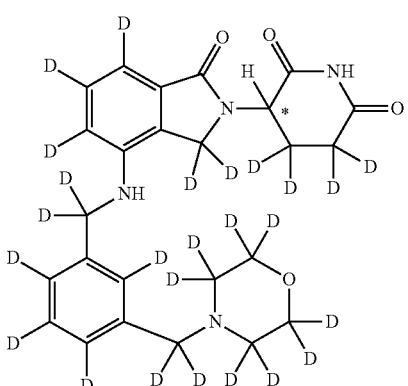

A822 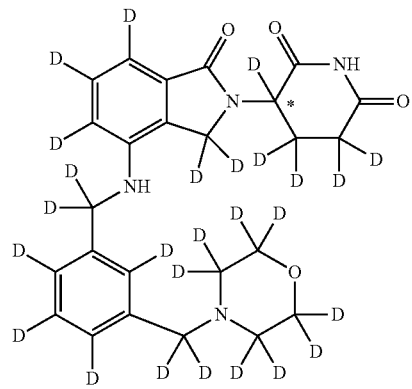
A823 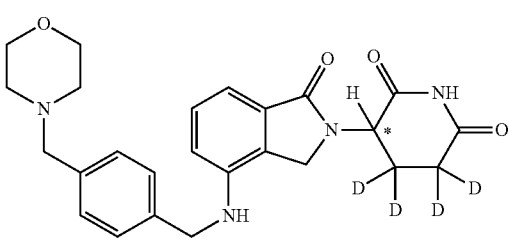
A824 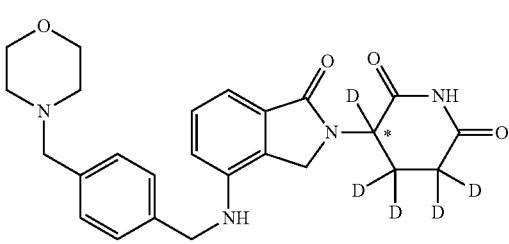
A825 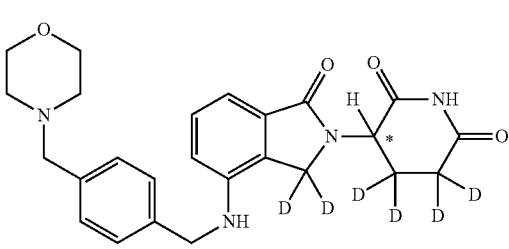
A826 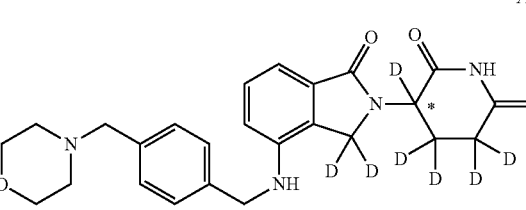
A827 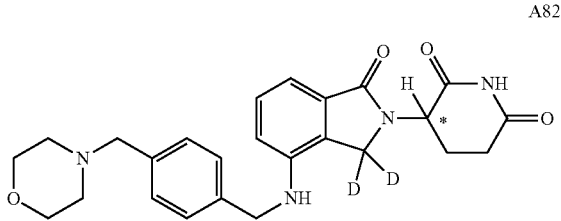
A828 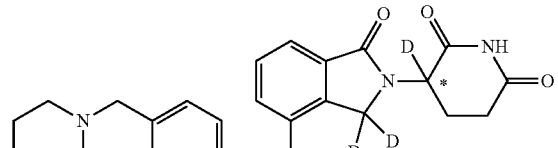
A829 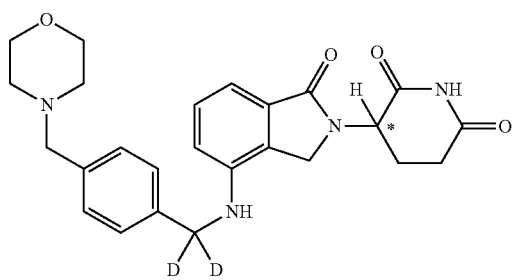
A830 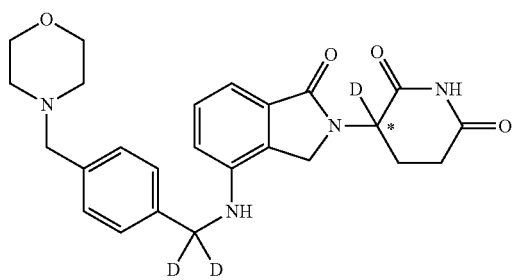
A831 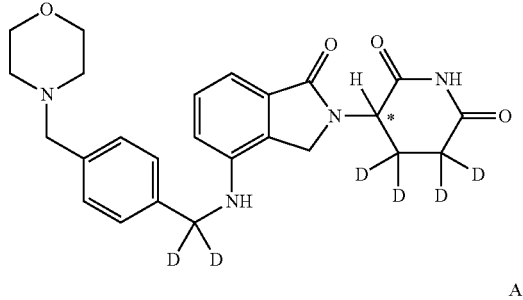
A832 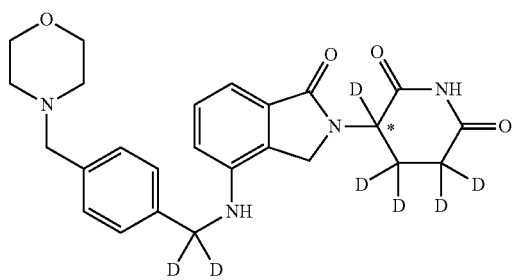
A833 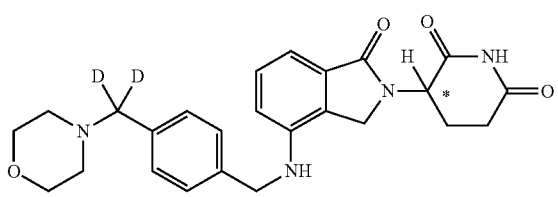

A834
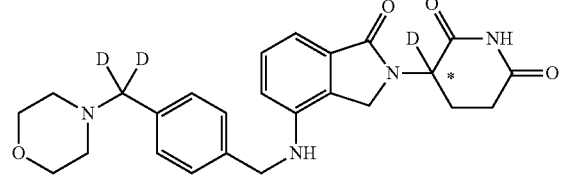
A835
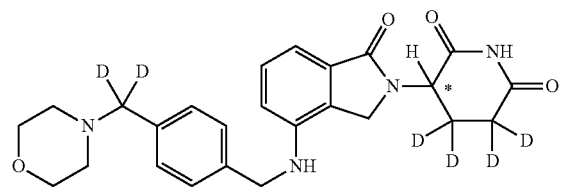
A836
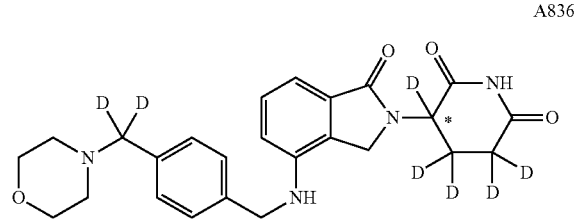
A837
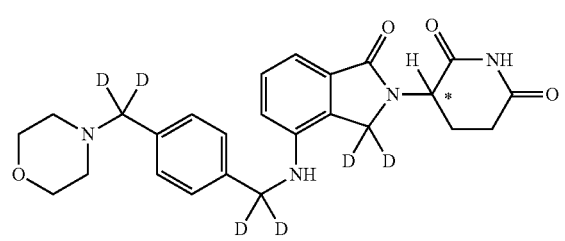
A838
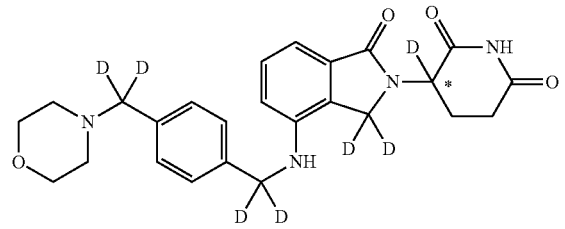
A839
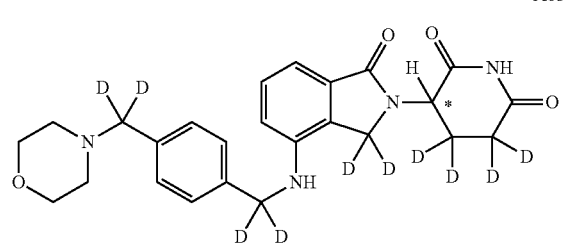
A840
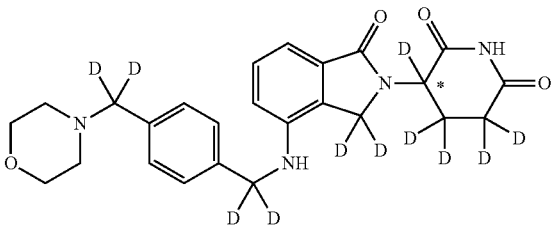
A841
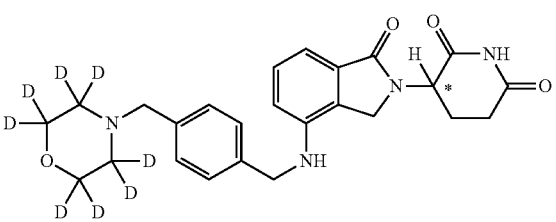
A842
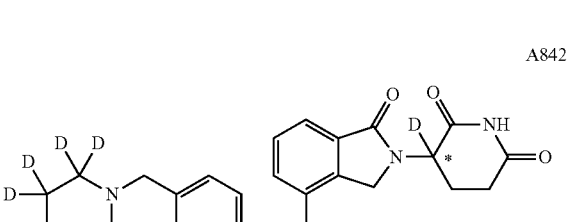
A843
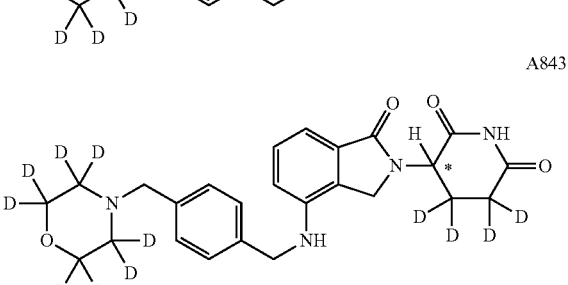
A844
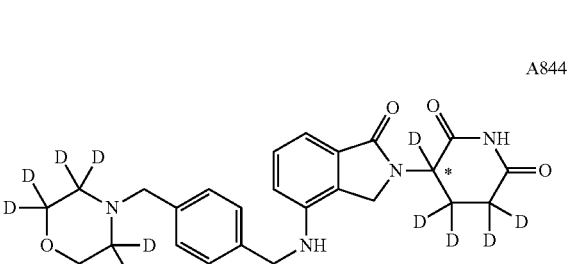
A845
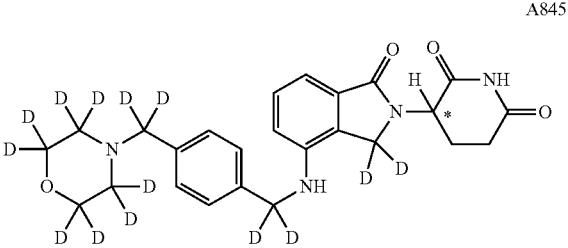

A846
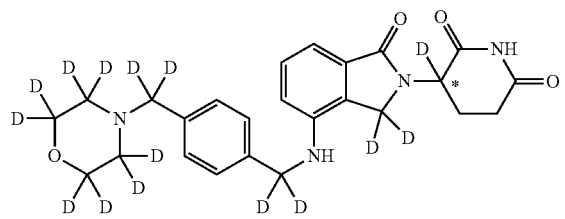
A847
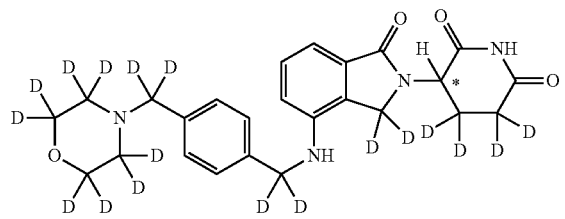
A848
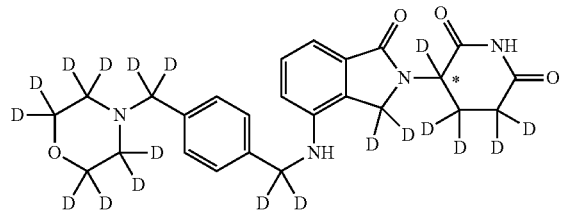
A849
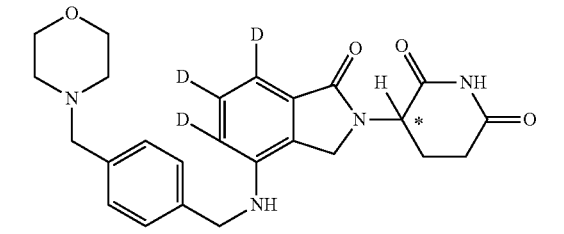
A850
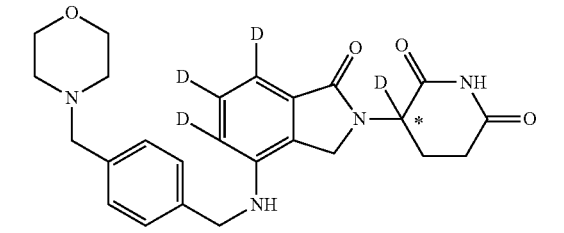
A851
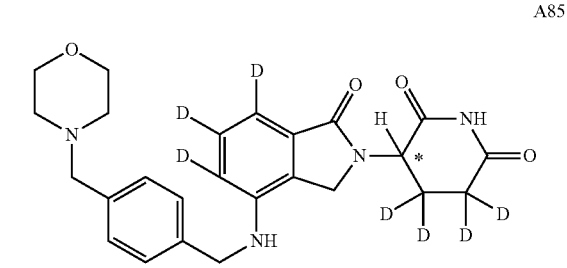
A852
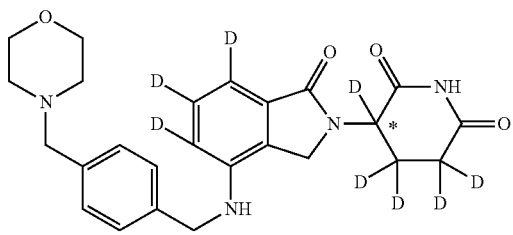
A853
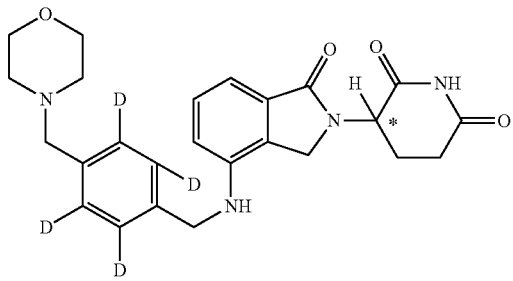
A854
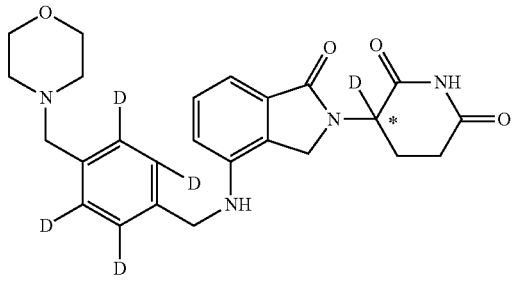
A855
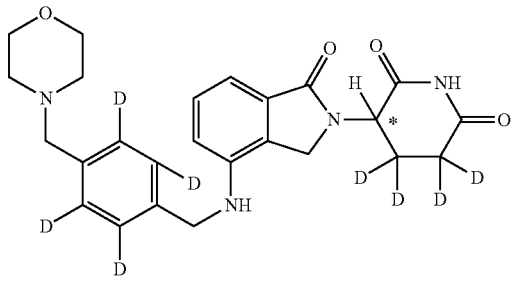
A856
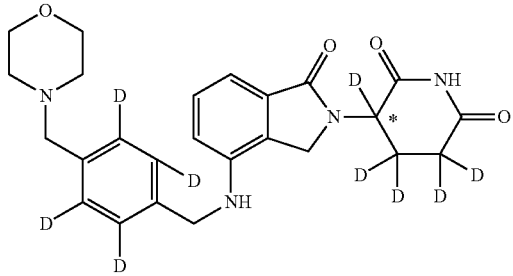

A857
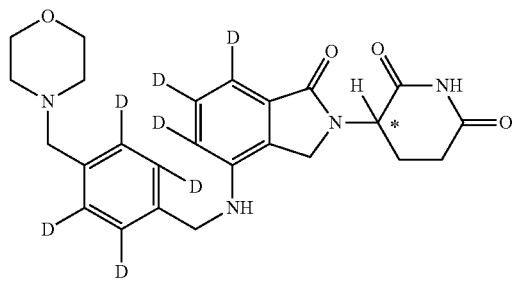
A858
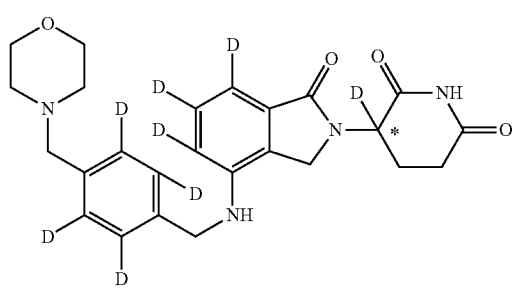
A859
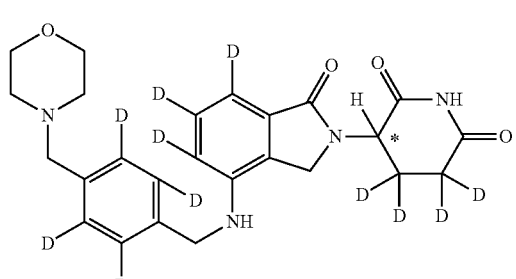
A860
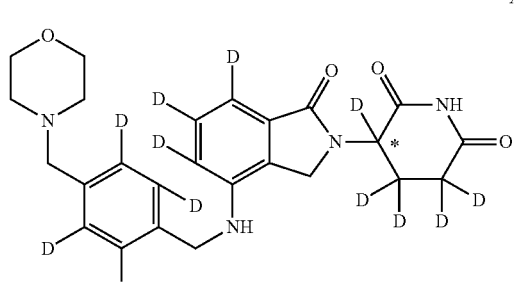
A861
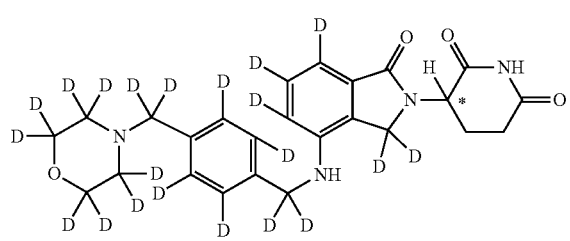
A862
A863
A864
A381
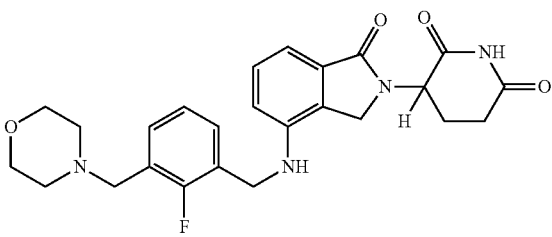
A865
A866
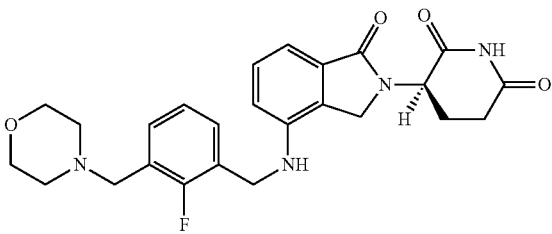

A867
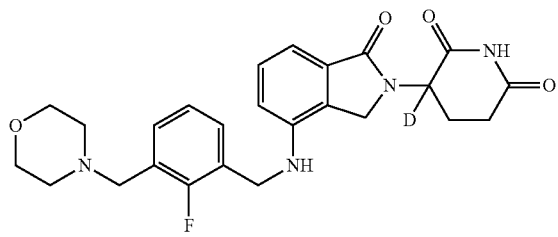
A872
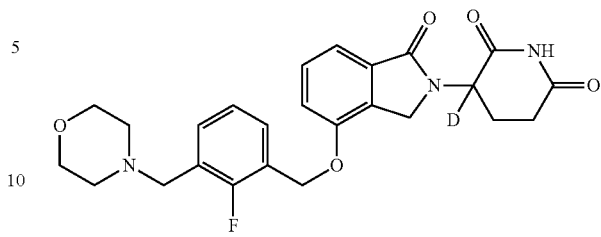
A400
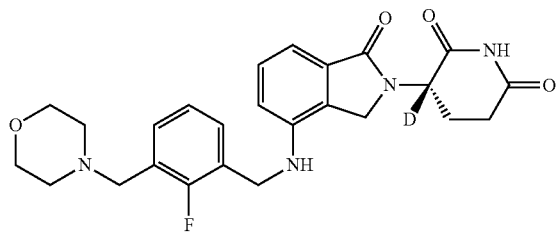
A404
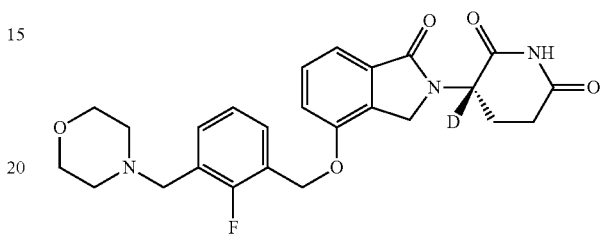
A868
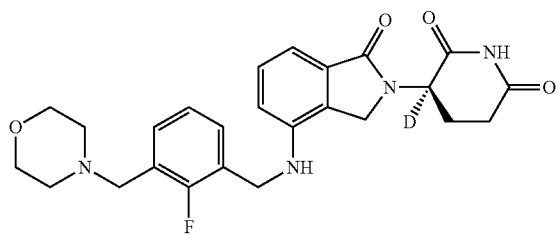
A871
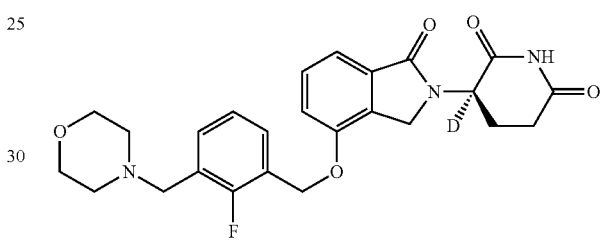
A399
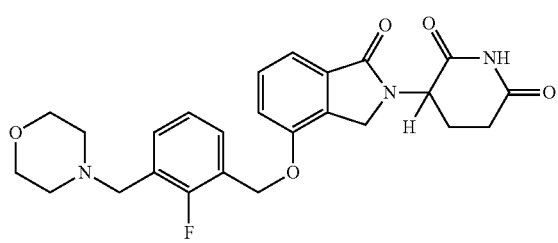
A873
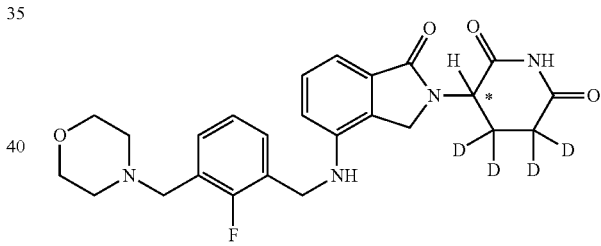
A869
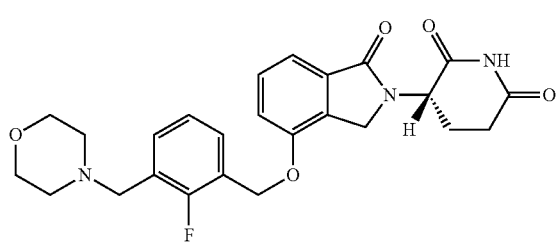
A874
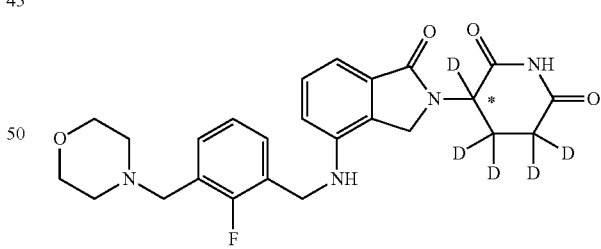
A870
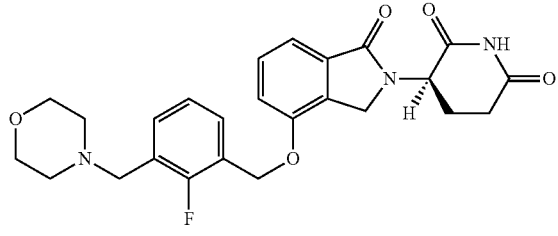
A875
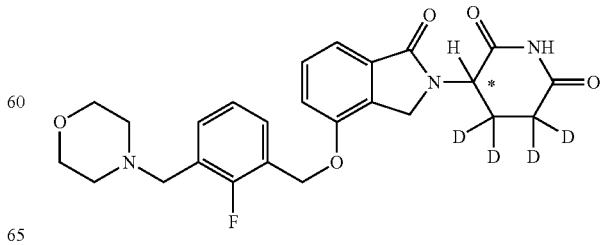

117
-continued
A876
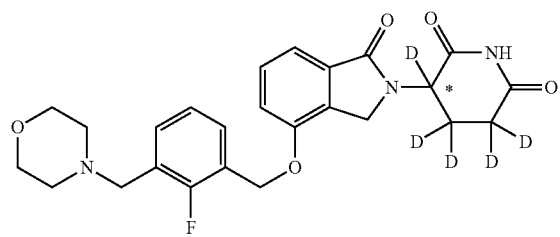
A877
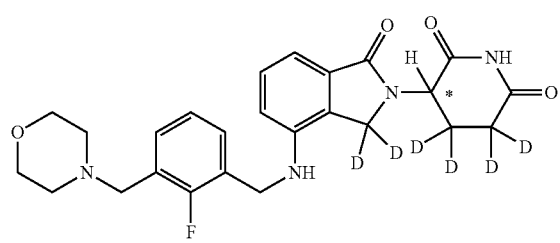
A878
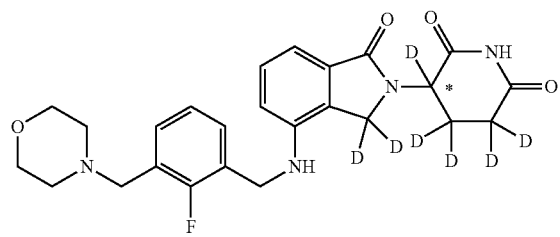
A879
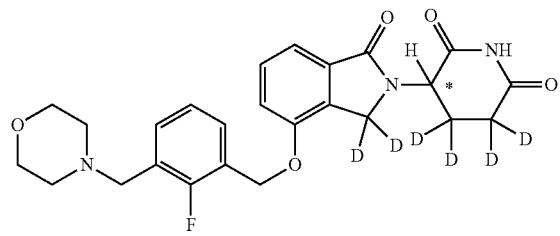
A880
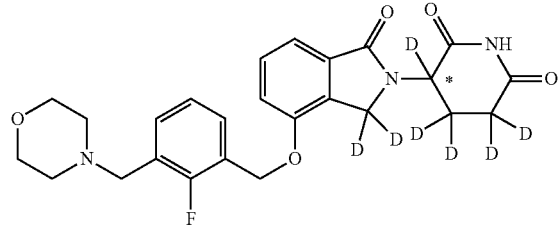
A881
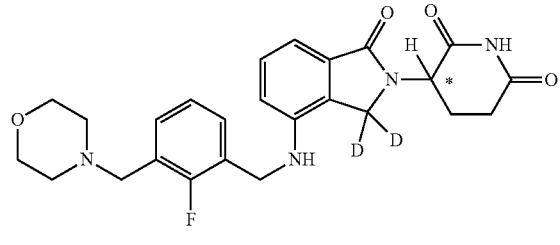
118
-continued
A882
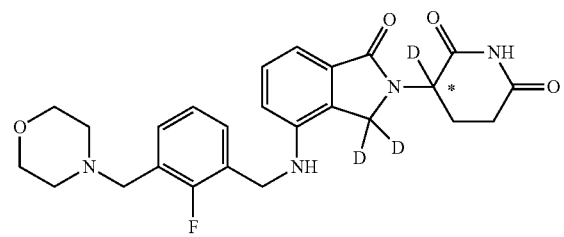
A883
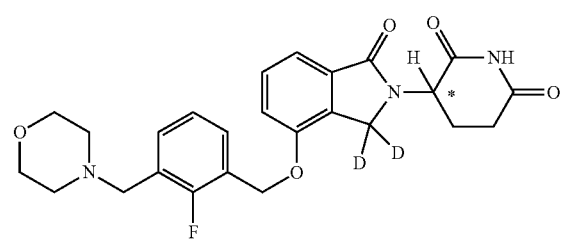
A884
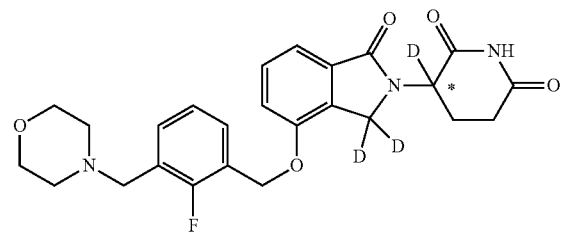
A885
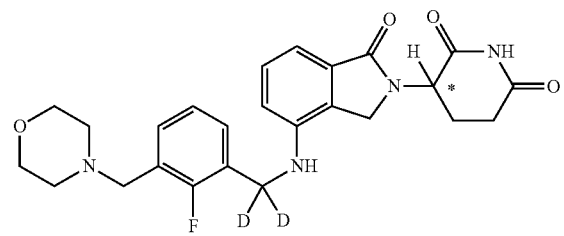
A886
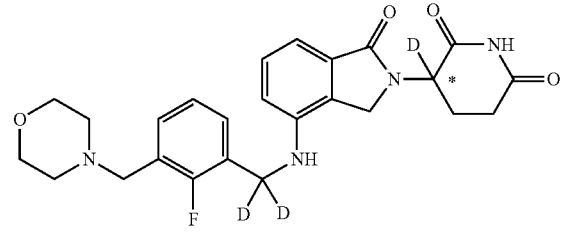
A887
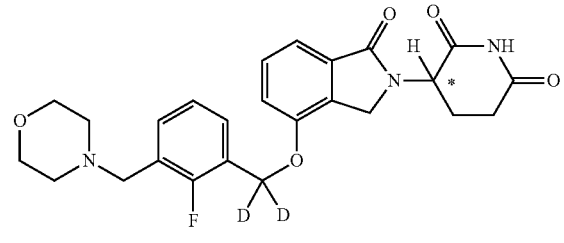

A888
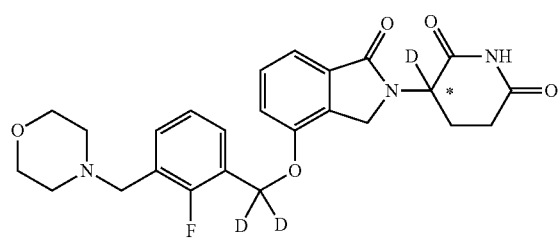
A889
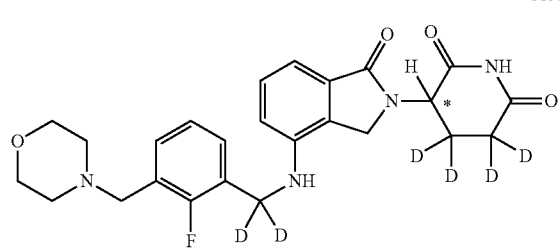
A890
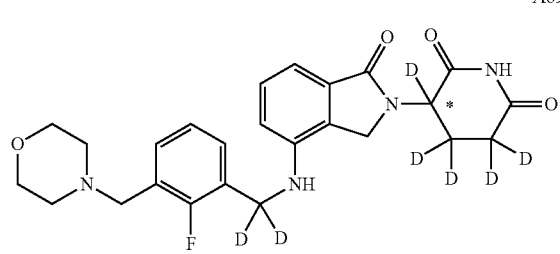
A891
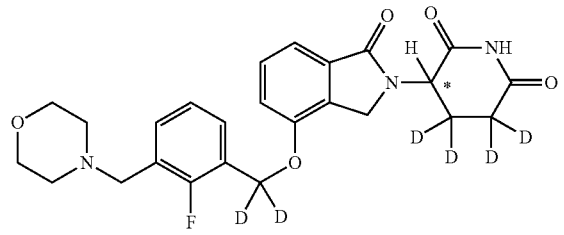
A892
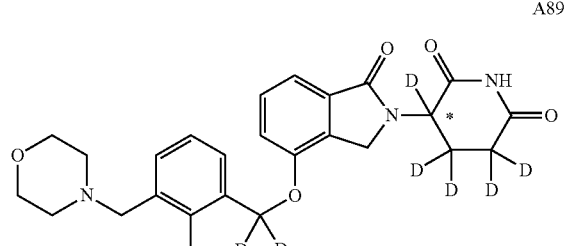
A893
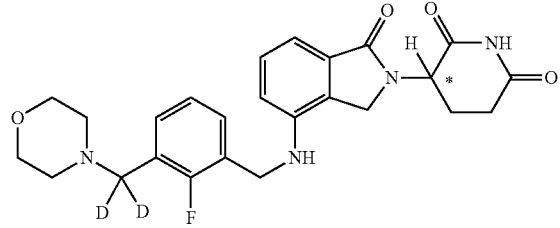
A894
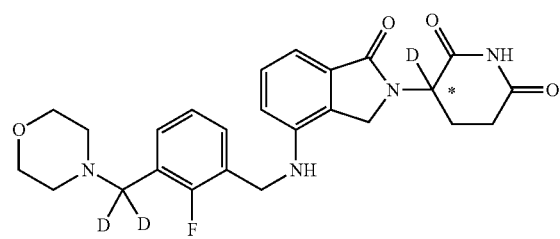
A895
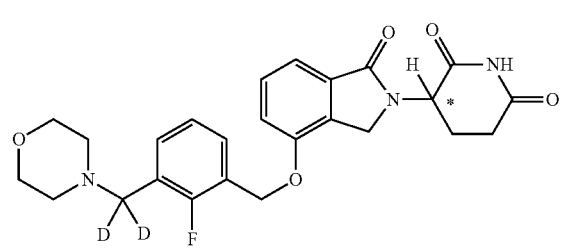
A896
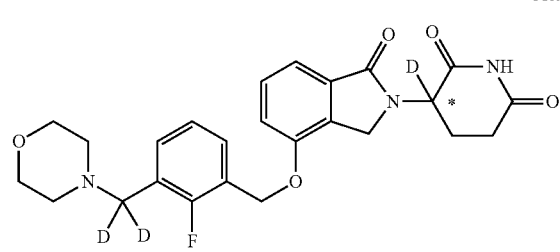
A897
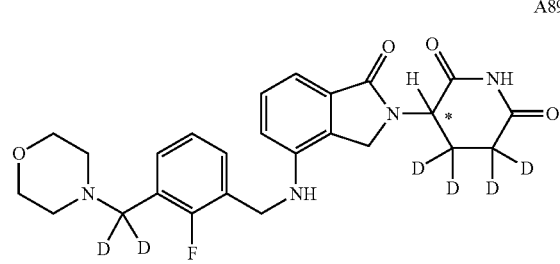
A898
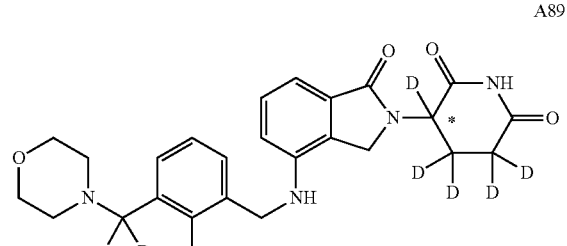
A899
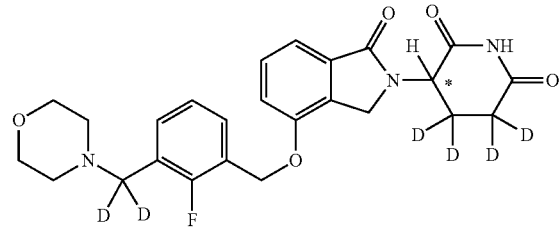

A900
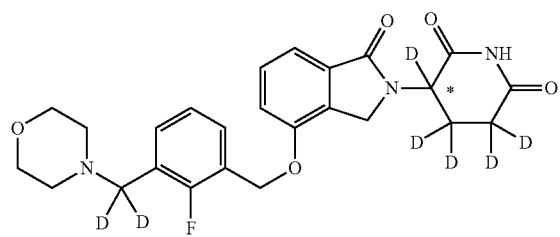
A901
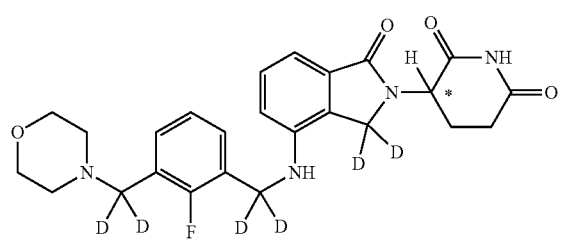
A902
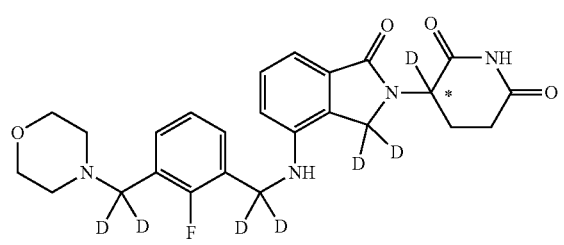
A903
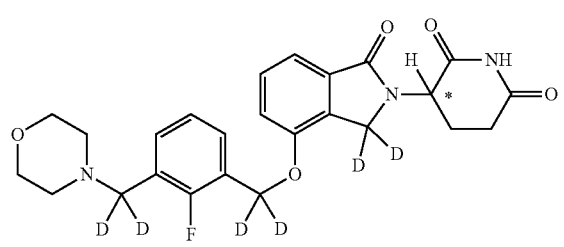
A904
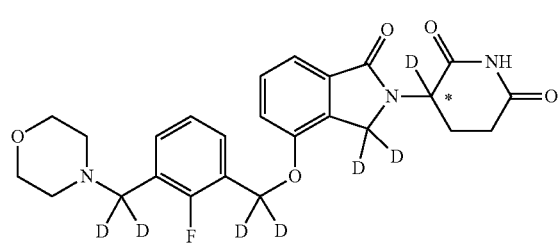
A905
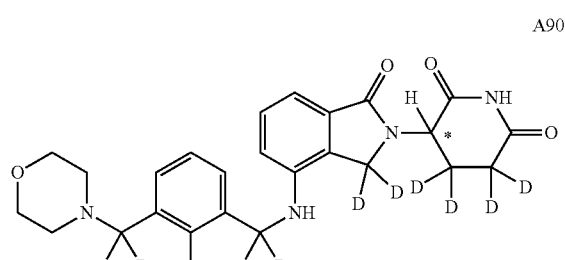
A906
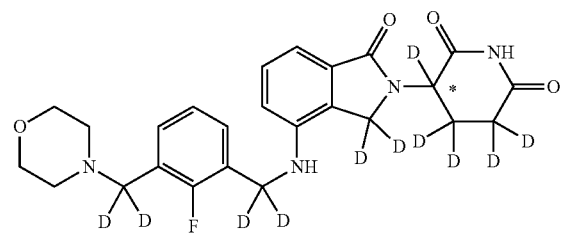
A907
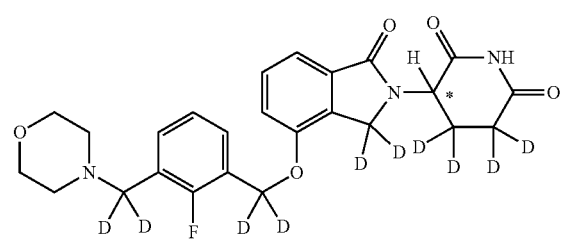
A908
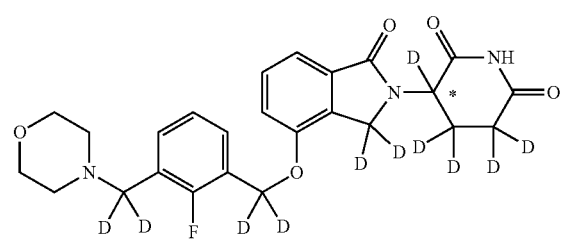
A909
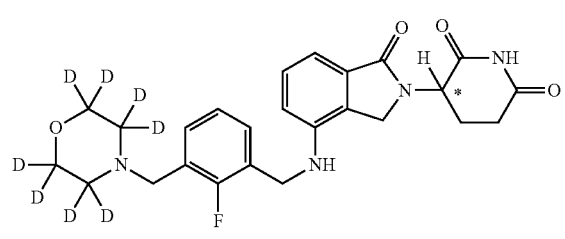
A910
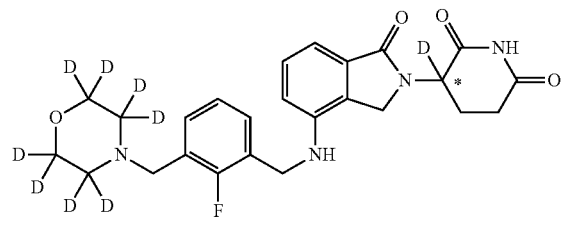
A911
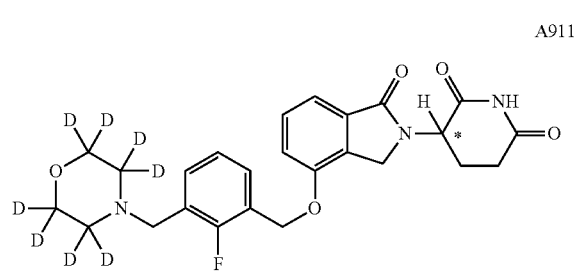

A912
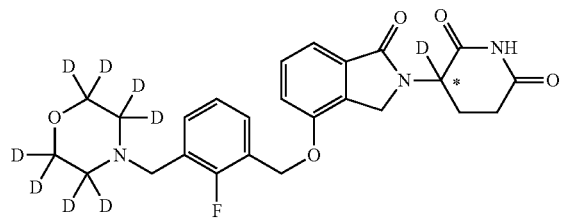
A913
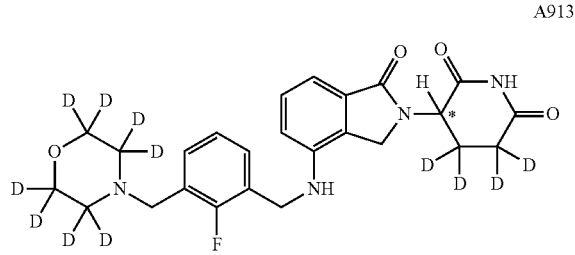
A914
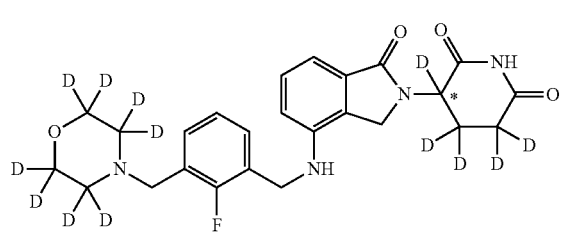
A915
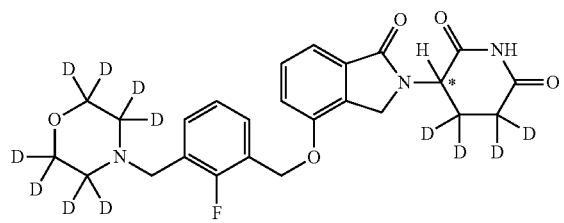
A916
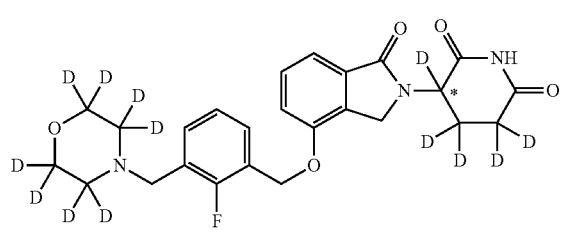
A917
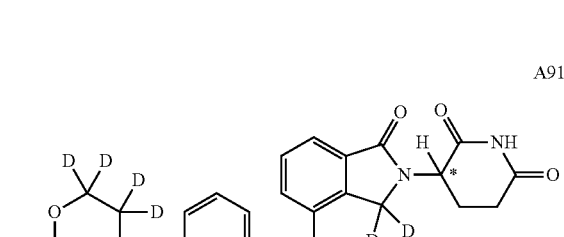
A918
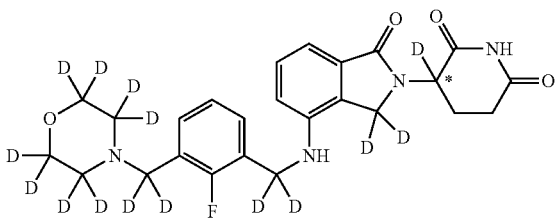
A919
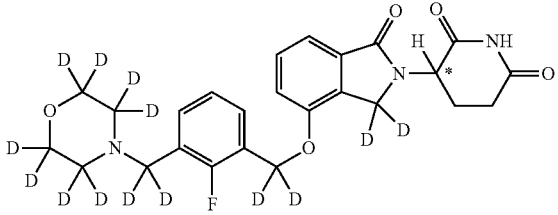
A920
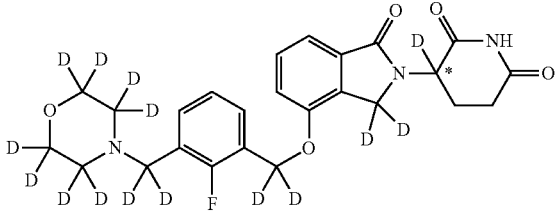
A921
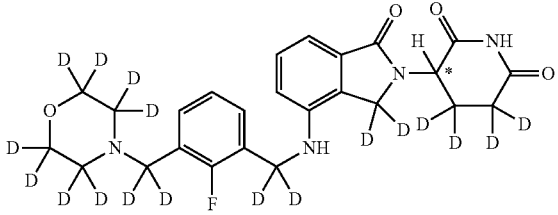
A922
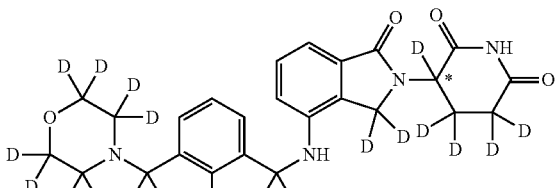
A923
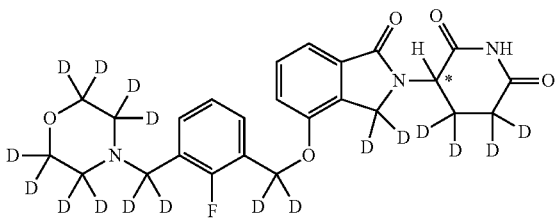

A924 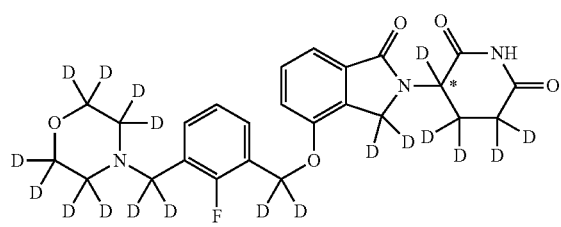
A925 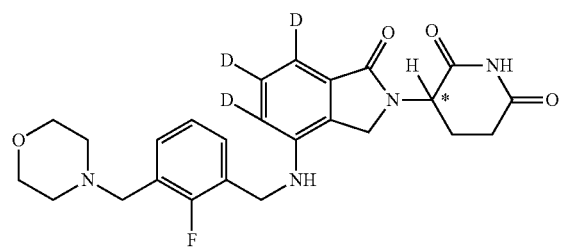
A926 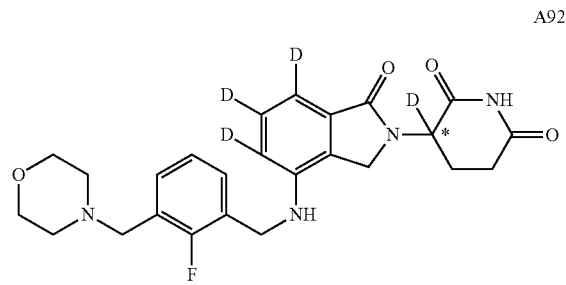
A927 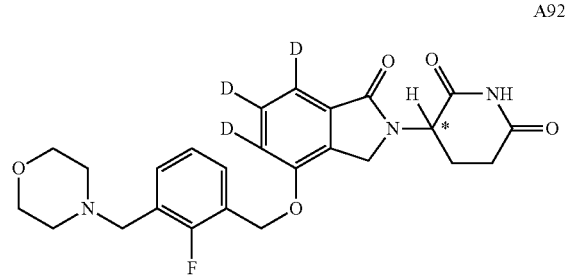
A928 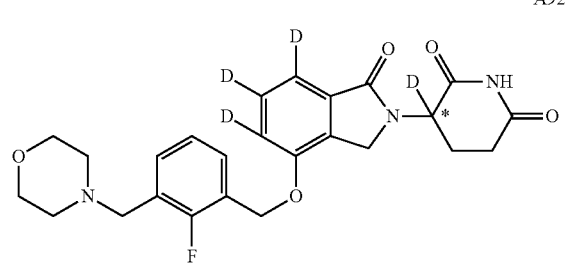
A929 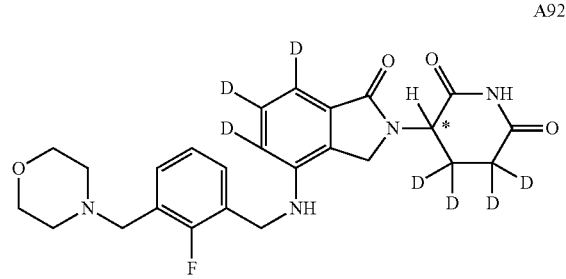
A930 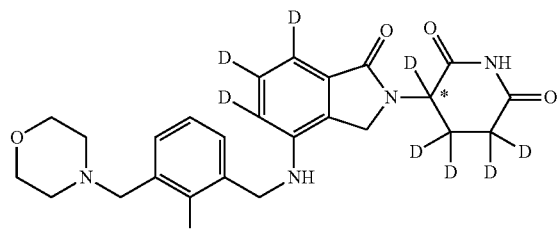
A931 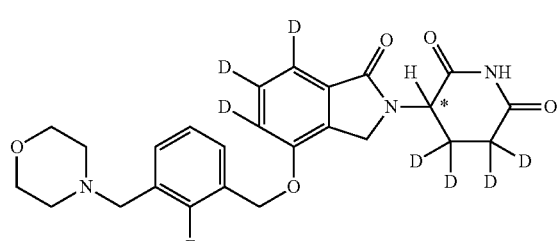
A932 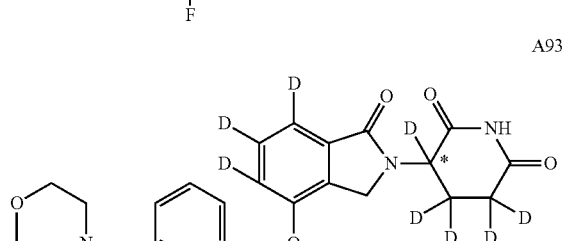
A933 
A934 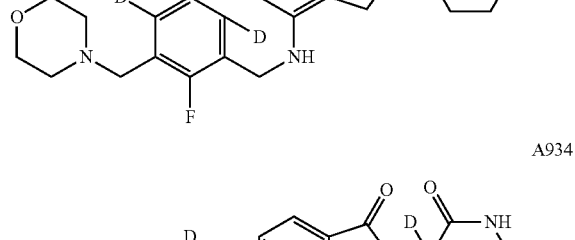
A935 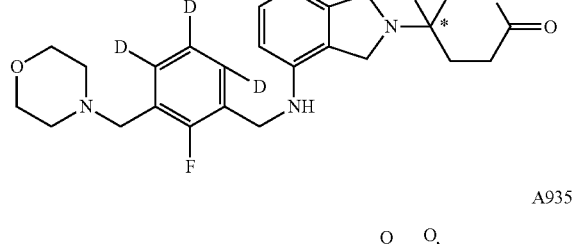

A936 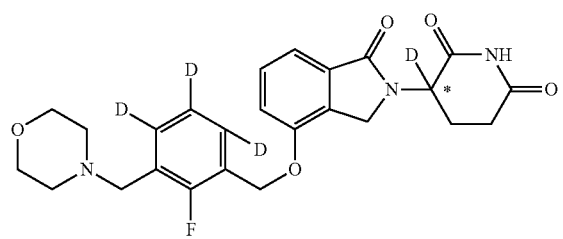
A937 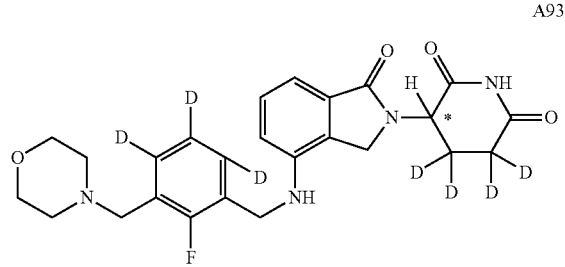
A938 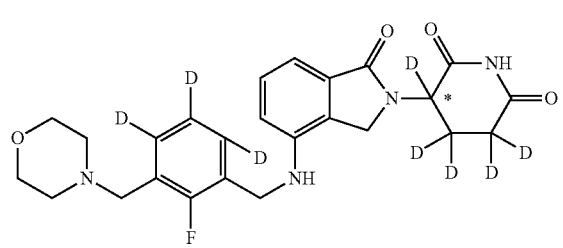
A939 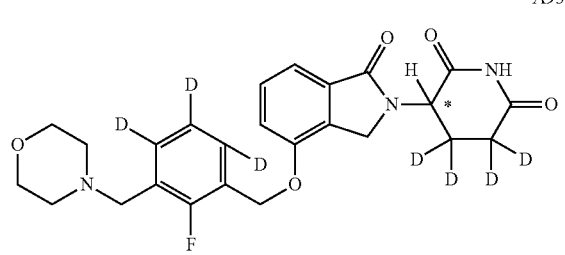
A940 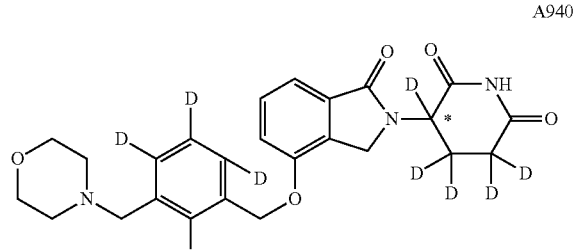
A941 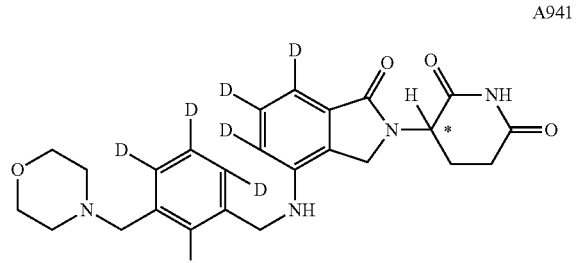
A942 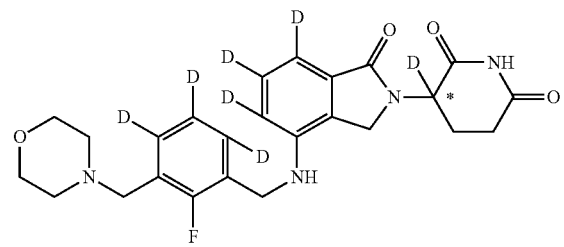
A943 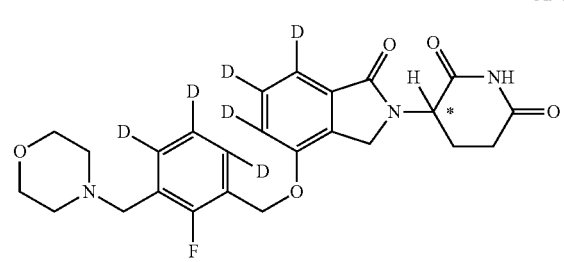
A944 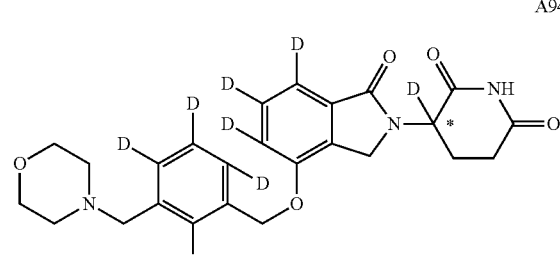
A945 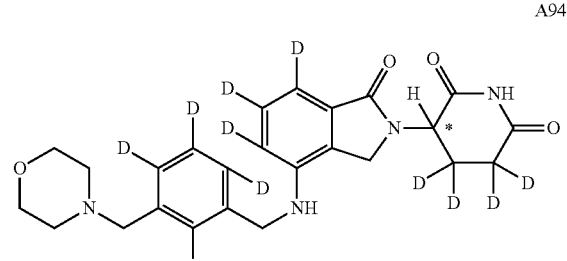
A946 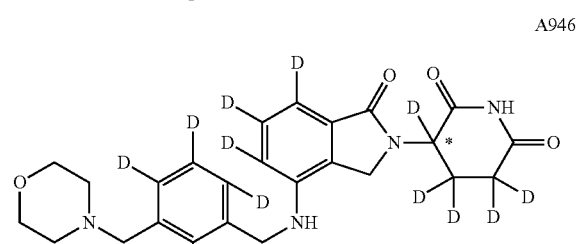
A947 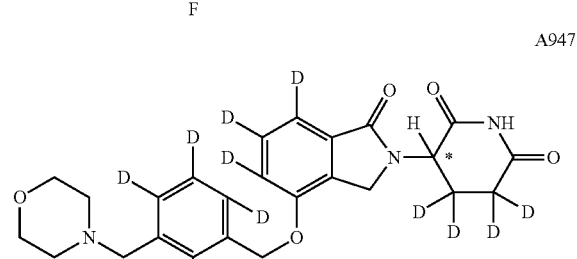

-continued
A948
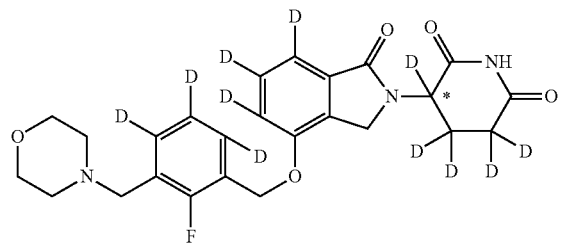
A949
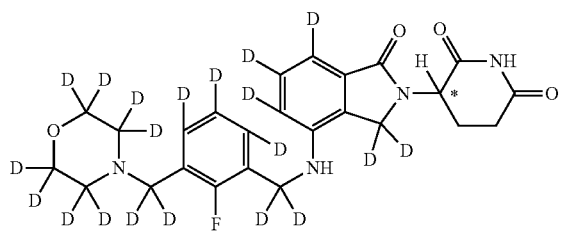
A950
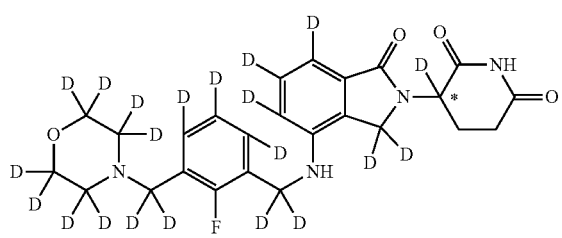
A951
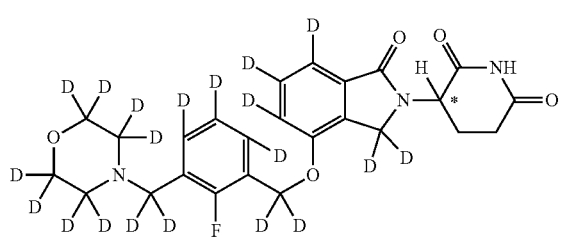
A952
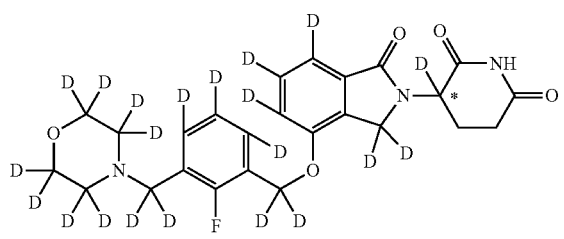
A953
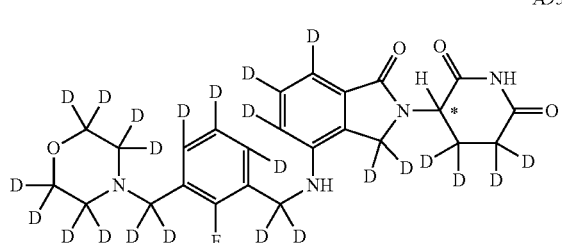
-continued
A954
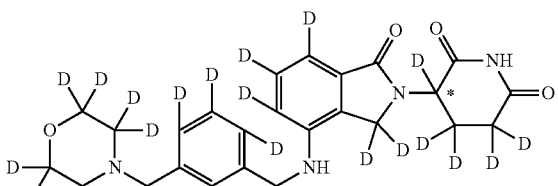
A955
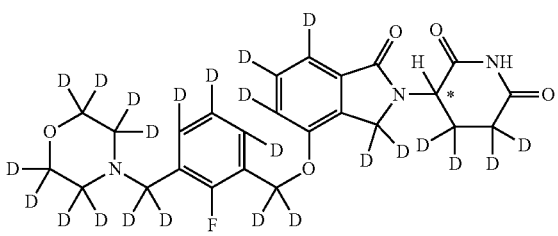
A956
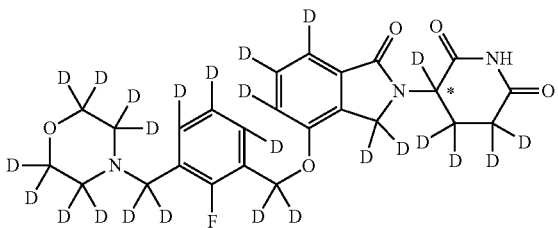
A382
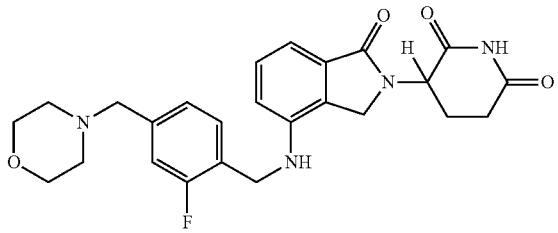
A957
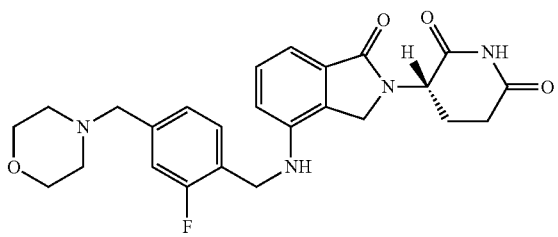
A958
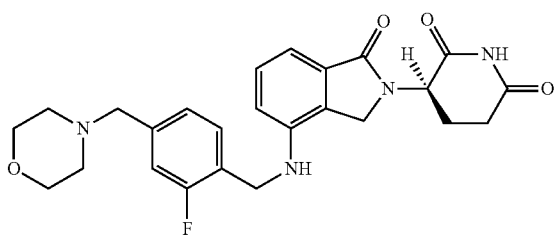

131 -continued

A426

A402

A959

A386

A960

A961

132 -continued

A425

A406

A962

A963

A964

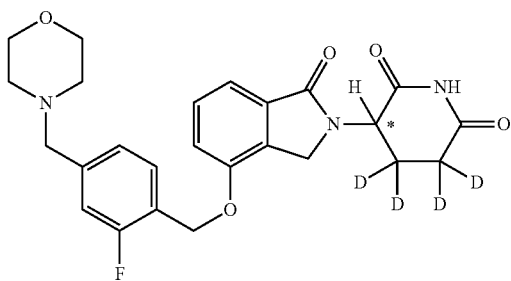
A965
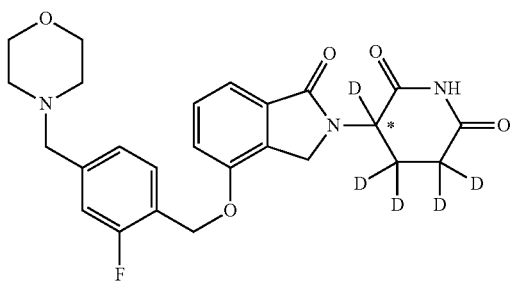
A966
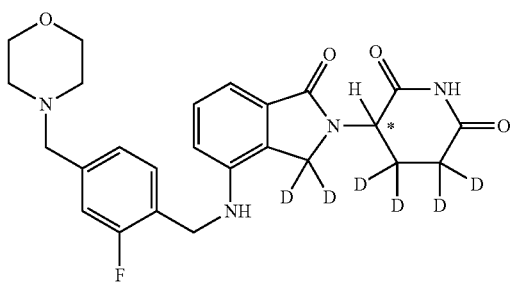
A967
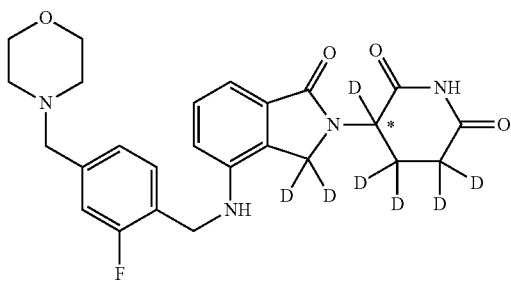
A968
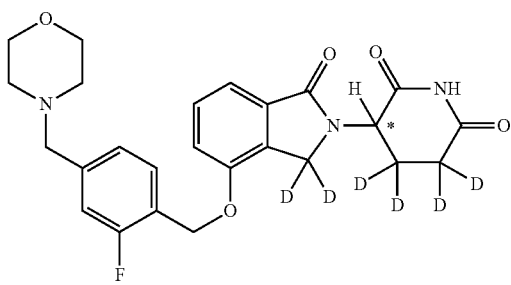
A969
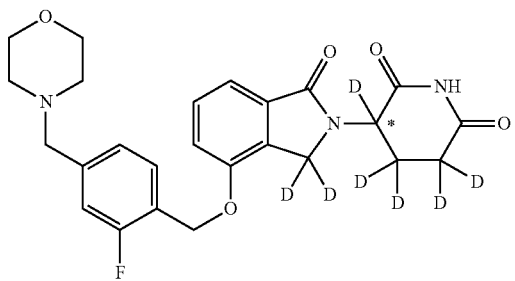
A970
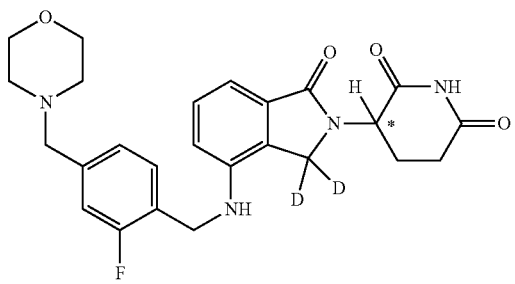
A971
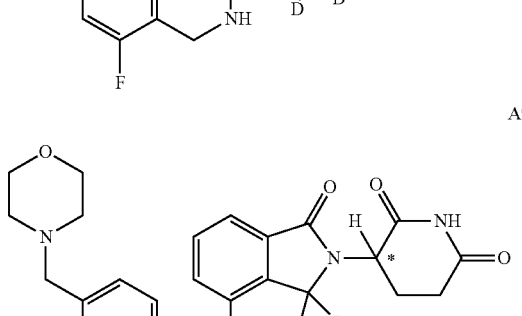
A972
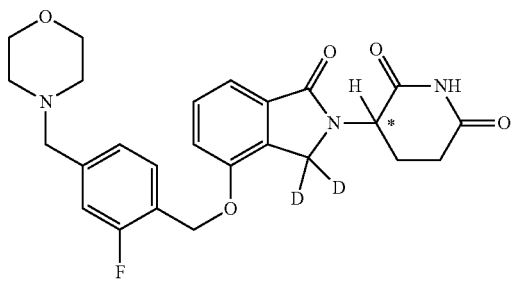
A973
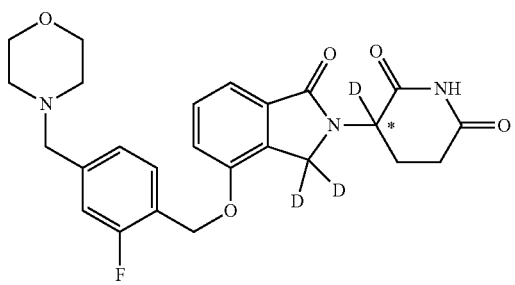
A974

A975
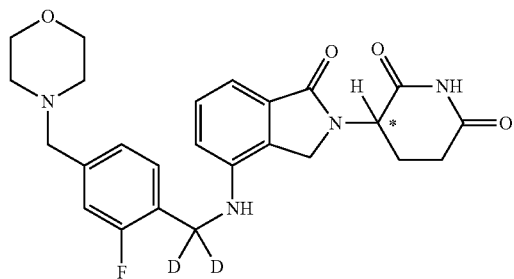
A976
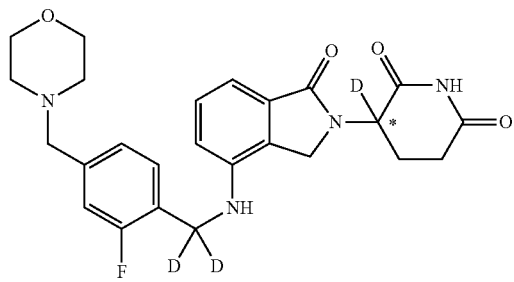
A977
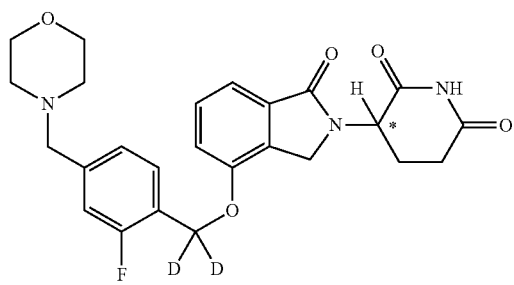
A978
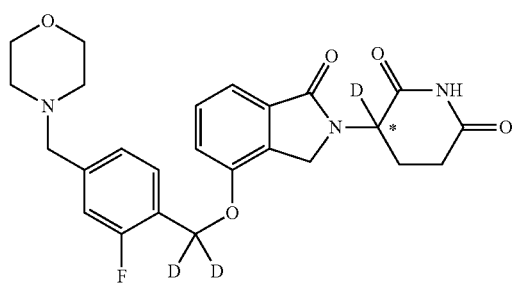
A979
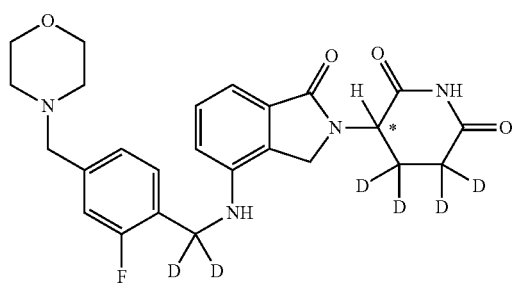
A980
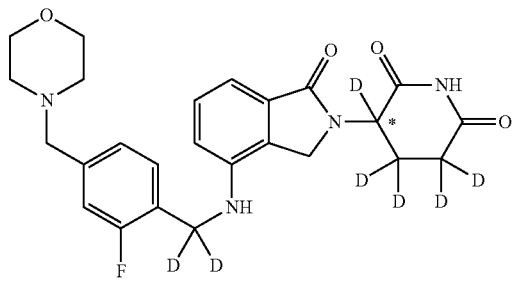
A981
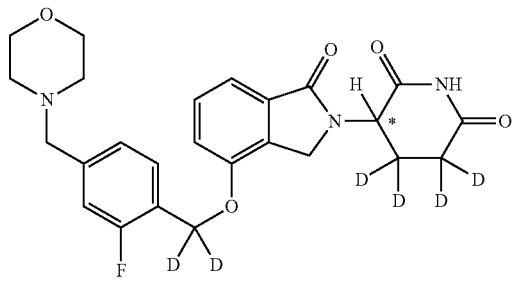
A982
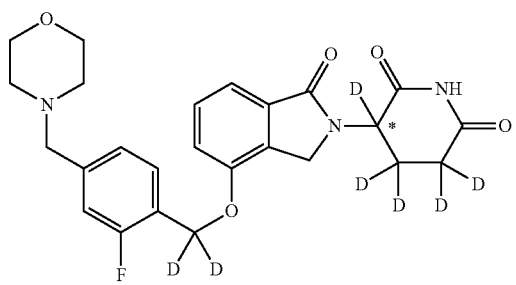
A983
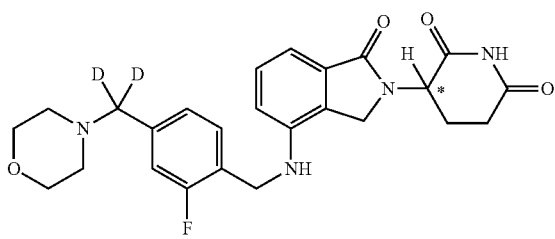
A984
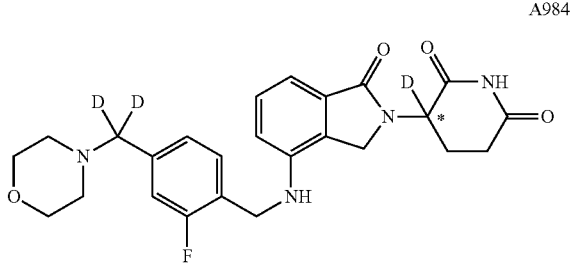

A985
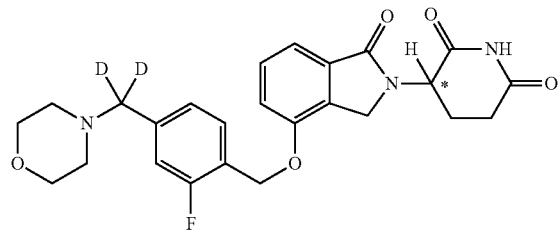
A986
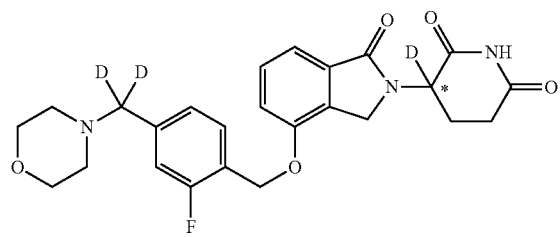
A987
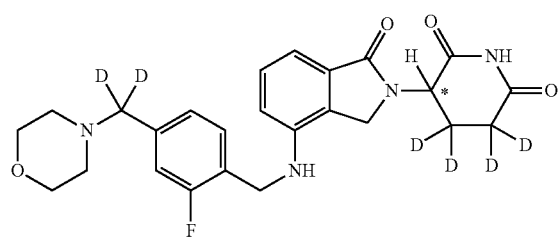
A988
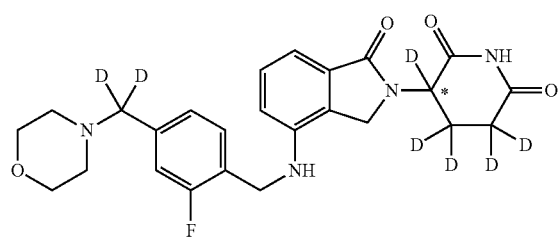
A989
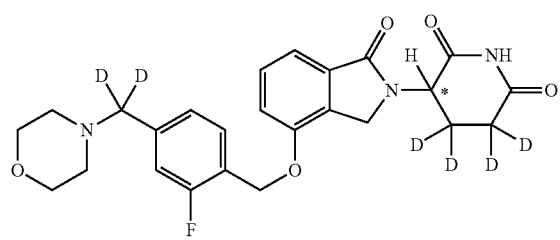
A990
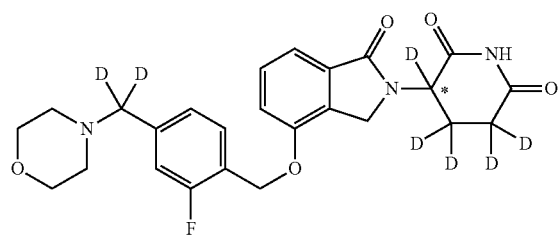
A991
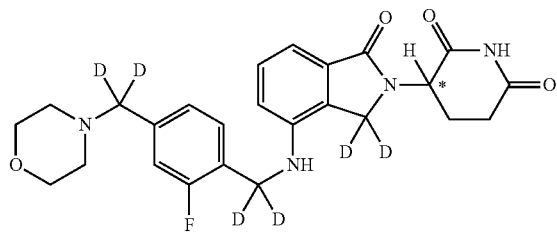
A992
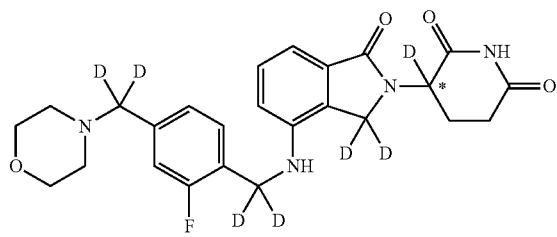
A993
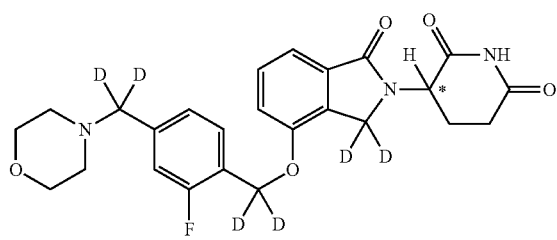
A994
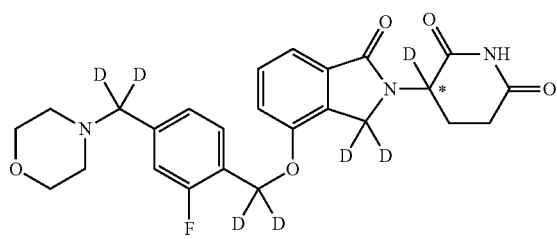
A995
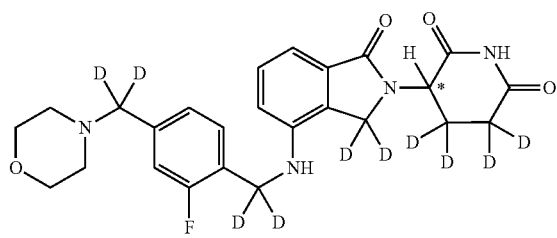
A996
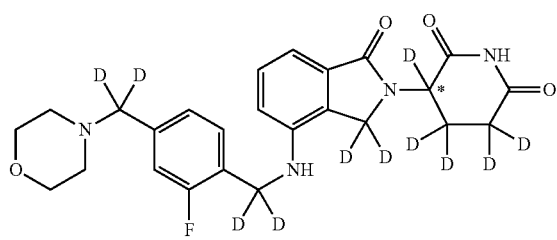

A997
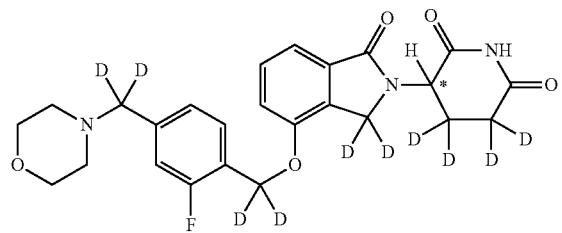
A998
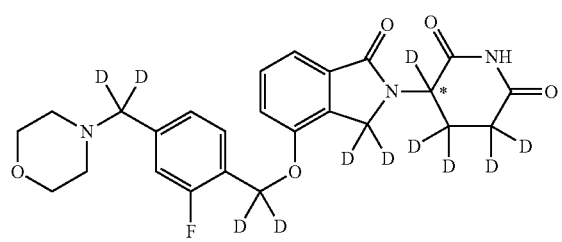
A999
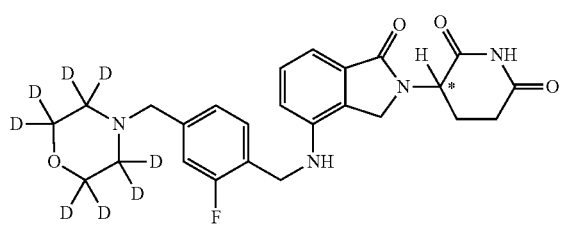
A1000
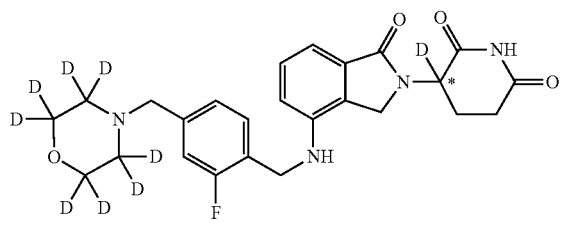
A1001
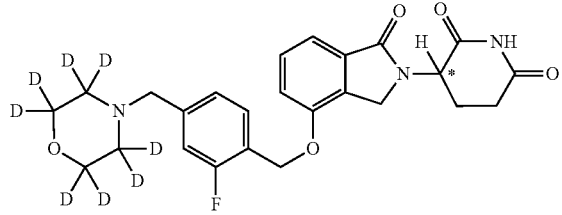
A1002
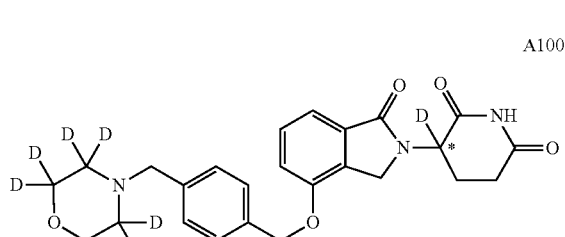
A1003
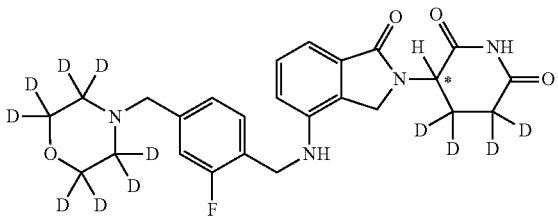
A1004
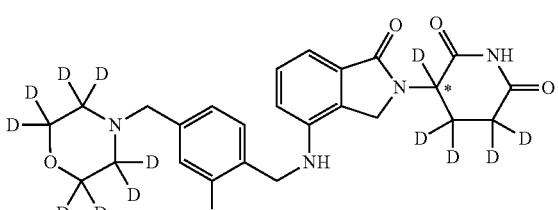
A1005
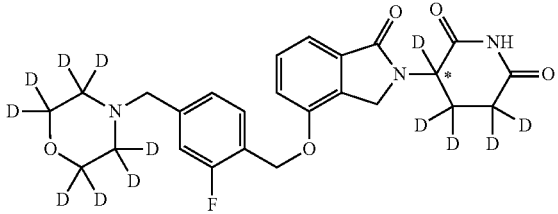
A1006
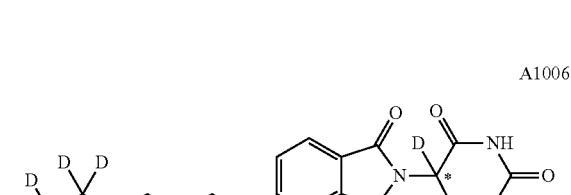
A1007
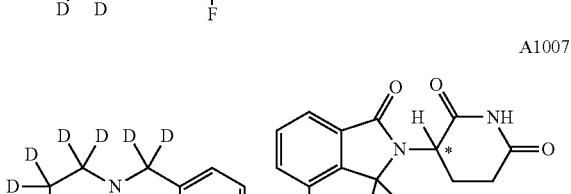
A1008
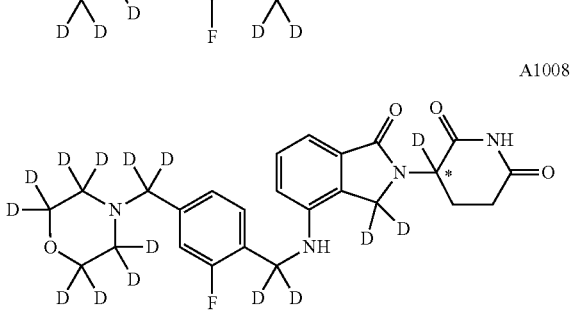

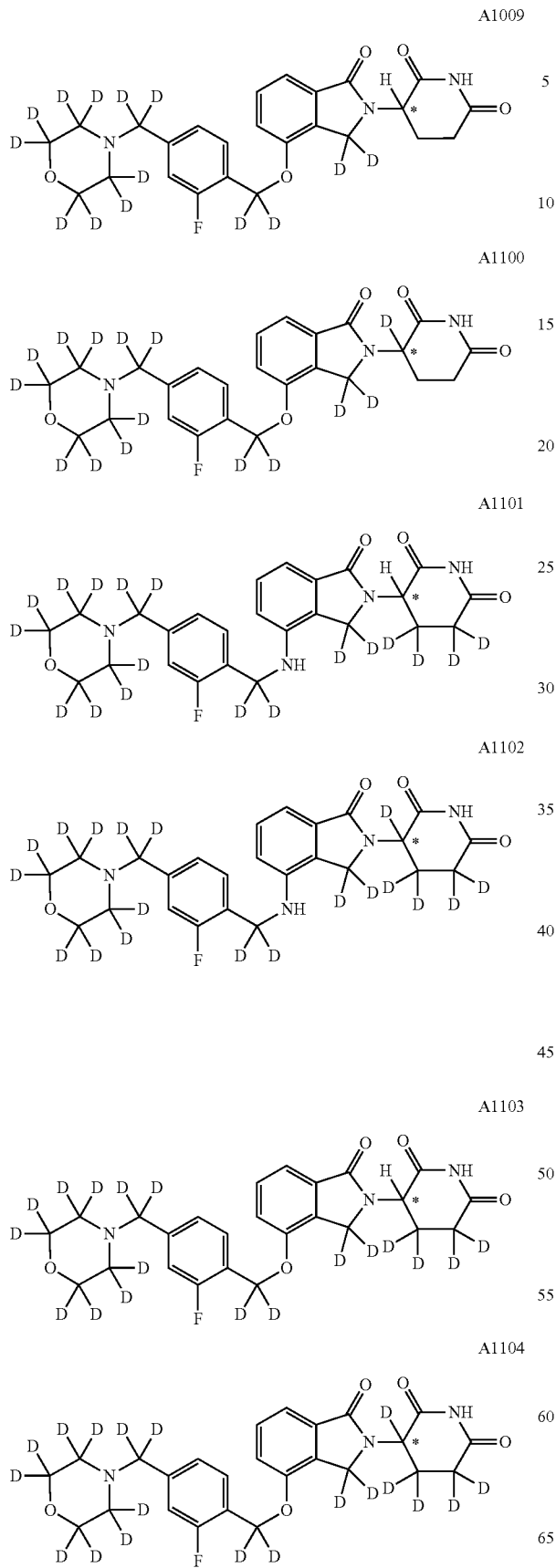
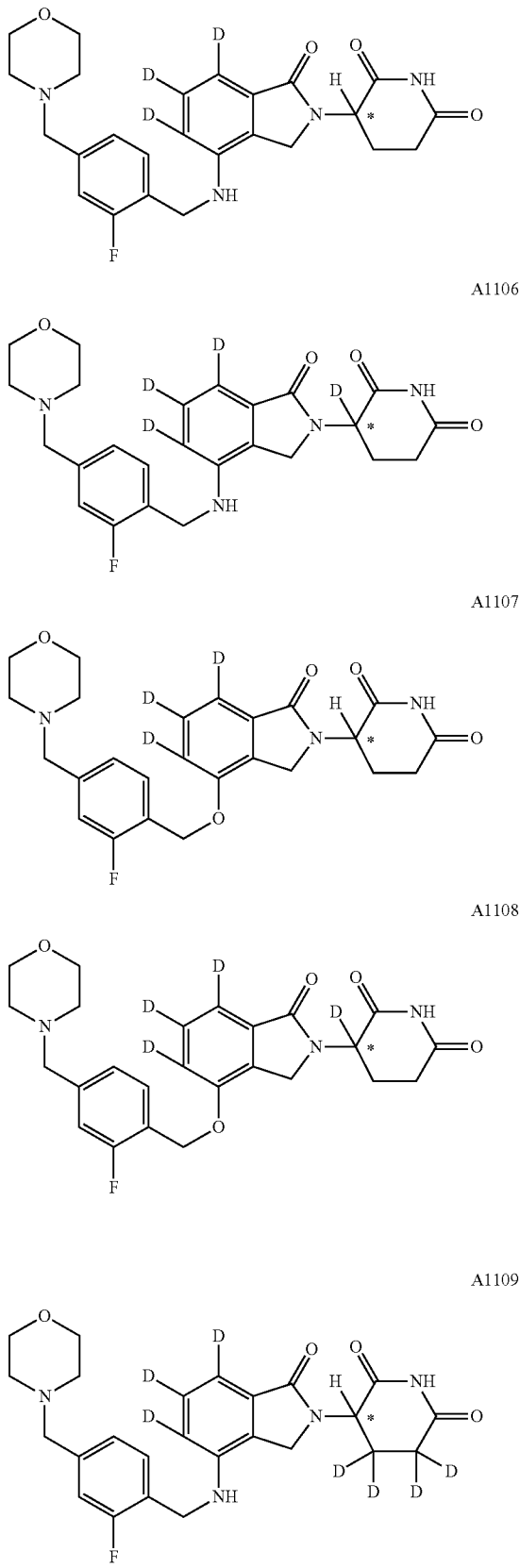

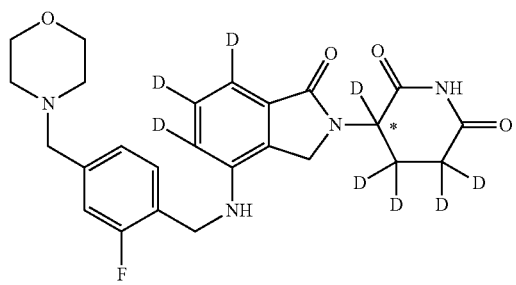
A1110
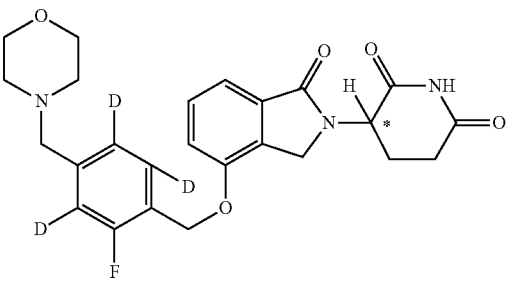
A1115
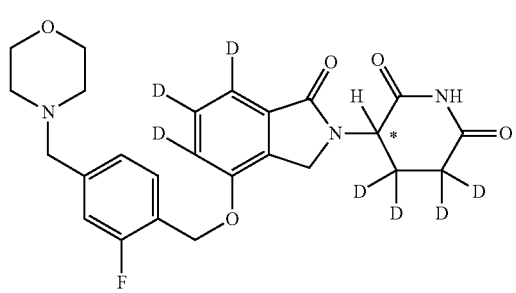
A1111
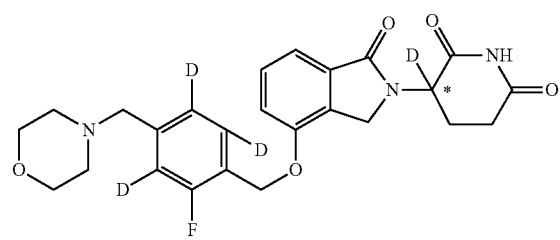
A1116
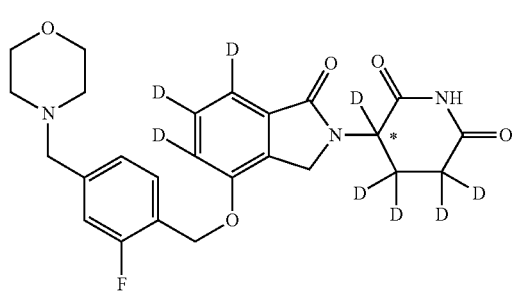
A1112
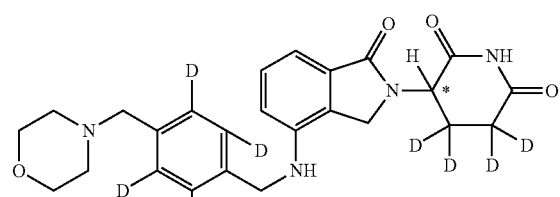
A1117
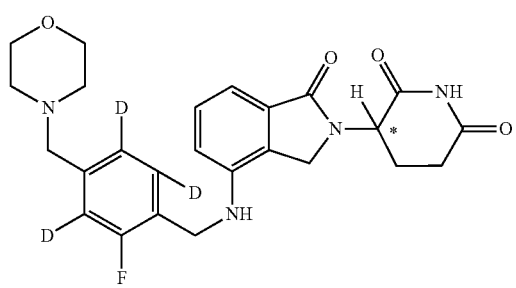
A1113
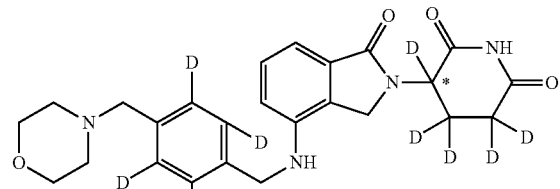
A1118
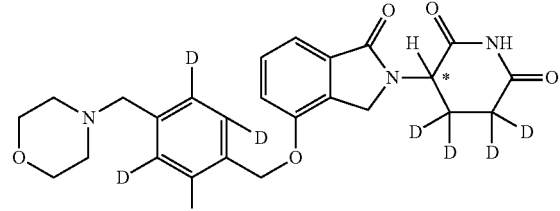
A1119
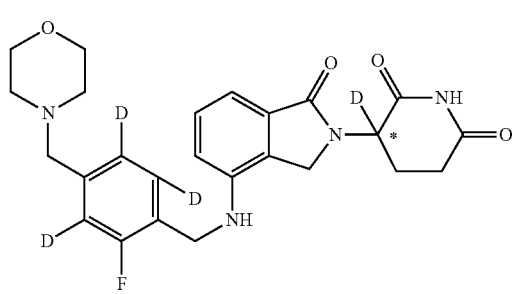
A1114
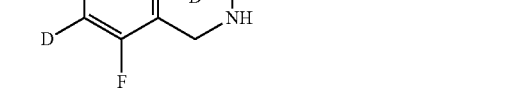
A1120

A1121
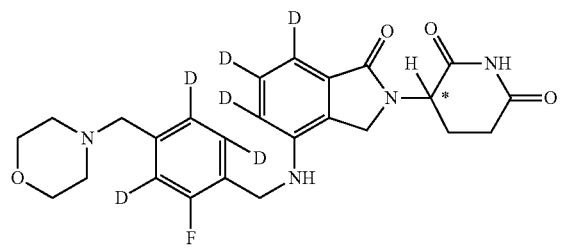
A1127
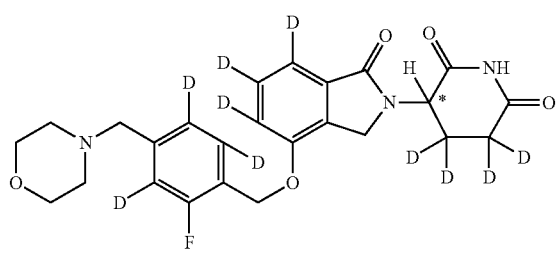
A1122
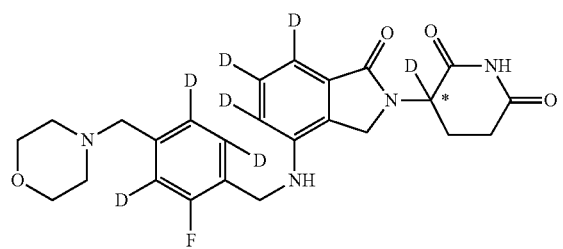
A1128
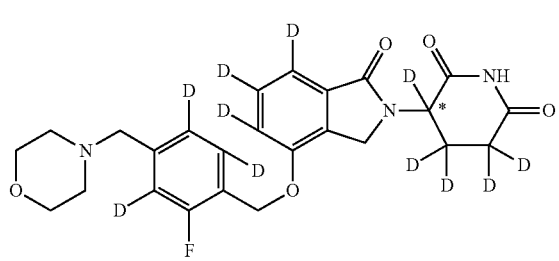
A1123
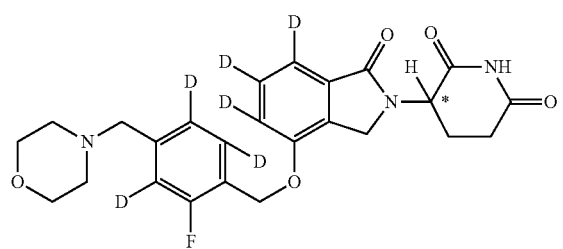
A1129
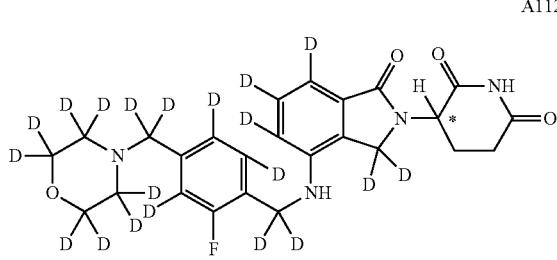
A1124
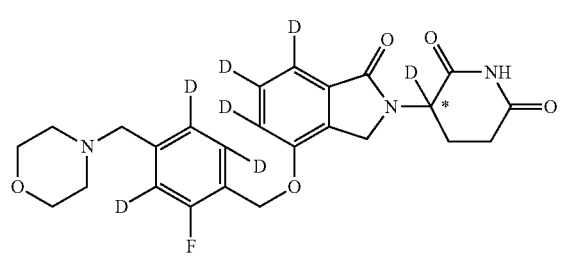
A1130
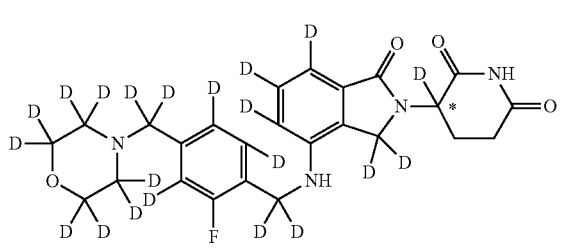
A1125
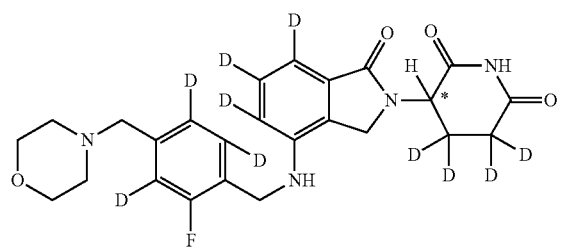
A1131
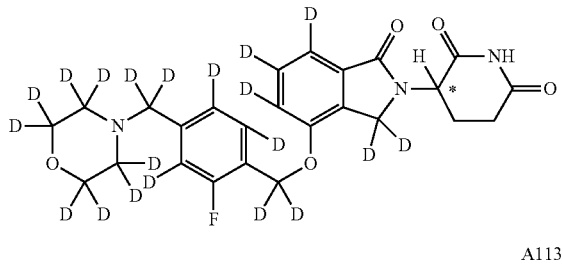
A1126
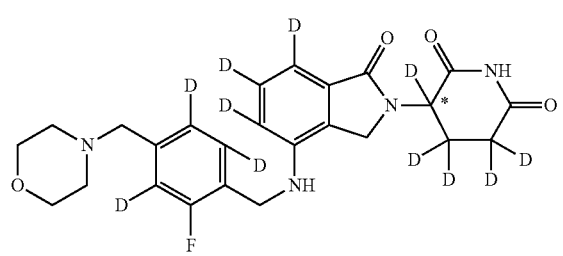
A1132
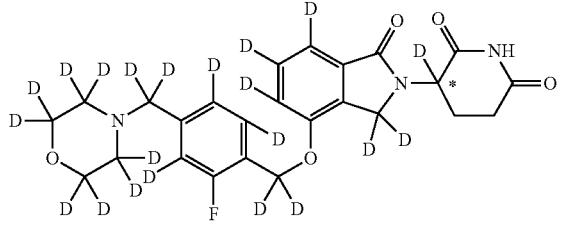

A1133
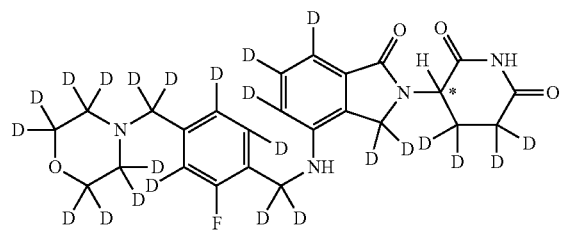
A1134
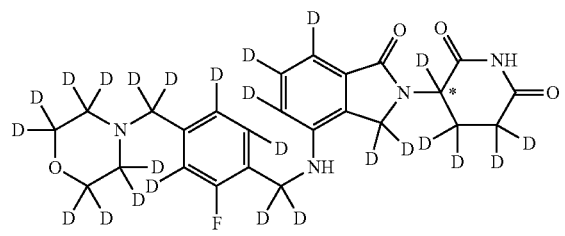
A1135
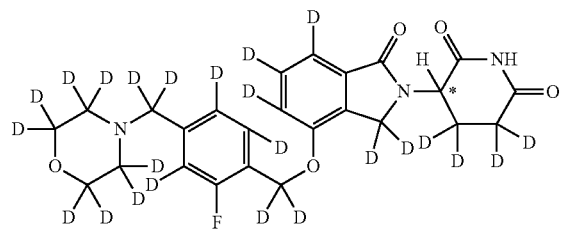
A1136
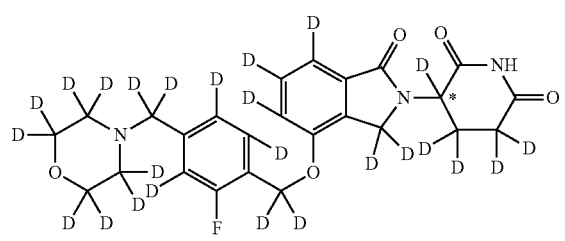
A383
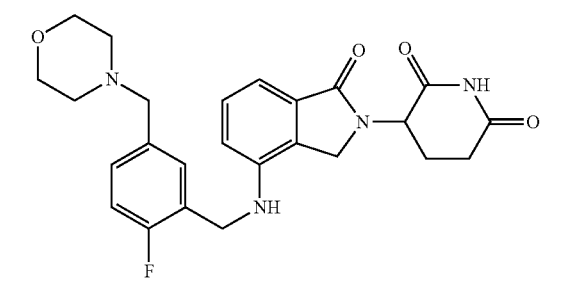
A1137
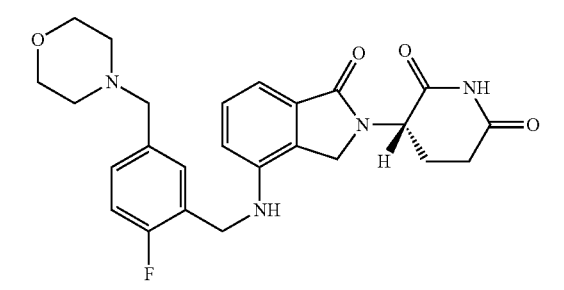
A1138
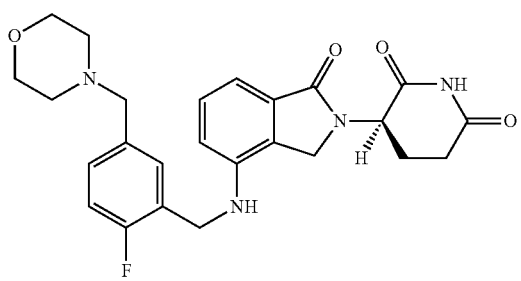
A1139
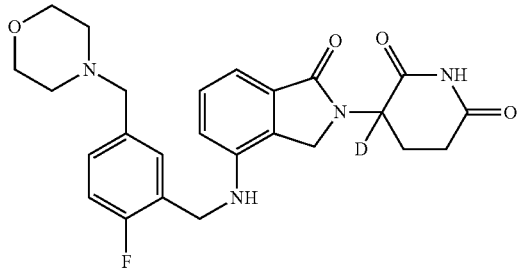
A401
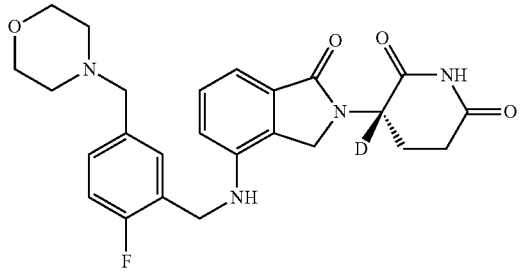
A1140
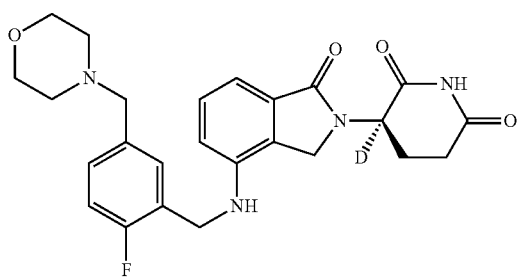
A398
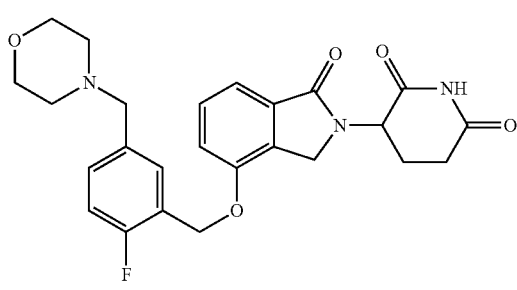

A1141
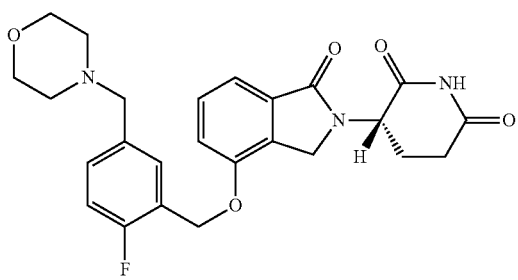
A1142
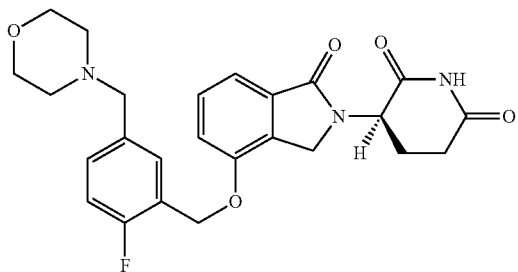
A1143
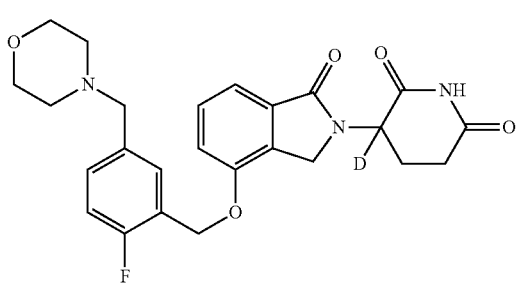
A403
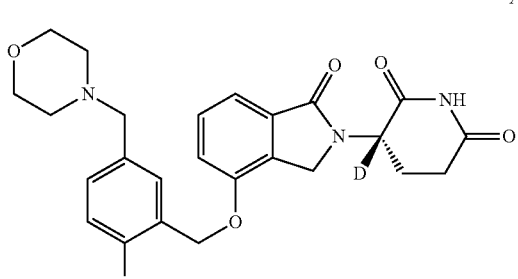
A1144
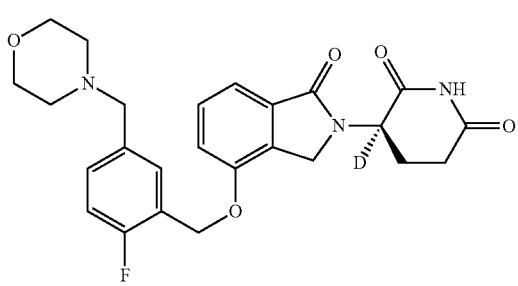
A1145
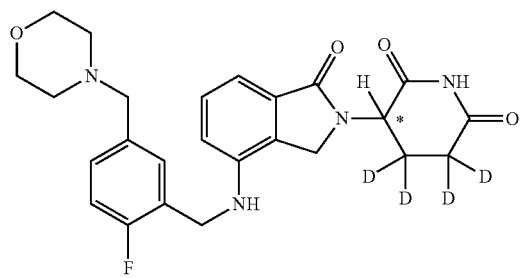
A1146
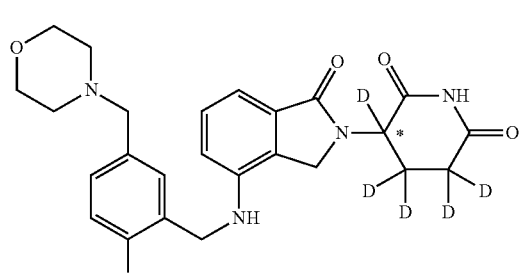
A1147
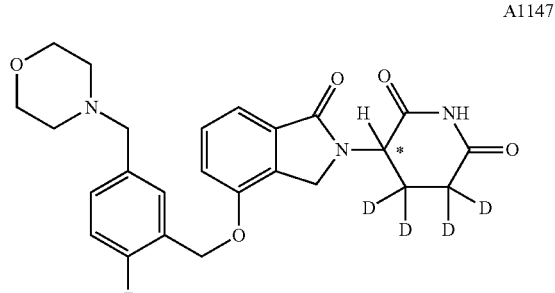
A1148
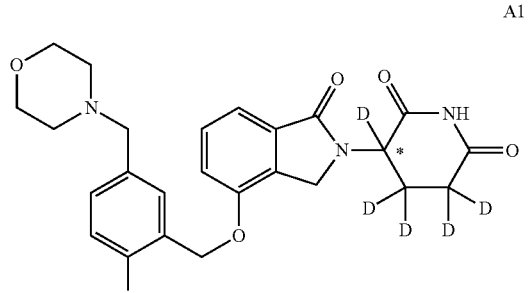
A1149
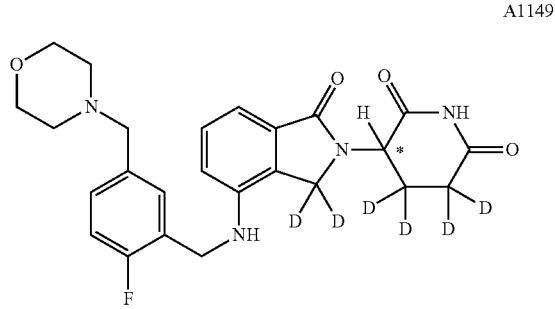

A1150
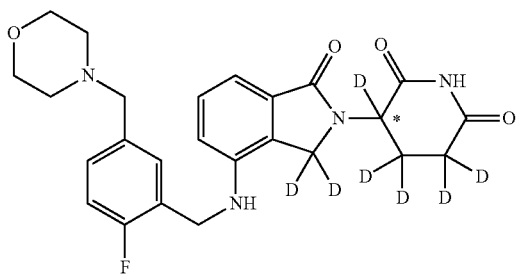
A1151
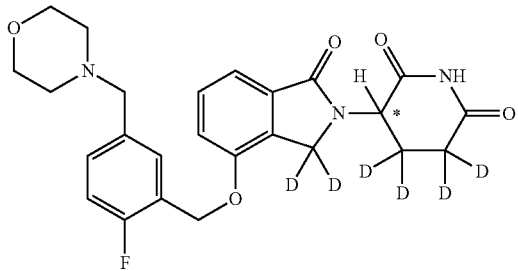
A1152
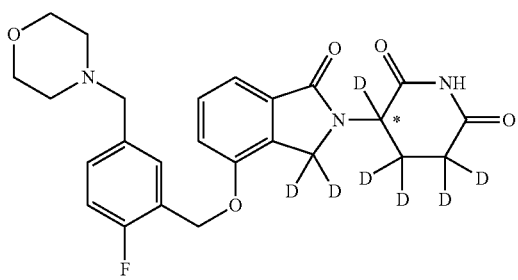
A1153
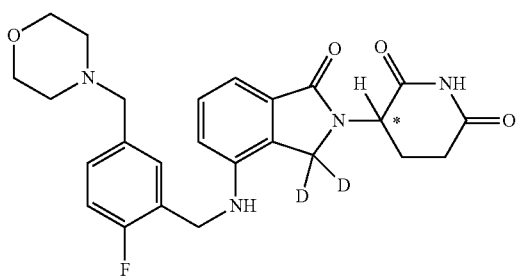
A1154
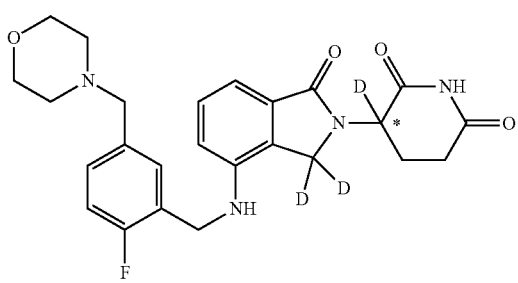
A1155
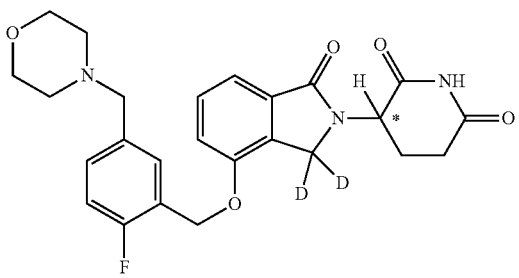
A1156
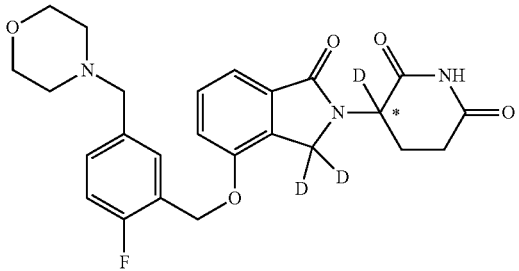
A1157
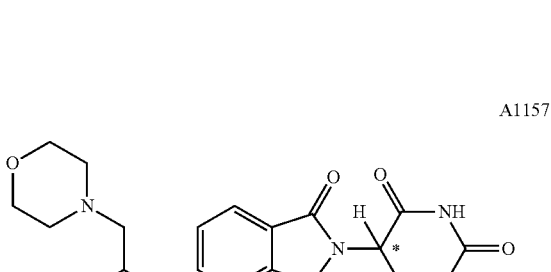
A1158
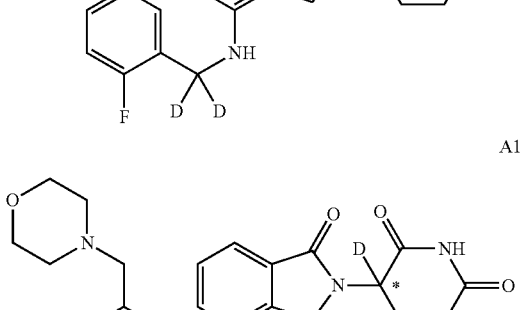
A1159
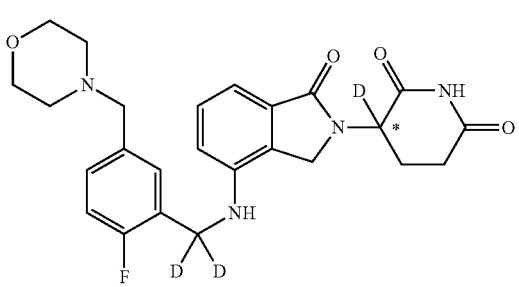

A1160

A1161

A1162

A1163

A1164

A1165

A1166

A1167

A1168

A1169

A1170
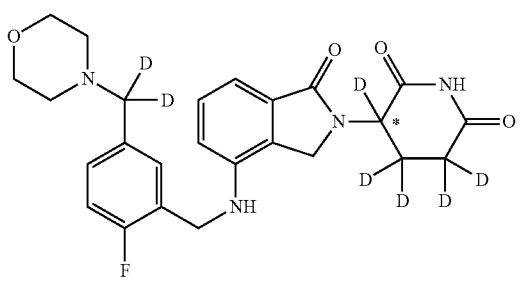
A1171
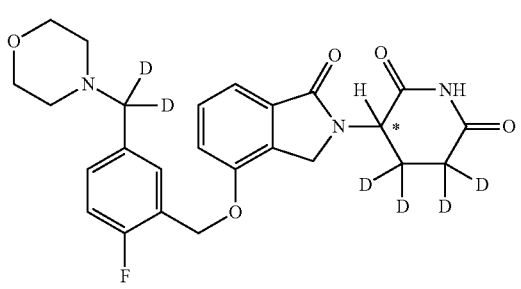
A1172
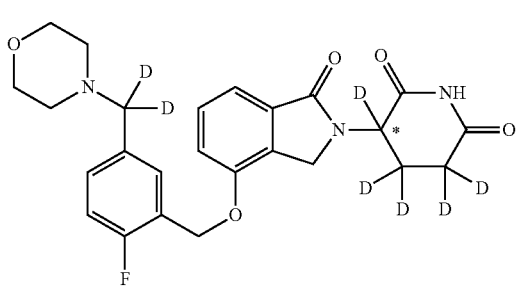
A1173
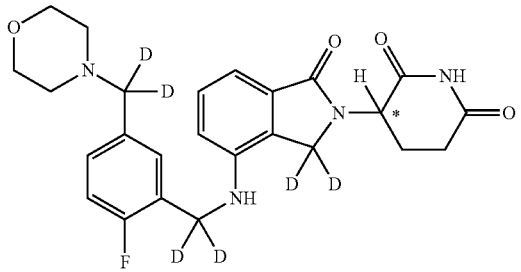
A1174
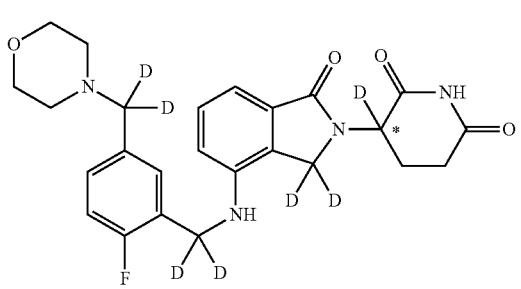
A1175
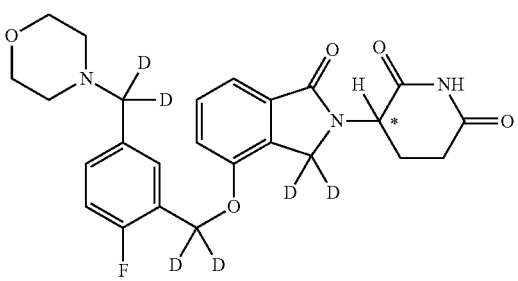
A1176
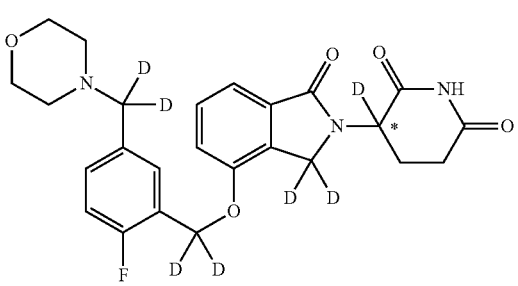
A1177
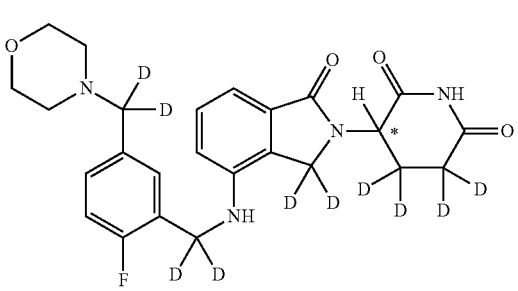
A1178
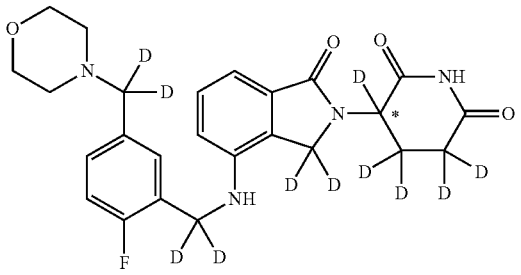
A1179
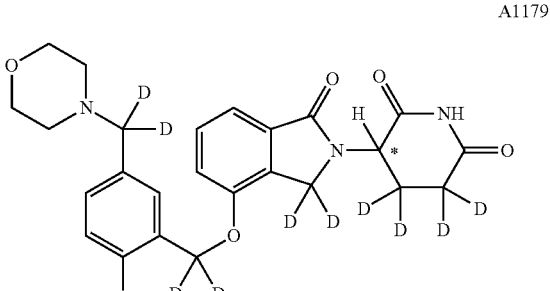

A1180
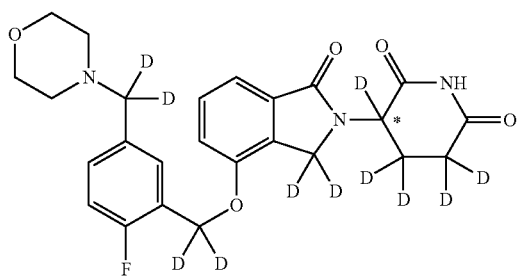
A1184
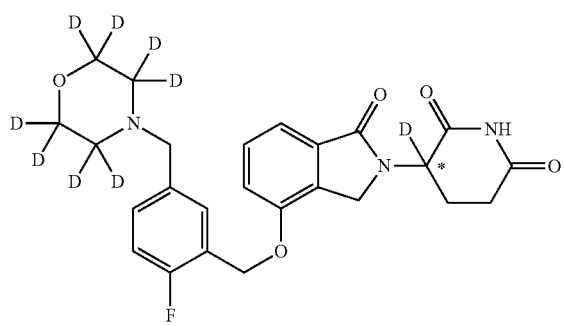
A1181
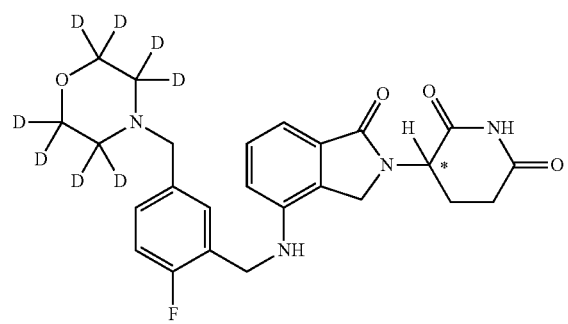
A1185
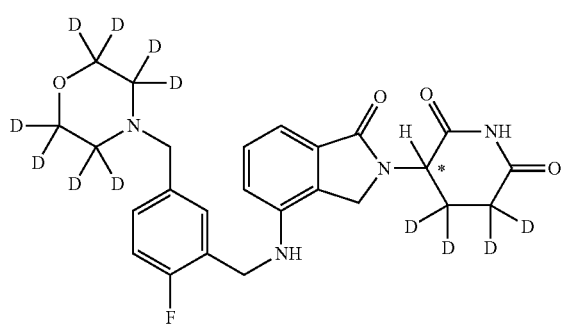
A1182
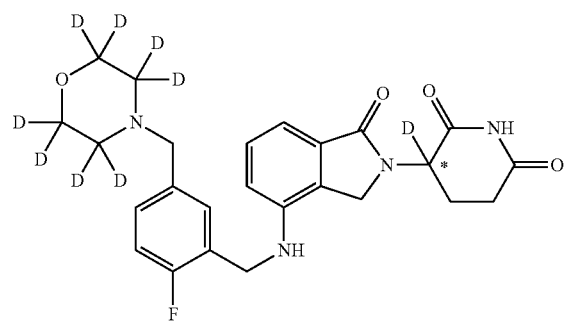
A1186
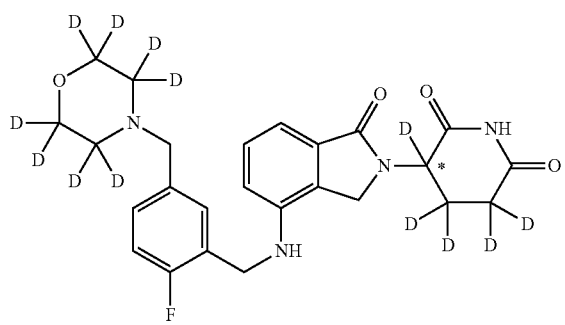
A1183
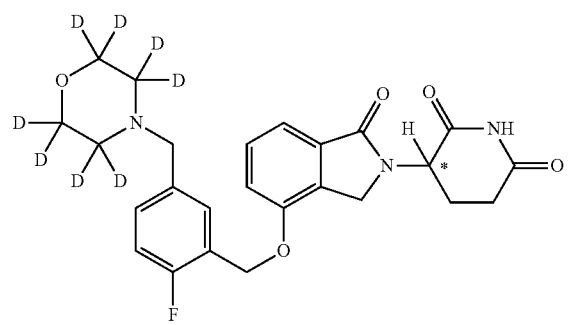
A1187
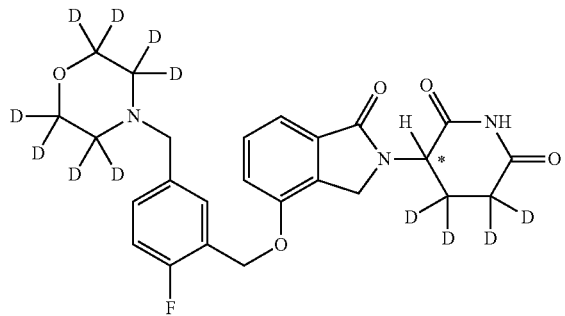

A1188
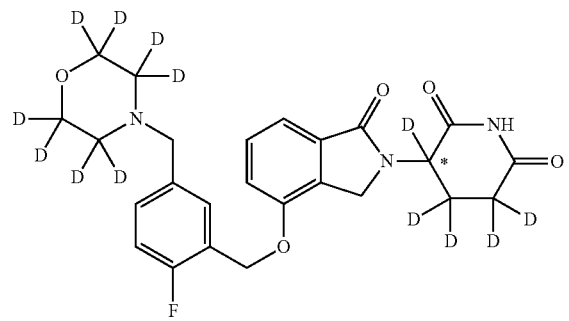
A1192
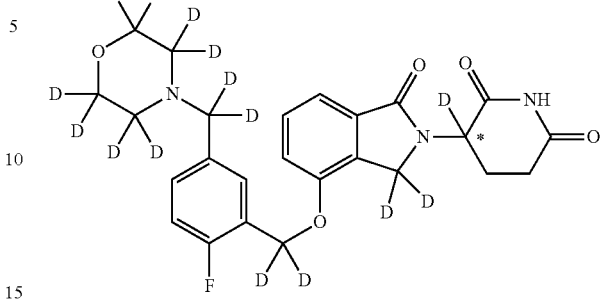
A1189
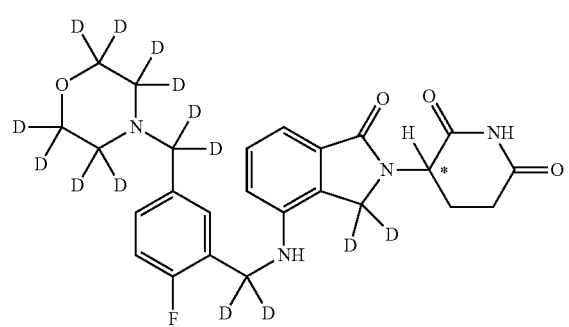
A1193
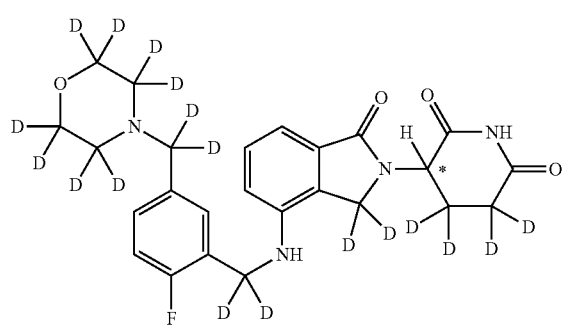
A1190
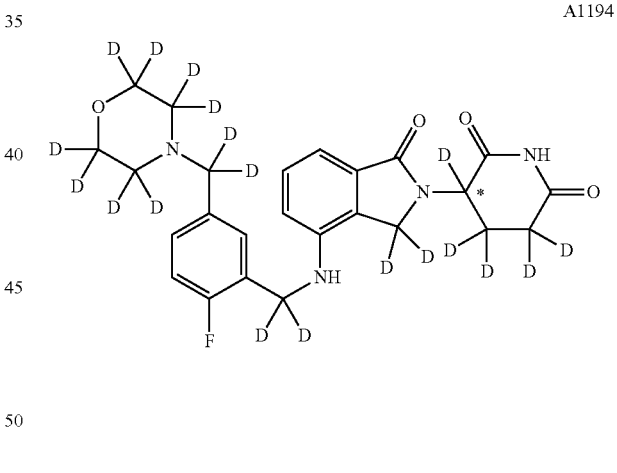
A1194
A1191
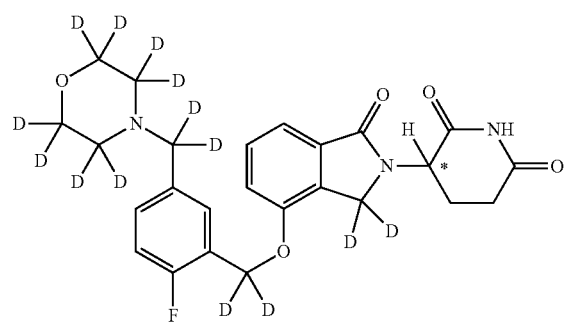
A1195
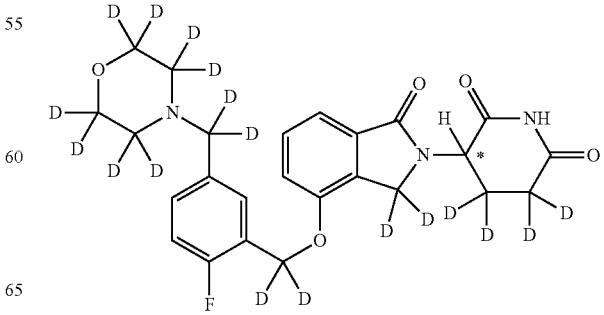

-continued
A1196
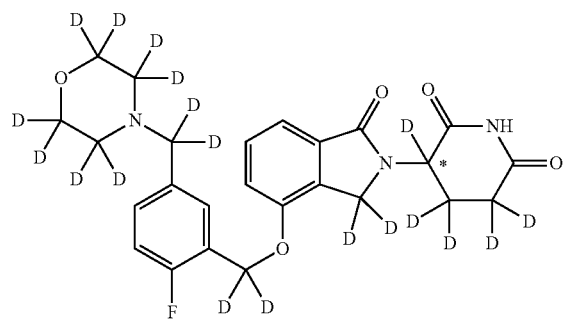
A1197
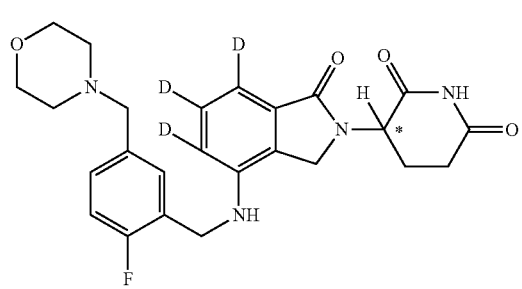
A1198
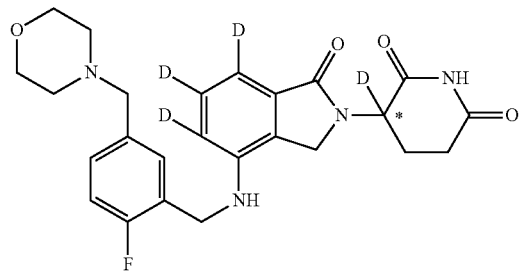
A1199
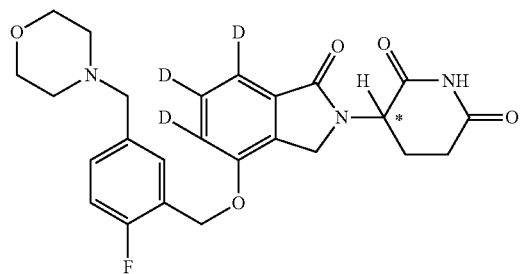
A1200
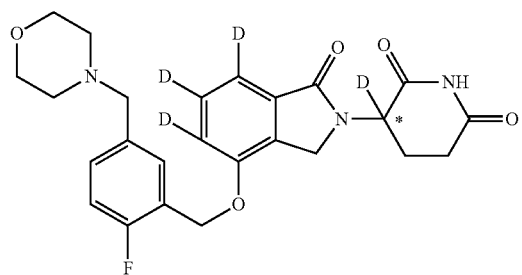
-continued
A1201
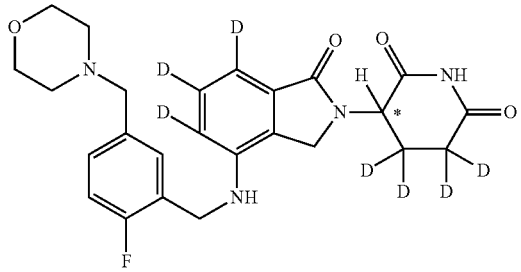
A1202
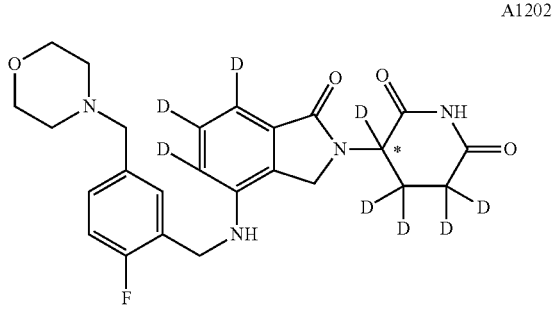
A1203
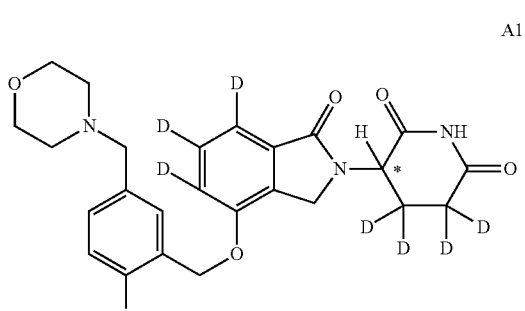
A1204
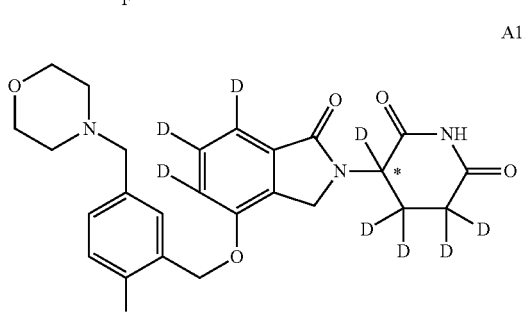
A1205
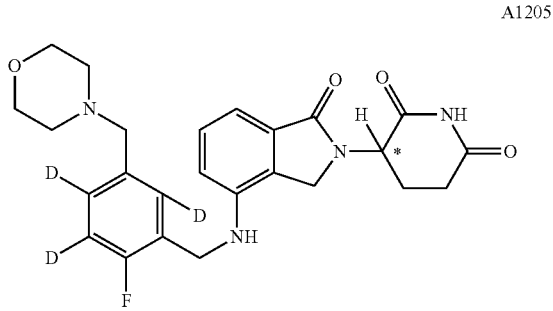

A1206
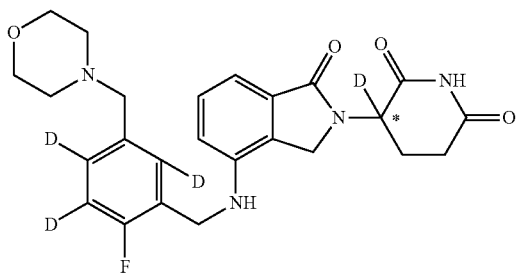
A1207
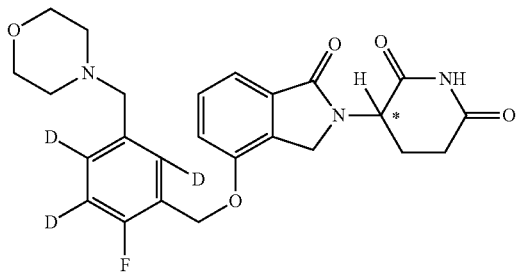
A1208
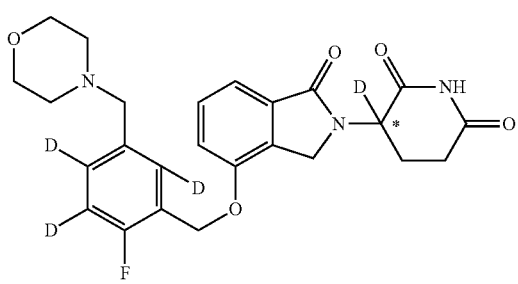
A1209
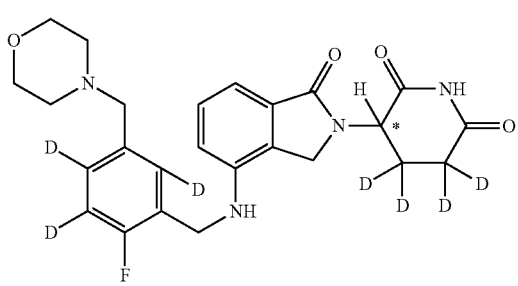
A1210
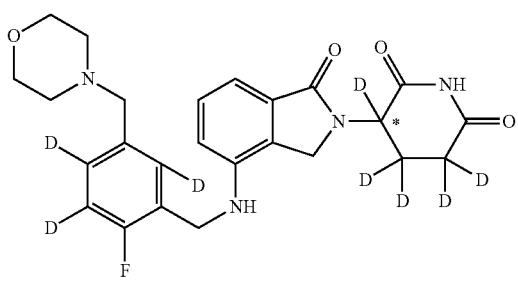
A1211
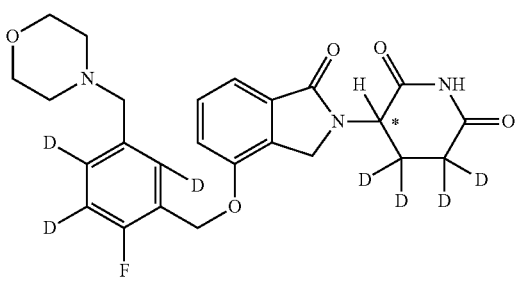
A1212
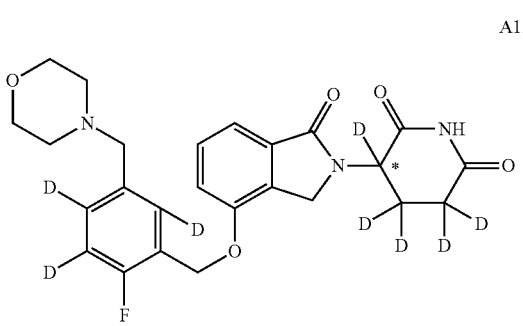
A1213
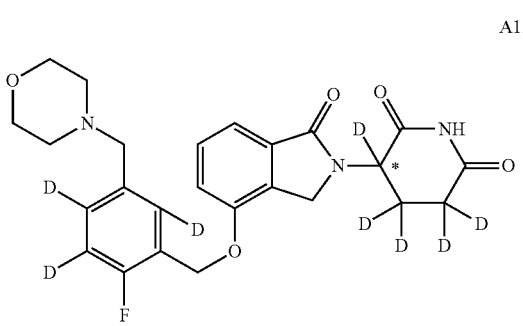
A1214
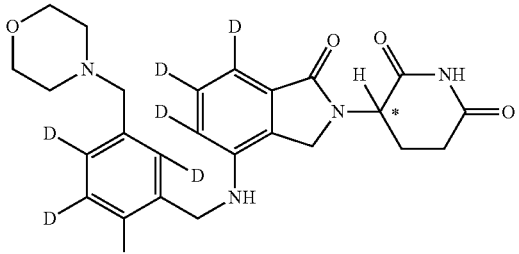
A1215
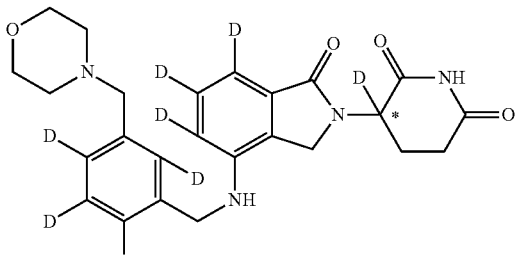

-continued
A1216
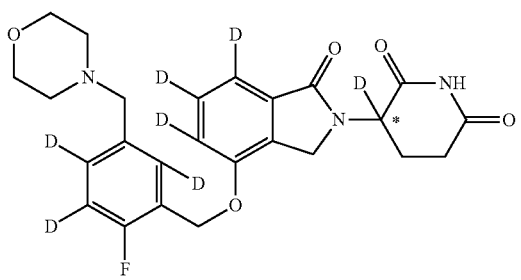
A1217
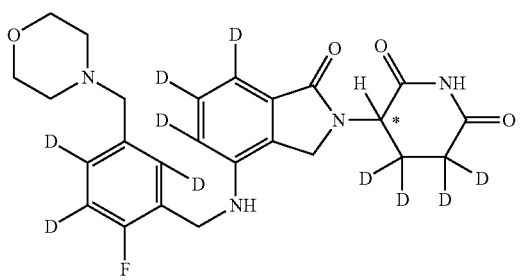
A1218
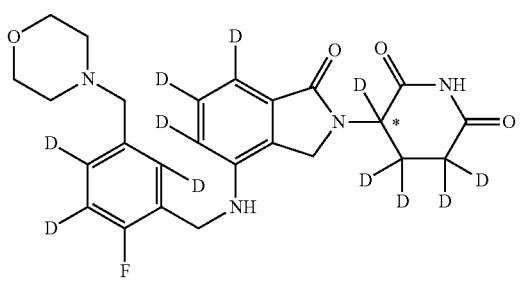
A1219
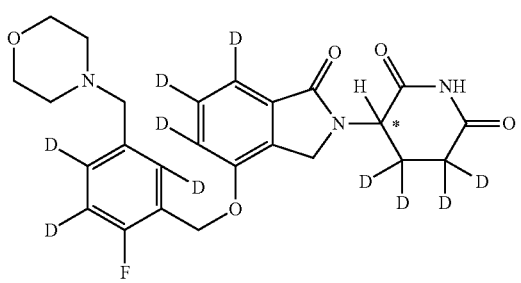
A1220
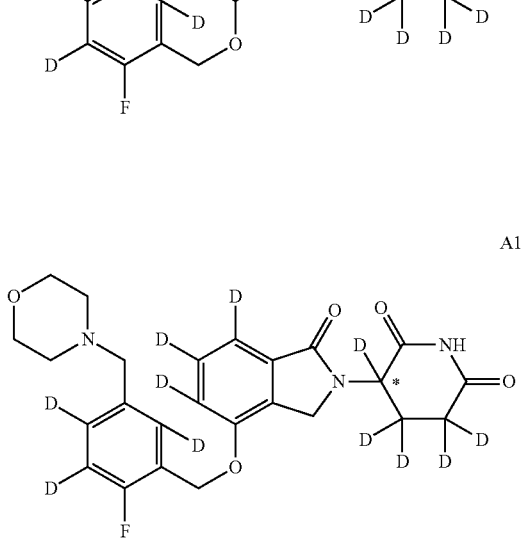
A1221
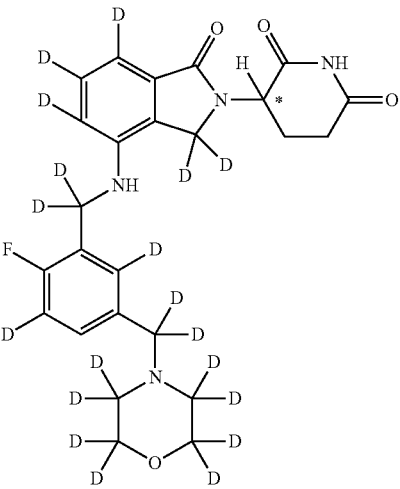
A1222
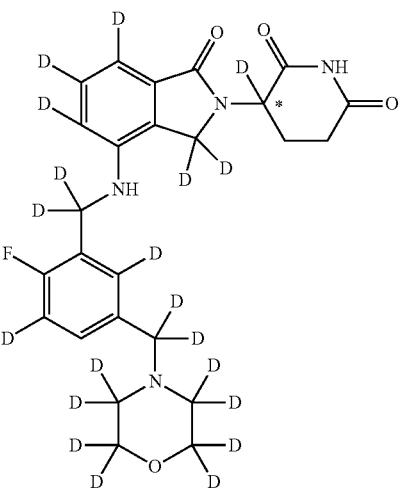
A1223
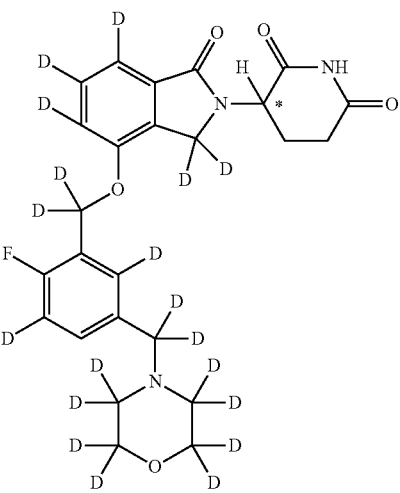

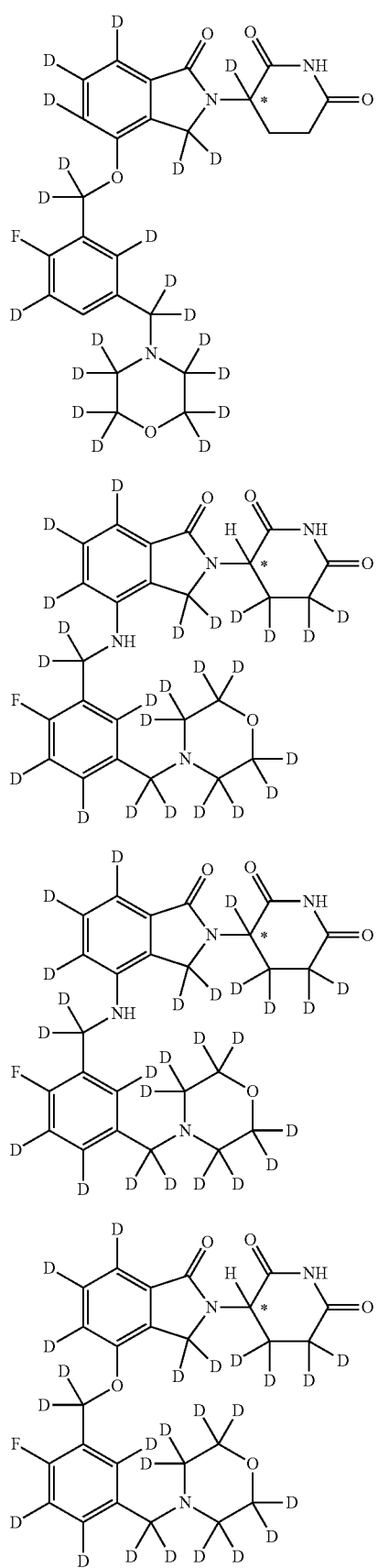
A1224
A1225
A1226
A1227
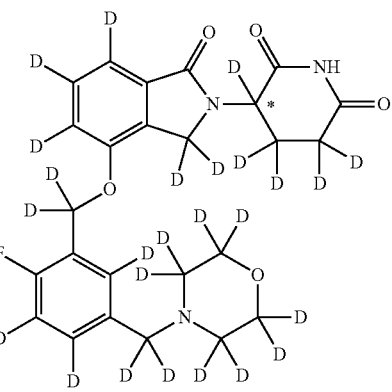
A1228
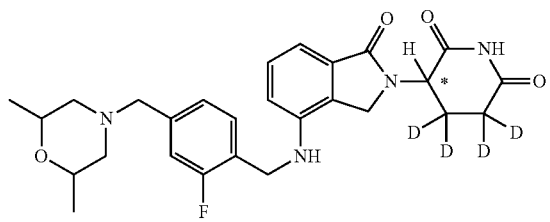
A1278
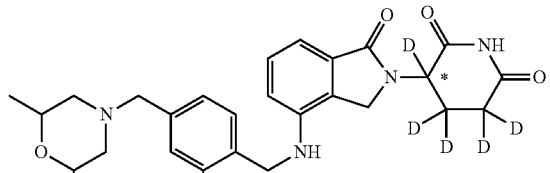
A1279
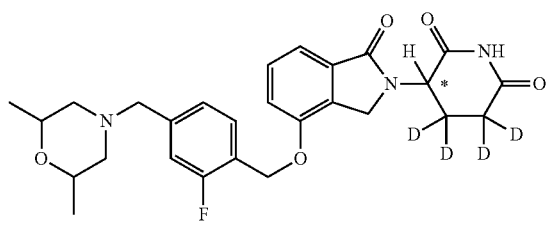
A1280
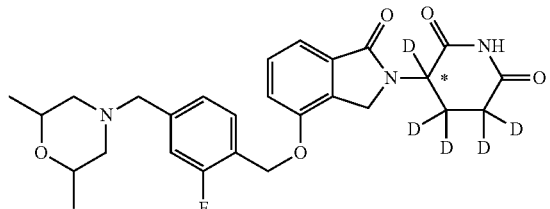
A1281
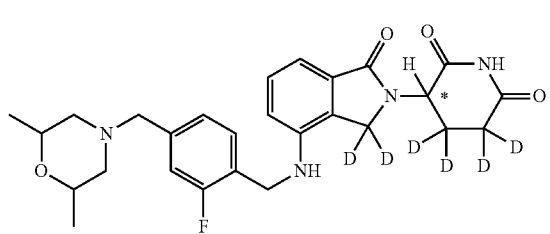
A1282

169
-continued

A1283

A1284

A1285

A1286

A1287

A1288

170
-continued

A1289

A1290

A1291

A1292

A1293

A1294

A1295
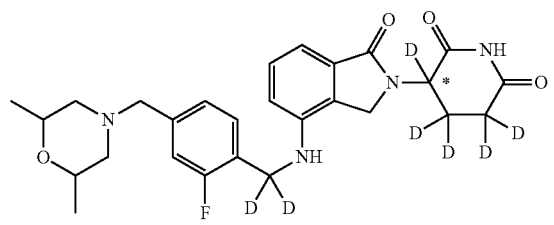
A1296
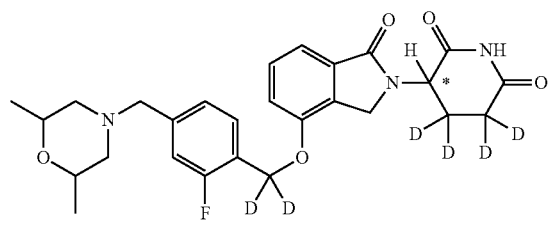
A1297
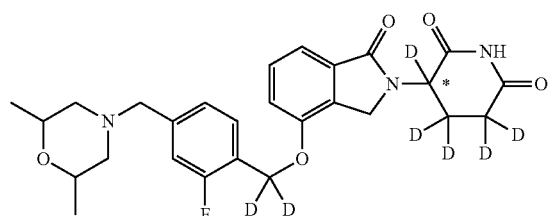
A1298
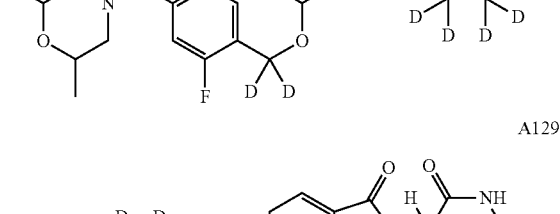
A1299
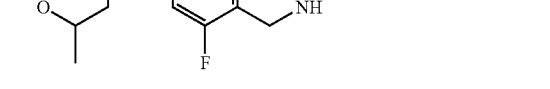
A1300
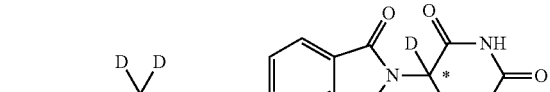
A1301
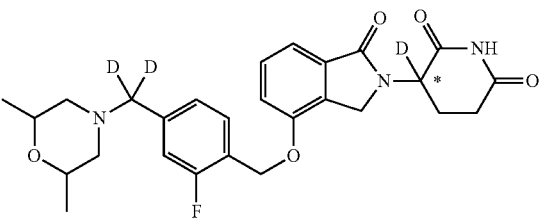
A1302
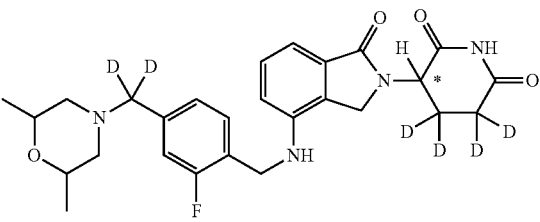
A1303
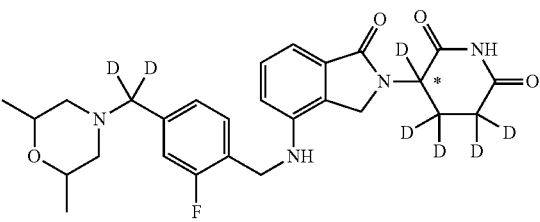
A1304
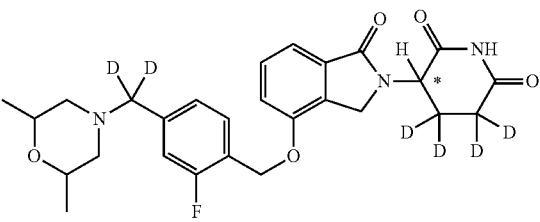
A1305
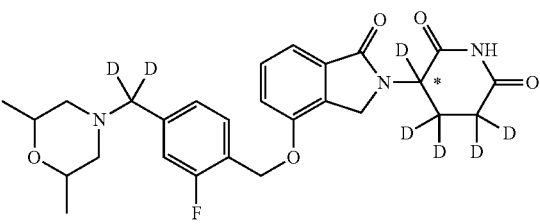
A1306
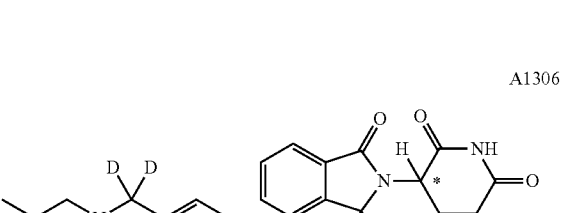

A1307
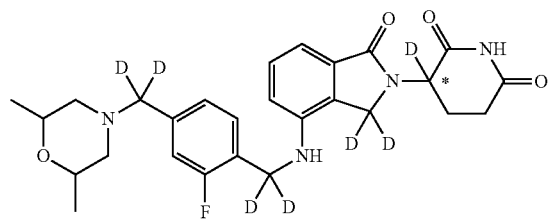
A1308
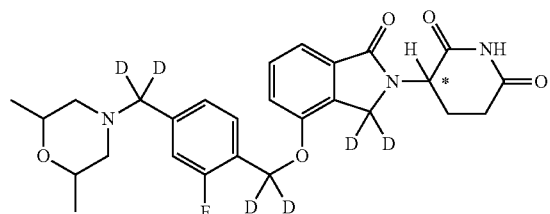
A1309
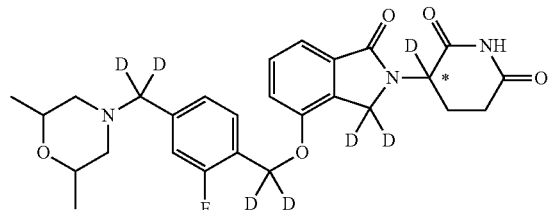
A1310
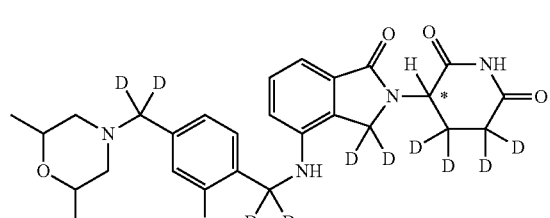
A1311
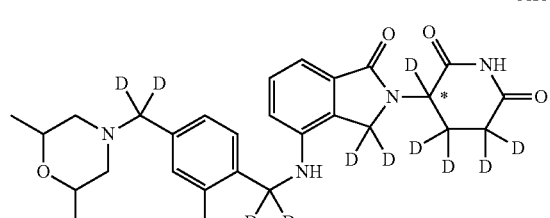
A1312
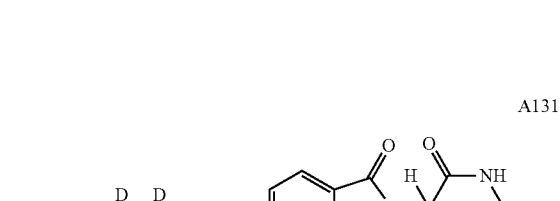
A1313
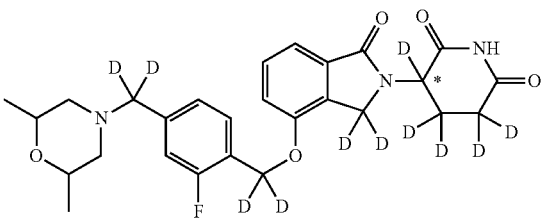
A1314
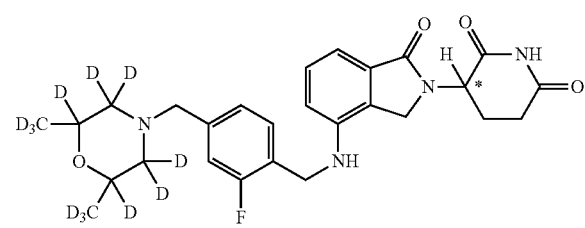
A1315
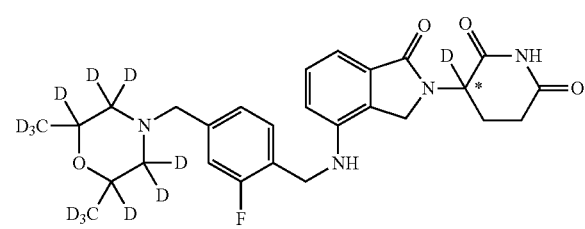
A1316
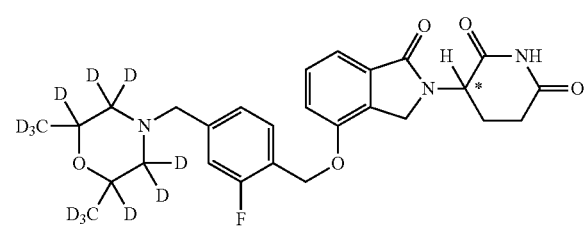
A1317
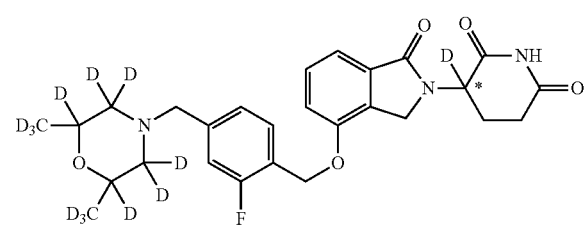
A1318
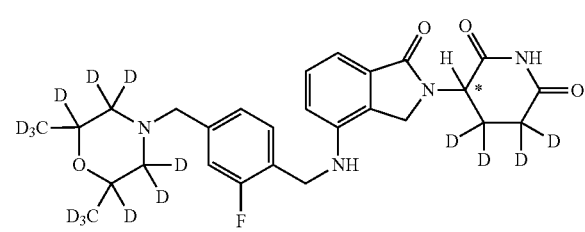

A1319
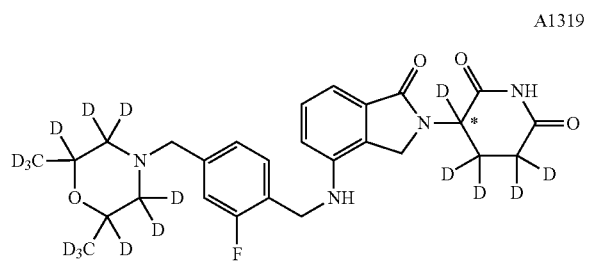
A1320
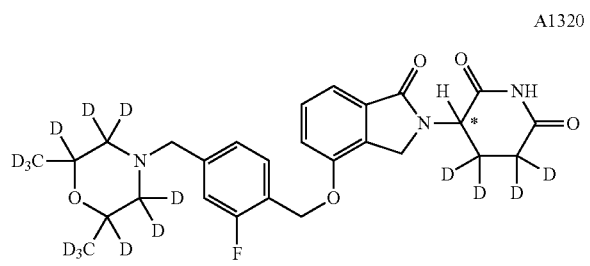
A1321
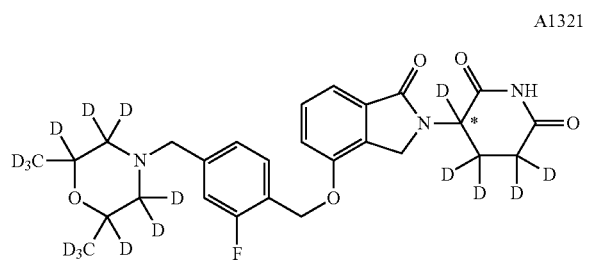
A1322
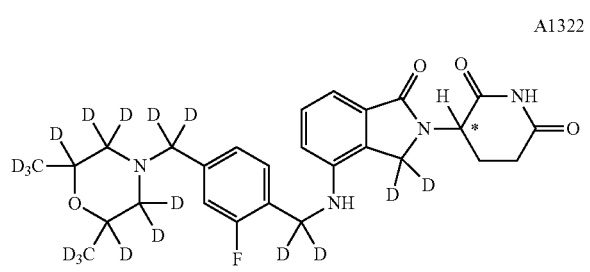
A1323
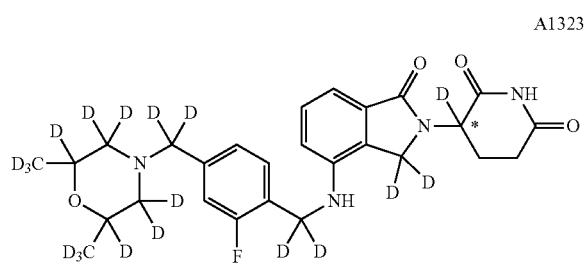
A1324
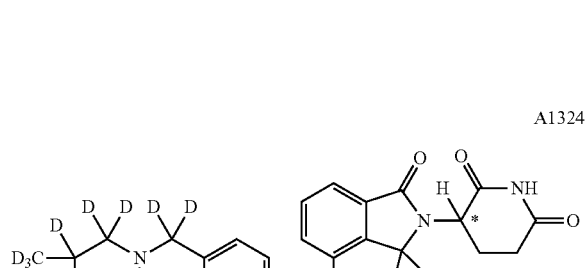
A1325
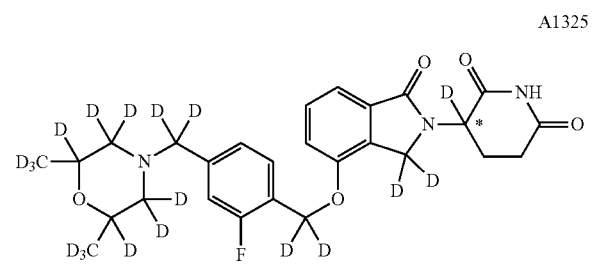
A1326
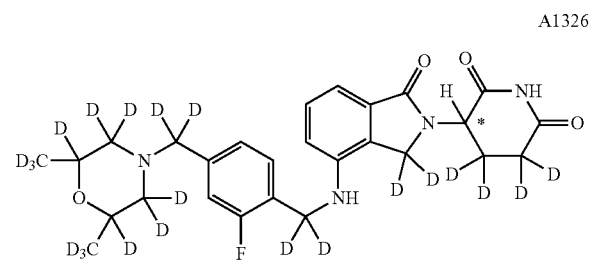
A1327
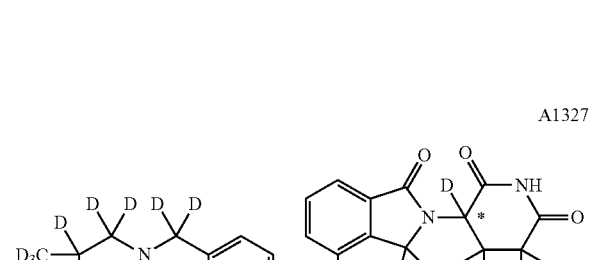
A1328
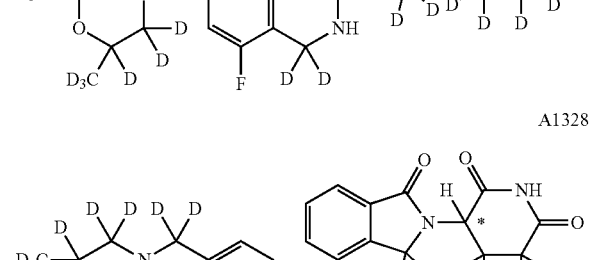
A1329
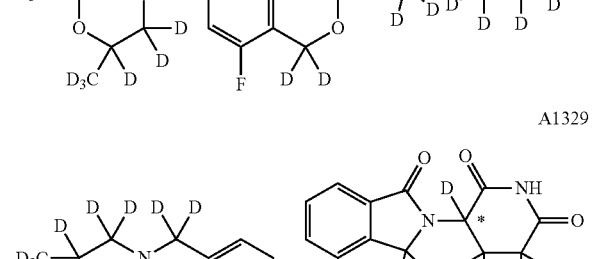
A1381
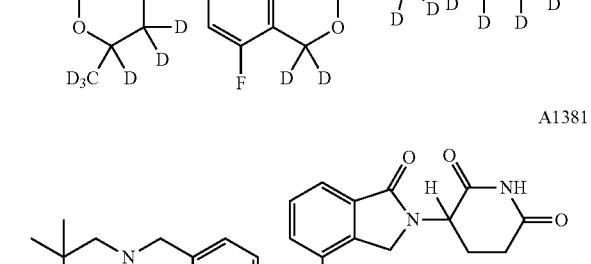

A1382
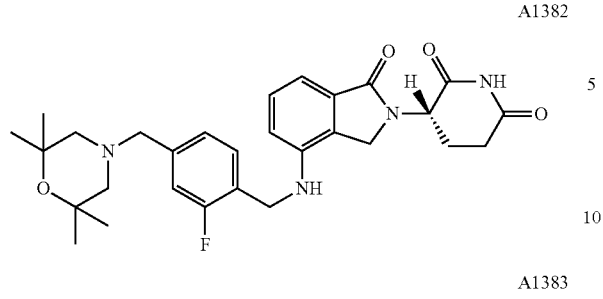
A1383
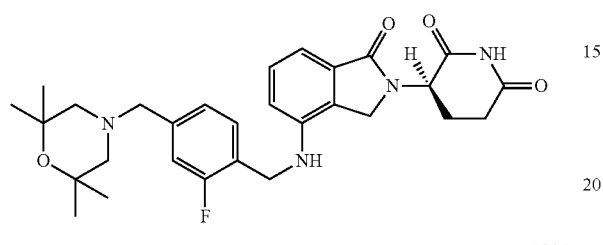
A1384
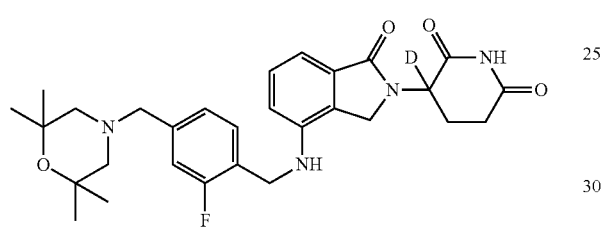
A1385
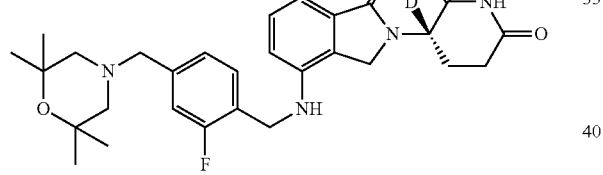
A1386
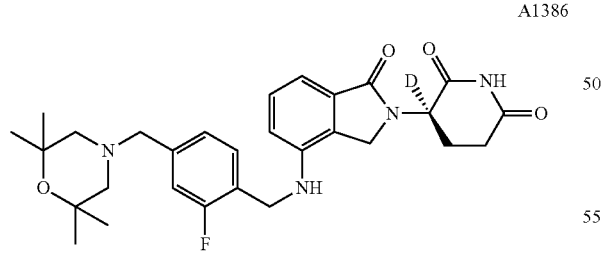
A1387
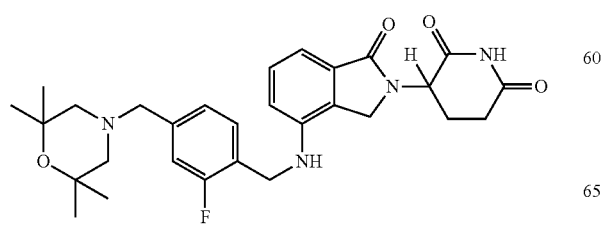
A1388
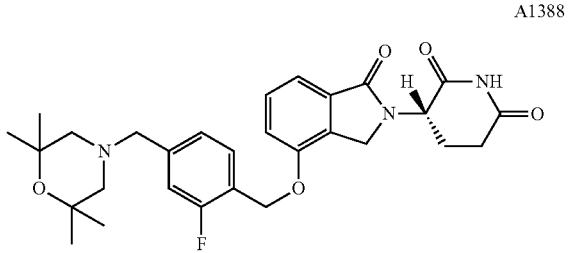
A1389
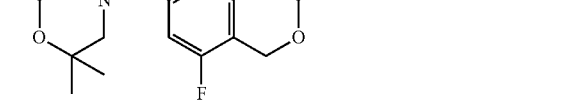
A1390
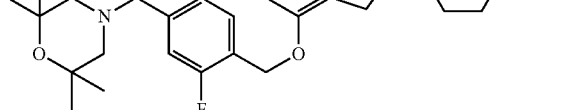
A1391
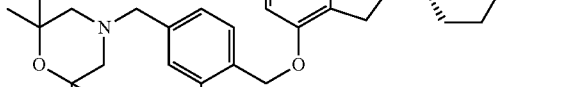
A1392
A1393
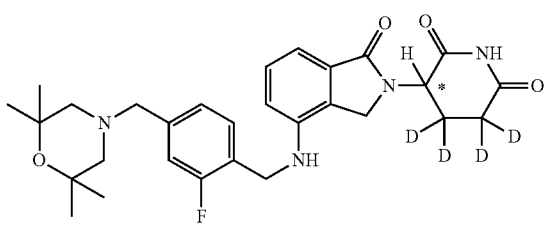

A1394
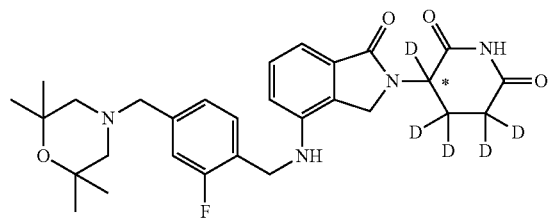
A1395
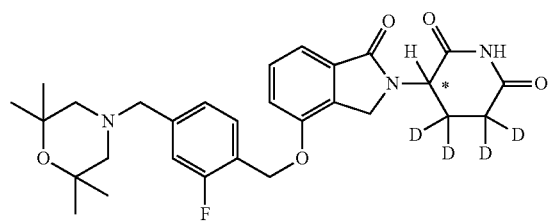
A1396
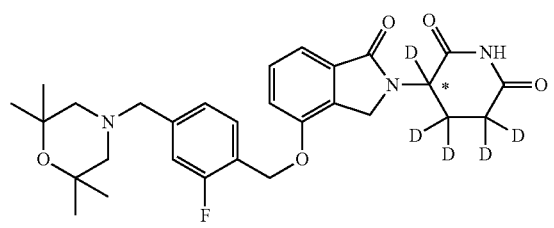
A1397
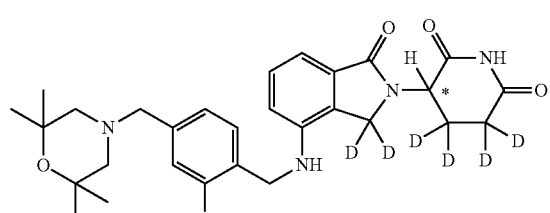
A1398
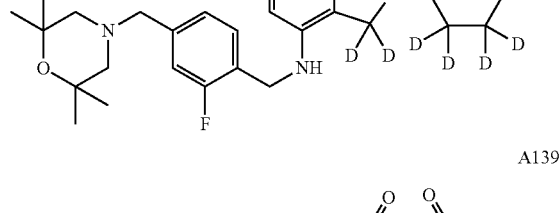
A1399
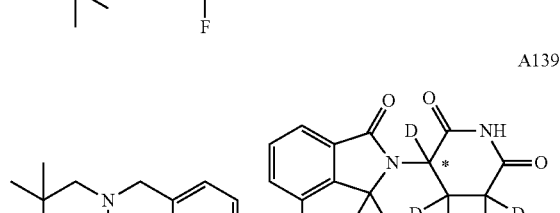
A1440
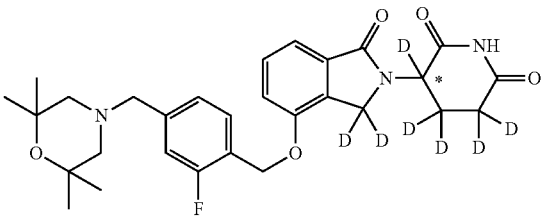
A1441
A1442
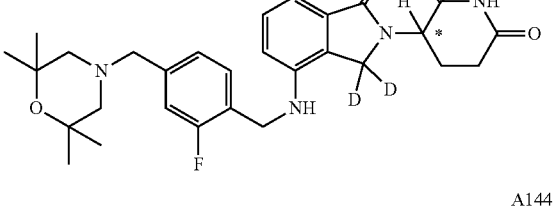
A1443
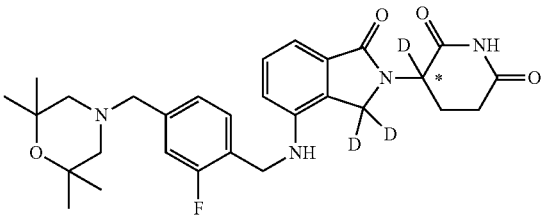
A1444
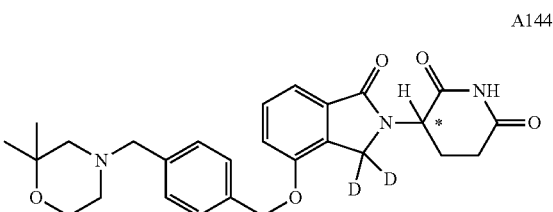
A1445
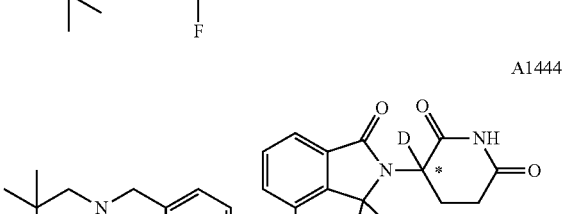

A1446
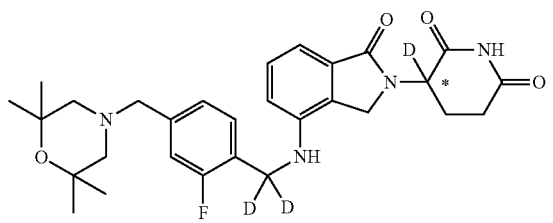
A1447
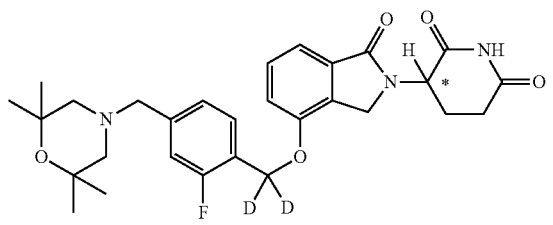
A1448
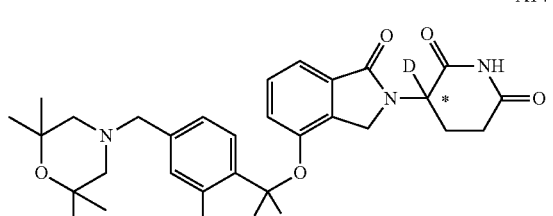
A1449

A1450
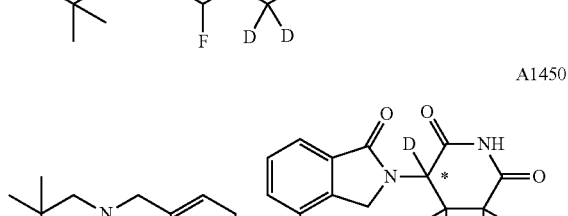
A1451

A1452
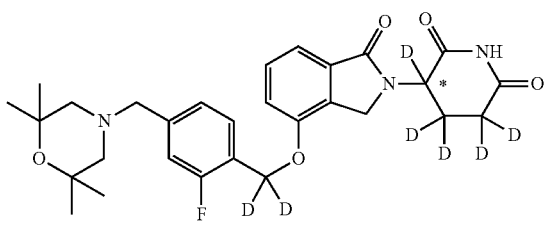
A1453
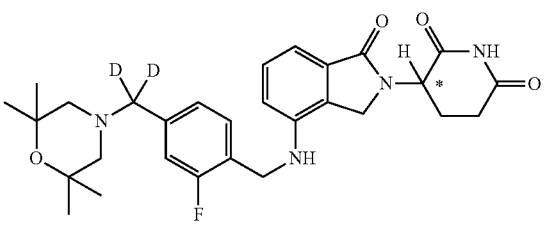
A1454
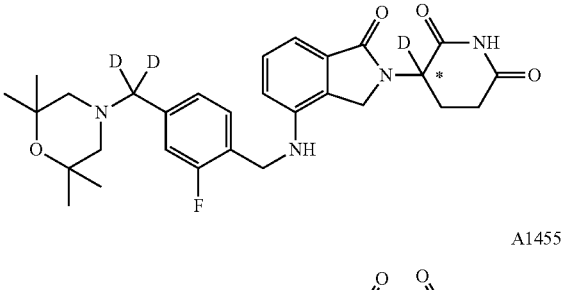
A1455
A1456
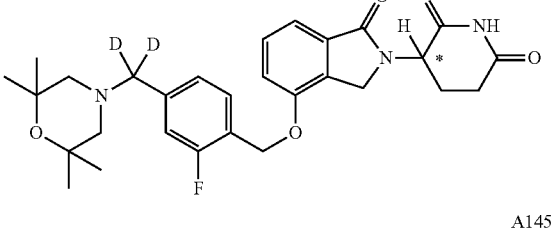
A1457
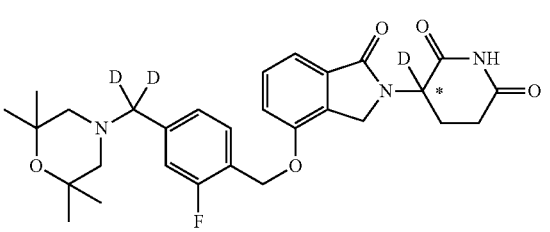

A1458
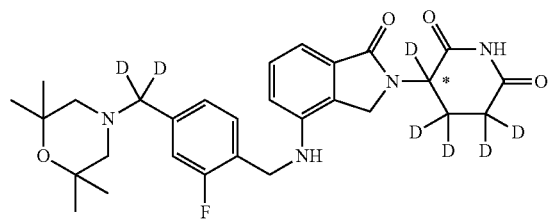
A1459
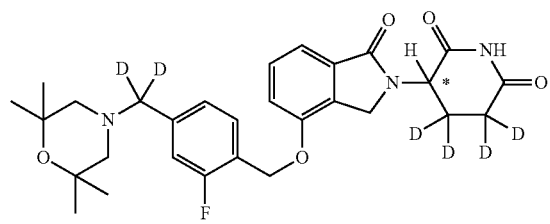
A1460
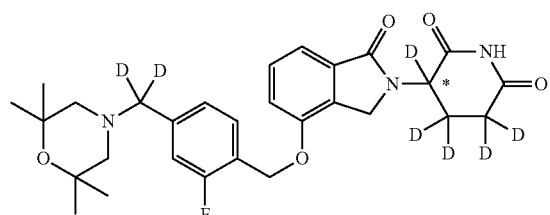
A1461
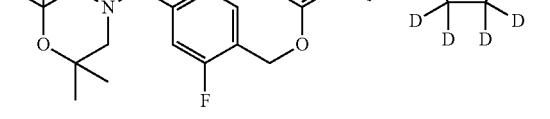
A1462
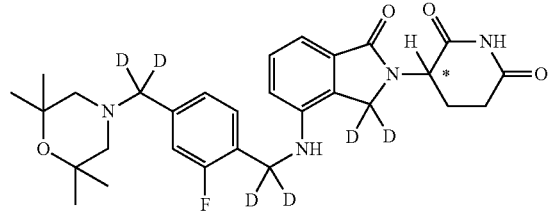
A1463
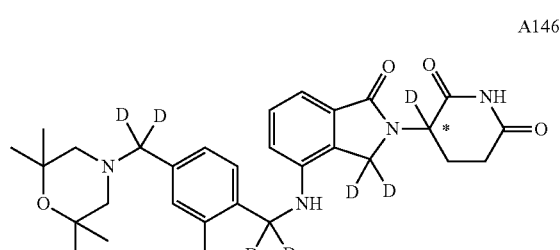
A1464
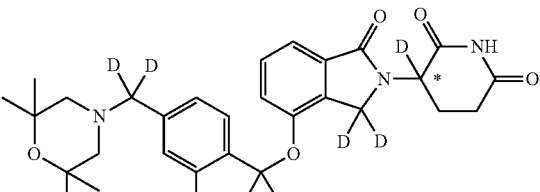
A1465
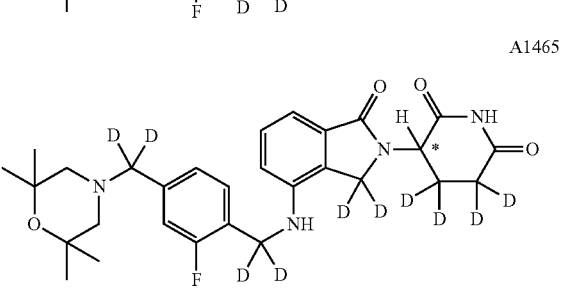
A1466
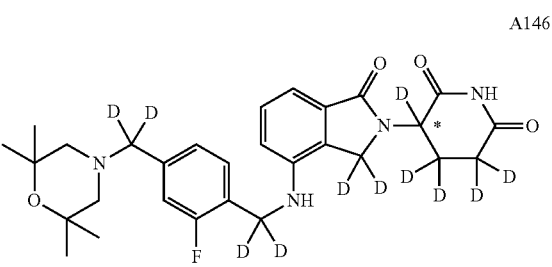
A1467
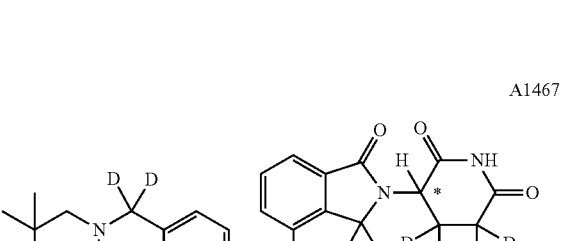
A1468
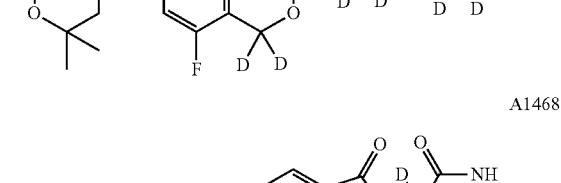
A1469
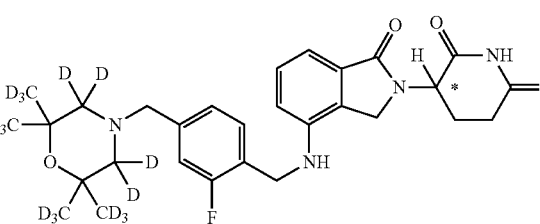

185
-continued

A1470

A1471

A1472

A1473

A1474

A1475

186
-continued

A1476

A1477

A1478

A1479

A1480

A1481

A1482
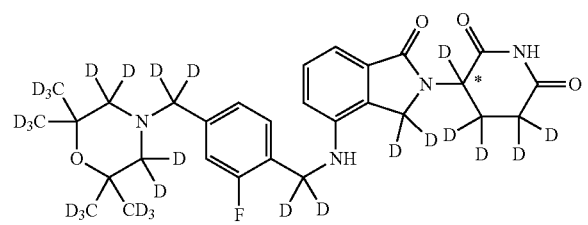
A1483
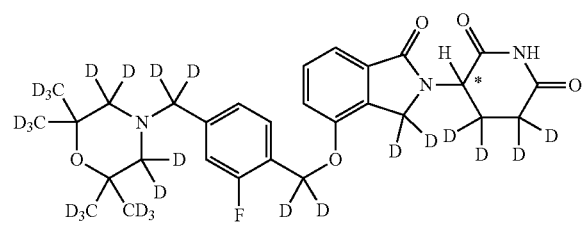
A1484
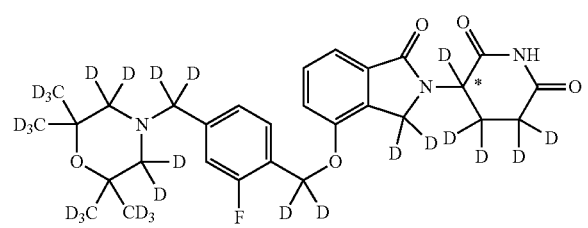
A1536
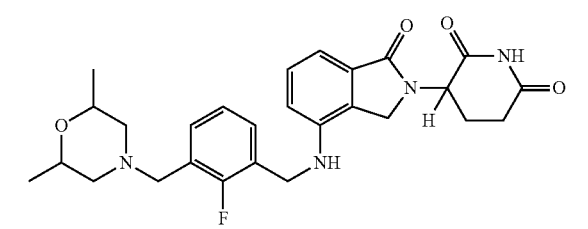
A1537
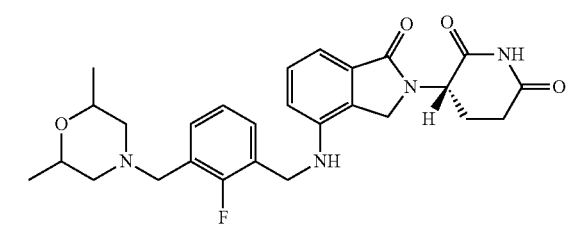
A1538
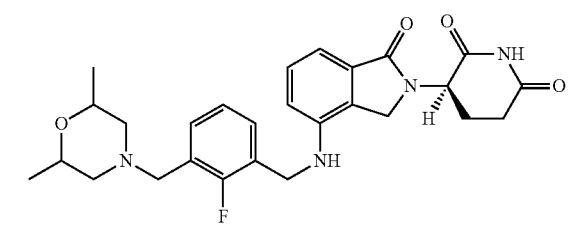
A1539
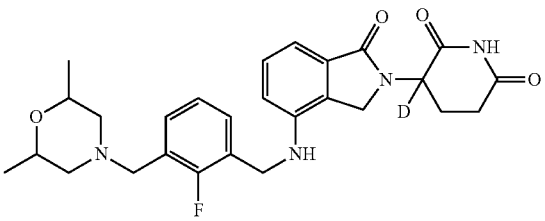
A1540
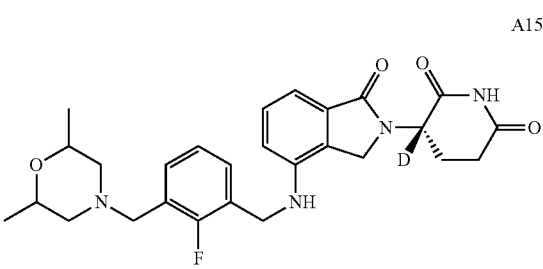
A1541
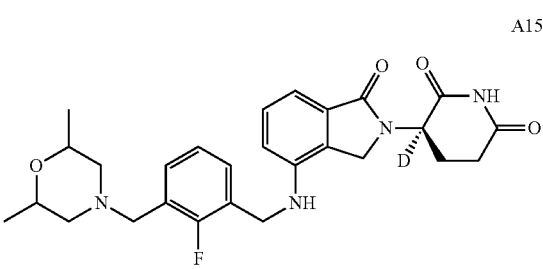
A1542
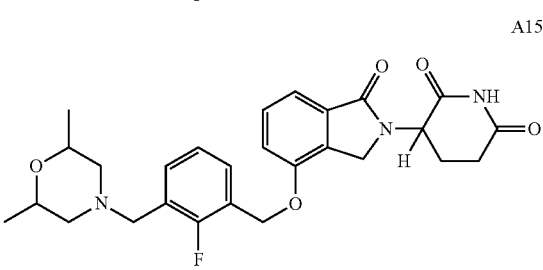
A1543
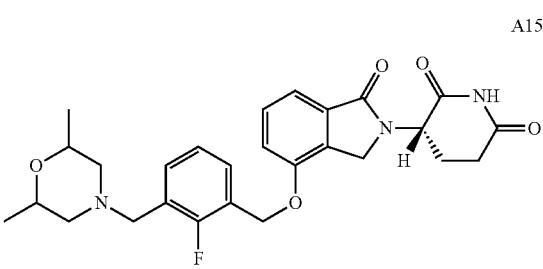
A1544
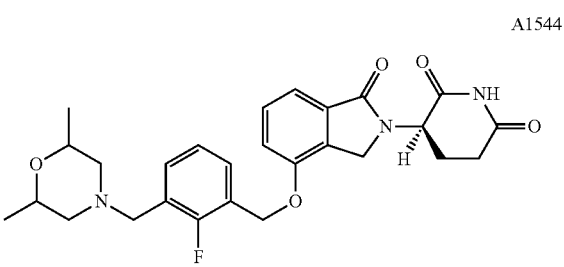

A1545
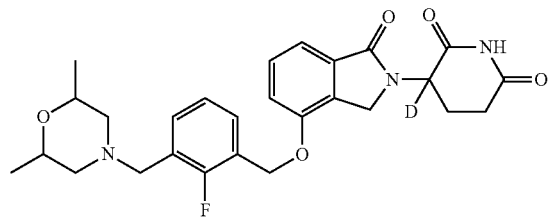
A1546
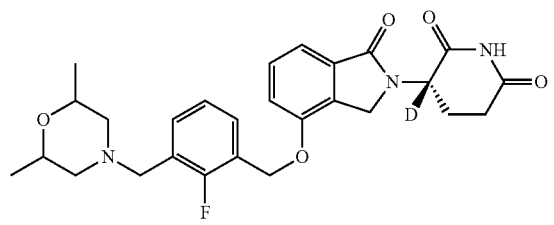
A1547
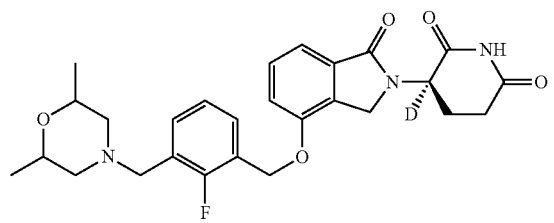
A1548
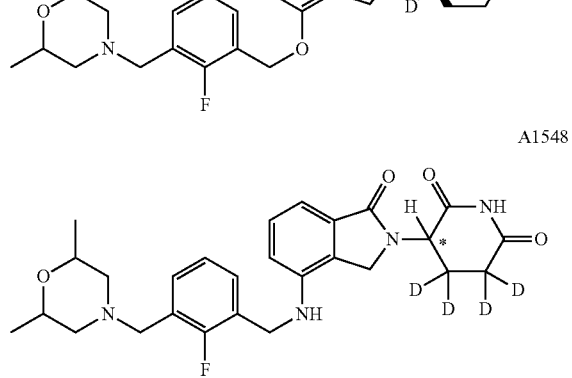
A1549
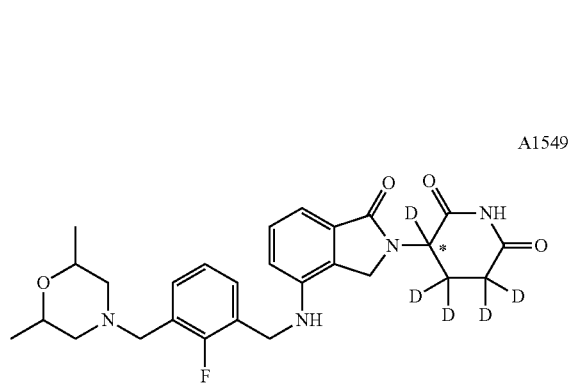
A1550
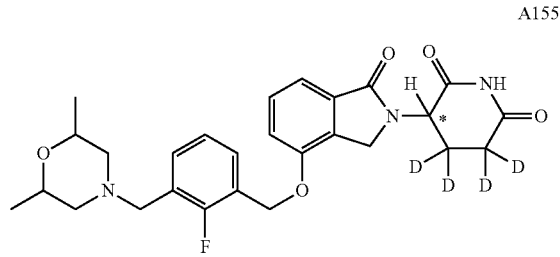
A1551
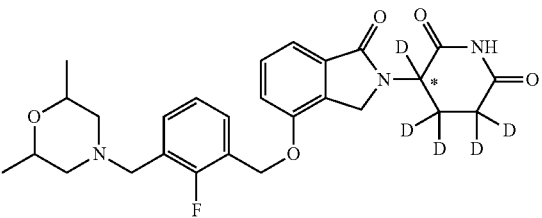
A1552
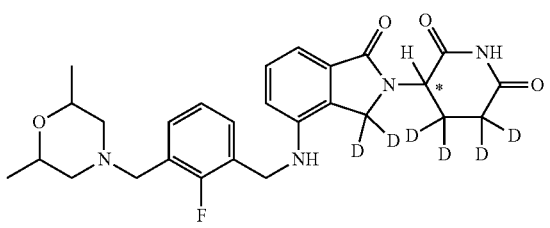
A1553
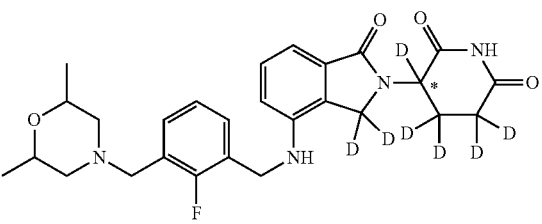
A1554
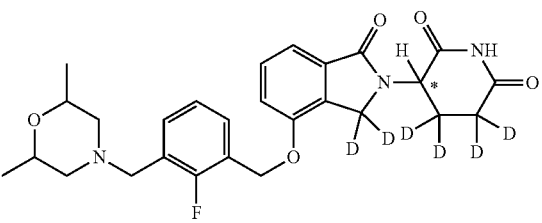
A1555
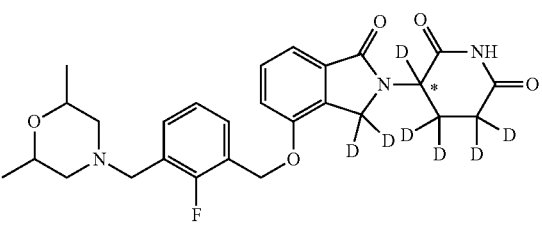
A1556
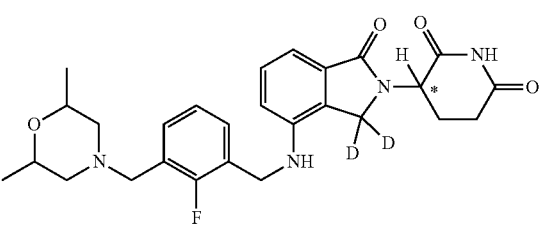

A1557

A1558
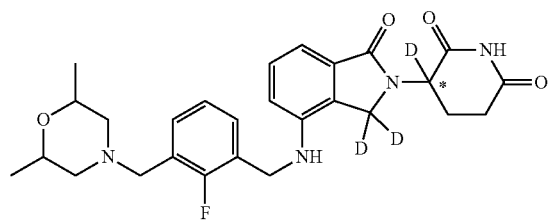
A1559

A1560
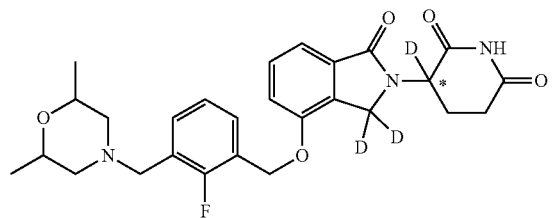
A1561
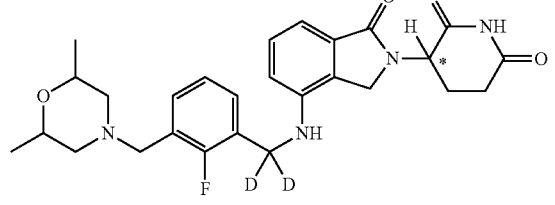
A1562
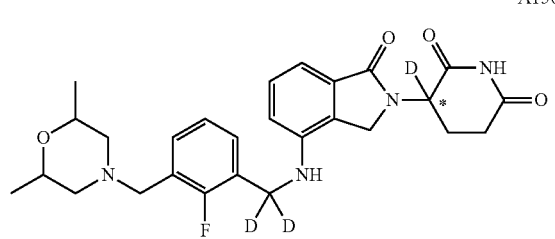
A1563

A1564
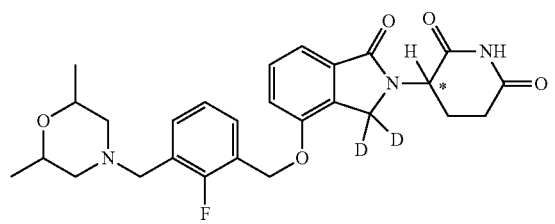
A1565

A1566
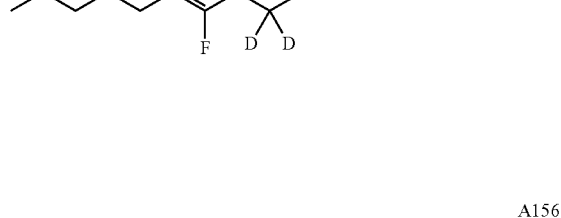
A1567
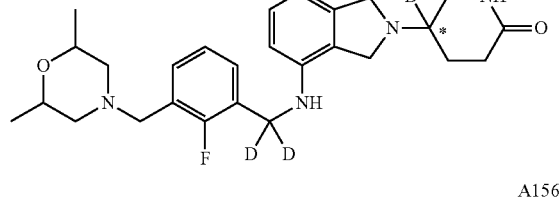
A1568
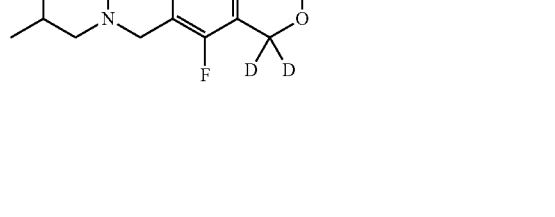

A1569
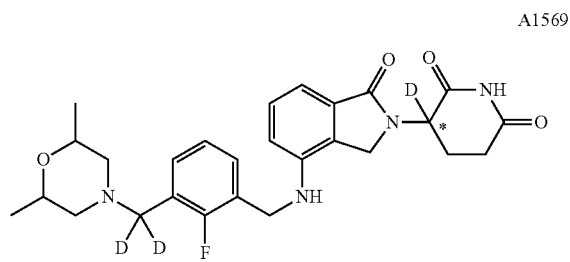
A1570
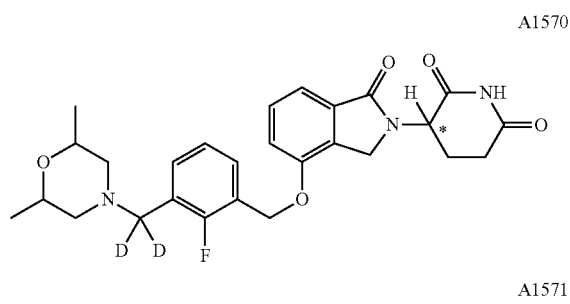
A1571
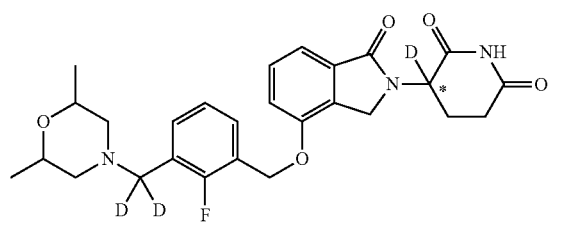
A1572
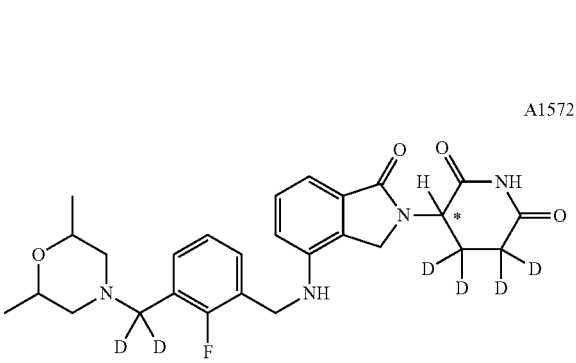
A1573
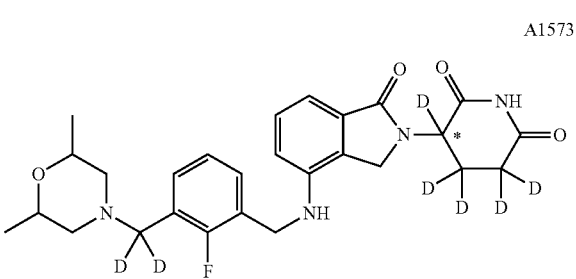
A1574
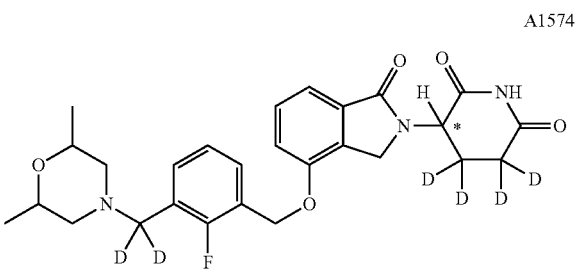
A1575
A1576
A1577
A1578
A1579
A1580
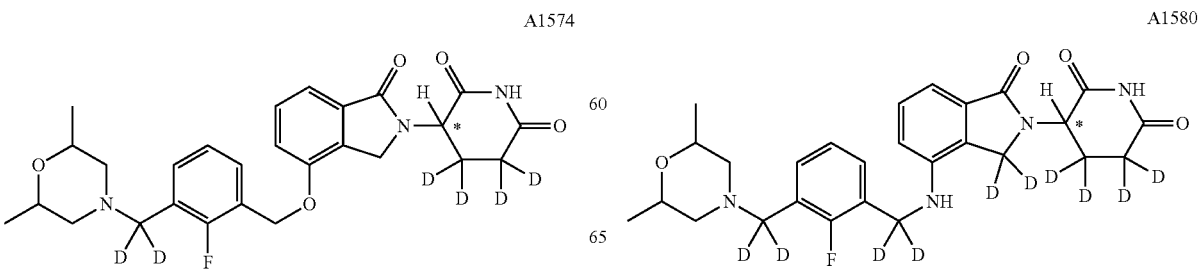

A1581
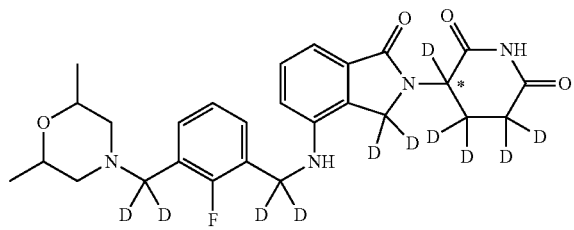
A1582
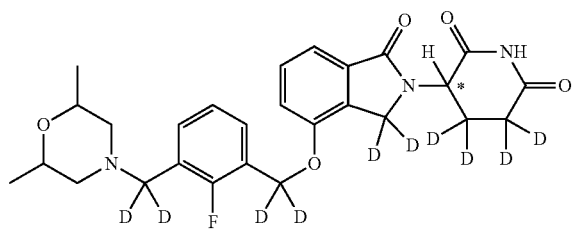
A1583
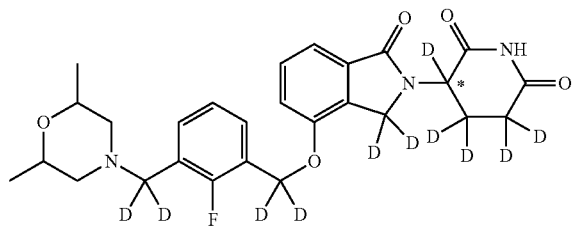
A1584
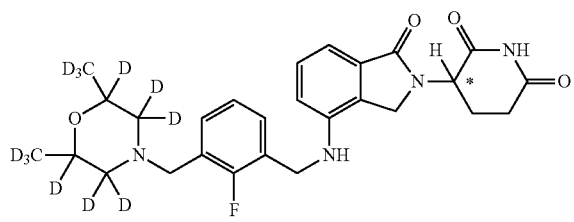
A1585
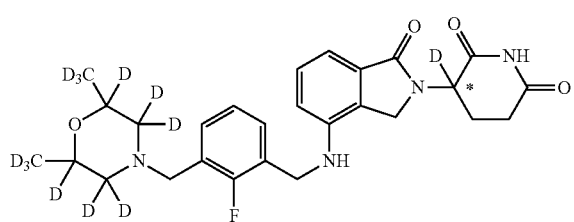
A1586

A1587
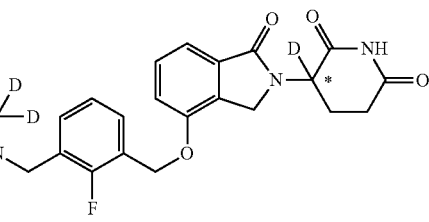
A1588
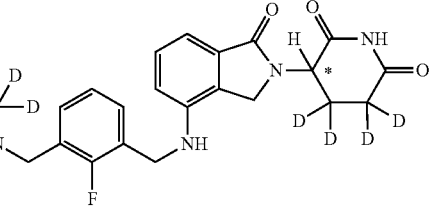
A1589
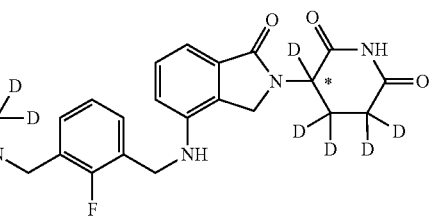
A1590
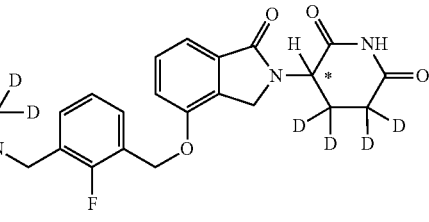
A1591
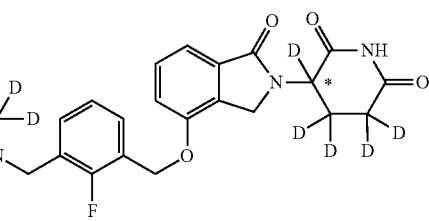
A1592
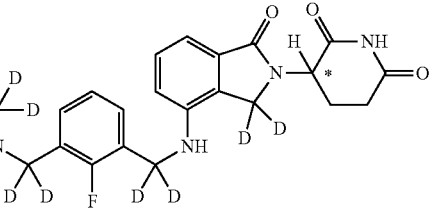

-continued

A1593

A1599

A1594

A1651

A1595

A1652

A1596

A1653

A1597

A1654

A1598

A1655

A1656
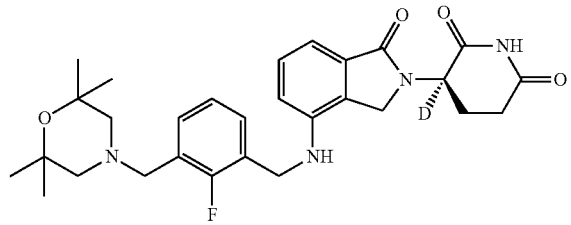
A1662
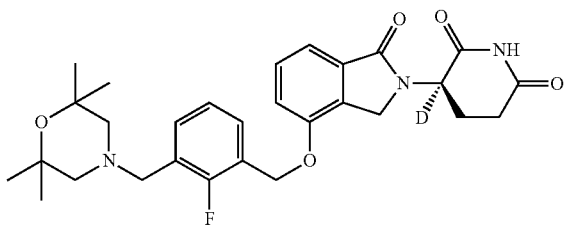
A1657
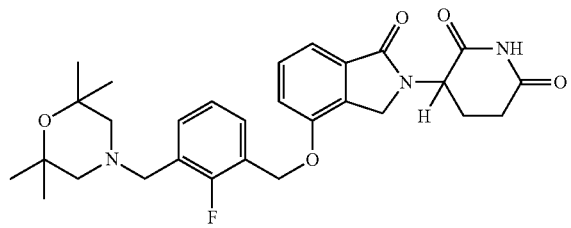
A1663
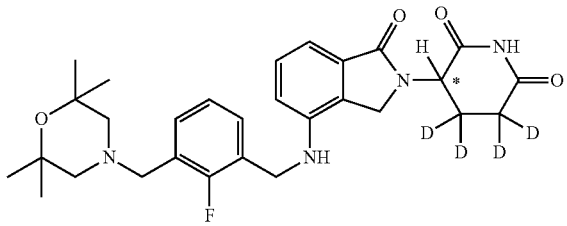
A1658
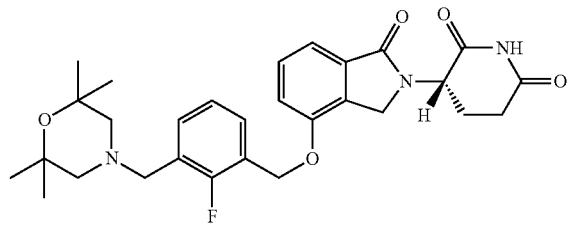
A1664
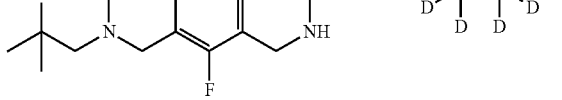
A1659
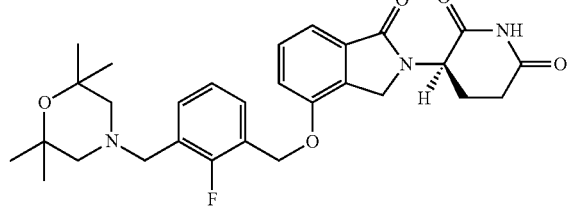
A1665
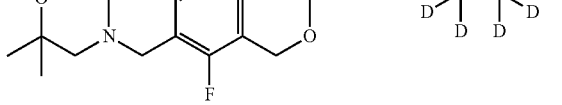
A1660
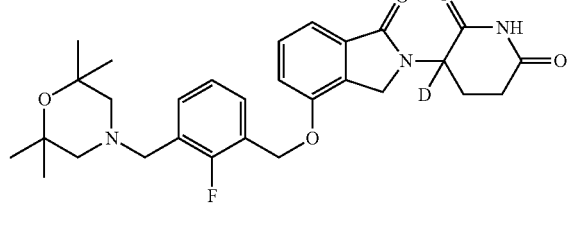
A1666
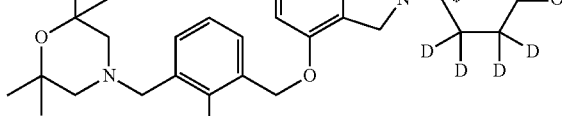
A1661
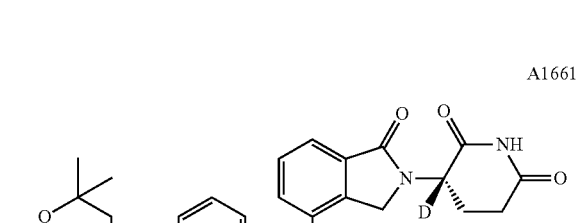
A1667
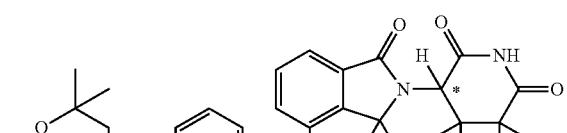
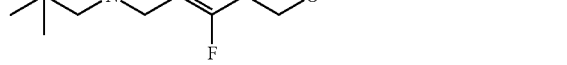

201
-continued
A1668
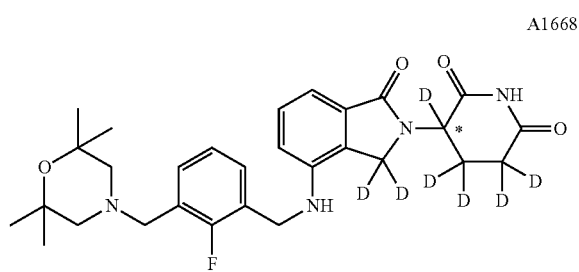
A1669
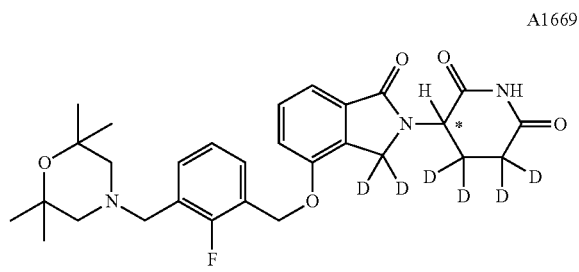
A1670
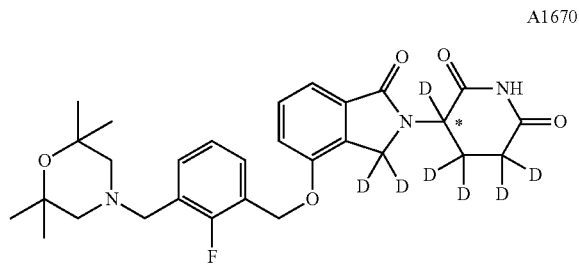
A1671
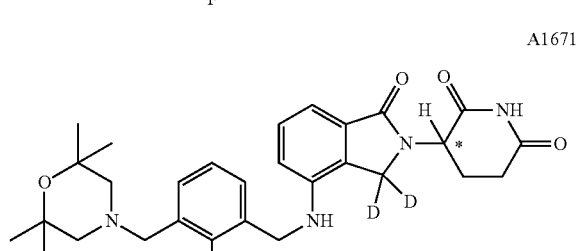
A1672
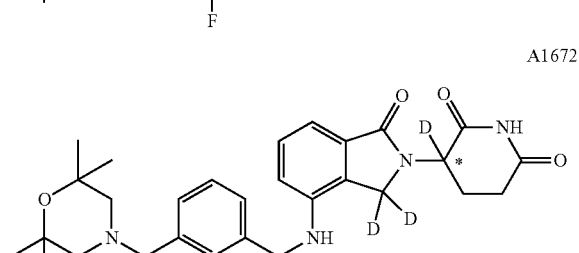
A1673
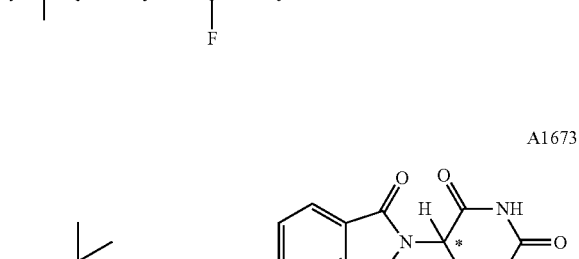
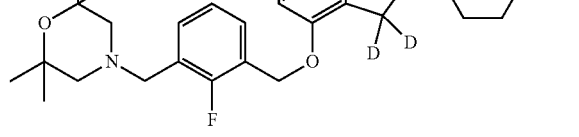
202
-continued
A1674
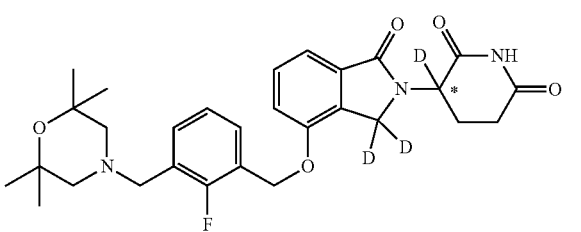
A1675
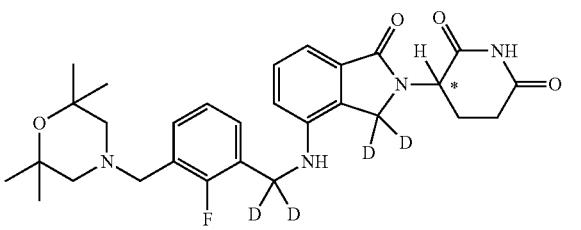
A1676
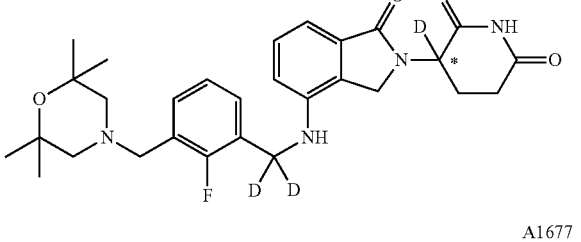
A1677
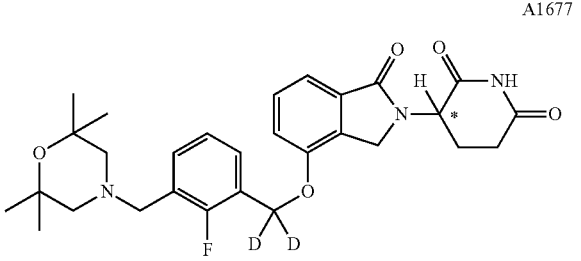
A1678
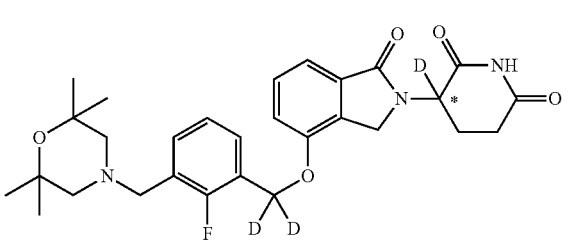
A1679

A1680
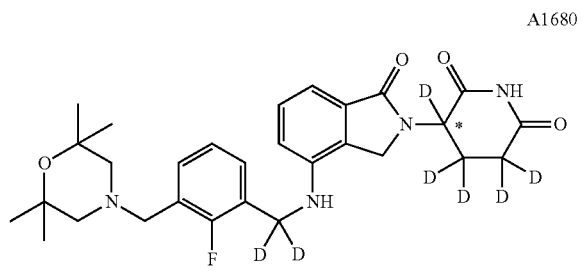
A1681
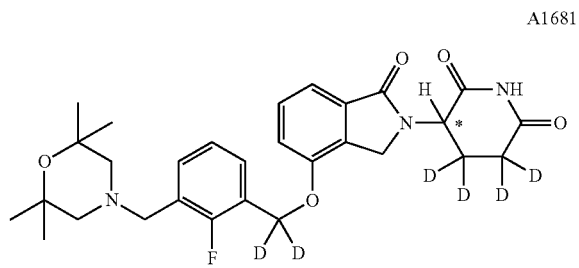
A1682
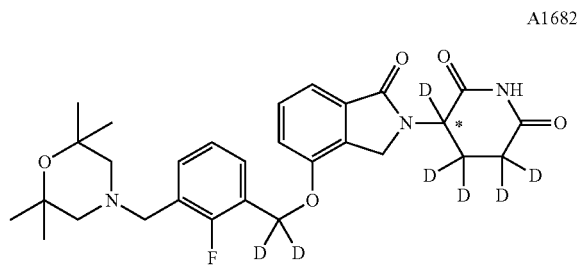
A1683

A1684
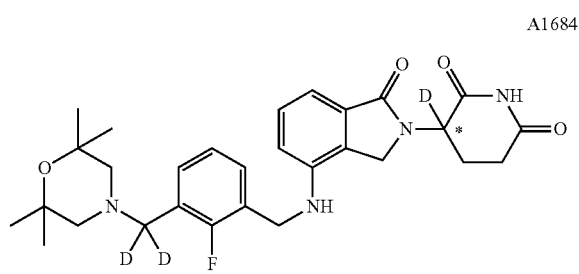
A1685
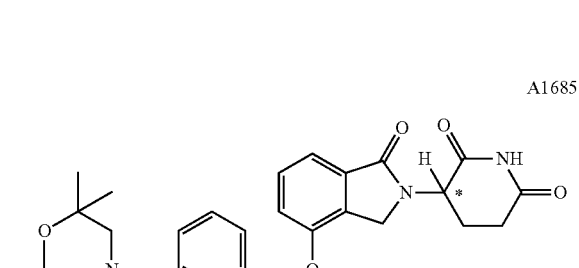
A1686

A1687
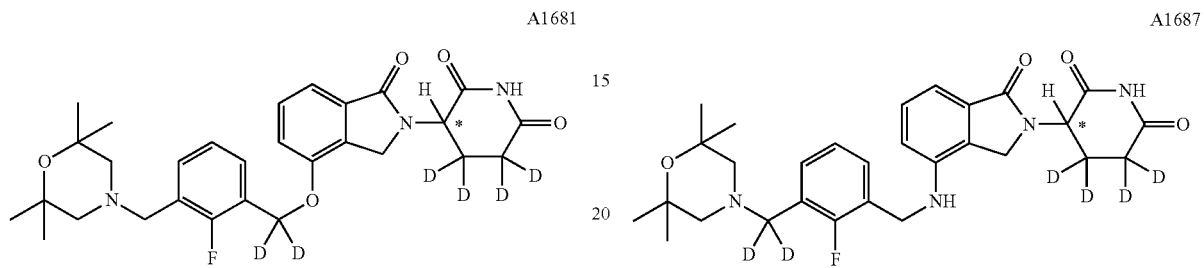
A1688

A1689
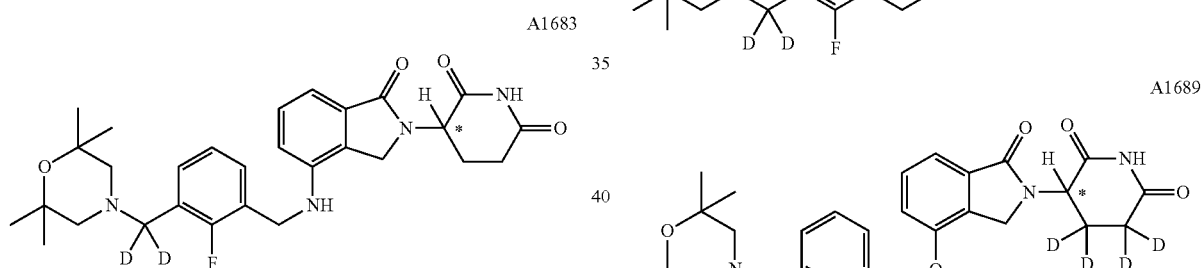
A1690
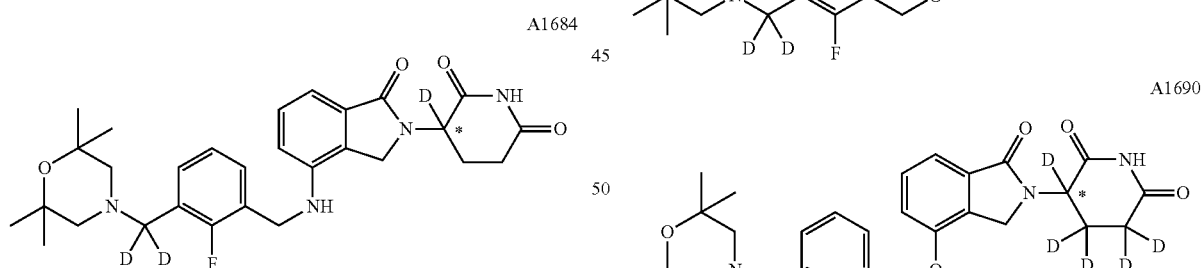
A1691
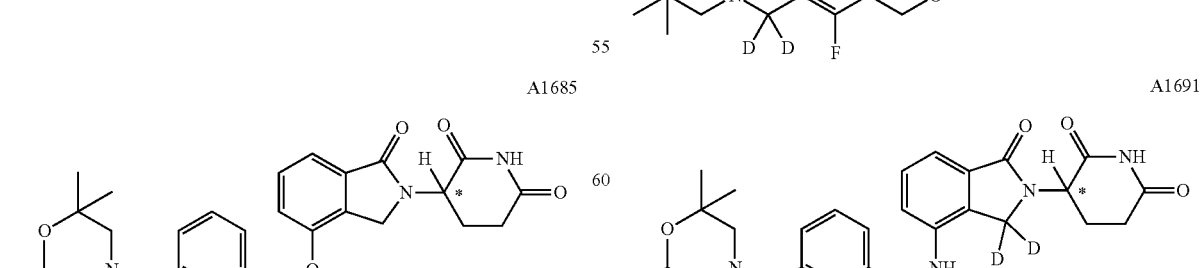

A1692
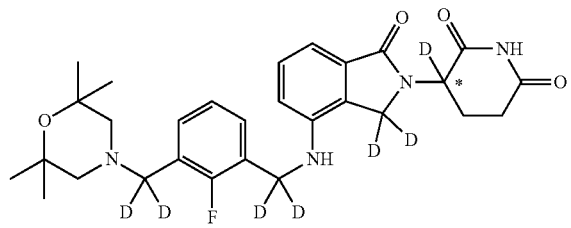
A1698
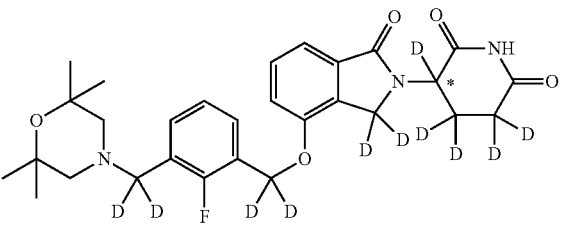
A1693
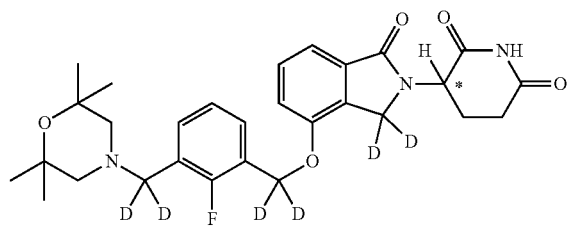
A1699
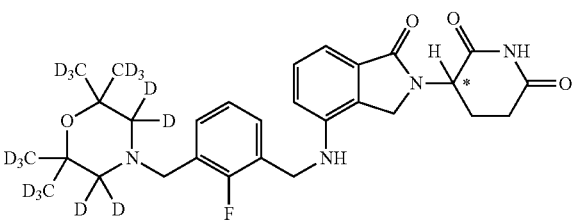
A1694
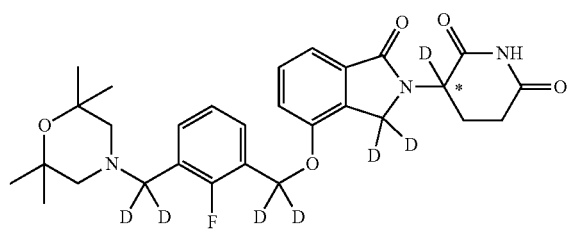
A1700
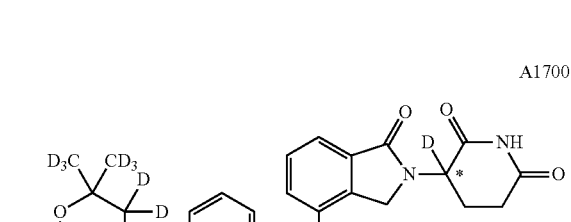
A1695
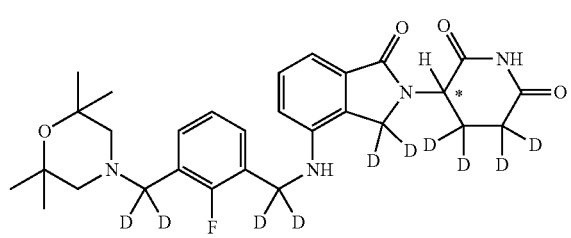
A1701
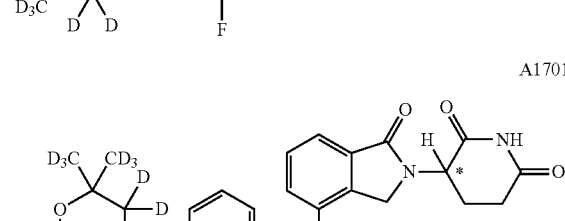
A1696
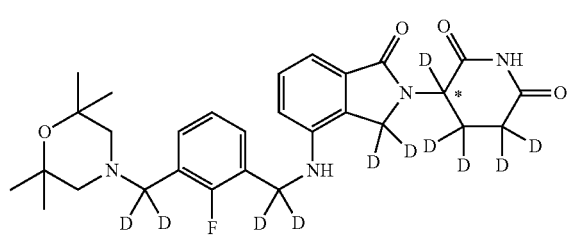
A1702
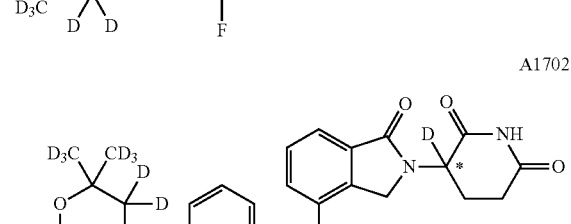
A1697
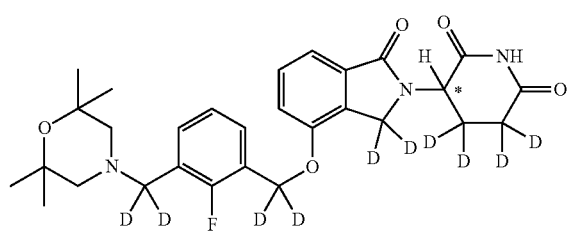
A1703
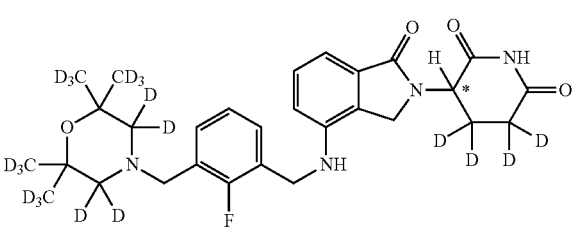

A1704
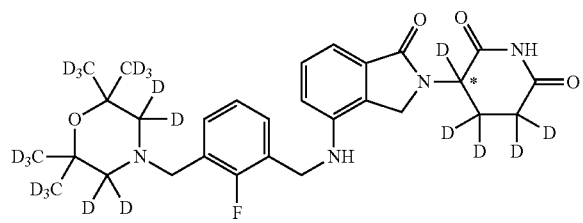
A1705
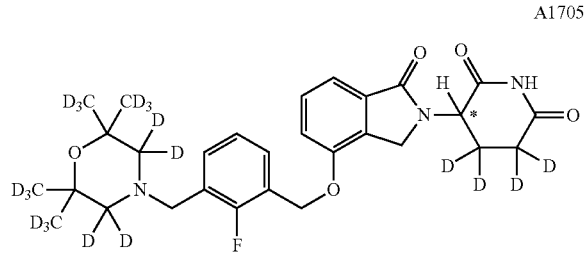
A1706

A1707
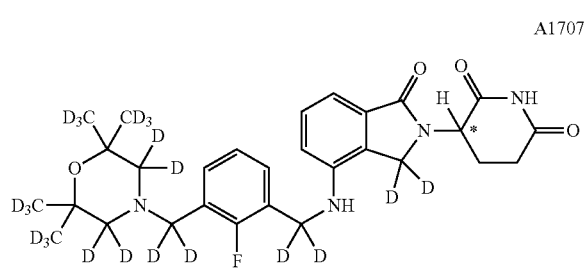
A1708

A1709
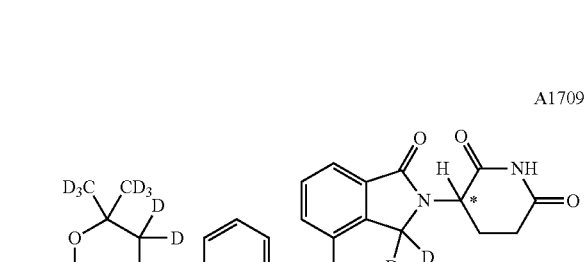
A1710
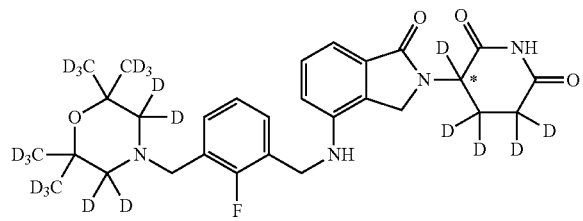
A1711
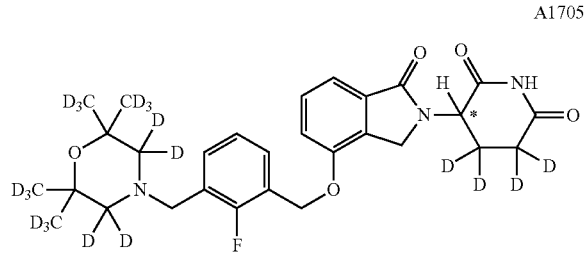
A1712
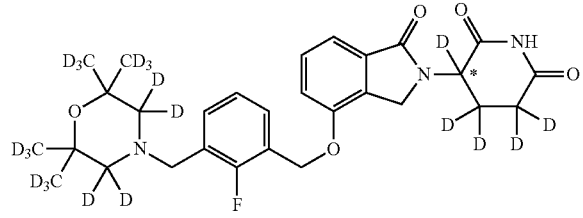
A1713
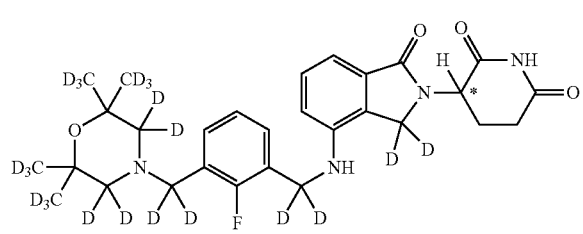
A1714
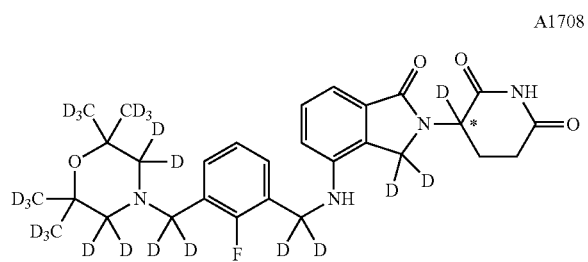
A1766
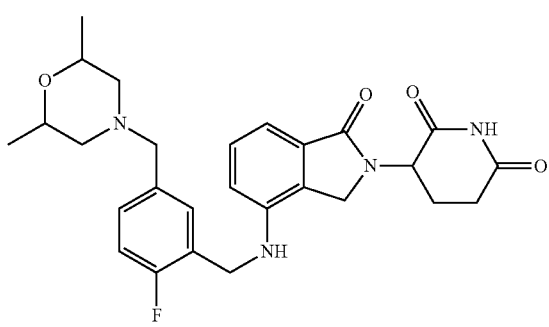

A1767
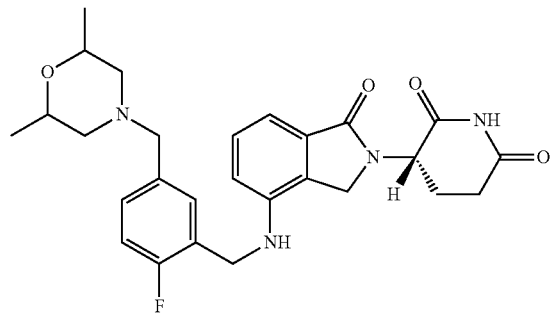
A1768
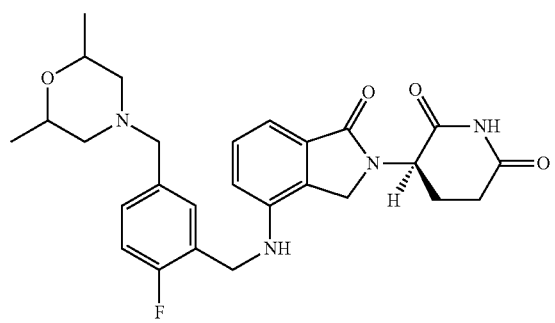
A1769
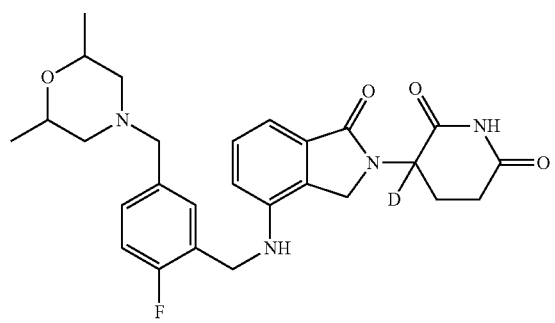
A1770
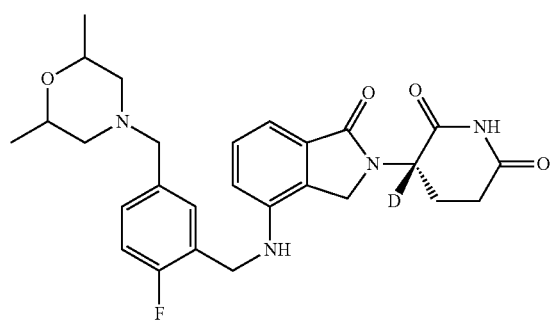
A1771
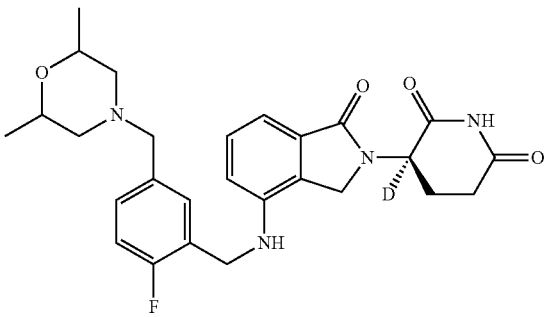
A1772
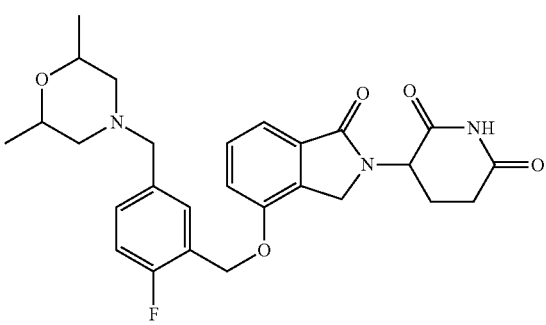
A1773
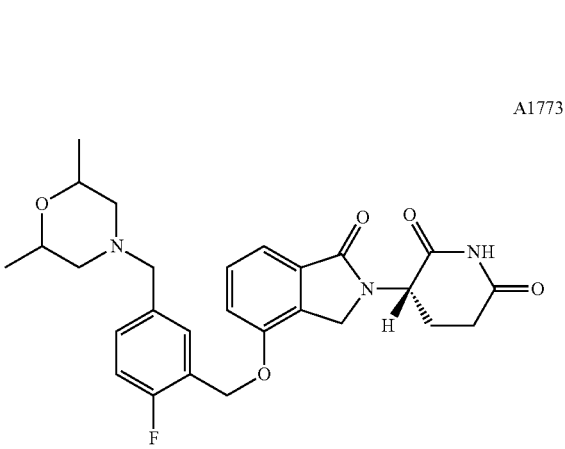
A1774
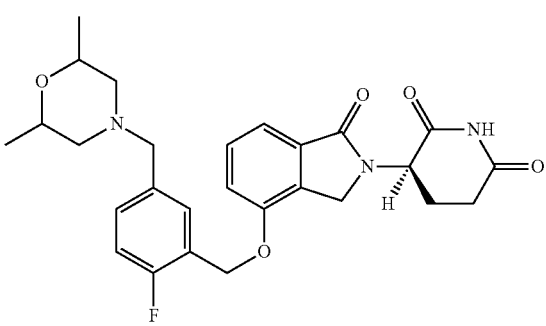

A1775
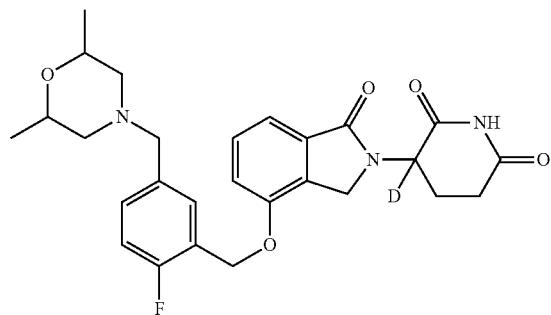
A1776
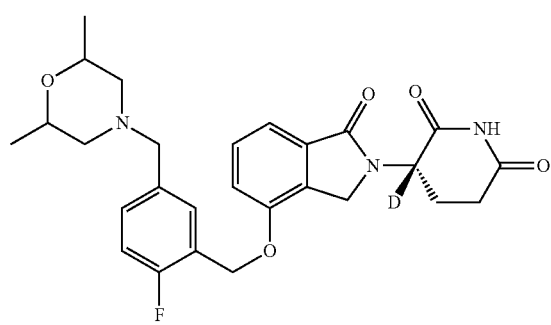
A1777
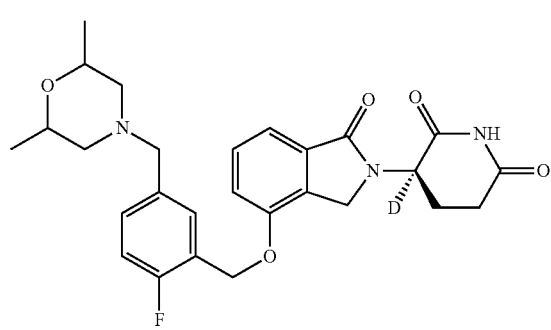
A1778
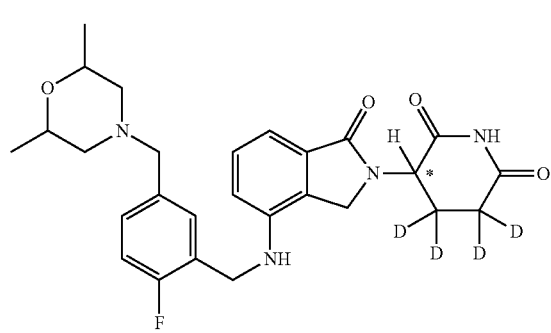
A1779
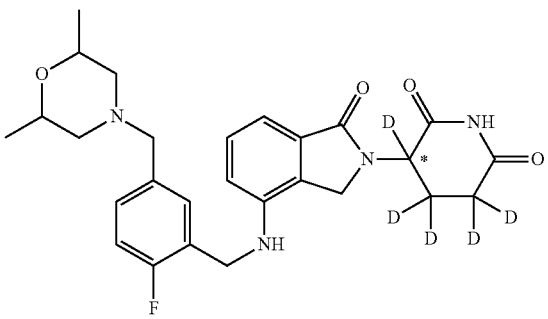
A1780
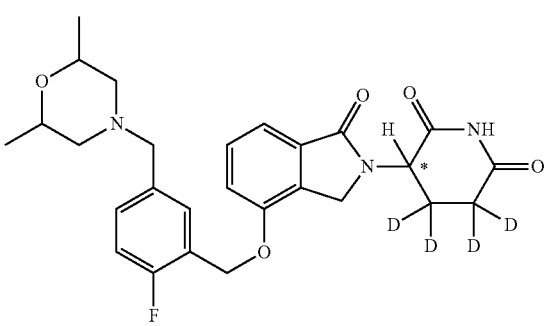
A1781
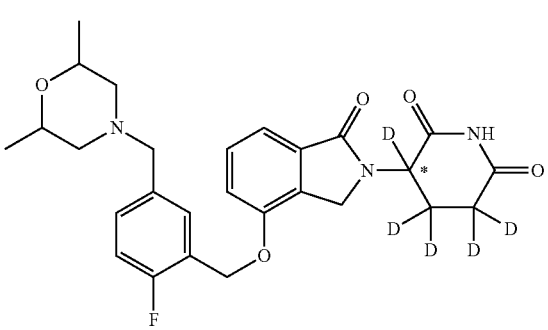
A1782
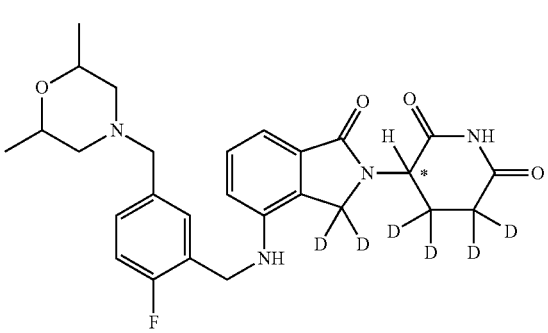

-continued
A1783
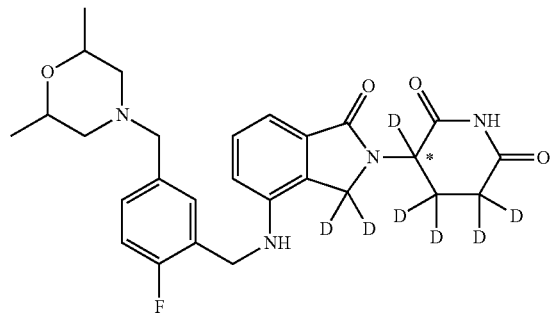
A1784
A1785
A1786
-continued
A1787
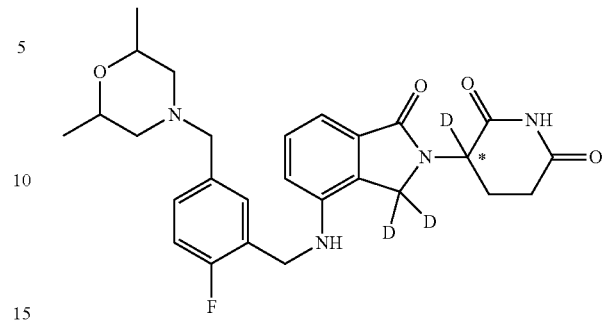
A1788
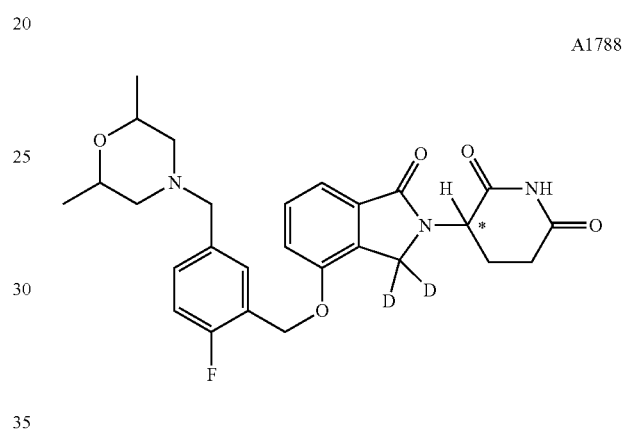
A1789
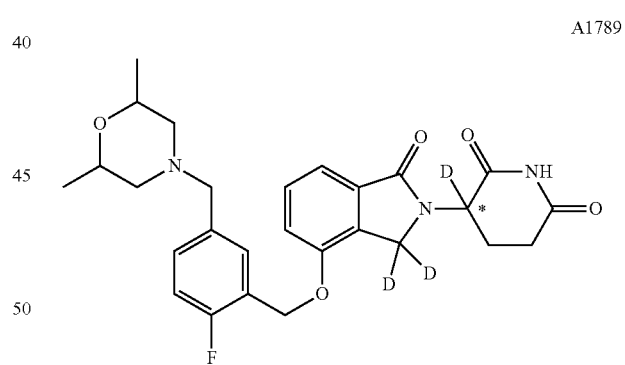
A1790
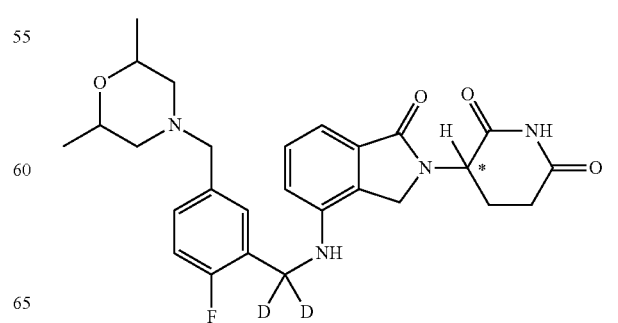

A1791
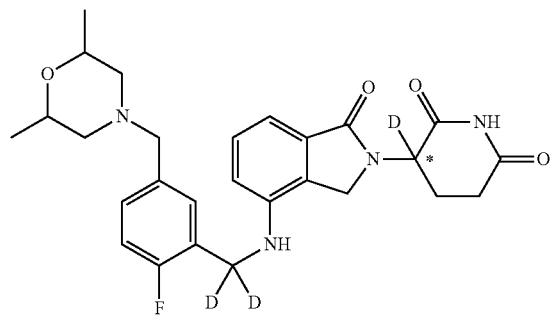
A1792
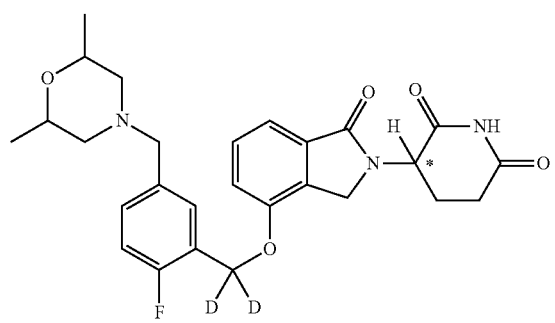
A1793
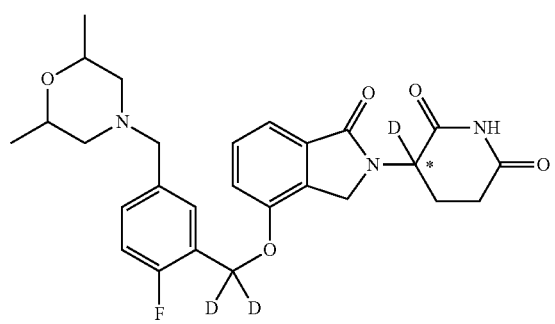
A1794
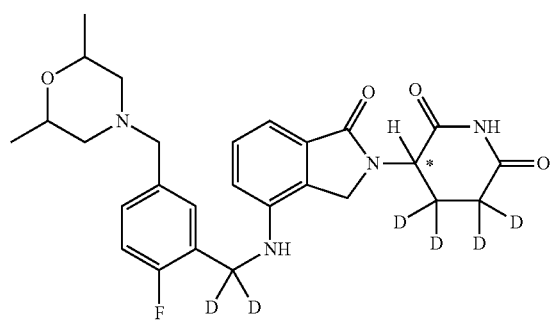
A1795
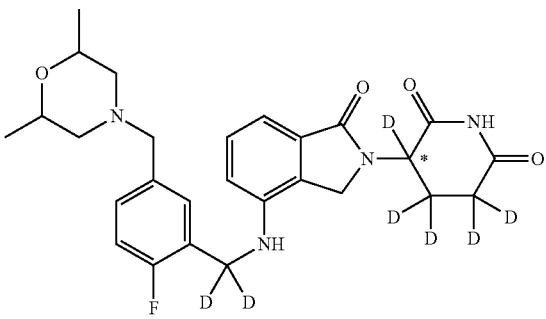
A1796
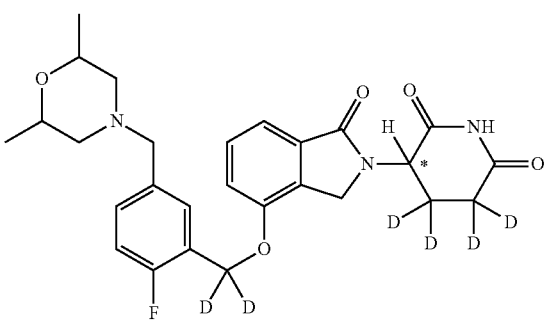
A1798
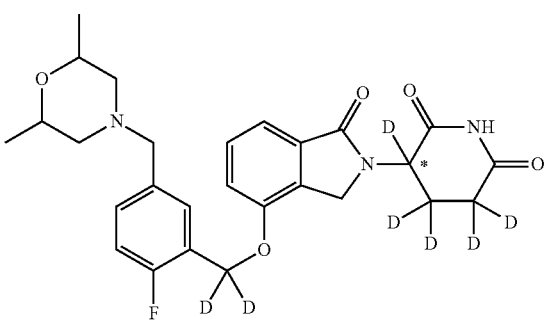
A1799
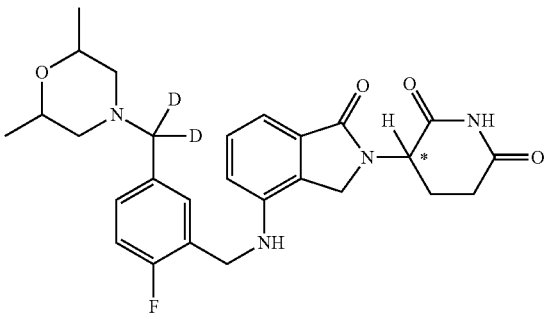

A1800
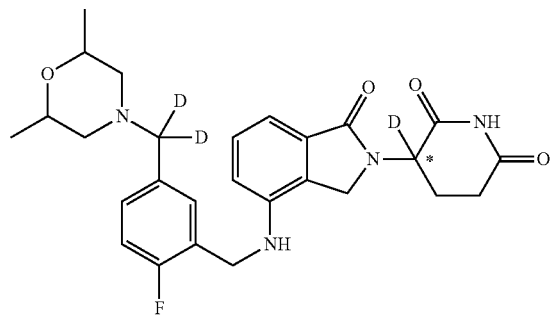
A1801
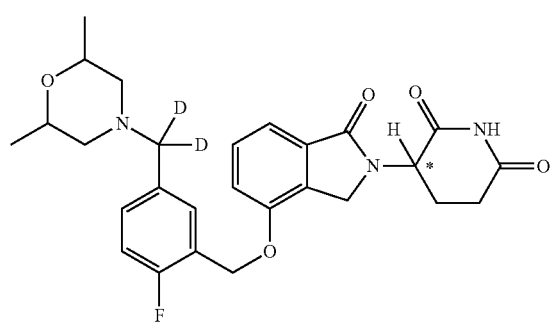
A1802
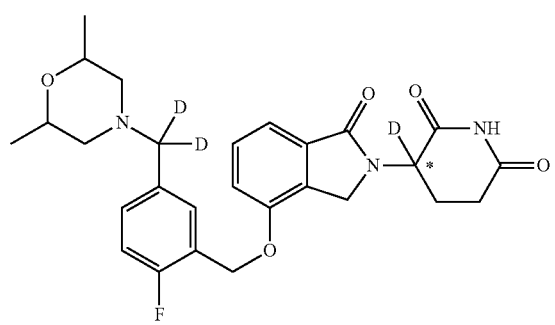
A1803
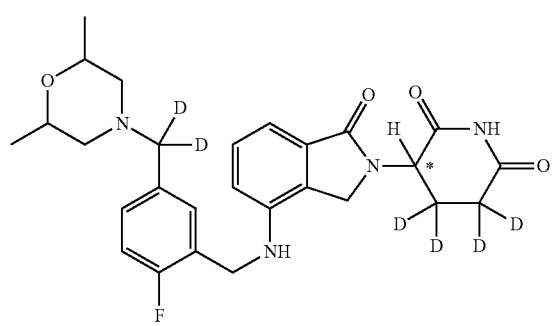
A1804
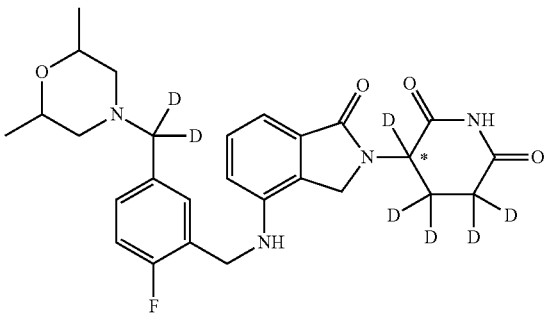
A1805
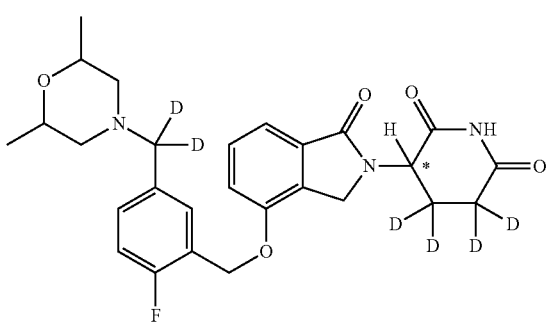
A1806
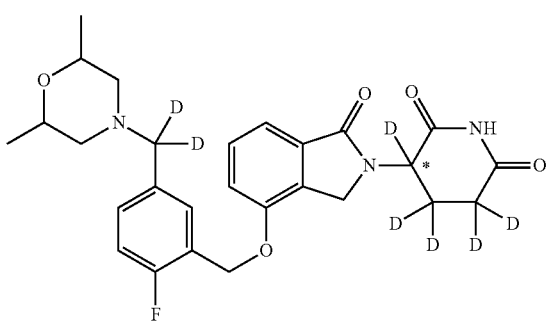
A1807
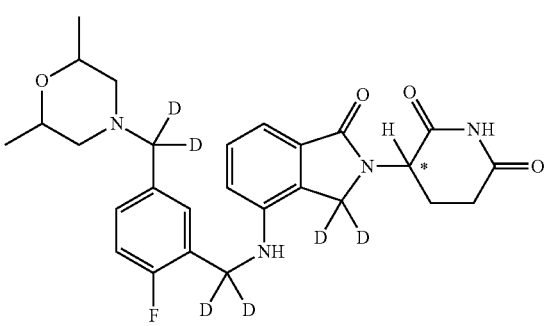

A1808
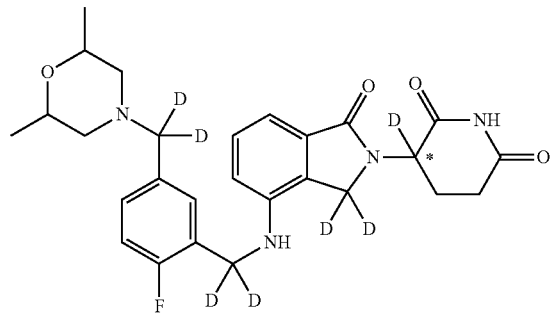
A1809
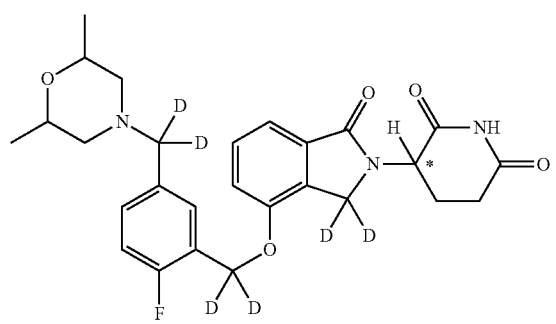
A1810
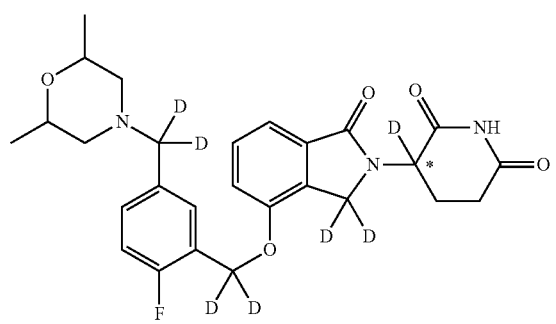
A1811
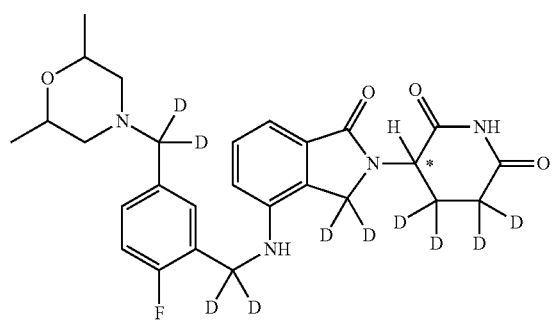
A1812
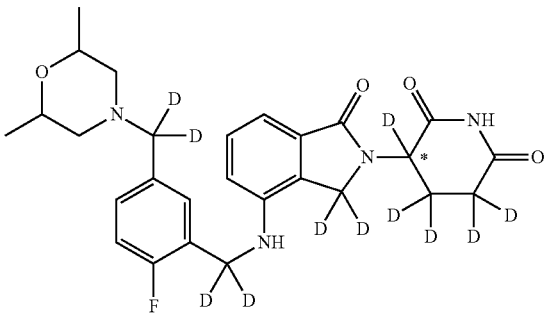
A1813
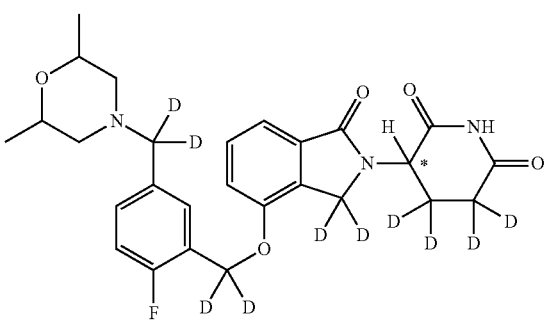
A1814
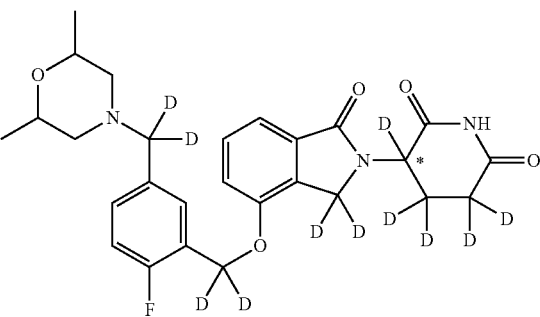
A1815
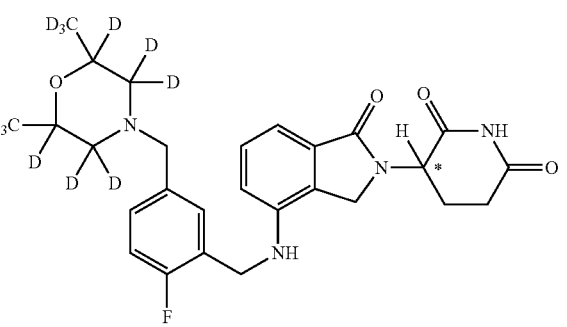

A1816
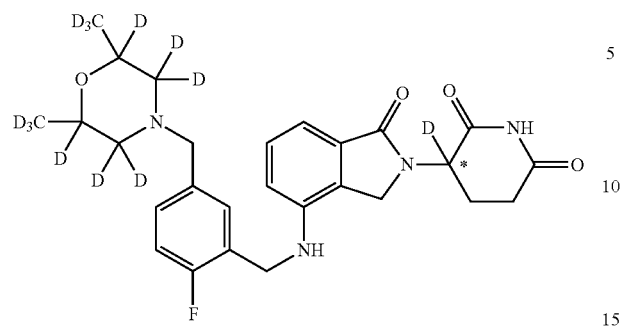
A1820
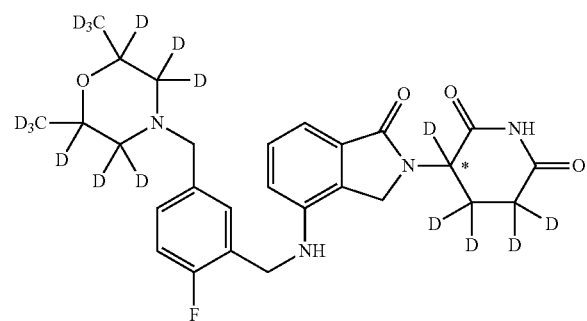
A1817
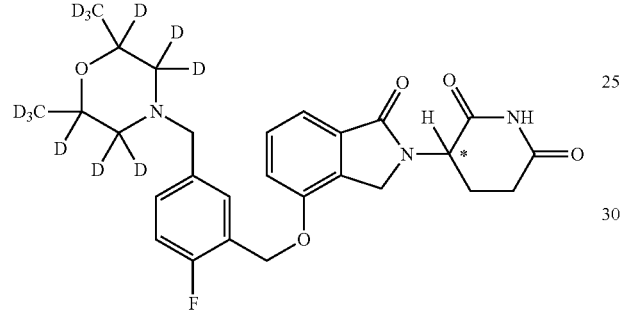
A1821
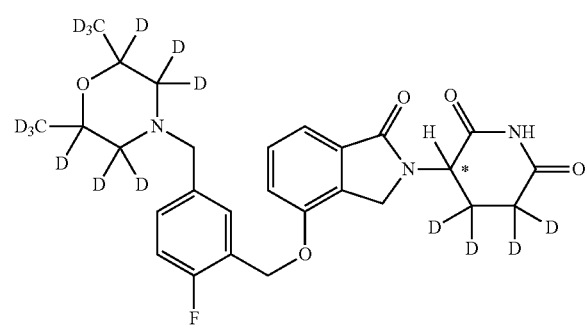
A1818
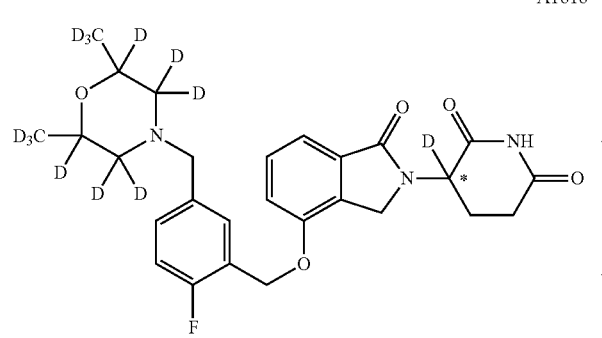
A1822
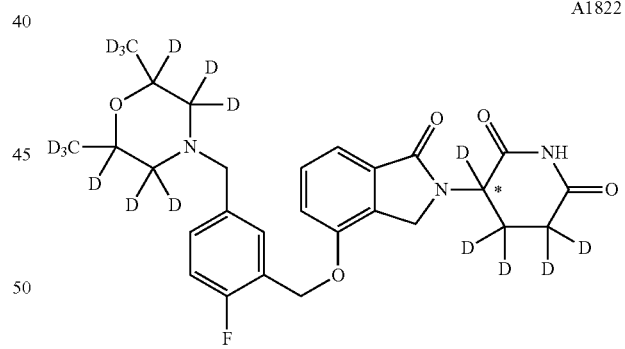
A1819
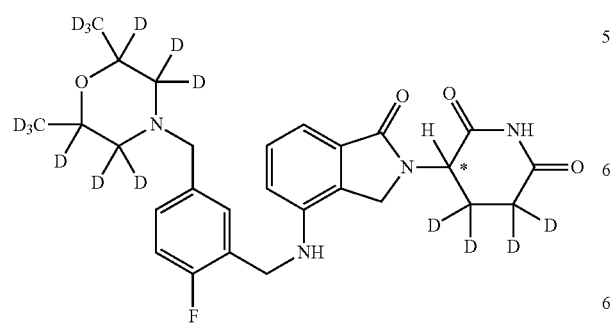
A1823
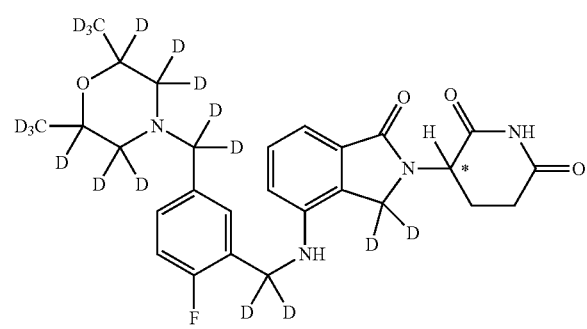

223
-continued
A1824
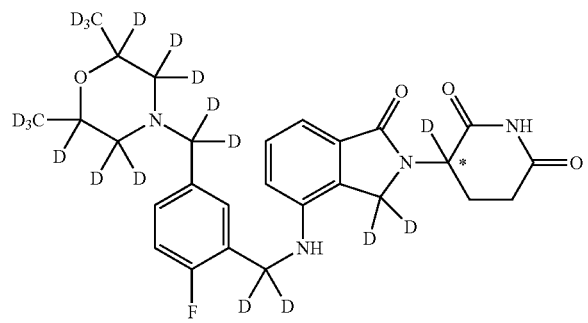
A1825
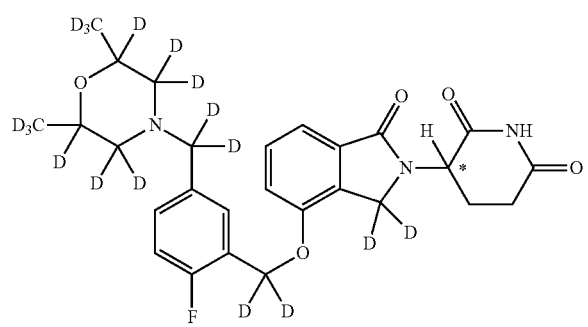
A1826
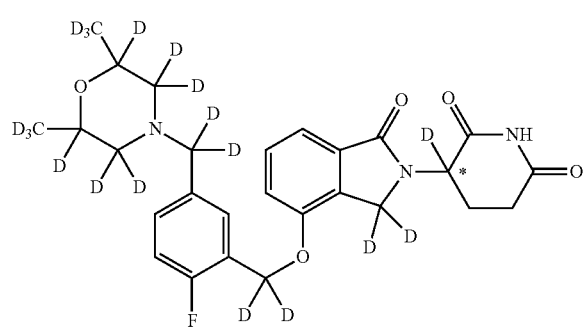
A1827
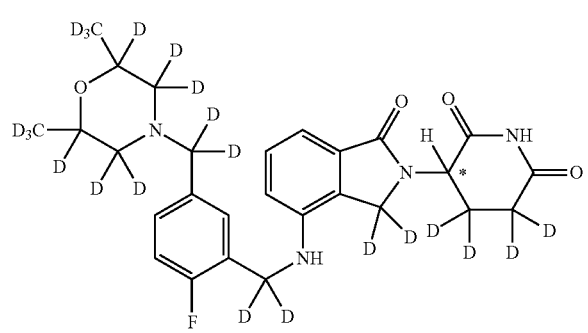
224
-continued
A1828
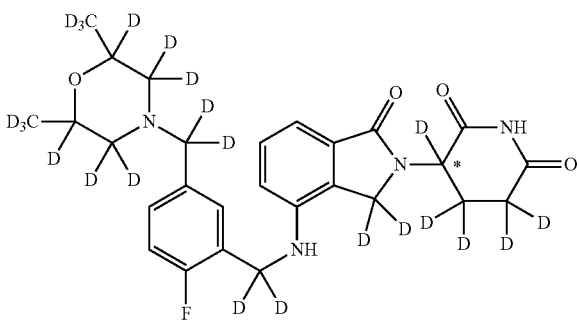
A1829
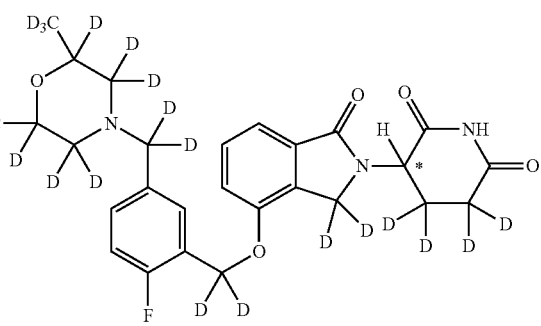
A1830
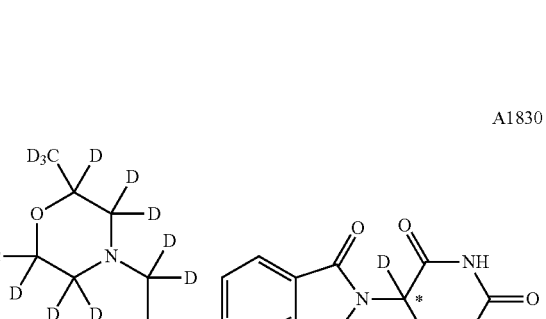
A1882
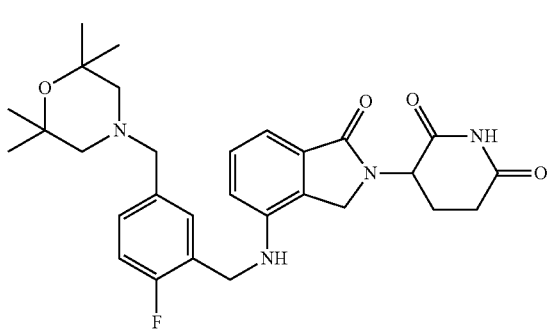

A1883
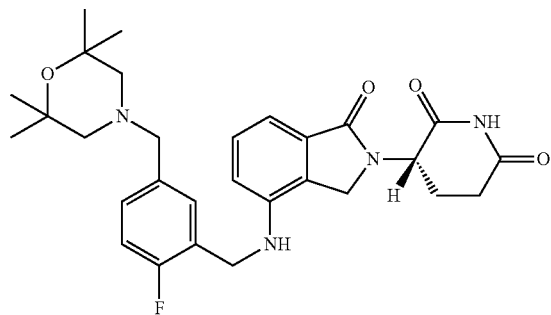
A1884
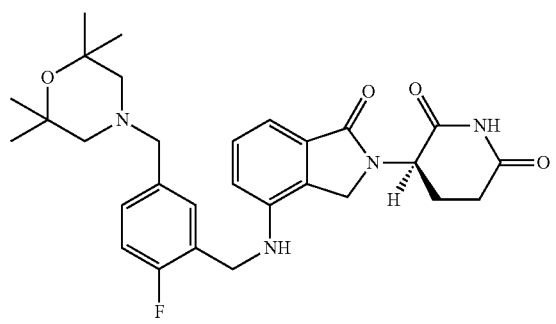
A1885
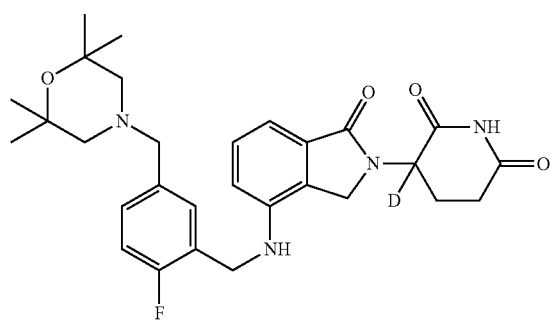
A1886
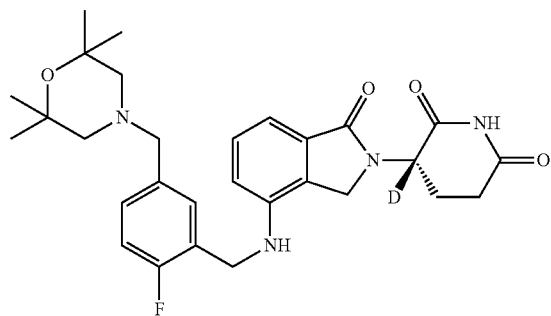
A1887
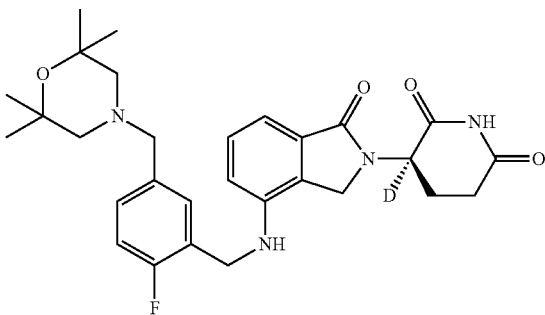
A1888
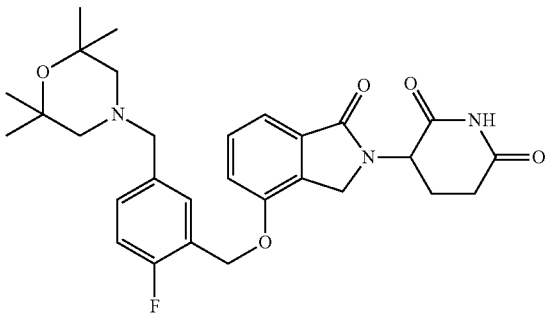
A1889
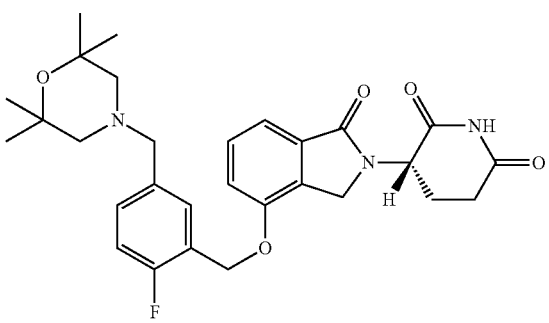
A1890
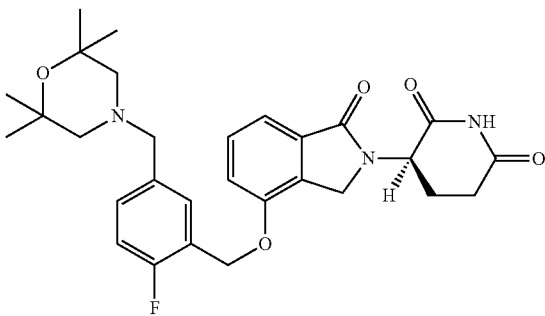

A1891
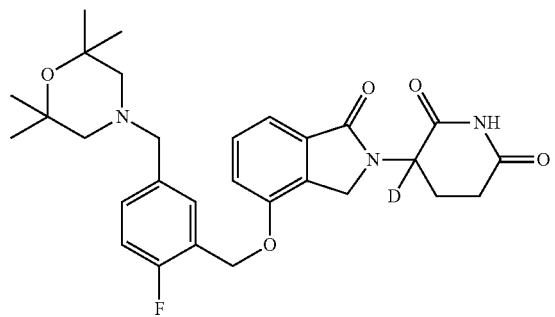
A1892
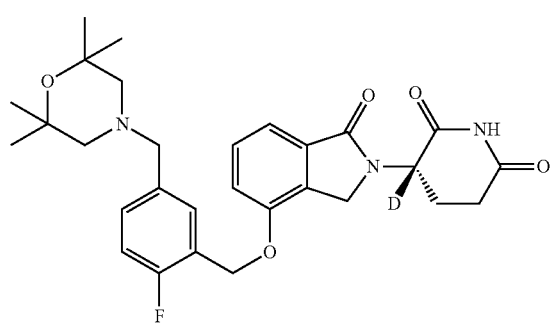
A1893
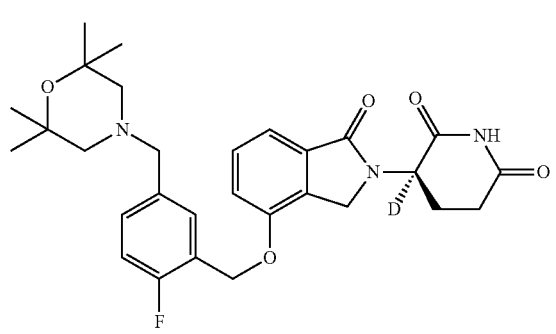
A1894
A1895
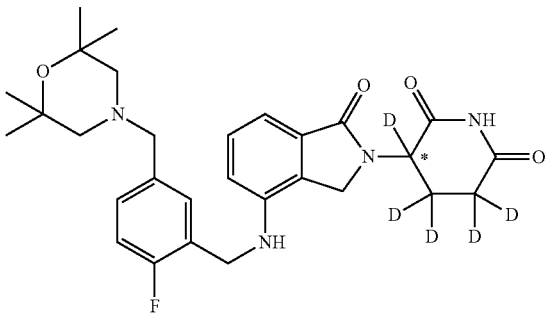
A1896
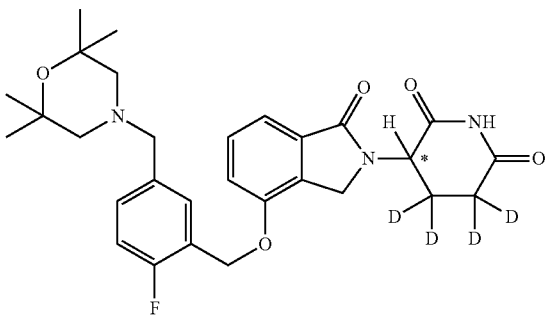
A1897
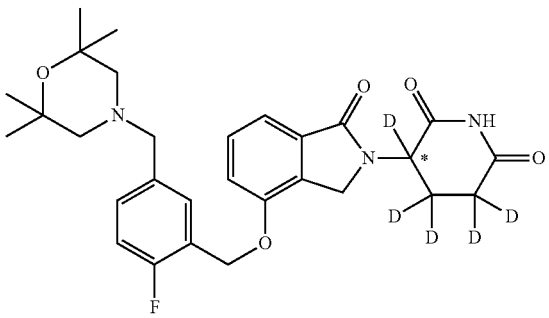
A1898
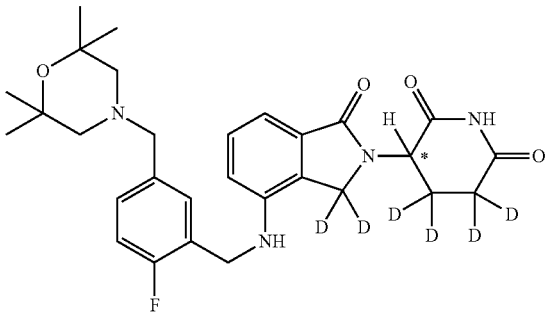

A1899
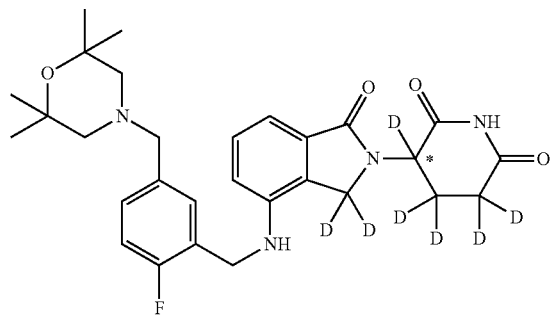
A1903
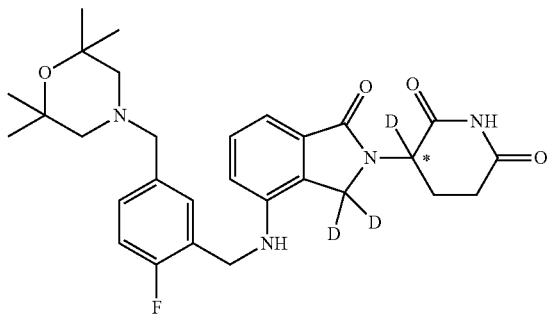
A1900
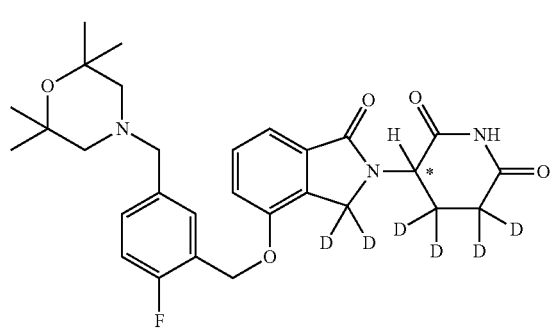
A1904
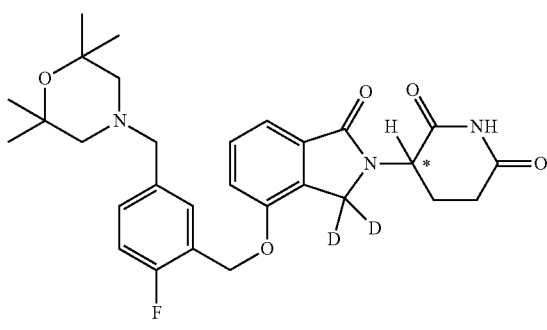
A1901
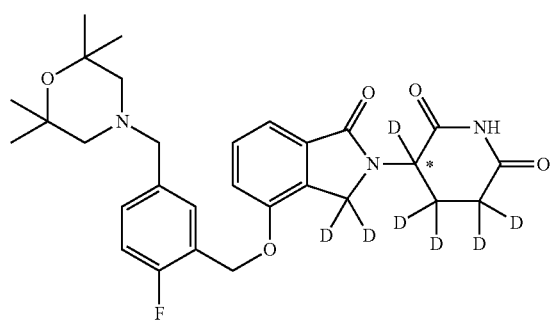
A1905
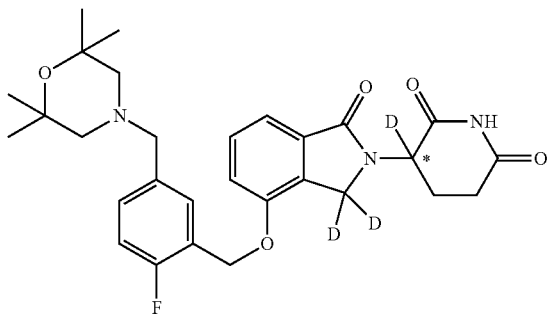
A1902
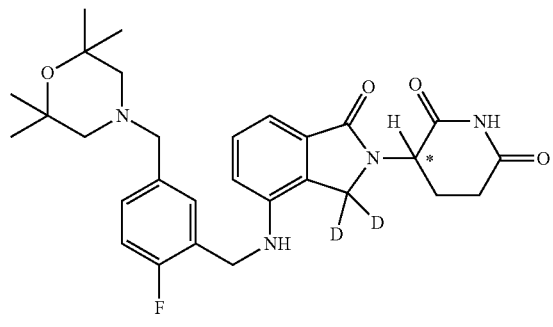
1906
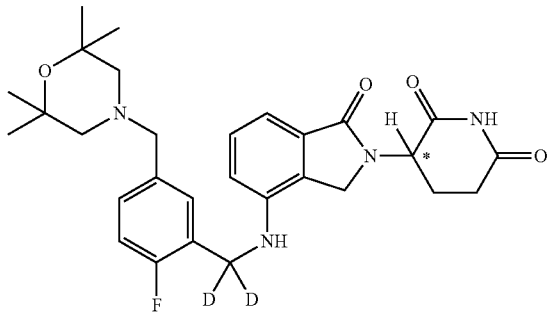

1907
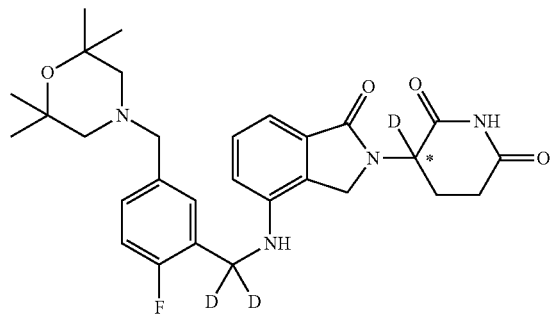
1908
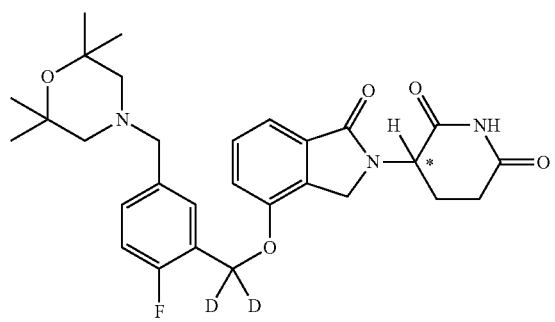
1909
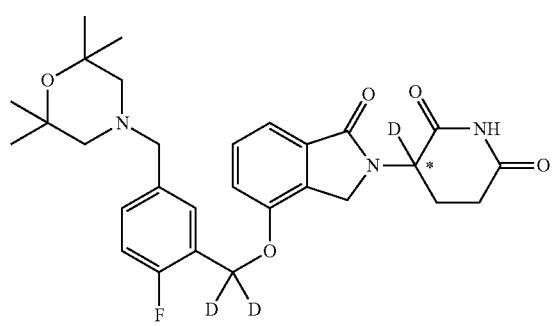
1910
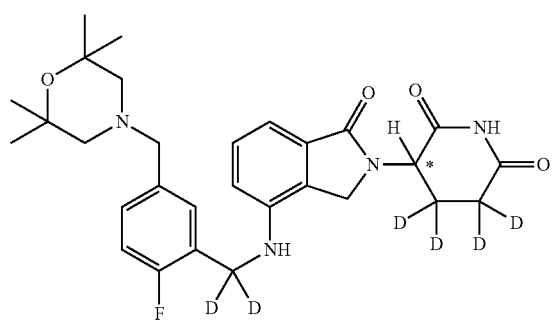
A1911
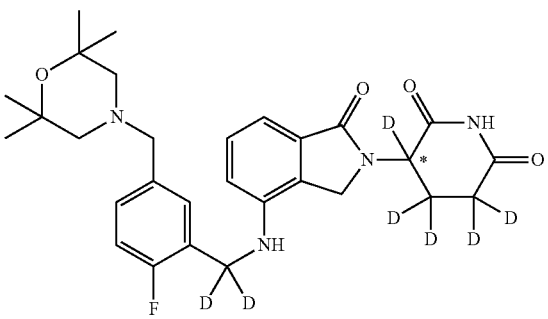
A1912
A1913
A1914
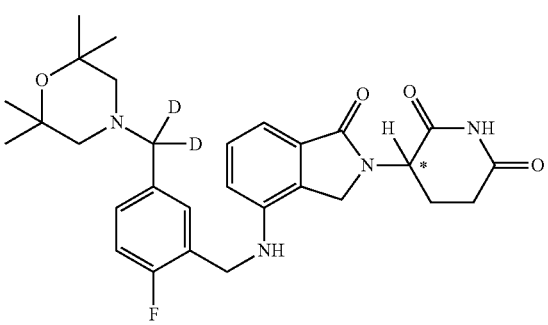

A1915
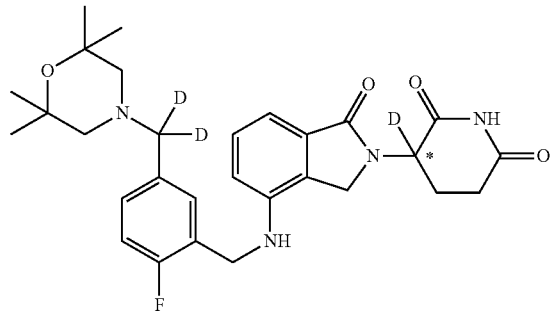
A1919
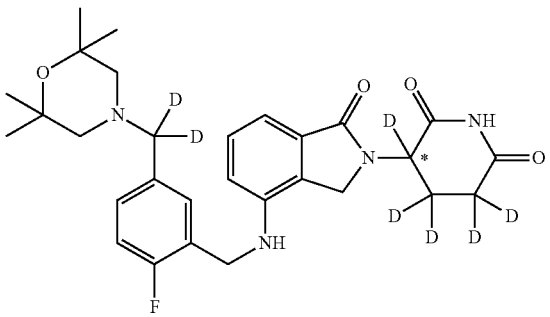
A1916
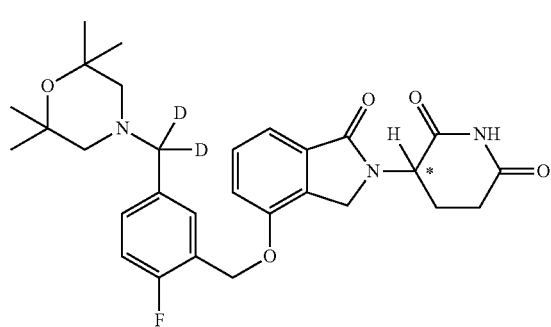
A1920
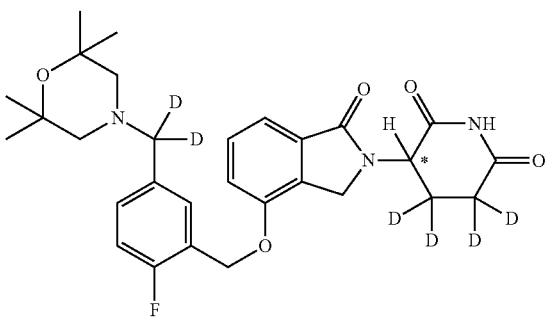
A1917
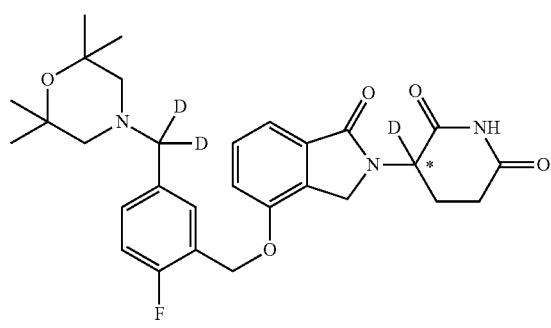
A1921
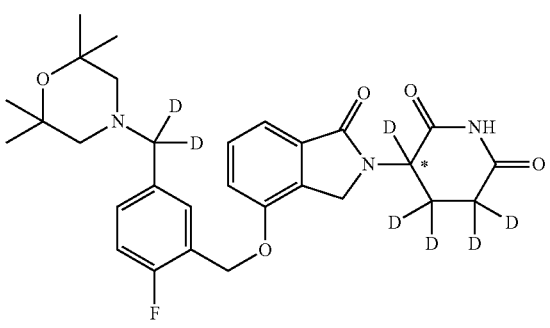
A1918
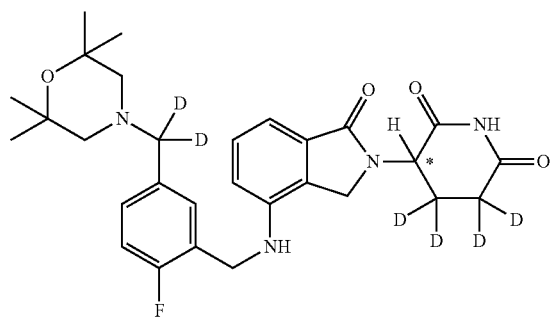
A1922
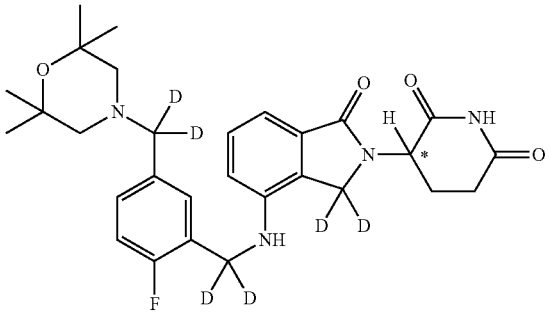

A1923
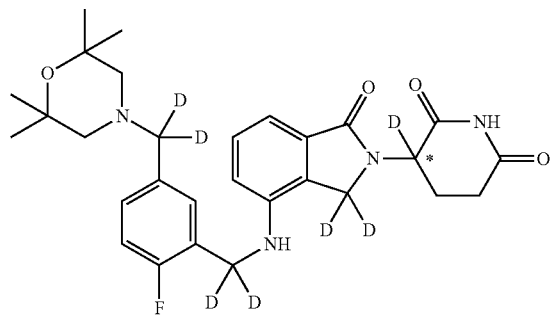
A1927
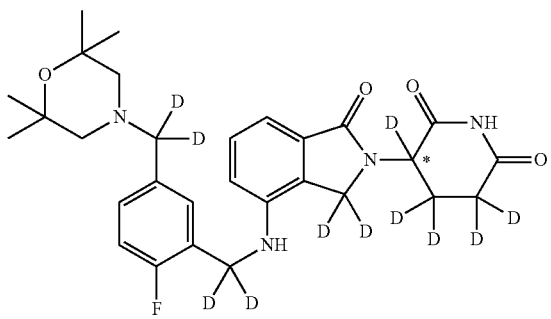
A1924
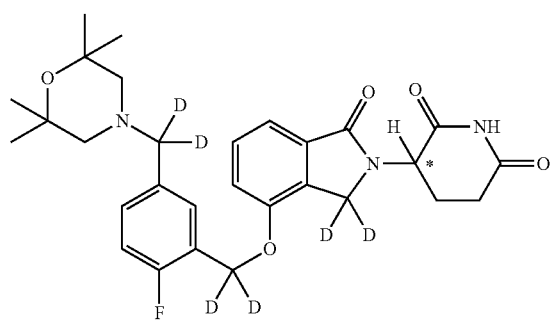
A1928
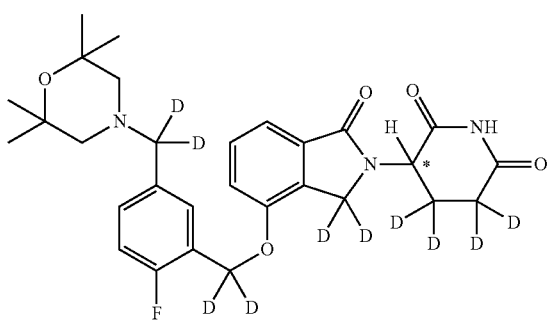
A1925
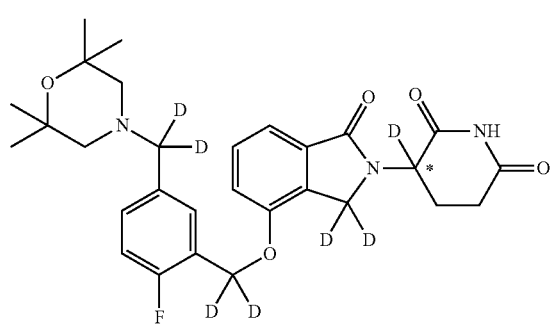
A1929
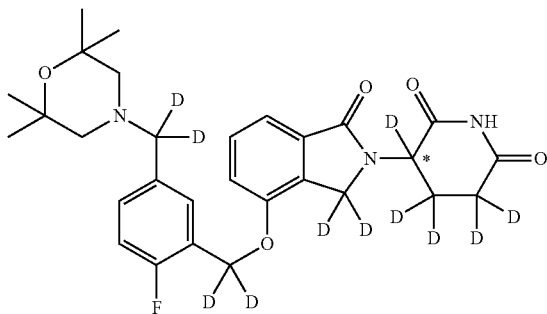
A1926
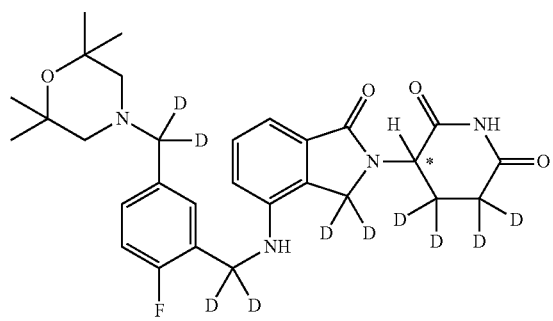
A1930
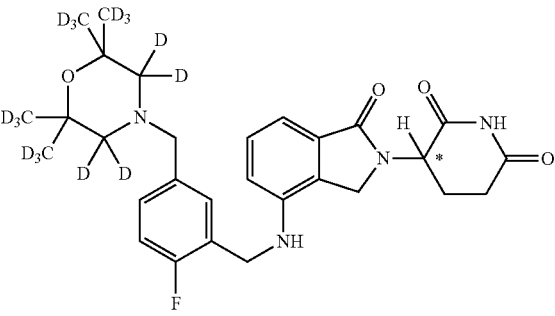

237
-continued
A1931
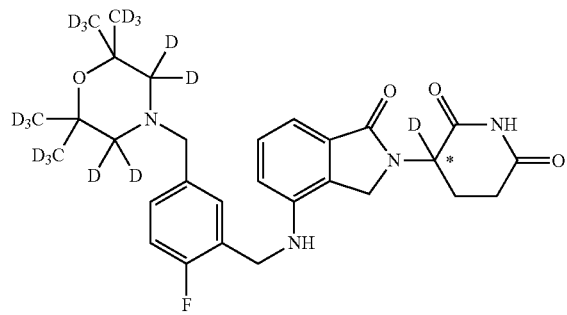
A1932
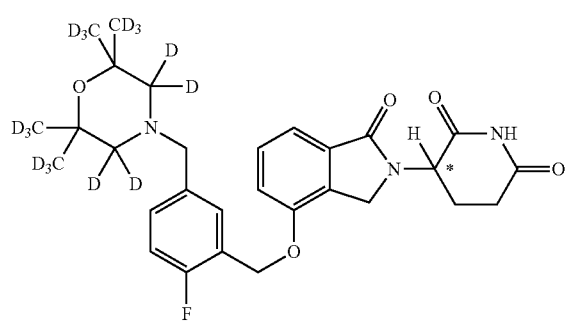
A1933
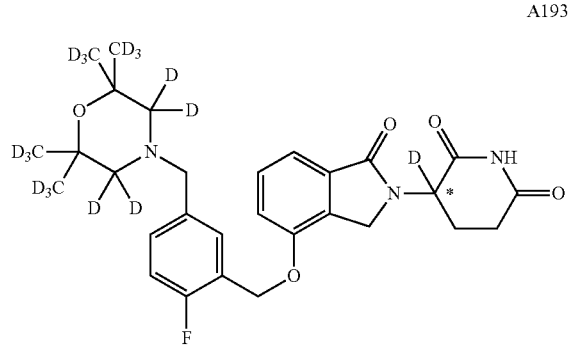
A1934
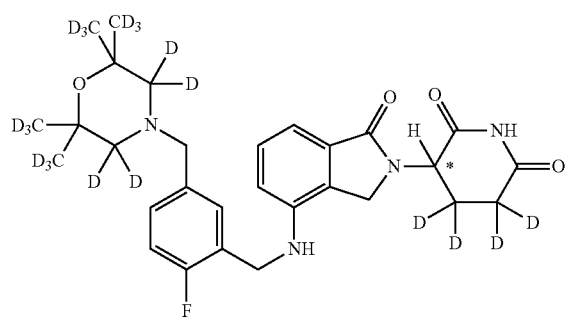
238
-continued
A1935
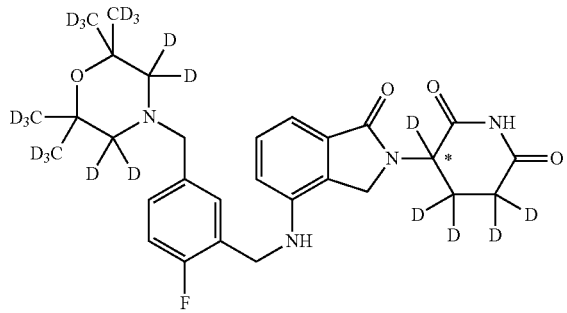
A1936
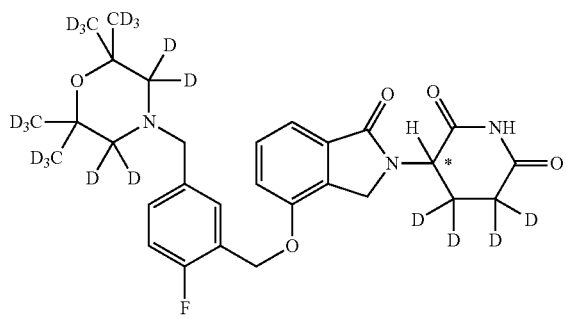
A1937
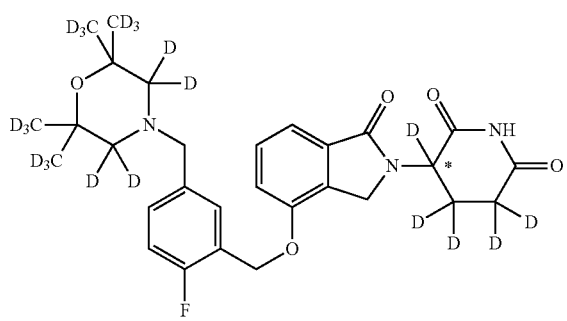
A1942
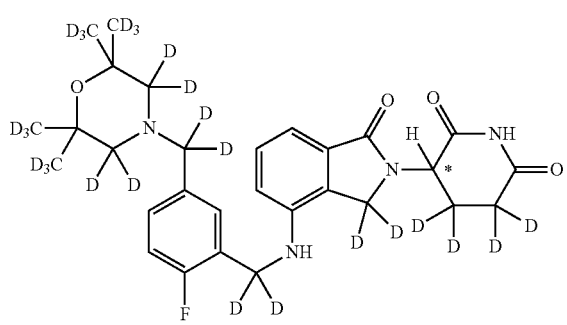

A1943

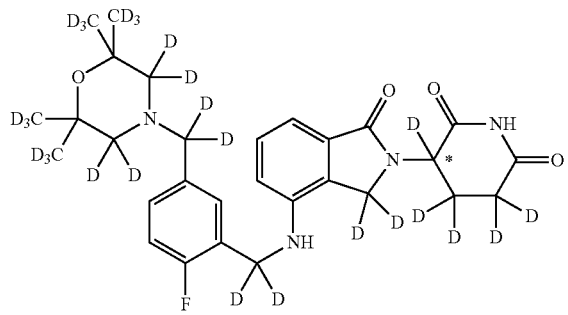

A1944

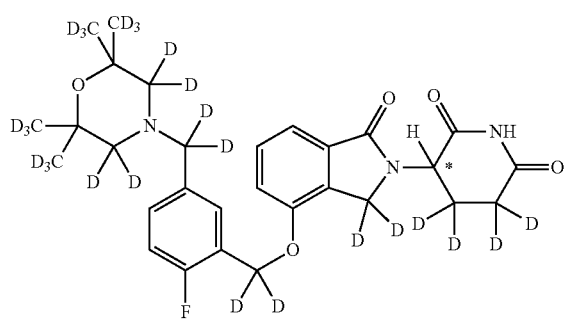

A1945

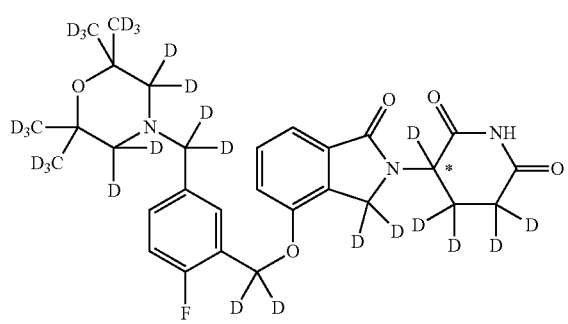

A1943

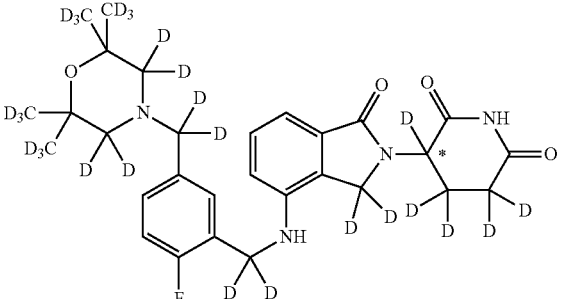

A1944

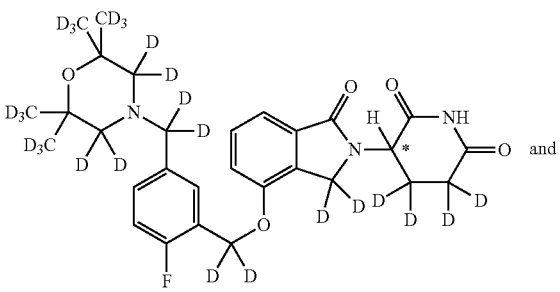

A1945

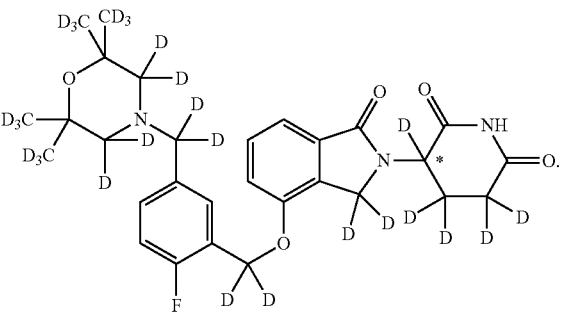

and

A1942

Deuterium (D or $^2$H) is a stable non radioactive isotope of hydrogen, its atomic weight is 2.0144. The hydrogen exists in the form of an isotopic mixture of H (hydrogen or protium), D ($^2$H or deuterium) and T ($^3$H or tritium) in natural, where the deuterium abundance is 0.0156%. According to the common technical knowledge in the field, of all the compounds whose structures contain natural hydrogen atoms, the hydrogen atom actually represents a mixture of H, D and T. Therefore, if a compound contains a deuterium whose abundance greater than its natural abundance 0.0156% at any position, these compounds should be considered to be non-natural or deuterium enriched, therefore, these compounds are novel relative to its non enriched analogues.

In the present invention, "deuterium enriched" compound refers to a compound of general formula (I), the pharmaceutically acceptable salt, solvate, polymorph, stereoisomer, isotopic compound, metabolite or prodrug thereof, where the deuterium abundance is greater than its natural abundance at any relevant position. Therefore, in the "deuterium enriched" compound, the deuterium abundance at the relevant position is likely between more than 0.0156% and 100%. The deuterium enriched position is represented by D, whereas the non deuterium enriched position is represented by H. According to the common technical knowledge in the field, the symbol H may be elided at the non deuterium enriched position. An example of a process for preparing a deuterium enriched compound is replacing the hydrogen with the deuterium, or employing deuterium-enriched starting material to synthesize the compound.

In the present invention, the percentage of the deuterium in the enriched deuterium or the deuterium abundance refers to molar percentage.

In the present invention, non deuterium enriched refers to the hydrogen in natural, which is in the form of a mixture of isotopes H (hydrogen or protium), D ($^2$H or deuterium) and T ($^3$H or tritium).

The present invention also provides a process for preparing the isoindoline derivative represented by general formula (I) which can be synthesized according to known processes with commercially available materials, preferably according to method A, which comprises carrying out a deprotection reaction with compound A-06(1) as below to give compound A(06a1); followed by an amidation reaction with compound A(06a1) as below to give the compound of general formula (I);

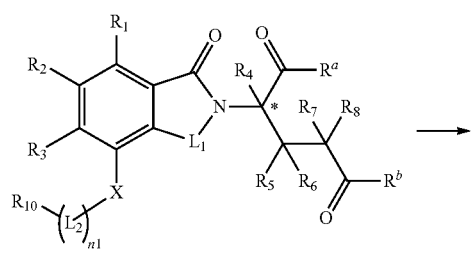

A-06(1)

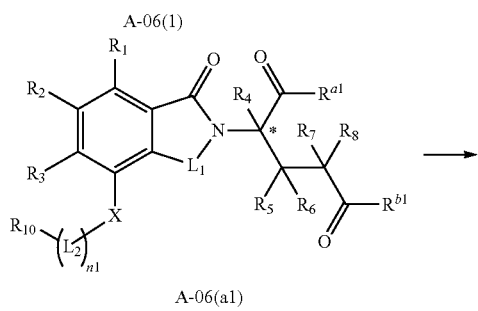

A-06(a1)

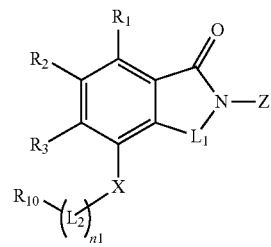

(I)

in the process of method A, in the definitions of compound A-06(1), compound A-06(a1) or the general formula (I), $L_1$, $L_2$, X, Z, *, $R_1$-$R_{10}$ and n1 are defined as above; one of $R^a$ and $R^b$ is

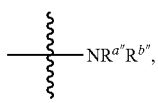

the other is

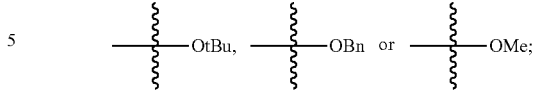

one of $R^{a1}$ and $R^{b1}$ is

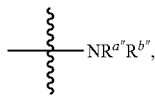

the other is

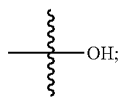

in the definition of

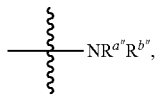

each of $R^{a''}$ and $R^{b''}$ is independently H or D.

In the general formula (I), when n1 is 0, the compound of general formula (I) may be further prepared according to method B, which comprises carrying out a reduction reaction with compound I-RS as below to give the compound of general formula (I);

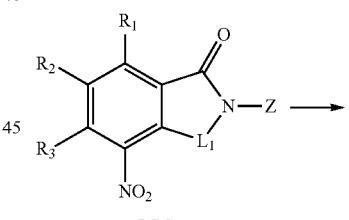

I-RS

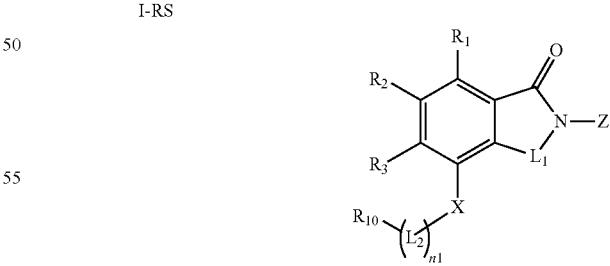

(I)

in the process of method B, in the definitions of compound I-RS or the general formula (I), $R_2$ is a halogen, n1 is 0, X is NH or ND, $R_{10}$ is H or D, $L_1$, Z, $R_1$ and $R_3$ are defined as above.

when n1 is 1 and X is NH or ND in the general formula (I), the compound of general formula (I) may be further prepared according to method C, which preferably comprises carrying our a reductive amination reaction with compound P-01 and

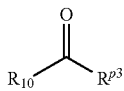

as below to give the compound of general formula (I)

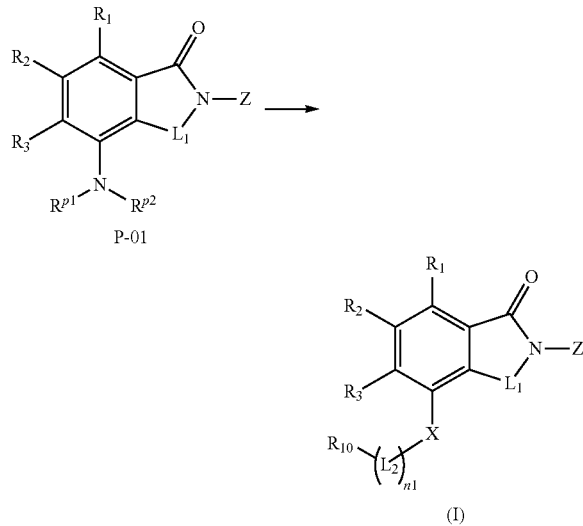

in the process of method C, in the definition of

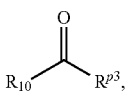

the compound P-01 or the general formula (I), X is NH or ND, n1 is 0, each of $R^{p1}$, $R^{p2}$ and $R^{p3}$ is independently H or D: $L_1$, $L_2$, Z, $R_1$, $R_2$ and $R_3$ are defined as above; in the definition of

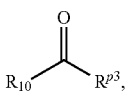

$R_{10}$ is

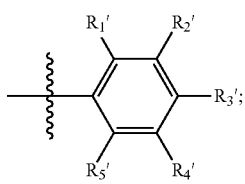

$R_1'$, $R_2'$, $R_3'$, $R_4'$ and $R_5'$ are defined as above.

In the process of method A, method B or method C, the steps and conditions of the deprotection reaction, the amidation reaction, the reduction reaction or the reductive amination reaction may be the conventional steps and conditions for such reaction in this field. Where the carbon atom labelled with * contained in Z in the compound A-06(1) or compound A-06(a1), compound I-RS, compound P-01 or general formula (I) is a chiral center, the compound A-06(1), compound A-06(a1), compound I-RS, compound P-01 or the general formula (I) can be isolated respectively by using a conventional chiral separation process in the field to give (R) configuration compound, enriched (R) configuration compound, (S) configuration compound or enriched (S) configuration compound in separate, and then being reacted accordingly to give the compound of general formula (I).

In the process of method A, when n1 is 0 in the general formula (I), the process for preparing the compound of general formula (I) may further comprise carrying out a reduction reaction with compound A-05(1) as below to give the compound A-06(1);

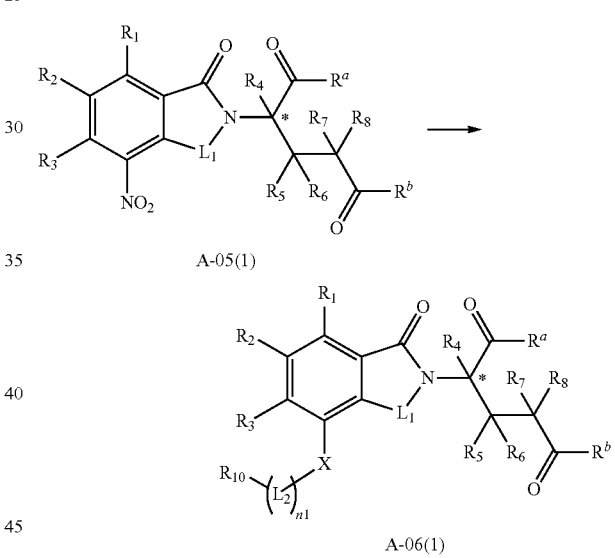

wherein, in the definitions of compound A-05(1) and A-06(1), $L_1$, $L_2$, $R_1$-$R_8$, $R^a$ and $R^b$ are defined as above; in the definition of compound A-06(1), X is NH or ND, n1 is 0; $R_{10}$ is H or D. The steps and conditions used for the reduction reaction can be conventional steps and conditions used for such reaction in this field.

In the process of method A, when X is NH or ND and n1 is 1 in the general formula (I), the process for preparing the compound of general formula (I) may further comprise carrying out a reductive amination reaction with compound A-05(2) and

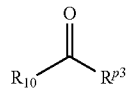

as below to give the compound A-06(1);

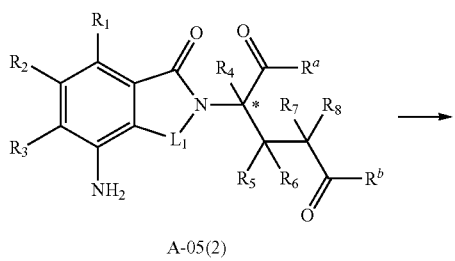

A-05(2)

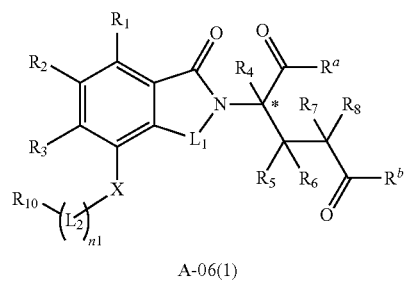

A-06(1)

wherein, in the definitions of compound A-05(2) and compound A-06(1), $L_1$, $L_2$, $R_1$-$R_8$, $R^a$ and $R^b$ are defined as above; in the definition of compound A-06(1), X is NH or ND and n1 is 1; in the definition of

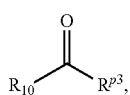

$R^{p3}$ is H or D; $R_{10}$ is

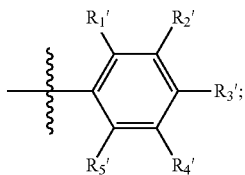

$R_1'$, $R_2'$, $R_3'$, $R_4'$ and $R_5'$ are defined as above. The steps and conditions used for the reductive amination reaction can be conventional steps and conditions used for such reaction in this field.

In the process of method A, when the X is O and n1 is 1 in the compound having a structure of general formula (I), the process for preparing the compound having a structure of general formula (I) may further comprise carrying out a nucleophilic substitution reaction with compound A-05(3) and

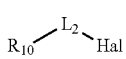

as below to give the compound A-06(1);

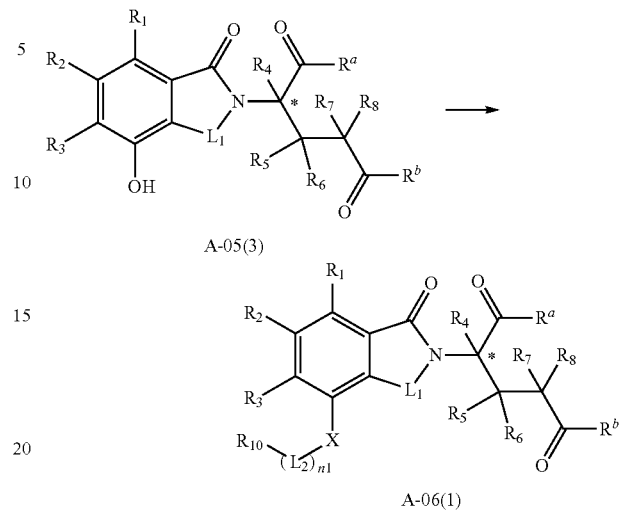

A-05(3)

A-06(1)

wherein, in the definitions of compound A-05(3) and compound A-06(1), $L_1$, $L_2$, $R_1$-$R_8$, $R^a$ and $R^b$ are defined as above; in the definition of compound A-06(1), X is O and n1 is 1; in the definition of

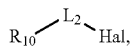

Hal is a halogen (e.g., F, Cl, Br or I); $R_{10}$ is

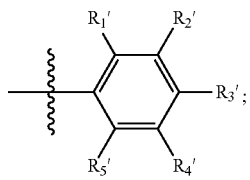

in the definitions of $R_{10}$, $R_1'$, $R_2'$, $R_3'$, $R_4'$ and $R_5'$ are defined as above. The steps and conditions used for the nucleophilic substitution reaction can be conventional steps and conditions used for such reaction in this field.

The process for preparing the compound A-06(1) may further comprise carrying out a coupling reaction with compound Q-03 and compound A-04(1), followed by deprotecting as below to give the compound A-05(3);

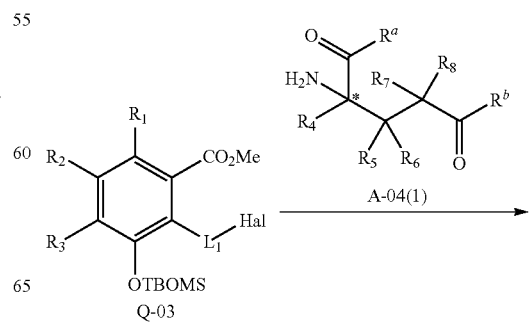

Q-03        A-04(1)

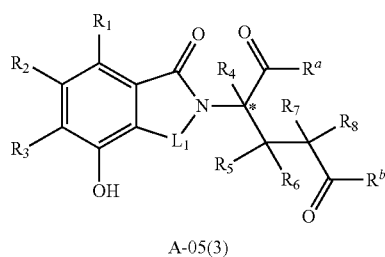

A-05(3)

wherein, in the definition of compound Q-03 or compound A-04(1), $L_1$, *, $R_1$-$R_8$ are defined as above, Hal is halogen (e.g. Cl, Br or I); one of $R^a$ and $R^b$ is

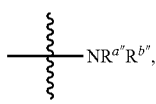

the other is

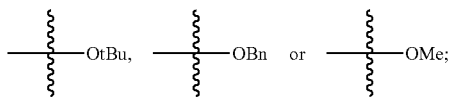

in the definition of

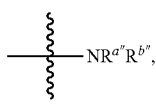

each of $R^{a''}$ and $R^{b''}$ is independently H or D.

The process for preparing the compound A-05(3) may further comprise protecting the commercially available starting material, phenol Q-01, with TBDMS to give Q-02, followed by reacting with a halogenated reagent (e.g. NBS) to give benzyl halide Q-03.

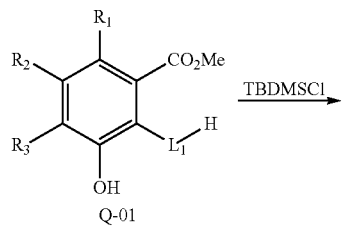

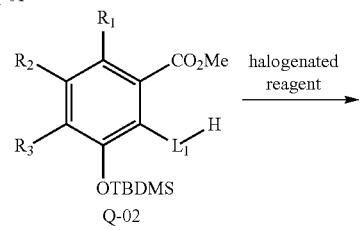

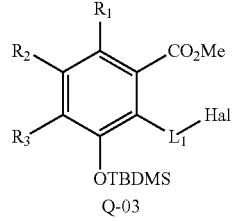

Q-03 wherein, in the definition of compound Q-01, $R_1$-$R_3$ and $L_1$ are defined as above.

In the process of method B, in process for preparing the compound having a structure of general formula (I), compound I-RS is prepared according to a common process for preparing such compound in this field, preferably, prepared according to method D or method E; method D preferably comprises carrying out a coupling reaction with compound A-03 and compound A-04(2) or the salt thereof as below to give compound I-RS;

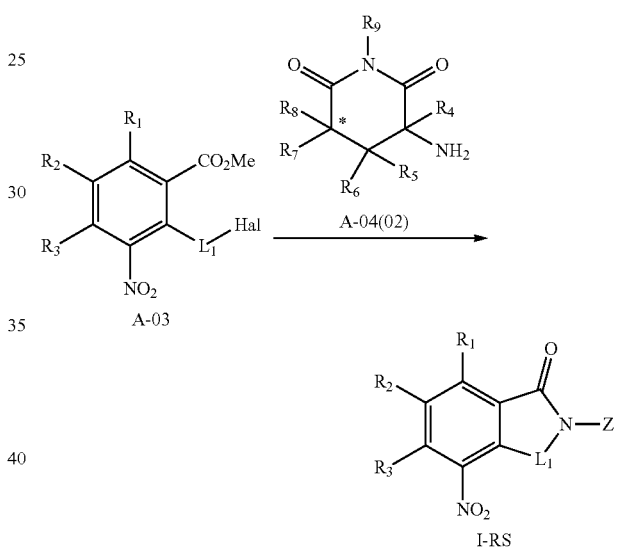

wherein, in the definition of compound A-03, A-04(2) or I-RS, $L_1$, Z, *, $R_1$-$R_8$ are defined as above; in the definition of compound A-03, Hal is a halogen (e.g. Cl, Br or I). The steps and conditions used for the coupling reaction can be conventional steps and conditions used for such reaction in this field.

Method E preferably comprises deprotecting compound A-05(1) as below to give compound A-06(a2), followed by carrying out a amidation reaction with compound A-06(a2) to give compound I-RS;

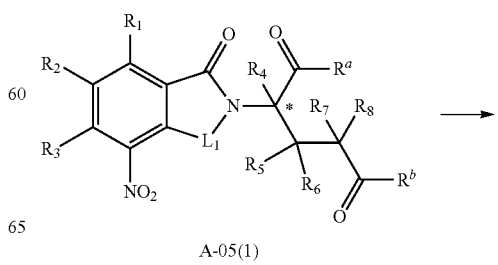

A-05(1)

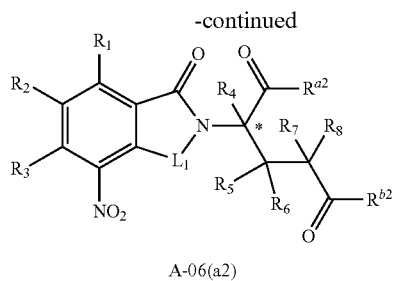

A-06(a2)

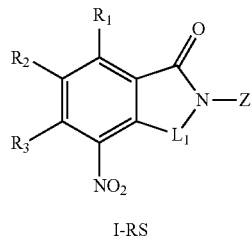

I-RS wherein, in the definition of compound A-05(1), A-06(a2) or I-RS, $L_1$, Z, *, $R_1$-$R_8$, $R^a$ and $R^b$ are defined as above; one of $R^{a2}$ and $R^{b2}$ is

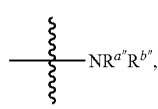

the other is

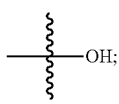

in the definition of

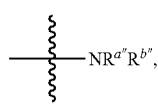

each of $R^{a''}$ and $R^{b''}$ is independently H or D. The steps and conditions used for the deprotecting reaction and amidation reaction can be conventional steps and conditions used for such reactions in this field.

In the process of method C, the process for preparing the compound having a structure of general formula (I) may further comprise carrying out a reduction reaction with compound I-RS as below to give compound P-01;

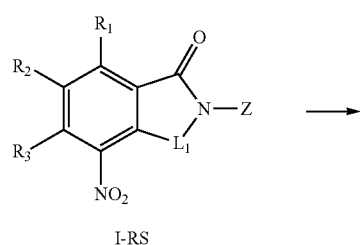

I-RS

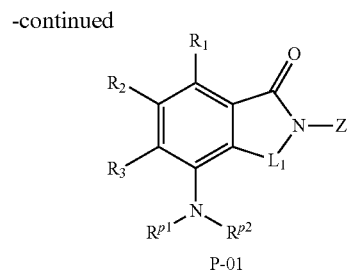

P-01

In the definition of compound I-RS or compound P-01, $R_2$ is H, D or a halogen; each of $R^{p1}$ and $R^{p2}$ is independently H or D; $L_1$, $L_2$, Z, $R_1$ and $R_3$ are defined as above. The steps and conditions used for the reduction reaction can be conventional steps and conditions used for such reaction in this field.

In the process of method A, the process for preparing compound A-06(1) may preferably further comprise carrying out a coupling reaction with compound A-03 and compound A-04(1) as below to give compound A-05(1);

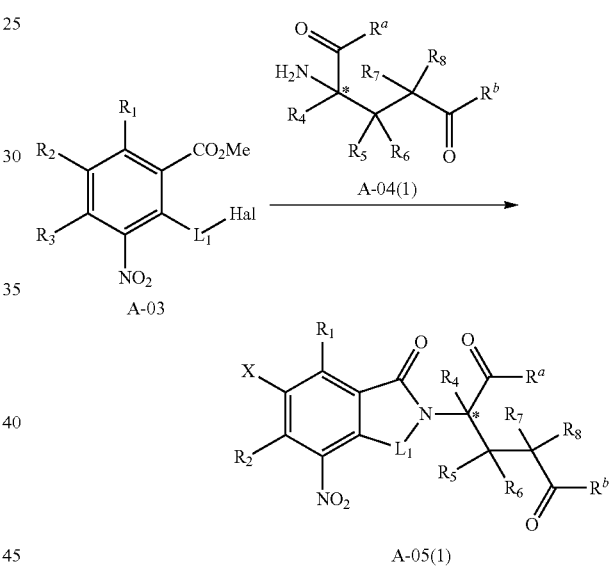

wherein, in the definition of compound A03, A-04(1) or A-05(1), $L_1$, *, $R_1$-$R_8$, $R^a$ and $R^b$ are defined as above; Hal is halogen (e.g. Cl, Br or I). The steps and conditions used for the coupling reaction can be conventional steps and conditions used for such reaction in this field.

The process for preparing the isoindoline derivative having a structure of formula (I) comprises the steps specifically reference to Scheme A and Scheme P:

Scheme A: coupling the benzyl halide A-03 with the amino acid derivative A-04(1) to give the product A-05(1), followed by deprotecting to give compound A-05(2), and being converted to amine A-06(1) by carrying out a reductive amination reaction with aldehyde

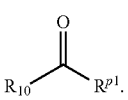

Ultimately, a deprotection reaction and a cyclization reaction are carried out to give the target compound (I), which is specifically as follows:

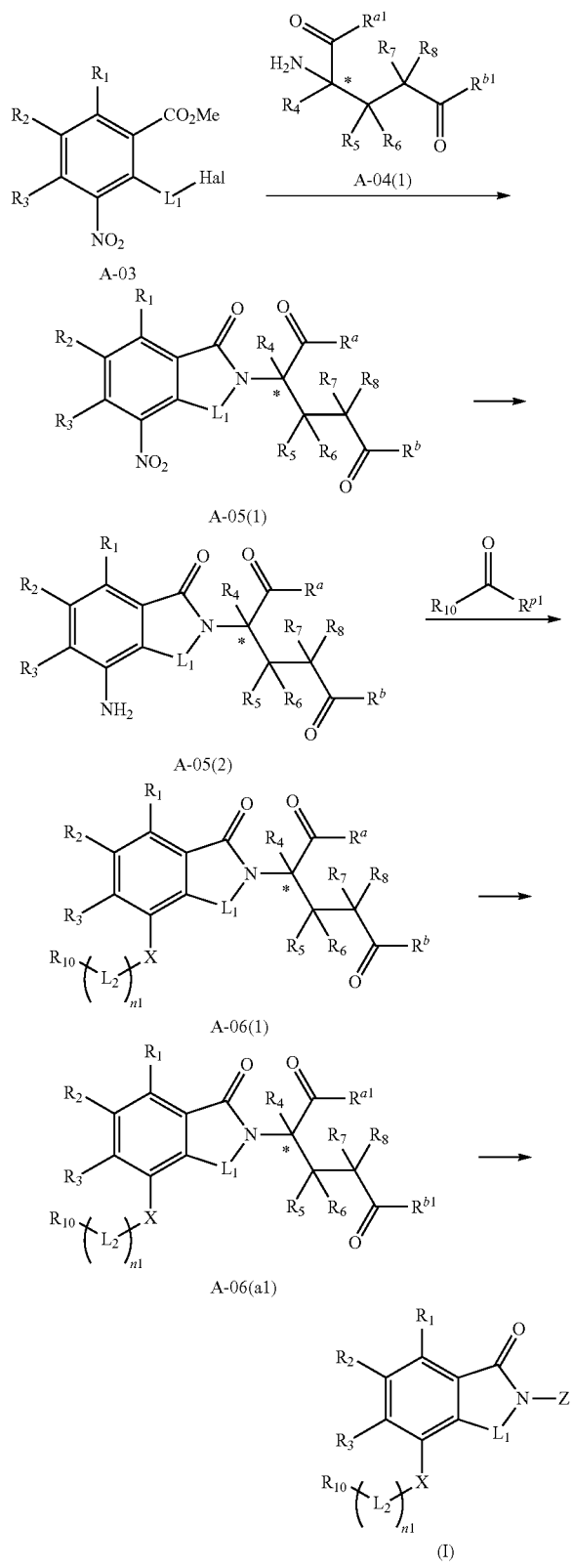

A-05(1)

A-05(2)

A-06(1)

A-06(a1)

(I)

In Scheme A, the definition of each letter and group is as above.

The starting material A-03 is commercially available or can be synthesized according to a known process (see Sbderberg et al. Org. Syn. (2003) 80, 75; U.S. Pat. No. 4,678,500; US 2012/0053159 and US 2007/0255076).

The amino acid derivative A-04 is commercially available or can be synthesized according to a known process (see Chen et al. Biotechnol. Lett. (1992) 14, 269; WO 2012/015986; WO 2012/068512; US 2012/0053159; Manesis et al. J. Org. Chem. (1987) 52, 5342: Stogniew et al. J. Labelled Compd. RAD. (1981) 18, 897; Blomquist et al. J. Org. Chem. (1966) 31, 4121), which specifically refers to Schemes F1, F2 and G.

Scheme F1:

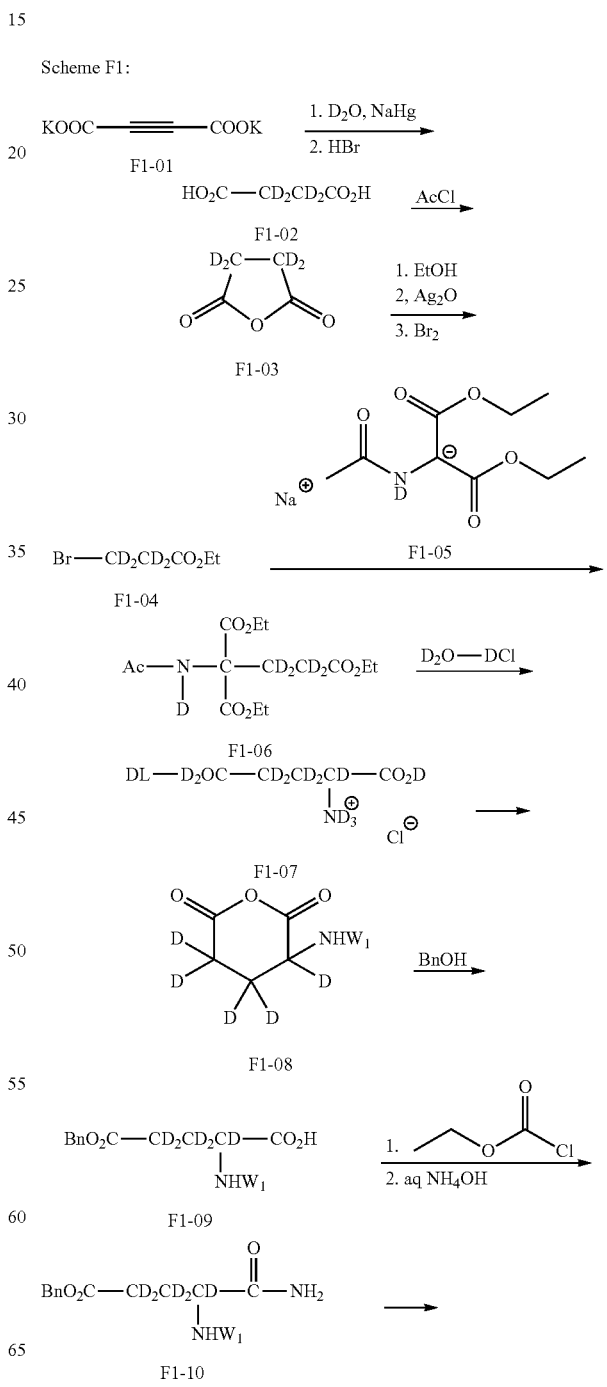

253

-continued

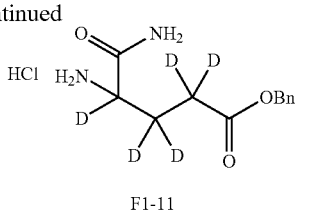

F1-11

F1-01 is reduced with Na—Hg in deuteroxide to give deuterium enriched F1-02. The diacid F1-02 is dehydrated with acetyl chloride to give acid anhydride F1-03, followed by reacting with anhydrous ethanol, silver oxide and bromine respectively to give bromo compound F1-04. F1-04 is treated with reagent F1-05(Blomquist et al. *J. Org. Chem.* (1966) 31, 4121) to give triethyl ester F1-06. F1-06 is heated in D₂O-DCl thereby forming deuterium enriched amino acid F1-07, followed by protecting amino group with an amino protecting group (e.g., Boc, Cbz), and convert acetic anhydride to acid anhydride F1-08 by dehydration. F1-08 is treated with benzyl alcohol followed by respectively reacting with ethyl chloroformate and aqueous ammonia, and finally deprotecting to give target compound F1-11. In the definition of F1-08, F1-09 and F1-10, W1 is a conventional amino protecting group in the art.

254

-continued

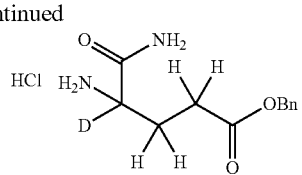

F2-11

F2-04 (commercially available) is treated with reagent F2-05 (Blomquist et al. J. Org. Chem. (1966) 31, 4121) to give triethyl ester F2-06. F2-06 is heated in D₂O-DCl thereby forming deuterium enriched amino acid F1-07, followed by protecting amino group with an amino protecting group (e.g., Boc, Cbz), and acetic anhydride is convert to acid anhydride F2-08 by dehydration. F2-08 is treated with benzyl alcohol, followed by respectively reacting with ethyl chloroformate and aqueous ammonia, and finally deprotecting to give target compound F2-11. In the definition of F2-08, F2-09 and F2-10, W1 is a conventional amino protecting group in the art.

Scheme F2:

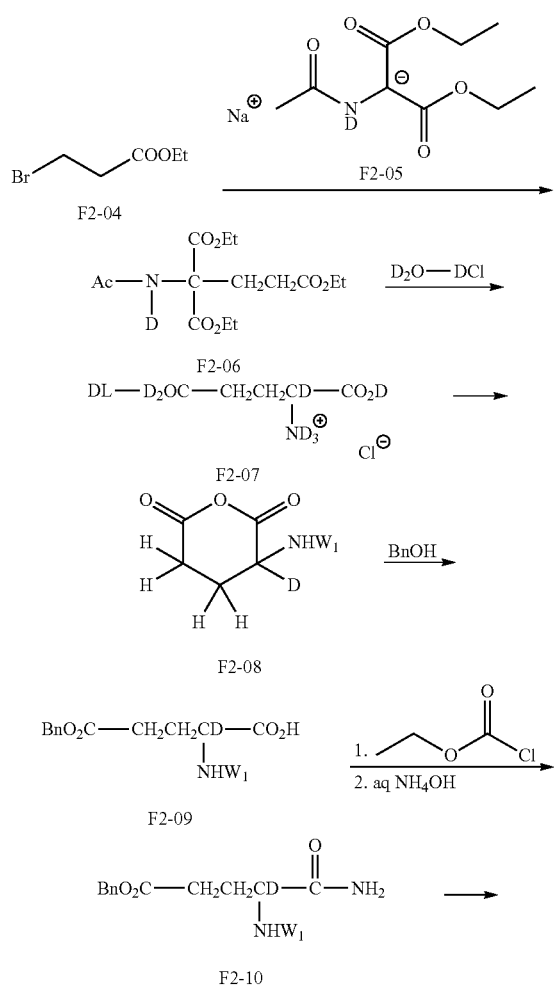

Scheme G:

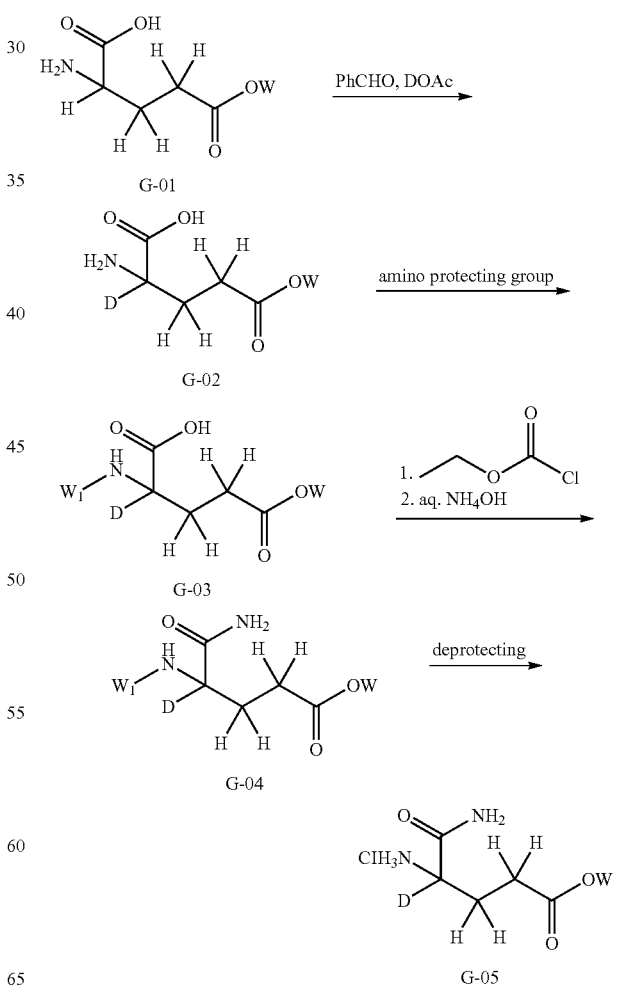

in Scheme G, W is

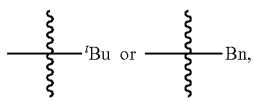

W1 is a conventional amino protecting group in the art, such as Boc, Cbz, etc.

Ester G-01 is treated with benzaldehyde in deuterated acetic acid to give deuterium enriched compound G-02. The amino group in G-02 is protected with an amino protecting group, followed by reacting respectively with ethyl chloroformate and aqueous ammonia to give amide G-04. The amino protecting group in G-04 can be removed according to a conventional deprotection process in the art (e.g., acidolysis or reduction) thereby converting to the target compound G-05.

Material A-03 is reacted with amino compound P-03 to give compound P-02, followed by reduction and reductive amination with aldehyde

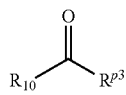

to give the compound having a structure of general formula (I). The amino compound P-03 is commercially available or can be synthesized according to a known process (see WO 2012/015986; WO 2012/068512; Muller et al. *Bioorganic & Medicinal Chemistry Letters* (1999) 9, 1625).

Scheme P:

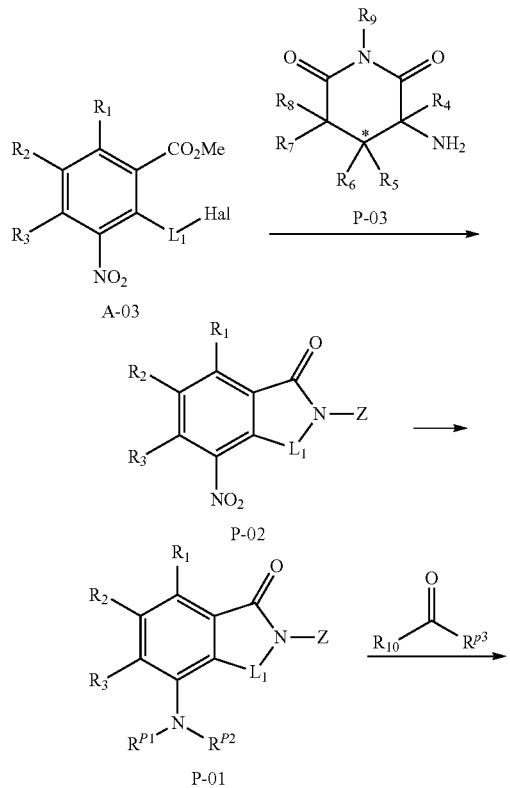

-continued

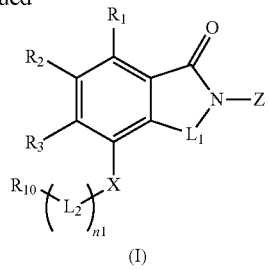

in Scheme P, the definition of each letter and group is as above.

The conditions and steps employed in the chemical reactions involved in the above-mentioned reaction routes can be conventional conditions and steps for such reactions in the art, and the compounds obtained by the above-mentioned processes can be further modified at peripheral positions to give other target compounds of the present invention.

The present invention also provides an intermediate compound A-06(1), A-06(a1), I-RS or P-01 for preparing the isoindoline derivative having a structure of general formula (I):

A-06(1)

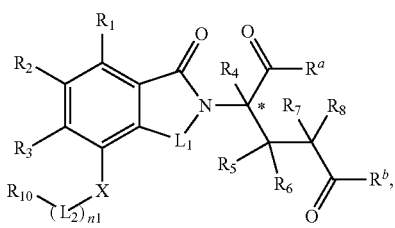

A-06(a1)

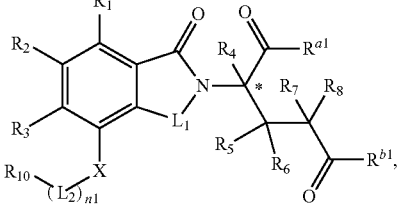

I-RS

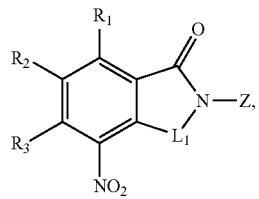

P-01

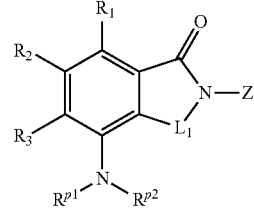

in the definition of compound A-06(1), A-06(a1), I-RS or P-01, $L_1$, $L_2$, n1, Z, *, $R_1$-$R_{10}$, $R^a$, $R^b$, $R^{a1}$, $R^{b1}$, $R^{p1}$ and $R^{p2}$ are defined as above; in the definition of compound A-06(1), one of $R^a$ and $R^b$ is

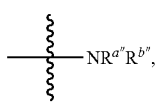

the other is

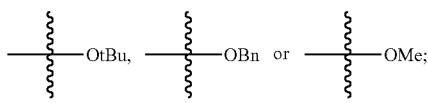

in the definition of compound A-06(a1), one of $R^{a1}$ and $R^{b1}$ is

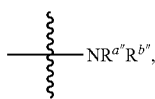

the other is

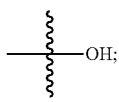

in the definition of

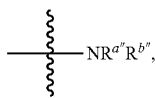

each of $R^{a''}$ and $R^{b''}$ is independently H or D; in the definiton of compound P-01, each of $R^{p1}$ and $R^{p2}$ is independently H or D.

The present invention also provides a pharmaceutical composition, the pharmaceutical composition comprises a therapeutically effective and/or prophylactically effective amount of the substance selected from the group consisting of the isoindoline derivatives having a structure of general formula (I), the pharmaceutically acceptable salt, the solvate, the polymorph, the stereoisomer, the isotopic compound, the metabolite and the prodrug thereof.

According to an embodiment of the present invention, the pharmaceutical composition may be formulated for any form of administration, including injection (intravenous), mucosal, oral administration (solid and liquid preparation), inhalation, ocular administration, rectal administration, topical or parenteral (infusion, injection, implantation, subcutaneous, vein, artery, intramuscular) administration. The pharmaceutical composition of the present invention can also be controlled release or delayed release dosage forms. Examples of solid oral preparation include but not limited to powder, capsule, caplet, soft capsule or tablet. Examples of liquid preparation administrated by oral or mucosal include but not limited to suspension, emulsion, elixir and solution. Examples of topical preparation include but not limited to emulsion, gel, ointment, cream, patch, paste, foam, lotion, drops or serum preparation. Examples of parenteral administration preparation include but not limited to injection solution, dry preparation which can be dissolved or suspended in a pharmaceutically acceptable carrier, injectable suspension and injectable emulsion. Examples of other suitable preparations of the compound having a structure of general formula (I), the pharmaceutically acceptable salt, the solvate, the polymorph, the stereoisomer, the isotopic compound, the metabolite or the prodrug thereof, include but not limited to eye drops and other ophthalmic preparations; aerosol, such as nasal spray or inhalation; liquid dosage forms suitable for parenteral administration; suppository and pastille.

The pharmaceutical composition of the present invention may further comprises a pharmaceutically acceptable excipient, such as those widely used in drug manufacture field. Excipients are mainly used to provide a safe, stable and functionalized pharmaceutical composition, and can also provide a process which makes the active ingredient dissolved at a desired rate or promotes the effective absorbtion of the active ingredients after a subject is administered. Excipients can be an inert filler, or provide some functions, such as stabilizing the overall pH value of the composition or preventing a degradation of the active ingredients of the composition.

According to an embodiment of the present invention, the pharmaceutically acceptable excipient may further comprise binder, suspending agent, emulsifier, diluent, filler, granulating agent, adhesive, disintegrating agent, lubricant, anti-adhesive agent, glidant, wetting agent, gelling agent, absorption retarder, dissolution inhibitor or reinforcing agent, adsorbent, buffer, chelating agent, preservative, colorant, flavoring agent and sweetening agent. Pharmaceutically acceptable carrier can be in many forms according to the required preparation. For example, for liquid oral preparation, suitable carriers and additives include water, glycols, oils, alcohols, flavoring agents, preservatives, colorants, etc. As another illustrative example, for solid oral preparation, suitable carriers and additives include starch, sugar, diluent, granulation agent, lubricant, adhesive, disintegrating agent, etc. The pharmaceutically acceptable carriers or excipients usually should be non-toxic. The pharmaceutical composition of the present invention may comprise one or more than one suitable carrier(s)/excipient(s). The amount and type of the excipient vary depending on the requirements. One skilled in the art can easily determine appropriate carrier(s)/excipient(s) to be added to the pharmaceutical composition of the present invention based on the contents disclosed herein.

The pharmaceutical composition of the present invention, which comprises a therapeutically effective or prophylactically effective amount of the substance selected from the group consisting of the compounds having a structure of general formula (I), the pharmaceutically acceptable salt, the solvate, the polymorph, the stereoisomer, the isotopic compound, the metabolite and the prodrug thereof, can be prepared based on the contens disclosed herein according to any processes known by one skilled in the art. For example, the pharmaceutical composition can be prepared by mixing the compound having a structure of general formula (I), the pharmaceutically acceptable salt, the solvate, the polymorph, the stereoisomer, the isotopic compound, the metabolite or the prodrug thereof, with a pharmaceutically acceptable carrier, based on common medicine pharmaceutical technology. The technology includes but not limited to a conventional mixing, dissolving, granulating, emulsifying, levigating, wrapping, embedding or freeze-dry process.

According to an embodiment of the present invention, in addition to the substance selected from the group consisting of the compounds having a structure of general formula (I), the pharmaceutically acceptable salt, the solvate, the polymorph, the stereoisomer, the isotopic compound, the metabolite and the prodrug thereof, the pharmaceutical composition may further comprise one or more than one other therapeutic agents. The other therapeutic agents that may be comprised in the pharmaceutical composition of the present invention are disclosed below. The amount and type of the other therapeutic agents depend on the disease, symptom or disorder to be treated or prevented, the severity of disease, symptom or disorder, the factors of the subject to be administered, such as age, weight, physical condition, etc, administration route, etc.

In some embodiments, the present invention relates to a controlled release preparation of the compound having a structure of general formula (I), the pharmaceutically acceptable salt, the solvate, the polymorph, the stereoisomer, the isotopic compound, the metabolite, or the prodrug thereof. As used herein, "controlled release preparation" refers to a preparation, wherein the therapeutic active ingredient of the composition has a controlled release rate, or a specific delay releasing to control the release site of the therapeutic active ingredient in the administered subject. One controlled release preparation may include a controlled release agent, such as a sustained release agent (sustained release or delayed release) and delayed release agent (delayed release).

As used herein, the term "sustained release" and "delayed release" refers to prolonging the release of the therapeutic active ingredient from the pharmaceutical composition. As used herein, the term "delayed release" refers to that the therapeutic active ingredient releases from the pharmaceutical composition at a specific site or in a required environment after the composition subjected to a subject reaches the required environment or goes through a certain period.

As used herein, the term "sustained release agent" and "delayed release agent" refers to a compound or an additive which controls the releasing of the therapeutic active ingredient from the composition, so as to make the release gradual and prolong the time of release. The sustained or delayed release agent may make the therapeutic active ingredient release within a specifically long period after the composition was subjected to a subject.

According to an embodiment of the present invention, the controlled release of the compound having a structure of general formula (I), the pharmaceutically acceptable salt, the solvate, the crystral form, the stereoisomer, the isotopic compound, the metabolite or the prodrug thereof from the composition of the present invention can be achieved by a variety of conditions, these conditions include but are not limited to pH value, temperature, enzyme, water or other physiological condition or compound. For example, the compound of the present invention may further include an enteric coating, wherein the enteric coating controls the release of the compound having a structure of general formula (I), the pharmaceutically acceptable salt, the solvate, the polymorph, the stereoisomer, the isotopic compound, the metabolite or the prodrug thereof, and allows a gradual and continuous release of which from the composition over a required period. This makes the compound have therapeutic or preventive effects over an prolonged period.

According to an embodiment of the present invention, the controlled release pharmaceutical composition may further comprise one or more than one other therapeutic agents or agentia as disclosed below.

One skilled in the art may be familiar with the appropriate controlled release preparations, sustained and delayed release agents based on the contents disclosed herein. Unrestrictive examples of the controlled release agents which can be incorporated into the pharmaceutical composition of the present invention in order to provide a controlled release composition include polymers, such as hydroxypropyl methyl cellulose, gel, permeable membrane, particle, liposome, microsphere and the combinations thereof. Any composition described herein may be suitable for the controlled release preparation, such as tablets, capsules, soft capsules and caplets.

According to an embodiment of the present invention, the therapeutic or prophylactic amount of the compound having a structure of general formula (I), the pharmaceutically acceptable salt, the solvate, the polymorph, the stereoisomer, the isotopic compound, the metabolite or the prodrug thereof, any pharmaceutical composition thereof and preparation etc., may be administrated to a subject over a period (drug delivery cycle) according to the process disclosed in the present invention, followed by a period free of the compound (non drug delivery cycle). The drug delivery cycle and non drug delivery cycle can be repeated for required times. The required length and time of the drug delivery cycle and non drug delivery cycle depend on the type and/or severity of the disease, the symptom or the disorder being treated or prevented, and the gender, age, weight of the subject, and other parameters (e.g., the subject's biological, physical and physiological conditions, etc.). One skilled in the art can sufficiently determine a suitable length and time for the drug delivery cycle and non drug delivery cycle based on the contents disclosed herein.

The compound having a structure of general formula (I), the pharmaceutically acceptable salt, the solvate, the polymorph, the stereoisomer, the isotopic compound, the metabolite or the prodrug thereof, can be used for multiple purposes including but not limited to, being used for manufacturing a medicament for treating or preventing a disease, symptom or disorder caused by TNF-α or related to the abnormal regulation of TNF-α activity.

Hence, in one general aspect, the present invention relates to a use of the therapeutically or prophylactically effective amount of the isoindoline derivative having a structure of general formula (I), the pharmaceutically acceptable salt, the solvate, the polymorph, the stereoisomer, the isotopic compound, the metabolite or the prodrug thereof in manufacturing a medicament for treating or preventing a disease, symptom or disorder. In another aspect, the invention relates to a process for treating or preventing a disease, symptom or disorder caused by TNF-α or related to abnormal regulation of TNF-α activity, the process comprises administering to a subject a therapeutically or prophylactically effective amount of the substance selected from the compound having a structure of general formula (I), the pharmaceutically acceptable salt, the solvate, the polymorph, the stereoisomer, the isotopic compound, the metabolite and the prodrug thereof. According to the process, examples of the disease, symptom or disorder to be treated or prevented include but not limited to cancers including solid tumors, TNF-α related disorders, diseases and disorders related to undesired angiogenesis, pains, macular degeneration (MD) syndrome, skin diseases, keratosis, respiratory system disease (such as pulmonary diseases), immunodeficiency diseases, central nervous system (CNS) diseases, autoimmune diseases, atherosclerosis, heredity, allergy, viruses, sleep disorders and related syndrome, inflammatory diseases, PDE-4 related diseases or IL-2 related diseases. Well-known examples of the diseases, symptoms or disorders in the field include but not limited to those described in PCT patent publications WO2012015986 and WO2006018182 and US patent publication US20100204227, some contents of which are incorporated herein by reference in their entireties.

In an embodiment, the disease, symptom or disorder is selected from neoplastic or cancerous diseases; autoimmune diseases, such as Addison's disease, ankylosing spondylitis, antiphospholipid antibody syndrome, atopic dermatitis, autoimmune alopecia areata, autoimmune hemolytic anemia, autoimmune hepatitis, autoimmune inner ear disease, autoimmune lymphoproliferative syndrome (Alps), behcet's disease, bullous pemphigoid, cardiomyopathy, celiac disease, chronic fatigue syndrome immune deficiency syndrome (CFIDS), chronic inflammatory demyelinating polyneuropathy, cicatricial pemphigoid, cold agglutinin disease, CREST syndrome, Crohn's disease, Dego's disease, dermatomyositis, juvenile dermatomyositis, discoid lupus erythematosus, eczema, essential mixed cryoglobulinemia, fibromyalgia-fiber myositis, Grave's disease, Guillain Barre syndrome, Hashimoto's thyroiditis, hidradenitis suppurativa, idiopathic pulmonary fibrosis, idiopathic thrombocytopenic purpura (ITP), idiopathic thrombocytopenic purpura, IgA nephropathy, insulin-dependent diabetes mellitus (type I), juvenile arthritis, lupus erythematosus, Meniere's disease, mixed connective tissue disease, multiple sclerosis, myasthenia gravis, pemphigus vulgaris, pernicious anemia, polyarteritis nodosa, polychondritis, polyglancular syndrome, polymyalgia rheumatica, polymyositis and dermatomyositis, primary agammaglobulinemia, primary biliary cirrhosis, psoriasis, Raynaud's phenomenon, Reiter's syndrome, rheumatic fever, rheumatoid arthritis, sarcoidosis, scleroderma, Sjogren's syndrome, systemic lupus erythematosus, stiffman syndrome, Takayasu's arteritis, temporal arteritis/giant cell arteritis, ulcerative colitis, uveitis, vasculitis, vitiligo, Wegener's granulomatosis and autoimmune Wilson's disease; pulmonary disease, such as asthma, chronic obstructive pulmonary disease; nervous system disease, such as Alzheimer's disease, Parkinson's disease, depression, epilepsy and bipolar disorder; cardiovascular disease, such as atherosclerosis, myocardial infarction, osteoporosis; metabolic disease, such as obesity, type II diabetes; adult respiratory distress syndrome; bone resorption disease, such as arthritis; hypercalcemia; graft versus host reaction; cerebral malaria; inflammatory disease, such as acne, arthritis, asthma, atherosclerosis, celiac disease, chronic prostatitis, colitis, Crohn's disease, dermatitis, diverticulitis, glomerular nephritis, hepatitis, hypersensitivity, inflammatory bowel disease, interstitial cystitis, irritable bowel syndrome (IBS), lupus erythematosus, nephritis, pelvic inflammatory disease, reperfusion injury, rheumatoid arthritis, sarcoidosis, graft rejection, ulcerative colitis, vasculitis, chronic pulmonary inflammatory disease, stroke, circulatory shock; HIV infection, AIDS and AIDS opportunistic infection; other diseases, such as, rheumatoid spondylitis, osteoarthritis and other arthritic disorder, septic shock, sepsis, endotoxic shock, graft-versus-host disease, emaciation, Cohn's disease, ulcerative colitis, leprosy nodular erythema, cAMP related disorders, such as septic shock, sepsis, endotoxic shock, hemodynamic shock and sepsis syndrome, ischemia reperfusion injury, malaria, Mycobacterial infection, meningitis, congestive heart failure, fibrotic disease, cachexia, transplant rejection, radiation injury, hyperoxia alveolar injury; viral infection, such as infections caused by herpes virus; viral conjunctivitis; or atopic dermatitis.

Examples of the neoplastic or cancerous diseases include but not limited to acute lymphoblastic leukemia, acute myeloid leukemia, acute myelogenous leukemia, karyotype acute myeloidleukemia, chronic lymphocytic leukemia, chronic myeloid leukemia, chronic granulocytic leukemia, hairy cell leukemia, myeloid leukemia, adrenocortical carcinoma, Burkitt's lymphoma, AIDS related lymphoma, cutaneous T-cell lymphoma, cutaneous B-cell lymphoma, diffuse large B-cell lymphoma, low grade follicular lymphoma, Hodgkin's lymphoma, non Hodgkin's lymphoma, multiple myeloma, smoldering myeloma, myelodysplastic syndrome, mantle cell lymphoma, indolent myeloma, chronic myeloproliferative disease, central nervous system (CNS) lymphoma, anal cancer, astrocytoma, Atypical teratoid/rhabdoid tumor, basal cell carcinoma, cholangiocarcinoma, bladder cancer, osteoma, teoid osteoma, osteochondroma, osteoblastoma, osteosarcoma, enchondroma, aneurysmal bone cyst, fibrous dysplasia of bone, chondrosarcoma, Ewing's sarcoma, fibrosarcoma, pleomorphic undifferentiated sarcoma, brain tumor, brainstem glioma, medulloblastoma, medullary epithelial tumor, pineal cell tumor, breast cancer, bronchial tumor, carcinoid tumor, cervical cancer, chordoma, colon cancer, colorectal cancer, craniopharyngioma, embryonal carcinoma, ependymoblastoma, ependymoma, esophageal cancer, olfactory neuroblastoma, extracranial germ cell tumor, gonadal germ cell tumor, cholangiocarcinoma, intraocular melanoma, retinoblastoma retinoblastoma, gallbladder carcinoma, gastric cancer, gastrointestinal stromal tumor, gestational trophoblastic tumor, glioma, head and neck cancer, liver cancer, hypopharyngeal carcinoma, intraocular melanoma, islet cell tumor, Capocci sarcoma, renal cell carcinoma, Langerhans cell histiocytosis, laryngeal cancer, lip and oral cancer, lung cancer, Merkel cell carcinoma, mesothelioma, multiple endocrine neoplasia syndrome, mycosis fungoides, nasal and sinus cancer, nasopharyngeal carcinoma, neuroblastoma, oral cancer, oropharyngeal cancer, ovarian cancer, ovarian epithelial carcinoma, ovarian germ cell tumor, low potential malignant tumor of ovary, pancreatic cancer, islet cell tumor, pancreatic carcinoma, papilloma, paraganglioma, parathyroid carcinoma, penile cancer, pharyngeal carcinoma, pheochromocytoma, plasma cell tumor, pleuropulmonary blastoma, hormone-refractory prostate cancer, androgen independent prostate cancer, androgen dependent phase IV non metastatic prostate cancer, hormone insensitive prostate cancer, chemotherapy insensitive prostate cancer, rectal cancer, retinal glioblastoma, rhabdomyosarcoma, salivary gland cancer, soft tissue sarcoma, uterine sarcoma, skin cancer (melanoma), squamous cell carcinoma, Merkel cell skin cancer, small bowel cancer, squamous cervical cancer, testicular cancer, throat cancer, thymoma and thymic carcinoma, thyroid cancer, urinary tract cancer, endometrial carcinoma, sarcoma of uterus, vagina cancer, vulvar cancer, astrocytoma, hepatocellular carcinoma, Waldenstrom macroglobulinemia, nephroblastoma.

In a preferred embodiment, the disease, symptom or disorder is selected from myelodysplastic syndrome, multiple myeloma, mantle cell lymphoma, diffuse large B cell lymphoma, central nervous system lymphoma, non Hodgkin's lymphoma; papillary and follicular thyroid carcinoma; breast cancer, prostate cancer, chronic lymphocytic leukemia, amyloidosis, type I complex regional pain syndrome, malignant melanoma, radiculopathy, myelofibrosis, glioblastoma, glioma sarcomatosum, malignant glioma, refractory plasma cell tumor, chronic myelomonocytic leukemia, follicular lymphoma, ciliary and chronic melanoma, iris melanoma, recurrent ocular melanoma, extraocular extension melanoma, solid tumor, T-cell lymphoma, erythroid lymphoma, monoblastic and monocytic leukemia; myeloid leukemia, brain tumors, meningiomas, spinal tumor, thyroid cancer, non-small cell lung cancer, ovarian cancer, renal cell carcinoma, myelofibrosis, Burkitt's lymphoma, Hodgkin's lymphoma, large cell lymphoma, astrocytoma, hepatocellular carcinoma, primary macroglobulinemia (Waldenstrom macroglobulinemia). In an embodiment, the cancer is metastatic. In another embodiment, the cancer is refractory or ineffective with the treatment of chemotherapy or radiation therapy.

The process for the treatment in the present invention comprises administering the pharmaceutical composition to a subject by any suitable processes, such as injection, mucosal, oral, inhalation, ocular, rectal, long-acting implant, liposome, emulsion or sustained release process.

One skilled in that art understands that the therapeutically effective or prophylactically effective amount of the compound used in the present invention may vary with factors, for a specific subject, such as age, diet, health, etc., the severity, complication and type of the symptom, disease or disorder to be treated or prevented, and the preparation used etc. According to the disclosures in present invention, one skilled in the art can easily determine required therapeutically effective or prophylactically effective amount of the compound administered to the subject, so as to induce the desired biological or medical response in the subject.

According to an embodiment of the present invention, the compound having a structure of general formula (I), the pharmaceutically acceptable salt, the solvate, the polymorph, the stereoisomer, the isotopic compound, the metabolite or the prodrug thereof can be used to regulate the activity or generation of TNF-α or IL-2. In an embodiment, when the term "regulate" is used to describe the activity or generation of a specific molecule, it refers to inhibiting the activity or generation of the molecule. However, in another embodiment, when the term "regulate" is used to describe the activity or generation of a specific molecule, it refers to decreasing or enhancing the activity or generation of the molecule.

Therefore, the present invention also provides a process for regulating the generation or activity of TNF-α or IL-2. According to an embodiment of the present invention, the compound having a structure of general formula (I), the pharmaceutically acceptable salt, the solvate, the polymorph, the stereoisomer, the isotopic compound, the metabolite or the prodrug thereof, or the composition thereof can be administered to a subject to regulate the generation and activity of TNF-α or IL-2, which can further be used for treating or preventing a disease, symptom or disorder associated with the abnormal regulation of TNF-α or IL-2, or characterized by the abnormal regulation of TNF- or IL-2.

In an preferred embodiment, the compound having a structure of general formula (I), the pharmaceutically acceptable salt, the solvate, the polymorph, the stereoisomer, the isotopic compound, the metabolite or the prodrug thereof, or the composition thereof is administered to a subject to regulate the generation and activity of TNF-α or IL-2 for treating or preventing cancer or inflammation.

In any processes described in the present invention, the compound having a structure of general formula (I), the pharmaceutically acceptable salt, the solvate, the polymorph, the stereoisomer, the isotopic compound, the metabolite or the prodrug thereof, can be used alone or in combination with radiation therapy or radioimmunotherapy and the like, and further may be used in combination with one or more than one therapeutic agent(s) which has pharmaceutical activity (hereinafter referred to as "other therapeutic agent(s)")

According to an embodiment of the present invention, the compound having a structure of general formula (I), the pharmaceutically acceptable salt, the solvate, the polymorph, the stereoisomer, the isotopic compound, the metabolite or the prodrug thereof used in combination with other therapeutic agent(s) can have synergistic effects when any diseases, symptoms or disorders is treated or prevented, according to the contents disclosed herein.

According to an embodiment of the present invention, the other therapeutic agent(s) may be a natural, semisynthetic or synthetic compound. In another embodiment, the other therapeutic agent(s) may be a small molecule, such as a synthetic organic or inorganic molecule, or a larger molecule or biomolecule, such as proteins or nucleic acids with pharmacologically activity. In other embodiment, the other therapeutic agent(s) may be an anti-angiogenic, immuno-regulation, immunotherapy, chemotherapeutic or hormone compound.

Examples of the other therapeutic agent(s) suitable for the present invention include, but not limited to, monoclonal and polyclonal antibody such as obinutuzumab (Gazyva®), nivolumab (Opdivo®), pembrolizumab (Keytruda®), elotuzumab, anti Her2/neu antibody (e.g. trastuzumab (trade name: Herceptin®) and pertuzumab (trade name: Omnitarg™): abciximab (trade name: ReoPro®), rituximab (trade name: Mabthera®), basiliximab (trade name: Simulect®), palivizumab (trade name: Synagis®), infliximab (trade name: Remicade®), trastuzumab (trade name: Herceptin®), alemtuzumab (trade name: Campath®), ibritumomab tiuxetan (trade name: Zevalin®), adalimumab (trade name: Humira®), omalizumab (trade name: Xolair®), tositumomab-I-131 (trade name: Bexxar®), cetuximab (trade name: Erbitux®), natalizumab (trade name: Tysabri®), tocilizumab (trade name: Actemra®), panitumumab (trade name: Vectibix®), ranibizumab (trade name: Lucentis®), eculizumab (trade name: Soliris®), certolizumab pegol (trade name: Cimzia®), golimumab (trade name: Simponi®), canakinumab (trade name: Ilaris®), ustekinumab (trade name: Stelara®), ofatumumab (trade name: Arzerra®), denosumab (trade name: Prolia®), motavizumab (trade name: Numax®), edrecolomab (trade name: Panorex®), raxibacumab (trade name: ABThrax®), belimumab (trade name: Benlysta®), ipilimumab (trade name: Yervoy®), brentuximab vedotin (trade name: Adcetris®), pertuzumab (trade name: Perjeta® or Omnitar™), ado-Trastuzumab emtansine (trade name: Adcyla®), anti-CD40 monoclonal antibody, anti-TNF-α antibody and VEGFR antibody (e.g., bevacizumab (trade name: Avastin™): Akt inhibitor: ALK inhibitor; AMPK inhibitor; antisensedigonucleotide; alkylating chemotherapeutic agent, such as nitrogen mustards (e.g., Cyclophosphamide), Mechlorethamine, HN2 (trade name: Mustardgen), Uramustine, uracil mustard, Melphalan, Chlorambucil, Ifosfamide and Bendamustine; Nitrosoureas (e.g., Carmustine), Lomustine and Streptozocin; alkyl sulfonate (e.g., Busulfan); and aziridines such as Thiotepa; chemotherapeutic agent based on platinum (e.g., Cisplatin, Carboplatin, Nedaplatin, Oxaliplatin, Satraplatin and Triplatin tetranitrate, Procarbazine, Altretamine, Dacarbazine, Mitozolomide and Temozolomide; APC inhibitor; apoptosis gene regulator; apoptosis regulator; ATM/ATR inhibitor: aurora kinase inhibitor; Axl inhibitor; Bcl-2 inhibitor; BCR/ABL antagonist; bFGF inhibitor; BTK inhibitor; casein kinase inhibitor (ICOS); cysteine proteinase inhibitor; CAR-T; CDK inhibitor such as palbociclib; ChK inhibitor; c-Kit inhibitor; c-Met inhibitor; EGFR inhibitor; c-Myc inhibitor; C-RET inhibitor; CSF-1R inhibitor; cytokine; DNA-PK inhibitor; dynein inhibitor; EGF receptor inhibitor; EGFR inhibitor; EGFR/ERBB inhibitor; liver protein receptor inhibitor; ERK inhibitor; estrogen agonist; estrogen antagonist; FAK inhibitor; FGFR inhibitor; FLT3 inhibitor; GF receptor antagonist; glutathione inhibitor; GSK-3 inhibitor; heat shock protein-90 inhibitor (e.g., 17-AAG); hemopoietic growth factor; HDAC inhibitor; androgen receptor inhibitor, androgen biosynthesis inhibitor; HER2 inhibitor; HIF inhibitor; histone deacetylase inhibitor (e.g., SAHA and LAQ 824); HSP inhibitor; IAP inhibitor; IGF-1R inhibitor; IkB kinase inhibitor; Insulin like growth factor-1 receptor inhibitor; integrin inhibitor; interferon agonist; interferon; interleukin; JAK inhibitor; JNK inhibitor; leukaemia inhibitory factor; leukocyte α interferon; lysophosphatidate acyltransferase inhibitor: matrilysin inhibitor; matrix metallo-proteinase inhibitor; Mdm2 inhibitor: MEK inhibitor: MIF inhibitor: mTOR inhibitor: oligonucleotide; P13K inhibitor (e.g., wortmannin); p38 MAPK inhibitor: p53 inhibitor: PAK inhibitor: PARP inhibitor; PDGFR inhibitor: PDK-1 inhibitor: PD-1 inhibitor; PDL-1 inhibitor phosphatase inhibitor; Pim inhibitor; PKC inhibitor; PLK inhibitor; immunomodulatory agent based on protein A; protein kinase C inhibitor; protein tyrosine phosphatase inhibitor: purine nucleoside phosphorylase inhibitor; RacGTPase inhibitor; Raf inhibitor; Ras farnesyl protein transferase inhibitor; Ras inhibitor; Ras-GAP inhibitor; ROCK inhibitor; S6 kinase inhibitor; signal transduction inhibitor; deacetylase inhibitor; Src inhibitor; STAT inhibitor; survivin inhibitor; Syk inhibitor; telomerase inhibitor; TNF-α inhibitor; topoisomerase inhibitor; Trk inhibitor; tyrosine kinase inhibitor; urokinase receptor antagonist; vascular endothelial growth factor receptor kinase inhibitor (e.g., PTK787); VDA inhibitor; VEGFR inhibitor (e.g., flk-1 specific kinase inhibitor, SU5416 and ptk787/zk222584); Wee1 inhibitor; and Wnt signaling pathway inhibitor.

Other specific therapeutic agent(s) suitable for the invention include, but are not limited to, acivicin; aclarubicin; acodazole hydrochloride; acronine; acylfulvene; adecypenol; adozelesin; aldesleukin; altretamine; ambamustine; ambomycin; ametantrone acetate; amidox; amifostine; aminolevulinic acid; amrubicin; amsacrine; anagrelide; anastrozole; andrographolide; antarelix; anthramycin; anti-dorsalizing morphogenetic protein-1; antineoplaston; aphidicolin glycinate; apurinic acid; ara-CDP-DL-PTBA; asparaginase; asperlin; asulacrine; atamestane; atrimustine; axinastatin 1; axinastatin 2: axinastatin 3; azacitidine; azasetron; azatoxin; azatyrosine; azetepa; azotomycin; balanol; batimastat; benzochlorins; benzodepa; benzoylstaurosPorine; beta lactam derivatives; β-alethine; betaclamycin B; betulinic acid; bicalutamide; bisantrene hydrochloride; bisaziridinylspermine; bisnafide dimesylate; bistratene A; bizelesin; bleomycin sulfate; bortezomib (gemcitabine); brequinar sodium; bretlate; bropirimine; budotitane; busulfan; buthionine sulfoximine; cactinomycin; calcipotriol; calphostin C; calusterone; camptothecin derivatives; capecitabine; caracemide; carbetimer; carboplatin; carboxamide-amino-triazole; carboxyamidotriazole; carboxyamidotriazole; carmustine; carubicin hydrochloride; carzelesin; castanospermine; cecropin B; cedefingol; celecoxib; cetrorelix; chlorambucil; chlorins; chloroquinoxaline sulfonamide; cicaprost; cirolemycin; cisplatin; cis-porphyrin; cladribine; clomifene analogues; clotrimazole; collismycin A; collismycin B; combretastatin A4; combretastatin derivatives; conagenin; crambescidin 816; crisnatol mesylate; crisnatol; cryptophycin 8; cryptophycin A analogues; curacin A; cyclopentanthraquinones; cyclophosphamide; cycloplatam; cyclosporin; cypemycin; cytarabine ocfosfate; cytarabine; cytostatin; dacarbazine; dacliximab; dactinomycin; daunorubicin hydrochloride; decitabine; dehydrodidemnin B; deslorelin; dexamethasone; dexifosfamide; ormaplatin; dex (ormaplatin); Dextrazoxane; dexverapamil; dezaguanine mesylate; dezaguanine; diaziquone; didemnin B; didox; diethylnorspermine; dihydro-5-azacytidine; dihydrotaxol, 9-)-; dioxamycin; diphenyl spiromustine; docetaxel; docosanol; dolasetron; doxifluridine; doxorubicin hydrochloride; doxorubicin; doxycycline; droloxifene citrate; droloxifene; dromostanolone propionate; dronabinol; duazomycin; duocarmycin SA; ebselen; ecomustine; edatrexate; edelfosine; edrecolomab; eflornithine hydrochloride; eflornithine; elemene; elotuzumab; elsamitrucin; emitefur; enloplatin; enpromate; epipropidine; epirubicin hydrochloride; epirubicin; epristeride; erbitux; erbulozole; esorubicin hydrochloride; estramustine derivatives; estramustine phosphate sodium; estramustine; etanercept; etanidazole; etoposide phosphate; etoposide; etoprine; exemestane; fadrozole hydrochloride; fadrozole; fazarabine; fenretinide; filgrastim; finasteride; flavopiridol; flezelastine; floxuridine; fluasterone; fludarabine phosphate; fludarabine; fluorocitabine; fluorodaunorunicin hydrochloride; fluorouracil; forfenimex; formestane; fosquidone; fostriecin sodium; fostriecin; fotemustine; gadolinium texaphyrin; gallium nitrate; galocitabine; ganirelix; gemcitabine hydrochloride; gemcitabine; hepsulfam; heregulin; hexamethylene bisacetamide; hydroxyurea; hypericin; ibandronic acid; ibrutinib; idarubicin hydrochloride; idarubicin; idoxifene; idramantone; ifosfamide; ilmofosine; ilomastat; imatinib, trade nam: Gleevec®; imiquimod; immunostimulant peptides; iobenguane; iododoxorubicin; ipomeanol, 4-)-; iproplatin; irinotecan hydrochloride; irinotecan; iroplact; irsogladine; isobengazole; isohomohalicondrin B; itasetron jasplakinolide; kahalalide F; lamellarin-N triacetate; lanreotide acetate; lanreotide; lapatinib, trade name: Tykerb®; leinamycin; lenograstim; lentinan sulfate; leptolstatin; letrozole; leuprolide acetate; leuprolide+estrogen+progesterone; leuprorelin; levamisole; liarozole hydrochloride; liarozole; lipophilic disaccharide peptide; lipophilic platinum analogues; lissoclinamide 7; lobaplatin; lombricine; lometrexol sodium; lometrexol; lomustine; lonidamine; losoxantrone hydrochloride; losoxantrone; loxoribine; lurtotecan; lutetium texaphyrin; lysofylline; lytic peptides; maitansine; Amannostatin A; marimastat; masoprocol; maspin; maytansine; mechlorethamine hydrochloride; megestrol acetate; melengestrol acetate; melphalan; menogaril; merbarone; mercaptopurine; meterelin; methioninase; methotrexate sodium; methotrexate; metoclopramide; metoprine; meturedepa; mifepristone; miltefosine; mirimostim; mitindomide; mitocarcin; mitocromin; mitogillin; mitoguazone; mitolactol; mitomalcin; mitomycin derivatives; mitomycin; mitonafide; mitosper; mitotane; mitotoxin fibroblast growth factor-saporinmitotoxin; mitoxantrone hydrochloride; mitoxantrone; mofarotene; molgramostim; mopidamol; mycaperoxide B; mycophenolic acid; myriaporone; N-acetyldinaline; nafarelin; nagrestip; naloxone+pentazocine; napavin; naphterpin; nartograstim; nedaplatin; nemorubicin; neridronic acid; nilutamide; nisamycin; nitrullyn; nivolumab (Opdivo®); nocodazole; nogalamycin; O6-benzylguanine; oblimersen (trade name: Genasense®; octreotide; okicenone; onapristone; ondansetron; oracin; ormaplatin; osaterone; oxaliplatin; oxaunomycin; oxisuran;

paclitaxel; paclitaxel derivatives; palauamine; palbociclib; palmitoylrhizoxin; pamidronic acid; panaxytriol; panomifene; panobinostat; parabactin; pazelliptine; pegaspargase; peldesine; peliomycin; pembrolizumab (Keytruda®); pentamustine; pentosan polysulfate sodium; pentostatin; pentrozole; peplomycin sulfate; perflubron; perfosfamide; perillyl alcohol; phenazinomycin; phenylacetate; picibanil; pilocarpine hydrochloride; pipobroman; piposulfan; pirarubicin; piritrexim; piroxantrone hydrochloride; placetin A; placetin B; platinum complex; plicamycin; plomestane; porfimer sodium; porfiromycin; prednimustine; metacortandracin; procarbazine hydrochloride; propyl bisacridone; prostaglandin J2; puromycin hydrochloride; puromycin; purpurins; pyrazofurin; pyrazoloacridine; raltitrexed; ramosetron; rapamycin; rapamycin derivatives (e.g., everolimus); merilimus; olcorolimus; ridaforolimus; sirolimus; temsirolimu (sirolimus, trade name: Torisel); umirolimus and (zotarolimus); retelliptine demethylated; rhenium Re 186 etidronate; rhizoxin; riboprine; ribozymes; RII retinamide; rohitukine; romurtide; roquinimex; rubiginone B1; ruboxyl; safingol hydrochloride; safingol; saintopin; SarCNU; sarcophytol A; sargramostim; Sdi 1 mimetics; semaxanib; semustine; simtrazene; sizofuran; sobuzoxane; sodium borocaptate; sodium phenylacetate; solverol; somatomedin binding protein; sonermin; sparfosate sodium; sparfosate; sparsomycin; spicamycin D; spirogermanium hydrochloride; spiromustine; spiroplatin; splenopentin; spongistatin 1; squalamine; stipiamide; streptonigrin; streptozocin; sulfinosine; sulofenur; suradista; suramin; swainsonine; talisomycin; tallimustine; tamoxifen methiodide; tauromustine; taxotere; taxotere; tecogalan sodium; tegafur; tellurapyrylium; teloxantrone hydrochloride; temoporfin; teniposide; teroxirone; teroxirone; tetrachlorodecaoxide; tetrazomine; thaliblastine; thiamiprine; thiocoraline; thioguanine); thiotepa; thrombopoietin mimetics; thrombopoietin; thymalfasin; thymotrinan; tiazofurin; tin ethyl etiopurpurin; tirapazamine; titanocene bichloride; topsentin; toremifene citrate; toremifene; trestolone acetate; tretinoin; triacetyluridine; triciribine phosphate; triciribine; trimetrexate glucoronate; trimetrexate; triptorelin; tropisetron; tubulozole hydrochloride; turosteride; tyrphostins; ubenimex; uracil mustard; uredepa; vapreotide; variolin B; velaresol; veramine; verdins; verteporfin; vinblastine sulfate; vincristine sulfate; vindesine sulfate; vindesine; vinepidine sulfate; vinglycinate sulfate; vinleurosine sulfate; (vinorelbine tartrate; vinorelbine; vinrosidine sulfate; vinxaltine; vinzolidine sulfate; vitaxin; vorozole; zanoterone; zeniplatin; zinostatin; 5-ethynyluracil and zorubicin hydrochloride.

In a preferred embodiment, the other therapeutic agent(s) is selected from a group consisting of elotuzumab, palbociclib, panobinostat, nivolumab, pembrolizumab, pemetrexed, topotecan, doxorubicin, bortezomib, gemcitabine, dacarbazine, dexamethasone, biaxin, vincristine, azacitidine, CAR-T, rituximab, trastuzumab, PD-1 inhibitor, PDL-1 inhibitor, HDAC inhibitor, androgen receptor inhibitor, androgen biosynthesis inhibitor, prednisone, docetaxel, clofarabine injection, Ublituximab, romidepsin, BTK inhibitor, erythropoietin, eltrombopag, minocycline and melphalan.

In an embodiment of the present invention, a composition containing the compound having a structure of general formula (I), the pharmaceutically acceptable salt, the solvate, the polymorph, the stereoisomer, the isotopic compound, the metabolite or the prodrug thereof, and one other therapeutic agent is administrated to a subject simultaneously. In another embodiment, the compound having a structure of general formula (I), the pharmaceutically acceptable salt, the solvate, the polymorph, the stereoisomer, the isotopic compound, the metabolite or the prodrug thereof, and one other therapeutic agent is administrated sequentially. In another embodiment, the compound having a structure of general formula (I), the pharmaceutically acceptable salt, the solvate, the polymorph, the stereoisomer, the isotopic compound, the metabolite or the prodrug thereof, and one other therapeutic agent is administrated separately. The other therapeutic agent can be administrated before, followed by or after the administration of the compound having a structure of general formula (I), the pharmaceutically acceptable salt, the solvate, the polymorph, the stereoisomer, the isotopic compound, the metabolite or the prodrug thereof.

One or more than one the other therapeutic agent, which can be administrated in combination with the compound having a structure of general formula (I), the pharmaceutically acceptable salt, the solvate, the polymorph, the stereoisomer, the isotopic compound, the metabolite or the prodrug thereof, depends on a variety of factors, such as the disease, symptom or disorder to be treated or prevented and so on. One skilled in the art can easily determine suitable the other therapeutic agent to be administrated in combination with the compound having a structure of general formula (I), the pharmaceutically acceptable salt, the solvate, the polymorph, the stereoisomer, the isotopic compound, the metabolite or the prodrug thereof, based on the contents disclosed.

The therapeutically effective amount of the other therapeutic agent used in the process of the present invention is known by one skilled in the art, and administration guidance can refer to the patents and applications published as well as Wells et al, eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000) and other medical literatures cited herein. However, one skilled in the art is capable of determining the optimal dose range of the other therapeutic agent.

According to an embodiment of the present invention, when being administered in combination with other therapeutic agent(s), the therapeutically effective amount of the compound having a structure of general formula (I), the pharmaceutically acceptable salt, the solvate, the polymorph, the stereoisomer, the isotopic compound, the metabolite or the prodrug thereof is less than the required therapeutically effective amount of the compound having a structure of general formula (I), the pharmaceutically acceptable salt, the solvate, the polymorph, the stereoisomer, the isotopic compound, the metabolite or the prodrug thereof when not in combination with other therapeutic agent(s). In another embodiment, the therapeutically effective amount of the other therapeutic agent(s) is less than that when the administration is free of the compound having a structure of general formula (I), the pharmaceutically acceptable salt, the solvate, the polymorph, the stereoisomer, the isotopic compound, the metabolite or the prodrug thereof. According to this, the side effects related to any drugs can be reduced to the lowest. Other potential advantages are, for example, improving the administration solution and/or lowering the cost of the drugs, obvious to one skilled in the art.

According to an embodiment of the present invention, when the compound having a structure of general formula (I), the pharmaceutically acceptable salt, the solvate, the polymorph, the stereoisomer, the isotopic compound, the metabolite or the prodrug thereof, and the other therapeutic agent(s) are administered to a subject to treat or prevent a disease, symptom or disorder, the compound having a structure of general formula (I), the pharmaceutically acceptable salt, the solvate, the polymorph, the stereoisomer, the isotopic compound, the metabolite or the prodrug thereof, and the other therapeutic agent(s) can be administered in the same way or different ways. The other therapeutic agent(s) can be administered in any ways described herein, including but not limited to, oral, inhalation, injection, ocular, mucosal, rectal, emulsion, liposome, long-acting implant or sustained release administration. The specific administration of the other therapeutic agent(s) depends on itself and the preparation, and the disease, symptom or disorder to be prevented or treated. According to the disclosures herein, one skilled in the art can determine the administration of other therapeutic agent(s).

This application refers or describes a variety of publications, literatures and patents, the purpose of citing or describing these references or incorporating these references by their enterties or discussing these references is to state the background of the present invention, not to mean that the contents of these references contribute to a part of the prior art of the present invention.

Unless otherwise defined, the technical and scientific terms used herein have the same meanings as those commonly understood by one skilled in the art. Otherwise, they have the meanings specified in the present description. All the patents, patent applications which have already been disclosed, and publications cited herein are incorporated herein by reference, just like elaborating in detailed herein. It should be noted that, unless otherwise indicated herein, the singular form used herein and in the attached claims contains a plural meaning.

As used herein, when the specific salt, composition, and excipient etc. are "pharmaceutical acceptable", it refers to that the salt, the composition, the excipient etc, are generally non-toxic, safe, and suitable for administering to a subject, preferably mammalian, more preferably human.

The term "pharmaceutically acceptable salt" herein refers to a pharmaceutically acceptable organic or inorganic salt. Examples of the salt include but are not limited to, sulfate, citrate, acetate, oxalate, chloride, bromide, iodide, nitrate, hydrosulfate, phosphate, acid phosphate, isonicotinic acid salt, lactate, salicylic acid salt, acid citrate, tartrate, oleate, tannic acid salt, pantothenate, bitartrate, ascorbate, succinate, maleate, gentisinate, fumarate, gluconate, glucuronate salt, saccharate, formate, benzoate, glutamate, methane sulfonate, ethane sulfonate, benzene sulfonate, p-toluene sulfonate, and embonate (i.e. 1-1-methylene-bis(2-hydroxy-3-naphthoate)). The compounds of the present invention may be used to form pharmaceutically acceptable salts with various amino acids. Suitable alkali salt includes but is not limited to, aluminum salt, calcium salt, lithium salt, magnesium salt, potassium salt, sodium salt, zinc salt, bismuth salt and diethanolamine salt. Review regarding pharmaceutically acceptable salts refers to Handbook of Pharmaceutical Salts: Properties, Selection, and Use (P. Heinrich Stahl and Camille G. Wermuth, ed., Wiley-VCH, 2002).

As used herein, the term "metabolite" refers to an active substance produced after the chemical structure of a drug molecule changes in vivo, the active substance is generally a derivative of the aforementioned drug molecule, and also can be chemically modified.

As used herein and unless otherwise specified, the term "polymorph" refers to one or more than one kind(s) of crystal structure formed by the different arrangement of molecules in the lattice space when crystallizing.

As used herein, the term "solvate" refers to a crystal form of the compound having a structure of general formula (I), the pharmaceutically acceptable salt, the polymorph, the stereoisomer, the isotopic compound, the metabolite or the prodrug thereof, which further has one or more than one kind(s) of solvent molecule(s) incorporated into the crystal structure. The solvate may include a stoichiometric amount or a non stoichiometric amount of solvent, and the solvent molecule in the solvent may exist in an ordered or non ordered arrangement. The solvate containing a non stoichiometric amount of solvent molecules may be formed by losing at least one solvent molecule (but not all) from the solvate. In a particular embodiment, a solvate refers to a hydrate, which means the crystal of the compound further includes water molecule, and water is used as a solvent.

As used herein and unless otherwise specified, the term "prodrug" refers to a derivative of the compound comprising a biologically reactive functional group, the biological reactive functional group can be cleaved from the compound or react in other ways to give the compound under biological conditions (in vivo or in vitro). Usually, the prodrug is inactive, or at least has lower activity than the compound, which makes the compound exhibit its activity until it is cleaved from the biologically reactive functional group. The biologically reactive functional group can be hydrolyzed or oxidized under biological conditions to give the compound. For instance, the prodrug may contain a biologically hydrolysable group. Examples of the biologically hydrolysable group include, but are not limited to, a biologically hydrolysable phosphate, a biologically hydrolysable ester, a biologically hydrolysable amide, a biologically hydrolysable carbonic ester, a biologically hydrolysable carbamate and a biologically hydrolysable ureide. Review regarding the prodrug refers to, such as J. Rautio et al., Nature Reviews Drug Discovery (2008) 7, 255-270 and Prodrugs: Challenges 和 Rewards (V. Stella et al. ed., Springer, 2007).

The compound having a structure of general formula (I) in the present invention, the pharmaceutically acceptable salt, the solvate, the polymorph, the stereoisomer, the isotopic compound, the metabolite or the prodrug thereof, can contain one or more than one asymmetric centers ("stereoisomer"). As used herein, the term "stereoisomer" refers to all stereoisomers including enantiomer, diastereoisomer, epimer, endo-exo isomer, atropisomer, regioisomer, cis- and trans-isomer. The "stereoisomer" herein also includes "pure stereoisomer" and "enriched stereoisomer" or "racemic isomer" of the various aforementioned stereoisomers. These stereoisomers can be prepared according to an asymmetric synthesis process, or separated, purified and enriched by a chiral separation process (including but not limited to thin layer chromatography, rotating chromatography, column chromatography, gas chromatography, high pressure liquid chromatography, etc.), as well as obtained by chiral separation by means of bonding (chemical binding etc.) or salifying (physical binding etc.) with other chiral compound(s). The term "pure stereoisomer" herein refers to that the mass content of a stereoisomer of the compound is no less than 95% relative to other stereoisomers of the compound. The term "enriched stereoisomer" herein refers to that the mass content of a stereoisomer of the compound is no less than 50% relative to other stereoisomers of the compound. The term "racemic isomer" herein refers to that the mass content of a stereoisomer of the compound is equal to that of other stereoisomers of the compound.

The term "isotopic compound" used herein refers to that there is one or more than one atomic isotope(s) with natural or non natural abundance contained in the compound having a structure of general formula (I), the pharmaceutically acceptable salt, the solvate, the polymorph, the stereoisomer, the isotopic compound, the metabolite or the prodrug thereof. Atomic isotopes with non natural abundance include, but are not limited to, deuterium ($^2$H or D), tritium ($^3$H or T), iodine-125 ($^{125}$I), phosphorus-32 ($^{32}$P), carbon-13 ($^{13}$C) or carbon-14 ($^{14}$C). The aforementioned isotopic compound can also be used as a therapeutic or diagnostic agent (i.e., internal developing agent) or research tool. All the isotopic variants of the compound of the present invention, whether or not radioactive, are included in the scope of the present invention.

The term "isotope enriched" used herein refers to that there is one or more than one atomic isotope(s) with natural or non natural abundance contained in the compound having a structure of general formula (I), the pharmaceutically acceptable salt, the solvate, the polymorph, the stereoisomer, the isotopic compound, the metabolite or the prodrug thereof. The term "isotope enriched" also refers to that the compound having a structure of general formula (I), the pharmaceutically acceptable salt, the solvate, the polymorph, the stereoisomer, the isotopic compound, the metabolite or the prodrug thereof, contains at least one isotopic atom with non natural abundance.

As used herein, the term "subject" refers to any animal to be treated or treated with the compound or the composition according to an embodiment of the present invention, mammalian is preferred, and human is optimal. The term "mammalian" used herein includes any mammals. Examples of mammal include but are not limited to cattle, horse, sheep, pig, cat, dog, mice, rat, rabbit, guinea pig, monkey, human, etc., human is optimal.

In an embodiment, the terms "treat" and "treating" refers to an improvement, prevention or reversal of a disease or condition or at least one of identifiable symptoms thereof, such as treating cancer, disorders related to undesirable angiogenesis or TNF-α by reducing or stabilizing the symptoms of cancer or a disease. In another embodiment, "treat" or "treating" refers to an improvement, prevention or reversal of at least one measurable body parameter of a disease or condition which is being treated, the disease or condition may not be identified in mammal, for example, treating cancer or a disorder related to undesired angiogenesis or TNF-α by inhibiting the generation of TNF-α or modulating the activity of TNF-α. However, in another embodiment, the term "treat" or "treating" refers to slower the progress of a disease or symptom, in physical, such as stabilizing identifiable symptoms, or in physiological, such as stabilizing physical parameters, or in both. In another embodiment, the term "treat" or "treating" refers to delaying the development of a disease or symptom.

In some embodiments, the compound is administered for a prevention purpose. As used herein, "prevent" or "preventing" refers to a reduction in a risk of given disease or symptom. In a preferred embodiment, the designated compound is administered to a subject for a prevention purpose, such as the subject with family history or tendency of cancer or autoimmune disease.

As used herein, "therapeutically effective amount" refers to an amount of the compound or the composition that can cause a biological or medical response (which is sought by researchers, veterinarians, physicians, or other clinicians) for an organism, an animal or a person, where may include relieving symptoms of the disease or symptom which is being treated. In a preferred embodiment, the therapeutically effective amount is an amount which is enough to effectively treat, improvedly treat or prevent cancer, symptom or disorder related to undesirable vascular or TNF-α.

The term "prophylactically effective amount" refers to an amount of an active compound or agent (sought by researchers, veterinarians, physicians or other clinicians), that can inhibit the development of a disease in a subject. A prophylactically effective amount of a compound refers to an amount of a therapeutic agent used alone or in combination with other active compound, which can provide a therapeutic benefit for treating or preventing the disease, symptom or disorder.

Unless otherwise specified, the singular form of the term used herein, "a" or "an", also includes a plural meaning.

Unless otherwise specified, the term "or" or "and" used herein refers to "and/or".

Unless otherwise specified, the " " or "-" in the specific group herein refers to a connection position.

Each preferred conditions aforementioned can be combined randomly without departing from the common knowledge in the art thereby forming various preferred embodiments of the present invention.

The reagents and starting materials used herein are all commercially available.

The positive effects achieved by the present invention are that the isoindoline derivative having a structure of general formula (I) can regulate the generation and/or activity of cytokines (e.g. TNF-α) so as to effectively treat cancer and inflammatory diseases.

EXAMPLES

Example 1. Compound I-28

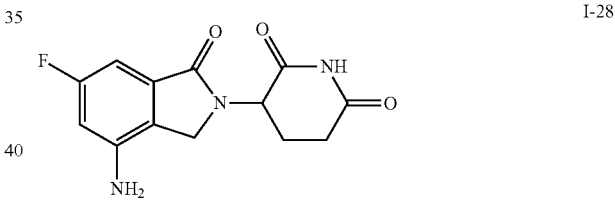

I-28

Step A. To a mixture of 5-fluoro-2-methylbenzoic acid (6.0 g, 39.0 mmol) in 98% H$_2$SO$_4$ (60 mL) was added 65% HNO$_3$ (3.3 g, 50.7 mmol) at −5 to 0° C., then the resulting mixture was stirred for 1 h at this temperature. The mixture was poured into 200 g ice-water, then extracted by MTBE (150 mL×3). The combined organic phase was washed with brine (20 mL), dried over Na$_2$SO$_4$, filtered and evaporated to dryness via rotary evaporation to afford 5-Fluoro-2-methyl-3nitro-benzoic acid (7.0 g, crude) as a yellow solid, which was used in the next step without further purification.

$^1$H NMR (DMSO-d$_6$. 300M Hz): δ 8.05 (dd, J=8.1 Hz, 3.0 Hz, 1H), 7.85 (dd, J=8.7, 3.0 Hz, 1H), 2.44 (s, 3H).

Step B. To a mixture of 5-Fluoro-2-methyl-3-nitro-benzoic acid (7.0 g, crude) in MeOH (70 mL) was added 98% H$_2$SO$_4$ (2 mL), then the resulting mixture was stirred for overnight at 70° C. The mixture was concentrated, then the residue was diluted by H$_2$O (50 mL) and EtOAc (150 mL). The aqueous layer was extracted by EtOAc (100 mL×2), the combined organic phase was washed with brine (30 mL), dried over Na$_2$SO$_4$, filtered and evaporated to dryness via rotary evaporation. The residue was purified by column chromatography on silica gel eluted with (PE:EtOAc=10:1 to 3:1) to afford methyl 5-fluoro-2-methyl-3-nitrobenzoate (3.5 g, yield 42%, two steps) as a light yellow solid.

¹H NMR (DMSO-d₆. 300M Hz): δ 8.10 (dd, J=8.1, 3.0 Hz, 1H), 7.88 (dd, J=8.7, 3.0 Hz, 1H), 3.86 (s, 3H), 2.41 (s, 3H).

Step C. To a mixture of methyl 5-fluoro-2-methyl-3-nitrobenzoate (3.5 g, 16.4 mmol) and benzoyl peroxide (388 mg, 1.6 mmol) in CCl₄ (40 mL) was added NBS (3.2 g, 18.1 mmol), then the resulting mixture was stirred for overnight at 95° C. The mixture was cooled to room temperature and filtered, and the filtrate was washed wish brine (20 mL) dried over Na₂SO₄, filtered and evaporated to dryness via rotary evaporation. The residue was purified by column chromatography on silica gel eluted with (PE:EtOAc=10:1-5:1) to afford methyl 2-(bromomethyl)-5-fluoro-3-nitrobenzoate (3.7 g, yield 77%) as a light yellow oil.

¹H NMR (DMSO-d₆, 300 MHz): δ 8.21-8.25 (dd, J=8.1, 3.0 Hz, 1H), 7.99-8.03 (dd, J=8.7, 2.7 Hz, 1H), 4.97 (s, 2H), 3.93 (s, 3H).

Step D. To a mixture of 3-aminopiperidine-2,6-dione hydrochloride (2.5 g, 15.1 mmol) and KHCO₃ (3.5 g, 34.2 mmol) in CH₃CN (80 mL) was added methyl 2-(bromomethyl)-5-fluoro-3-nitrobenzoate (4.0 g, 13.7 mmol), then the resulting mixture was stirred for overnight at 95° C. The mixture was concentrated, then poured into 100 g ice-water, then mixture was stirred for 0.5 h. The mixture was filtered and the solid was washed with H₂O (50 mL×3), dried to afford compound I-28A [3-(6-fluoro-4-nitro-1-oxoisoindolin-2-yl)piperidine-2,6-dione] (3.8 g, yield 90%) as a yellow solid.

¹H NMR (DMSO-d₆. 400 MHz): δ 11.04 (s, 1H), 8.38 (dd, J=8.8, 2.4 Hz, 1H), 8.11 (dd, J=6.8, 2.4 Hz, 1H), 5.18 (dd, J=13.2, 5.2 Hz, 1H), 4.88 (d, J=19.2 Hz, 1H), 4.78 (d, J=19.2 Hz, 1H), 2.87-2.96 (m, 1H), 2.54-2.63 (m, 2H), 2.01-2.05 (m, 1H).

Step E. A mixture of compound I-28A (2.8 g, 9.1 mmol) and Pd/C (10%, 280 mg, 50% water) in DMF (30 mL) was stirred for 6 h under 50 Psi H₂ at room temperature. The mixture was filtered and solid was washed with DMF (50 mL×1). The filtrate was concentrated then poured into H₂O (100 mL) and stirred for 0.5 h. The mixture was filtered, the solid was washed with H₂O (50 mL×3), dried, to afford a crude product (2.1 g, yield: 84%) as an off-white solid. 200 mg of the above crude product was purified by Prep-HPLC to afford I-28 [3-(4-amino-6-fluoro-1-oxoisoindolin-2-yl)piperidine-2,6-dione] (148.8 mg) as an off-white solid.

¹H NMR (DMSO-d₆. 400 MHz): 11.01 (s, 1H), 6.55-6.63 (m, 2H), 5.79 (s, 2H), 5.10 (dd, J=13.2, 4.8 Hz, 1H), 4.18 (d, J=17.2 Hz, 1H), 4.08 (d, J=17.2 Hz, 1H), 2.87-2.95 (m, 1H), 2.59-2.63 (m, 1H), 2.27-2.31 (m, 1H), 2.02-2.06 (m, 1H). LCMS: 278.1 ([M+1]⁺).

Compounds I-01 to I-27 can be prepared according to the method described in Example 1.

Example 2. Synthesis of Compound I-29 and I-30

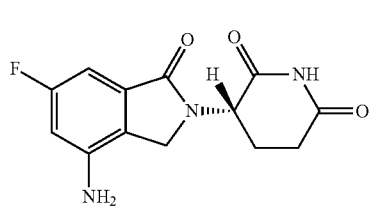

I-29

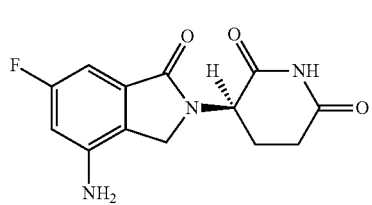

I-30

800 mg of compound I-28 in 28 mL DMF was separated by chiral HPLC (Column: CHIRALPAK IA, 5 μm, 30×250 mm; Mobile Phase: CH₃CN; Flow Rate: 21 mL/min; Temperature: 26-28° C.; Wave Length: 230 nm; Injection: 350 uL) to afford 300 mg I-29 and 260 mg I-30.

I-29: [Rt-4.81 min; >99% ee; ¹H NMR (DMSO-d₆. 400 MHz): δ 11.01 (s, 1H), 6.55-6.63 (m, 2H), 5.80 (s, 2H), 5.07-5.12 (m, 1H), 4.18 (d, J=16.8 Hz, 1H), 4.08 (d, J=16.8 Hz, 1H), 2.87-2.93 (m, 1H), 2.59-2.63 (m, 1H), 2.27-2.31 (m, 1H), 2.02-2.07 (m, 1H). LCMS: 278.1 ([M+1]⁺)].

I-30: [Rt=7.08 min; >97.5% ee; ¹H NMR (DMSO-d₆. 400 MHz): δ 11.01 (s, 1H), 6.55-6.63 (m, 2H), 5.79 (s, 2H), 5.08-5.12 (m, 1H), 4.19 (d, J=17.2 Hz, 1H), 4.08 (d, J=17.2 Hz, 1H), 2.87-2.95 (m, 1H), 2.59-2.64 (m, 1H), 2.27-2.31 (m, 1H), 2.04-2.07 (m, 1H). LCMS: 278.1 ([M+1]⁺)].

Example 3, Compound I-31 and I-32

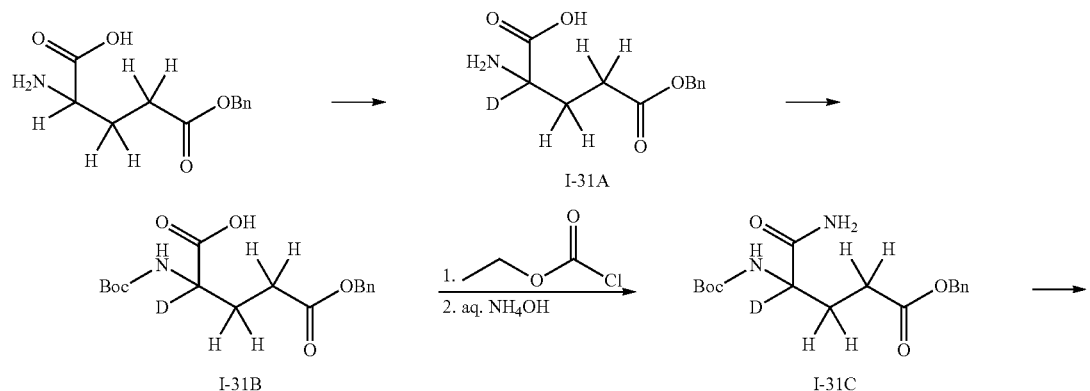

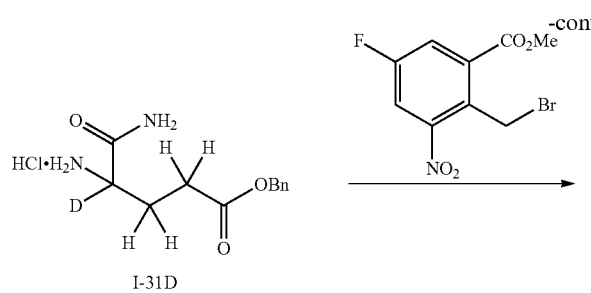
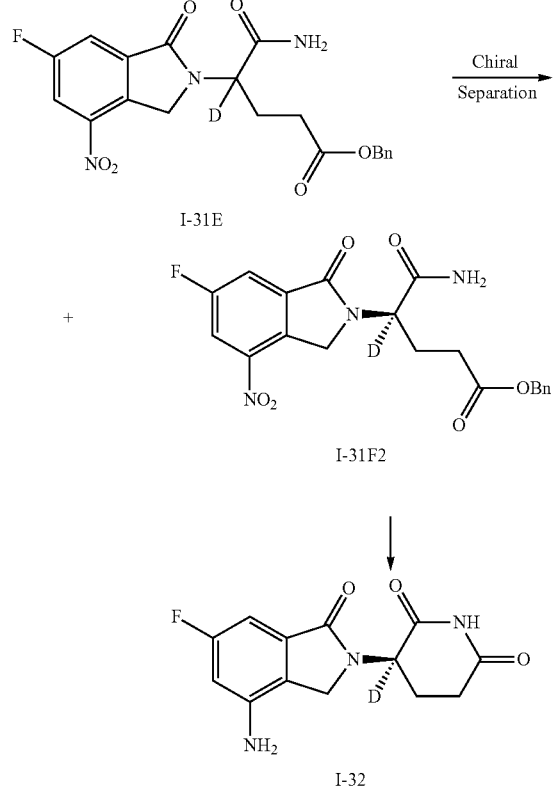

Step A: To a solvent of (S)-2-amino-5-(benzyloxy)-5-oxopentanoic acid (50.0 g, 221 mmol) in CH₃CO₂D (150 mL) was added benzaldehyde (1.34 g, 12.6 mmol), the mixture was heated to 65° C. and stirred for 18 hours. The reaction mixture was concentrated and the resulted solid was triturated with MeOH (25 mL), CH₃CN (50 mL) and t-BuOMe (200 mL) for 30 mins, the filtered cake was rinsed with t-BuOMe (200 mL) and dried. The product was subject to the same procedure to afford compound I-31A, (32.5 g, yield=65%).

$^1$H NMR (CD₃OD+D₂O, 300 MHz): δ 7.33-7.42 (m, 5H), 5.14 (s, 2H), 3.70 (t, <0.05H), 2.58-2.63 (m, 2H), 2.13-2.17 (m, 2H).

Step B: To a mixture of THF (600 mL) and H₂O (600 mL) was added compound I-31A (32.5 g, 137 mmol). NaHCO₃ (12.6 g, 150 mmol) was added to the above mixture in ice-water bath, After 10 min, (BOC)₂O (32.7 g, 150 mmol) was added slowly, the reaction mixture was stirred for 4 hours at room temperature. THF was removed under reduced pressure (in vacuum), Sat. NaHCO₃ solution was added to dissolve the residue, the mixture was extract with t-BuOMe (200 mL×2). The aqueous phase was cooled with ice-water bath and adjusted to PH=1 with 3N HCl, then extracted with EtOAc (300 mL×2), combined organic layers was dried over Na₂SO₄, filtrated and concentrated to afford I-31B (46.5 g, yield 100%) as white solid, which was used in the next step without further purification.

$^1$H NMR (CD₃OD, 300 MHz): δ 7.29-7.35 (m, 5H), 5.12 (s, 2H), 4.13 (br s, 0.05H), 2.45-2.50 (m, 2H), 2.12-2.21 (m, 1H), 1.85-1.94 (m, 1H), 1.42 (s, 9H).

Step C: To a solution of I-31B (46.5 g, 137 mmol) in THF (500 mL), cooled to 5° C., was added N-methyl morpholine (NMM) (16.5 g, 164 mmol) and Ethyl chlorocarbonate (17.8 g, 164 mmol) slowly. The reaction was stirred at 0-5° C. for 1 hour. 150 mL of saturated NH₃.H₂O was added to the reaction mixture and then stirred for 2 hours at room temperature. EtOAc (200 mL) was added and the organic phase was separated, aqueous layer was extracted with EtOAc (200 mL), the combined the organic phase was washed with NaHCO₃ aqueous (200 mL×2) and brine (200 mL) as sequence, dried over Na₂SO₄, filtered and concentrated to afford I-31C (41 g, 90%) as white solid.

$^1$H NMR (DMSO-d₆, 300 MHz): δ 7.30-7.41 (m, 5H), 7.24 (s, 1H), 6.99 (s, 1H), 6.79 (s, 1H), 5.06 (s, 2H), 3.90 (m, <0.05H), 2.33-2.38 (m, 2H), 1.70-1.94 (m, 2H), 1.35 (s, 9H).

Step D: To a solution of I-31C (41.0 g, 121 mmol) in 1,4-dioxane (200 mL) was added a solution of 6N HCl in 1,4-dioxane (300 mL), the mixture was stirred for 2 hours at room temperature. The reaction mixture was concentrated under reduced pressure (in vacuum) to afford a solid, which was triturated with t-BuOMe (200 mL), and filtrated and dried to afford product I-31D (31.3 g, yield 95%) as a white solid.

$^1$H NMR (DMSO-d₆, 400 MHz): δ 8.37 (br s, 3H), 8.04 (s, 1H), 7.56 (s, 1H), 7.33-7.38 (m, 5H), 5.10 (s, 2H), 3.77 (t, <0.05H), 2.48-2.52 (m, 2H), 2.01-2.05 (m, 2H).

Step E: A mixture of methyl 2-(bromomethyl)-5-fluoro-3-nitrobenzoate (31.8 g, 108.9 mmol) and compound I-31D (29.7 g, 109 mmol) and Et₃N (22.1 g, 218 mmol) in CH₃CN (550 mL) was stirred at 75° C. for overnight. The mixture was concentrated. The residue was triturated with CH₃CN (100 mL) to afford Compound I-31E (34.5 g, yield 76.2%) as a pale yellow solid.

¹H NMR (DMSO-d₆. 300 MHz): δ 8.33 (dd, J=8.7, 2.4 Hz, 1H), 8.04 (dd, J=6.9, 2.4 Hz, 1H), 7.66 (s, 1H), 7.26-7.36 (m, 6H), 4.82-5.05 (m, 4H), 2.20-2.39 (m, 3H), 2.06-2.15 (m, 1H).

Step F: Compound I-31E was subjected to chiral HPLC (Column: DAICEL CHIRALPAK IA, 10 μm, 25×250 mm; Mobile Phase: MeOH/DCM=80/20(V/V); Flow Rate: 30 mL/min; Temperature: 35° C.; Wave Length: 254 nm) separation to afford two compounds I-31F1 [¹H NMR (DMSO-d₆. 300 MHz): δ 8.31-8.35 (m, 1H), 8.03 (dd, J=7.2, 2.1 Hz, 1H), 7.66 (s, 1H), 7.29-7.35 (m, 6H), 4.83-5.04 (m, 4H), 2.22-2.40 (m, 3H), 2.06-2.16 (m, 1H)] and I-31F2 [¹H NMR (DMSO-d₆. 300 MHz): δ 8.33 (dd, J=9.3, 2.4 Hz, 1H), 8.03 (dd, J=7.2, 2.4 Hz, 1H), 7.67 (s, 1H), 7.29-7.36 (m, 6H), 4.83-5.05 (m, 4H), 2.20-2.42 (m, 3H), 2.09-2.16 (m, 1H).].

Compound I-32: A mixture of compound I-31F2, (2.2 g, 5.3 mmol) and Pd/C (10%, 200 mg, 50% water) in anhydrous MeOH (30 mL) was stirred for 4 h under 50 Psi H₂ at room temperature. The mixture was filtered and filtrate was concentrated, the resulting solid was added into DCE (15 mL) and stirred for 5 mins, then the mixture was concentrated to afford an off-white solid residue (1.4 g). The above solid (1.1 g, 3.7 mmol) was dissolved in dry THF (10 mL) and DCE (40 mL), and then SOCl₂ (0.74 g, 9.3 mmol) was slowly added to the mixture at −30° C., after stirring for 2 h, pyridine (1.1 g, 9.3 mmol) was added and stirred for 40 mins at this temperature, Et₃N (1.3 g, 13 mmol) was added and then the mixture was stirred for 2 h. H₂O (0.1 mL) was added, and then the mixture was concentrated to dryness, the residue was dissolved in H₂O (5 mL) and extracted with EtOAc (70 mL×5), dried over Na₂SO₄, filtered and concentrated. The residue was purified by Prep-HPLC to afford I-32 (340 mg, yield 33%, ee: 99%) as a pale green solid.

¹H NMR (DMSO-d₆. 400 MHz): 11.00 (s, 1H), 6.56-6.61 (m, 2H), 5.78 (s, 2H), 5.05-5.11 (m, 0.05H), 4.17 (d, J=17.1 Hz, 1H), 4.05 (d, J=17.1 Hz, 1H), 2.84-2.96 (m, 1H), 2.56-2.62 (m, 1H), 2.20-2.32 (m, 1H), 1.98-2.05 (m, 1H). LCMS: 279.1 ([M+1]⁺).

Compound I-31: Following the same synthetic method as compound I-32, compound I-31F1 was converted to I-31 (99% ee). ¹H NMR (DMSO-d₆. 400 MHz): 10.99 (s, 1H), 6.52-6.61 (m, 2H), 5.71 (br s, 2H), 5.08 (dd, J=18.0, 7.2 Hz, 0.04H) 4.17 (d, J=17.4 Hz, 1H), 4.06 (d, J=17.4 Hz, 1H), 2.83-2.96 (m, 1H), 2.47-2.62 (m, 1H), 2.21-2.32 (m, 1H), 1.98-2.05 (m, 1H). LCMS: 279.1 ([M+1]⁺).

Example 4: Compound I-01

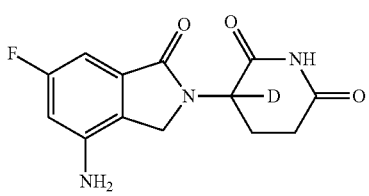

I-01

Following the procedure in above mentioned Example 3, compound I-01 of example 4 was obtained using racemic I-31E.

¹H NMR (DMSO-d₆. 300 MHz): δ 10.94 (br s, 1H), 6.52-6.61 (m, 2H), 5.78 (s, 2H), 5.05-5.11 (m, 0.05H), 4.16 (d, J=16.8 Hz, 1H), 4.05 (d, J=16.8 Hz, 1H), 2.84-2.96 (m, 1H), 2.54-2.62 (m, 1H), 2.21-2.31 (m, 1H), 1.98-2.04 (m, 1H). LCMS: 279.1 ([M+1]⁺).

Compounds I-33 to I-56 can be prepared according to the synthetic method shown in Example 2 or 3 with appropriate starting material.

Example 5: Compound A195

3-(4-((2-fluoro-5-methoxybenzyl)amino)-1-oxoisoindolin-2-yl)piperidine-2,6-dione, A195

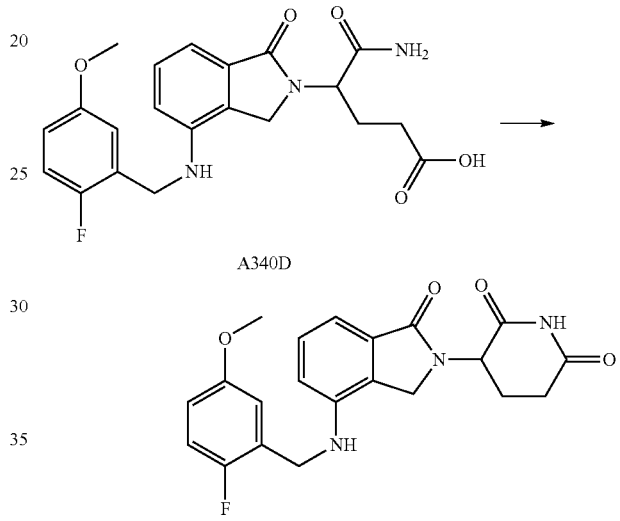

To a solution of A340D (40 mg, 0.096 mmol) in CH₃CN (3 mL) was added CDI (20 mg, 0.13 mmol). The reaction mixture was stirred overnight at 90° C. under N2. After concentration under reduced pressure, the residue was dissolved in DCM (30 mL), washed with 0.1N HCl (10 mL), sat. aq. NaHCO₃ (10 mL), and then sat. NaCl (10 mL), dried over Na₂SO₄, filtered and concentrated under reduced pressure. The crude product was then purified by prep-TLC (DCM/MeOH=25:1) 2 times to give compound A195 (46 mg, yield 81%) as white solid.

¹H NMR (DMSO-d₆, 300 MHz): δ 10.98 (s, 1H), 7.23 (t, J=7.8 Hz, 1H), 7.11 (t, J=9.6 Hz, 1H), 6.90-6.95 (m, 2H), 6.78-6.84 (m, 1H), 6.66 (d, J=7.8 Hz, 1H), 6.24 (t, J=5.7 Hz, 1H), 5.10 (dd, J=13.2, 5.4 Hz, 1H), 4.36 (d, J=5.4 Hz, 2H), 4.30 (d, J=17.7 Hz, 1H), 4.17 (d, J=17.7 Hz, 1H), 3.65 (s, 3H), 2.85-2.97 (m, 1H), 2.57-2.64 (m, 1H), 2.24-2.36 (m, 1H), 2.00-2.07 (m, 1H). LCMS: 398.1 ([M+1]⁺).

Compounds of examples 6-7 were prepared according to the synthetic method shown in example 5 with corresponding starting materials to replace A340D.

Example 6: Compound A196

3-(4-((2-fluoro-3-methoxybenzyl)amino)-1-ox-oisoindolin-2-yl)piperidine-2,6-dione A196

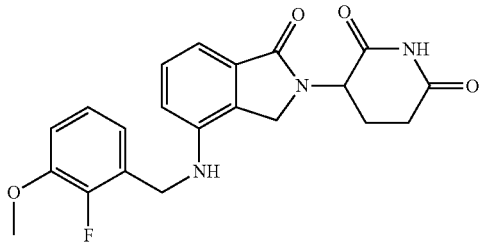

¹H NMR (DMSO-d₆, 300 MHz): δ 11.00 (s, 1H), 7.21 (t, J=7.8 Hz, 1H), 7.00-7.04 (m, 2H), 6.90-6.95 (m, 2H), 6.62 (d, J=7.8 Hz, 1H), 6.30 (t, J=6.0 Hz, 1H), 5.10 (dd, J=13.2, 5.7 Hz, 1H), 4.40 (d, J=6.0 Hz, 2H), 4.28 (d, J=17.4 Hz, 1H), 4.16 (d, J=17.4 Hz, 1H), 3.81 (s, 3H), 2.85-2.97 (m, 1H), 2.56-2.63 (m, 1H), 2.26-2.32 (m, 1H), 1.99-2.07 (m, 1H). LCMS: 398.1 ([M+1]⁺).

Example 7: Compound A197

3-(4-((2-fluoro-3-methoxybenzyl)amino)-1-ox-oisoindolin-2-yl)piperidine-2,6-dione A197

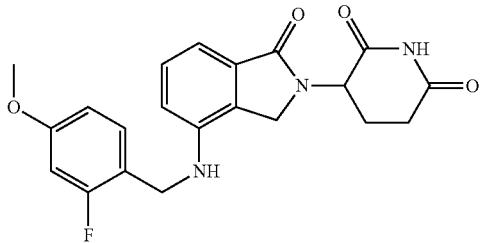 [SMILES: COc1ccc(CNc2cccc3c2CN(C2CCC(=O)NC2=O)C3=O)c(F)c1]

¹H NMR (DMSO-d₆, 300 MHz): δ 11.00 (s, 1H), 7.19-7.31 (m, 2H), 6.92 (d, J=7.2 Hz, 1H), 6.80 (dd, J=12.0, 2.4 Hz, 1H), 6.71 (dd, J=8.4, 2.4 Hz, 1H), 6.65 (d, J=7.8 Hz, 1H), 6.20 (t, J=5.7 Hz, 1H), 5.10 (dd, J=13.2, 5.1 Hz, 1H), 4.24-4.33 (m, 3H), 4.14 (d, J=17.1 Hz, 1H), 3.72 (s, 3H), 2.85-2.97 (m, 1H), 2.57-2.62 (m, 1H), 2.21-2.36 (m, 1H), 1.98-2.05 (m, 1H). LCMS: 398.1 ([M+1]⁺).

Example 8: Compound A318

3-(6-fluoro-4-((2-fluoro-3-methoxybenzyl)amino)-1-oxoisoindolin-2-yl)-piperidine-2,6-dione A318

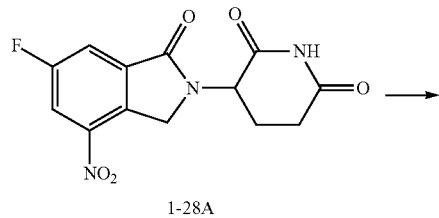

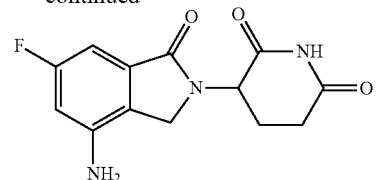

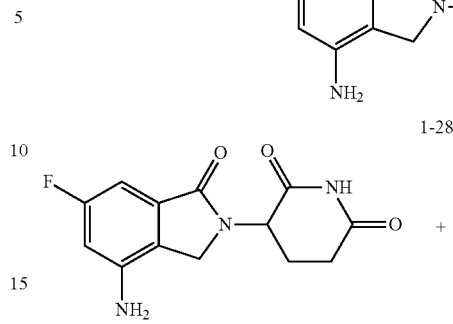

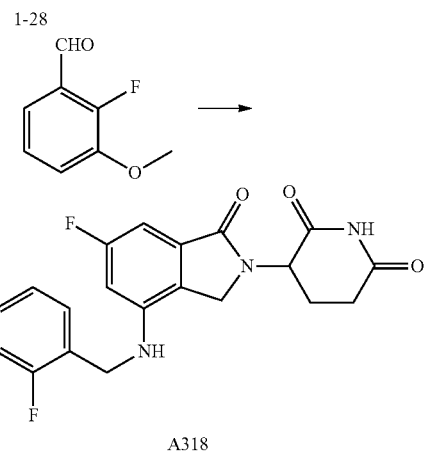

Step A. To a mixture of compound I-28A (1.0 g, 3.3 mmol) in DMF (10 mL) was added Pd/C (0.18 g, 10%, 50% wet) and degassed with H₂ 3 times. The mixture was stirred at 25° C. for 5 hours under 50 psi H₂ pressure. Then the reaction mixture was filtered and concentrated, then triturated with PE/EtOAc (5:1, 10 mL×3) to give 1-28 (crude, 0.9 g) as a green solid.

¹H NMR (DMSO-d₆, 300 MHz): δ 10.98 (s, 1H), 6.52-6.61 (m, 2H), 5.77 (s, 2H), 5.07 (dd, J=5.4, 13.2 Hz, 1H), 4.17 (d, J=17.1 Hz, 1H), 4.06 (d, J=17.1 Hz, 1H), 2.83-2.95 (m, 1H), 2.55-2.62 (m, 1H), 2.20-2.34 (m, 1H), 1.97-2.07 (m, 1H).

Step B. To a solution of compound I-28 and 2-fluoro-3-methoxybenzaldehyde (85 mg, 0.551 mmol) in AcOH (3 mL) was added dichloroethane (15 mL) and stirred for 1 hour. Then NaBH(OAc)₃ (235 mg, 1.09 mmol) was added and the mixture was stirred for 18 hours. Another portion of NaBH(OAc)₃ (50 mg, 0.236 mmol) was added and the mixture was heated to 30° C. for 8 hours. Then another portion of 2-fluoro-3-methoxybenzaldehyde (30 mg, 0.195 mmol) was added and the mixture was stirred at 40° C. for 16 hours. The mixture was concentrated and purified by prep-TLC to give crude product, which was triturated with MeOH (1 mL) to give A318 (30 mg, yield: 20%) as an off-white solid.

¹H NMR (DMSO-d₆, 300 MHz): δ 11.00 (s, 1H), 7.05-7.07 (m, 2H), 6.91-6.94 (m, 1H), 6.61-6.65 (m, 2H), 6.44 (dd, J=1.8, 12.9 Hz, 1H), 5.06-5.12 (m, 1H), 4.39 (d, J=5.7 Hz, 2H), 4.26 (d, J=17.1 Hz, 1H), 4.13 (d, J=17.1 Hz, 1H), 3.81 (s, 3H), 2.86-2.90 (m, 1H), 2.57-2.63 (m, 1H), 2.24-2.30 (m, 1H), 2.02-2.06 (m, 1H). LCMS: 416.1 ([M+1]⁺).

Compounds of Examples 9-10 were prepared according to the synthetic method shown in example 8 with corresponding starting material to replace 2-fluoro-3-methoxybenzaldehyde in step B.

Example 9: Compound A319

3-(6-fluoro-4-((2-fluoro-4-methoxybenzyl)amino)-1-oxoisoindolin-2-yl)-piperidine-2,6-dione, A319

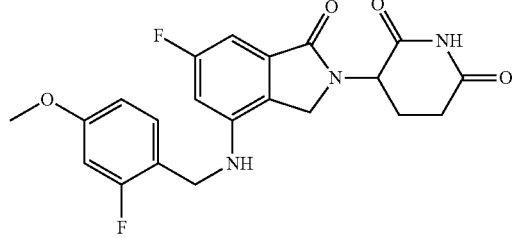

A319

$^1$H NMR (DMSO-d$_6$, 300 MHz): δ 11.00 (s, 1H), 7.30 (t, J=9.0 Hz, 1H), 6.71-6.84 (m, 2H), 6.55-6.64 (m, 2H), 6.47 (dd, J=2.1, 12.6 Hz, 1H), 5.05-5.11 (m, 1H), 4.31 (d, J=5.1 Hz, 2H), 4.24 (d, J=17.4 Hz, 1H), 4.11 (d, J=17.4 Hz, 1H), 3.73 (s, 3H), 2.84-2.96 (m, 1H), 2.57-2.62 (m, 1H), 2.19-2.34 (m, 1H), 2.03-2.06 (m, 1H). LCMS: 416.1 ([M+1]$^+$).

Example 10: Compound A320

3-(6-fluoro-4-((2-fluoro-5-methoxybenzyl)amino)-1-oxoisoindolin-2-yl)-piperidine-2,6-dione A320

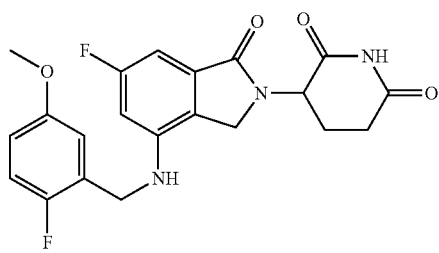

A320

$^1$H NMR (DMSO-d$_6$, 300 MHz): δ 11.00 (s, 1H), 7.12 (t, J=9.3 Hz, 1H), 6.81-6.94 (m, 2H), 6.60-6.66 (m, 2H), 6.48 (dd, J=2.4, 12.6 Hz, 1H), 5.06-5.12 (m, 1H), 4.36 (d, J=5.4 Hz, 2H), 4.27 (d, J=17.7 Hz, 1H), 4.14 (d, J=17.7 Hz, 1H), 3.67 (s, 3H), 2.83-2.97 (m, 1H), 2.57-2.62 (m, 1H), 2.20-2.35 (m, 1H), 2.00-2.08 (m, 1H). LCMS: 416.1 ([M+1]$^+$).

Example 11: Compound A327

3-(6-fluoro-4-((4-(morpholinomethyl)benzyl)oxy)-1-oxoisoindolin-2-yl)-piperidine-2,6-dione, A327

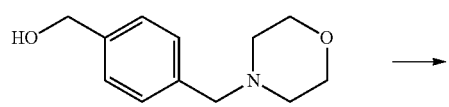

-continued

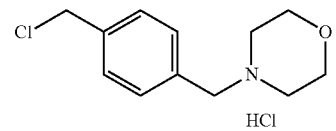

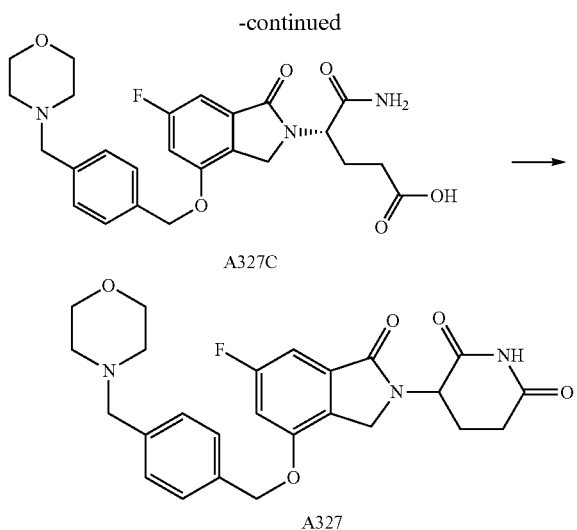

A327C

A327

Step A. To a mixture of (4-(morpholinomethyl)phenyl)methanol (1.5 g, 7.2 mmol) in DCM (20 mL) was added $SOCl_2$ (2.6 g, 21.8 mmol) slowly at 0° C., then the resulting mixture was stirred overnight at 25° C. LCMS shown the reaction was finished. The reaction mixture was concentrated, to afford the crude product 4-(4-(chloromethyl)benzyl)morpholine hydrochloride (1.9 g) as an off-white solid.

$^1$H NMR (DMSO-$d_6$. 400 M Hz): δ 11.70 (br s, 1H), 7.65-7.67 (m, 2H), 7.50-7.52 (m, 2H), 4.79 (s, 2H), 4.32-4.33 (m, 2H), 3.81-3.93 (m, 4H), 3.16-3.19 (m, 2H), 3.02-3.11 (m, 2H).

Step B. To a mixture of methyl 5-fluoro-2-methyl-3-nitrobenzoate (2.0 g, 9.4 mmol) and Pd/C (10%, 200 mg, 50% water) in MeOH (20 mL) was stirred at room temperature overnight under 50 Psi $H_2$. TLC and LCMS shown the reaction was finished. The mixture was filtered and the solid was washed with MeOH (50 mL×1), the filtrate was concentrated to afford methyl 3-amino-5-fluoro-2-methylbenzoate (1.3 g crude) as a colorless oil.

$^1$H NMR (DMSO-$d_6$. 300 M Hz), δ 6.57-6.60 (m, 1H), 5.44 (s, 2H), 3.77 (s, 3H), 2.11 (s, 3H).

Step C. To a mixture of methyl 3-amino-5-fluoro-2-methylbenzoate (1.3 g crude) and 100/a $H_2SO_4$ (43 g, 42.6 mmol) in MeOH (20 mL) was added $NaNO_2$ (750 mg, 10.87 mmol) at 0° C. under $N_2$, then the resulting mixture was stirred for 1 h at this temperature. Then 50% $H_2SO_4$ (42.6 g, 213 mmol) was added to the reactor, the mixture was stirred for 1 h at 100° C. TLC shown the reaction was finished. The reaction mixture was concentrated, the residue was diluted with $H_2O$ (20 mL) and EtOAc (100 mL). The aqueous layer was extracted by EtOAc (100 mL×3). The combined organic phase was dried over $Na_2SO_4$, filtered and evaporated to dryness via rotary evaporation. The residue was purified by column chromatography on silica gel eluted with (PE:EtOAc=50:1) to afford methyl 5-fluoro-3-hydroxy-2-methylbenzoate (660 mg, yield: 38% for two steps) as a light yellow solid.

$^1$H NMR (DMSO-$d_6$, 400 MHz): δ 10.25 (s, 1H), 6.93-6.96 (m, 1H), 6.78-6.82 (m, 1H), 3.81 (s, 3H), 2.23 (s, 3H).

Step D. A mixture of methyl 5-fluoro-3-hydroxy-2-methylbenzoate (1.2 g, 6.5 mmol) and imidazole (1.33 g, 19.5 mmol) in DCM (20 mL) was added TBDMSCl (1.96 g, 13.0 mmol) under N2 at 0° C., then the mixture was stirred for 10 minutes Then was stirred for 2 h at 25° C. TLC shown the reaction was finished. The mixture was washed with $H_2O$ (50 mL), the aqueous layer was extracted by DCM (150 mL×3), the combined organic phase was dried over $Na_2SO_4$, filtered and evaporated to dryness via rotary evaporation. The residue was purified by column chromatography on silica gel eluted with (PE:EtOAc=20:1-10:1) to afford methyl 3-((tert-butyldimethylsilyl)oxy)-5-fluoro-2-methylbenzoate (1.4 g yield: 72%) as a light yellow oil.

$^1$H NMR (DMSO-$d_6$, 400 MHz): δ 7.12-7.15 (m, 1H), 6.84-6.87 (m, 1H), 3.82 (s, 3H), 2.26 (s, 3H), 0.98 (s, 9H), 0.23 (s, 6H).

Step E. To a mixture of methyl 3-((tert-butyldimethylsilyl)oxy)-5-fluoro-2-methylbenzoate (1.4 g, 4.7 mmol) and NBS (1.0 g 5.6 mmol) in $CCl_4$ (20 mL) was added benzoyl peroxide (0.12 g, 0.5 mmol) under $N_2$, the mixture was stirred for overnight at 80° C. TLC shown the reaction was finished. The mixture was filtered then the solid was washed with DCM (50 mL), the organic phase was washed with $H_2O$ (50 mL), the aqueous layer was extracted by DCM (100 mL×3), the combined organic phase was dried over $Na_2SO_4$, filtered and evaporated to dryness via rotary evaporation. The residue was purified by column chromatography on silica gel eluted with (PE:EtOAc=100:1) to afford methyl 2-(bromomethyl)-3-((tert-butyldimethylsilyl)oxy)-5-fluorobenzoate (1.4 g, purity: 90%) as a white solid.

$^1$H NMR (DMSO-$d_6$, 400 MHz): δ 7.28-7.31 (m, 1H), 7.00-7.03 (m, 1H), 4.93 (s, 2H), 3.91 (s, 3H), 1.07 (s, 9H), 0.36 (s, 6H).

Step F. To a mixture of methyl 2-(bromomethyl)-3-((tert-butyldimethylsilyl)oxy)-5-fluorobenzoate (500 mg, 1.33 mmol) and (S)-tert-butyl-4,5-diamino-5-oxopentanoate hydrochloride (349 mg, 1.46 mmol) and $Et_3N$ (405 mg, 4.0 mmol) in $CH_3CN$ (10 mL) was stirred for overnight under $N_2$ at 80° C. TLC shown the reaction was finished. The mixture was concentrated, the residue was added to THF (10 mL), and then TBAF (4 mL, 1 M in THF) was added to the reactor dropwise. The mixture was stirred for 0.5 h at room temperature. TLC shown the reaction was finished. The mixture was concentrated, the residue was purified by column chromatography on silica gel eluted with (PE:EtOAc=5:1-1:1-EtOAc) to afford A327A (200 mg, yield: 34%, for 3 steps) as a light yellow solid.

$^1$H NMR (MeOD, 400 MHz): δ 6.95-6.98 (m, 1H), 6.72-6.76 (m, 1H), 4.90-4.94 (m, 1H), 4.54 (d, J=17.6 Hz, 1H), 4.42 (d, J=17.6 Hz, 1H), 2.25-2.30 (m, 3H), 2.16-2.21 (m, 1H), 1.39 (s, 9H).

Step G. To a mixture of A327A (200 mg, 0.57 mmol) and 4-(4-(chloromethyl)benzyl)morpholine hydrochloride (445 mg, crude) in dry DMF (10 mL), under $N_2$ at room temperature, was added $K_2CO_3$ (393 mg, 2.90 mmol). The mixture was stirred at room temperature for overnight. LCMS shown the reaction was not finished. Another portion of 4-(4-(chloromethyl)benzyl)morpholine hydrochloride (445 mg, crude) was added to the reactor, the reaction mixture was stirred for 6 h. The mixture was concentrated, then the residue was diluted by $H_2O$ (10 mL) and EtOAc (30 mL). The aqueous layer was extracted by EtOAc (10 mL×3), the combined organic phase was dried over $Na_2SO_4$, filtered and evaporated to dryness via rotary evaporation. The residue was purified by column chromatography on silica gel eluted with (PE:EtOAc=5:1~1:1~EtOAc) to afford A327B (250 mg, yield: 81%) as a white solid.

$^1$H NMR (DMSO-$d_6$, 400 MHz): δ 7.57 (s, 1H), 7.44-7.46 (m, 2H), 7.34-7.36 (m, 2H), 7.19-7.27 (m, 2H), 7.06-7.08 (m, 1H), 5.23 (s, 2H), 4.68-4.72 (m, 1H), 4.50 (d, J=17.6 Hz, 1H), 4.39 (d, J=17.6 Hz, 1H), 3.56-3.58 (m, 4H), 3.47 (s, 2H), 2.30-2.38 (m, 4H), 2.13-2.17 (m, 3H), 2.00-2.05 (m, 1H), 1.32 (s, 9H).

Step H. To a mixture of A327B (250 mg, 0.46 mmol) in dry DCM (10 mL) was added TFA (4 mL) under $N_2$ at 0° C. The mixture was stirred for 4 h. TLC shown the reaction was finished. The mixture was concentrated to give A327C (230 mg crude) as a pale yellow solid.

Step I. To a mixture of A327C (230 mg crude) in $CH_3CN$ (15 mL) was added CDI (115 mg, 0.71 mmol) under $N_2$ at room temperature. After finishing adding, the mixture was stirred for overnight at 95° C. LCMS shown the reaction was finished. The mixture was concentrated, The residue was purified by prep-HPLC to afford A327 (24 mg, yield: 11%, two steps) as a yellow solid.

$^1$H NMR (DMSO-$d_6$, 400 MHz): δ 10.98 (s, 1H), 7.43-7.45 (m, 2H), 7.28-7.35 (m, 3H), 7.11-7.13 (m, 1H), 5.23 (s, 2H), 5.08-5.13 (m, 1H), 4.39 (d, J=17.2 Hz, 1H), 4.23 (d, J=17.2 Hz, 1H), 3.55-3.58 (m, 4H), 3.47 (s, 2H), 2.87-2.91 (m, 1H), 2.54-2.59 (m, 1H), 2.42-2.45 (m, 1H), 2.35-2.41 (m, 4H), 1.97-1.99 (m, 1H). LCMS: 468.2 ([M+1]$^+$).

Example 12: Compound A329

3-(4-((2-fluoro-4-methoxybenzyl)oxy)-1-oxoisoindolin-2-yl)piperidine-2,6-dione, A329

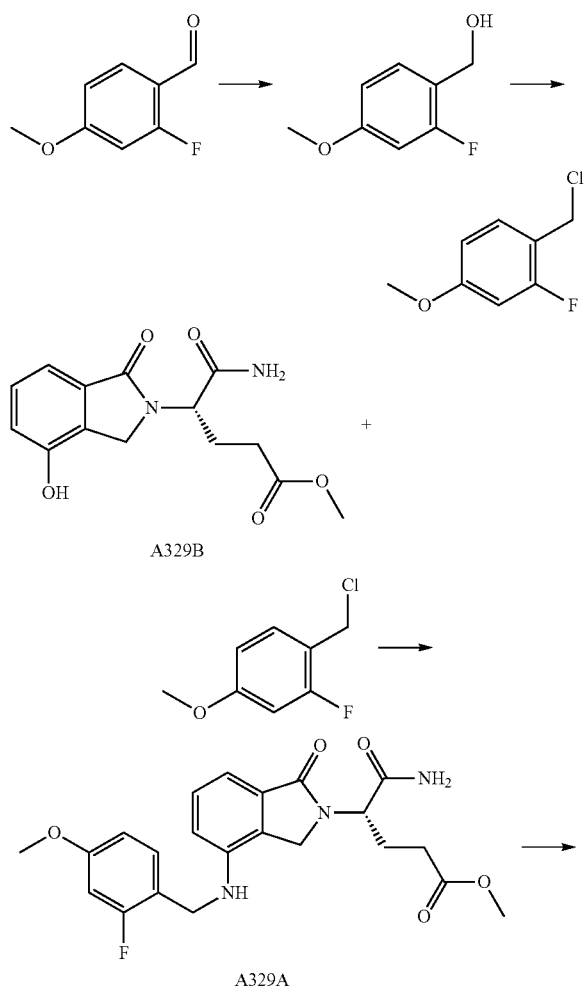

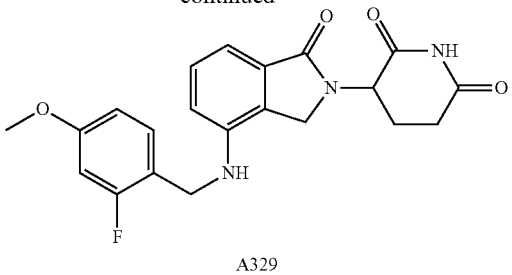

A329

Step A. To a solution of 2-fluoro-4-methoxybenzaldehyde (1.0 g, 6.49 mmol) in MeOH (10 mL) were added $NaBH_4$ (370 mg, 9.74 mmol) at room temperature, the mixture was stirred for 1 h. TLC shown the reaction was finished. HCl (1 N) was added to quench the reaction and pH was adjusted to 4-5. DCM (50 mL) and water (40 mL) was added and water layer was extracted with DCM (50 mL×2), the combined organic phase was washed with brine (50 mL), dried over $Na_2SO_4$, filtration, concentrated to give the product (2-fluoro-4-methoxyphenyl)methanol (910 mg, yield: 90%) as a light yellow oil, without further purification for the next step.

$^1$H NMR (DMSO-$d_6$, 300 MHz): δ 7.31 (t, J=8.4 Hz, 1H), 6.72-6.76 (m, 2H), 5.08 (t, J=5.7 Hz, 1H), 4.43 (d, J=5.7 Hz, 2H), 3.73 (m, 3H).

Step B. To a solution of (2-fluoro-4-methoxyphenyl)methanol (400 mg, 2.56 mmol) in dry DCM (10 mL) was added $SOCl_2$ (458 mg, 3.85 mmol) at room temperature, the mixture was stirred for 3h. LCMS shown the reaction was finished. The reaction mixture was concentrated to give 1-(chloromethyl)-2-fluoro-4-methoxybenzene (450 mg) as a light yellow oil which was used next step without further purification.

$^1$H NMR (DMSO-$d_6$, 300 MHz): δ 7.42 (t, J=8.7 Hz, 1H), 6.85 (dd, J=12.0, 2.7 Hz, 1H), 6.77 (dd, J=11.4, 2.7 Hz, 1H), 4.72 (s, 2H), 3.76 (s, 3H).

Step C. To a solution of A329B (200 mg, 0.68 mmol) in DMF (15 mL) were added $K_2CO_3$ (283 mg, 2.05 mmol) and [1-(chloromethyl)-2-fluoro-4-methoxybenzene] (239 mg, 1.37 mmol) at room temperature, the mixture was stirred overnight at room temperature. LCMS shown the reaction was not finished. Additional [1-(chloromethyl)-2-fluoro-4-methoxybenzene] (100 mg, 0.57 mmol) was added and stirred for 3 hr. LCMS shown the reaction was finished. The reaction mixture was concentrated and EtOAc (50 mL) and water (30 mL) was added and water layer was extracted with EtOAc (50 mL×2), the combined organic phase was washed with brine (50 mL), dried over $Na_2SO_4$, filtered, and then concentrated to give a residue. The residue was purified by prep-TLC (MeOH/DCM=1/20) to give A329A (190 mg, yield: 65%) as a white solid.

$^1$H NMR (DMSO-$d_6$, 300 MHz): δ 7.57 (br s, 1H), 7.45-7.54 (m, 2H), 7.36 (d, J=8.1 Hz, 1H), 7.30 (d, J=7.5 Hz, 1H), 7.17 (br s, 1H), 6.87-6.92 (m, 1H), 6.81-6.85 (m, 1H), 5.19 (s, 2H), 4.69-4.74 (m, 1H), 4.47 (d, J=17.7 Hz, 1H), 4.33 (d, J=17.7 Hz, 1H), 3.79 (s, 3H), 3.50 (s, 3H), 2.13-2.27 (m, 3H), 2.00-2.10 (m, 1H),

Step D. To a solution of A329A (190 mg, 0.44 mmol) in DMF (10 mL) were added $K_2CO_3$ (183 mg, 1.33 mmol), the mixture was stirred at 80° C. overnight under $N_2$. LCMS shown the reaction was finished. The reaction mixture was filtered and the filtrate was concentrated to give a residue. The residue was purified by prep-HPLC and freeze-dried to give A329 (120 mg, yield: 68%) as a white solid.

¹H NMR (DMSO-d₆, 300 MHz): δ 10.79 (br s, 1H), 7.48-7.54 (m, 2H), 7.33-7.41 (m, 2H), 6.89 (dd, J=12.3, 2.4 Hz, 1H), 6.81 (dd, J=8.4, 2.4 Hz, 1H), 5.19 (s, 2H), 5.08-5.13 (m, 1H), 4.35 (d, J=17.7 Hz, 1H), 4.18 (d, J=17.7 Hz, 1H), 3.78 (s, 3H), 2.84-2.94 (m, 1H), 2.57-2.61 (m, 1H), 2.38-2.46 (m, 1H), 1.92-2.00 (m, 1H).

LCMS: 399.1 ([M+1]₊).

Compounds in example 13-14 were prepared according to the procedure described for example 12, with corresponding starting material to replace 2-fluoro-4-methoxybenzaldehyde in step A.

Example 13: Compound A331

3-(4-((2-fluoro-5-methoxybenzyl)oxy)-1-oxoisoindolin-2-yl)piperidine-2,6-dione, A331

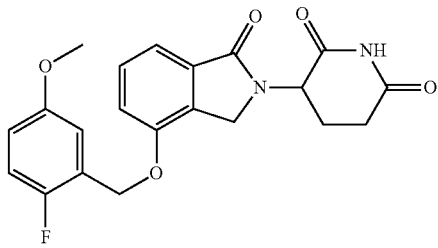 [SMILES: COc1ccc(F)c(COc2cccc3c2CN(C2CCC(=O)NC2=O)C3=O)c1]

¹H NMR (DMSO-d₆, 300 MHz): δ 10.65 (br s, 1H), 7.51 (t, J=7.8 Hz, 1H), 7.34-7.40 (m, 2H), 7.13-7.23 (m, 2H), 6.93-6.99 (m, 1H), 5.25 (s, 2H), 5.10 (dd, J=10.2, 5.1 Hz, 1H), 4.39 (d, J=17.7 Hz, 1H), 4.23 (d, J=17.7 Hz, 1H), 3.74 (s, 3H), 2.84-2.96 (m, 1H), 2.54-2.60 (m, 1H), 2.39-2.47 (m, 1H), 1.93-2.00 (m, 1H). LCMS: 399.1 ([M+1]⁺).

Example 14: Compound A334

3-(4-((2-fluoro-3-methoxybenzyl)oxy)-1-oxoisoindolin-2-yl)piperidine-2,6-dione, A334

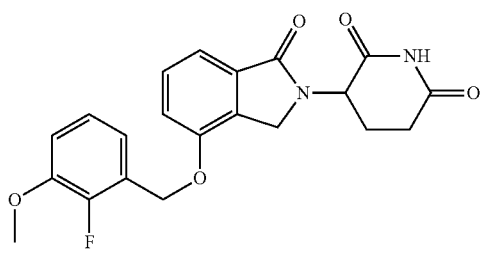 [SMILES: COc1cccc(COc2cccc3c2CN(C2CCC(=O)NC2=O)C3=O)c1F]

¹H NMR (DMSO-d₆. 400 MHz): 10.96 (s, 1H), 7.50 (t, J=7.6 Hz, 1H), 7.34-7.38 (m, 2H), 7.13-7.20 (m, 3H), 5.28 (s, 2H), 5.10 (dd, J=12.8, 4.4 Hz, 1H), 4.38 (d, J=17.6 Hz, 1H), 4.22 (d, J=17.6 Hz, 1H), 3.85 (s, 3H), 2.87-2.90 (m, 1H), 2.50-2.58 (m, 1H), 2.40-2.43 (m, 1H), 1.95-1.98 (m, 1H). LCMS: 399.1 ([M+1]⁺).

Example 15: Compound A336

3-[4-(2-Fluoro-benzyloxy)-1-oxo-1,3-dihydro-isoindol-2-yl]-piperidine-2,6-dione, A336

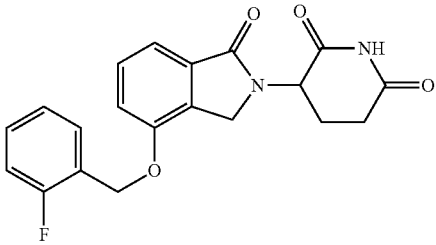 [SMILES: O=C1CCC(N2Cc3c(OCc4ccccc4F)cccc3C2=O)C(=O)N1]

¹H NMR (DMSO-d₆. 400 MHz): 10.92 (s, 1H), 6.53-6.63 (m, 1H), 7.50 (t, J=8.0 Hz, 1H), 7.40-7.47 (m, 2H), 7.36 (t, J=8.0 Hz, 1H), 7.23-7.29 (m, 2H), 5.30 (s, 2H), 5.11 (dd, J=12.8, 5.2 Hz, 1H), 4.38 (d, J=17.6 Hz, 1H), 4.23 (d, J=17.6 Hz, 1H), 2.86-2.95 (m, 1H), 2.54-2.59 (m, 1H), 2.38-2.47 (m, 1H), 1.97-2.00 (m, 1H). LCMS: 369.1 ([M+1]⁺).

Example 16: Compound A340

(S)-3-(4-((2-fluoro-5-methoxybenzyl)amino)-1-oxoisoindolin-2-yl)piperidine-2,6-dione, A340

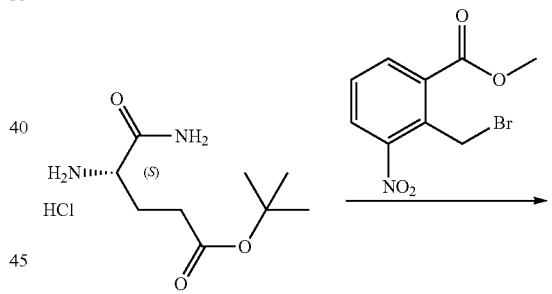

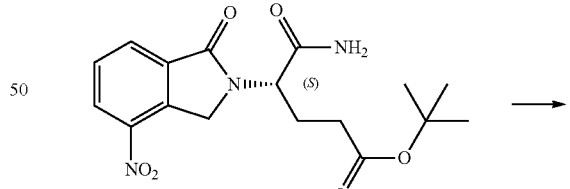

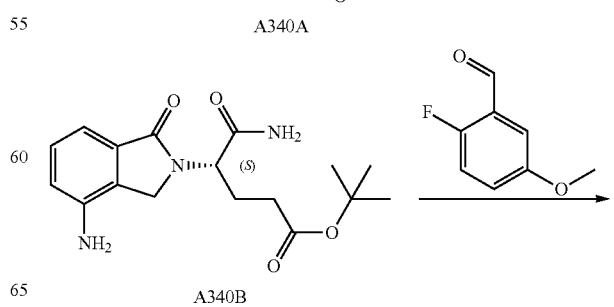

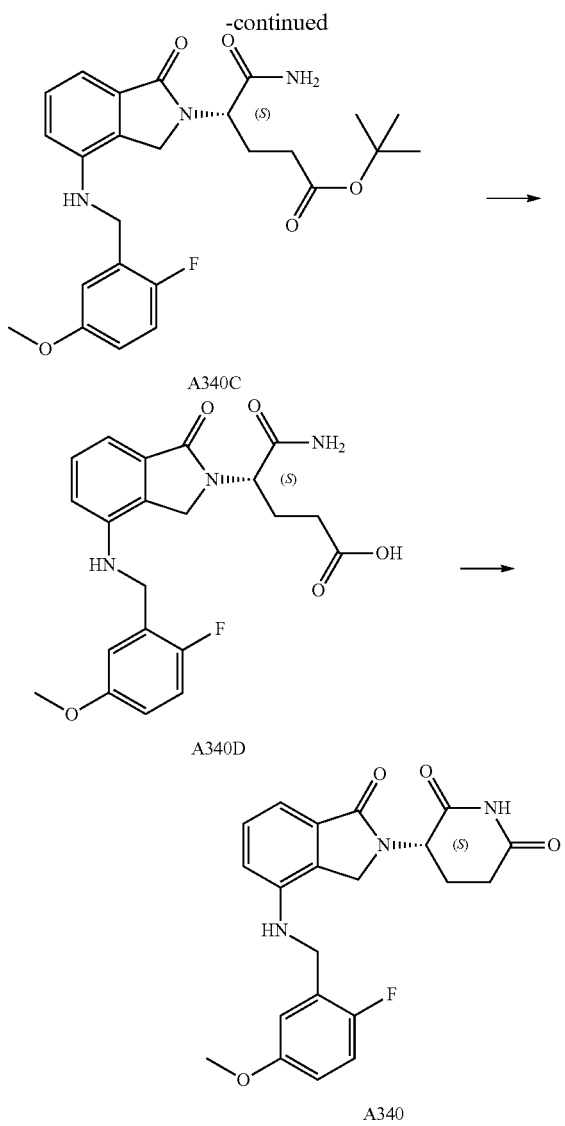

Step A. To a solution of methyl 2-(bromomethyl)-3-nitrobenzoate (2.00 g, 7.30 mmol) in CH₃CN (40 mL) were added (S)-tert-butyl 4,5-diamino-5-oxopentanoate hydrochloride (1.91 g, 8.00 mmol) and Et₃N (1.63 g, 16.1 mmol) under N₂, the mixture was stirred at 75° C. overnight. TCL shown the reaction was finished. The reaction mixture was concentrated and EtOAc (50 mL) and water (50 mL) were added, the water layer was extracted with EtOAc (50 mL×2), the combined organic phases were washed with brine (50 mL), dried over Na₂SO₄, filtered, concentrated to give a crude product. The crude product was triturated with PE/EtOAc (4/1, v/v), then filtered to give A340A (2.2 g, 83% yield) as a white solid.

¹H NMR (DMSO-d₆, 300 MHz): δ 8.45 (dd, J=0.9, 8.1 Hz, 1H), 8.16 (dd, J=0.9, 8.1 Hz, 1H), 7.82 (t, J=8.1 Hz, 1H), 7.65 (br s, 1H), 7.27 (br s, 1H), 5.05 (d, J=19.5 Hz, 1H), 4.90 (d, J=19.5 Hz, 1H), 4.75-4.80 (m, 1H), 2.14-2.27 (m, 3H), 2.00-2.10 (m, 1H), 1.33 (s, 9H).

Step B. To a solution of A340A (1.20 g, 3.30 mmol) in MeOH was added Pd/C (10%/o, 200 mg, 50% water), degassed with H₂ 3 times the mixture was stirred at 25° C. overnight under H₂ (50 Psi). LCMS shown the reaction was finished. Pd/C was removed by filtration and the filtrate was concentrated to give A340B (1.19 g, crude) as a light yellow solid which was used for next step without further purification.

¹H NMR (DMSO-d₆, 300 MHz): δ 7.50 (br s, 1H), 7.11-7.16 (m, 2H), 6.85 (d, J=7.2 Hz, 1H), 6.74 (d, J=7.2 Hz, 1H), 5.41 (br s, 2H), 4.68-4.73 (m, 1H), 4.38 (d, J=17.7 Hz, 1H), 4.16 (d, J=17.7 Hz, 1H), 2.09-2.19 (m, 3H), 1.92-2.01 (m, 1H), 1.32 (s, 9H).

Step C. To a solution of A340B (1.00 g, crude) and 2-Fluoro-5-methoxy-benzaldehyde (601 mg, 3.90 mmol) in MeOH (10 mL) was added AcOH (0.5 mL), the mixture was stirred at 25° C. for 3 hours. Pd/C (10%, 200 mg, 50% water) was added, degassed with H₂ 3 times and stirred at 25° C. overnight under H₂ (balloon). LCMS shown the reaction was finished. Pd/C was removed by filtration and the filtrate was concentrated to give a residue. The residue was purified by column chromatography on slica gel (PE/EtOAc=1/4) to give the desired product A340C (1.15 g, yield: 88%, for two steps) as a light yellow solid.

¹H NMR (DMSO-d₆, 300 MHz): δ 7.56 (br s, 1H), 7.09-7.24 (m, 3H), 6.91-6.96 (m, 2H), 6.80-6.85 (m, 1H), 6.63 (d, J=8.4 Hz, 1H), 6.34-6.38 (m, 1H), 4.74 (dd, J=10.2, 4.5 Hz, 1H), 4.50 (d, J=18.0 Hz, 1H), 4.37 (d, J=6.0 Hz, 2H), 4.28 (d, J=18.0 Hz, 1H), 3.67 (s, 3H), 2.12-2.21 (m, 3H), 1.91-2.02 (m, 1H), 1.33 (s, 9H).

Step D. To a solution of A340C (1.15 g, 2.44 mmol) in DCM (20 mL) cooled to 0° C. was added dropwise TFA (4 mL), the mixture was stirred overnight at 25° C. The reaction mixture was concentrated under reduced pressure. The residue was purified by flash chromatography on C18 (40% acetonitrile in water) then was freeze-dried to afford A340D (800 mg, yield: 79%) as a light yellow solid.

¹H NMR (DMSO-d₆, 400 MHz): δ 12.14 (br s, 1H), 7.57 (br s, 1H), 7.10-7.23 (m, 3H), 6.91-6.96 (m, 2H), 6.81-6.85 (m, 1H), 6.63 (d, J=8.0 Hz, 1H), 6.35 (t, J=6.0 Hz, 1H), 4.72-4.76 (m, 1H), 4.51 (d, J=17.6 Hz, 1H), 4.37 (d, J=5.6 Hz, 2H), 4.31 (d, J=17.6 Hz, 1H), 3.67 (s, 3H), 2.18-2.23 (m, 3H), 1.96-2.02 (m, 1H).

Step E. A solution of A340D (700 mg, 1.69 mmol) in dry DCM (70 mL) was cooled to −40° C. under N₂, SOCl₂ (1.00 g, 8.40 mmol) was slowly added to the mixture at −40° C., then a solution of DMF (10 mg) in DCM (1 mL) was added and stirred for 2 h, and then pyridine (666 mg, 8.42 mmol) was added dropwise and stirred for 40 mins at this temperature, Et₃N (852 mg, 8.42 mmol) was added and then the mixture was stirred for 2 h. LCMS shown the reaction was finished. H₂O (10 mL) was added to quench the reaction, the water layer was extracted with DCM (20 mL×2), the combined organic phase was washed with brine (50 mL×1), dried over Na₂SO₄, filtered, concentrated to give a residue. The residue was purified by Prep-HPLC to give A340 (460 mg, yield: 68%, ee: 98%) as a pale green solid.

¹H NMR (DMSO-d₆, 300 MHz): δ 11.00 (br s, 1H), 7.23 (t, J=7.8 Hz, 1H), 7.11 (t, J=9.6 Hz, 1H), 6.90-6.95 (m, 2H), 6.78-6.84 (m, 1H), 6.65 (d, J=8.1 Hz, 1H), 6.26 (t, J=6.0 Hz, 1H), 5.10 (dd, J=13.2, 5.1 Hz, 1H), 4.37 (d, J=6.0 Hz, 2H), 4.30 (d, J=17.1 Hz, 1H), 4.17 (d, J=17.1 Hz, 1H), 3.65 (s, 3H), 2.85-2.96 (m, 1H), 2.56-2.63 (m, 1H), 2.24-2.37 (m, 1H), 2.00-2.07 (m, 1H). LCMS: 398.1 ([M+1]⁺).

Example 17: Compound A341

(R)-3-(4-((2-fluoro-5-methoxybenzyl)amino)-1-oxoisoindolin-2-yl)piperidine-2,6-dione, A341

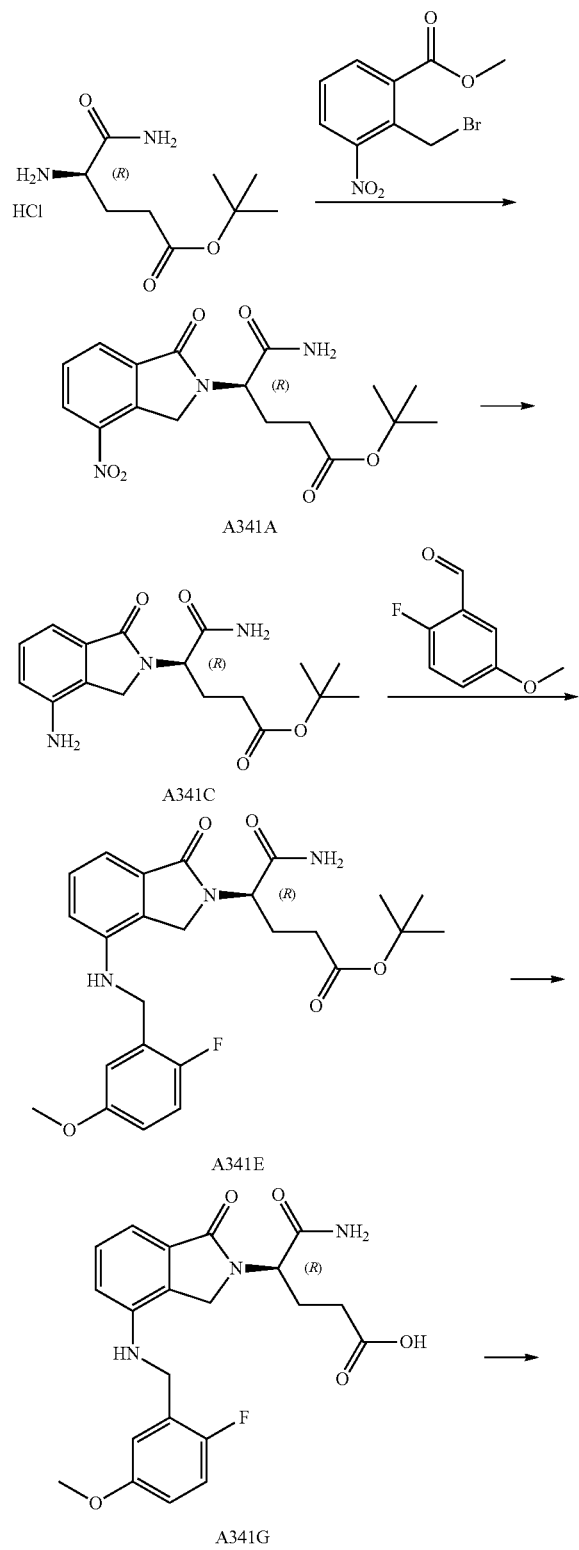

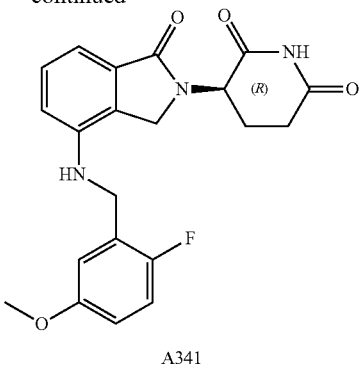

A341

Step A. To a solution of 2-Bromomethyl-3-nitro-benzoic acid methyl ester (1.00 g, 3.65 mmol) in $CH_3CN$ (50 mL) were added (R)-tert-butyl 4,5-diamino-5-oxopentanoate hydrochloride (955 mg, 4.00 mmol) and $Et_3N$ (815 mg, 8.05 mmol), the mixture was stirred 75° C. overnight under $N_2$. TLC shown the reaction was finished. The reaction mixture was concentrated and EtOAc (50 mL) and water (50 mL) were added, the water layer was extracted with EtOAc (50 mL×2), the combined organic phase was washed with brine (50 mL), dried over $NaZSO_4$, filtered, and concentrated to give a crude product. The crude product was purified by column chromatography on slica gel (PE/EtOAc=1/4), to give A341A (800 mg, yield: 60%) as a white solid.

$^1H$ NMR (DMSO-d, 300 MHz): δ 8.45 (d, J=6.0 Hz, 1H), 8.16 (d, J=5.4 Hz, 1H), 7.82 (t, J=6.0 Hz, 1H), 7.64 (br s, 1H), 7.27 (br s, 1H), 5.05 (d, J=14.4 Hz, 1H), 4.91 (d, J=14.4 Hz, 1H), 4.76-4.80 (m, 1H), 2.15-2.25 (m, 3H), 2.02-2.11 (m, 1H), 1.33 (s, 9H).

Step B. To a solution of A341A (800 mg, 2.20 mmol) in MeOH was added Pd/C (100%, 80 mg, 50(955 m water), the mixture was stirred at 25° C. overnight under Hz (50 Psi). LCMS showed the reaction completed. Pd/C was removed by filtration and the filtrate was concentrated to give a crude product A341C (680 rag, 93% yield) as a light yellow solid. The crude product was used for next step without further purification.

$^1H$ NMR (DMSO-$d_6$, 300 MHz): δ 7.54 (br s, 1H), 7.13-7.18 (m, 2H), 6.88 (d, J=7.2 Hz, 1H), 6.76 (d, J=7.8 Hz, 1H), 5.44 (br s, 2H), 4.70-4.75 (m, 1H), 4.41 (d, J=17.7 Hz, 1H), 4.18 (d, J=17.7 Hz, 1H), 2.09-2.21 (m, 3H), 1.92-2.06 (m, 1H), 1.34 (s, 9H).

Step C. To a solution of A341C (680 mg, 2.04 mmol) and 2-Fluoro-5-methoxy-benzaldehyde (472 mg, 3.06 mmol) in MeOH was added AcOH (0.5 mL), the mixture was stirred at 25° C. for 3 hours. Pd/C (10%, 50 mg, 50% water) was added, degassed with $H_2$ 3 times and stirred at 25° C. overnight under $H_2$ (balloon). LCMS showed the reaction completed. Pd/C was removed by filtration and the filtrate was concentrated to give a residue. The residue was purified by column chromatography on slica gel (PE/EtOAc=1/4) to give the desired product A341E (650 mg, yield: 68%) as a light yellow solid.

$^1H$ NMR (DMSO-$d_6$, 400 MHz): δ 7.56 (br s, 1H), 7.18-7.23 (m, 2H), 7.12 (t, J=9.2 Hz, 1H), 6.91-6.95 (m, 2H), 6.81-6.85 (m, 1H), 6.63 (d, J=8.0 Hz, 1H), 6.36 (t, J=5.6 Hz, 1H), 4.72-4.76 (m, 1H), 4.50 (d, J=17.6 Hz, 1H), 4.37 (d, J=6.0 Hz, 2H), 4.29 (d, J=17.6 Hz, 1H), 3.67 (s, 3H), 2.14-2.22 (m, 3H), 1.94-2.04 (m, 1H), 1.33 (s, 9H).

Step D. To a solution of A341E (650 mg, 1.38 mmol) in DCM (20 mL) cooled to 0° C. was added dropwise TFA (4 mL), the mixture was warmed slowly to 25° C. and stirred overnight. The reaction mixture was concentrated under reduced pressure (in vacuum) to remove solution. The residue was purified by flash chromatography on C18 (40% acetonitrile in water) then was freeze-dried to afford A341G (450 mg, yield: 79%) as a light yellow solid.

¹H NMR (DMSO-d₆, 300 MHz): δ 7.56 (br s, 1H), 7.07-7.22 (m, 3H), 6.89-6.94 (m, 2H), 6.78-6.83 (m, 1H), 6.61 (d, J=7.8 Hz, 1H), 6.34 (t, J=6.3 Hz, 1H), 4.69-4.73 (m, 1H), 4.50 (d, J=17.7 Hz, 1H), 4.35 (d, J=5.7 Hz, 2H), 4.29 (d, J=17.7 Hz, 1H), 3.65 (s, 3H), 2.12-2.19 (m, 3H), 1.93-1.98 (m, 1H).

Step E. To a solution of A341G (450 mg, 1.08 mmol) dissolved in dry DCM (50 mL) cooled to −40° C. under N₂, SOCl₂ (644 mg, 5.41 mmol) was slowly added to the mixture at −40° C. under N₂, then a solution of DMF (10 mg) in DCM (1 mL) was added and stirred for 2 hrs, pyridine (428 mg, 5.41 mmol) was added dropwise and stirred for 40 mins at this temperature, Et₃N (547 mg, 5.41 mmol) was added and then the mixture was stirred for 2 h. LCMS showed the reaction completed. H₂O (10 mL) was added to quench the reaction, the water layer was extracted with DCM (30 mL×2), the combined organic phase was washed with brine (50 mL), dried over Na₂SO₄, filtered, concentrated to give a residue. The residue was purified by Prep-HPLC to give A341 (260 mg, yield: 61%, ee: 96%) as a pale green solid.

¹H NMR (DMSO-d₆, 300 MHz): δ 10.98 (br s, 1H), 7.23 (t, J=7.8 Hz, 1H), 7.11 (t, J=9.3 Hz, 1H), 6.90-6.95 (m, 2H), 6.78-6.84 (m, 1H), 6.65 (d, J=8.1 Hz, 1H), 6.26 (t, J=6.0 Hz, 1H), 5.10 (dd, J=13.2, 5.1 Hz, 1H), 4.36 (d, J=5.7 Hz, 2H), 4.30 (d, J=17.1 Hz, 1H), 4.17 (d, J=17.1 Hz, 1H), 3.65 (s, 3H), 2.85-2.97 (m, 1H), 2.56-2.63 (m, 1H), 2.22-2.35 (m, 1H), 2.00-2.07 (m, 1H). LCMS: 398.1 ([M+1]⁺).

Example 18: Compound A342

(R)-3-deuterium-3-(4-((2-fluoro-5-methoxybenzyl)amino)-1-oxoisoindolin-2-yl)piperidine-2,6-dione, A342

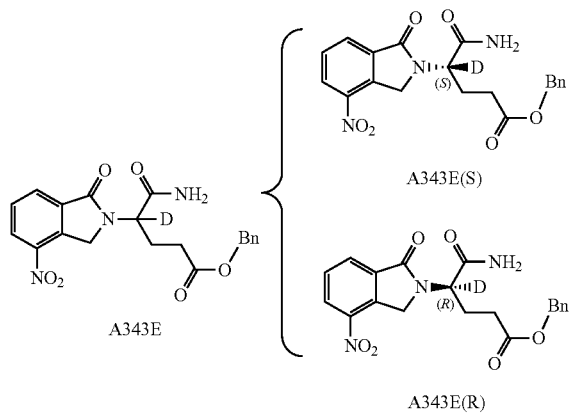

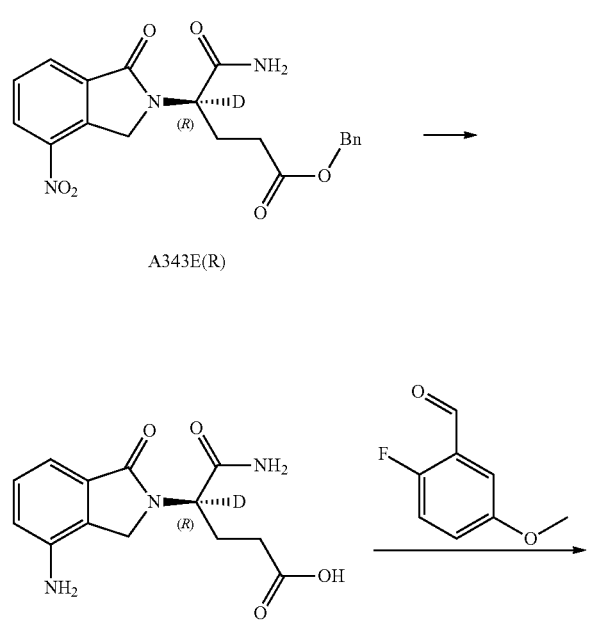

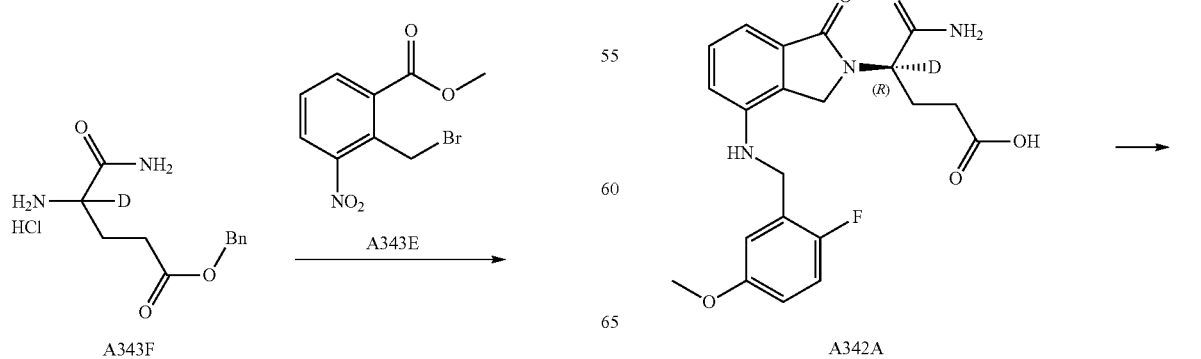

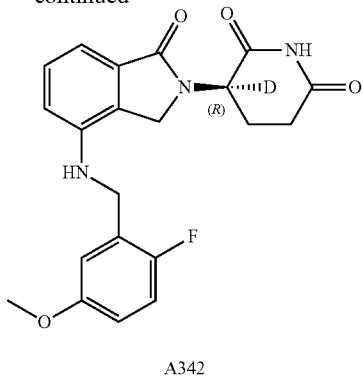

A342

Step A. To a solution of A343F (31.7 g, 115.7 mmol) in CH$_3$CN (560 mL) were added A343G (31.5 g, 115.1 mmol) and Et$_3$N (23.3 g, 231.0 mmol), the mixture was stirred at 75° C. overnight under N$_2$. The reaction mixture was concentrated and EtOAc (50 mL) and 4N HCl aqueous solution (150 mL) were added, the mixture was filtered and the cake was washed with water (30 mL) and dried, while the filtrate was extracted with EtOAc (250 mL×2), the combined organic phase was washed with brine (30 mL), dried over Na$_2$SO$_4$, filtration, concentrated to give a crude product. The combined solid was triturated with CH$_3$CN (40 mL×2), filtered to give A343E (37 g, 81% yield) as a white solid. Compound A343E was subjected to chiral separation to afford Peak 1 A343E(S) (14.4 g, yield: 77.8%, Rt=7.30 min, 100% ee) and Peak 2 A342E(R) (14.8 g, yield: 80%, Rt=11.87 min, 100% ee) as a white solid.

Chiral Separation conditions: Column: CHIRALPAK IE, Particle size: 10 μm, Dimensious: 50×250 mm: Wave Length: 254 nm; Mobile Phase: MeOH/DCM=80/20 (V/V); Injection: 48 mL; Flow Rate: 60 mL/min; Temperature: 35° C. Solvent: Mobile Phase, 17.1 mg/mL.

A343E(S): $^1$H NMR (DMSO-d$_6$, 300 MHz): δ 8.43 (d, J=8.1 Hz, 1H), 8.13 (d, J=7.5 Hz, 1H), 7.79 (t, J=8.1 Hz, 1H), 7.66 (br s, 1H), 7.26-7.35 (m, 6H), 4.86-5.07 (m, 4H), 2.42-2.21-2.43 (m, 3H), 2.06-2.16 (m, 1H).

A342E(R): $^1$H NMR (DMSO-d$_6$, 300 MHz): δ 8.43 (d, J=8.4 Hz, 1H), 8.13 (d, J=7.2 Hz, 1H), 7.77-7.82 (m, 1H), 7.65 (br s, 1H), 7.35-7.23-7.35 (m, 6H), 4.86-5.07 (m, 4H), 2.20-2.42 (m, 3H), 2.06-2.15 (m, 1H).

Step B. To a solution of A342E(R) (2.5 g, 6.3 mmol) in MeOH (150 mL) and THF (150 mL) was added Pd/C (10%, 500 mg, 50% water), the mixture was stirred overnight under H$_2$ (50 Psi) at 25° C. LCMS showed the reaction completed. Pd/C was removed by filtration and the filtrate was concentrated to give a crude product which was co-evaporated with CH$_3$CN/DCE (50 mL/150 mL), and then the solid was dissolved in THF (300 mL) and concentrated to give A342C (1.68 g, 97% yield) as a white solid, which was used in the next step without further purification.

$^1$H NMR (DMSO-d$_6$, 300 MHz): δ 12.11 (br s, 1H), 7.54 (s, 1H), 7.11-7.16 (m, 2H), 6.85 (d, J=7.8 Hz, 1H), 6.74 (d, J=7.8 Hz, 1H), 5.43 (br s, 2H), 4.68-4.73 (m, 0.02H), 4.41 (d, J=17.4 Hz, 1H), 4.17 (d, J=17.4 Hz, 1H), 2.10-2.18 (m, 3H), 1.94-1.97 (m, 1H).

Step C: To a solution of A342C and 2-Fluoro-5-methoxy-benzaldehyde (831 mg, 5.39 mmol) in MeOH was added AcOH (0.5 mL), the mixture was stirred at 25° C. for 20 hours. Pd/C (10%, 100 mg, 50% water) was added, degassed with H$_2$ 3 times and stirred at 25° C. overnight under H$_2$ (balloon). LCMS showed the reaction completed. Pd/C was removed by filtration and the filtrate was concentrated to give a residue. The residue was purified by flash chromatography on C18 (CH$_3$CN: H$_2$O=5%-35%, 30 min; 35%-45%, 30 min; 45%-55% 20 min) then was freeze-dried to afford A342A (800 mg, yield: 53%) as a light yellow solid.

$^1$H NMR (DMSO-d$_6$, 300 MHz): δ 12.10 (br s, 1H), 7.56 (br s, 1H), 7.07-7.22 (m, 3H), 6.89-6.94 (m, 2H), 6.78-6.83 (m, 1H), 6.61 (d, J=8.1 Hz, 1H), 6.34 (t, J=6.0 Hz, 1H), 4.70-4.74 (m, 0.03H), 4.50 (d, J=17.7 Hz, 1H), 4.35 (d, J=5.7 Hz, 2H), 4.28 (d, J=17.7 Hz, 1H), 3.65 (s, 3H), 2.10-2.21 (m, 3H), 1.92-2.02 (m, 1H).

Step D: To a solution of A342A (450 mg, 1.10 mmol) in dry DCM (50 mL) cooled to −40° C. under N$_2$, SOCl$_2$ (572 mg, 4.81 mmol) was slowly added to the mixture at −40° C. under N$_2$, then a solution of DMF (10 mg) in DCM (1 mL) was added, stirring for 2 hr, then pyridine (380 mg, 4.80 mmol) was added dropwise at this temperature, stirring for 40 mins, then Et$_3$N (486 mg, 4.80 mmol) was added and then the mixture was stirred for 2 h. LCMS showed the reaction completed. H$_2$O (10 mL) was added to quench the reaction, the water layer was extracted with DCM (30 mL×2), the combined organic phase was washed with brine (50 mL), dried over Na$_2$SO$_4$, filtered, concentrated to give a residue. The residue was purified by flash chromatography on C18 (CH$_3$CN: H$_2$O=5%-35%, 30 min; 35%-45%, 30 min; 45%-55% 20 min) to give A342 (220 mg, yield: 58%, ee: 99%) as a light yellow solid.

$^1$H NMR (DMSO-d$_6$, 300 MHz): δ 11.00 (br s, 1H), 7.23 (t, J=7.8 Hz, 1H), 7.11 (t, J=9.6 Hz, 1H), 6.90-6.95 (m, 2H), 6.79-6.84 (m, 1H), 6.65 (d, J=7.8 Hz, 1H), 6.26 (t, J=5.4 Hz, 1H), 5.07-5.14 (m, 0.01H), 4.36 (d, J=5.7 Hz, 2H), 4.30 (d, J=17.1 Hz, 1H), 4.17 (d, J=17.1 Hz, 1H), 3.65 (s, 3H), 2.85-2.97 (m, 1H), 2.57-2.63 (m, 1H), 2.24-2.34 (m, 1H), 2.00-2.06 (m, 1H).

LCMS: 399.1 ([M+1]$^+$).

Compound of example 19 was prepared according to the synthetic method described for example 18, with corresponding starting material to replace A342E(R) in step B.

Example 19: A343

(S)-3-deuterium-3-(4-((2-fluoro-5-methoxybenzyl)amino)-1-oxoisoindolin-2-yl)piperidine-2,6-dione, A343

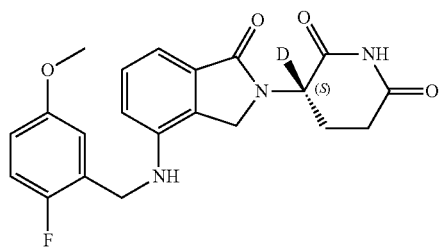

$^1$H NMR (DMSO-d$_6$, 300 MHz): δ 11.00 (br s, 1H), 7.23 (t, J=8.1 Hz, 1H), 7.11 (t, J=9.6 Hz, 1H), 6.90-6.95 (m, 2H), 6.78-6.84 (m, 1H), 6.65 (d, J=8.1 Hz, 1H), 6.26 (t, J=6.3 Hz, 1H), 5.07-5.13 (m, 0.02H), 4.36 (d, J=5.7 Hz, 2H), 4.29 (d, J=17.1 Hz, 1H), 4.17 (d, J=17.1 Hz, 1H), 3.65 (s, 3H), 2.85-2.97 (m, 1H), 2.56-2.64 (m, 1H), 2.24-2.34 (m, 1H), 2.00-2.05 (m, 1H). LCMS: 399.1 ([M+1]$^+$).

Example 20: Compound A346

(S)-3-(4-((4-(morpholinomethyl)benzyl)amino)-1-oxoisoindolin-2-yl) piperidine-2,6-dione, A346

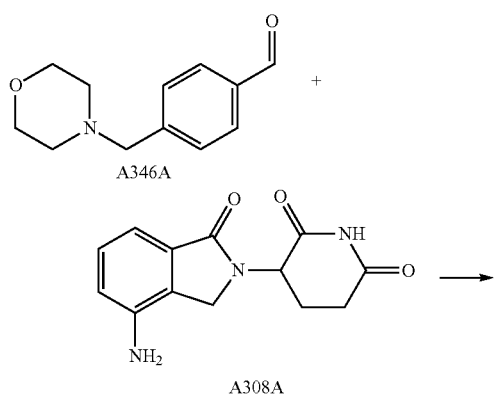

A346A (119 mg, 0.58 mmol) and compound A308A (100 mg, 0.39 mmol) was dissolved in AcOH (2.5 mL) and DCM (2.5 mL) and the solution was stirred for 1 hour at 30° C. NaBH(OAc)₃ (246 mg, 1.16 mmol) was added and the reaction mixture was stirred for 18 hours under N₂. TCL showed the reaction completed. The solvent was removed and sat aq NaHCO₃ (5 mL) was added to adjust pH to 8. The mixture was extracted with DCM (25 mL×5) and the combined organic layer was dried over Na₂SO₄, filtered, concentrated and triturated with PE/EtOAc (1/1) (25 mL×2) to give 250 mg crude product, which was purified by prep-HPLC to give A346 (140 mg, 80% yield) as a white solid.

¹H NMR (DMSO-d₆, 300 MHz): δ 11.00 (s, 1H), 0.7.16-7.33 (m, 5H), 6.90 (d, J=7.2 Hz, 1H), 6.62 (d, J=7.8 Hz, 1H), 6.33 (t, J=5.7 Hz, 1H), 5.07-5.13 (m, 1H), 4.35 (d, J=5.4 Hz, 2H), 4.29 (d, J=17.1 Hz, 1H), 4.16 (d, J=17.1 Hz, 1H), 3.53 (t, J=4.5 Hz, 4H), 3.39 (s, 2H), 2.85-2.93 (m, 1H), 2.58-2.63 (m, 1H), 2.28-2.31 (m, 5H), 2.01-2.06 (m, 1H).

LCMS: 449.2 ([M+1]⁺).

Compounds in examples 12-45 was prepared according to the procedure described for example 20, with corresponding starting materials to replace A346A.

Example 21: Compound A359

3-(4-((2-fluoro-3-hydroxybenzyl)amino)-1-oxoisoindolin-2-yl)piperidine-2,6-dione, A359

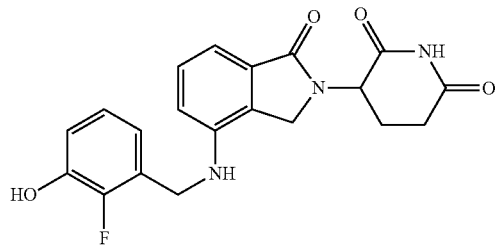 [SMILES: N#Cc1cccc(CNc2cccc3c2CN(C2CCC(=O)NC2=O)C3=O)c1F]

¹H NMR (DMSO-d₆, 300 MHz): δ 10.96 (br, 1H), 9.79 (br, 1H), 7.21 (t, J=7.8 Hz, 1H), 6.73-6.93 (m, 4H), 6.63 (d, J=7.8 Hz, 1H), 6.25 (t, J=6.0 Hz, 1H), 5.10 (dd, J=13.2, 5.1 Hz, 1H), 4.37 (d, J=5.7 Hz, 2H), 4.28 (d, J=17.4 Hz, 1H), 4.15 (d, J=17.4 Hz, 1H), 2.85-2.97 (m, 1H), 2.57-2.63 (m, 1H), 2.22-2.36 (m, 1H), 2.01-2.05 (m, 1H). LCMS: 384.1 ([M+1]⁺).

Example 22: Compound A360

3-(((2-(2,6-dioxopiperidin-3-yl)-1-oxoisoindolin-4-yl)amino)methyl)-2-fluorobenzonitrile, A360

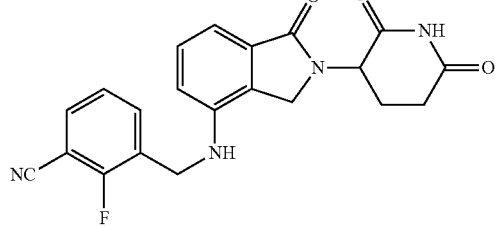

¹H NMR (300 MHz, DMSO-d₆): δ 11.03 (s, 1H), 7.81-7.86 (m, 1H), 7.71-7.76 (m, 1H), 7.36 (t, J=7.8 Hz, 1H), 7.25 (t, J=7.8 Hz, 1H), 6.97 (d, J=7.5 Hz, 1H), 6.66 (d, J=7.8 Hz, 1H), 6.41 (t, J=5.7 Hz, 1H), 5.13, (dd, J=12.9, 5.1 Hz, 1H), 4.50 (d, J=5.7 Hz, 1H), 4.32 (d, J=17.1 Hz, 1H), 4.19 (d, J=17.1 Hz, 1H), 2.87-2.95 (m 1H), 2.50-2.65 (m 1H), 2.29-2.34 (m 1H), 2.02-2.07 (m 1H).

Example 23: Compound A361

3-(((2-(2,6-Dioxopiperidin-3-yl)-1-oxoisoindolin-4-yl)amino)methyl)-2-fluorobenzamide, A361

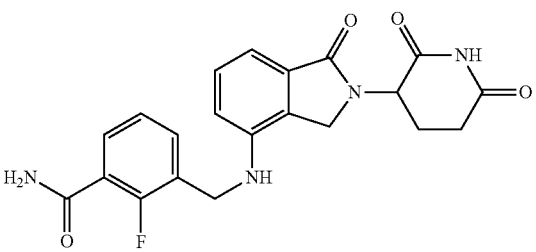 [SMILES: NC(=O)c1cccc(CNc2cccc3c2CN(C2CCC(=O)NC2=O)C3=O)c1F]

¹H NMR (DMSO-d₆, 300 MHz): δ 11.02 (s, 1H), 7.75 (s, 1H), 7.63 (s, 1H), 7.45-7.53 (m, 2H), 7.16-7.27 (m, 2H), 6.96 (d, J=7.2 Hz, 1H), 6.64 (d, J=8.1 Hz, 1H), 6.35-6.38 (m, 1H), 5.13 (dd, J=13.2, 4.8 Hz, 1H), 4.46 (d, J=5.4 Hz, 2H), 4.33 (d, J=17.4 Hz, 1H), 4.20 (d, J=17.4 Hz, 1H), 2.87-2.98 (m, 1H), 2.60-2.65 (m, 1H), 2.25-2.39 (m, 1H), 2.03-2.07 (m, 1H). LCMS: 411.1 ([M+1]⁺).

Example 24: Compound A362

3-(((2-(2,6-Dioxopiperidin-3-yl)-1-oxoisoindolin-4-yl)amino)methyl)-2-fluoro-N-methylbenzamide, A362

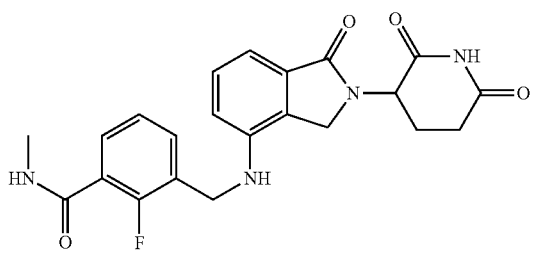 [SMILES: CNC(=O)c1cccc(CNc2cccc3c2CN(C2CCC(=O)NC2=O)C3=O)c1F]

¹H NMR (DMSO-d₆, 300 MHz): δ 11.01 (s, 1H), 8.28 (d, J=3.3 Hz, 1H), 7.46 (t, J=7.2 Hz, 2H), 7.15-7.26 (m, 2H), 6.95 (d, J=7.5 Hz, 1H), 6.63 (d, J=8.4 Hz, 1H), 6.37 (t, J=5.7 Hz, 1H), 5.12 (dd, J=13.5, 4.8 Hz, 1H), 4.45 (d, J=5.1 Hz, 2H), 4.32 (d, J=17.4 Hz, 1H), 4.20 (d, J=17.4 Hz, 1H), 2.87-2.99 (m, 1H), 2.78 (d, J=4.8 Hz, 3H), 2.60-2.65 (m, 1H), 2.25-2.39 (m, 1H), 1.99-2.11 (m, 1H). LCMS: 425.1 ([M+1]⁺).

Example 25: Compound A363

3-(4-((5-(2-(Dimethylamino)ethoxy)-2-fluorobenzyl)amino)-1-oxoisoindolin-2-yl)piperidine-2,6-dione, A363

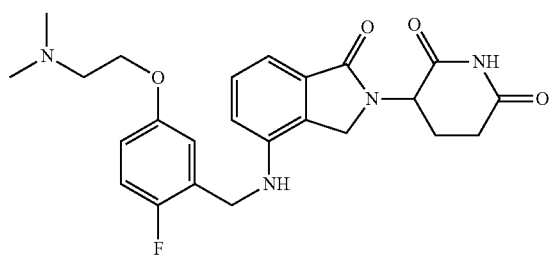 [SMILES: CN(C)CCOc1ccc(F)c(CNc2cccc3c2CN(C2CCC(=O)NC2=O)C3=O)c1]

¹H NMR (DMSO-d₆, 300 MHz): δ 11.02 (s, 1H), 7.24 (t, J=8.1 Hz, 1H), 7.11 (t, J=9.3 Hz, 1H), 6.90-6.96 (m, 2H), 6.80-6.86 (m, 1H), 6.65 (d, J=8.4 Hz, 1H), 6.29 (t, J=6.0 Hz, 1H), 5.12 (dd, J=13.2, 4.8 Hz, 1H), 4.29-4.39 (m, 3H), 4.19 (d, J=17.1 Hz, 1H), 3.94 (t, J=5.7 Hz, 2H), 2.87-2.99 (m, 1H), 2.51-2.65 (m, 3H), 2.24-2.38 (m, 1H), 2.15 (s, 6H), 2.00-2.10 (m, 1H). LCMS: 455.2 ([M+1]⁺).

Example 26: Compound A364

3-(4-((2-fluoro-5-hydroxybenzyl)amino)-1-oxoisoindolin-2-yl)piperidine-2,6-dione, A364

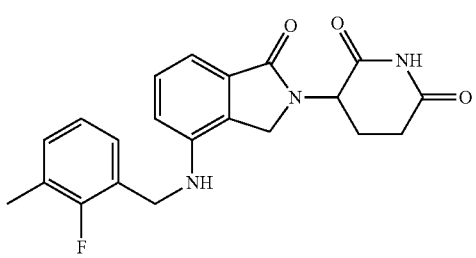 [SMILES: Cc1cccc(CNc2cccc3c2CN(C2CCC(=O)NC2=O)C3=O)c1F]

¹H NMR (300 MHz, DMSO-d₆): δ 11.01 (s, 1H), 9.24 (s, 1H), 7.22 (t, J=7.8 Hz, 1H), 6.92-6.99 (m, 2H), 6.70-6.73 (m, 1H), 6.55-6.60 (m, 2H), 6.31 (t, J=5.7 Hz, 1H), 5.11, (dd, J=13.2, 5.1 Hz, 1H), 4.27-4.34 (m, 3H), 4.17 (d, J=17.1 Hz, 1H), 2.86-2.96 (m 1H), 2.57-2.64 (m 1H), 2.24-2.33 (m 1H), 2.02-2.06 (m 1H).

Example 27: Compound A367

3-(4-((2-fluoro-3-methylbenzyl)amino)-1-oxoisoindolin-2-yl)piperidine-2,6-dione, A367

¹H NMR (DMSO-d₆, 300 MHz): δ 11.03 (s, 1H), 7.14-7.26 (m, 3H), 6.93-7.04 (m, 2H), 6.64 (d, J=7.5 Hz, 1H), 6.30 (br s, 1H), 5.09-5.16 (m, 1H), 4.42 (s, 2H), 4.31 (d, J=17.4 Hz, 1H), 4.18 (d, J=17.4 Hz, 1H), 2.89-2.98 (m, 1H), 2.59-2.65 (m, 1H), 2.25-2.46 (m, 4H), 2.02-2.07 (m, 1H). LCMS: 382.2 ([M+1]⁺).

Example 28: Compound A368

3-(4-((2-fluoro-5-(2-morpholinoethoxy)benzyl)amino)-1-oxoisoindolin-2-yl)piperidine-2,6-dione, A368

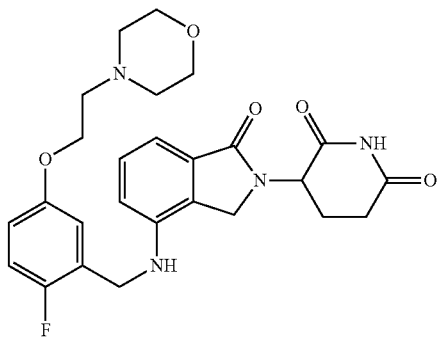 [SMILES: O=C1CCC(N2Cc3c(NCc4cc(OCCN5CCOCC5)ccc4F)cccc3C2=O)C(=O)N1]

$^1$H NMR (DMSO-d$_6$, 300 MHz): δ 10.98 (s, 1H), 7.23 (t, J=7.5 Hz, 1H), 7.09 (t, J=9.6 Hz, 1H), 6.79-6.95 (m, 3H), 6.64 (d, J=7.5 Hz, 1H), 6.24 (br, 1H), 5.10 (dd, J=13.2, 5.1 Hz, 1H), 4.36 (d, J=5.7 Hz, 2H), 4.30 (d, J=17.1 Hz, 1H), 4.18 (d, J=17.1 Hz, 1H), 3.97 (t, J=5.7 Hz, 2H), 3.51 (t, J=4.5 Hz, 4H), 2.85-2.97 (m, 1H), 2.56-2.63 (m, 3H), 2.27-2.39 (m, 5H), 2.00-2.05 (m, 1H). LCMS: 497.2 ([M+1]$^+$).

Example 29: Compound A369

3-(4-((2-fluoro-5-(3-morpholinopropoxy)benzyl)amino)-1-oxoisoindolin-2-yl)piperidine-2,6-dione, A369

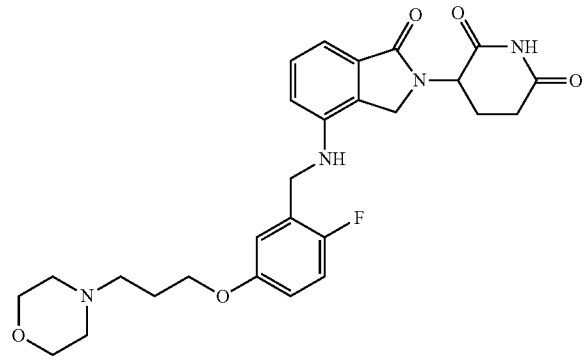 [SMILES: O=C1CCC(N2Cc3c(NCc4cc(OCCCN5CCOCC5)ccc4F)cccc3C2=O)C(=O)N1]

$^1$H NMR (DMSO-d$_6$, 300 MHz): δ 11.00 (s, 1H), 7.22 (t, J=7.8 Hz, 1H), 7.09 (t, J=9.3 Hz, 1H), 6.88-6.95 (m, 2H), 6.77-6.83 (m, 1H), 6.63 (d, J=8.1 Hz, 1H), 6.27 (t, J=5.7 Hz, 1H), 5.11 (dd, J=13.2, 5.4 Hz, 1H), 4.36 (d, J=5.7 Hz, 2H), 4.30 (d, J=17.4 Hz, 1H), 4.17 (d, J=17.4 Hz, 1H), 3.88 (t, J=6.3 Hz, 2H), 3.52 (t, J=3.9 Hz, 4H), 2.85-2.96 (m, 1H), 2.57-2.63 (m, 1H), 2.22-2.41 (m, 7H), 1.99-2.05 (m, 1H), 1.73-1.84 (m, 2H). LCMS: 511.2 ([M+1]$^+$).

Example 30: Compound A370

3-(4-((2-fluoro-5-(2-methoxyethoxy)benzyl)amino)-1-oxoisoindolin-2-yl)piperidine-2,6-dione, A370

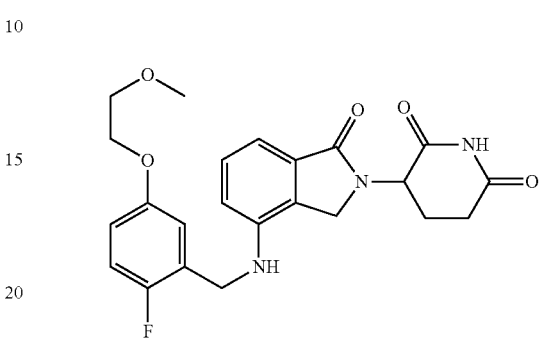

$^1$H NMR (300 MHz, DMSO-d$_6$): δ 10.98 (s, 1H), 7.23 (t, J=7.8 Hz, 1H), 7.06-7.12 (m, 1H), 6.90-6.95 (m, 2H), 6.79-6.84 (m, 1H), 6.64 (d, J=8.1 Hz, 1H), 6.24 (t, J=5.4 Hz, 1H), 5.10 (dd, J=13.2, 5.1 Hz, 1H), 4.28-4.38 (m, 3H), 4.19 (d, J=17.1 Hz, 1H), 3.96-3.99 (m, 2H), 3.55-3.58 (m, 2H), 3.23 (s, 3H), 2.85-2.95 (m 1H), 2.57-2.64 (m 1H), 2.24-2.36 (m 1H), 1.98-2.09 (m 1H).

Example 31: Compound A371

3-(((2-(2,6-Dioxopiperidin-3-yl)-1-oxoisoindolin-4-yl)amino)methyl)-4-fluorophenyl methylcarbamate, A371

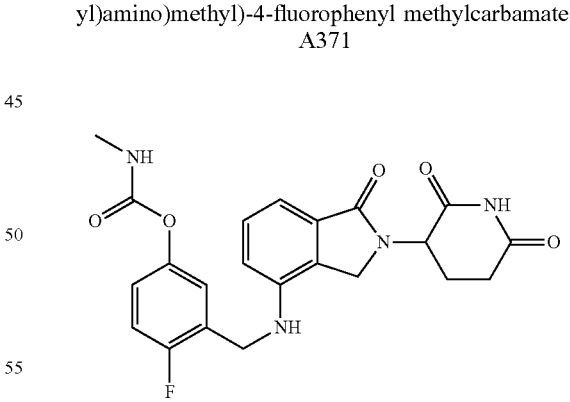

$^1$H NMR (DMSO-d$_6$, 300 MHz): δ 11.00 (s, 1H), 7.52-7.56 (m, 1H), 7.15-7.25 (m, 2H), 6.93-7.06 (m, 3H), 6.63 (d, J=7.8 Hz, 1H), 6.28-6.32 (m, 1H), 5.10 (dd, J=13.5, 4.5 Hz, 1H), 4.40 (d, J=4.8 Hz, 2H), 4.30 (d, J=17.4 Hz, 1H), 4.18 (d, J=17.4 Hz, 1H), 2.84-2.97 (m, 1H), 2.59-2.69 (m, 4H), 2.23-2.37 (m, 1H), 1.99-2.08 (m, 1H). LCMS: 441.1 ([M+1]$^+$).

Example 32: Compound A372

3-(4-((2-fluoro-3-(methylamino)benzyl)amino)-1-oxoisoindolin-2-yl)piperidine-2,6-dione, A372

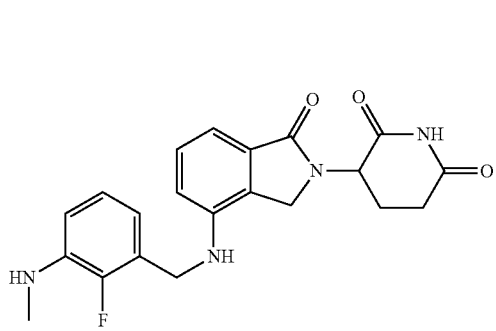 [SMILES: CNc1cccc(CNc2cccc3c2CN(C2CCC(=O)NC2=O)C3=O)c1F]

$^1$H NMR (DMSO-d$_6$, 300 MHz): δ 10.99 (s, 1H), 7.21 (t, J=7.8 Hz, 1H), 6.85-6.92 (m, 2H), 6.63 (d, J=8.1 Hz, 1H), 6.48-6.55 (m, 2H), 6.21 (t, J=5.4 Hz, 1H), 5.48-6.49 (m, 1H), 5.09 (dd, J=13.2, 5.1 Hz, 1H), 4.35 (d, J=5.4 Hz, 2H), 4.27 (d, J=17.4 Hz, 1H), 4.15 (d, J=17.4 Hz, 1H), 2.85-2.97 (m, 1H), 2.69 (d, J=4.5 Hz, 3H), 2.49-2.63 (m, 1H), 2.21-2.35 (m, 1H), 1.98-2.05 (m, 1H). LCMS=397.1 ([M+1]$^+$)

Example 33: Compound A375

3-(4-((2-fluoro-5-(2-hydroxyethoxy)benzyl)amino)-1-oxoisoindolin-2-yl)piperidine-2,6-dione, A375

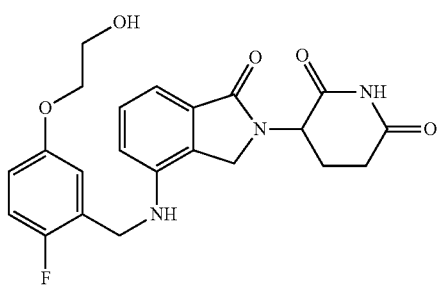 [SMILES: O=C1CCC(N2Cc3c(NCc4cc(OCCO)ccc4F)cccc3C2=O)C(=O)N1]

$^1$H NMR (DMSO-d$_6$, 300 MHz): δ 9.35 (br s, 1H), 7.22 (t, J=8.1 Hz, 1H), 7.10 (t, J=9.3 Hz, 1H), 6.88-6.95 (m, 2H), 6.78-6.83 (m, 1H), 6.63 (d, J=8.4 Hz, 1H), 6.31 (t, J=6.0 Hz, 1H), 5.11 (dd, J=13.5, 5.1 Hz, 1H), 4.82 (br s, 1H), 4.37 (d, J=5.7 Hz, 2H), 4.30 (d, J=17.1 Hz, 1H), 4.17 (t, J=17.1 Hz, 1H), 3.85 (t, J=4.8 Hz, 2H), 3.62 (t, J=4.8 Hz, 2H), 2.85-2.97 (m, 1H), 2.55-2.65 (m, 1H), 2.24-2.36 (m, 1H), 2.01-2.05 (m, 1H). LCMS: 428.1 [(M+1)$^+$].

Example 34: Compound A376

3-(4-((2-fluoro-5-(2-(pyrrolidin-1-yl)ethoxy)benzyl)amino)-1-oxoisoindolin-2-yl)piperidine-2,6-dione, A376

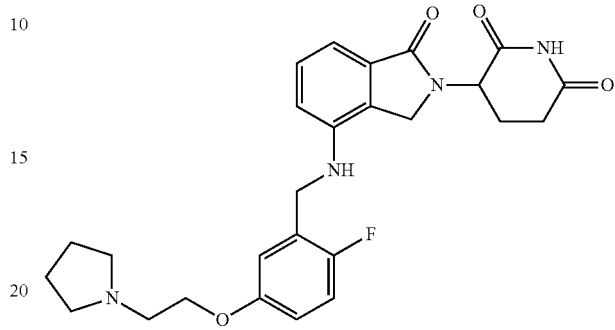

$^1$H NMR (300 MHz, DMSO-d$_6$): δ 11.02 (s, 1H), 7.22 (t, J=8.1 Hz, 1H), 7.06-7.13 (m, 1H), 6.89-6.95 (m, 2H), 6.78-6.84 (m, 1H), 6.63 (d, J=7.8 Hz, 1H), 6.29 (t, J=5.7 Hz, 1H), 5.11, (dd, J=13.2, 5.1 Hz, 1H), 4.27-4.37 (m, 3H), 4.17 (d, J=17.1 Hz, 1H), 3.94 (t, J=6.0 Hz, 1H), 2.85-2.97 (m 1H), 2.57-2.69 (m 3H), 2.22-2.42 (m 5H), 1.98-2.06 (m, 1H), 1.56-1.66 (m 4H).

Example 35: Compound A377

3-(4-((2-fluoro-5-(2-(4-methylpiperazin-1-yl)ethoxy)benzyl)amino)-1-oxoisoindolin-2-yl)piperidine-2,6-dione, A377

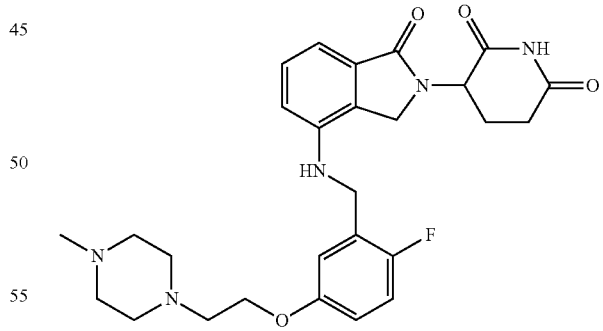

$^1$H NMR (300 MHz, DMSO-d$_6$): δ 11.03 (s, 1H), 7.22 (t, J=7.8 Hz, 1H), 7.09 (t, J=9.6 Hz, 1H), 6.91-6.95 (m, 2H), 6.79-6.89 (m, 1H), 6.63 (d, J=8.1 Hz, 1H), 6.29 (t, J=6.0 Hz, 1H), 5.11 (dd, J=13.5, 4.8 Hz, 1H), 4.27-4.37 (m, 3H), 4.17 (d, J=17.4 Hz, 1H), 3.94 (t, J=5.7 Hz, 2H), 2.85-2.98 (m, 1H), 2.55-2.62 (m, 4H), 2.20-2.42 (m, 8H), 2.12 (s, 3H), 1.98-2.07 (m, 1H). LCMS: 510.2 ([M+1]$^+$).

Example 36: Compound A378

3-(((2-(2,6-dioxopiperidin-3-yl)-1-oxoisoindolin-4-yl)amino)methyl)-4-fluorophenyl dimethylcarbamate, A378

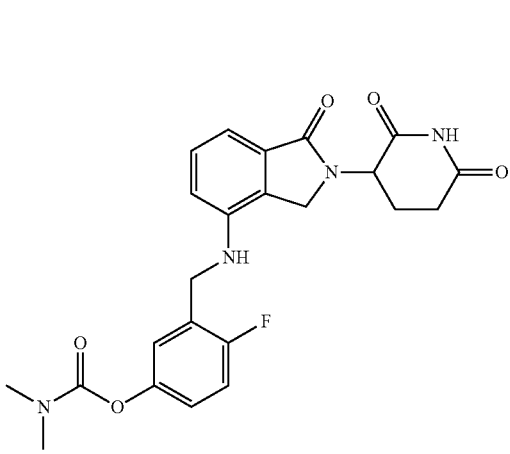 [SMILES: CN(C)C(=O)Oc1ccc(F)c(CNc2cccc3c2CN(C2CCC(=O)NC2=O)C3=O)c1]

$^1$H NMR (300 MHz, DMSO-d$_6$): δ 11.00 (s, 1H), 7.17-7.26 (m, 2H), 7.08-7.11 (m, 1H), 6.94-7.04 (m, 2H), 6.78-6.84 (m, 1H), 6.62 (d, J=8.1 Hz, 1H), 6.30 (t, J=5.9 Hz, 1H), 5.11, (dd, J=13.2, 5.4 Hz, 1H), 4.40 (d, J=5.7 Hz, 1H), 4.31 (d, J=17.4 Hz, 1H), 4.18 (d, J=17.4 Hz, 1H), 2.84-2.96 (m 7H), 2.57-2.63 (m 1H), 2.23-2.37 (m 1H), 2.00-2.05 (m 1H).

Example 37: Compound A382

3-(4-((2-fluoro-5-(3-morpholinopropoxy)benzyl)amino)-1-oxoisoindolin-2-yl)piperidine-2,6-dione, A382

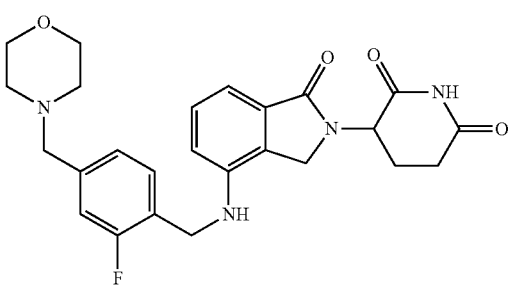 [SMILES: O=C1CCC(N2Cc3c(NCc4ccc(CN5CCOCC5)cc4F)cccc3C2=O)C(=O)N1]

$^1$H NMR (DMSO-d$_6$, 300 MHz): δ 11.00 (s, 1H), 7.32 (t, J=7.8 Hz, 1H), 7.22 (t, J=7.8 Hz, 1H), 7.05-7.13 (m, 2H), 6.93 (d, J=7.5 Hz, 1H), 6.64 (d, J=7.8 Hz, 1H), 6.28 (t, J=6.3 Hz, 1H), 5.07-5.13 (m, 1H), 4.38 (d, J=5.7 Hz, 2H), 4.28 (d, J=17.4 Hz, 1H), 4.16 (d, J=17.4 Hz, 1H), 3.54 (t, J=4.5 Hz, 4H), 3.42 (s, 2H), 2.85-2.97 (m, 1H), 2.57-2.63 (m, 1H), 2.26-2.38 (m, 5H), 2.00-2.09 (m, 1H). LCMS: 467.2 ([M+1]$^+$).

Example 38: Compound A383

3-(4-((2-fluoro-5-(morpholinomethyl)benzyl)amino)-1-oxoisoindolin-2-yl)piperidine-2,6-dione, A383

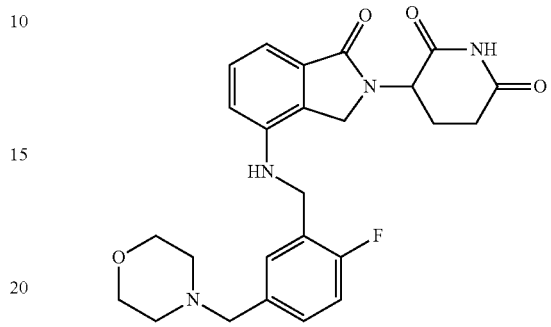

$^1$H NMR (DMSO-d$_6$, 300 MHz): δ 10.98 (br s, 1H), 7.34 (d, J=0.9 Hz, 1H), 7.10-7.32 (m, 3H), 6.95 (d, J=7.5 Hz, 1H), 6.64 (d, J=7.8 Hz, 1H), 6.27 (br s, 1H), 5.12 (dd, J=13.5, 5.1 Hz, 1H), 4.43 (d, J=5.7 Hz, 2H), 4.32 (d, J=17.1 Hz, 1H), 4.21 (d, J=17.1 Hz, 1H), 3.45-3.48 (m, 4H), 3.38 (s, 2H), 2.87-2.99 (m, 1H), 2.30-2.36 (m, 1H), 2.23-2.25 (m, 4H), 2.22-2.36 (m, 1H), 2.01-2.09 (m, 1H). LCMS=467.2 [(M+1)$^+$].

Example 39: Compound A381

3-(4-((2-fluoro-3-(morpholinomethyl)benzyl)amino)-1-oxoisoindolin-2-yl)piperidine-2,6-dione, A381

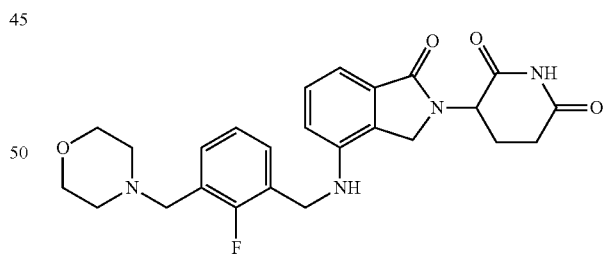

$^1$H NMR (DMSO-d$_6$, 300 MHz): δ 11.02 (s, 1H), 7.20-7.31 (m, 3H), 7.10 (t, J=7.8 Hz, 1H), 6.95 (d, J=7.5 Hz, 1H), 6.65 (d, J=8.1 Hz, 1H), 6.31 (t, J=5.7 Hz, 1H), 5.12 (dd, J$_1$=13.8 Hz, J$_2$=5.4 Hz, 1H), 4.43 (d, J=5.4 Hz, 2H), 4.31 (d, J=17.4 Hz, 1H), 4.19 (d, J=17.4 Hz, 1H), 3.53-3.58 (m, 6H), 2.87-2.99 (m, 1H), 2.57-2.66 (m, 1H), 2.24-2.39 (m, 5H), 2.00-2.10 (m, 1H). LCMS=467.2 [(M+1)$^+$].

Example 40: Compound A384

3-(4-((3-amino-2-fluorobenzyl)amino)-1-oxoisoindolin-2-yl)piperidine-2,6-dione, A384

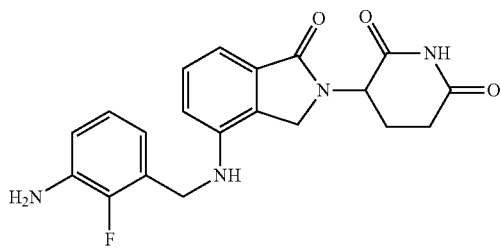 [SMILES: Nc1cccc(CNc2cccc3c2CN(C2CCC(=O)NC2=O)C3=O)c1F]

¹H NMR (DMSO-d₆, 300 MHz): δ 9.76 (br s, 1H), 7.23 (t, J=8.1 Hz, 1H), 6.93 (d, J=7.5 Hz, 1H), 6.77 (t, J=7.8 Hz, 1H), 6.61-6.67 (m, 2H), 6.49-6.54 (m 1H), 6.22 (t, J=5.7 Hz, 1H), 5.09-5.15 (m, 3H), 4.35 (d, J=5.4 Hz, 2H), 4.29 (d, J=17.4 Hz, 1H), 4.17 (d, J=17.4 Hz, 1H), 2.87-2.99 (m, 1H), 2.58-2.67 (m, 1H), 2.23-2.36 (m, 1H), 2.00-2.10 (m, 1H). LCMS=383.1 ([M+1]⁺).

Example 41: Compound A388

N-(3-(((2-(2,6-dioxopiperidin-3-yl)-1-oxoisoindolin-4-yl)amino)methyl)-2-fluorophenyl)acetamide, A388

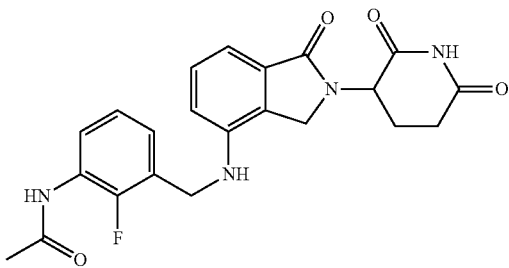 [SMILES: CC(=O)Nc1cccc(CNc2cccc3c2CN(C2CCC(=O)NC2=O)C3=O)c1F]

¹H NMR (DMSO-d₆, 300 MHz): δ 10.96 (br s, 1H), 9.71 (s, 1H), 7.74 (t, J=6.9 Hz, 1H), 7.22 (t, J=7.8 Hz, 1H), 7.02-7.13 (m, 2H), 6.93 (d, J=7.5 Hz, 1H), 6.64 (d, J=7.8 Hz, 1H), 6.31 (t, J=6.0 Hz, 1H), 5.10 (dd, J=12.9, 5.1 Hz, 1H), 4.42 (d, J=5.4 Hz, 2H), 4.29 (d, J=17.1 Hz, 1H), 4.16 (d, J=17.1 Hz, 1H), 2.85-2.95 (m, 1H), 2.55-2.64 (m, 1H), 2.22-2.36 (m, 1H), 1.99-2.07 (m, 4H). LCMS=425.1 [(M+1)⁺].

Example 42: Compound A389

3-(((2-(2,6-dioxopiperidin-3-yl)-1-oxoisoindolin-4-yl)amino)methyl)-2-fluorobenzenesulfonamide, A389

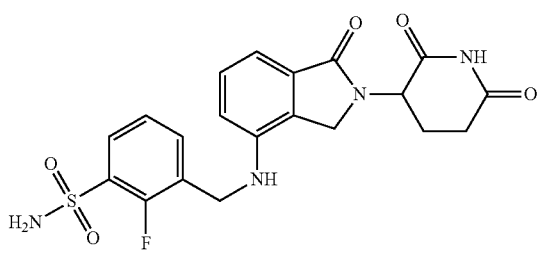 [SMILES: NS(=O)(=O)c1cccc(CNc2cccc3c2CN(C2CCC(=O)NC2=O)C3=O)c1F]

¹H NMR (300 MHz, DMSO-d₆): δ 11.02 (s, 1H), 7.85-7.88 (m, 1H), 7.73-7.78 (m, 1H), 7.39-7.45 (m, 3H), 7.24 (t, J=7.8 Hz, 1H), 6.96 (d, J=7.5 Hz, 1H), 6.63 (d, J=8.1 Hz, 1H), 6.43 (t, J=6.0 Hz, 1H), 5.11, (dd, J=13.2, 5.1 Hz, 1H), 4.46 (d, J=5.4 Hz, 2H), 4.29 (d, J=17.4 Hz, 1H), 4.18 (d, J=17.4 Hz, 1H), 2.85-2.97 (m 1H), 2.58-2.63 (m 1H), 2.24-2.36 (m 5H), 2.02-2.07 (m 1H).

Example 43: Compound A387

3-(4-((2-fluoro-5-(methylamino)benzyl)amino)-1-oxoisoindolin-2-yl)piperidine-2,6-dione, A387

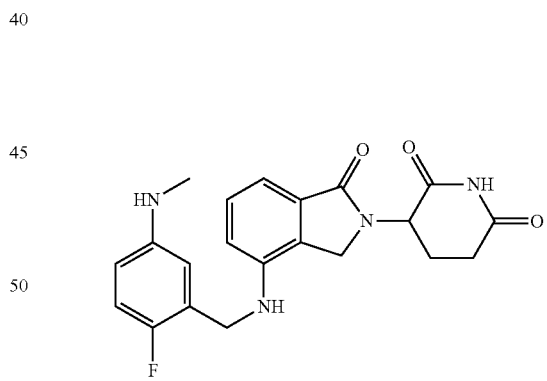

¹H NMR (DMSO-d₆, 300 MHz): δ 11.02 (s, 1H), 7.22 (t, J=7.5 Hz, 1H), 6.87-6.93 (m, 2H), 6.62 (d, J=8.1 Hz, 1H), 6.50-6.53 (m, 1H), 6.31-6.36 (m, 1H), 6.25 (t, J=5.7 Hz, 1H), 5.47-5.52 (m, 1H), 5.11 (dd, J=4.8, 13.2 Hz, 1H), 4.25-4.30 (m, 3H), 4.15 (d, J=17.4 Hz, 1H), 2.85-2.97 (m, 1H), 2.54-2.63 (m, 4H), 2.22-2.37 (m, 1H), 1.99-2.06 (m, 1H). LCMS: 397.21 ([M+1]⁺).

Example 44: Compound A396

3-(4-((2-fluoro-4-hydroxybenzyl)amino)-1-oxoisoindolin-2-yl)piperidine-2,6-dione, A396

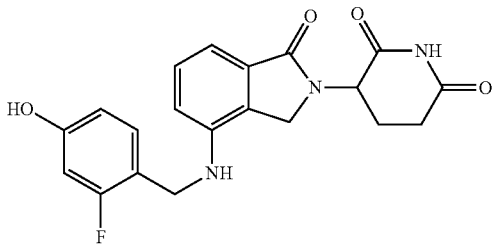 [SMILES: O=C1CCC(N2Cc3c(NCc4ccc(O)cc4F)cccc3C2=O)C(=O)N1]

$^1$H NMR (DMSO-$d_6$, 300 MHz): δ 11.00 (br s, 1H), 9.74 (br s, 1H), 7.14-7.25 (m, 2H), 6.92 (d, J=7.2 Hz, 1H), 6.66 (d, J=8.1 Hz, 1H), 6.52-6.55 (m, 2H), 6.13 (t, J=6.0 Hz, 1H), 5.07-5.13 (m, 1H), 4.24-4.29 (m, 3H), 4.14 (d, J=17.1 Hz, 1H), 2.87-2.97 (m, 1H), 2.56-2.65 (m, 1H), 2.21-2.36 (m, 1H), 1.98-2.06 (m, 1H). LCMS: 384.1 [(M+1)$^+$]

Example 45: Compound A391

[3-(4-((5-amino-2-fluorobenzyl)amino)-1-oxoisoindolin-2-yl)piperidine-2,6-dione], A391

Step A: compound A391G was prepared according to the synthetic method shown in Example 20, with corresponding starting material to replace A346A.

$^1$H NMR (DMSO-$d_6$, 400 MHz): δ 11.03 (s, 1H), 9.31 (s, 1H), 7.37-7.44 (m, 2H), 7.24 (t, J=7.6 Hz, 1H), 7.09 (t, J=9.2 Hz, 1H), 6.95 (d, J=7.2 Hz, 1H), 6.62 (d, J=8.0 Hz, 1H), 6.33 (t, J=5.6 Hz, 1H), 5.11-5.16 (m, 1H), 4.36 (t, J=5.2 Hz, 2H), 4.29 (d, J=16.8 Hz, 1H), 4.19 (d, J=17.2 Hz, 1H), 2.89-2.98 (m, 1H), 2.60-2.64 (m, 1H), 2.26-2.37 (m, 1H), 2.03-2.06 (m, 1H), 1.42 (s, 9H).

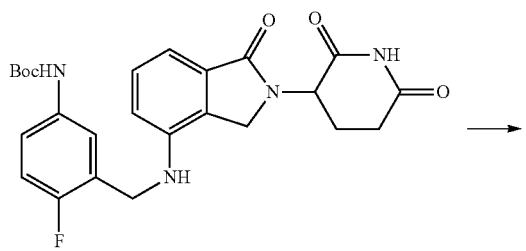

A391G

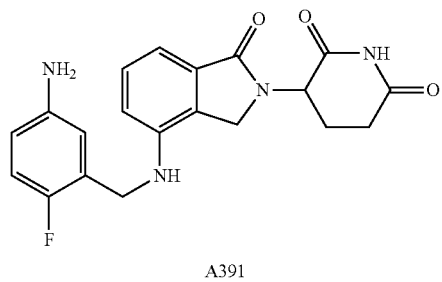

A391

Step B: To a solution of A391G (400 mg, 0.83 mmol) in DCM (12 mL) was added CF$_3$COOH (4 m L), and the solution was stirred for 0.5 hours at 35° C. The solvent was removed and the residue was dissolved with 4 mL CH$_3$CN and 100 mg Et$_3$N, then purified by prep-HPLC to give A391 (130 mg, yield: 41%) as a white solid.

$^1$H NMR (DMSO-$d_6$, 400 MHz): δ 10.83 (s, 1H), 9.37 (t, J=5.6 Hz, 1H), 8.03 (d, J=8.8 Hz, 2H), 7.78-7.86 (m, 3H), 7.58 (s, 1H), 7.50 (d, J=8.0 Hz, 2H), 7.17 (s, 1H), 4.64 (d, J=5.6 Hz, 2H), 4.50-4.54 (m, 1H), 2.37-2.41 (m, 1H), 2.21-2.26 (m, 1H), 1.89-1.93 (m, 2H). LCMS: 523.1 ([M+1]$^+$).

Example 46: Compound A397

3-(4-((5-amino-2-fluorobenzyl)amino)-1-oxoisoindolin-2-yl)piperidine-2,6-dione, A397

Step A: Compound A397A was prepared according to the synthetic method shown in Example 20, with corresponding starting material to replace A346A.

$^1$H NMR (DMSO-$d_6$, 400 MHz): δ 11.04 (br s, 1H), 9.54 (br s, 1H), 7.38 (d, J=12.8 Hz, 1H), 7.22-7.28 (m, 2H), 7.13 (d, J=8.4 Hz, 1H), 6.94 (d, J=7.6 Hz, 1H), 6.65 (d, J=8.0 Hz, 1H), 6.24 (t, J=5.6 Hz, 1H), 5.10-5.14 (m, 1H), 4.27-4.34 (m, 3H), 4.17 (d, J=17.2 Hz, 1H), 2.89-2.97 (m, 1H), 2.64-2.67 (m, 1H), 2.25-2.36 (m, 1H), 2.03-2.06 (m, 1H), 1.46 (s, 9H).

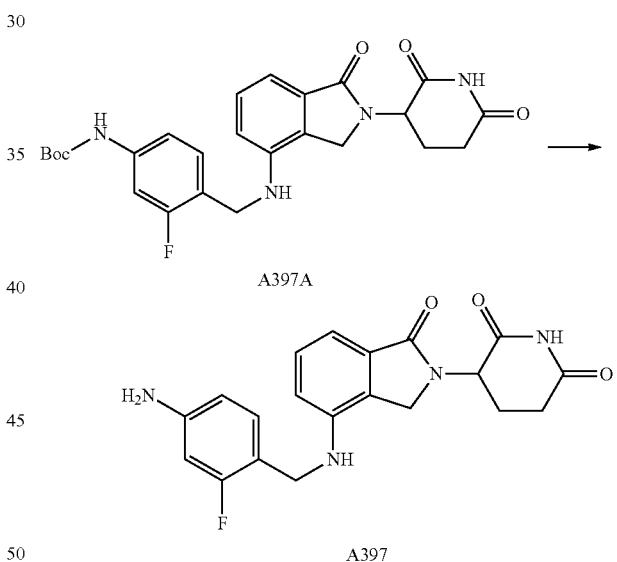

Step B: To a solution of compound A397A (100 mg, 0.21 mmol) in dioxane (20 mL) was added a solution of 6 N HCl in dioxane, the mixture was stirred for 2.5 h. The reaction mixture was concentrated and the residue was dissolved in DMF (10 mL) and adjust pH=7-8 with Sat. NaHCO$_3$, filtered. The filtrate was concentrated and the residue was purified by Prep-HPLC to give the desired product A397 (35 mg, yield: 44%) as a light yellow solid.

$^1$H NMR (DMSO-$d_6$, 400 MHz): δ 11.02 (br s, 1H), 7.24 (t, J=8.4 Hz, 1H), 7.02 (t, J=8.4 Hz, 1H), 6.93 (d, J=7.6 Hz, 1H), 6.69 (d, J=8.0 Hz, 1H), 6.04 (t, J=5.6 Hz, 1H), 5.30 (br s, 2H), 5.09-5.14 (m, 1H), 4.25 (d, J=17.2 Hz, 1H), 4.20 (d, J=5.6 Hz, 1H), 4.14 (d, J=17.2 Hz, 1H), 2.88-2.97 (m, 1H), 2.59-2.64 (m, 1H), 2.24-2.35 (m, 1H), 2.02-2.08 (m, 4H). LCMS: 383.2 [(M+1)$^+$].

Example 47: Compound A373

(S)-3-deuterium-3-(4-((4-(morpholinomethyl)benzyl)amino)-1-oxoisoindolin-2-yl)piperidine-2,6-dione, A373

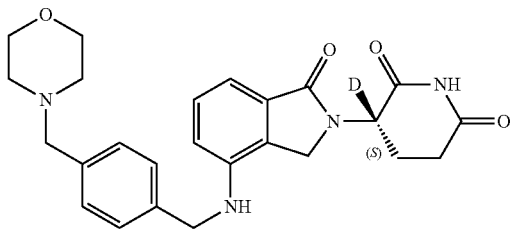

Step A: To a solution of A373C [4-(morpholinomethyl)benzaldehyde] (0.8 g, 3.9 mmol) and A356C (0.7 g, 2.5 mmol) in MeOH (100 mL) was added AcOH (1 mL) and the mixture was stirred overnight at 40° C. under $N_2$. Then Pd/C (50% wet, 10%, 150 mg) was added to the reaction mixture and degassed with $H_2$ 3 times. The mixture was stirred for 5 hours at 1 atm hydrogen pressure. The reaction mixture was filtered and the filtrate was concentrated and purified by RP-HPLC to give A373A (1.0 g, yield: 86%) as a light yellow solid.

$^1$H NMR (DMSO-d6, 300 MHz): δ 9.96 (br, 1H), 7.59 (s, 1H), 7.41-7.49 (m, 4H), 7.11-7.18 (m, 2H), 6.87 (d, J=7.2 Hz, 1H), 6.54 (d, J=8.1 Hz, 1H), 4.25-4.55 (m, 7H), 3.93 (d, J=12.0 Hz, 2H), 3.58 (t, J=12.3 Hz, 2H), 3.01-3.24 (m, 4H), 2.13-2.21 (m, 3H), 1.93-2.00 (m, 1H).

Step B: To a solution of A373A (200 mg, 0.428 mmol) in THF (12 mL) and DCM (12 mL) was added $SOCl_2$ (204 mg, 1.71 mmol in 1.7 mL DCM) at −40° C. and the mixture was stirred at −40° C. for 2 hours under $N_2$. Then pyridine (135 mg, 1.71 mmol) was added to the reaction mixture and stirred for 30 minutes. Then $Et_3N$ (173 mg, 1.71 mmol) was added and the reaction mixture was allowed to warm to room temperature. Water (0.5 mL) was added to quench the reaction and the mixture was concentrated and purified by reversed-phase Prep-HPLC (mobile phase:water/acetonitrile) 2 times to give A373 (20 mg, yield: 10%) as a white solid.

$^1$H NMR (DMSO-d6, 300 MHz): δ 11.02 (s, 1H), 7.15-7.34 (m, 5H), 6.89 (d, J=7.2 Hz, 1H), 6.61 (d, J=7.8 Hz, 1H), 6.38 (t, J=4.8 Hz, 1H), 5.08-5.14 (m, 0.04H), 4.35 (d, J=5.1 Hz, 2H), 4.29 (d, J=17.4 Hz, 1H), 4.16 (d, J=17.4 Hz, 1H), 3.55 (br s, 4H), 3.42 (br.s, 2H), 2.85-2.98 (m, 1H), 2.57-2.63 (m, 1H), 2.24-2.34 (m, 5H), 1.99-2.05 (m, 1H).

LCMS: 450.2 ([M+1]$^+$).

Example 48: Compound A374

2-(3-(((2-(2,6-dioxopiperidin-3-yl)-1-oxoisoindolin-4-yl)amino)methyl)-4-fluorophenoxy)ethyl pyrrolidine-1-carboxylate, A374

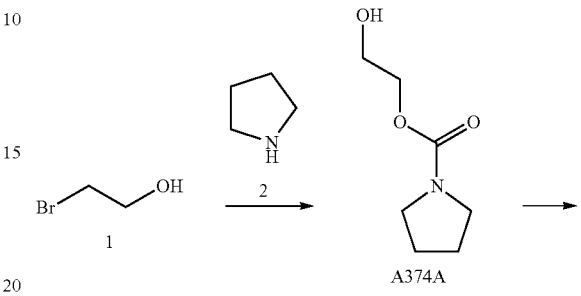

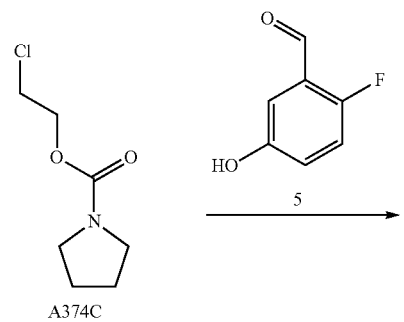

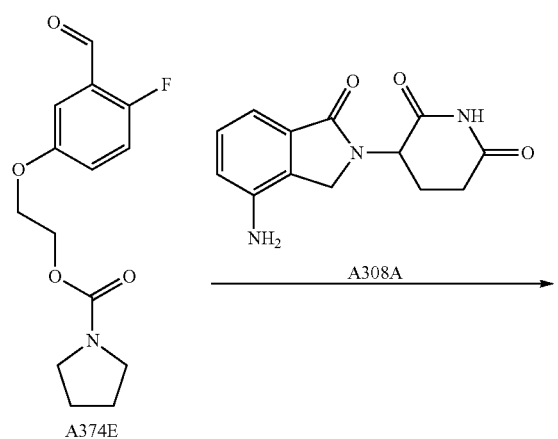

-continued

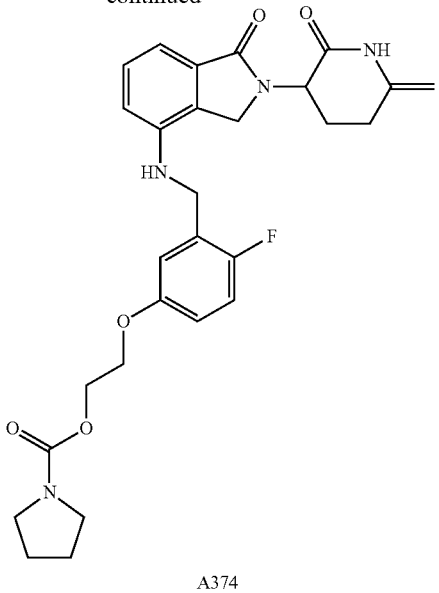

A374

Step A. A mixture of pyrrolidine (3.77 g 53 mmol), 2-bromoethanol (6.25 g, 50 mmol) and K₂CO₃ (6.9 g 50 mmol) in CH₃CN (70 mL) was heated to reflux and stirred overnight under N₂. The reaction mixture was filtered and concentrated, and purified via column chromatography on silica gel (DCM:MeOH=100:1 to 10:1) to give A374A (4 g, 50% yield) as a light yellow oil.

¹H NMR (CDCl₃, 300 MHz): δ 4.25-4.28 (m, 2H), 3.80-3.85 (m, 2H), 3.36-3.43 (m, 4H), 2.92 (t, J=5.7, 1H), 1.88-1.92 (m, 4H).

Step B. To a solution of A374A (2.3 g, 14.4 mmol) in CHCl₃ (50 mL) was added SOCl₂ (3.6 g, 30.0 mmol) and the reaction mixture was stirred for 1.5 h under reflux. The reaction mixture was concentrated to give crude A374C (2.0 g, yield: 78%) as a white solid.

¹H NMR (CDCl₃, 300 MHz): δ 4.21 (t, J=5.7, 2H), 3.77 (t, J=5.7, 2H), 3.21-3.32 (m, 4H), 1.75-1.83 (m, 4H).

Step C. A mixture of A374C (802 mg, 4.52 mmol), 2-fluoro-5-hydroxybenzaldehyde (280 mg, 2.0 mmol) and K₂CO₃ (828 mg, 6.0 mmol) in DMF (10 mL) was heated to 90° C. and stirred overnight under N₂. The reaction mixture was poured into ice water (100 mL), stirred and filtered. The cake was washed with water (20 mL) and then dissolved in EtOAc (50 mL), dried and concentrated to give product A374E (560 mg) as a white solid which was used in next step without purification.

¹H NMR (CDCl₃, 300 MHz): δ 10.32 (s, 1H), 7.31-7.34 (m, 1H), 7.09-7.17 (m, 2H), 4.42 (t, J=5.1 Hz, 2H), 4.20 (t, J=5.1 Hz, 2H) 3.30-3.41 (m, 4H), 1.85 (br s, 4H).

Step D. A solution of A374E (206 mg, 0.732 mmol), A308A (150 mg, 0.578 mmol) and AcOH (6 mL) in dichloromethane (6 mL) was stirred for 4 hours at room temperature. NaBHCN (109 mg, 1.74 mmol) was added and the reaction mixture was stirred at room temperature overnight under N₂. The solvent was removed and the residue was dissolved in CH₃CN and purified by prep-HPLC to give A374 (105 mg, 35% yield) as a white solid.

¹H NMR (DMSO-d₆, 300 MHz): δ 11.00 (s, 1H), 7.20-7.25 (m, 1H), 7.11 (t, J=9.3 Hz, 1H), 6.93-6.95 (m, 2H), 6.82-6.87 (m, 1H), 6.64 (d, J=8.1 Hz, 1H), 6.24-6.29 (m, 1H), 5.11 (dd, J=13.5, 5.1 Hz, 1H), 4.33-4.37 (m, 2H), 4.20-4.27 (m, 4H), 4.08-4.14 (m, 2H), 3.12-3.22 (m, 4H), 2.86-2.97 (m, 1H), 2.62-2.71 (m, 1H), 2.24-2.33 (m, 1H), 2.01-2.06 (m, 1H), 1.69-1.77 (m, 4H). LCMS: 525.2 ([M+1]⁺).

Example 49: Compound A349

[3-(4-((3,4-dimethoxybenzyl)amino)-1-oxoisoindolin-2-yl)piperidine-2,6-dione], A349

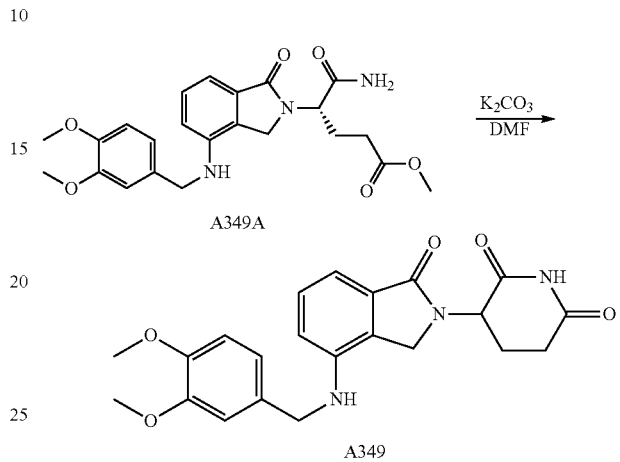

To a solution of compound A349A (100 mg, 0.23 mmol) in DMF (5 mL) were added K₂CO₃ (47.0 mg, 0.34 mmol), the mixture was stirred 80° C. (oil bath) overnight under N₂. TCL showed the reaction was finished. The reaction mixture was filtrated and the filtrate was concentrated to give a residue. The residue was purified by RP-HPLC to give A349 (40 mg, 43% yield) as a white solid.

¹H NMR (DMSO-d₆, 300 MHz): δ 11.02 (s, 1H), 7.20 (t, J=7.5 Hz, 1H), 7.01 (s, 1H), 6.85-6.92 (m, 3H), 6.68 (d, J=7.8 Hz, 1H), 6.24-6.28 (m, 1H), 5.08-5.14 (m, 1H), 4.25-4.33 (m, 3H), 4.18 (d, J=17.1 Hz, 1H), 3.72 (s, 3H), 3.70 (s, 3H), 2.87-2.99 (m, 1H), 2.59-2.65 (m, 1H), 2.24-2.37 (m, 1H), 2.00-2.08 (m, 1H). LCMS: 410.2 ([M+1]⁺)

Example 50: Compound A350

3-(4-((3,4-dimethylbenzyl)amino)-1-oxoisoindolin-2-yl)piperidine-2,6-dione, A350

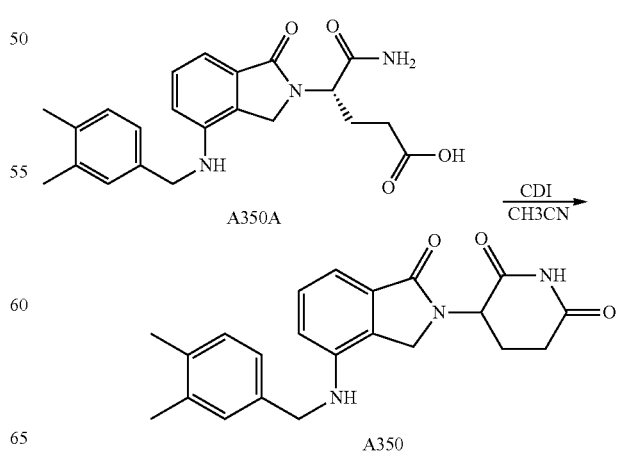

To a solution of A350A (100 mg, 0.25 mmol) in CH₃CN (5 mL) were added CDI (62.0 mg, 0.38 mmol), the mixture was stirred 95° C. (oil bath) overnight under N₂. TCL showed the reaction was finished. The reaction mixture was filtered and concentrated to give a residue. The residue was purified by RP-HPLC to give A350 (61 mg, yield: 65%) as a white solid.

¹H NMR (DMSO-d₆, 300 MHz): δ 11.01 (s, 1H), 7.15-7.21 (m, 2H), 7.04-7.10 (m, 2H), 6.91 (d, J=7.2 Hz, 1H), 6.62 (d, J=8.1 Hz, 1H), 6.27-6.31 (m, 1H), 5.11 (dd, J=13.2, 5.1 Hz, 1H), 4.28-4.33 (m, 3H), 4.18 (d, J=17.7 Hz, 1H), 2.87-2.99 (m, 1H), 2.60-2.65 (m, 1H), 2.24-2.37 (m, 1H), 2.19 (s, 3H), 2.17 (s, 3H), 2.02-2.07 (m, 1H). LCMS: 378.2 ([M+1]⁺).

Compounds in examples 51-55 were prepared according to the procedure described in example 50, with corresponding starting materials to replace A350A.

Example 51: Compound A351

3-(4-((4-fluoro-3-methylbenzyl)amino)-1-oxoisoindolin-2-yl)piperidine-2,6-dione, A351

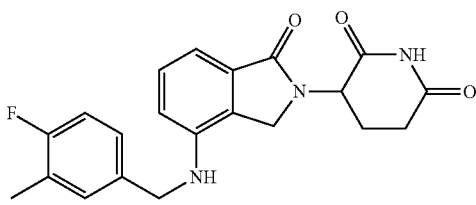 [SMILES: Cc1cc(CNc2cccc3c2CN(C2CCC(=O)NC2=O)C3=O)ccc1F]

¹H NMR (DMSO-d₆, 300 MHz): δ 11.02 (s, 1H), 7.29 (d, J=6.0 Hz, 1H), 7.18-7.23 (m, 2H), 7.06 (t, J=9.6 Hz, 1H), 6.92 (d, J=7.2 Hz, 1H), 6.63 (d, J=7.8 Hz, 1H), 6.34 (t, J=6.0 Hz, 1H), 5.12 (dd, J=13.2, 5.1 Hz, 1H), 4.28-4.33 (m, 3H), 4.18 (d, J=17.4 Hz, 1H), 2.87-2.99 (m, 1H), 2.59-2.65 (m, 1H), 2.26-2.37 (m, 1H), 2.21 (s, 3H), 2.01-2.08 (m, 1H). LCMS: 382.1 ([M+1]⁺).

Example 52: Compound A352

3-(4-((3-chloro-4-methylbenzyl)amino)-1-oxoisoindolin-2-yl)piperidine-2,6-dione, A352

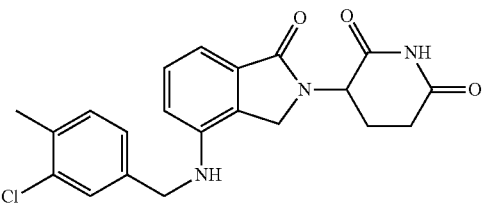 [SMILES: Cc1ccc(CNc2cccc3c2CN(C2CCC(=O)NC2=O)C3=O)cc1Cl]

¹H NMR (DMSO-d₆, 300 MHz): δ 11.01 (s, 1H), 7.41 (s, 1H), 7.17-7.30 (m, 3H), 6.92 (d, J=7.5 Hz, 1H), 6.61 (d, J=8.1 Hz, 1H), 6.39 (t, J=6.0 Hz, 1H), 5.12 (dd, J=13.2, 5.4 Hz, 1H), 4.29-4.37 (m, 3H), 4.18 (d, J=17.1 Hz, 1H), 2.87-2.99 (m, 1H), 2.59-2.65 (m, 1H), 2.25-2.39 (m, 4H), 2.02-2.07 (m, 1H). LCMS: 398.1 ([M+1]⁺).

Example 53: Compound A353

3-(4-((3-fluoro-4-methylbenzyl)amino)-1-oxoisoindolin-2-yl)piperidine-2,6-dione, A353

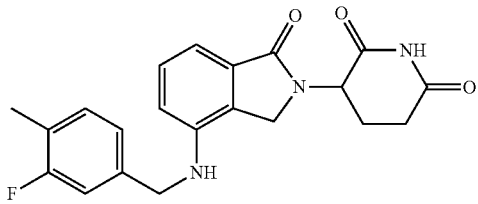 [SMILES: Cc1ccc(CNc2cccc3c2CN(C2CCC(=O)NC2=O)C3=O)cc1F]

¹H NMR (DMSO-d₆, 300 MHz): δ 11.02 (s, 1H), 7.11-7.24 (m, 4H), 6.92 (d, J=7.2 Hz, 1H), 6.61 (d, J=7.5 Hz, 1H), 6.36-6.40 (m, 1H), 5.12 (dd, J=13.5, 5.1 Hz, 1H), 4.29-4.37 (m, 3H), 4.19 (d, J=17.4 Hz, 1H), 2.86-2.99 (m, 1H), 2.59-2.65 (m, 1H), 2.24-2.39 (m, 1H), 2.18 (s, 3H), 2.01-2.07 (m, 1H). LCMS: 382.1 ([M+1]⁺).

Example 54: Compound A354

3-(4-((3-chloro-4-methoxybenzyl)amino)-1-oxoisoindolin-2-yl)piperidine-2,6-dione, A354

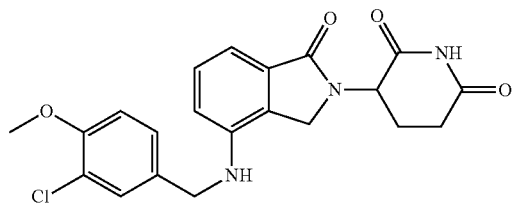 [SMILES: COc1ccc(CNc2cccc3c2CN(C2CCC(=O)NC2=O)C3=O)cc1Cl]

¹H NMR (DMSO-d₆, 300 MHz): δ 11.02 (s, 1H), 7.44 (d, J=1.8 Hz, 1H), 7.32 (dd, J=8.4, 1.8 Hz, 1H), 7.21 (t, J=7.8 Hz, 1H), 7.09 (d, J=8.7 Hz, 1H), 6.93 (d, J=7.2 Hz, 1H), 6.65 (d, J=8.1 Hz, 1H), 6.35 (t, J=5.9 Hz, 1H), 5.09-5.15 (m, 1H), 4.28-4.33 (m, 3H), 4.18 (d, J=16.8 Hz, 1H), 3.81 (s, 3H), 2.87-2.99 (m, 1H), 2.58-2.67 (m, 1H), 2.24-2.37 (m, 1H), 2.01-2.09 (m, 1H). LCMS: 414.1 ([M+1]⁺).

Example 55: Compound A355

3-(4-((3,5-dimethoxybenzyl)amino)-1-oxoisoindolin-2-yl)piperidine-2,6-dione, A355

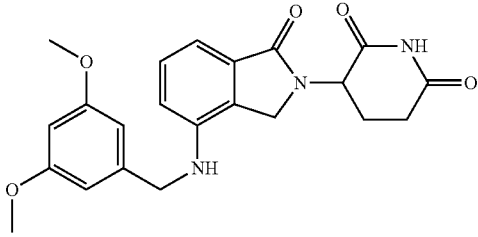 [SMILES: COc1cc(CNc2cccc3c2CN(C2CCC(=O)NC2=O)C3=O)cc(OC)c1]

¹H NMR (DMSO-d₆, 300 MHz): δ 11.03 (s, 1H), 7.18-7.24 (m, 1H), 6.92 (d, J=7.5 Hz, 1H), 6.64 (d, J=8.4 Hz, 1H), 6.55 (d, J=2.1 Hz, 2H), 6.31-6.35 (m, 2H), 5.12 (dd, J=13.2, 4.8 Hz, 1H), 4.28-4.34 (m, 3H), 4.19 (d, J=16.8 Hz, 1H), 3.33 (s, 6H), 2.87-2.99 (m, 1H), 2.58-2.67 (m, 1H), 2.26-2.37 (m, 1H), 2.02-2.08 (m, 1H). LCMS: 410.2 ([M+1]$^+$).

Example 56: Compound A356

(S)-3-deuterium-3-(4-((2-fluoro-4-methoxybenzyl)amino)-1-oxoisoindolin-2-yl)piperidine-2,6-dione, A356

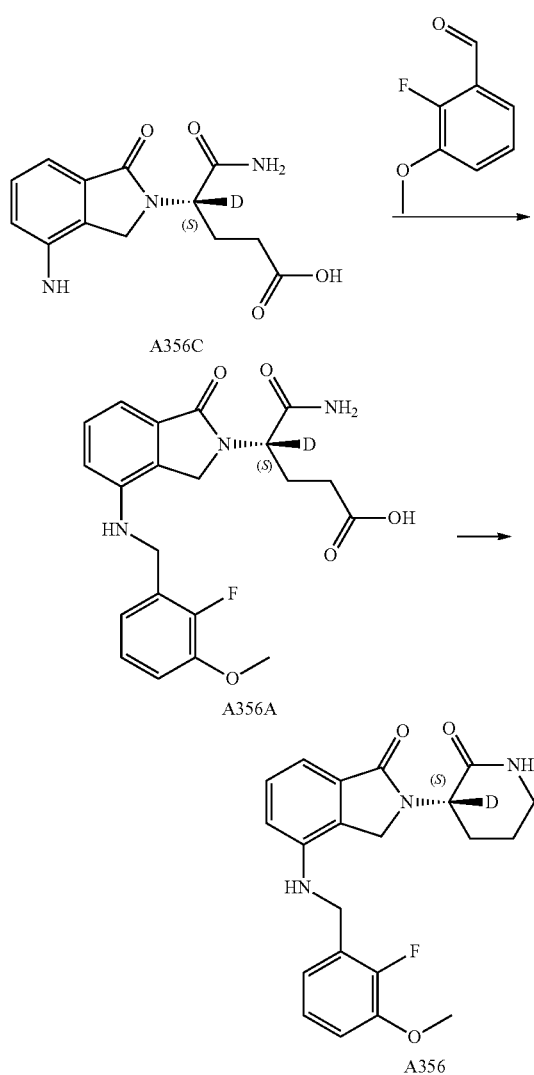

Step A. To a solution of A356C (300 mg, 1.08 mmol) and 2-Fluoro-4-methoxy-benzaldehyde (249 mg, 1.62 mmol) in MeOH (30 mL) was added glacial AcOH (0.5 mL), the mixture was stirred at 30° C. (oil bath) for 5 hours. Pd/C (10%, 100 mg, 50% water) was added and stirred at 30° C. (oil bath) overnight under H$_2$ (balloon). Pd/C was removed by filtration and the filtrate was concentrated to give a residue. The residue was purified by flash chromatography on C18 (CH$_3$CN: H$_2$O=5%-35%, 30 min; 35%-45%, 30 min; 45%-55% 20 min) then was freeze-dried to afford A356A (160 mg, yield: 35%) as a light yellow solid.

$^1$H NMR (DMSO-d$_6$, 300 MHz): δ 12.06 (br s, 1H), 7.55 (br s, 1H), 7.29 (t, J=9.0 Hz, 1H), 7.16-7.22 (m, 2H), 6.88 (d, J=7.5 Hz, 1H), 6.80 (dd, J=12.6, 2.4 Hz, 1H), 6.71 (dd, J=8.7, 2.7 Hz, 1H), 6.61 (d, J=8.1 Hz, 1H), 6.28 (t, J=6.0 Hz, 1H), 4.68-4.74 (m, 0.01H), 4.48 (d, J=17.7 Hz, 1H), 4.23-4.31 (m, 3H), 3.72 (s, 3H), 2.10-2.19 (m, 3H), 1.93-2.01 (m, 1H).

Step B. To a solution of A356A (160 mg, 0.39 mmol) in dry DCM (20 mL) cooled to −40° C. under N$_2$, SOCl$_2$ (229 mg, 1.92 mmol) was slowly added to the mixture at −40° C. under N$_2$, then a solution of DMF (5 mg) in DCM (1 mL) was added. The reaction mixture was stirred at −40° C. for 2 hr, pyridine (152 mg, 1.92 mmol) was added dropwise, stirred for 40 minutes at this temperature, Et$_3$N (195 mg, 1.92 mmol) was added and then the reaction mixture was stirred at −40° C. for 2 h. LCMS showed the reaction was finished. H$_2$O (10 mL) was added to quench the reaction, the water layer was extracted with DCM (30 mL×2), the combined organic phase was washed with brine (50 mL), dried over Na$_2$SO$_4$, filtered, concentrated to give a residue. The residue was purified by flash chromatography on C18 (CH$_3$CN: H$_2$O=5%-35%, 30 min; 35%-45%, 30 min; 45%-55% 20 min) to give A356 (70 mg, yield: 46%, ee: 97%) as a white solid.

$^1$H NMR (DMSO-d$_6$, 300 MHz): δ 10.99 (br s, 1H), 7.31 (t, J=9.0 Hz, 1H), 7.24 (t, J 7.8 Hz, 1H), 6.94 (d, J=7.2 Hz, 1H), 6.82 (dd, J=12.3, 2.7 Hz, 1H), 6.71-6.75 (m, 1H), 6.68 (d, J=7.8 Hz, 1H), 6.20 (t, J=6.0 Hz, 1H), 5.08-5.14 (m, 0.04H), 4.26-4.35 (m, 3H), 4.17 (d, J=16.8 Hz, 1H), 3.74 (s, 3H), 2.87-2.97 (m, 1H), 2.57-2.66 (m, 1H), 2.25-2.34 (m, 1H), 2.00-2.09 (m, 1H). LCMS: 399.1 ([M+1]$_+$).

Compound in example 57 was prepared according to the procedure described in example 56, with corresponding starting material to replace 2-Fluoro-4-methoxy-benzaldehyde in step A.

Example 57: Compound A357

(S)-3-deuterium-3-(4-((2-fluoro-3-methoxybenzyl)amino)-1-oxoisoindolin-2-yl)piperidine-2,6-dione, A357

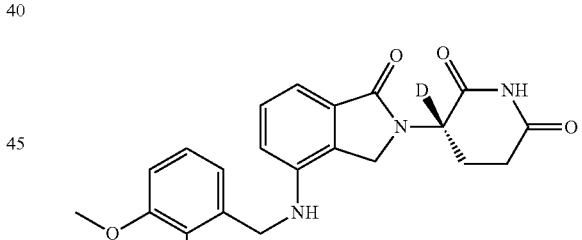

$^1$H NMR (DMSO-d$_6$, 300 MHz): δ 11.00 (br s, 1H), 7.21 (t, J=7.8 Hz, 1H), 7.00-7.07 (m, 2H), 6.89-6.93 (m, 2H), 6.78-6.84 (m, 1H), 6.61 (d, J=8.4 Hz, 1H), 6.30 (t, J=5.4 Hz, 1H), 5.07-5.13 (m, 0.03H), 4.40 (d, J=5.7 Hz, 2H), 4.28 (d, J=17.1 Hz, 1H), 4.16 (d, J=17.1 Hz, 1H), 3.81 (s, 3H), 2.85-2.97 (m, 1H), 2.57-2.63 (m, 1H), 2.24-2.34 (m, 1H), 2.00-2.06 (m, 1H). LCMS: 399.1 ([M+1]$^+$).

Example 58: Compound A379

(S)-3-deuterium-3-(4-((2-fluoro-5-methoxybenzyl)oxy)-1-oxoisoindolin-2-yl)piperidine-2,6-dione, A379

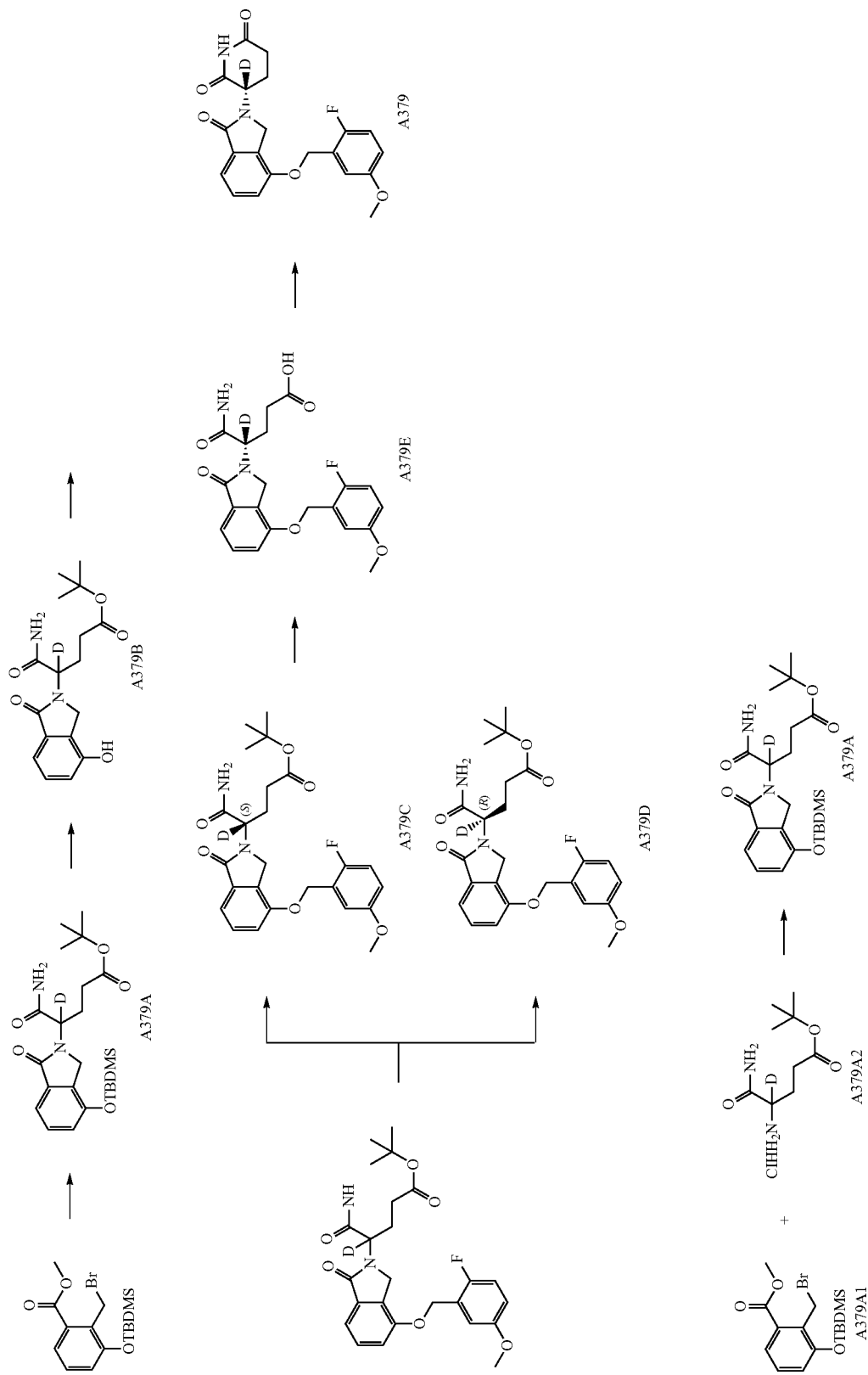

Step A. To a mixture of A379A1 (10.0 g, 27.8 mmol) and A379A2 (8.01 g, 33.4 mmol) in CH₃CN (250 mL) were added DIPEA (7.92 g, 61.3 mmol), the mixture was stirred 45° C. overnight under N₂. The reaction mixture was concentrated and DCM (300 mL) and H₂O (100 mL) were added, the water phase was extracted with DCM (200 mL×1), the combined organic phase was washed with brine (200 mL), dried over Na₂SO₄, filtered, concentrated to give a crude product A379A (12.3 g) as a yellow solid.

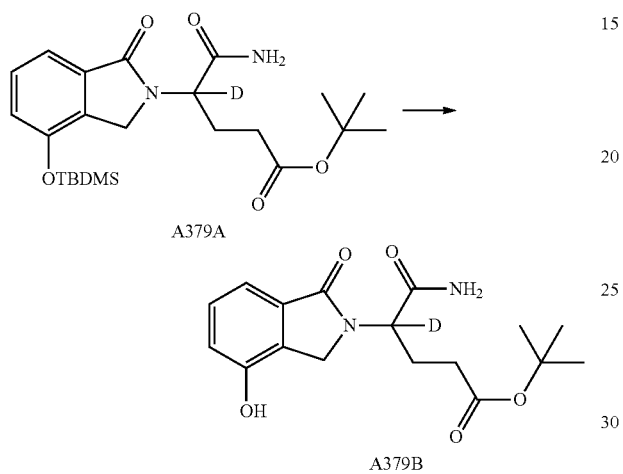

Step B. To a solution of A379A (12.3 g, crude) in THF (100 mL) was added 1N TBAF in THF (100 mL), the mixture was stirred overnight at 25° C. LCMS showed the reaction was finished. EtOAc (200 mL) and H₂O (200 mL) were added, the water phase was extracted with EtOAc (200 mL×2), the combined organic phase was washed with brine (300 mL), dried over Na₂SO₄, filtered, concentrated to give a residue. The residue was triturated with EtOAc (20 mL), filtered, washed with EtOAc (10 mL), then dried to give A379B (5.7 g) as white solid. The filtrate was concentrated and purified by column chromatography on silica gel (PE/EtOAc=1:4) to give additional 1.5 g A379B as a white solid; (overall yield: 77%, for two steps).

¹H NMR (DMSO-d₆, 300 MHz): δ 10.01 (s, 1H), 7.54 (br s, 1H), 7.29 (t, J=7.8 Hz, 1H), 7.12-7.16 (m, 2H), 6.96 (dd, J=8.1, 0.6 Hz, 1H), 4.66-4.71 (m, 0.01H), 4.47 (d, J=17.7 Hz, 1H), 4.29 (d, J=17.7 Hz, 1H), 2.08-2.17 (m, 3H), 1.95-2.02 (m, 1H), 1.31 (s, 9H).

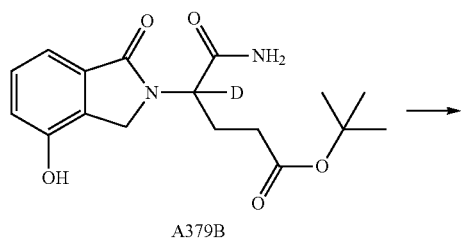

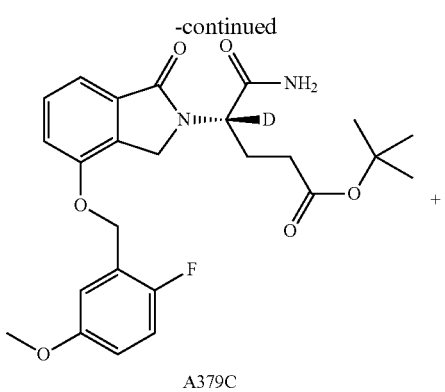

Step C. To a solution of A379B (1.18 g, 3.52 mmol) and 2-(chloromethyl)-1-fluoro-4-methoxybenzene (1.23 g, 7.04 mmol) in DMF (20 mL) was added K₂CO₃ (972 mg, 7.03 mmol), the mixture was stirred overnight at room temperature. LCMS showed the reaction was finished. The reaction mixture was concentrated and EtOAc (50 mL) and H₂O (30 mL) were added, the water phase was extracted with EtOAc (50 mL), the combined organic phase was washed with brine (50 mL), dried over Na₂SO₄, filtered, concentrated to give a residue. The residue was purified by column chromatography on silica gel (MeOH/DCM=1/30) to give a white product (1.46 g, 87% yield). The white solid was subjected to chiral separation to give A379C (650 mg) and A379D (650 mg).

Conditions of Chiral Separation:

Mobile Phase: Hexane/EtOH=40/60 (V/V), sample concentration: 100 mg/ml in Mobile Phase; Column: CHIRALPAK IC; 20 mm(I.D)×250 mm(L); 5 um; temperature: 35° C.; Injection Volume: 250 μL; Flow Rate: 10 mL/min; Wave Length: 205 nm. A379C: ¹H NMR (DMSO-d₆, 300 MHz): δ 7.55 (br s, 1H), 7.46 (t, J=8.1 Hz, 1H), 7.28-7.34 (m, 2H), 7.11-7.21 (m, 3H), 6.92-6.97 (m, 1H), 5.22 (s, 2H), 4.49 (d, J=18.0 Hz, 1H), 4.36 (d, J=18.0 Hz, 1H), 3.73 (s, 3H), 2.05-2.13 (m, 3H), 1.96-2.02 (m, 1H), 1.30 (s, 9H).

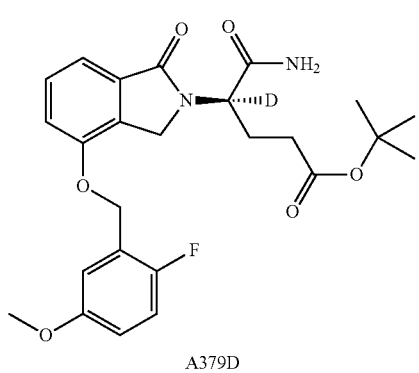

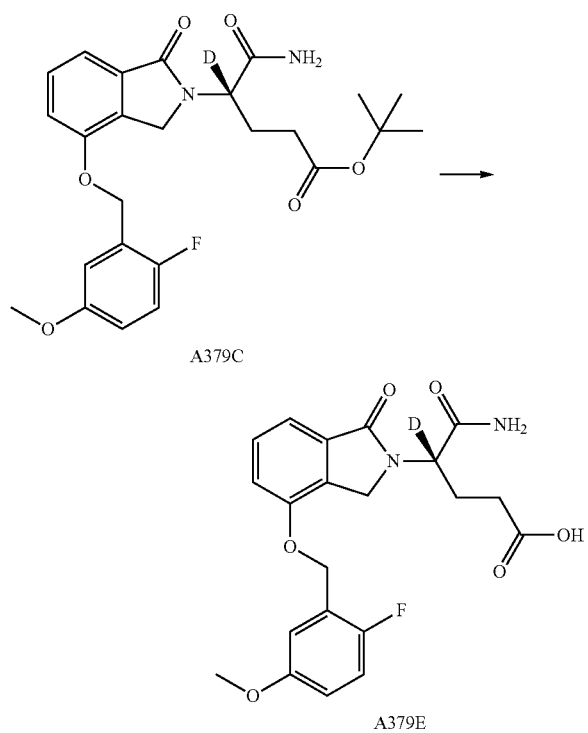

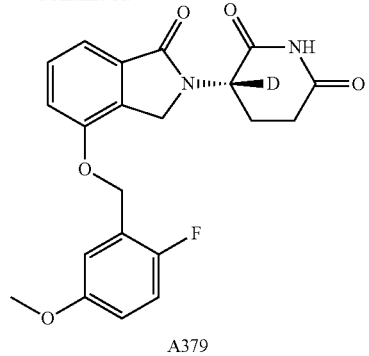

Step E: To a solution of A379E (366 mg, 0.88 mmol) in dry DCM (35 mL) and THF (5 mL) under $N_2$ at −40° C., was slowly added $SOCl_2$ (522 mg, 4.39 mmol), and then a solution of DMF (5 mg) in DCM (1 mL). The reaction mixture was stirred at −40° C. for 1 h, pyridine (347 mg, 4.39 mmol) was added, after 40 mins $Et_3N$ (444 mg, 4.39 mmol) was added and then the mixture was stirred for 1 h at −40° C. LCMS showed the reaction was finished. $H_2O$ (10 mL) was added to quench the reaction, the water layer was extracted with DCM (50 mL), the combined organic phase was washed with brine (50 mL), dried over $Na_2SO_4$, filtered, concentrated to give a residue. The crude product was purified by C18 to give A379 (270 mg, yield: 77%, ee: 100%) as a white solid.

$^1$H NMR (DMSO-$d_6$, 300 MHz): δ 10.96 (br s, 1H), 7.49 (t, J=8.1 Hz, 1H), 7.32-7.38 (m, 2H), 7.11-7.21 (m, 2H), 6.91-6.97 (m, 1H), 5.23 (s, 2H), 5.06-5.12 (m, 0.01H), 4.37 (d, J=17.4 Hz, 1H), 4.21 (d, J=17.4 Hz, 1H), 3.72 (s, 3H), 2.82-2.94 (m, 1H), 2.57-2.60 (m, 1H), 2.38-2.48 (m, 1H), 1.92-1.97 (m, 1H). LCMS=400.1 ([M+1]$^+$).

Compound in example 59 was prepared according to the procedure described for example 58, with corresponding starting material to replace 2-(chloromethyl)-1-fluoro-4-methoxybenzene in step C.

Step D. To a solution of A379C (650 mg, 1.37 mmol) in DCM (20 mL) at 0° C. was added dropwise TFA (10 mL), the mixture was warmed to room temperature and stirred for overnight. The reaction mixture was concentrated under reduced pressure (in vacuum). The residue was dissolved in $CH_3CN$ (4 mL) and purified by flash chromatography on C18 (40% acetonitrile in water) then was freeze-dried to afford A379E (566 mg, yield: 99%) as a light yellow solid.

$^1$H NMR (DMSO-$d_6$, 300 MHz): δ 12.08 (br s, 1H), 7.58 (br s, 1H), 7.46 (t, J=8.1 Hz, 1H), 7.28-7.35 (m, 2H), 7.11-7.21 (m, 3H), 6.92-6.97 (m, 1H), 5.22 (s, 2H), 4.51 (d, J=17.7 Hz, 1H), 4.37 (d, J=17.7 Hz, 1H), 3.73 (s, 3H), 2.08-2.20 (m, 3H), 1.96-2.05 (m, 1H).

Example 59: Compound A380

(S)-3-deuterium-3-(4-((2-fluoro-3-methoxybenzyl)oxy)-1-oxoisoindolin-2-yl)piperidine-2,6-dione, A380

$^1$H NMR (DMSO-$d_6$, 300 MHz): δ 10.95 (br s, 1H), 7.49 (t, J=7.8 Hz, 1H), 7.31-7.37 (m, 2H), 7.07-7.19 (m, 3H), 5.26 (s, 2H), 5.05-5.11 (m, 0.01H), 4.36 (d, J=17.4 Hz, 1H), 4.20 (d, J=17.4 Hz, 1H), 3.83 (s, 3H), 2.82-2.94 (m, 1H), 2.51-2.60 (m, 1H), 2.37-2.46 (m, 1H), 1.92-1.99 (m, 1H). LCMS=400.1 ([M+1]$^+$).

Example 60: Compound A393

(S)-3-deuterium-3-(4-((2-fluoro-4-methoxybenzyl)oxy)-1-oxoisoindolin-2-yl)piperidine-2,6-dione, A393

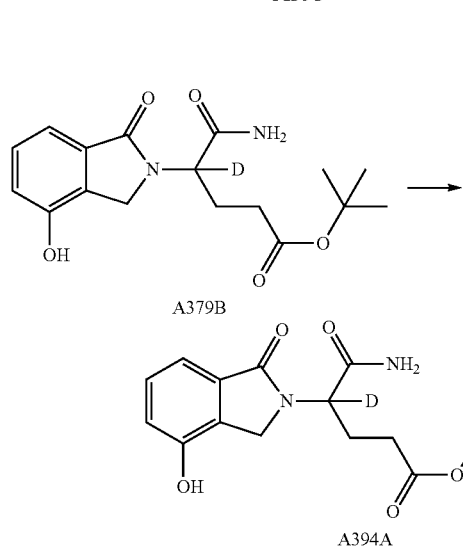

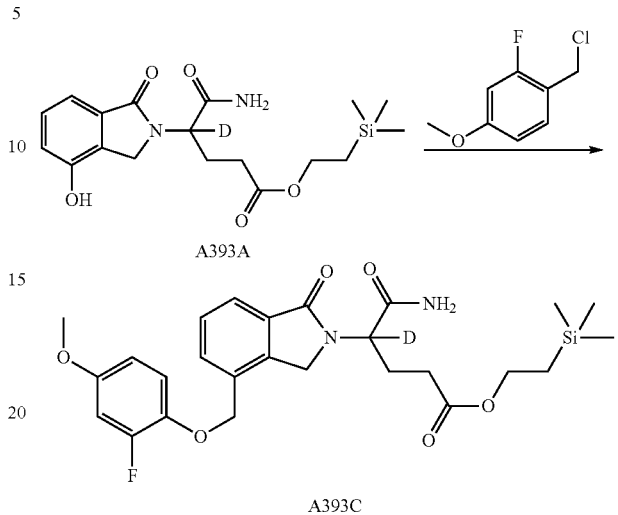

Step A: To a solution of A379B (2.0 g, 6.0 mmol) in DCM (30 mL) was added TFA (5 mL), after stirring for 3 hours at 25° C., the reaction mixture was concentrated to afford a residue (1.7 g). The residue (1.7 g) was dissolved in DMF (5 mL) and treated with 2-(trimethylsilyl)ethanol (3.55 g, 30 mmol), EDCI (2.3 g, 12.0 mmol) and DMAP (733 mg, 6.0 mmol). The reaction mixture was stirred overnight at 35° C., and then concentrated. The residue was purified by column chromatography on silica gel (DCM/MeOH=40:1) to give A393A (1.6 g, 70%).

$^1$H NMR (DMSO-$d_6$, 300 MHz): δ 9.99 (s, 1H), 7.54 (s, 1H), 7.28 (t, J=7.8 Hz, 1H), 7.11-7.14 (m, 2H), 6.96 (d, J=7.8 Hz, 1H), 4.47 (d, J=18.0 Hz, 1H), 4.28 (d, J=18.0 Hz, 1H), 3.92-3.99 (m, 2H), 2.00-2.25 (m, 4H), 0.80-0.85 (m, 2H), 0.04 (s, 9H).

Step B: To a solution of A393A (1.02 g, 2.70 mmol) in DMF (20 mL) was added K$_2$CO$_3$ (750 mg, 5.40 mmol) and 1-Chloromethyl-2-fluoro-4-methoxy-benzene (720 mg, 4.10 mmol), this mixture was warm to 30° C. and stirred for 17 hours, then this mixture was filtered and concentrated to afford a crude oil, which was purified by column chromatography on silica gel (DCM/MeOH=60/1) to afford A393C (1.0 g, 72%).

$^1$H NMR (DMSO-$d_6$, 300 MHz): δ 7.43-7.54 (m, 3H), 7.26-7.35 (m, 2H), 7.14 (s, 1H), 6.80-6.90 (m, 2H), 5.16 (s, 2H), 4.45 (d, J=17.4 Hz, 1H), 4.30 (d, J=17.4 Hz, 1H), 3.92-3.98 (m, 2H), 3.77 (s, 3H), 2.01-2.22 (m, 4H), 0.79-0.84 (m, 2H).

Step C: Chiral Separation

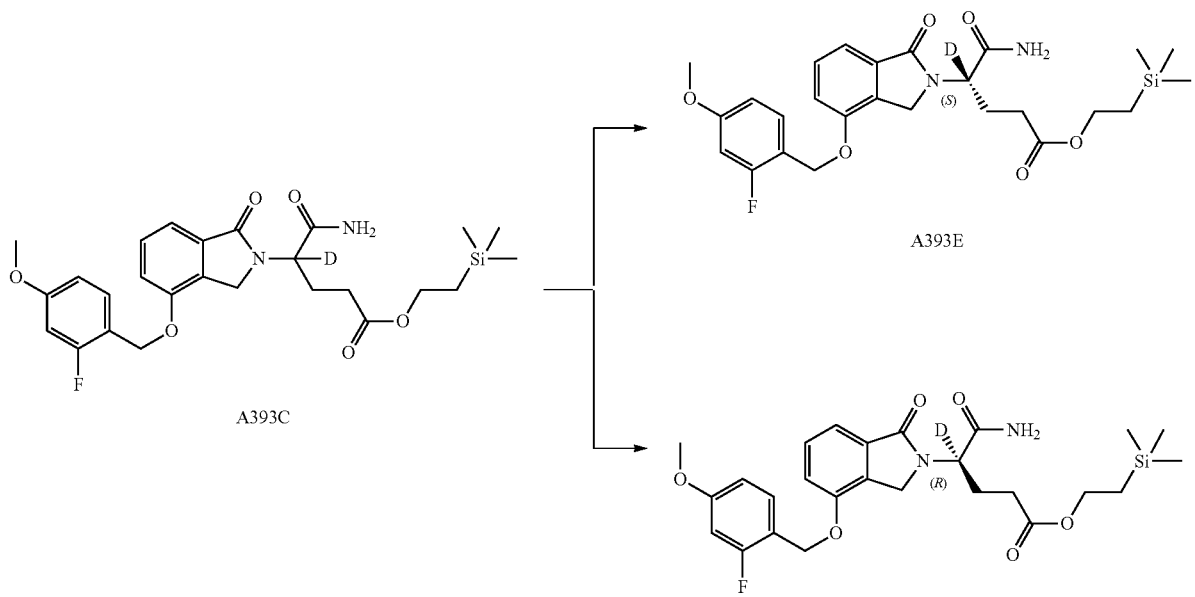

Chiral Separation Conditions:

Mobile Phase: MeOH/EtOH=50/50 (V/V); Sample: 120 mg/mL in Mobile Phase; Column: IF; 20 mm(I.D)×250 mm(L); 5 um; Temperature: 35° C.; Injection volume: 300 L; Flow Rate: 9 mL/min; Wave length: 205 nm.

A393E $^1$H NMR (DMSO-d$_6$, 300 MHz): δ 7.59 (s, 1H), 7.45-7.54 (m, 2H), 7.36 (d, J=7.8 Hz, 1H), 7.29 (d, J=7.2 Hz, 1H), 7.20 (s, 1H), 6.80-6.92 (m, 2H), 5.18 (s, 2H), 4.47 (d, J=17.4 Hz, 1H), 4.32 (d, J=17.4 Hz, 1H), 3.92-4.01 (m, 2H), 3.78 (s, 3H), 2.01-2.20 (m, 4H), 0.80-0.85 (m, 2H), 0.04 (s, 9H).

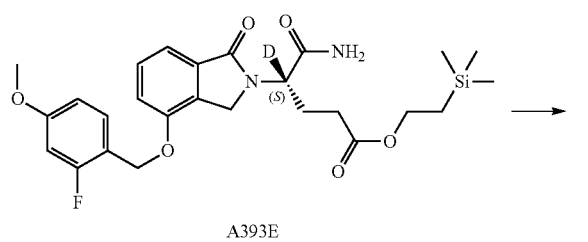

A393E

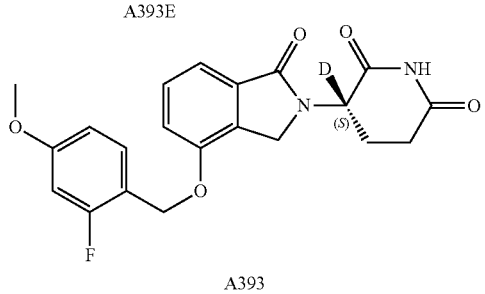

A393

Step D: To a solution of A393E (500 mg, 0.97 mmol) in THF (5 mL) was added TBAF (1N/THF, 5 mL), this mixture was stirred at 50° C. overnight, filtered and concentrated, the residue was purified by column chromatography (C18) to afford an intermediate (420 mg), To a solution of this intermediate (300 mg) in DCM (15 mL) and DMF (1 mL) at −40° C. was added SOCl$_2$ (428 mg, 3.60 mmol). The reaction mixture was stirred for 2 hours, pyridine (281 mg, 3.60 mmol) was added, the mixture was stirred for another 30 min and then Et$_3$N (363 mg, 3.60 mmol) was added and stirred for additional 1 hr at −40° C. The reaction mixture was treated with water (80 mL) and extracted with DCM (80 mL×3), combined organic layers and was dried over Na$_2$SO$_4$, filtered and concentrated and purified by Prep-HPLC to give A393 (200 mg, 72%, for two steps).

$^1$H NMR (DMSO-d$_6$, 300 MHz): δ 10.95 (s, 1H), 7.48-7.53 (m, 2H), 7.32-7.40 (m, 2H), 6.80-6.91 (m, 2H), 5.19 (s, 2H), 4.35 (d, J=17.4 Hz, 1H), 4.19 (d, J=17.4 Hz, 1H), 3.78 (s, 3H), 2.84-2.96 (m, 1H), 2.37-2.59 (m, 2H), 1.93-1.99 (m, 1H). LCMS: 400.1 ([M+1]$^+$).

Compound of example 61 was prepared according to the procedure described for example 60, with corresponding starting material to replace compound A393E.

Example 61: Compound A392

(R)-3-deuterium-3-(4-((2-fluoro-4-methoxybenzyl)oxy)-1-oxoisoindolin-2-yl)piperidine-2,6-dione, A392

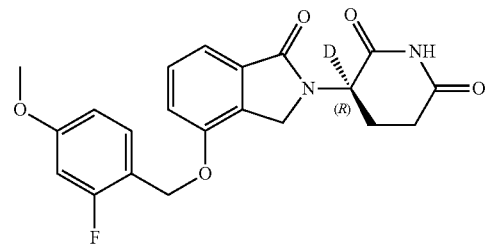

$^1$H NMR (DMSO-d$_6$, 300 MHz): δ 10.95 (s, 1H), 7.48-7.53 (m, 2H), 7.32-7.40 (m, 2H), 6.80-6.91 (m, 2H), 5.19 (s, 2H), 5.07-5.13 (m, 0.05H), 4.35 (d, J=17.7 Hz, 1H), 4.19 (d, J=17.7 Hz, 1H), 3.78 (s, 3H), 2.84-2.96 (s, 1H), 2.36-2.59 (m, 2H), 1.93-1.98 (m, 1H). LCMS: 400.1 ([M+1]$^+$).

Example 62: Compound A385

3-(4-((2-fluoro-3-(methylamino)benzyl)oxy)-1-oxoisoindolin-2-yl)piperidine-2,6-dione, A385

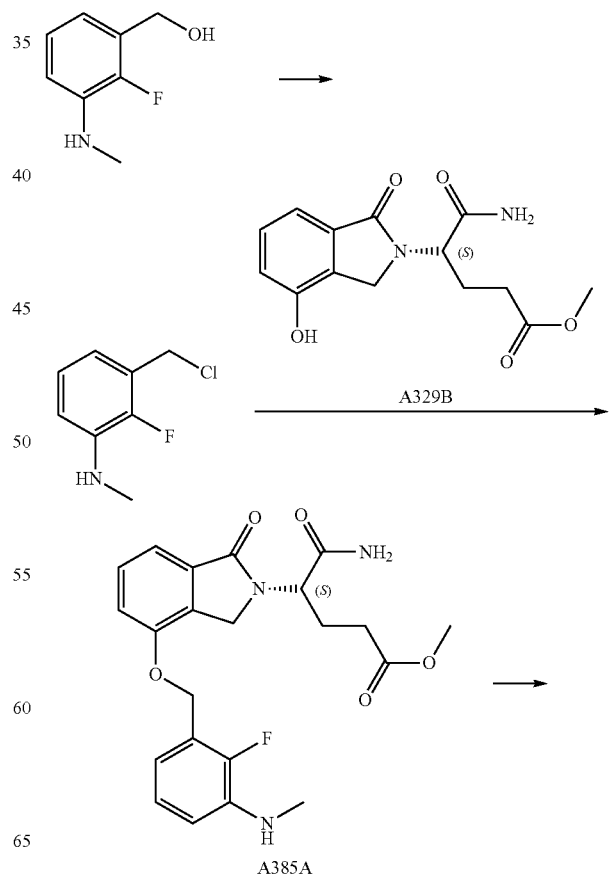

A385A

329

-continued

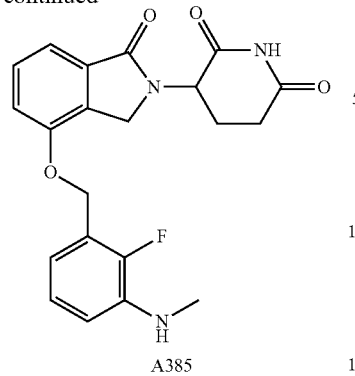

A385

Step A. To a solution of (2-fluoro-3-(methylamino)phenyl)methanol in DCM (10 mL) was added SOCl$_2$ (0.5 mL), the mixture was stirred for 4 h. The reaction mixture was concentrated to give crude product 3-(chloromethyl)-2-fluoro-N-methylaniline hydrochloride (430 mg) as a yellow solid which was used in the next step without further purification.

$^1$H NMR (DMSO-d$_6$, 300 MHz): δ 9.97 (br s, 2H), 7.05 (t, J=8.1 Hz, 1H), 6.84-6.92 (m, 2H), 4.72 (s, 2H), 2.74 (s, 3H).

Step B. To a solution of A329B (300 mg, 1.03 mmol) in DMF (10 mL) was added 3-(chloromethyl)-2-fluoro-N-methylaniline hydrochloride (259 mg) and K$_2$CO$_3$ (355 mg, 2.57 mmol), the mixture was stirred overnight. LCMS showed the reaction was not finished. Additional 3-(chloromethyl)-2-fluoro-N-methylaniline hydrochloride (150 mg) and K$_2$CO$_3$ (100 mg, 0.72 mmol) were added and the mixture was stirred overnight. The reaction mixture was concentrated and EtOAc (20 mL) and H$_2$O (10 mL) was added. The water layer was extracted by EtOAc (20 mL×2), the combined organic layer was washed by brine (20 mL), dried over Na$_2$SO$_4$, filtered, concentrated to give a residue. The residue was purified by Prep-TLC (petroleum ether/EtOAc=1/4) to give compound A385A (242 mg, 55% yield) as a white solid.

$^1$H NMR (DMSO-d$_6$, 300 MHz): δ 7.55 (br s, 1H), 7.45 (t, J=7.8 Hz, 1H), 7.27-7.33 (m, 2H), 7.15 (br s, 1H), 6.99 (t, J=8.1 Hz, 1H), 6.61-6.71 (m, 2H), 5.59 (br s, 1H), 5.20 (s, 2H), 4.70 (dd, J=10.5, 4.5 Hz, 1H), 4.47 (d, J=17.7 Hz, 1H), 4.33 (d, J=17.7 Hz, 1H), 3.48 (s, 3H), 2.71 (d, J=4.2 Hz, 3H), 2.12-2.25 (m, 3H), 1.99-2.09 (m, 1H).

Step C. To a solution of A385A (242 mg, 0.56 mmol) in DMF (10 mL) was added K$_2$CO$_3$ (234 mg, 1.69 mmol), the mixture was stirred overnight at 80° C. The reaction mixture was concentrated under reduced pressure and the residue was purified by prep-HPLC then freeze-dried to give A385 (100 mg, 45% yield) as a white solid.

$^1$H NMR (DMSO-d$_6$, 300 MHz): δ 10.71 (br s, 1H), 7.50 (t, J=8.1 Hz, 1H), 7.32-7.38 (m, 2H), 7.00 (t, J=7.8 Hz, 1H), 6.63-6.72 (m, 2H), 5.61-5.62 (m, 1H), 5.23 (s, 2H), 5.10 (dd, J=13.2, 5.1 Hz, 1H), 4.37 (d, J=17.7 Hz, 1H), 4.21 (d, J=17.7 Hz, 1H), 2.84-2.96 (m, 1H), 2.72 (d, J=4.8 Hz, 3H), 2.51-2.60 (m, 1H), 2.37-2.47 (m, 1H), 1.93-2.00 (m, 1H). LCMS=398.1 ([M+1]$^+$)

Compounds in examples 63-66 were prepared according to the procedure described for example 62, with corresponding starting materials to replace 3-(chloromethyl)-2-fluoro-N-methylaniline hydrochloride in step B.

330

Example 63: Compound A390

3-(4-((2-fluoro-5-(methylamino)benzyl)oxy)-1-oxoisoindolin-2-yl)piperidine-2,6-dione, A390

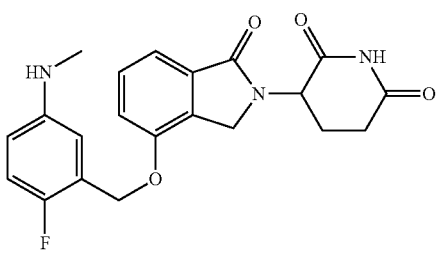

$^1$H NMR (DMSO-d$_6$, 300 MHz): δ 10.97 (s, 1H), 7.48 (t, J=7.8 Hz, 1H), 7.33 (t, J=7.2 Hz, 2H), 6.96 (t, J=9.3 Hz, 1H), 6.63-6.66 (m, 1H), 6.46-6.51 (m, 1H), 5.58-5.63 (m, 1H), 5.16 (s, 2H), 5.06-5.12 (m, 1H), 4.35 (d, J=17.4 Hz, 1H), 4.19 (d, J=17.4 Hz, 1H), 2.83-2.95 (m, 1H), 2.54-2.62 (m, 4H), 2.34-2.45 (m, 1H), 1.91-1.99 (m, 1H). LCMS: 398.1 ([M+1]$^+$).

Example 64: Compound A398

3-(4-((2-fluoro-5-(morpholinomethyl)benzyl)oxy)-1-oxoisoindolin-2-yl)-piperidine-2,6-dione, A398

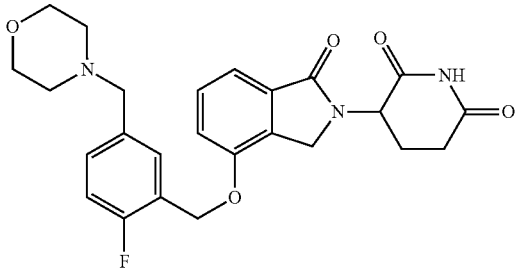 [SMILES: O=C1CCC(N2Cc3c(OCc4cc(CN5CCOCC5)ccc4F)cccc3C2=O)C(=O)N1]

$^1$H NMR (DMSO-d$_6$, 300 MHz): δ 10.92 (br s, 1H), 7.46-7.51 (m, 2H), 7.31-7.37 (m, 3H), 7.16-7.22 (m, 1H), 5.27 (s, 2H), 5.05-5.11 (m, 1H), 4.35 (d, J=17.4 Hz, 1H), 4.20 (d, J=17.4 Hz, 1H), 3.50-3.53 (m, 4H), 3.43 (s, 2H), 2.82-2.92 (m, 1H), 2.53-2.60 (m, 1H), 2.34-2.44 (m, 1H), 2.23-2.29 (m, 4H), 1.90-2.00 (m, 1H). LCMS=468.2 [(M+1)$^+$].

Example 65: Compound A399
3-(4-((2-fluoro-3-(morpholinomethyl)benzyl)oxy)-1-oxoisoindolin-2-yl)piperidine-2,6-dione, A399
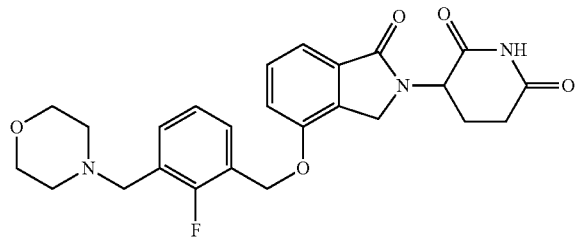 [SMILES: O=C1CCC(N2Cc3c(OCc4cccc(CN5CCOCC5)c4F)cccc3C2=O)C(=O)N1]
$^1$H NMR (DMSO-d$_6$, 300 MHz): δ 10.98 (s, 1H), 7.49-7.54 (m, 2H), 7.34-7.45 (m, 3H), 7.19-7.24 (m, 1H), 5.29 (s, 2H), 5.08-5.14 (m, 1H), 4.39 (d, J=17.7 Hz, 1H), 4.22 (d, J=17.7 Hz, 1H), 3.50-3.57 (m, 6H), 2.84-2.98 (m, 1H), 2.54-2.60 (m, 1H), 2.34-2.47 (m, 5H), 1.92-2.01 (m, 1H). LCMS: 468.2 ([M+1]$^+$).
Example 66: Compound A407
3-(4-((2-fluoro-4-(morpholinomethyl)benzyl)amino)-1-oxoisoindolin-2-yl)piperidine-2,6-dione, A407
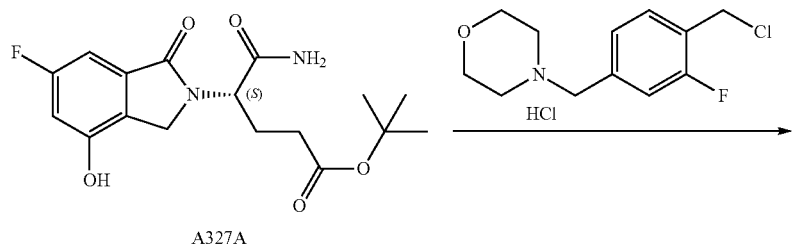
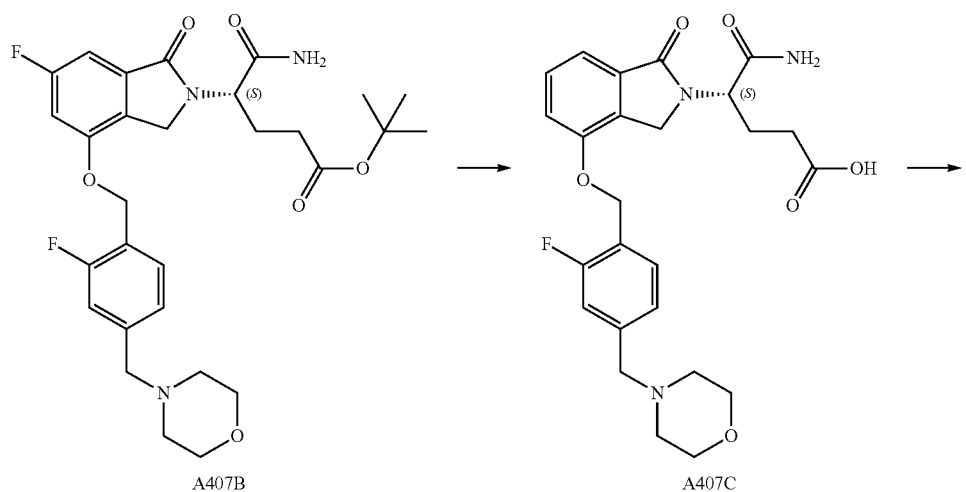

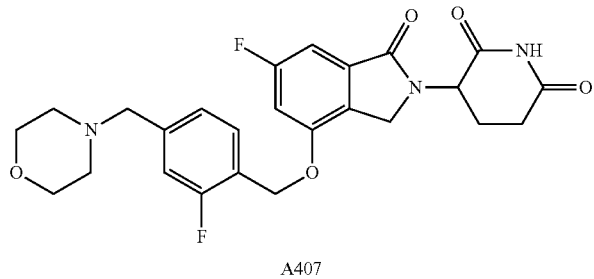

A407

Step A: To a solution of A327A (300 mg, 0.85 mmol) and 4-(4-(chloromethyl)-3-fluorobenzyl)morpholine hydrochloride (359 mg, 1.28 mmol) in DMF (15 mL) was added K$_2$CO$_3$ (352 mg, 2.55 mmol), the mixture was stirred overnight at 40° C. The reaction mixture was filtered and the filtrate was concentrated to give a residue. The residue was purified by Prep-TLC (MeOH/DCM=1/15) to give a white solid A407B (430 mg, 90% yield).

$^1$H NMR (DMSO-d$_6$, 300 MHz): δ 7.51-7.56 (m, 2H), 7.33 (dd, J=11.4, 1.5 Hz, 1H), 7.17-7.21 (m, 3H), 7.07 (dd, J=7.5, 1.5 Hz, 1H), 5.24 (s, 2H), 4.66-4.69 (m, 1H), 4.44 (d, J=17.7 Hz, 1H), 4.32 (d, J=17.7 Hz, 1H), 3.55-3.58 (m, 4H), 3.48 (s, 2H), 2.29-2.39 (m, 4H), 2.05-2.18 (m, 3H), 1.95-2.01 (m, 1H), 1.29 (s, 9H).

Step B: To a solution of A407B (430 mg, 0.77 mmol) in DCM (20 mL) was added dropwise TFA (5 mL) at room temperature, the mixture was stirred for 3 hours at 25° C. LCMS showed the reaction was finished. The reaction mixture was concentrated under reduced pressure (in vacuum) to afford A407C (387 mg, yield 100%) as a yellow solid.

$^1$H NMR (DMSO-d$_6$, 300 MHz): δ 10.33 (br s, 1H), 7.71 (t, J=7.8 Hz, 1H), 7.61 (s, 1H), 7.33-7.47 (m, 3H), 7.19 (s, 1H), 7.09-7.11 (m, 1H), 5.31 (s, 2H), 4.69-4.72 (m, 1H), 4.48 (d, J=17.7 Hz, 1H), 4.38 (s, 2H), 4.35 (d, J=17.7 Hz, 1H), 3.89-3.99 (m, 2H), 3.57-3.67 (m, 2H), 3.14-3.34 (m, 4H), 2.10-2.17 (m, 3H), 1.95-2.01 (m, 1H).

Step C: To a solution of A407C (215 mg, 0.39 mmol) in CH$_3$CN (15 mL) was added CDI (190 mg, 1.17 mmol), the mixture was refluxed overnight under N$_2$. LCMS showed the reaction was finished. The reaction mixture was concentrated to give a residue and purified by Prep-HPLC to give A407 (80 mg, yield: 43%) as a white solid.

$^1$H NMR (DMSO-d$_6$, 300 MHz): δ 10.96 (br s, 1H), 7.51-7.56 (m, 1H), 7.34-7.39 (m, 1H), 7.11-7.21 (m, 3H), 5.25 (s, 2H), 5.05-5.11 (m, 1H), 4.33 (d, J=18.0 Hz, 1H), 4.16 (d, J=18.0 Hz, 1H), 3.54-3.57 (m, 4H), 3.48 (s, 2H), 2.82-2.94 (m, 1H), 2.49-2.56 (m, 1H), 2.30-2.44 (m, 5H), 1.91-1.99 (m, 1H). LCMS=486.2 ([M+1]$^+$).

Example 67: A403

(S)-3-deuterium-3-(4-((2-fluoro-5-(morpholinomethyl)benzyl)oxy)-1-oxoisoindolin-2-yl)piperidine-2,6-dione, A403

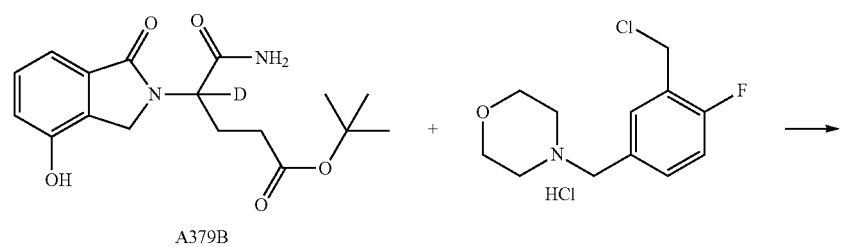

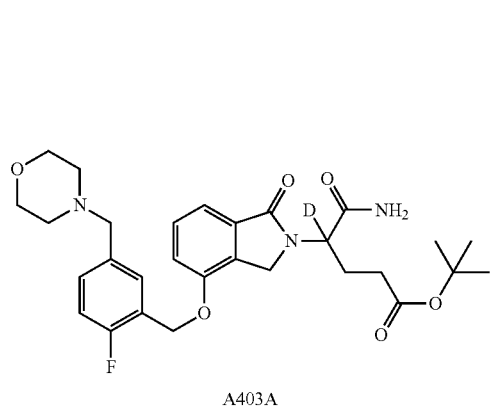

A403A

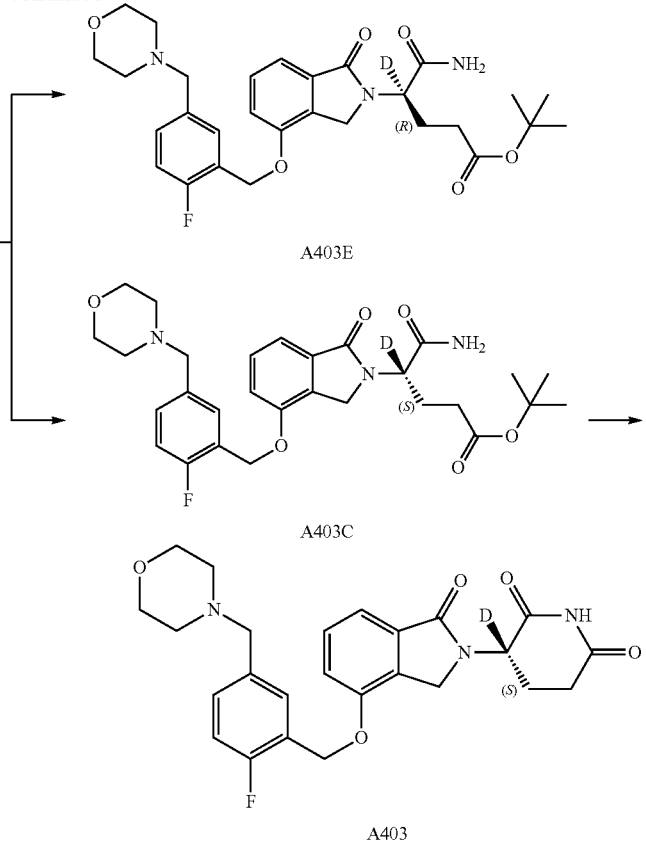

A403E

A403C

A403

Step A: To a solution of compound A379B (1.0 g, 3.59 mmol) and 4-(3-(chloromethyl)-4-fluorobenzyl)morpholine hydrochloride (1.23 g, 7.05 mmol) in DMF (20 mL) was added $K_2CO_3$ (972 mg, 7.04 mmol), the mixture was stirred overnight at 25° C. Filtration and the filtrate was concentrated to give a residue. The residue was purified by column chromatography on silica gel to give a white solid A403A (1.3 g, 80% yield).

$^1$H NMR (DMSO-$d_6$, 300 MHz): δ 7.54 (br s, 1H), 7.43-7.49 (m, 2H), 7.28-7.34 (m, 3H), 7.14-7.22 (m, 2H), 5.26 (s, 2H), 4.67-4.72 (m, 0.05H), 4.50 (d, J=17.4 Hz, 1H), 4.33 (d, J=17.4 Hz, 1H), 3.49-3.56 (m, 4H), 3.44 (s, 2H), 2.25-2.34 (m, 4H), 2.09-2.15 (m, 3H), 1.94-2.03 (m, 1H), 1.29 (s, 9H).

Step B: Chiral Separation

A403A was chiral separated to give A403C (500 mg) and A403E (500 mg).

Chiral Separation conditions: Mobile Phase: Hexane/IPA=70/30(V/V); Sample concentration: 100 mg/mL; Column: CHIRALPAK IA; 30 mm (I.D)×250 mm(L); 5 μm, Temperature: 35° C.; Wave Length: 205 nm; Injection: 250 uL; Flow Rate: 50 mL/min.

A403C:

(S)-tert-butyl 5-amino-4-(4-((2-fluoro-5-(morpholinomethyl)benzyl)oxy)-1-oxoisoindolin-2-yl)-5-oxo-pentanoate

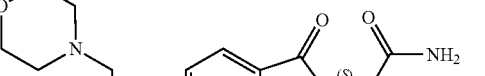

$^1$H NMR (DMSO-$d_6$, 300 MHz): δ 7.55 (br s, 1H), 7.43-7.49 (m, 2H), 7.28-7.34 (m, 3H), 7.16-7.22 (m, 2H), 5.26 (s, 2H), 4.66-4.71 (m, 1H), 4.49 (d, J=17.4 Hz, 1H), 4.33 (d, J=17.4 Hz, 1H), 3.51-3.53 (m, 4H), 3.43 (s, 23H), 2.26-2.33 (m, 4H), 2.02-2.16 (m, 3H), 1.94-1.99 (m, 1H), 1.29 (s, 9H).

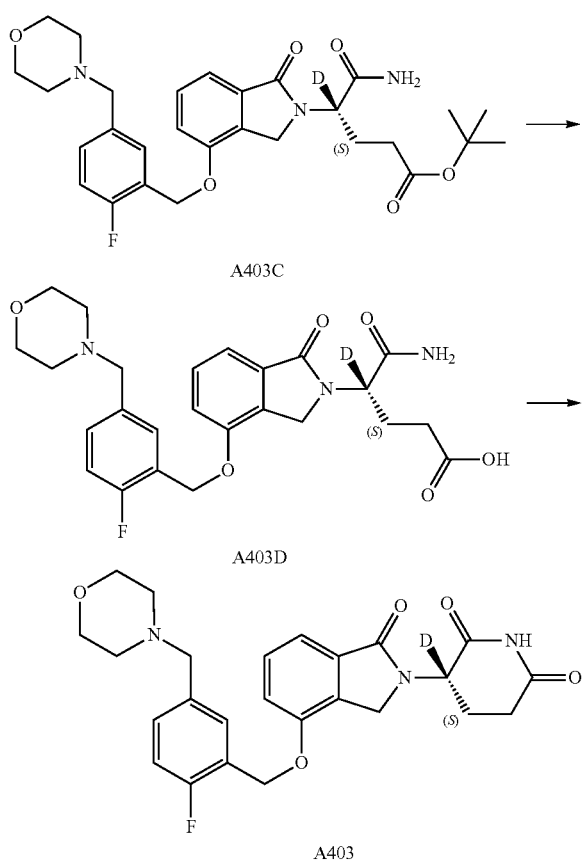

A403C

A403D

A403

Step C: To a solution of A403C (500 mg, 1.0 mmol) in DCM (12 mL) cooled to 0° C. was added TFA (3 mL) dropwise, the mixture was warmed slowly to 25° C. and stirred overnight. The reaction mixture was concentrated under reduced pressure (in vacuum). The residue was dissolved in CH$_2$Cl$_2$ (20 mL) and sat. NaHCO$_3$ was added to adjust pH=8-9, the mixture was concentrated and the residue was purified by flash chromatography on C18 (CH$_3$CN: H$_2$O=5-40%, 40 min) to afford A403D (400 mg, yield: 82%) as a light yellow solid.

$^1$H NMR (DMSO-d$_6$, 300 MHz): δ 7.93 (br s, 1H), 7.41-7.49 (m, 2H), 7.26-7.32 (m, 3H), 7.16-7.22 (m, 1H), 7.06 (br s, 1H), 5.25 (s, 2H), 5.05-5.13 (m, 0.00H), 4.60 (d, J=17.7 Hz, 1H), 4.30 (d, J=17.7 Hz, 1H), 3.50-3.52 (m, 4H), 3.42 (s, 2H), 2.22-2.32 (m, 4H), 2.03-2.10 (m, 1H), 1.81-1.94 (m, 3H).

Step D: To a solution of A403D (400 mg, 0.82 mmol) in dry DMF (1 mL), dry DCM (40 mL) and THF (20 mL) cooled to –40° C. under N$_2$, SOCl$_2$ (488 mg, 4.1 mmol) was slowly added to the mixture at –40° C. The reaction mixture was stirred for 1 h, and then pyridine (324 mg, 4.1 mmol) was added, after 40 mins Et$_3$N (415 mg, 4.1 mmol) was added, and then the mixture was stirred for 1 h. LCMS showed the reaction was finished. DCM (50 mL) and H$_2$O (2 mL) was added to quench the reaction, the water layer was extracted with DCM (50 mL×2), the combined organic phase was washed with brine (50 mL), dried over Na$_2$SO$_4$, filtered, concentrated to give a residue. The crude product was purified by C18 (CH$_3$CN: H$_2$O=5%-45%, 40 min) to give A403 (300 mg, yield: 78%, ee: 99%) as a white solid.

$^1$H NMR (DMSO-d$_6$, 300 MHz): δ 10.96 (br s, 1H), 7.46-7.51 (m, 2H), 7.31-7.37 (m, 3H), 7.16-7.22 (m, 1H), 5.27 (s, 2H), 5.05-5.13 (m, 0.04H), 4.35 (d, J=17.7 Hz, 1H), 4.19 (d, J=17.7 Hz, 1H), 3.5.-3.53 (m, 4H), 3.43 (s, 2H), 2.82-2.94 (m, 1H), 2.49-2.58 (m, 1H), 2.36-2.41 (m, 1H), 2.26-2.32 (m, 4H), 1.91-1.98 (m, 1H). LCMS=469.2 ([M+1]$^+$).

Compounds in examples 68 and 69 were prepared according to the procedure described for example 67, with corresponding starting materials to replace 4-(3-(chloromethyl)-4-fluorobenzyl)morpholine hydrochloride.

Example 68: Compound A404

(S)-3-deuterium-3-(4-((2-fluoro-3-(morpholinomethyl)benzyl)oxy)-1-oxoisoindolin-2-yl)piperidine-2,6-dione, A404

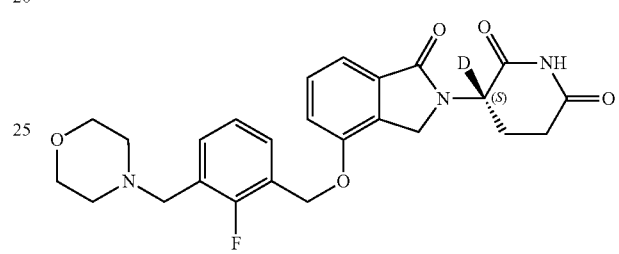

$^1$H NMR (DMSO-d$_6$, 300 MHz): δ 10.94 (s, 1H), 7.45-7.53 (m, 2H), 7.31-7.42 (m, 3H), 7.17-7.21 (m, 1H), 5.28 (s, 2H), 4.37 (d, J=18.0 Hz, 1H), 4.21 (d, J=18.0 Hz, 1H), 3.51-3.62 (m, 6H), 2.82-2.95 (m, 1H), 2.57-2.62 (m, 1H), 2.28-2.42 (m, 5H), 1.91-2.01 (m, 1H). LCMS: 469.2 ([M+1]$^+$).

Example 69: Compound A406

(S)-3-deuterium-3-(4-((2-fluoro-4-(morpholinomethyl)benzyl)oxy)-1-oxoisoindolin-2-yl)piperidine-2,6-dione, A406

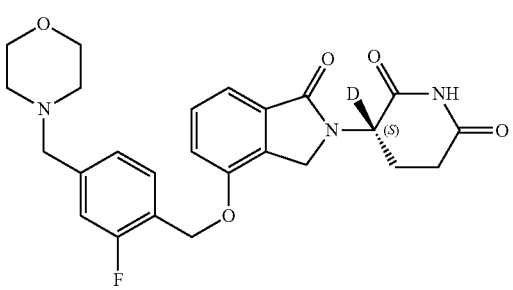

$^1$H NMR (DMSO-d$_6$, 300 MHz): δ 10.98 (s, 1H), 7.47-7.55 (m, 2H), 7.31-7.38 (m, 2H), 7.16-7.20 (m, 2H), 5.24 (s, 2H), 5.06-5.12 (m, 0.04H), 4.35 (d, J=18.0 Hz, 1H), 4.19 (d, J=18.0 Hz, 1H), 3.55 (br, 4H), 3.47 (s, 2H), 2.82-2.94 (m, 1H), 2.48-2.57 (m, 1H), 2.33-2.42 (m, 5H), 1.91-1.96 (m, 1H). LCMS: 469.2 ([M+1]$^+$).

Example 70: Compound A400

(S)-3-deuterium-3-(4-((2-fluoro-3-(morpholinomethyl)benzyl)amino)-1-oxoisoindolin-2-yl)piperidine-2,6-dione, A400

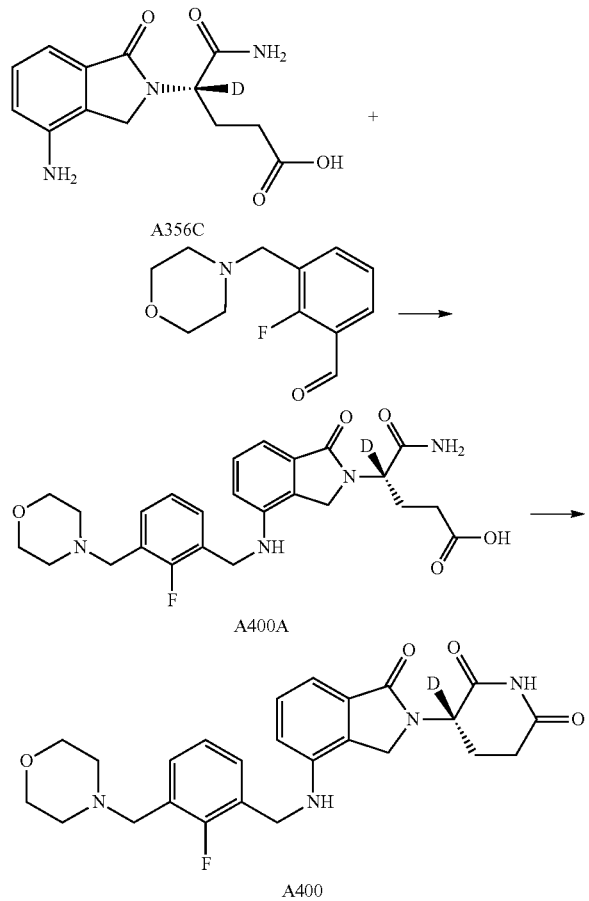

Step A: To a solution of compound A356C (400 mg, 1.44 mmol) in MeOH (30 mL) was added 2-fluoro-3-(morpholinomethyl)benzaldehyde (481 mg, 2.16 mmol) and AcOH (0.5 mL). The reaction mixture was stirred overnight at 30° C., then Pd/C (150 mg, 10%, 50% water) was added under $H_2$ atmosphere, the mixture was stirred for 3 hours, filtered and concentrated to afford product A400A (580 mg).

$^1$H NMR (DMSO-$d_6$, 300 MHz): δ 7.57 (br s, 1H), 7.06-7.31 (m, 5H), 6.88-6.90 (m, 1H), 6.58-6.60 (m, 1H), 6.37 (s, 1H), 4.26-4.54 (m, 4H), 3.47-3.66 (m, 6H), 2.23-2.37 (m, 4H), 2.07-2.15 (m, 3H), 1.85-1.97 (m, 1H).

Step B: To a solution of crude A400A (480 mg, 0.99 mmol) in DCM (20 mL) cooled to −40° C., was added DMF (1 mL), then SOCl$_2$ (589 mg, 4.95 mmol) was added and stirred for 2 hours, pyridine (383 mg, 4.95 mmol) was added, the mixture was stirred for 30 min, and then Et$_3$N (501 mg, 4.95 mmol) was added. The reaction mixture was stirred for another 1 hour at −40° C. and then quenched with water (80 mL), extracted with DCM (80 mL×3). The combined organic phase was dried over Na$_2$SO$_4$, filtered and concentrated to afford a crude oil, which was purified by column chromatographer on silica gel (DCM/MeOH=40/1) to give product A400 (251 mg, 54%).

$^1$H NMR (DMSO-$d_6$, 300 MHz): δ 11.02 (s, 1H), 7.20-7.31 (m, 3H), 7.10 (t, J=7.8 Hz, 1H), 6.95 (d, J=7.5 Hz, 1H), 6.65 (d, J=7.8 Hz, 1H), 6.29-6.32 (m, 1H), 5.09-5.15 (m, 0.05H), 4.43 (d, J=5.1 Hz, 2H), 4.31 (d, J=17.1 Hz, 1H), 4.19 (d, J=17.1 Hz, 1H), 3.49-3.64 (m, 6H), 2.87-2.99 (m, 1H), 2.58-2.65 (m, 1H), 2.25-2.44 (m, 5H), 2.01-2.06 (m, 1H). LCMS: 468.2 ([M+1]$^+$).

Compounds in example 71 and 72 were prepared according to the procedure described for example 70, with corresponding starting materials to replace 2-fluoro-3-(morpholinomethyl)benzaldehyde in step A.

Example 71: Compound A401

(S)-3-deuterium-3-(4-((2-fluoro-5-(morpholinomethyl)benzyl)amino)-1-oxoisoindolin-2-yl)piperidine-2,6-dione A401

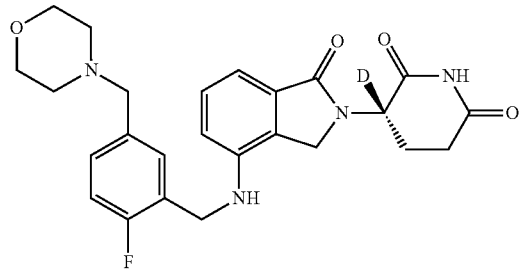

$^1$H NMR (DMSO-$d_6$, 400 MHz): δ 11.03 (br s, 1H), 7.32 (d, J=6.8 Hz, 1H), 7.12-7.23 (m, 3H), 6.94 (d, J=7.6 Hz, 1H), 6.62 (d, J=8.0 Hz, 1H), 6.34 (t, J=6.0 Hz, 1H), 5.11-5.16 (m, 0.4H), 4.42 (d, J=5.6 Hz, 2H), 4.31 (d, J=16.8 Hz, 1H), 4.20 (d, J=17.2 Hz, 1H), 3.42-3.49 (m, 4H), 3.37 (s, 2H), 2.89-2.98 (m, 1H), 2.58-2.67 (m, 1H), 2.28-2.35 (m, 1H), 2.18-2.26 (m, 4H), 2.02-2.06 (m, 1H). LCMS: 468.2 [(M+1)$^+$].

Example 72: Compound A402

(S)-3-deuterium-3-(4-((2-fluoro-4-(morpholinomethyl)benzyl)amino)-1-oxoisoindolin-2-yl)piperidine-2,6-dione, A402

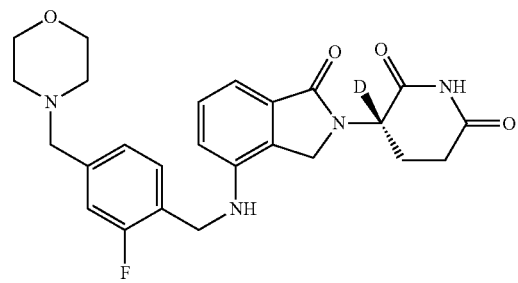

$^1$H NMR (DMSO-$d_6$, 300 MHz): δ 11.01 (s, 1H), 7.30-7.35 (m, 1H), 7.22 (t, J=7.8 Hz, 1H), 7.05-7.13 (m, 2H), 6.92 (d, J=7.5 Hz, 1H), 6.64 (d, J=8.1 Hz, 1H), 6.27-6.31 (m, 1H), 5.08-5.14 (m, 0.05H), 4.38 (d, J=5.4 Hz, 2H), 4.28 (d, J=17.4 Hz, 1H), 4.16 (d, J=17.4 Hz, 1H), 3.54 (br s, 4H), 3.42 (s, 2H), 2.85-2.97 (m, 1H), 2.56-2.62 (m, 1H), 2.24-2.31 (m, 5H), 1.98-2.06 (m, 1H). LCMS: 468.2 ([M+1]$^+$).

Example 73: Compound A405

3-(6-fluoro-4-((4-(morpholinomethyl)benzyl)amino)-1-oxoisoindolin-2-yl)piperidine-2,6-dione, A405

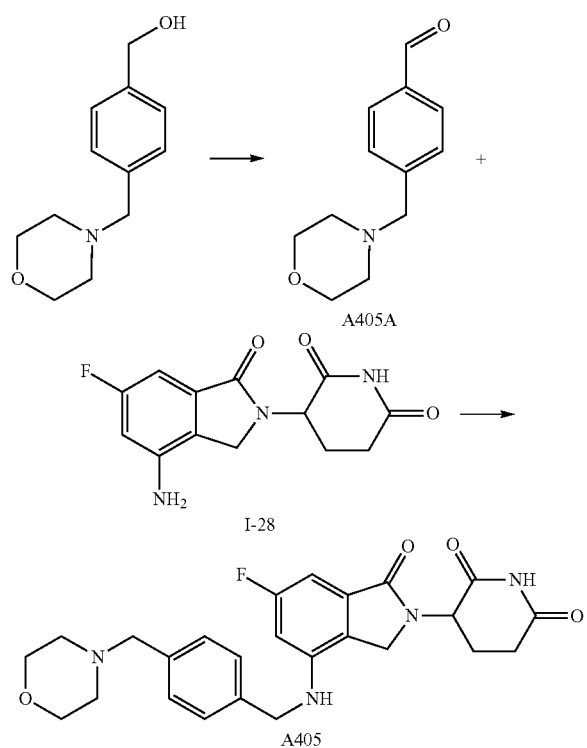

Step A: To a solution of DMSO (156 mg, 2.0 mmol) in DCM (10 mL) at −70° C. under N₂ was added (COCl)₂ (152 mg, 1.2 mmol). The reaction mixture was stirred for 30 minutes at −70° C. A solution of (4-(morpholinomethyl)phenyl) methanol (207 mg, 1.0 mmol) in DCM (3 mL) was added and the reaction mixture was stirred for 1 hour. Et₃N (405 mg, 4.0 mmol) was added dropwise to the reaction mixture and the mixture was stirred for 1 hour at −70° C., then the temperature was allowed to warm up to 25° C., the reaction mixture was quenched with H₂O (10 mL) and NaHCO₃ solution (5 mL) was added. The mixture was separated and the aqueous layer was extracted with 10 mL DCM. The combined organic layer was concentrated, and purified via column chromatography (PE:EtOAc=2:1) to give A405A (180 mg, yield: 88%) as a light yellow oil.

¹H NMR (CDCl₃, 300 MHz): δ 9.99 (s, 1H), 7.84 (d, J=7.8 Hz, 2H), 7.51 (d, J=8.1 Hz, 2H), 3.70-3.73 (m, 4H), 3.57 (s, 2H), 2.46 (t, J=4.2 Hz, 4H).

Step B: To a solution of A405A (111 mg, 0.54 mmol) and I-28 (100 mg, 0.36 mmol) in DCM (6 mL) was added HOAc (6 mL) and the reaction mixture was stirred for 3 hour at 25° C. NaBH₃CN (45 mg, 0.72 mmol) was added and the reaction mixture was stirred at room temperature overnight. Additional A405A (40 mg, 0.14 mmol) was added and the mixture was stirred at 40° C. for 6 hours. The solvent was removed and NaHCO₃ solution (10 mL) and DCM (25 mL) was added and separated. The aqueous layer was extracted with DCM (20 mL×2). The combined organic layer was concentrated and purified by prep-HPLC then freeze-dried to give a solid, which was added to 5 mL sat. NaHCO₃ solution to adjust pH=8 and then extracted with DCM (5 mL×5), the organic solution was combined, concentrated to give A405 (50 mg, 30% yield) as a white solid.

¹H NMR (DMSO-d₆, 300 MHz): δ 11.01 (s, 1H), 7.23-7.33 (m, 4H), 6.72 (br s, 1H), 6.60 (dd, J=1.8 Hz, 7.5 Hz, 1H), 6.42 (dd, J=2.1 Hz, 12.6 Hz, 1H), 5.09 (dd, J=5.1 Hz, 13.2 Hz, 1H), 4.35 (d, J=5.4 Hz, 2H), 4.27 (d, J=17.4 Hz, 1H), 4.14 (d, J=17.4 Hz, 1H), 3.53 (br s, 4H), 3.41 (s, 2H), 2.84-2.96 (m, 1H), 2.57-2.63 (m, 1H), 2.21-2.31 (m, 5H), 2.01-2.05 (m, 1H). LCMS: 467.2 ([M+1]⁺).

Example 74: Compound A386

3-(4-((2-fluoro-4-(morpholinomethyl)benzyl)oxy)-1-oxoisoindolin-2-yl)piperidine-2,6-dione, A386

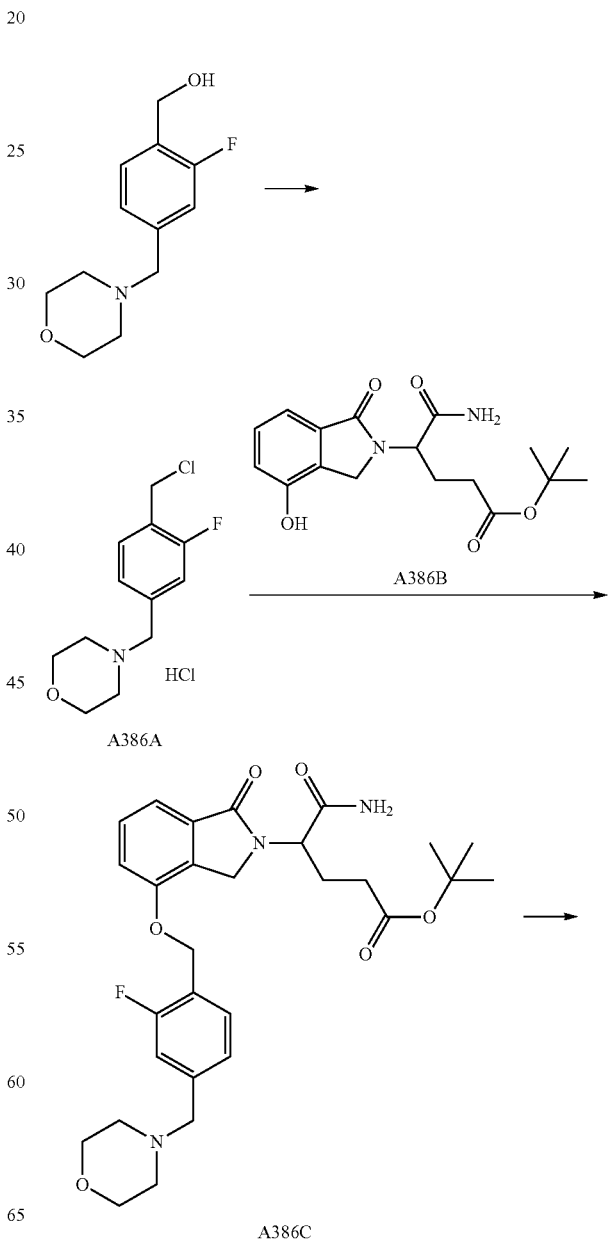

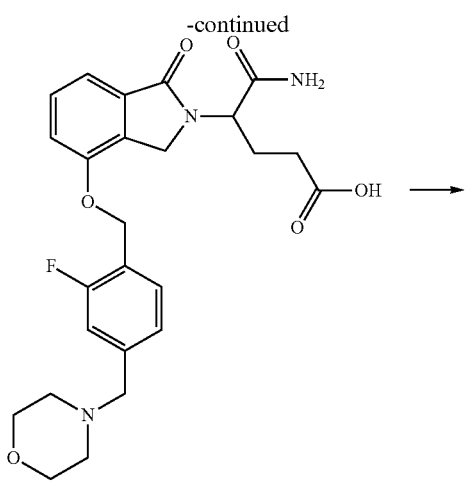

A386E

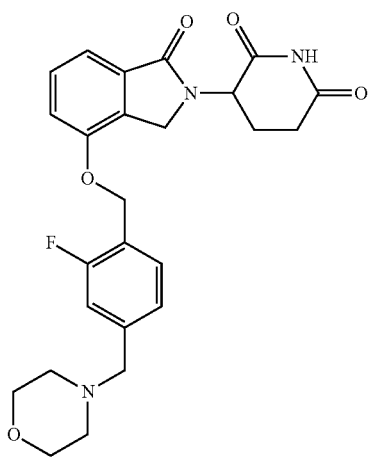

A386

Step A: A solution of (2-fluoro-4-(morpholinomethyl) phenyl)methanol (1.0 g, 4.4 mmol) in chloroform (25 mL) was added SOCl$_2$ (1.1 g, 9.2 mmol) and the mixture was heated to reflux for 2 hours. The solvent was removed in vacuum and co-evaporated with chloroform (25 mL×2) to give A386A (1.2 g, yield: 97%) as a white solid.

$^1$H NMR (DMSO-d6, 400 MHz): δ 11.98 (br s, 1H), 7.70 (d, J=10.8 Hz, 1H), 7.63 (t, J 8.0 Hz, 1H), 7.70 (d, J=7.6 Hz, 1H), 4.82 (s, 2H), 4.37 (d, J=4.8 Hz, 2H), 3.86-3.93 (m, 4H), 3.07-3.21 (m, 4H).

Step B: A mixture of A386A and A386B (0.8 g, 2.4 mmol), K$_2$CO$_3$ (1.3 g, 9.6 mmol) in DMF (20 mL) was degassed with N$_2$ and heated to 40° C. and stirred for 18 hours. The reaction mixture was poured into 100 mL ice water and extracted with EtOAc (20 mL×5). The combined organic layer was washed with 20 mL water, 20 mL brine and dried over Na$_2$SO$_4$, filtered, concentrated, and purified by column chromatography on silica gel (PE: EtOAc=2:1 to 1:1) to give A386C (1.2 g, yield: 92%) as a white solid.

$^1$H NMR (CDCl$_3$, 300 MHz): δ 7.37-7.47 (m, 3H), 7.10-7.16 (m, 3H), 6.30 (br s, 1H), 5.33 (br s, 1H), 5.18 (s, 2H), 4.86-4.91 (m, 1H), 4.36-4.51 (m, 2H), 3.71-3.74 (m, 4H), 3.51 (s, 2H), 2.45-2.48 (m, 4H), 2.09-2.40 (m, 4H), 1.42 (s, 9H).

Step C: A solution of A386C (1.2 g, 2.2 mmol) in DCM (30 mL) was added TFA (15 mL) and stirred at 35° C. for 2 hours. The reaction mixture was concentrated and purified by prep-HPLC to give A386E (1.4 g, yield: 64%) as a light yellow solid.

$^1$H NMR (DMSO-d$_6$, 300 MHz): δ 12.05 (br s, 1H), 7.56 (br s, 2H), 7.47 (t, J=8.1 Hz, 1H), 7.29-7.36 (m, 4H), 7.15-7.22 (m, 1H), 5.25 (s, 2H), 4.68-4.73 (m, 1H), 4.50 (d, J=17.7 Hz, 1H), 4.36 (d, J=17.7 Hz, 1H), 3.56-3.60 (m, 6H), 2.26-2.45 (m, 2H), 1.94-2.16 (m, 4H), 1.72-1.77 (m, 2H).

Step D: To a solution of A386E (421 mg, 0.867 mmol) in DCM/THF (50 mL/5 mL) at −40° C. was added SOCl$_2$ (516 mg, 4.33 mmol, as solution in 10 mL DCM). The mixture was stirred at −40° C. to −20° C. for 2 hours and pyridine (339 mg, 4.33 mmol) was added and the reaction mixture was stirred at −40° C. for 0.5 hours. Et$_3$N (438 mg, 4.33 mmol) was added and the mixture was allowed to warm to 25° C. slowly. H$_2$O (0.5 mL) was added and then filtered. The filter cake was dissolved with CH$_3$CN (5 mL) and un-dissolved solid was filtered off, and CH$_3$CN was removed to give crude product. The DCM layer of the reaction mixture was washed with water (25 mL×2) and brine (25 mL) and concentrated to give additional crude product. The combined crude product was purified by prep-HPLC twice to give A386 (105 mg, yield: 26%) as a white solid.

$^1$H NMR (DMSO-d$_6$, 300 MHz): δ 10.95 (s, 1H), 7.49-7.58 (m, 2H), 7.34-7.40 (m, 2H), 7.17-7.21 (m, 2H), 5.26 (s, 2H), 5.07-5.13 (m, 1H), 4.38 (d, J=17.7 Hz, 1H), 4.22 (d, J=17.7 Hz, 1H), 3.58 (br s, 4H), 3.49 (br s, 2H), 2.84-2.96 (m, 1H), 2.56-2.60 (m, 1H), 2.30-2.43 (m, 5H), 1.92-2.02 (m, 1H).

Example 75: Compound A425

3-deuterium-3-(4-((2-fluoro-5-(morpholinomethyl) benzyl)oxy)-1-oxoisoindolin-2-yl)piperidine-2,6-dione, A425

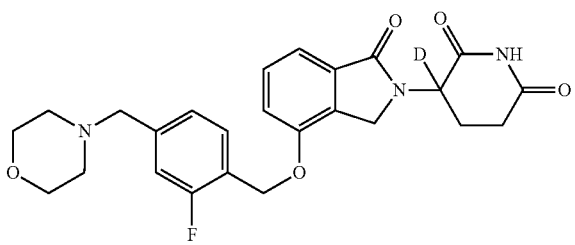 [SMILES: [2H]C1(N2Cc3c(OCc4ccc(CN5CCOCC5)cc4F)cccc3C2=O)CCC(=O)NC1=O]

Compound A425 in Example 75 was prepared according to the procedure described in example 67, with racemic A403A as appropriate starting material.

$^1$H NMR (DMSO-d$_6$, 300 MHz): δ 10.95 (s, 1H), 7.49-7.57 (m, 2H), 7.33-7.40 (m, 2H), 7.18-7.22 (m, 2H), 5.26 (s, 2H), 4.37 (d, J=17.7 Hz, 2H), 4.21 (d, J=17.7 Hz, 1H), 3.58-3.62 (m, 4H), 3.49 (s, 2H), 2.84-2.96 (m, 1H), 2.27-2.58 (m, 6H), 1.93-1.99 (m, 1H). LCMS=469.2 ([M+1]$^+$).

Example 76: Compound A427

3-deuterium-3-(4-((4-((2,6-dimethylmorpholino)methyl)-2-fluorobenzyl)oxy)-1-oxoisoindolin-2-yl)piperidine-2,6-dione, A427

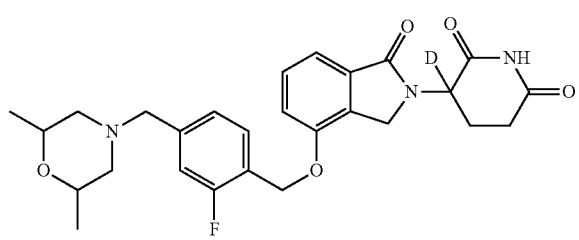 [SMILES: [2H]C1(N2Cc3c(OCc4ccc(CN5CC(C)OC(C)C5)cc4F)cccc3C2=O)CCC(=O)NC1=O]

Compound A427 in Example 76 was prepared according to the procedure described in example 67, with appropriate starting material to replace 4-(3-(chloromethyl)-4-fluorobenzyl)morpholine hydrochloride.

$^1$H NMR (DMSO-$d_6$, 300 MHz): δ 10.97 (s, 1H), 7.49-7.58 (m, 2H), 7.34-7.41 (m, 2H), 7.17-7.21 (m, 2H), 5.26 (s, 2H), 4.38 (d, J=17.7 Hz, 1H), 4.21 (d, J=17.7 Hz, 1H), 3.54-3.61 (m, 2H), 3.47 (s, 2H), 2.84-2.96 (m, 1H), 2.53-2.68 (m, 3H), 2.38-2.44 (m, 1H), 1.93-1.99 (m, 1H), 1.66 (t, J=10.5 Hz, 2H), 1.02 (d, J=6.0 Hz, 6H). LCMS: 497.2 ([M+1]$^+$).

Example 77: Compound A426

3-deuterium-3-(4-((2-fluoro-4-(morpholinomethyl)benzyl)amino)-1-oxoisoindolin-2-yl)piperidine-2,6-dione, A426

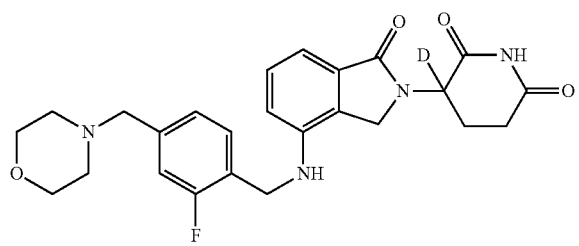 [SMILES: [2H]C1(N2Cc3c(NCc4ccc(CN5CCOCC5)cc4F)cccc3C2=O)CCC(=O)NC1=O]

Compound A426 in Example 77 was prepared according to the procedure described in example 70, with racemic A400A as appropriate starting material.

$^1$H NMR (DMSO-$d_6$, 300 MHz): δ 11.00 (s, 1H), 7.32 (t, J=8.1 Hz, 1H), 7.22 (t, J=7.8 Hz, 1H), 7.05-7.13 (m, 2H), 6.93 (d, J=7.5 Hz, 1H), 6.64 (d, J=8.1 Hz, 1H), 6.27 (t, J=6.0 Hz, 1H), 5.07-5.13 (m, 0.01H), 4.38 (d, J=5.4 Hz, 2H), 4.28 (d, J=17.1 Hz, 1H), 4.16 (d, J=17.1 Hz, 1H), 3.52-3.55 (m, 4H), 3.42 (s, 2H), 2.85-2.97 (m, 1H), 2.56-2.65 (m, 1H), 2.23-2.35 (m, 5H), 1.99-2.06 (m, 1H). LCMS: 468.2 ([M+1]$^+$).

Example 78: Compound A428

3-deuterium-3-(4-((4-((2,6-dimethylmorpholino)methyl)-2-fluorobenzyl)amino)-1-oxoisoindolin-2-yl)piperidine-2,6-dione, A428

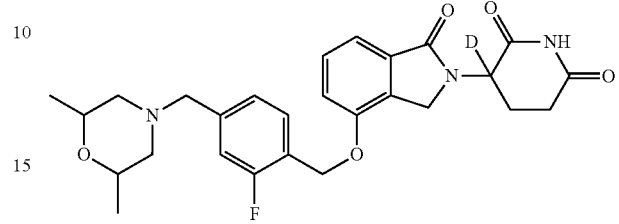

Compound A428 in Example 78 was prepared according to the procedure described in example 70, with appropriate starting material to replace 2-fluoro-3-(morpholinomethyl)benzaldehyde in step A.

$^1$H NMR (DMSO-$d_6$, 300 MHz): δ 11.02 (s, 1H), 7.34 (t, J=7.8 Hz, 1H), 7.24 (t, J=7.8 Hz, 1H) 7.06-7.13 (m, 2H), 6.95 (d, J=7.5 Hz, 1H), 6.67 (d, J=7.8 Hz, 1H), 6.28 (t, J=5.7 Hz, 1H), 4.40 (d, J=5.1 Hz, 2H), 4.30 (d, J=17.1 Hz, 1H), 4.18 (d, J=17.1 Hz, 1H), 3.52-3.61 (m, 2H), 3.42 (s, 2H), 2.87-2.99 (m, 1H), 2.59-2.65 (m, 3H), 2.35-2.25 (m, 1H), 2.01-2.06 (m, 1H), 1.63 (t, J=10.5 Hz, 2H), 1.01 (d, J=6.0 Hz, 6H). LCMS: 496.2 ([M+1]+).

Effect Examples

TNF-α Activity Inhibiting Assay

Peripheral blood from healthy volunteers was collected and collected with EDTA anticoagulant tubes. After being diluted 5-fold with 1640 medium (Gibco, catalog number 11875-093, USA), the blood was added to 96-well cell culture plates (Costar, catalog number 3599, USA) and then treated with 10 μL solution of the compound of general formula (I) of the present invention in DMSO (Sigma, catalog number D2650, USA). The final concentration of the compound was 100 nM, and the final concentration of DMSO was 0.2%. After incubation for 60 minutes in an incubator at 37° C. under 5% $CO_2$, 10 μL LPS (Sigma, catalog number L-2880, USA) was added to the reaction system, and the final concentration was 10 ng/mL. After further culturing for 6 hours in the incubator at 37° C. under 5% $CO_2$, the supernatant was collected. The content of TNF-α was determined by ELISA (BD Biosciences, catalog number 555212, USA). Absorbance was detected at $OD_{450}$ nm with a microplate reader, with OD 650 nm as reference. The control, a solution containing 0.2% DMSO medium, was as 0% inhibition. Raw data and standard curves were recorded. The four-parameter drug inhibition curve was plotted by XL-fit software and the inhibition rate of each compound was calculated, as shown in Table 1.

TABLE 1

| Compound | Inhibitory Rate on TNF-α (%) | Compound | Inhibitory Rate on TNF-α (%) | Compound | Inhibitory Rate on TNF-α (%) |
|---|---|---|---|---|---|
| I-01 | >50 | I-28 | >50 | I-29 | >50 |
| I-31 | >50 | I-32 | >50 | A386 | ≥50 |
| A196 | ≥50 | A360 | <50 | A387 | ≥50 |
| A197 | ≥50 | A361 | ≥50 | A388 | ≥50 |
| A318 | <50 | A362 | <50 | A389 | <50 |

TABLE 1-continued

| Compound | Inhibitory Rate on TNF-α (%) | Compound | Inhibitory Rate on TNF-α (%) | Compound | Inhibitory Rate on TNF-α (%) |
|---|---|---|---|---|---|
| A319 | <50 | A363 | <50 | A390 | ≥50 |
| A320 | <50 | A364 | <50 | A391 | ≥50 |
| A327 | <50 | A367 | ≥50 | A392 | ≥50 |
| A329 | ≥50 | A368 | ≥50 | A393 | <50 |
| A331 | ≥50 | A369 | ≥50 | A396 | <50 |
| A334 | ≥50 | A370 | <50 | A397 | <50 |
| A340 | <50 | A371 | ≥50 | A398 | ≥50 |
| A341 | <50 | A372 | ≥50 | A399 | ≥50 |
| A342 | <50 | A373 | ≥50 | A400 | ≥50 |
| A343 | ≥50 | A374 | ≥50 | A401 | ≥50 |
| A346 | ≥50 | A375 | <50 | A402 | ≥50 |
| A349 | <50 | A376 | ≥50 | A403 | ≥50 |
| A350 | <50 | A377 | <50 | A404 | ≥50 |
| A351 | <50 | A378 | <50 | A405 | <50 |
| A352 | <50 | A379 | <50 | A406 | ≥50 |
| A353 | <50 | A380 | <50 | A407 | <50 |
| A354 | <50 | A381 | ≥50 | A425 | ≥50 |
| A355 | <50 | A382 | ≥50 | A426 | ≥50 |
| A356 | ≥50 | A383 | ≥50 | A427 | ≥50 |
| A357 | ≥50 | A384 | ≥50 | A428 | ≥50 |
| A359 | ≥50 | A385 | ≥50 | Lenalidomide | <50 |

Cell Proliferation Assay

MM.1S cells (myeloma cells) (ATCC, catalog number CRL-2974) were seeded at $1.8\times10^3$ per well to a 96-well culture plate containing RPMI-1964 medium (Gibco, catalog number A10491-01), and were incubated in an incubator for 24 hours at 37° C. under 5% $CO_2$. Compounds were prepared as 20 mM stock solutions with DMSO (Sigma, catalog number D2650), and were diluted with the medium to the desired concentration (the final concentration of DMSO was 0.5%) and then were added to each well, incubated in an incubator for 72 hours at 37° C. under 5% $CO_2$. Then, 20 μL MTS (Promega, catalog number G3581) was added to each well, and further incubated for 1-4 hours in an incubator at 37° C. under 5% $CO_2$. $OD_{490}$ nm was detected with $OD_{650}$ nm as reference. The control, a solution containing 0.5% DMSO medium, was as 0% inhibition. GraphPad Prism 5 was used, slope was allowed to change to make the dose-effect curve and $IC_{50}$ values were calculated, shown in table 2 for details.

TABLE 2

| Compound | IC$_{50}$ values of MMIS Inhibition | Compound | IC$_{50}$ values of MMIS Inhibition | Compound | IC$_{50}$ values of MMIS Inhibition |
|---|---|---|---|---|---|
| I-28 | A | I-30 | A | I-29 | A |
| I-31 | A | I-32 | B | A386 | A |
| A195 | A | A359 | A | A387 | A |
| A196 | A | A360 | A | A388 | A |
| A197 | A | A361 | A | A389 | A |
| A318 | B | A362 | B | A390 | B |
| A319 | B | A363 | B | A391 | B |
| A320 | B | A364 | A | A392 | A |
| A327 | A | A367 | A | A393 | A |
| A329 | A | A368 | A | A396 | B |
| A331 | A | A369 | A | A397 | A |
| A334 | A | A370 | B | A398 | A |
| A336 | A | A371 | A | A399 | A |
| A340 | A | A372 | A | A400 | A |
| A341 | A | A373 | A | A401 | A |
| A342 | B | A374 | A | A402 | A |
| A343 | A | A375 | B | A403 | A |
| A346 | A | A376 | A | A404 | A |
| A349 | B | A377 | B | A405 | B |
| A350 | A | A378 | B | A406 | A |
| A351 | A | A379 | A | A407 | A |
| A352 | A | A380 | A | A425 | A |
| A353 | A | A381 | A | A426 | A |
| A354 | A | A382 | A | A427 | A |
| A355 | B | A383 | A | A428 | A |
| A356 | A | A384 | A | Lenalidomide | B |
| A357 | A | A385 | A | / | / |

Note:
A: <300 nM;
B:: ≥300 nM

CTG Cell Proliferation Assay

Rec-1 cells (Mantle cell lymphoma cells) (ATCC, catalog number CRL-3004), Namalwa.CSN/70 cells (Burkitt lymphoma cells) (DSMZ, catalog number ACC-70), and WSU-DLCL-2 cells (diffuse large B cell lymphoma cells) (DSMZ, catalog number ACC-575) were seeded at $(5-15)\times10^3$ per well to a 96-well plate with transparent bottom and white wall (Corning, catalog number CLS3903) containing specific medium. The plate was placed in an incubator and incubated for 24 hours at 37° C. under 5% $CO_2$. Compounds were prepared as 150 mM stock solutions with DMSO (Sigma, catalog number 276855), and were diluted with the medium to the desired concentration (the final concentration of DMSO was 0.2%) and then were added to each well, incubated in an incubator for 72-120 hours at 37° C. under 5% $CO_2$. Then, 100 μl CellTiter-Glo® cell activity assay reagent (Promega, catalog number G7570) was added to each well. Mixing proceeded for 10 minutes on a shaker to induce cytolysis. The 96-well plate was placed at room temperature for 10 minutes to make the luminous signal stable. A white base film was pasted at the bottom of the culture plate. EnSpire was used to test the plate. Data were processed by XLfit software, and $IC_{50}$ values were obtained and shown in table 3 for details.

TABLE 3

| Compound | IC$_{50}$ Value of WSU-DLCL2 Inhibition | IC$_{50}$ Value of Rec-1 Inhibition | IC$_{50}$ Value of Namalwa.CSN/70 Inhibition |
|---|---|---|---|
| Lenalidomide | D | B | D |
| I-28 | D | A | D |
| I-29 | D | A | D |
| I-30 | D | A | D |
| I-31 | C | A | D |
| I-32 | D | B | D |
| A195 | D | A | D |
| A324 | B | B | D |
| A329 | D | A | C |
| A334 | D | A | D |
| A356 | C | A | B |
| A357 | C | A | B |
| A381 | C | A | D |
| A382 | A | A | D |
| A383 | C | B | D |
| A386 | A | A | D |
| A399 | C | A | D |
| A400 | C | B | D |
| A402 | A | A | D |
| A403 | C | A | D |
| A404 | C | A | D |
| A406 | A | A | D |
| A407 | C | A | D |

TABLE 3-continued

| Compound | IC$_{50}$ Value of WSU-DLCL2 Inhibition | IC$_{50}$ Value of Rec-1 Inhibition | IC$_{50}$ Value of Namalwa.CSN/70 Inhibition |
| --- | --- | --- | --- |
| A427 | C | A | D |
| A428 | D | A | C |

Note:
A: <100 nM;
B: 100-400 nM;
C: 401 nM-300 μM;
D: >300 μM.

It is to be understood that the foregoing description of the preferred embodiments is intended to be purely illustrative of the principles of the invention, rather than exhaustive thereof, and that changes and variations will be apparent to those skilled in the art, and that the present invention is not intended to be limited other than expressly set forth in the following claims.

What is claimed is:

1. An isoindoline derivative having a structure of general formula (I), a pharmaceutically acceptable salt, a polymorph, a stereoisomer, an isotopic compound, or a metabolite thereof;

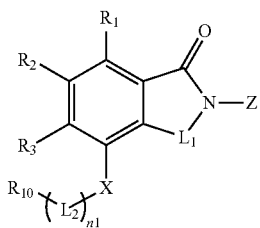
(I)

in the general formula (I), n1 is selected from 0 or 1;
Z is

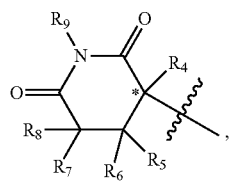

wherein the carbon atom labelled by * is an asymmetric center;
each of $R_1$, $R_3$, $R_4$, $R_5$, $R_6$, $R_7$, $R_8$ and $R_9$ is independently selected from H or D;
$R_2$ is selected from H, D or a halogen;
each of $L_1$ and $L_2$ is independently selected from CD$_2$, CHD or CH$_2$;
X is selected from NH, ND or O;
$R_{10}$ is H, D or

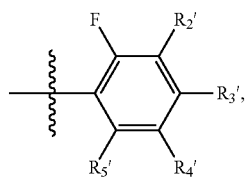

wherein each of $R_2'$, $R_3'$, $R_4'$ and $R_5'$ is independently selected from H, D, a halogen, a cyano, a hydroxy,

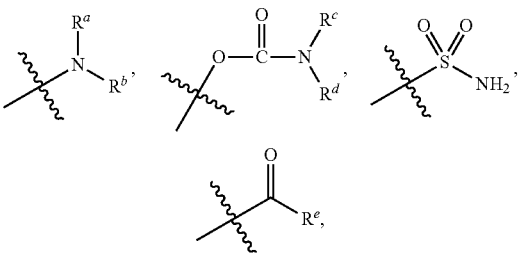

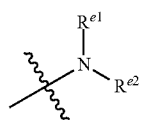

a substituted or unsubstituted (C$_1$-C$_{12}$)alkyl, a substituted or unsubstituted (C$_1$-C$_{12}$)alkoxy, a (C$_2$~C$_{20}$)heterocycloalkyl or deuterated (C$_2$~C$_{20}$)heterocycloalkyl; wherein each of R$^a$ and R$^b$ is independently H, a (C$_1$-C$_{12}$)alkyl, or a (C$_1$-C$_{12}$)alkylacyl; each of R$^c$ and R$^d$ is independently H or a (C$_1$-C$_{12}$)alkyl; R$^e$ is

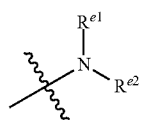

or a (C$_2$~C$_{20}$)heterocycloalkyl; each of R$^{e1}$ and R$^{e2}$ is independently H or a (C$_1$-C$_{12}$)alkyl;

the substituent contained in the substituted (C$_1$-C$_{12}$) alkoxy is selected from the group consisting of D, a halogen, a hydroxy, a (C$_1$-C$_{12}$)alkoxy, a (C$_2$~C$_{20}$)heterocycloalkyl, a (C$_2$~C$_{20}$)heterocycloalkyl substituted with a (C$_1$-C$_{12}$)alkyl,

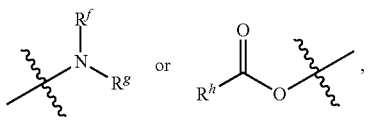

wherein each of R$^f$ and R$^g$ is independently H or a (C$_1$-C$_{12}$) alkyl; R$^h$ is a (C$_2$~C$_{20}$)heterocycloalkyl;

the substituent contained in the substituted (C$_1$-C$_{12}$)alkyl is selected from the group consisting of D, a (C$_2$~C$_{20}$) heterocycloalkyl, a deuterated (C$_2$~C$_{20}$)heterocycloalkyl, a (C$_2$~C$_{20}$)heterocycloalkyl substituted with a (C$_1$-C$_{12}$)alkyl, or a (C$_2$~C$_{20}$)heterocycloalkyl substituted with a deuterated (C$_1$-C$_{12}$)alkyl;

when more than one substituents are contained in the substituted (C$_1$-C$_{12}$)alkoxy or the substituted (C$_1$-C$_{12}$) alkyl, the substituents are the same or different;

in each of the groups mentioned above, the heteroatom of the (C$_2$~C$_{20}$)heterocycloalkyl contained in the (C$_2$~C$_{20}$)heterocycloalkyl, the deuterated (C$_2$~C$_{20}$)heterocycloalkyl, the (C$_2$~C$_{20}$)heterocycloalkyl substituted with a (C$_1$-C$_{12}$)alkyl or the (C$_2$~C$_{20}$)heterocycloalkyl substituted with a deuterated (C$_1$-C$_{12}$)alkyl, is selected from the group consisting of O, N and S;

provided that in the general formula (I), when n1 is 0, $R_1$, $R_3$ and $R_{10}$ are H or D, X is NH or ND, $R_2$ is a halogen;

provided that in the general formula (I), when n1 is 1, $R_{10}$ is

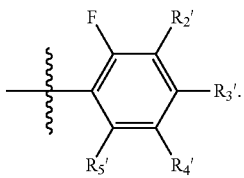

2. The isoindoline derivative having a structure of general formula (I), the pharmaceutically acceptable salt, the polymorph, the stereoisomer, the isotopic compound, or the metabolite thereof according to claim 1, wherein, in the general formula (I), the asymmetric center refers to an achiral carbon, (S) configuration carbon, enriched (S) configuration carbon, (R) configuration carbon, enriched (R) configuration carbon or racemate;

and/or, in the general formula (I), Z is selected from the group consisting of

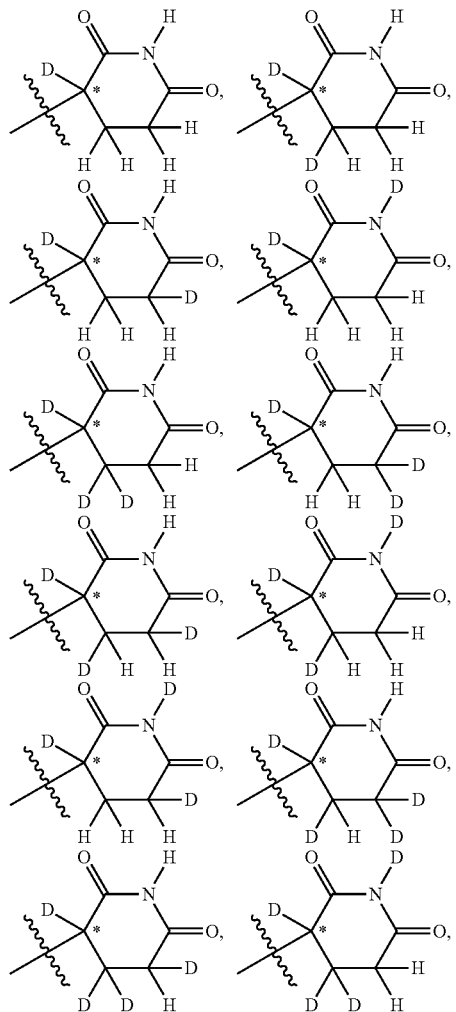

-continued

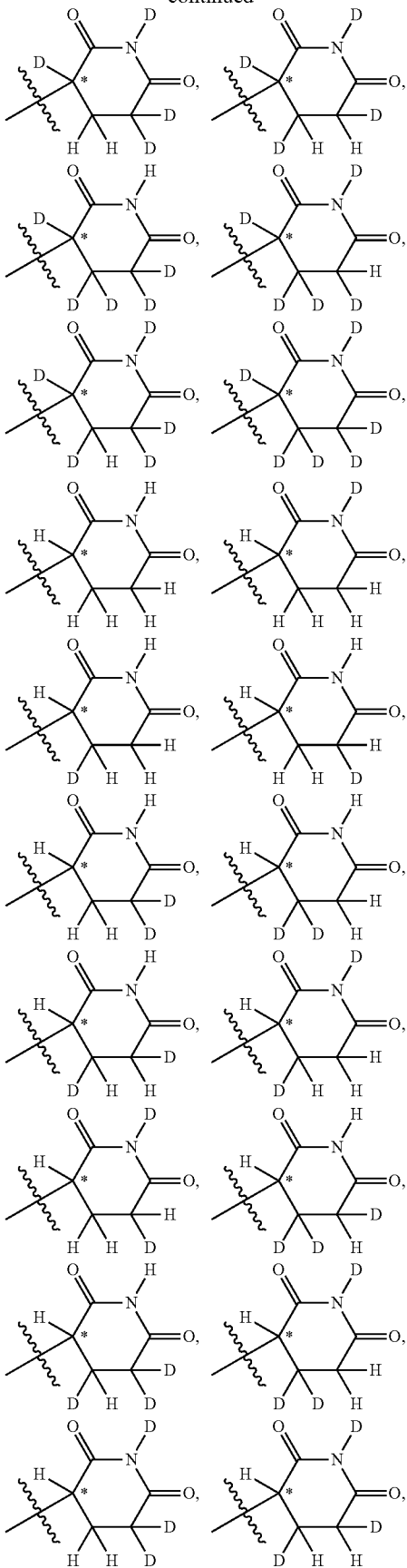

-continued

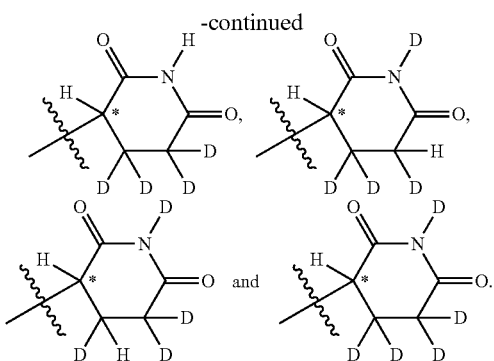

3. The isoindoline derivative having a structure of general formula (I), the pharmaceutically acceptable salt, the polymorph, the stereoisomer, the isotopic compound, or the metabolite thereof according to claim 1, wherein,
in the general formula (I), the $(C_2\text{~}C_{20})$heterocycloalkyl, the $(C_2\text{~}C_{20})$heterocycloalkyl contained in the deuterated $(C_2\text{~}C_{20})$heterocycloalkyl, the $(C_2\text{~}C_{20})$heterocycloalkyl substituted with a $(C_1\text{-}C_{12})$alkyl, or the $(C_2\text{~}C_{20})$heterocycloalkyl substituted with a deuterated $(C_1\text{-}C_{12})$alkyl is preferably a $(C_2\text{-}C_6)$heterocycloalkyl containing 1 or 2 heteroatom(s) selected from N or O; and/or, in the general formula (I), when $R_{10}$ is

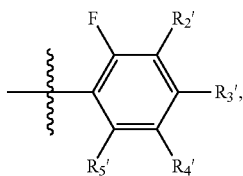

each of $R_2'$, $R_3'$, $R_4'$ and $R_5'$ is independently selected from

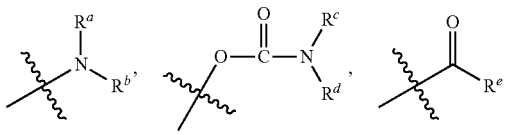

or a substituted $(C_1\text{-}C_{12})$alkoxy, each of $R^a$ and $R^b$ is independently a $(C_1\text{-}C_{12})$alkyl or a $(C_1\text{-}C_{12})$alkylacyl, each of $R^c$ and $R^d$ is independently a $(C_1\text{-}C_{12})$alkyl; $R^e$ is

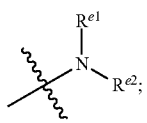

each of $R^{e1}$ and $R^{e2}$ is independently a $(C_1\text{-}C_{12})$alkyl; the substituent contained in the substituted $(C_1\text{-}C_{12})$alkoxy is

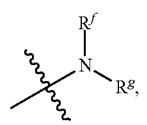

and each of $R^f$ and $R^g$ is independently a $(C_1\text{-}C_{12})$alkyl, the structure of the $(C_1\text{-}C_{12})$alkylacyl is

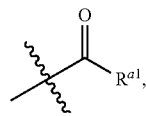

$R^{a1}$ is a $(C_1\text{-}C_{12})$alkyl; in the definition of $R^a$, $R^b$, $R^{a1}$, $R^c$, $R^d$, $R^{e1}$, $R^{e2}$, $R^f$ or $R^g$, the $(C_1\text{-}C_{12})$alkyl is a $(C_1\text{-}C_4)$alkyl; and/or, in the general formula (I), when $R_{10}$ is

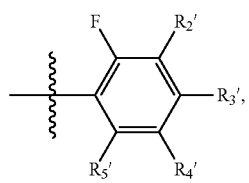

each of $R_2'$, $R_3'$, $R_4'$ and $R_5'$ is independently selected from a substituted $(C_1\text{-}C_{12})$alkoxy, and when the substituent contained in the substituted $(C_1\text{-}C_{12})$alkoxy is selected from a $(C_1\text{-}C_{12})$alkoxy, the $(C_1\text{-}C_{12})$alkoxy is a $(C_1\text{-}C_4)$alkoxy; and/or, in the general formula (I), when $R_{10}$ is

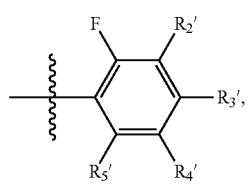

each of $R_2'$, $R_3'$, $R_4'$ and $R_5'$ is independently selected from a substituted $(C_1\text{-}C_{12})$alkoxy, and when the substituent in the substituted $(C_1\text{-}C_{12})$alkoxy is selected from

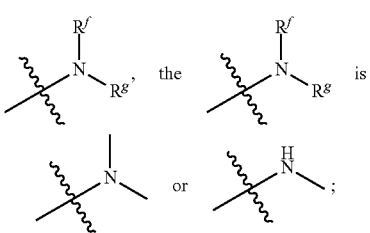

in the general formula (I), when $R_{10}$ is

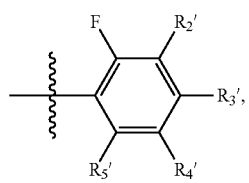

each of $R_2'$, $R_3'$, $R_4'$ and $R_5'$ is independently selected from a substituted $(C_1\text{-}C_{12})$alkoxy, and when the substituent contained in the substituted $(C_1\text{-}C_{12})$alkoxy is selected from

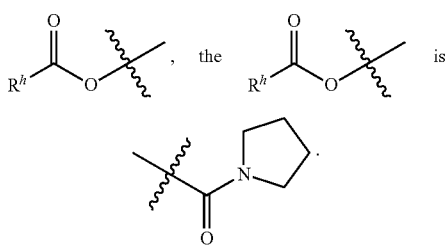, the 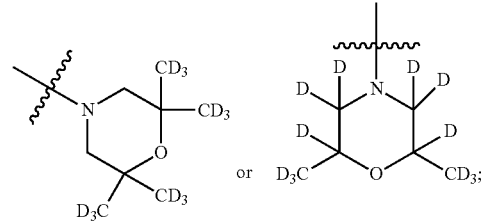 is

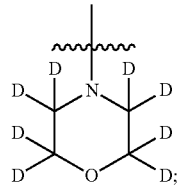

4. The isoindoline derivative having a structure of general formula (I), the pharmaceutically acceptable salt, the polymorph, the stereoisomer, the isotopic compound, or the metabolite thereof according to claim 3, wherein, the $(C_2\sim C_6)$heterocycloalkyl is pyrrolidine, morpholinyl or piperazinyl; the $(C_1-C_{12})$alkyl contained in the $(C_2\sim C_{20})$heterocycloalkyl substituted with a $(C_1-C_{12})$alkyl or the $(C_2\sim C_{20})$heterocycloalkyl substituted with a deuterated $(C_1-C_{12})$alkyl is a $(C_1-C_4)$alkyl; the deuterated $(C_2\sim C_{20})$heterocycloalkyl is

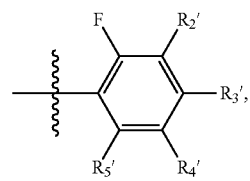

the $(C_2\sim C_{20})$heterocycloalkyl substituted with a $(C_1-C_{12})$ alkyl is

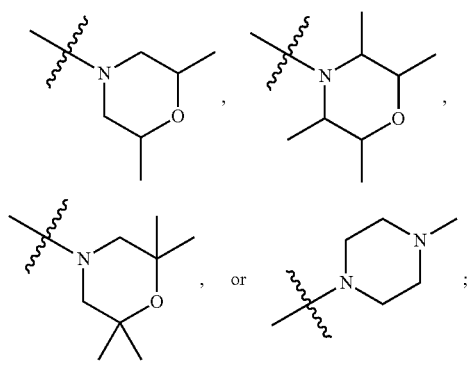

the $(C_2\sim C_{20})$heterocycloalkyl substituted with a deuterated $(C_1-C_{12})$alkyl is

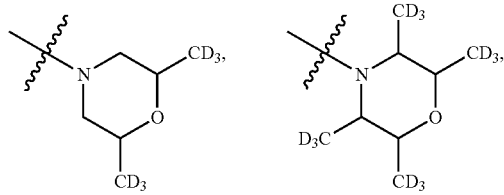

and/or, in the definition of each of $R^a$, $R^b$, $R^{a1}$, $R^c$, $R^d$, $R^{e1}$, $R^{e2}$, $R^f$ and $R^g$, the $(C_1-C_{12})$alkyl is a $(C_1-C_4)$alkyl; the $(C_1-C_4)$alkyl is a methyl, an ethyl, a n-propyl, an iso-propyl, a n-butyl, an iso-butyl or a tert-butyl;

and/or, in the general formula (I), when $R_{10}$ is

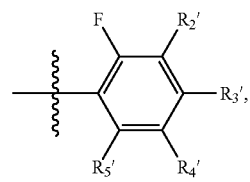

each of $R_2'$, $R_3'$, $R_4'$ and $R_5'$ is independently selected from a substituted $(C_1-C_{12})$alkoxy, and when the substituent contained in the substituted $(C_1-C_{12})$alkoxy is selected from a $(C_1-C_4)$alkoxy, the $(C_1-C_4)$alkoxy is a methoxy, an ethoxy, a n-propoxy, an isopropoxy, a n-butoxy, an isobutoxy, or a tert-butoxy.

5. The isoindoline derivative having a structure of general formula (I), the pharmaceutically acceptable salt, the polymorph, the stereoisomer, the isotopic compound, or the metabolite thereof according to claim 1, wherein, in the general formula (I), when $R_{10}$ is

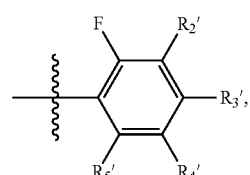

each of $R_2'$, $R_3'$, $R_4'$ and $R_5'$ is independently selected from a halogen, the halogen is F, Cl, Br or I;

and/or, in the general formula (I), when $R_{10}$ is

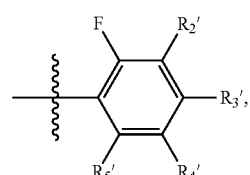

and each of $R_2'$, $R_3'$, $R_4'$ and $R_5'$ is independently selected from a substituted or unsubstituted $(C_1-C_{12})$alkyl, the substituted or unsubstituted $(C_1-C_{12})$alkyl is a substituted or unsubstituted $(C_1-C_4)$alkyl;

and/or, in the general formula (I), when $R_{10}$ is

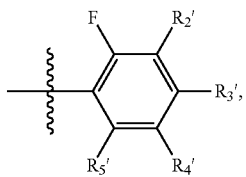

and each of $R_2'$, $R_3'$, $R_4'$ and $R_5'$ is independently selected from a substituted or unsubstituted $(C_1\text{-}C_{12})$alkoxy, the substituted or unsubstituted $(C_1\text{-}C_{12})$alkoxy is a substituted or unsubstituted $(C_1\text{-}C_4)$alkoxy;

and/or, in the general formula (I), when $R_{10}$ is

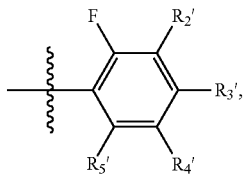

and each of $R_2'$, $R_3'$, $R_4'$ and $R_5'$ is independently selected from

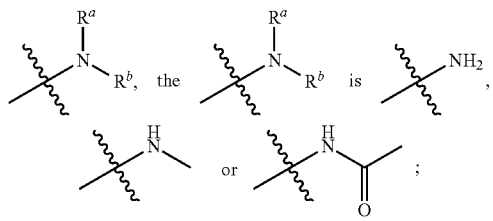

and/or, in the general formula (I), when $R_{10}$ is

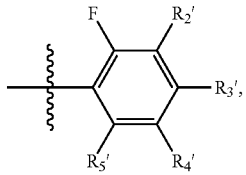

and each of $R_3'$, $R_4'$ and $R_5'$ is independently selected from

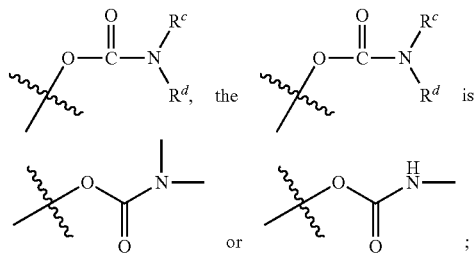

and/or, in the general formula (I), when $R_{10}$ is

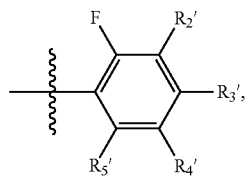

and each of $R_2'$, $R_3'$, $R_4'$ and $R_5'$ is independently selected from

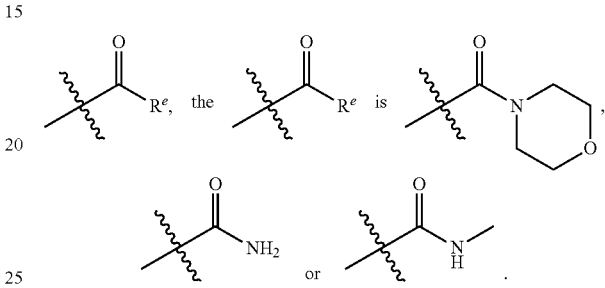

6. The isoindoline derivative having a structure of general formula (I), the pharmaceutically acceptable salt, the polymorph, the stereoisomer, the isotopic compound, or the metabolite thereof according to claim 5, wherein, in the general formula (I), when $R_{10}$ is

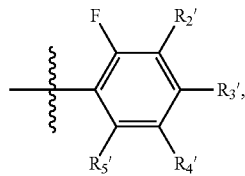

and each of $R_2'$, $R_3'$, $R_4'$ and $R_5'$ is independently selected from a substituted or unsubstituted $(C_1\text{-}C_4)$alkyl, the substituted or unsubstituted $(C_1\text{-}C_4)$alkyl is a substituted or unsubstituted methyl, a substituted or unsubstituted ethyl, a substituted or unsubstituted propyl, a substituted or unsubstituted isopropyl, a substituted or unsubstituted n-butyl, a substituted or unsubstituted isobutyl, or a substituted or unsubstituted tert-butyl; the substituted $(C_1\text{-}C_{12})$alkyl is

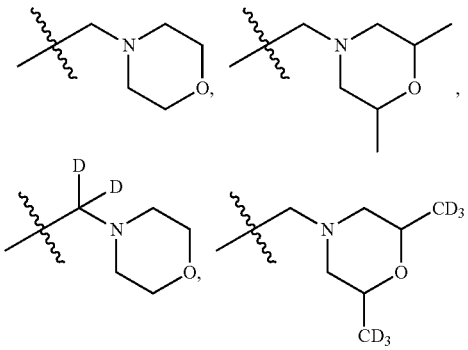

-continued

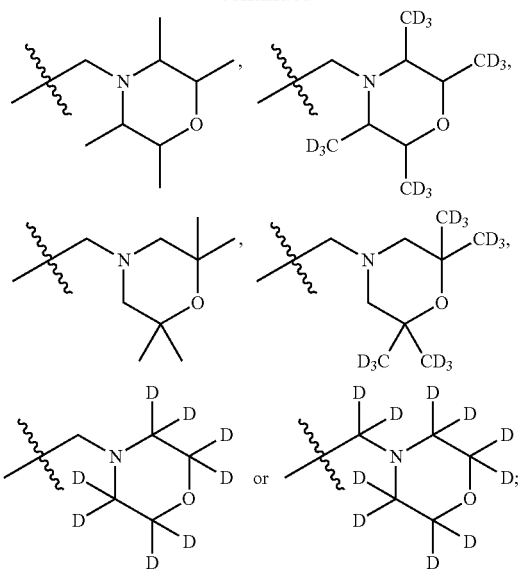

and/or, in the general formula (I), when $R_{10}$ is

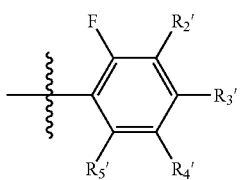

and each of $R_2'$, $R_3'$, $R_4'$ and $R_5'$ is independently selected from a substituted or unsubstituted $(C_1\text{-}C_4)$alkoxy, the substituted or unsubstituted $(C_1\text{-}C_4)$alkoxy is a substituted or unsubstituted methoxy, a substituted or unsubstituted ethoxy, a substituted or unsubstituted n-propoxy, a substituted or unsubstituted n-butoxy, a substituted or unsubstituted isobutoxy, or a substituted or unsubstituted tert-butoxy, the substituted $(C_1\text{-}C_{12})$alkoxy is

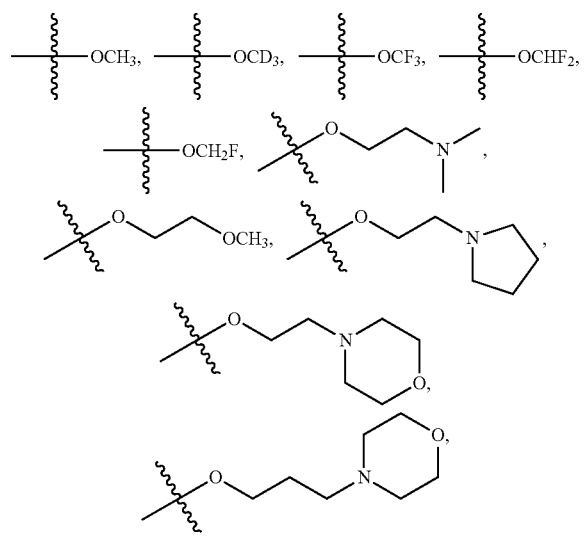

-continued

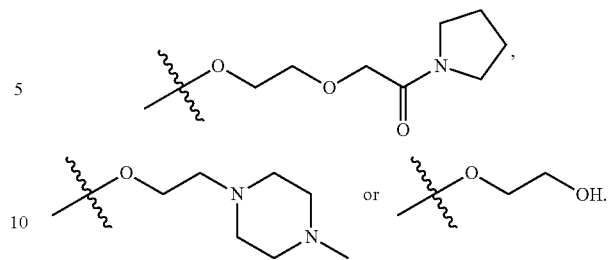

7. The isoindoline derivative having a structure of general formula (I), the pharmaceutically acceptable salt, the polymorph, the stereoisomer, the isotopic compound, or the metabolite thereof according to claim 1, wherein, in the definition of $R_{10}$, the

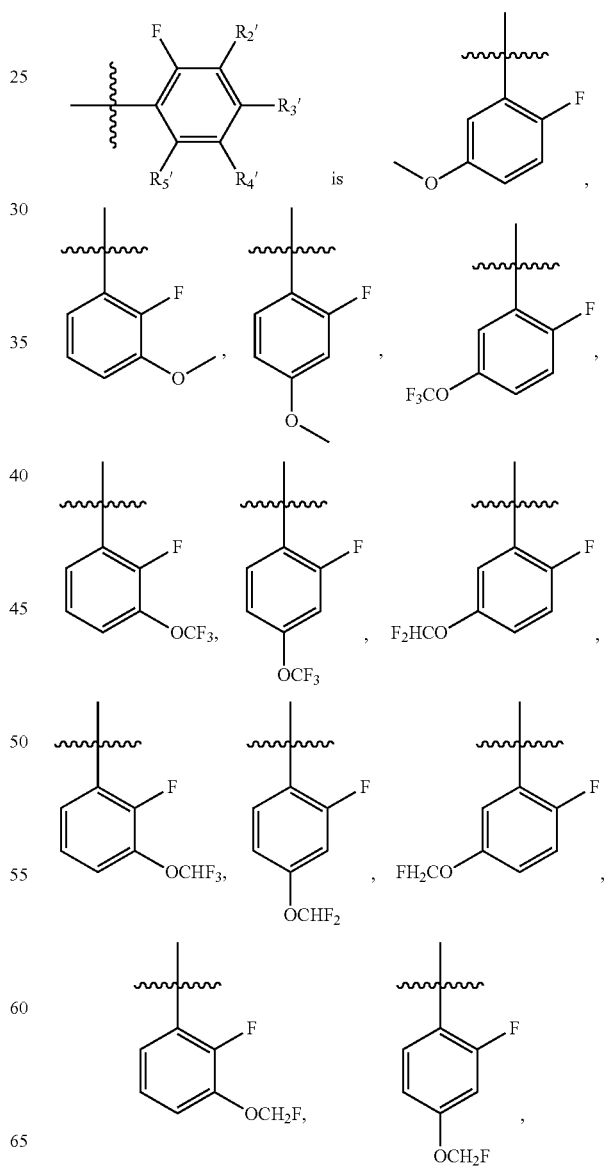

-continued
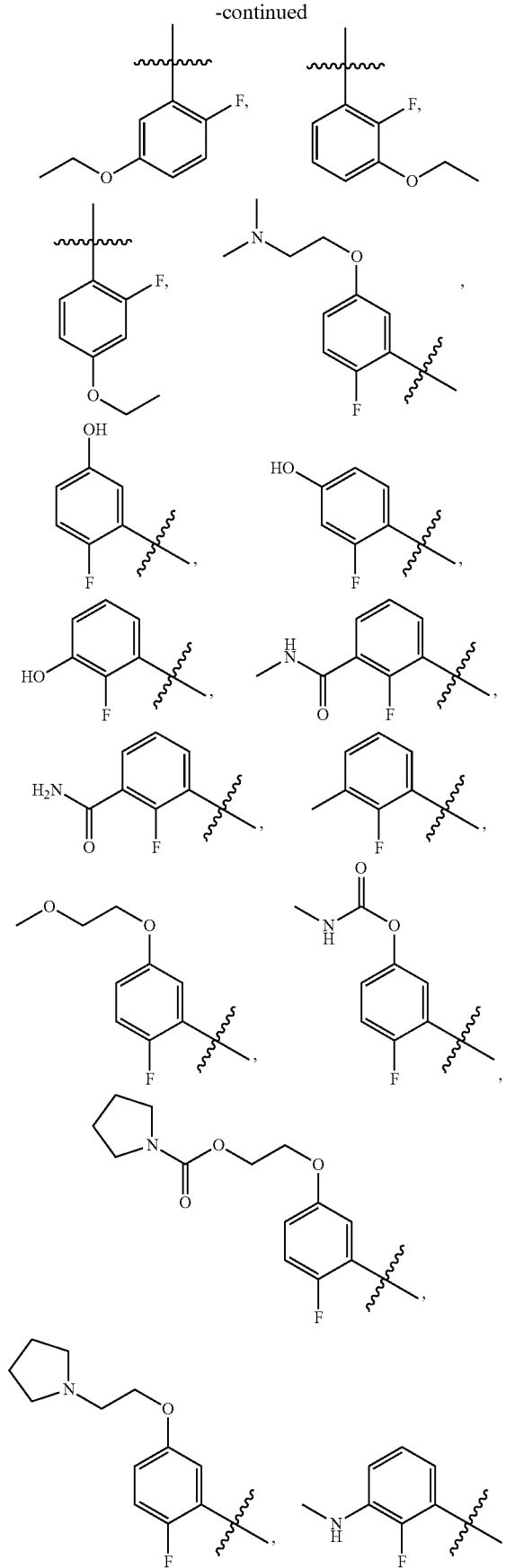
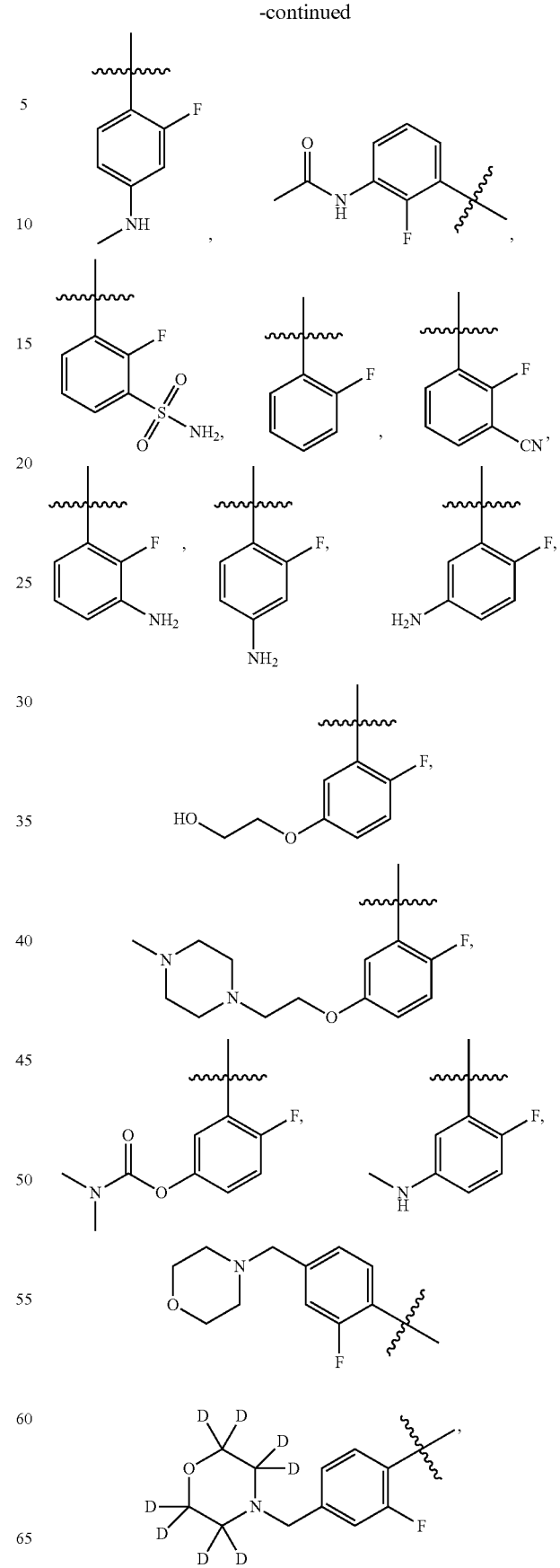

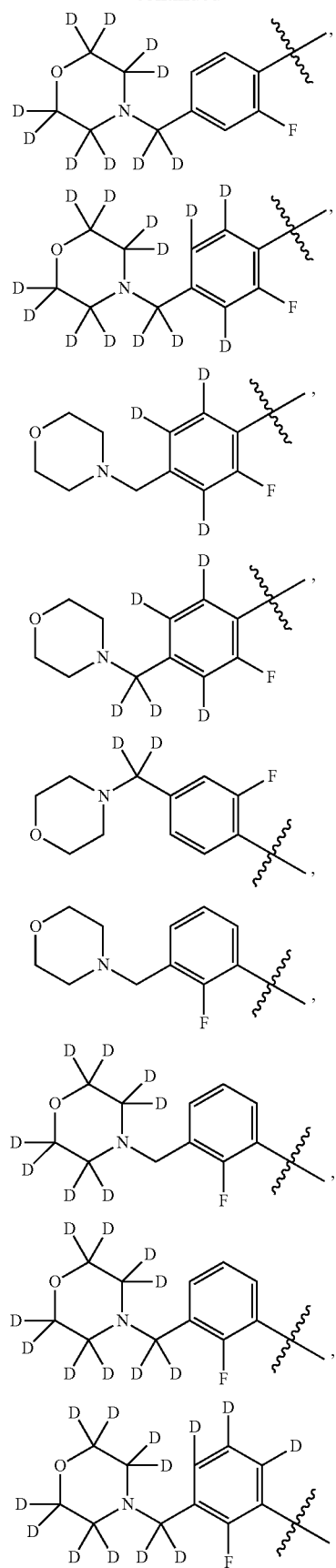
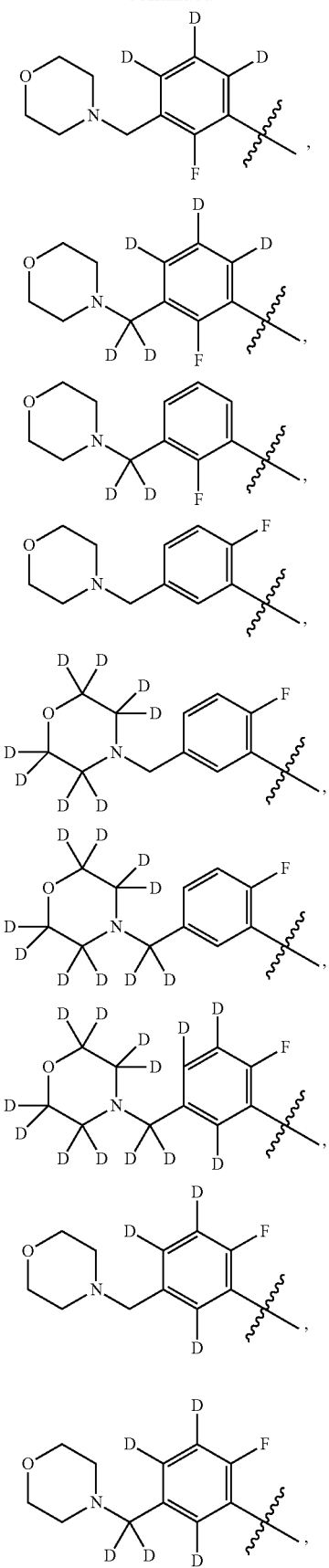

365
-continued
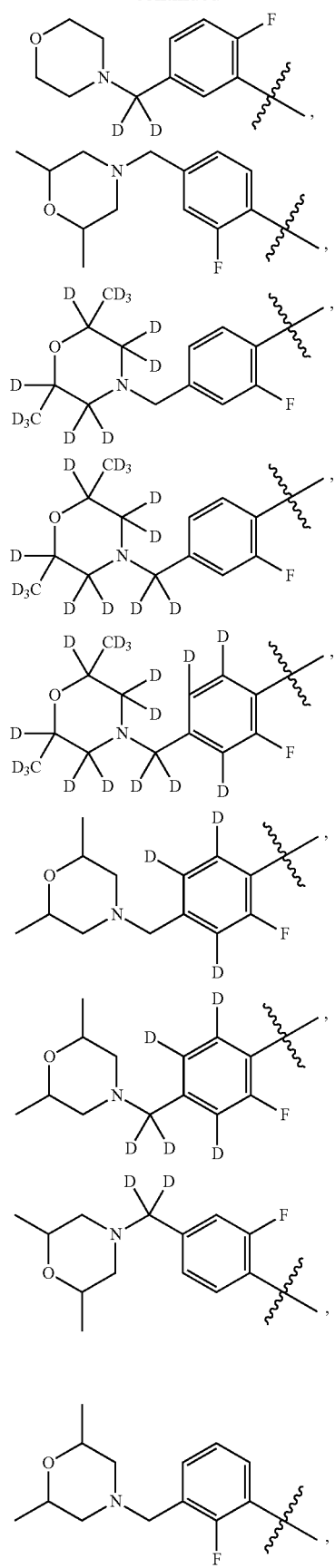
366
-continued
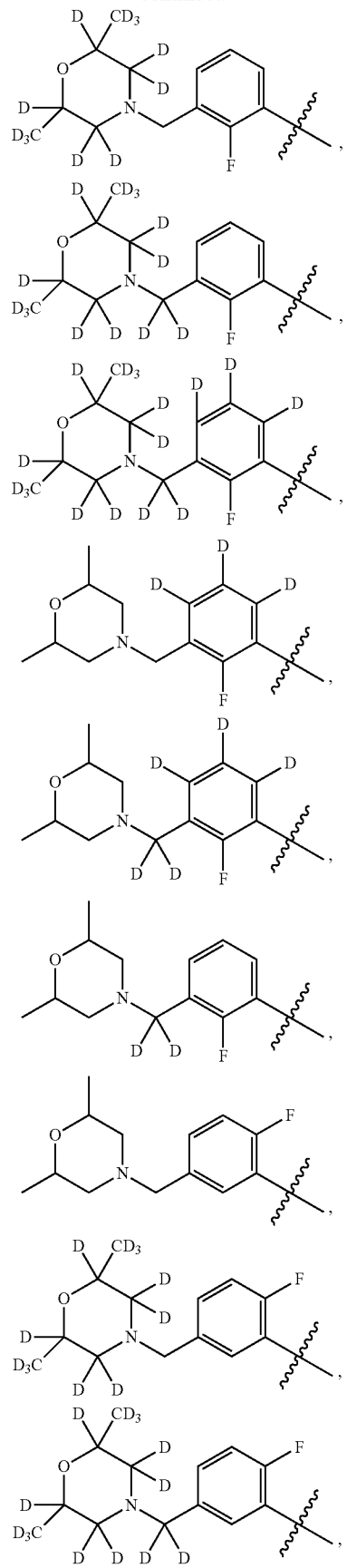

367
-continued
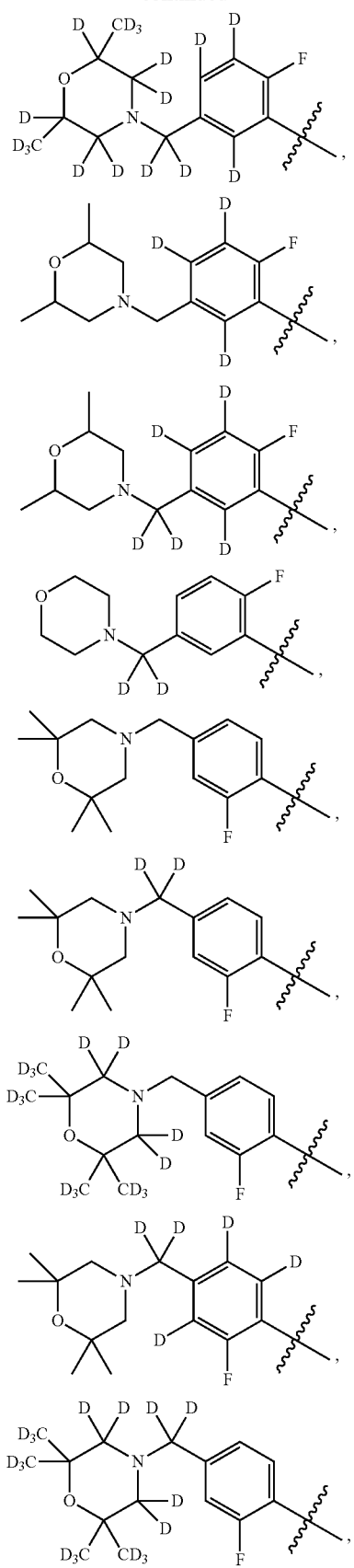
368
-continued
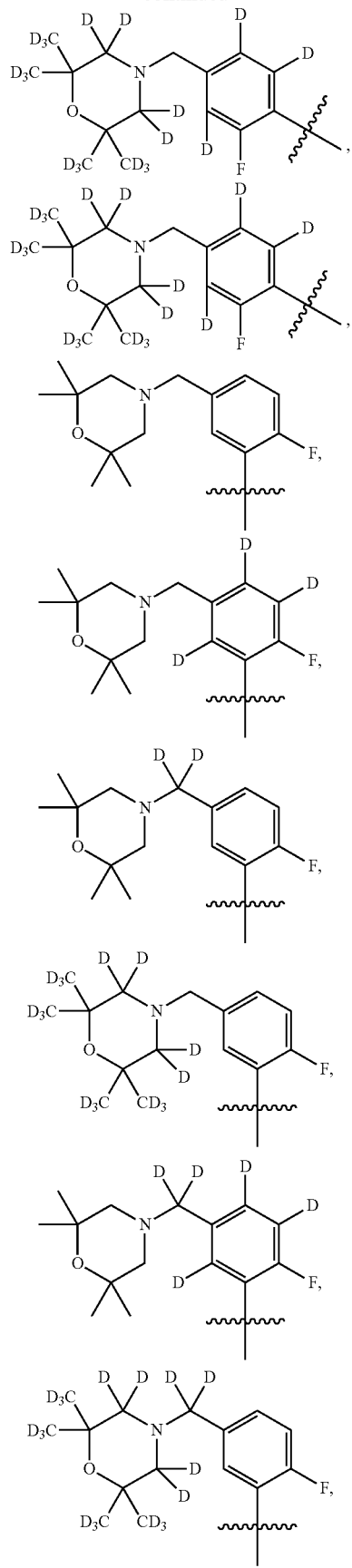

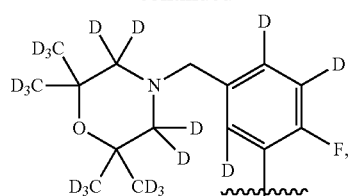
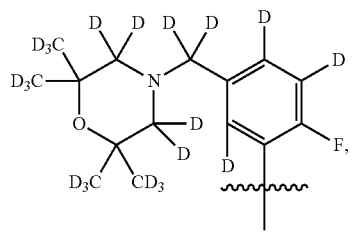
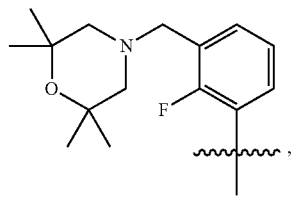
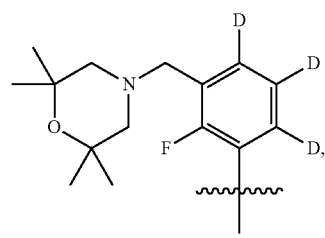
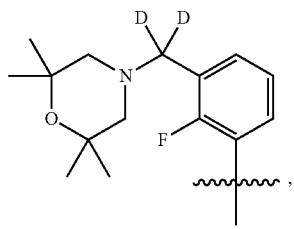
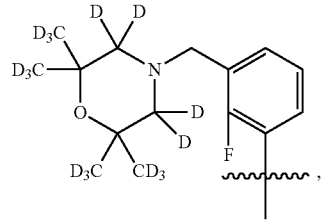
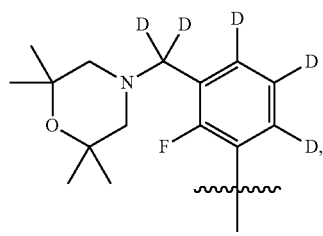
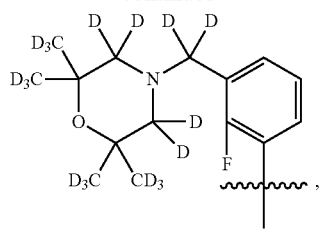
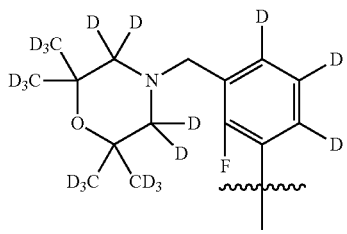
or
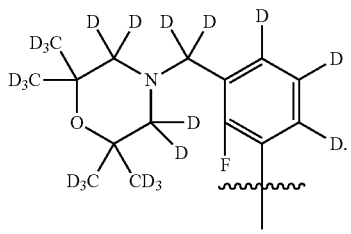
8. The isoindoline derivative having a structure of general formula (I), the pharmaceutically acceptable salt, the polymorph, the stereoisomer, the isotopic compound, or the metabolite thereof according to claim 1, wherein the compound having a structure of general formula (I) is selected from the group consisting of
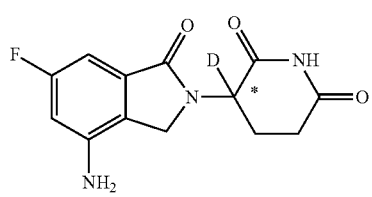
I-01
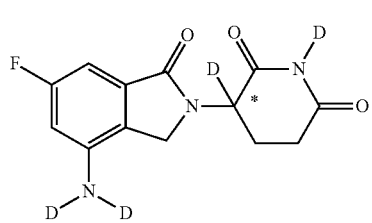
I-02
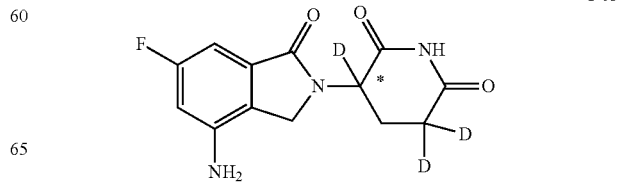
I-03

I-04
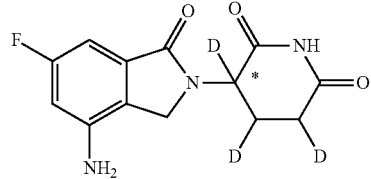
I-05
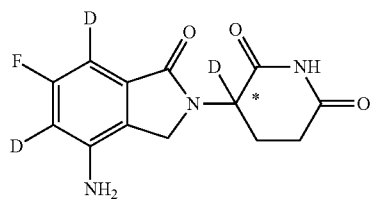
I-06
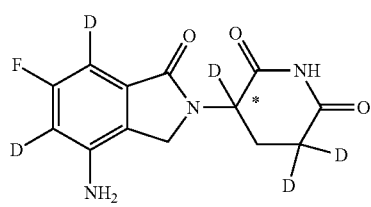
I-07
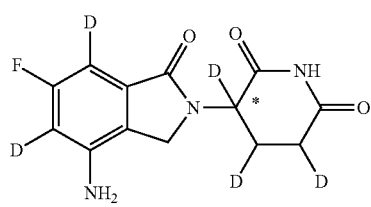
I-08
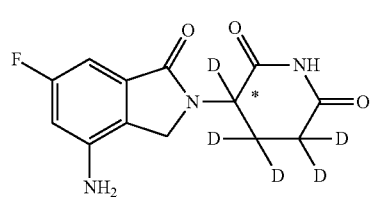
I-09
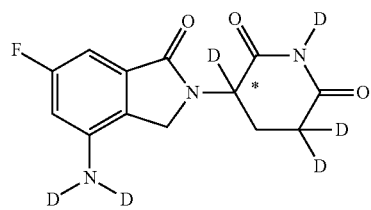
I-10
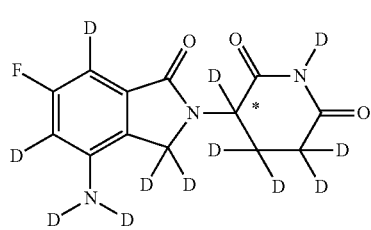
I-11
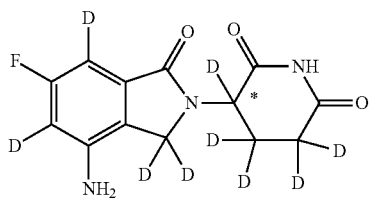
I-12
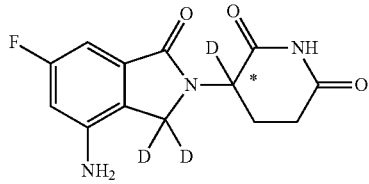
I-13
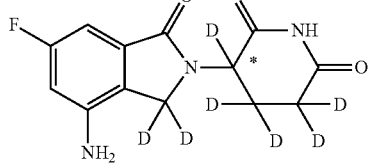
I-14
I-15
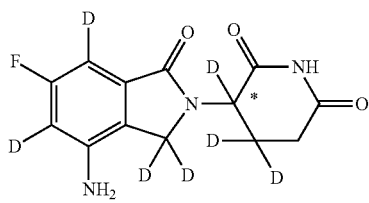
I-16
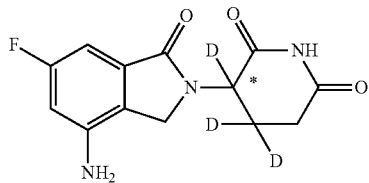
I-17
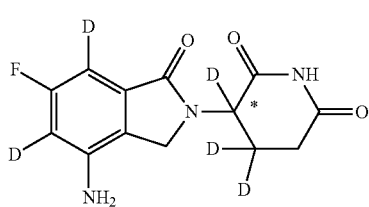
I-18

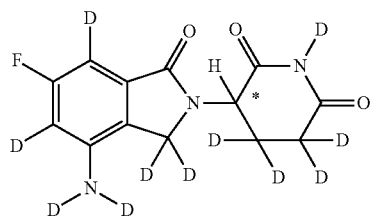 I-19
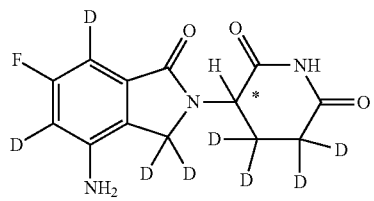 I-20
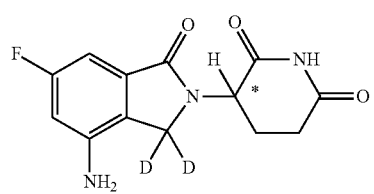 I-21
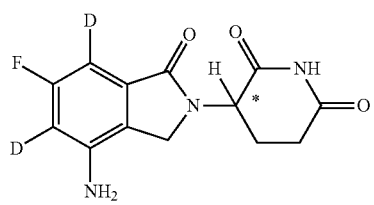 I-22
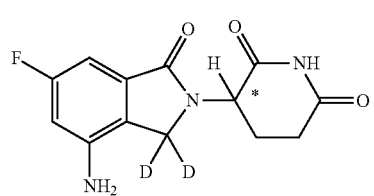 I-23
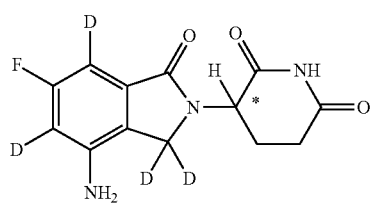 I-24
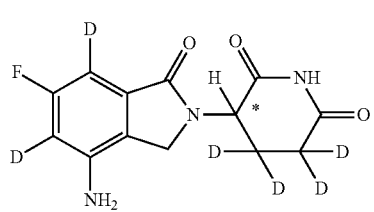 I-25
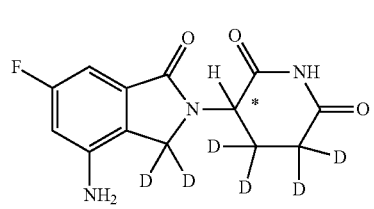 I-26
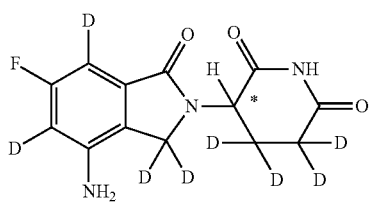 I-27
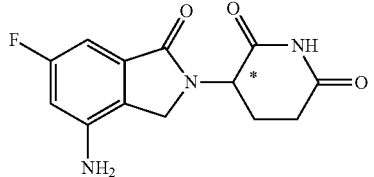 I-28
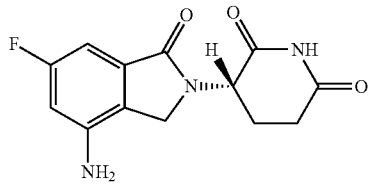 I-29
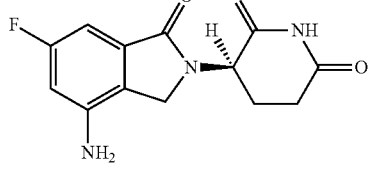 I-30
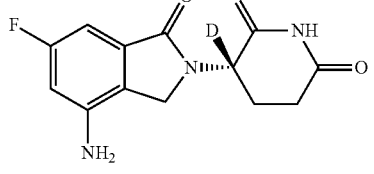 I-31
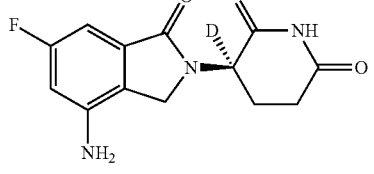 I-32
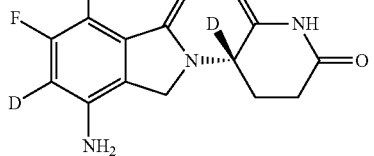 I-33
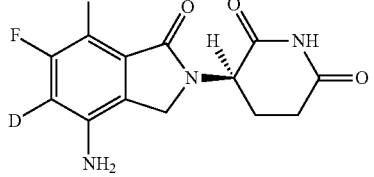 I-34

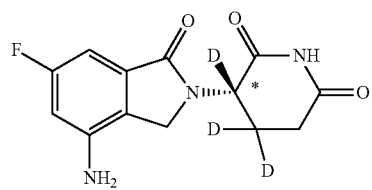
I-35
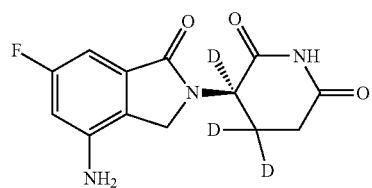
I-36
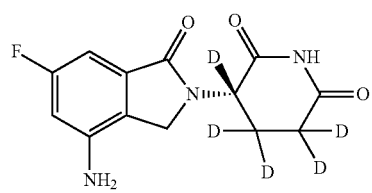
I-37
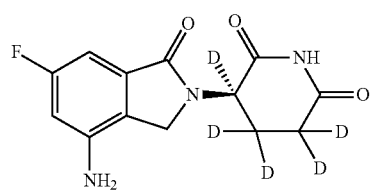
I-38
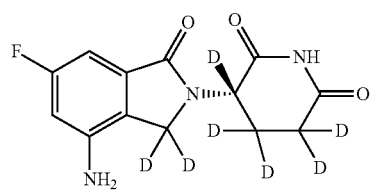
I-39
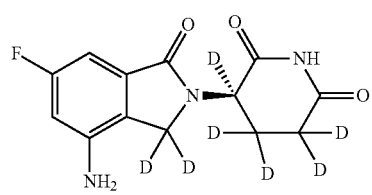
I-40
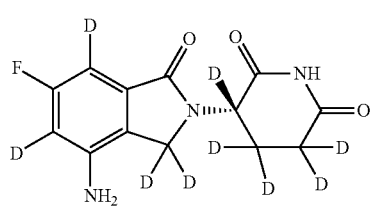
I-41
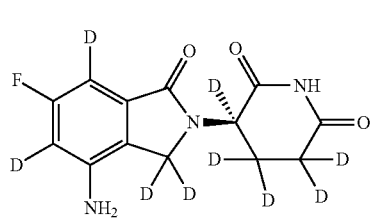
I-42
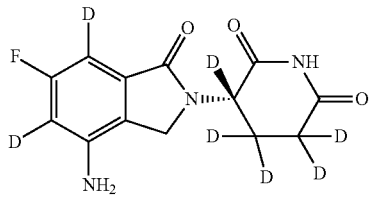
I-43
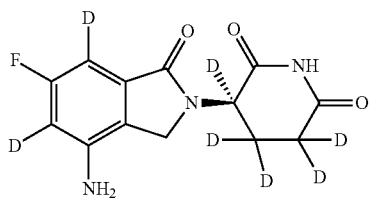
I-44
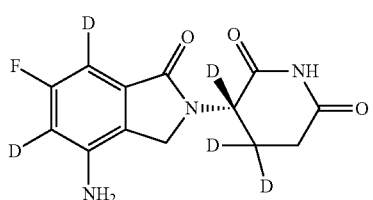
I-45
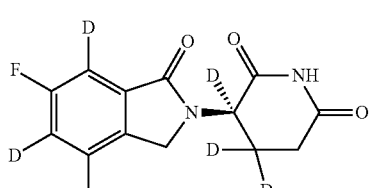
I-46
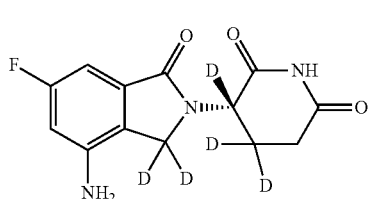
I-47
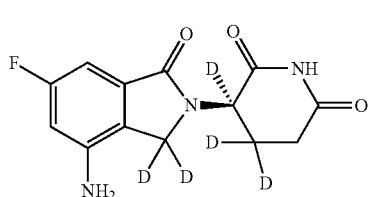
I-48
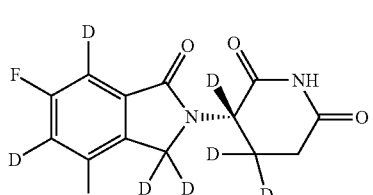
I-49
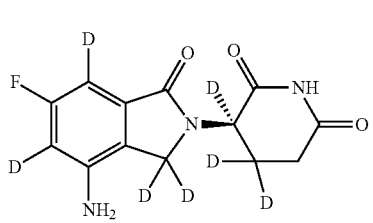
I-50

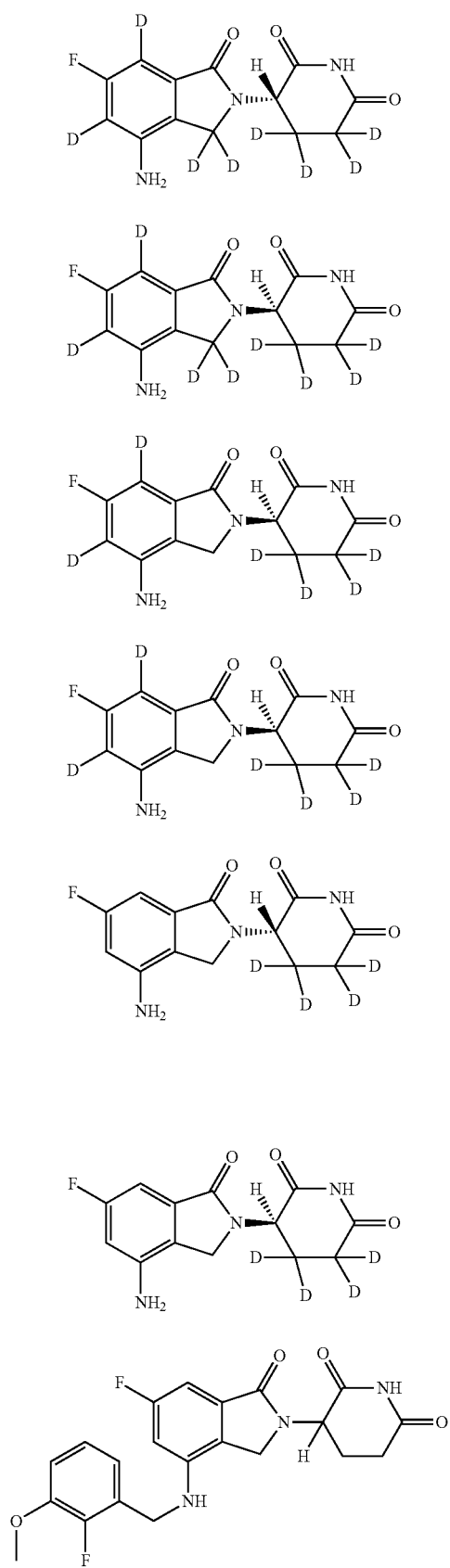
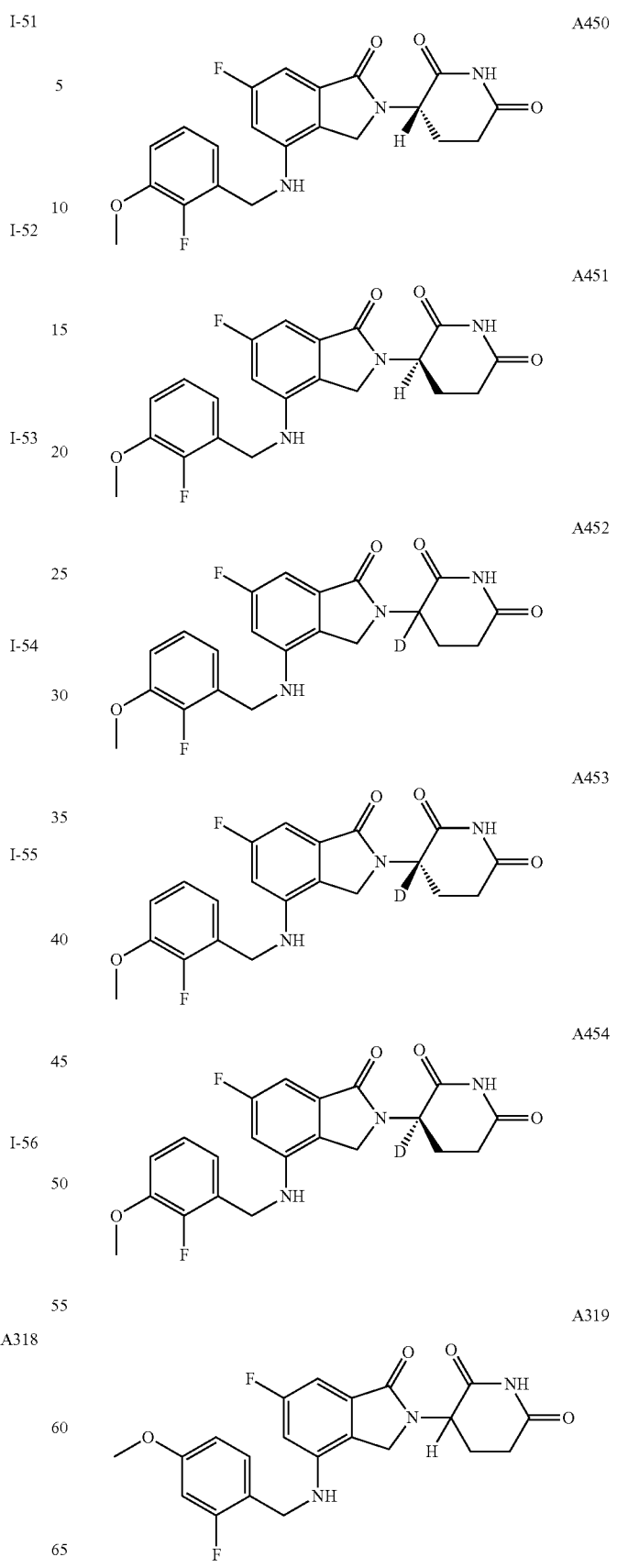

A455
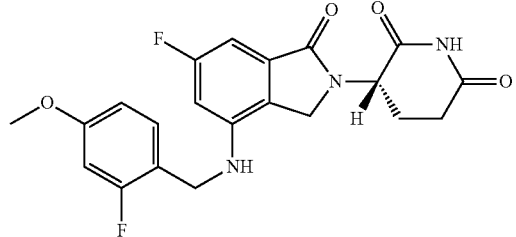
A456
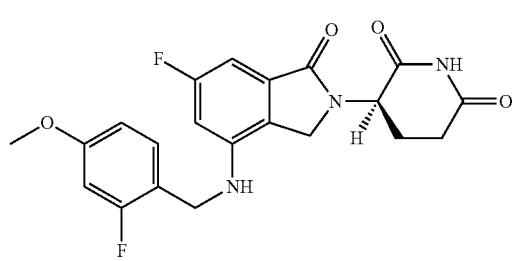
A457
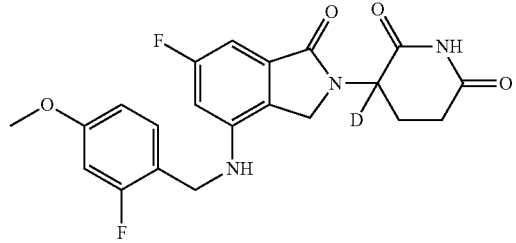
A458
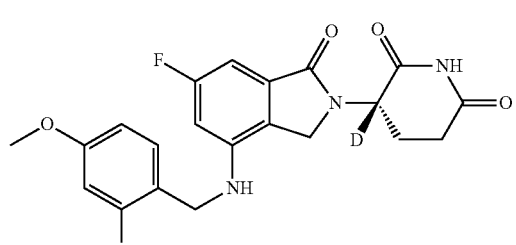
A459
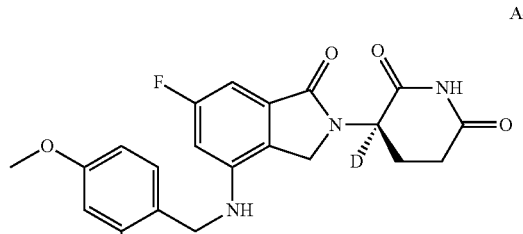
A320
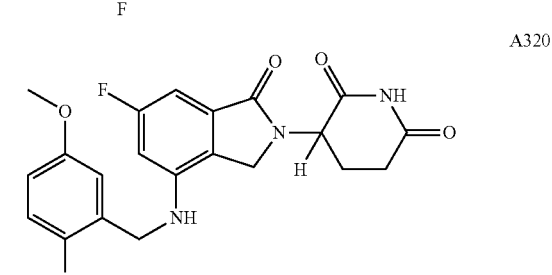
A460
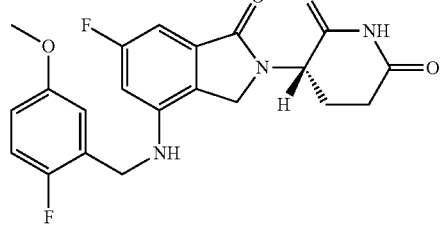
A461
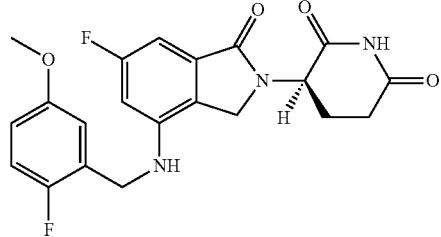
A462
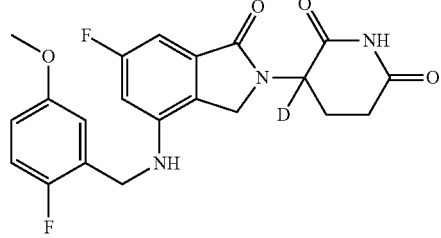
A463
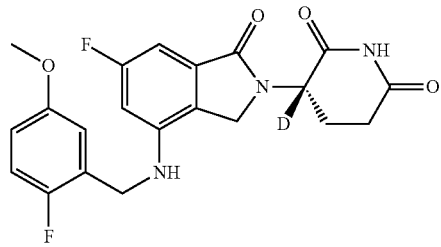
A464
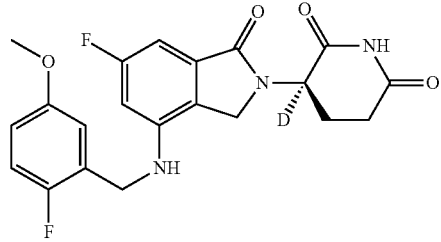
A196
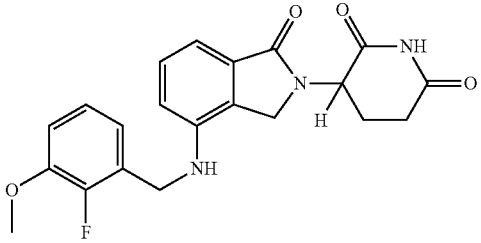

A465
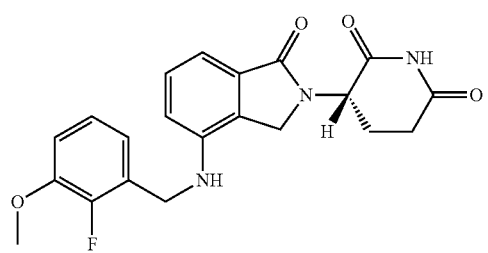
A466
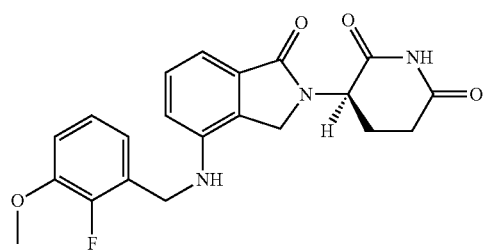
A467
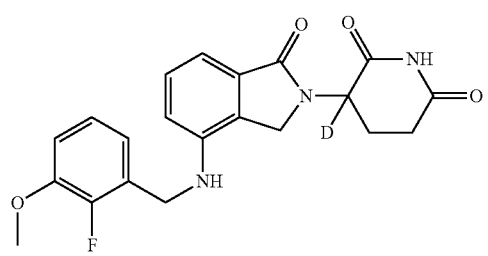
A357
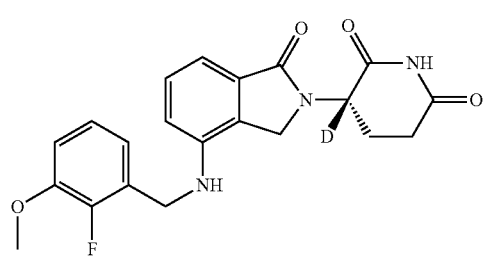
A468
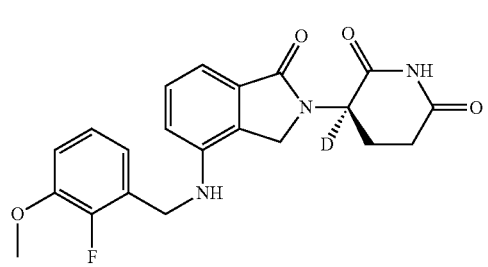
A197
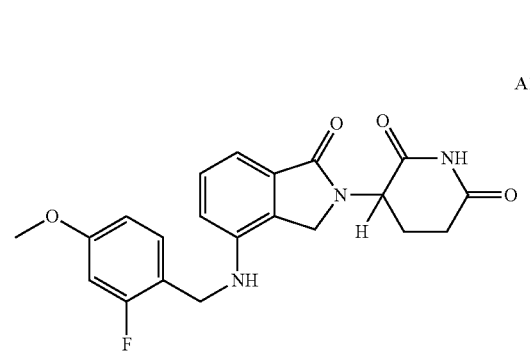
A469
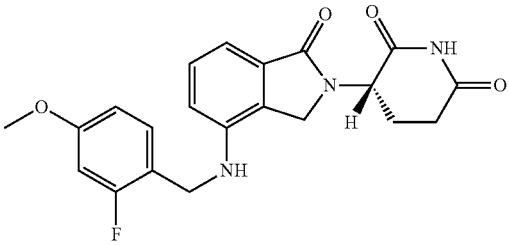
A470
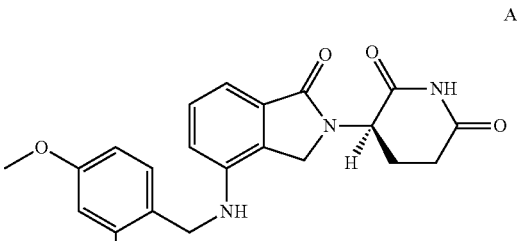
A340
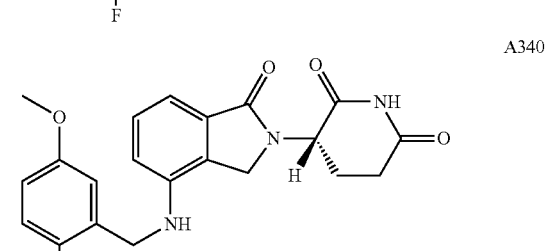
A356
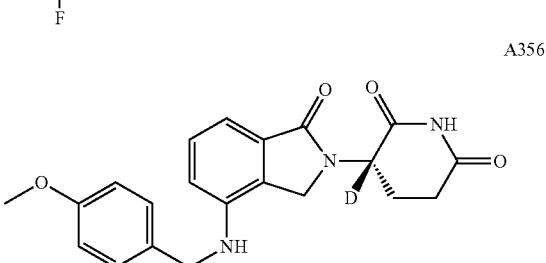
A471
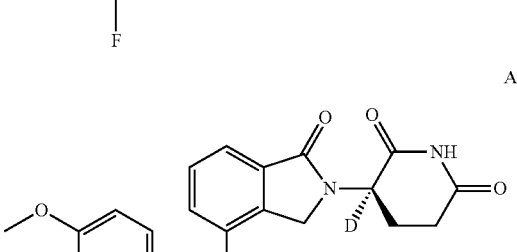
A195
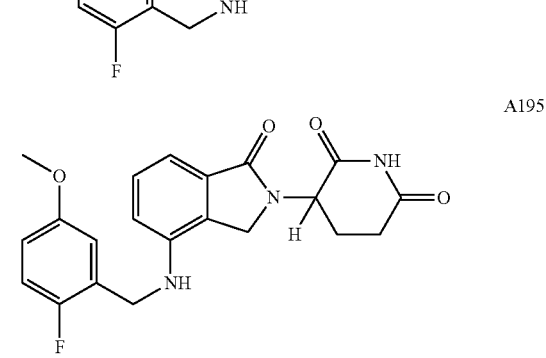

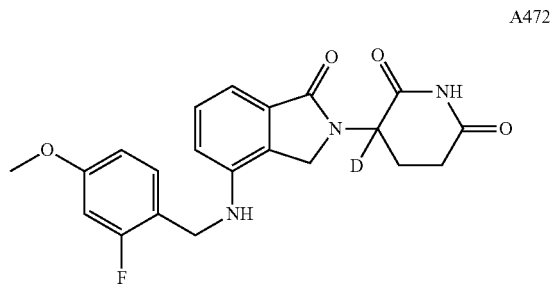
A472
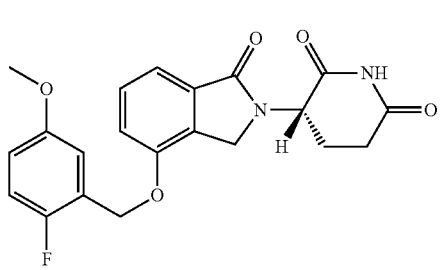
A484
A341
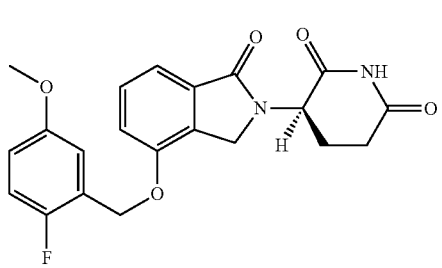
A485
A473
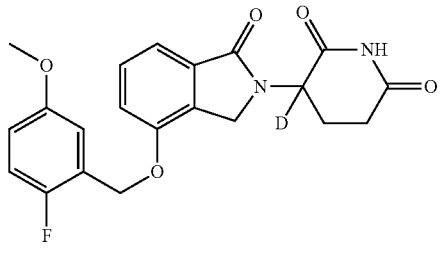
A486
A343
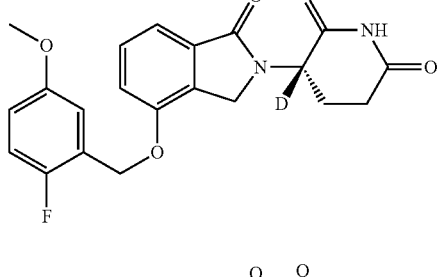
A379
A342
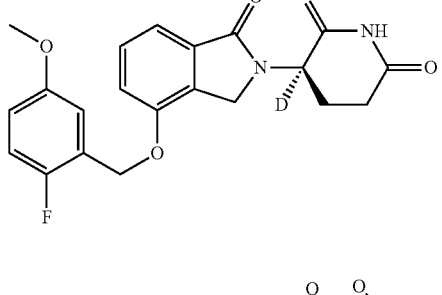
A487
A331
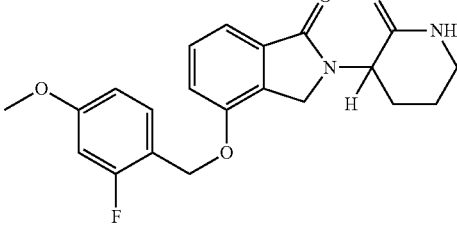
A329

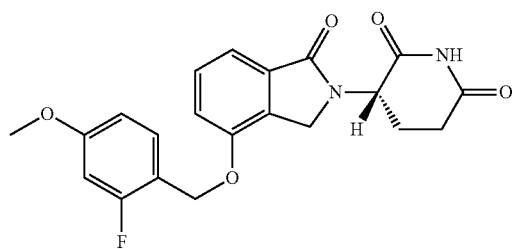
A488
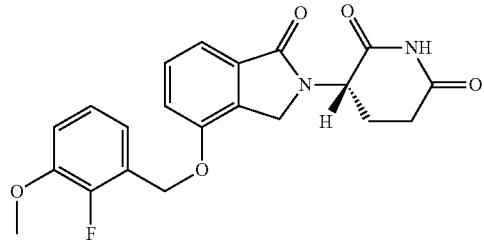
A491
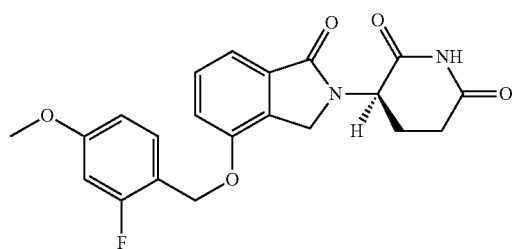
A489
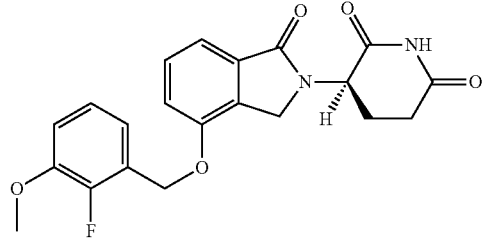
A492
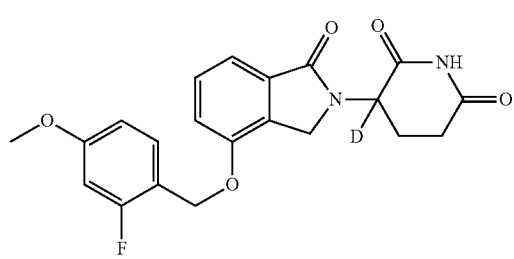
A490
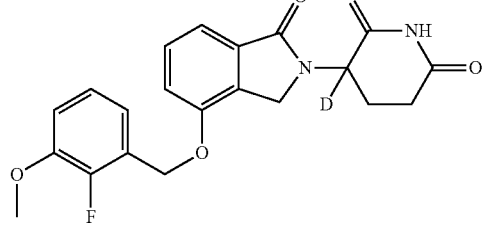
A493
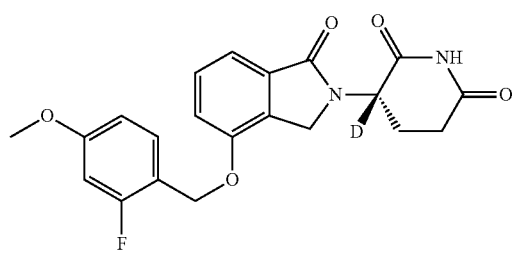
A393
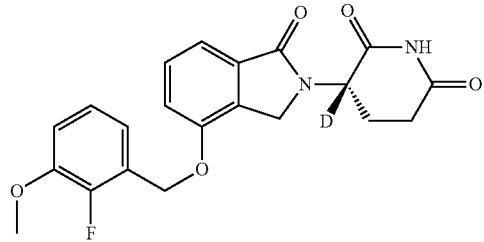
A380
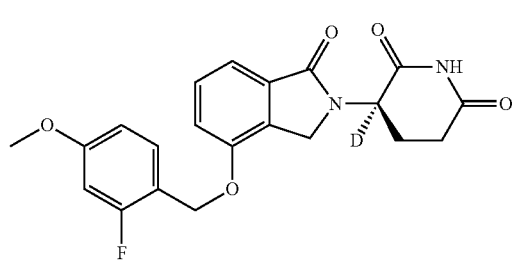
A392
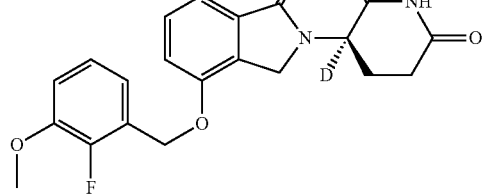
A494
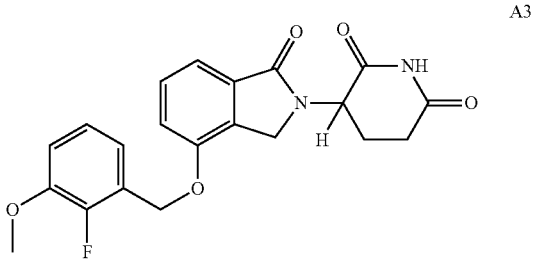
A334
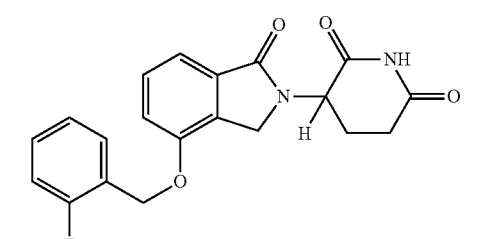
A336

A579
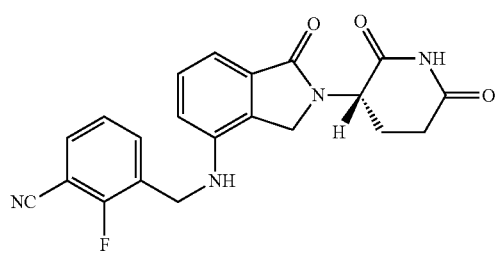
A580
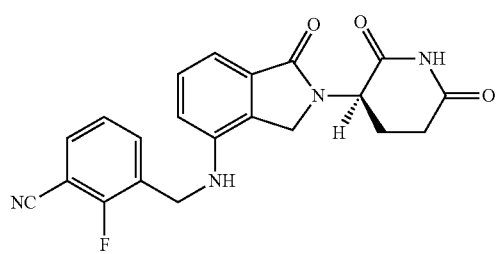
A581
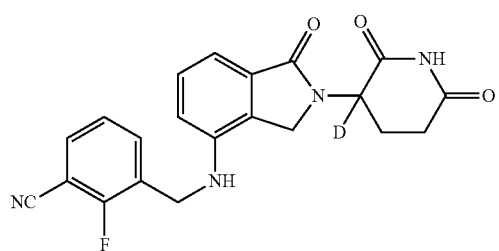
A582
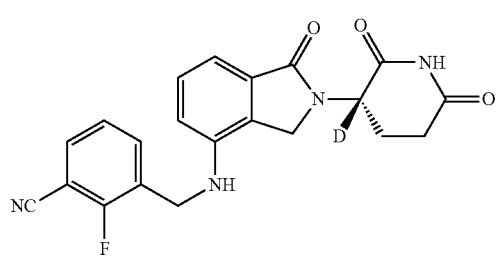
A583
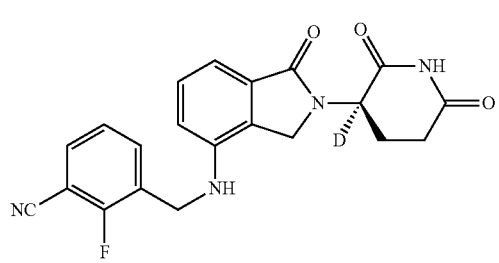
A367
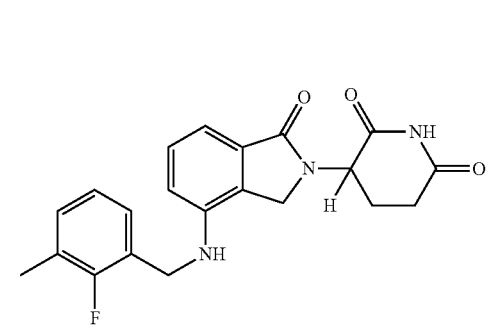
A584
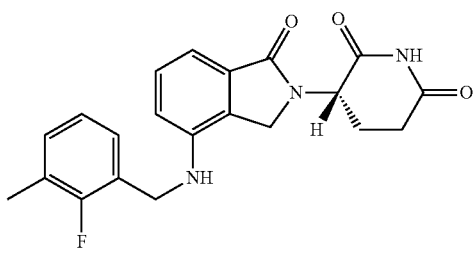
A585
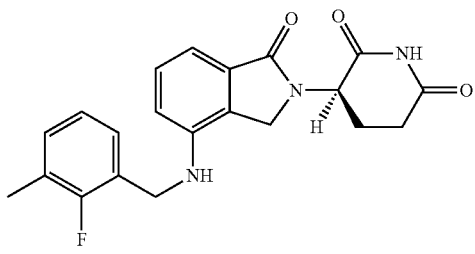
A586
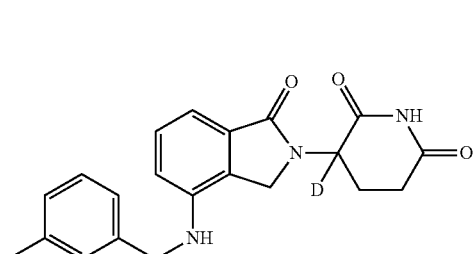
A587
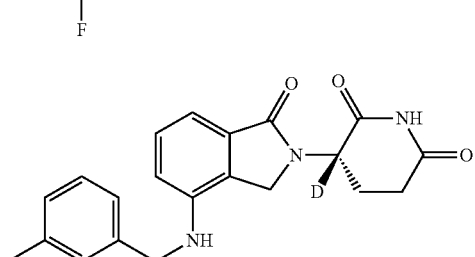
A588
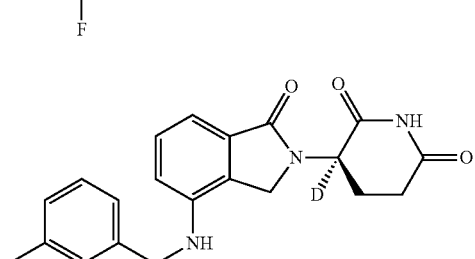
A361
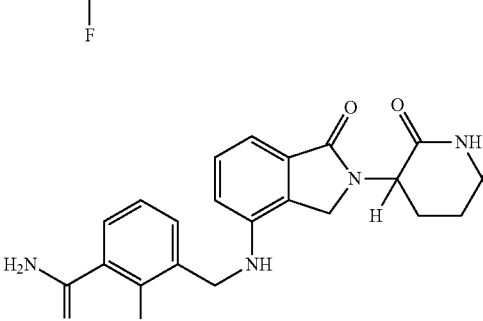

A589
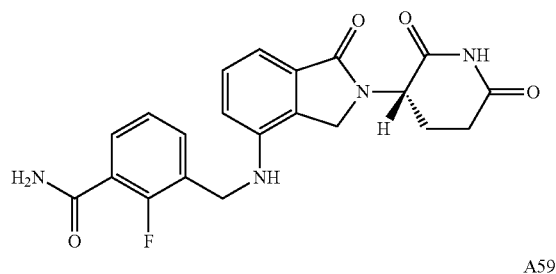
A590
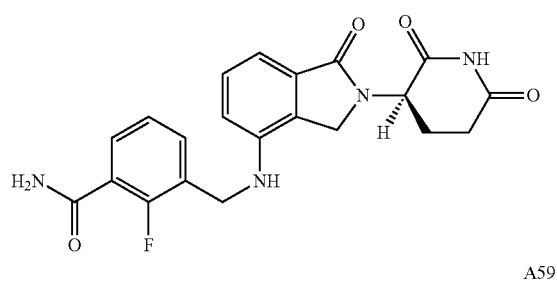
A591
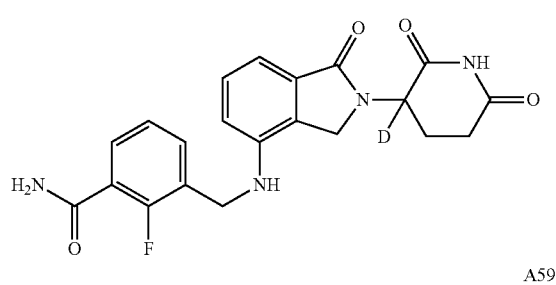
A592
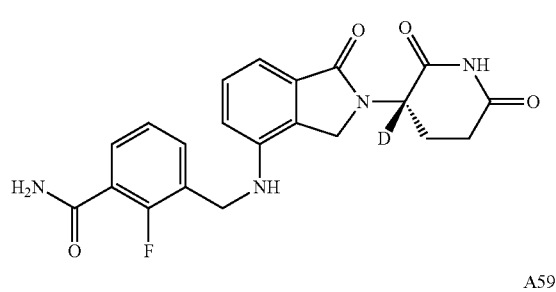
A593
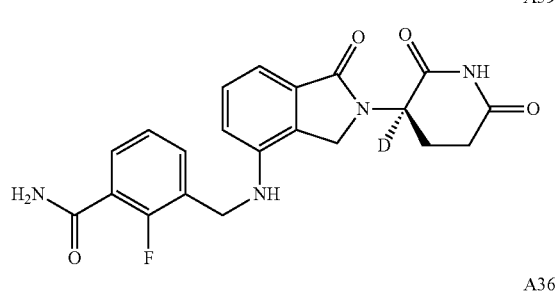
A362
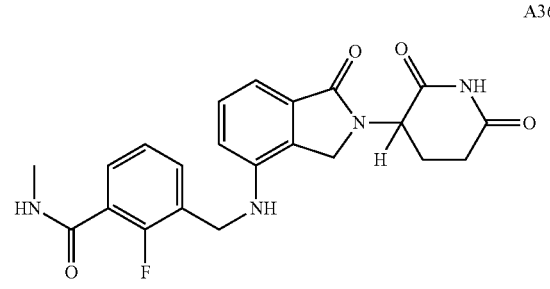
A594
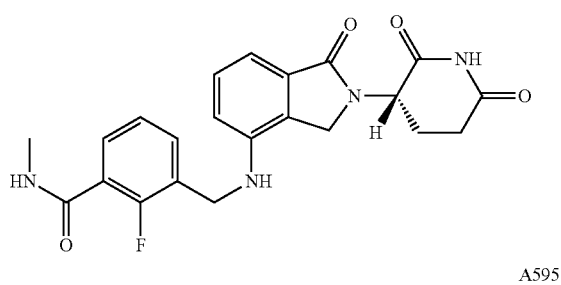
A595
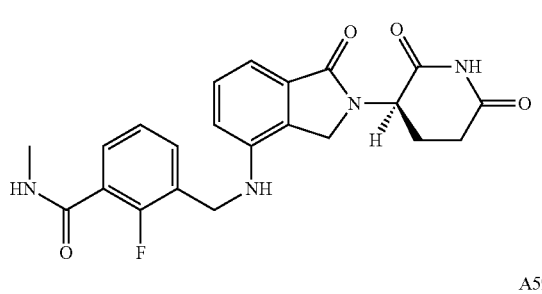
A596
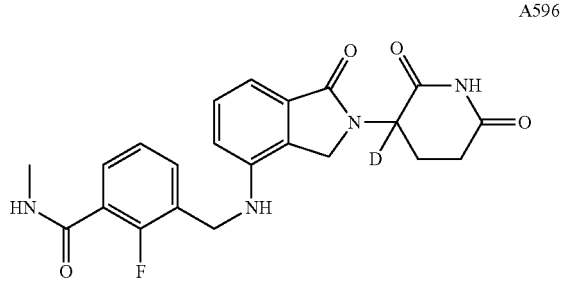
A597
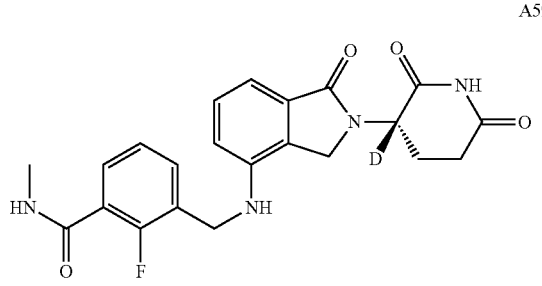
A598
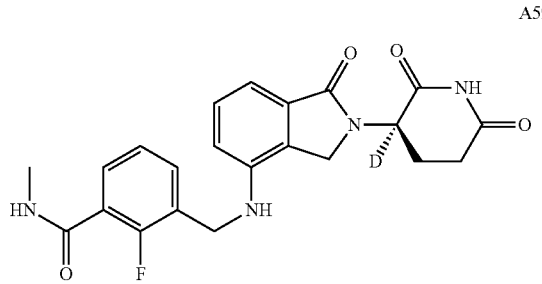
A364

A599
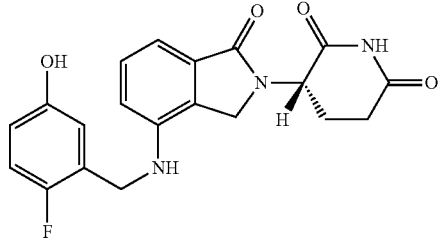
A600
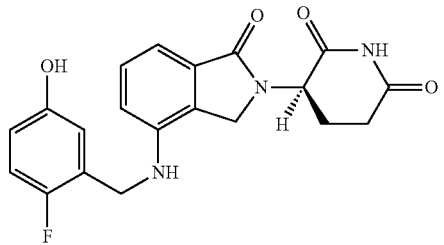
A601
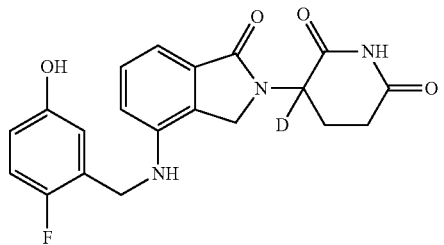
A602
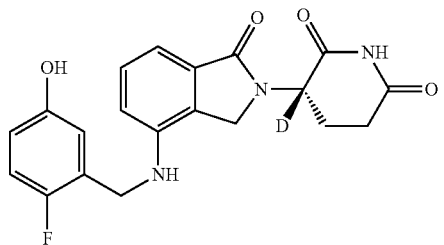
A603
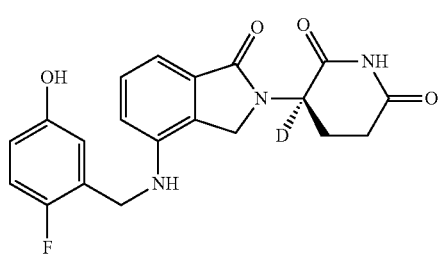
A615
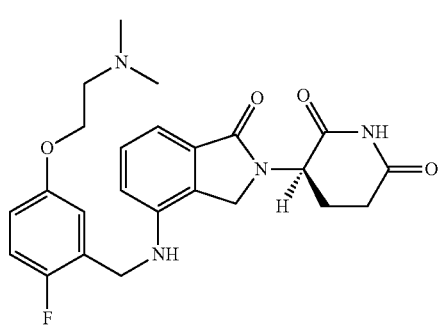
A616
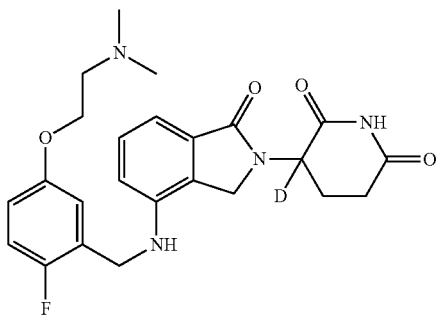
A617
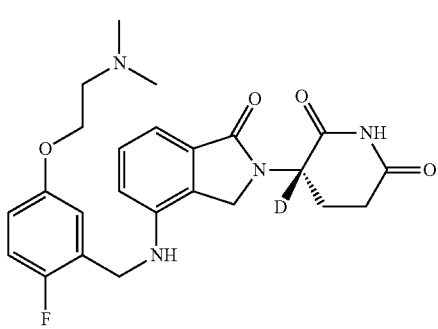
A618
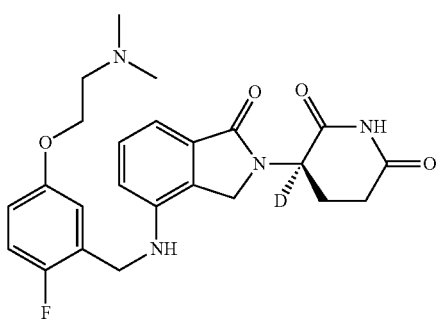
A370
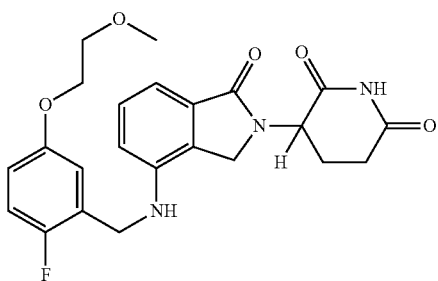
A619
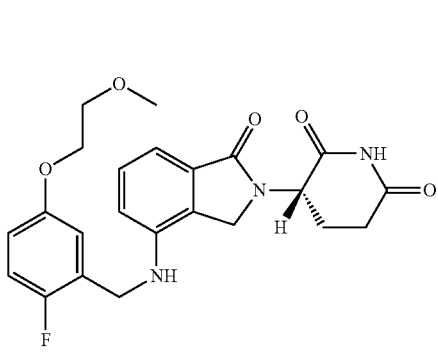

A620
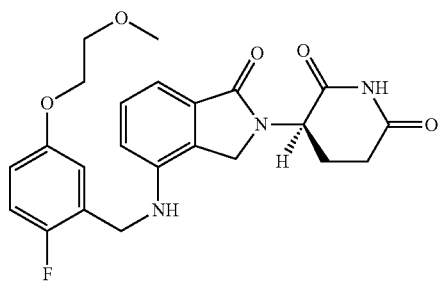
A621
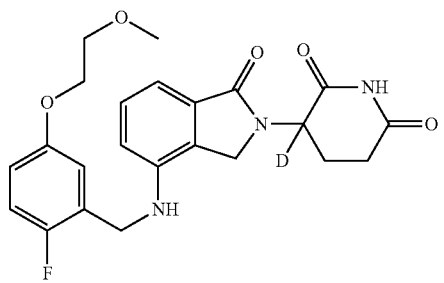
A622
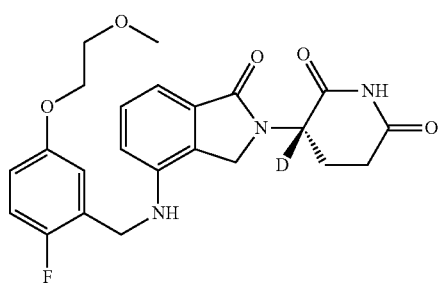
A623
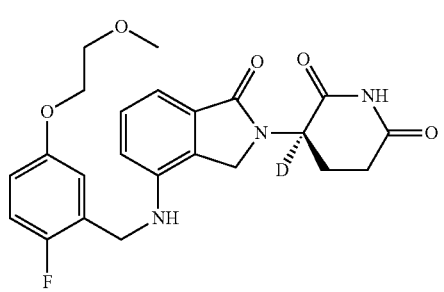
A376
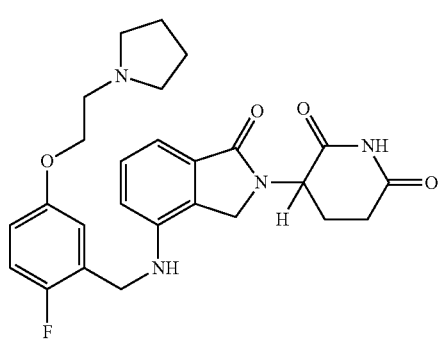
A624
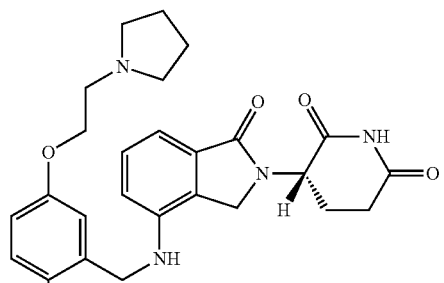
A625
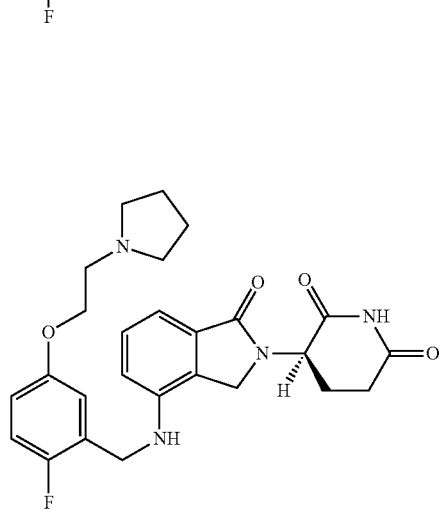
A626
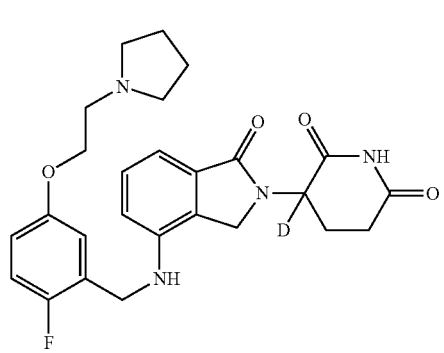
A627
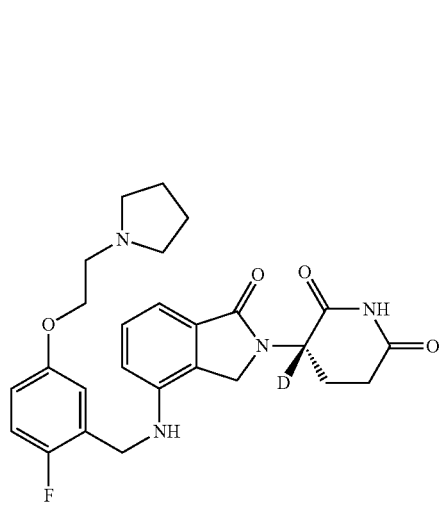

397
-continued
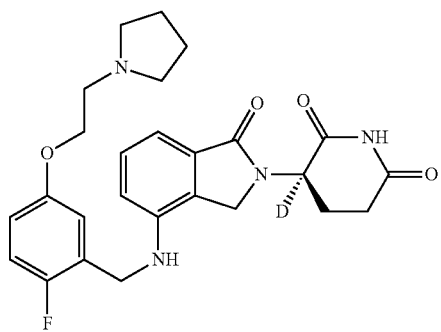
A628
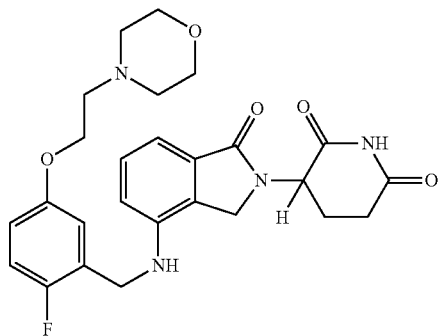
A368
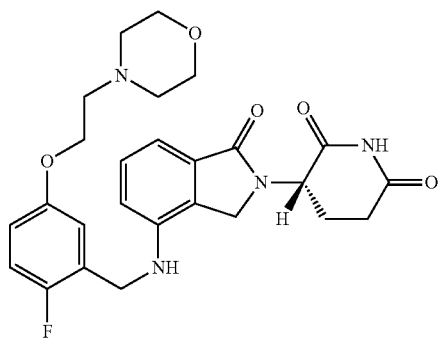
A629
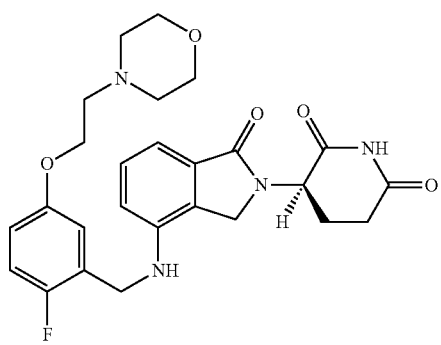
A630
398
-continued
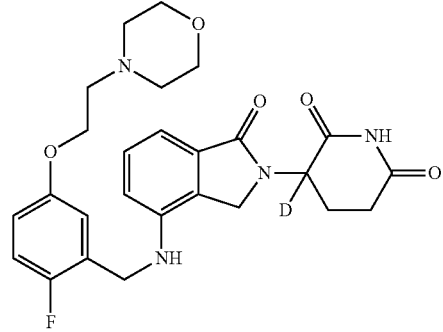
A631
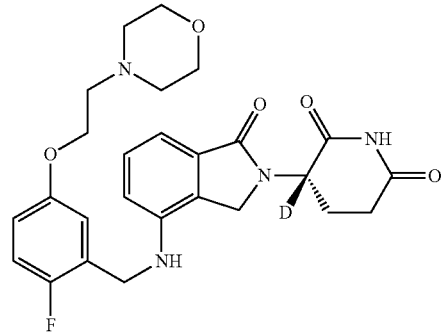
A632
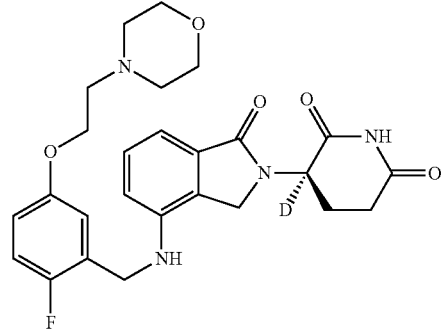
A633
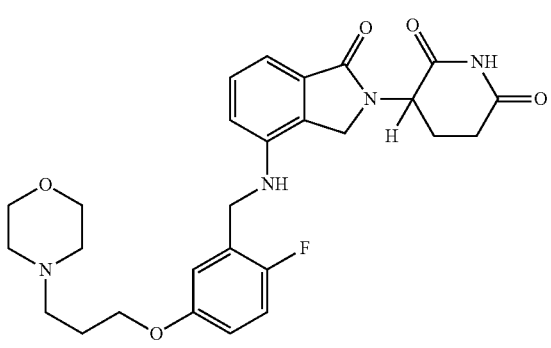
A369

A634
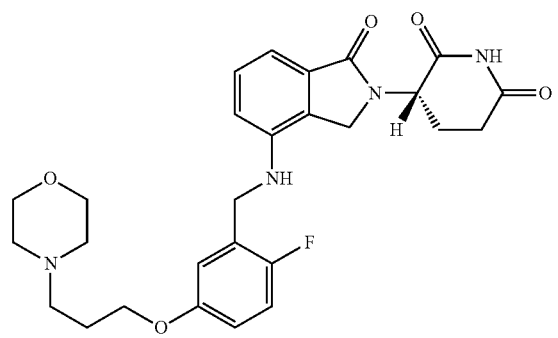
A635
A636
A637
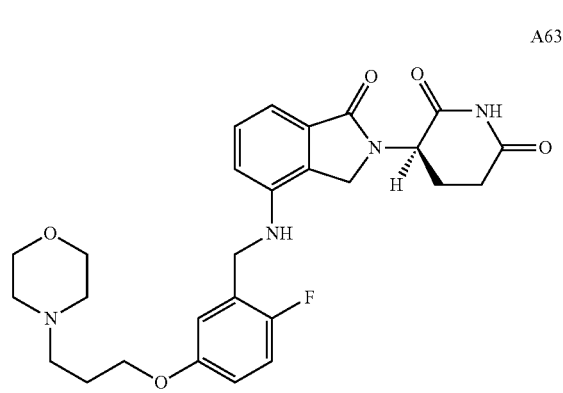
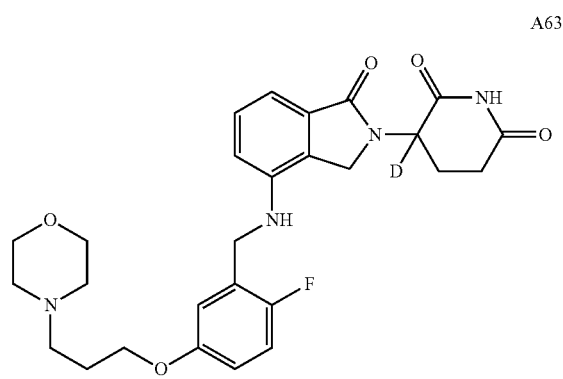
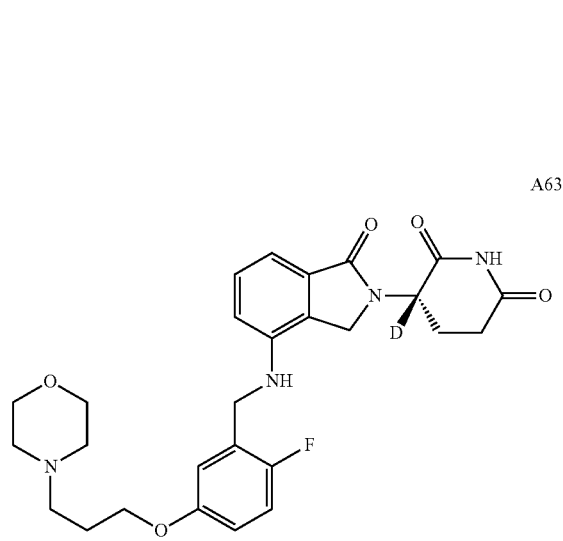
A638
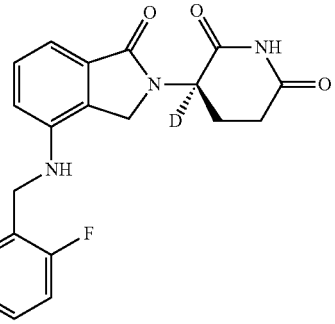
A372
A639
A640
A641
A642
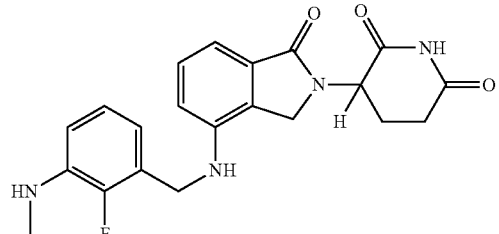
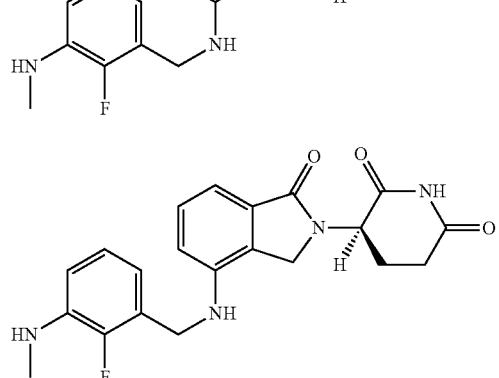
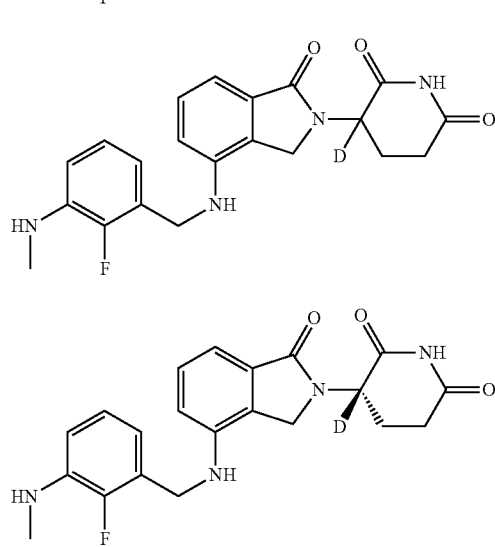

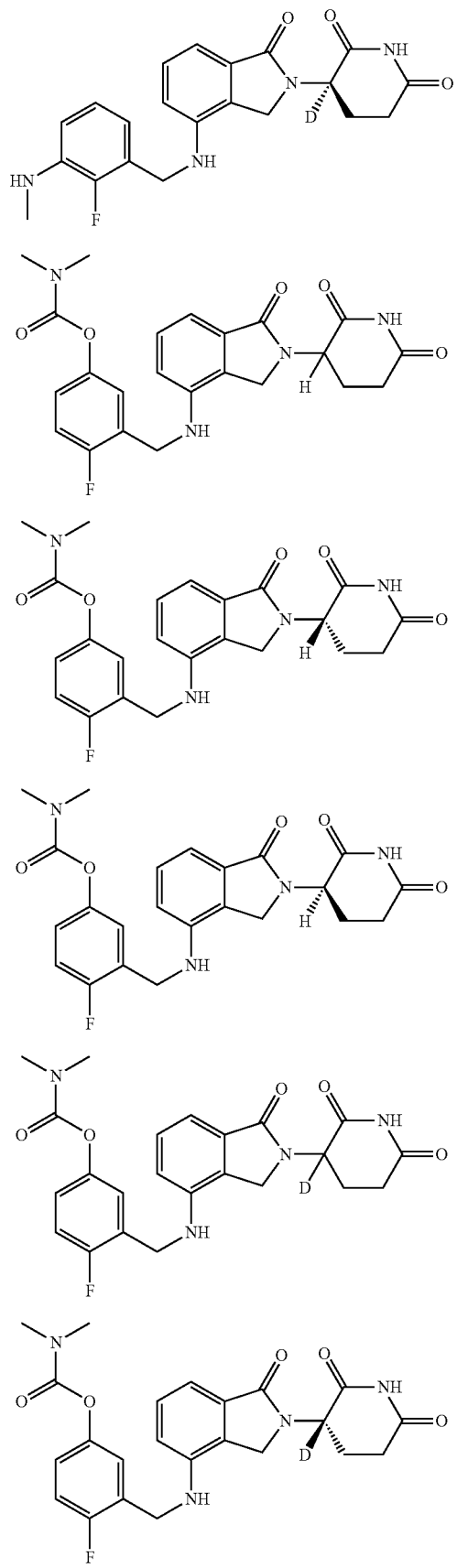
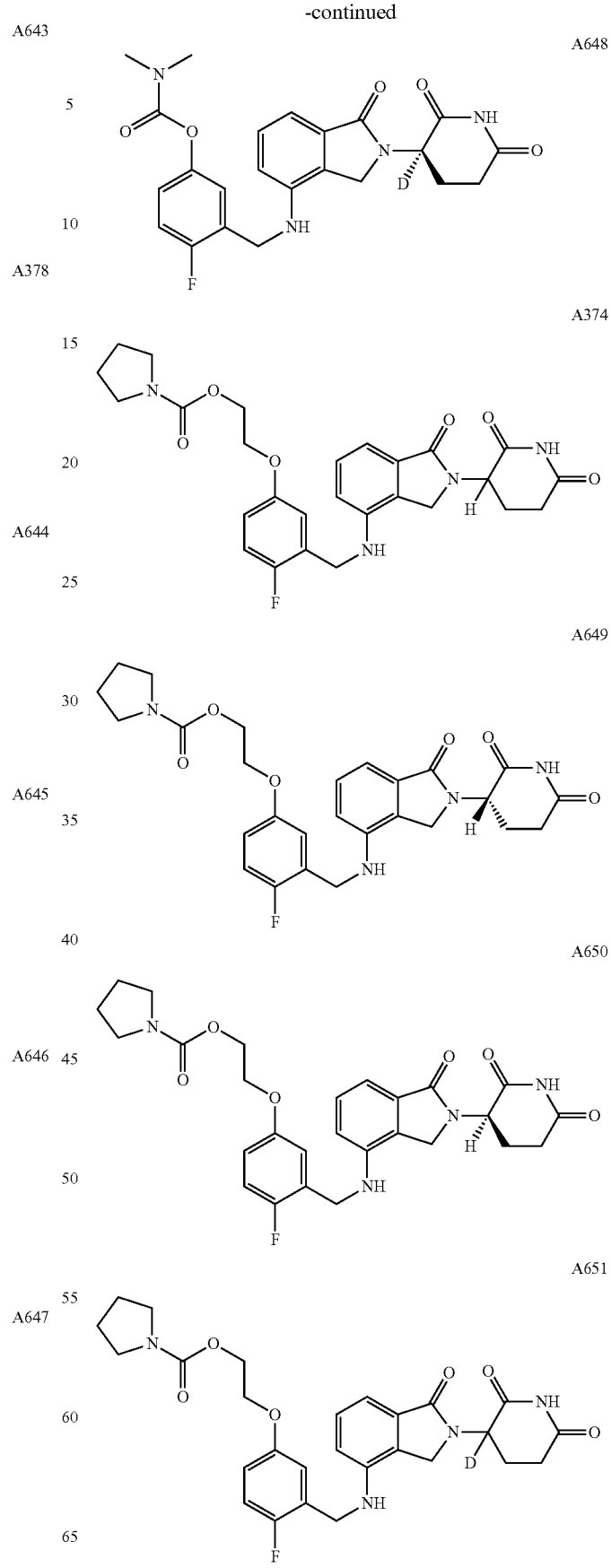

A652
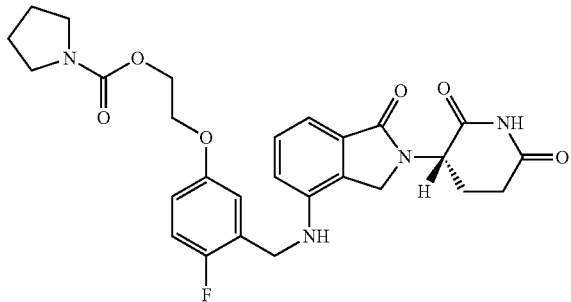
A653
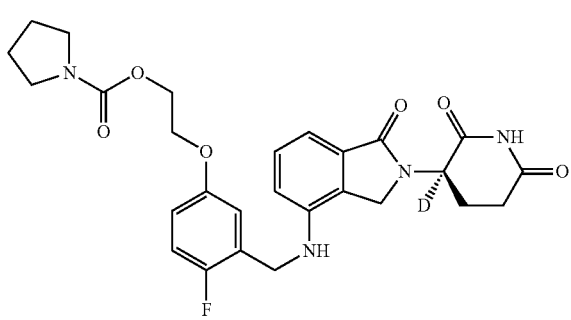
A375
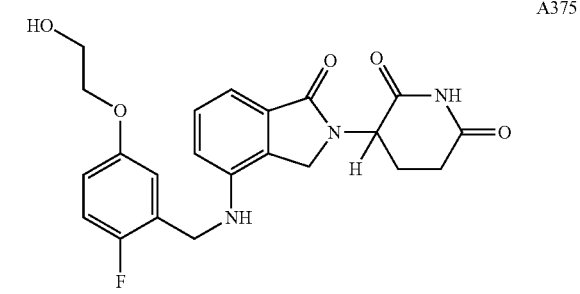
A654
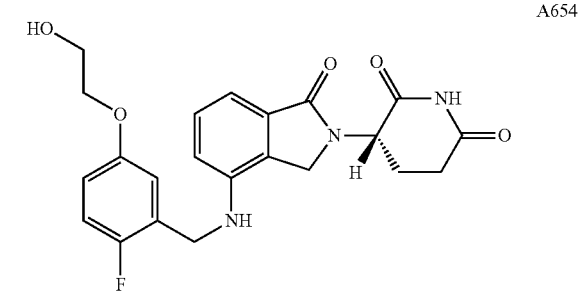
A655
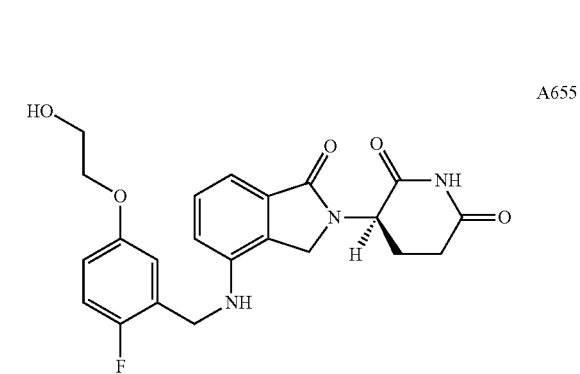
A656
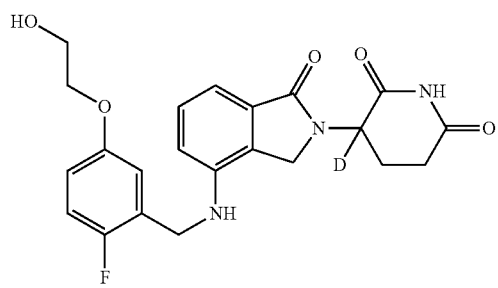
A390
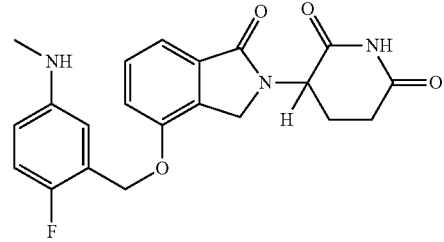
A657
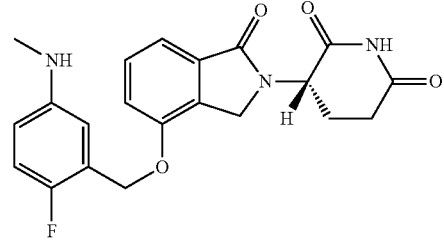
A658
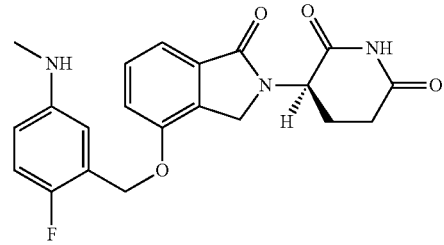
A659
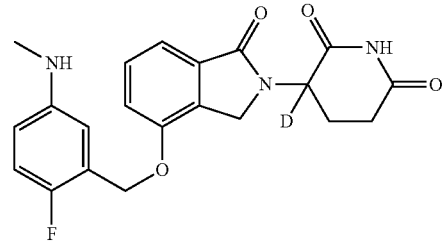
A660
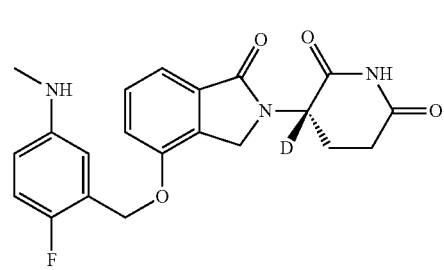

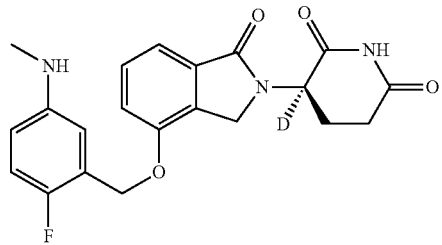
A661
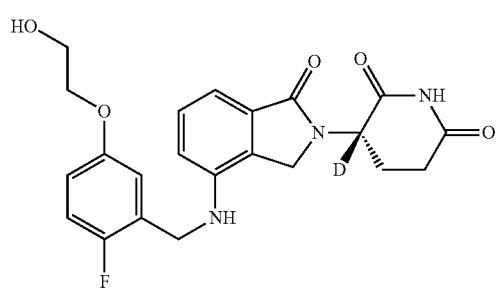
A662
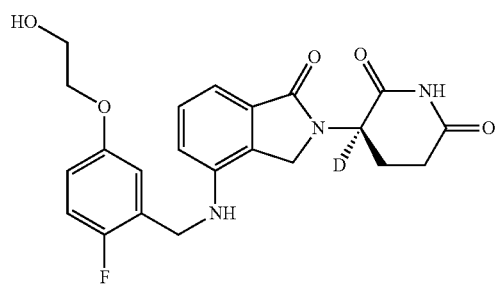
A663
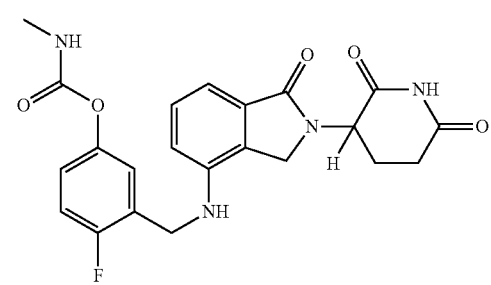
A371
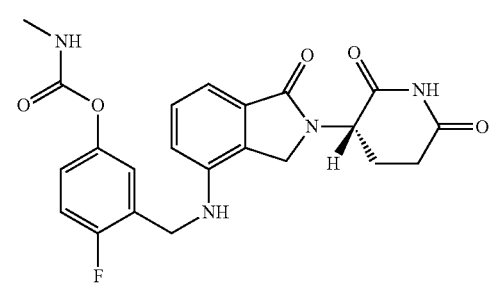
A664
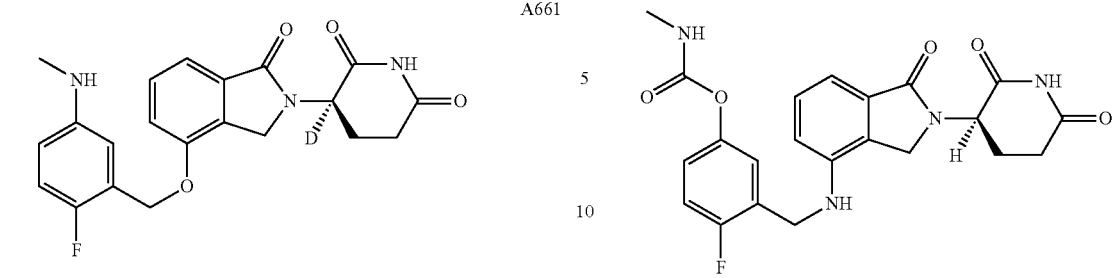
A665
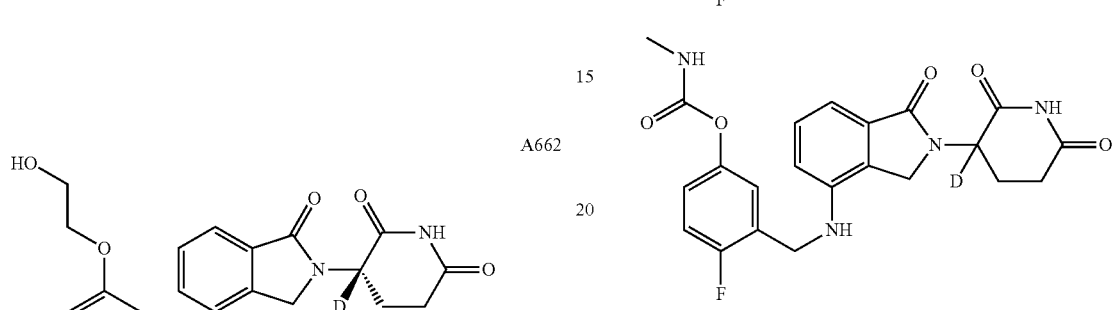
A666
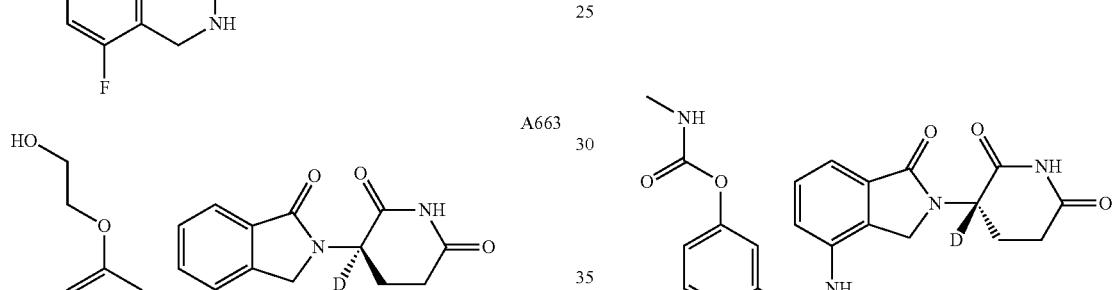
A667
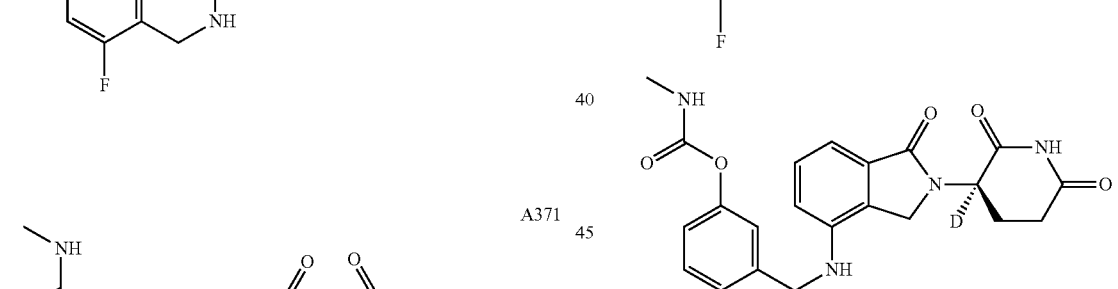
A668
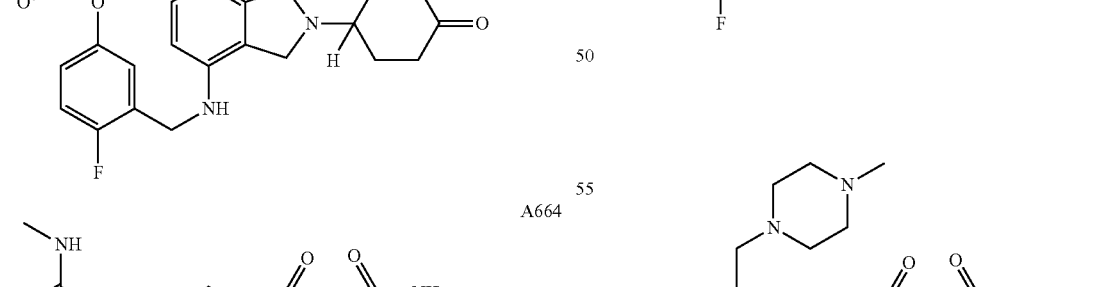
A377
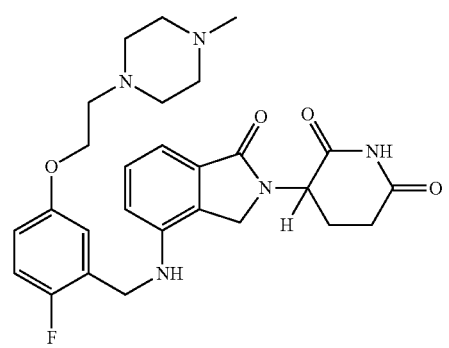

A669 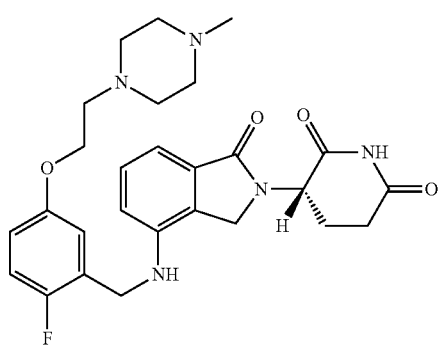
A670 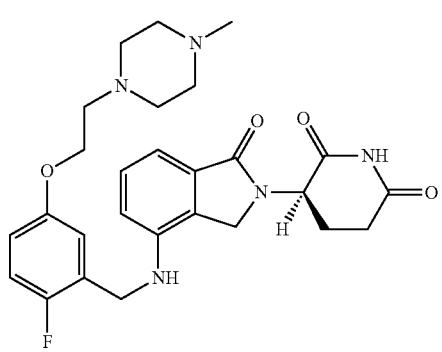
A671 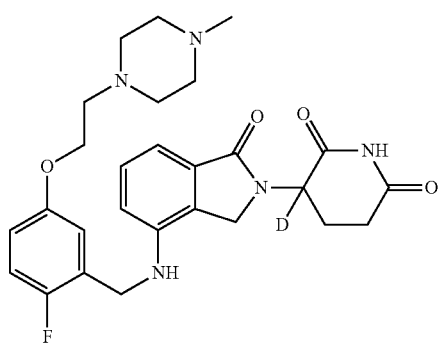
A672 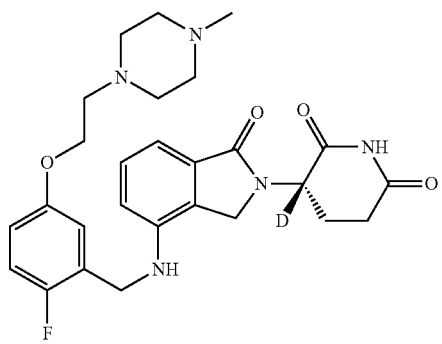
A673 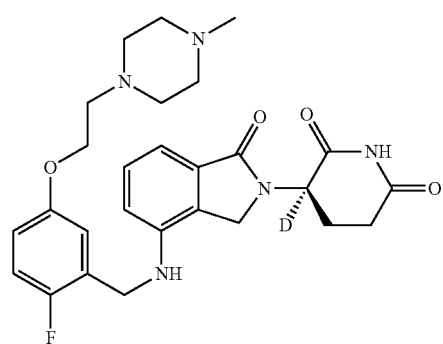
A385 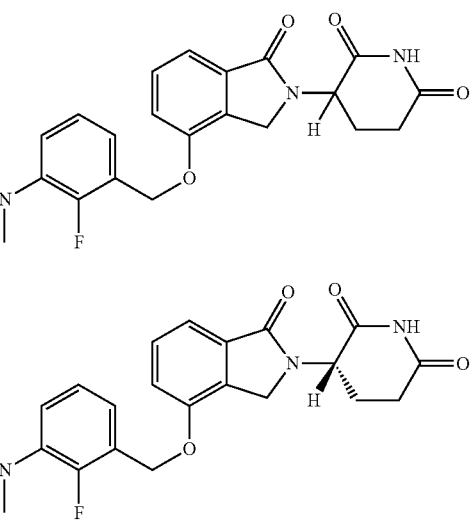
A674 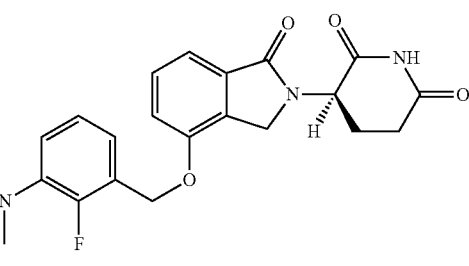
A675 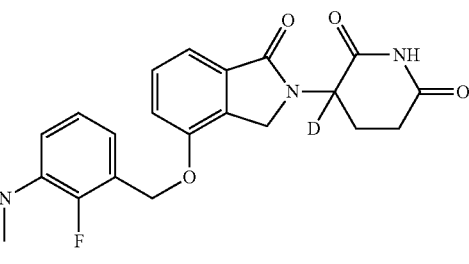
A676 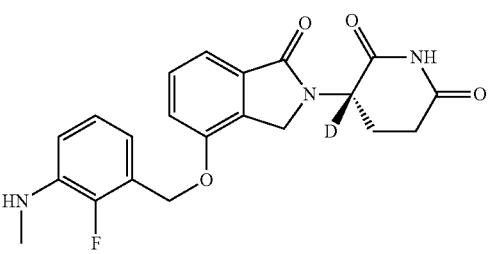
A677

A678
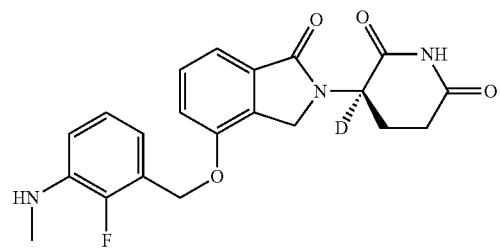
A394
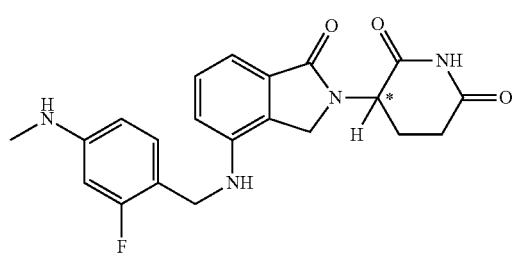
A679
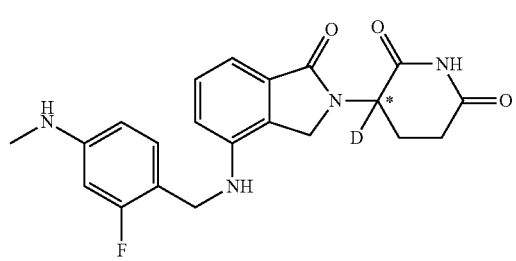
A387
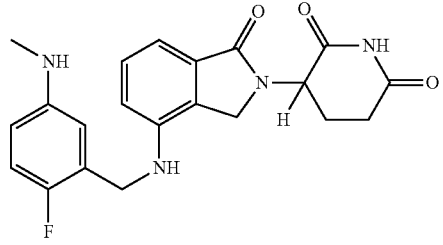
A680
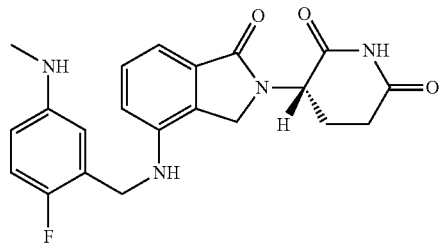
A681
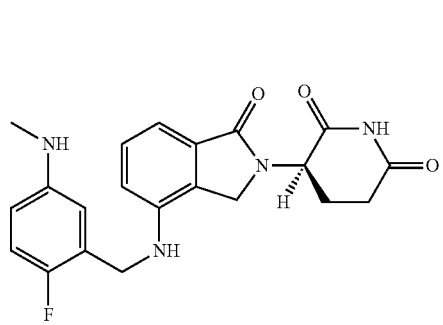
A682
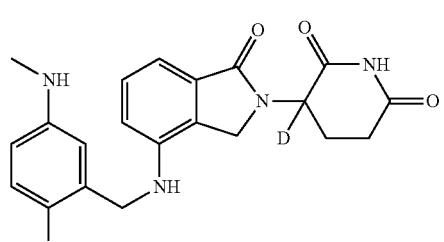
A683
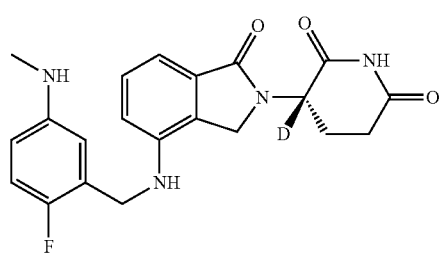
A684
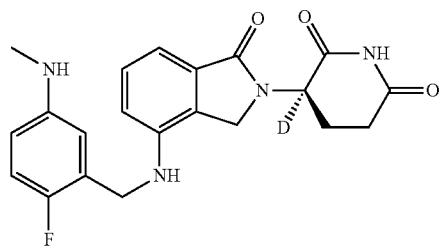
A389
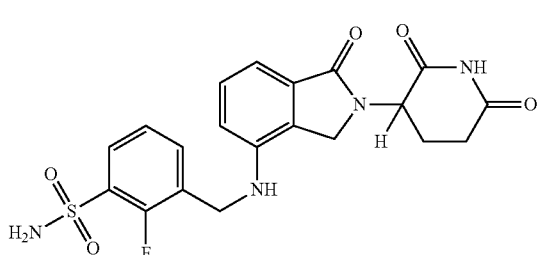
A685
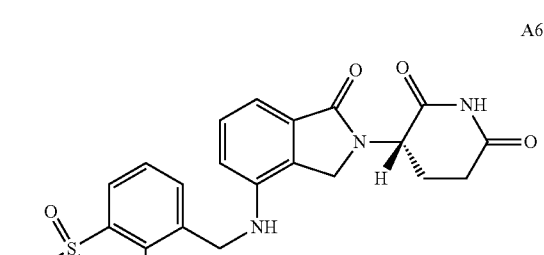
A686
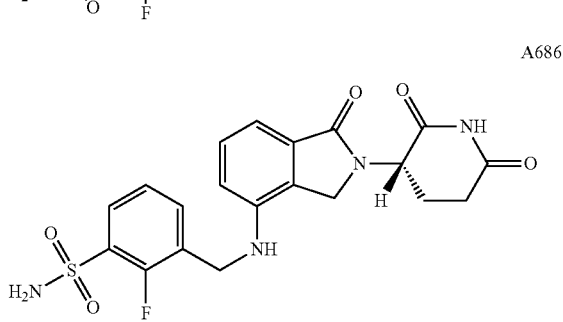

A687
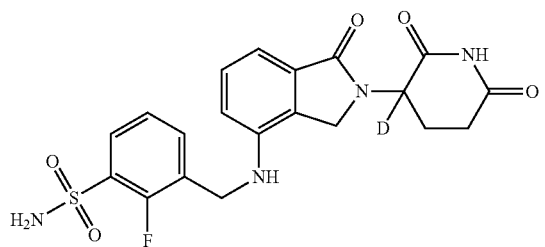
A692
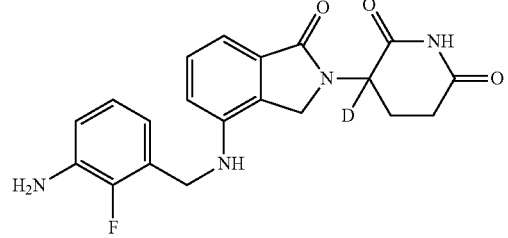
A688
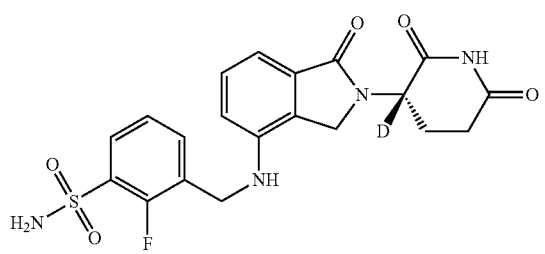
A693
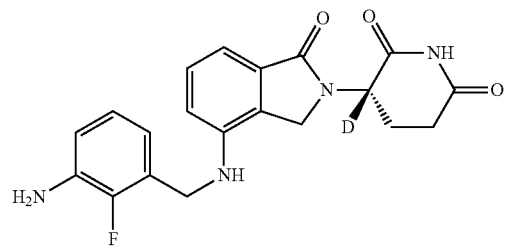
A689
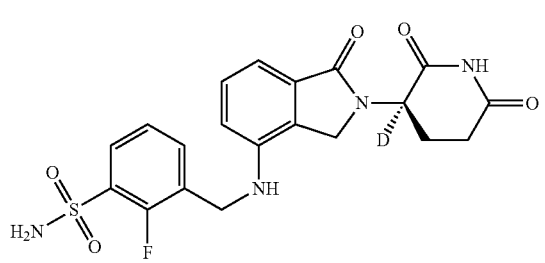
A694
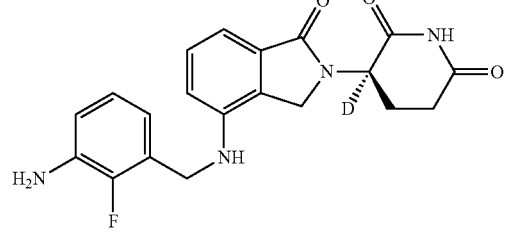
A384
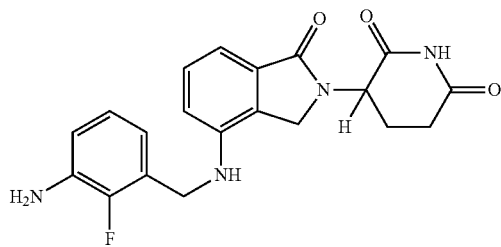
A388
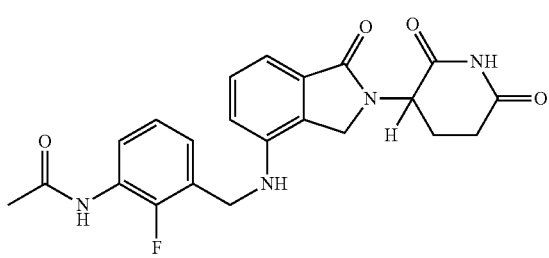
A690
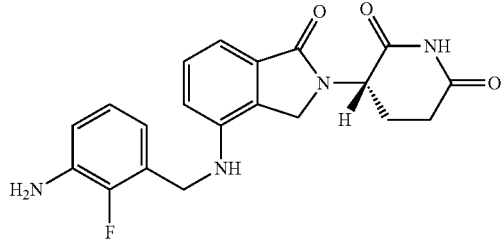
A695
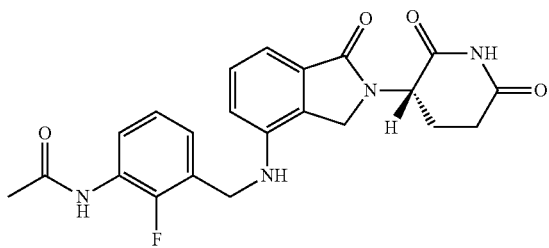
A691
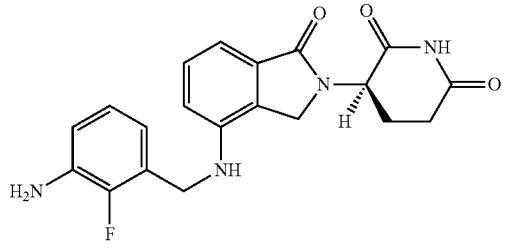
A696
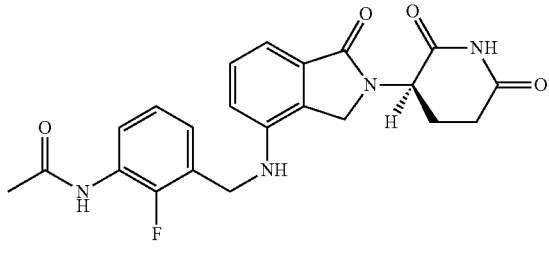

413
-continued
A697
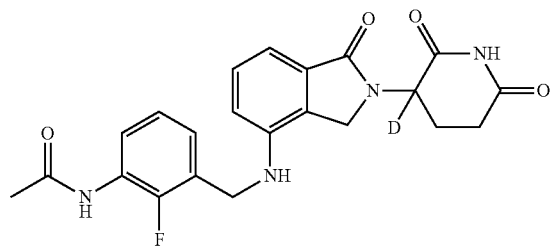
A698
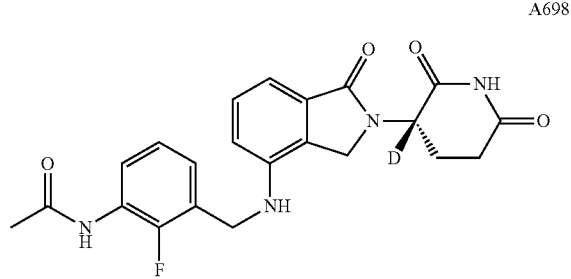
A699
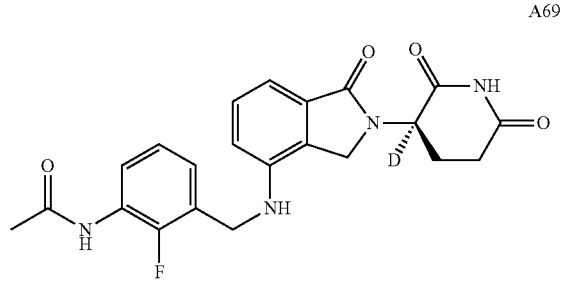
A397
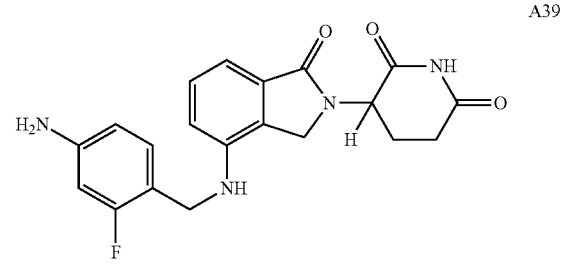
A700
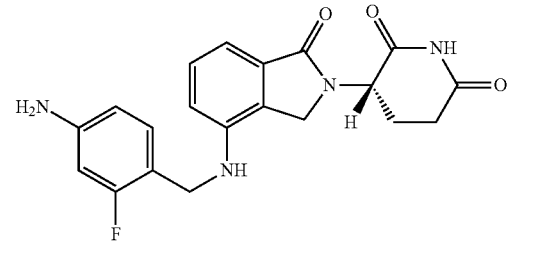
A701
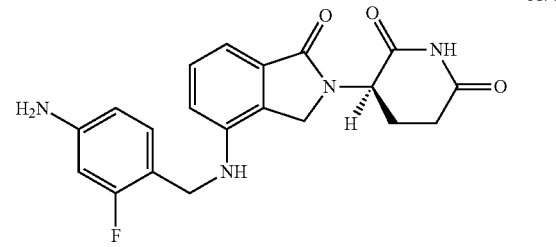
414
-continued
A702
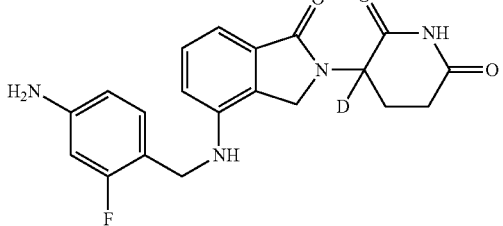
A703
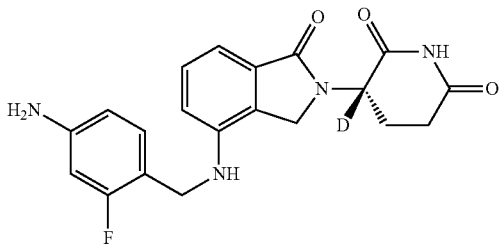
A704
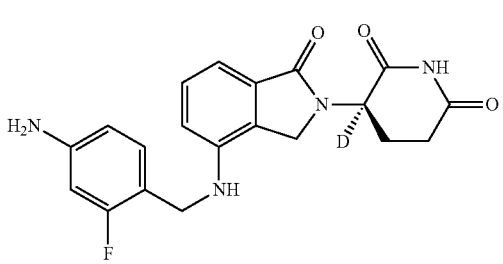
A391
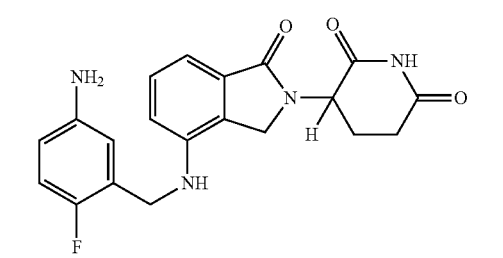
A705
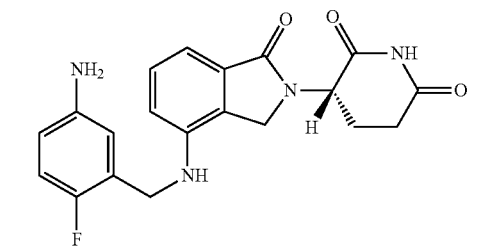
A706

A707
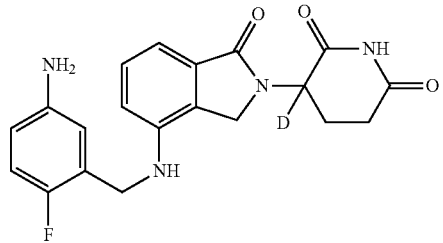
A708
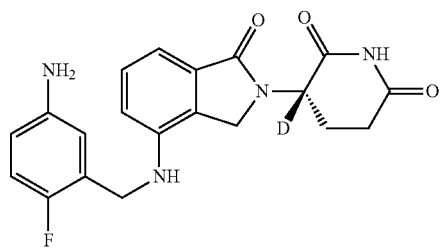
A709
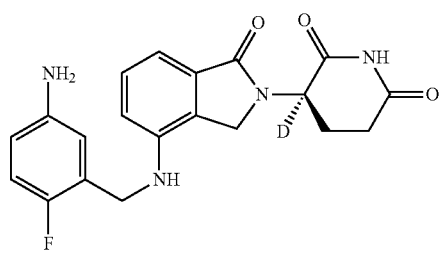
A710
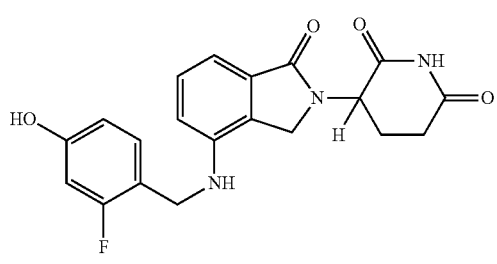
A711
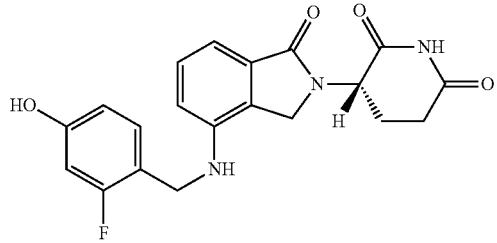
A396
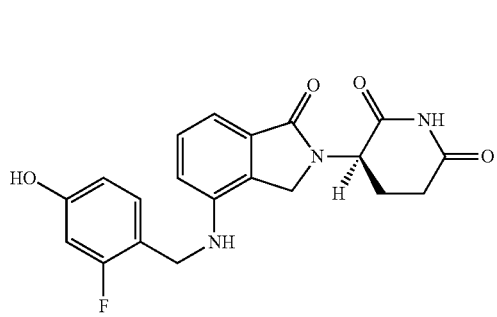
A712
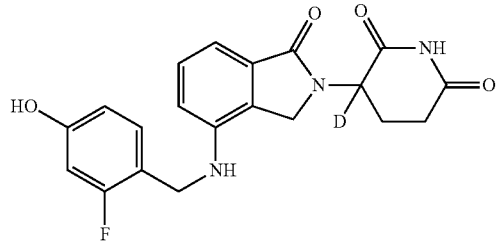
A713
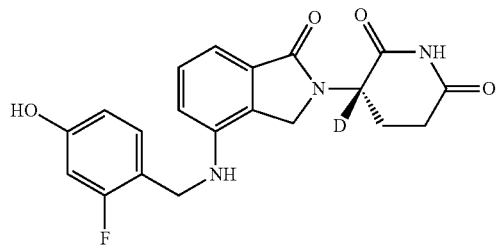
A714
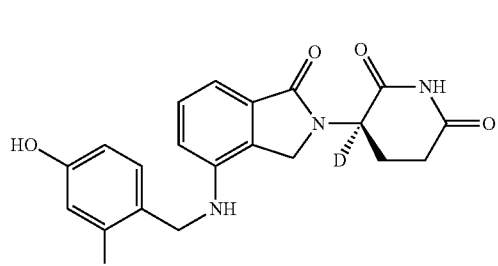
A407
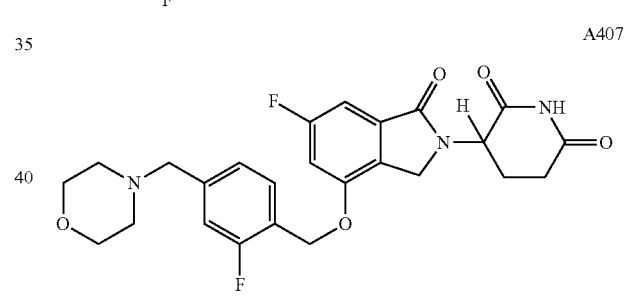
A720
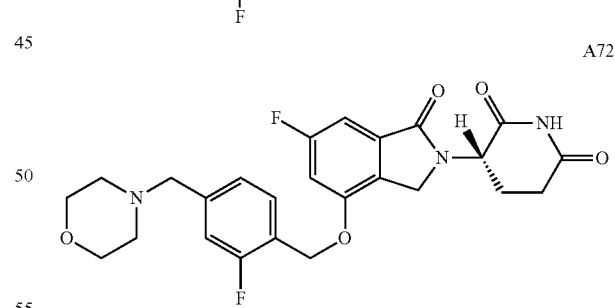
A721
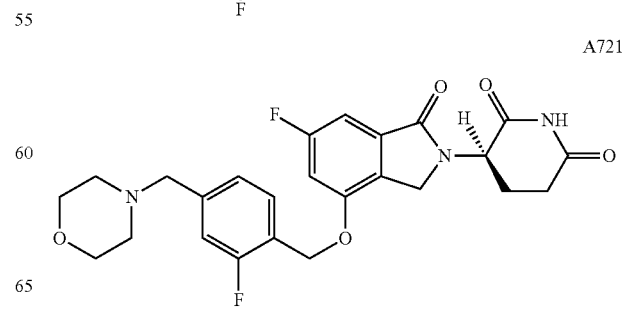

A722 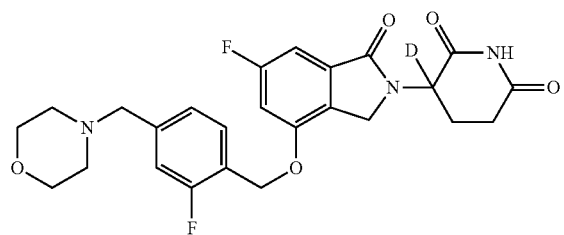
A723 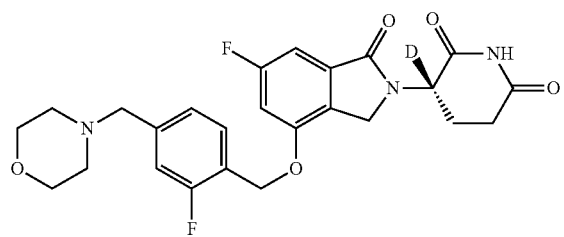
A724 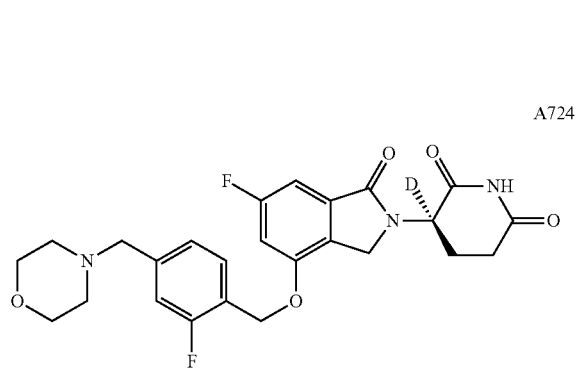
A725 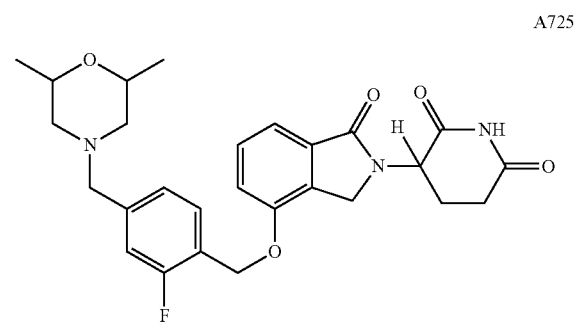
A726 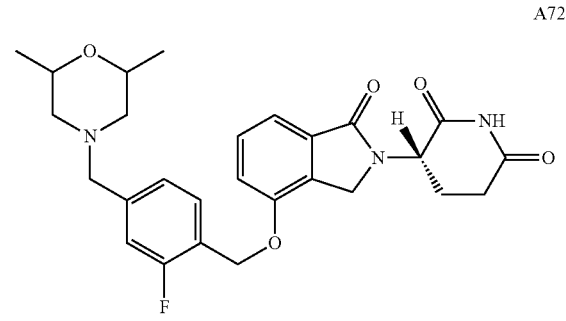
A727 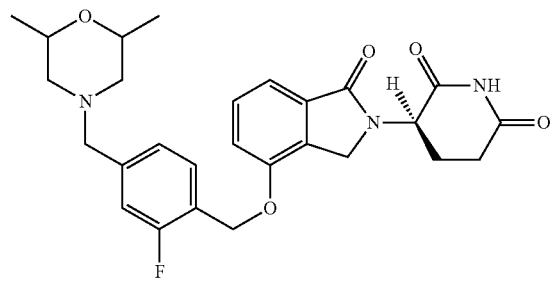
A427 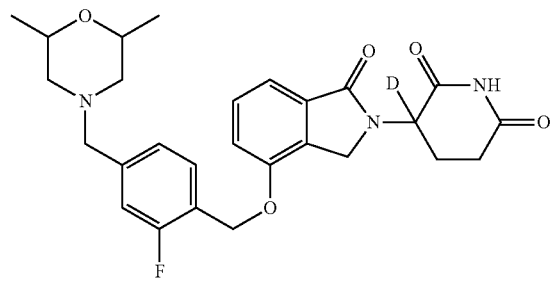
A728 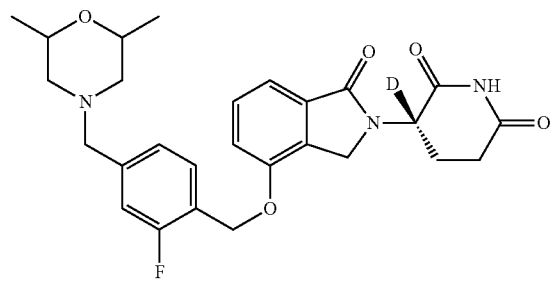
A729 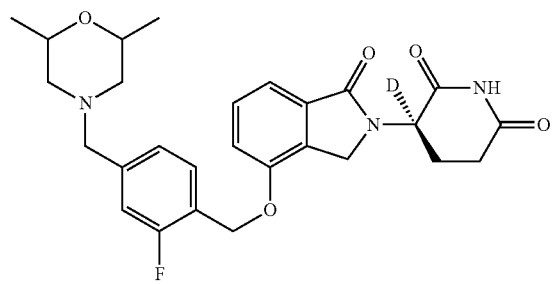
A730 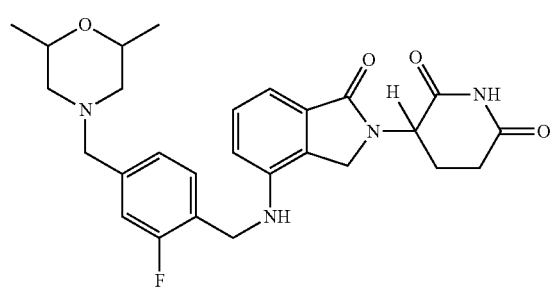

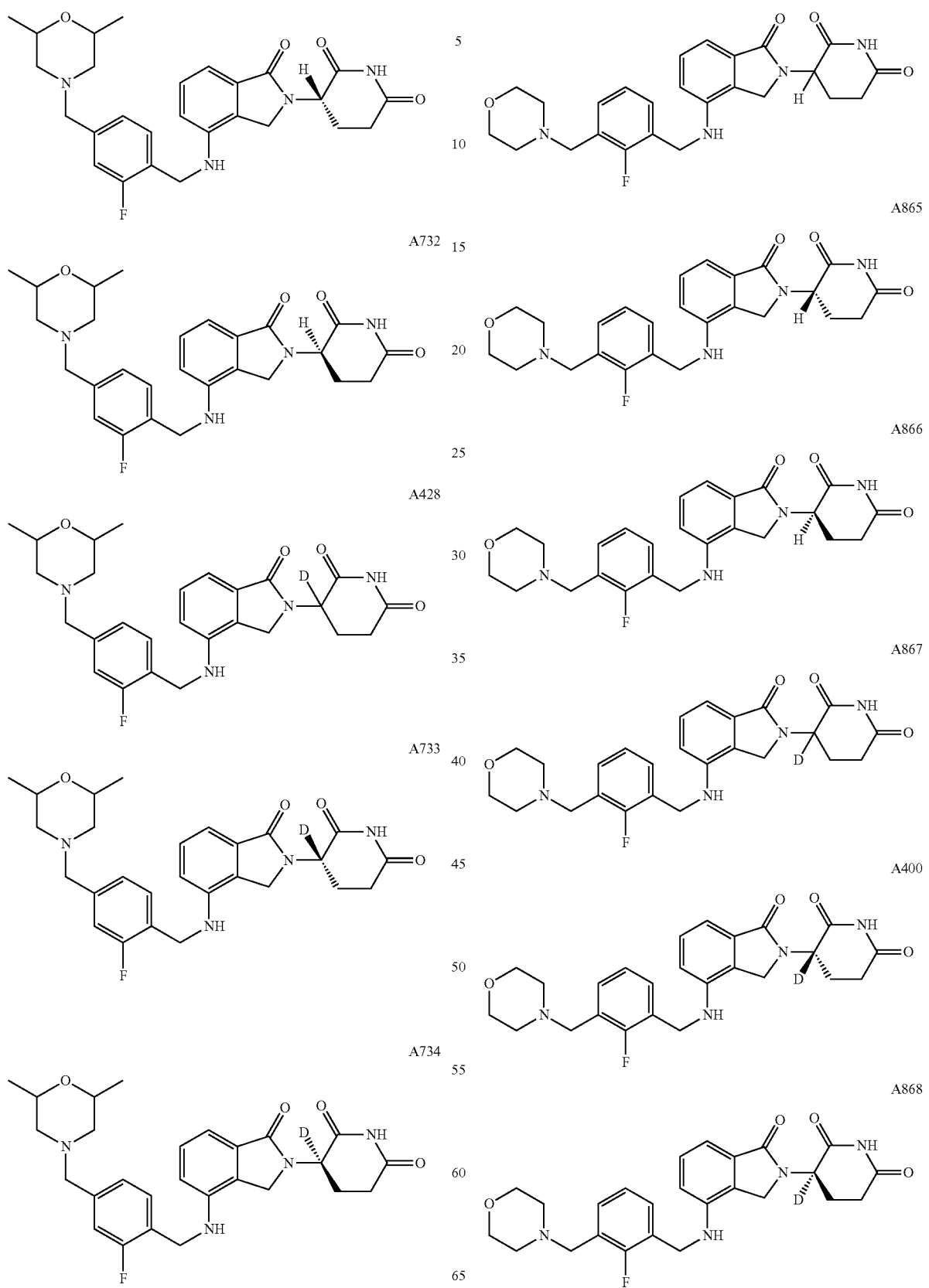

421
-continued
A399
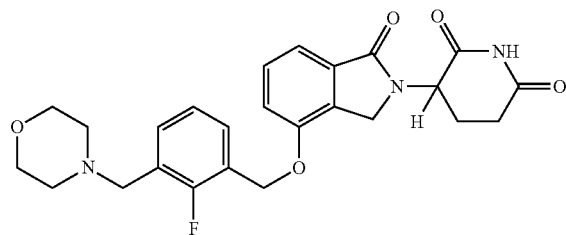
A869
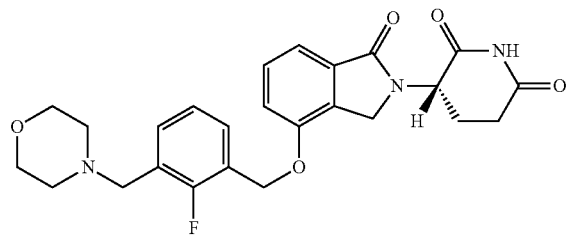
A870
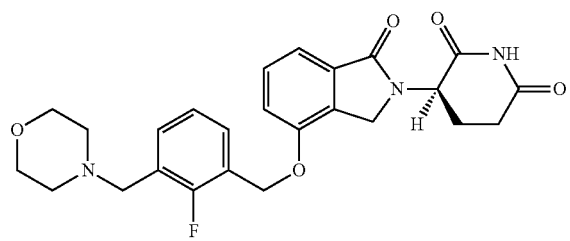
A872
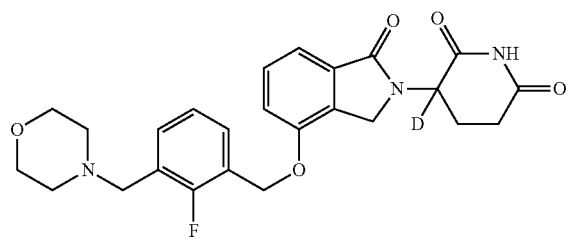
A404
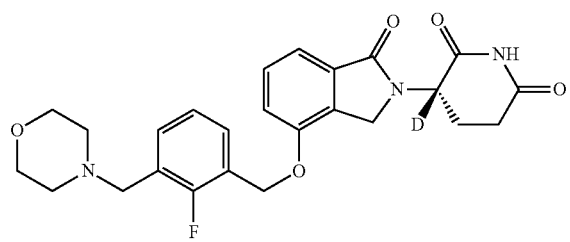
A871
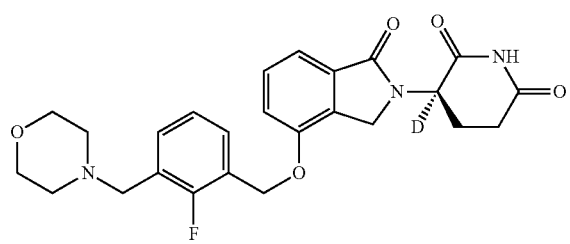
422
-continued
A873
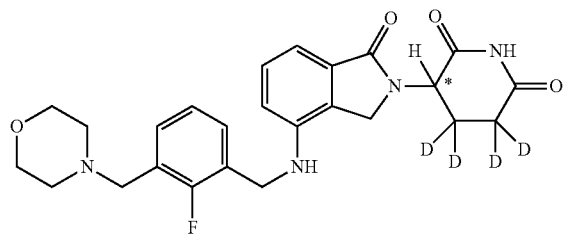
A874
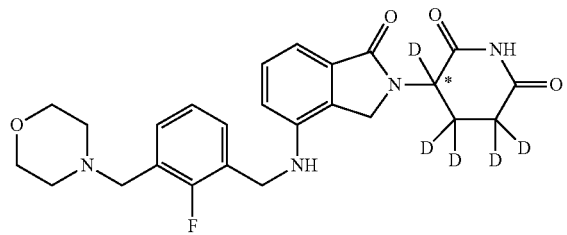
A875
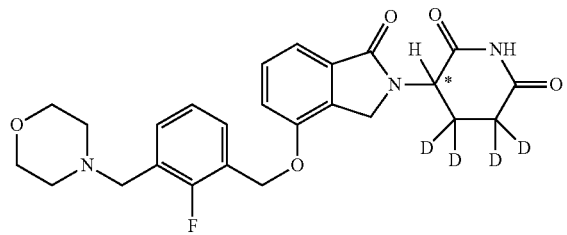
A876
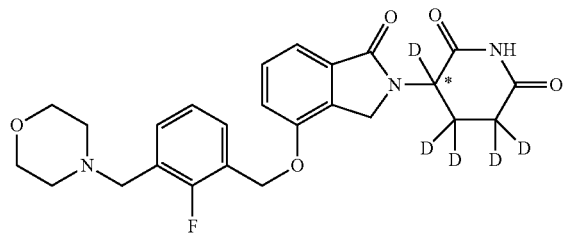
A877
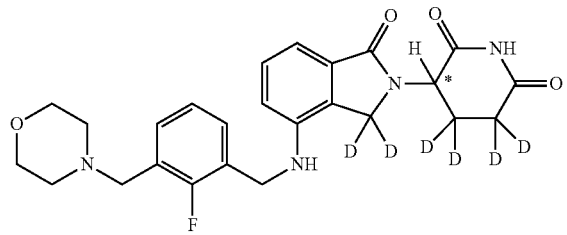
A878
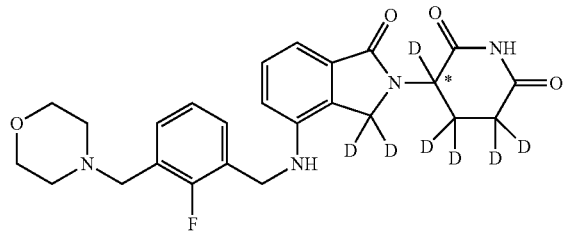

A879
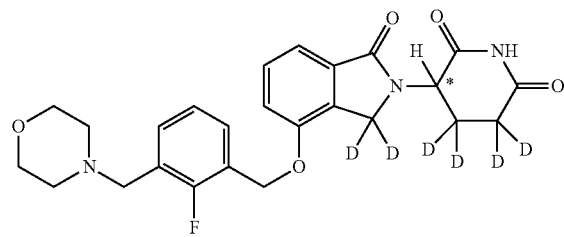
A885
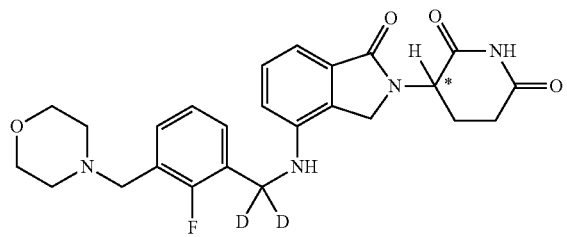
A880
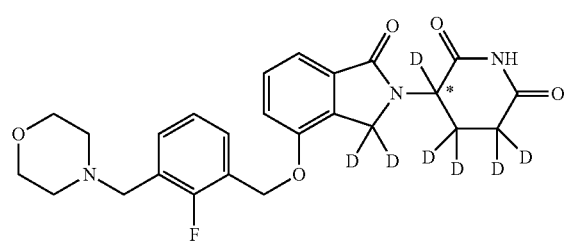
A886
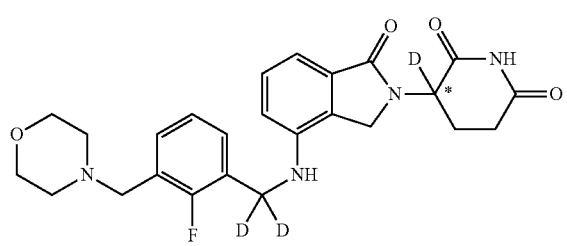
A881
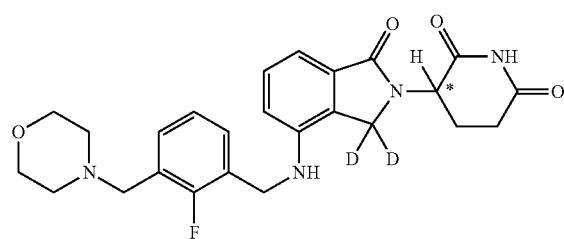
A887
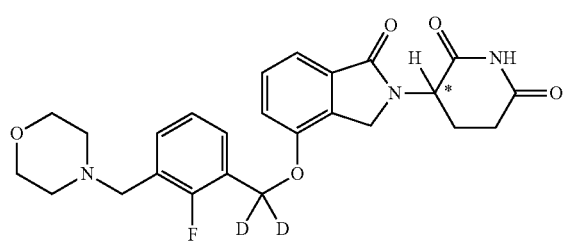
A882
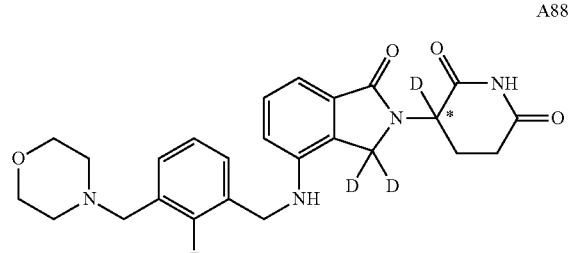
A888
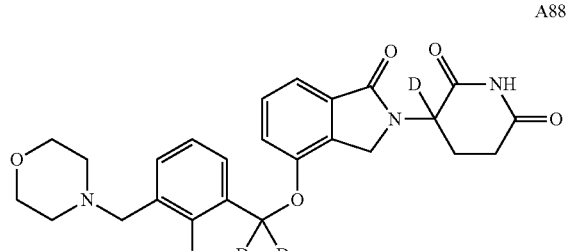
A883
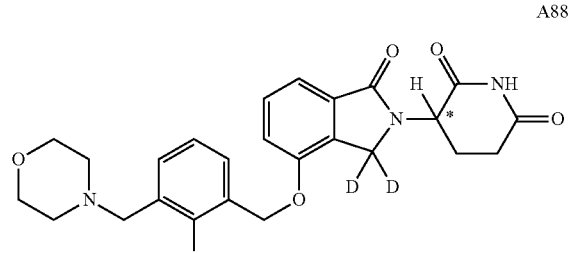
A889
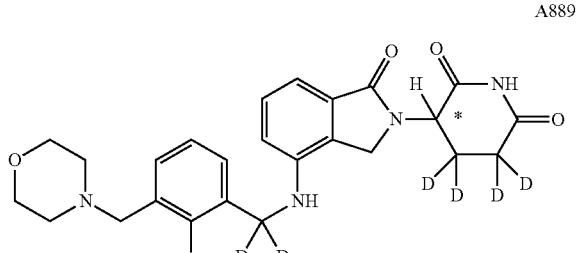
A884
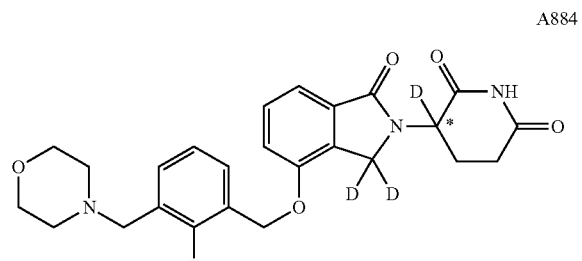
A890
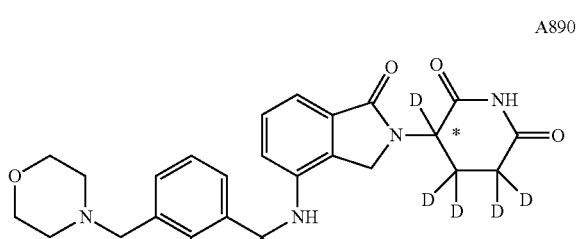

A891 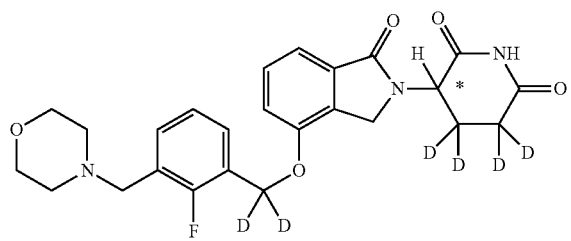
A897 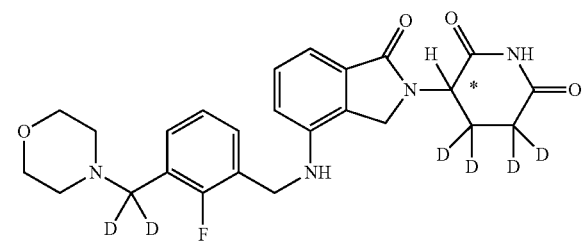
A892 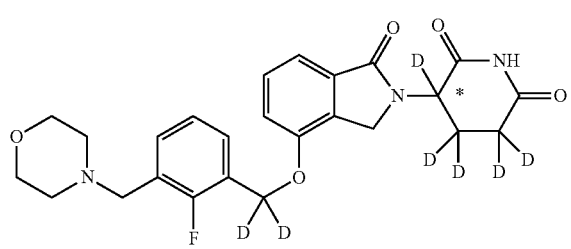
A898 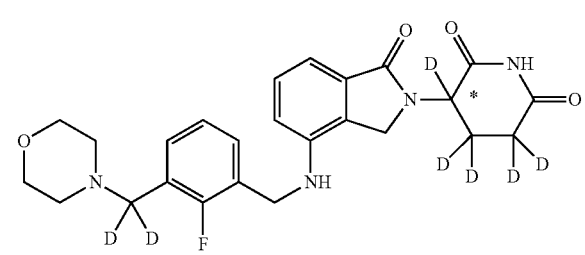
A893 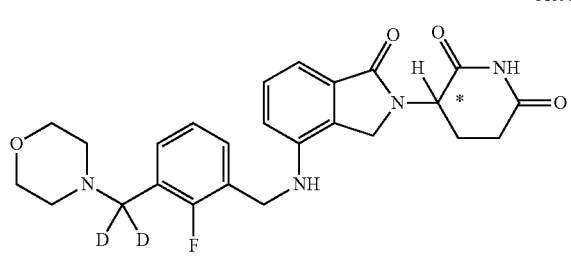
A899 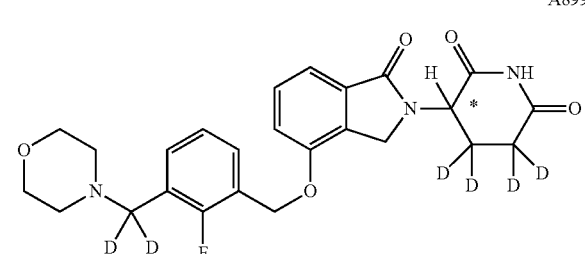
A894 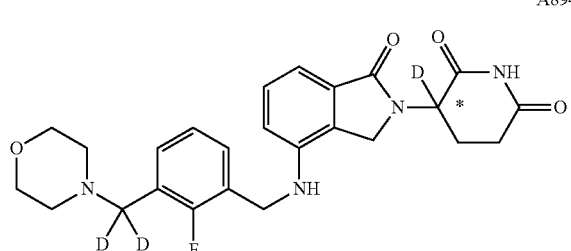
A900 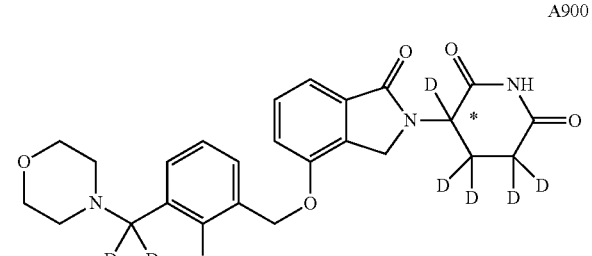
A895 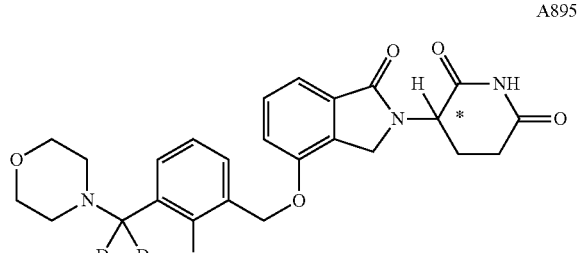
A901 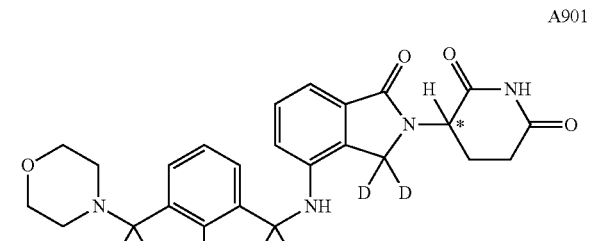
A896 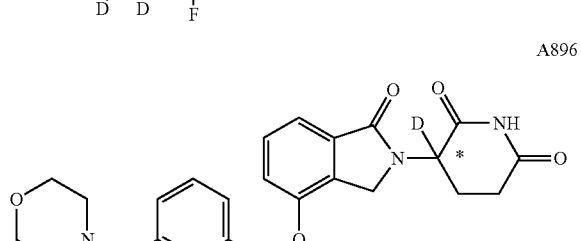
A902 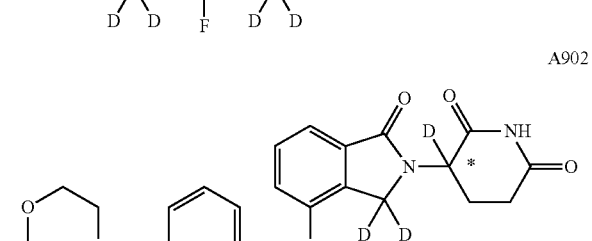

-continued
A903
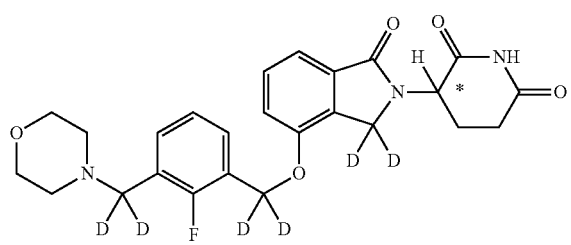
A904
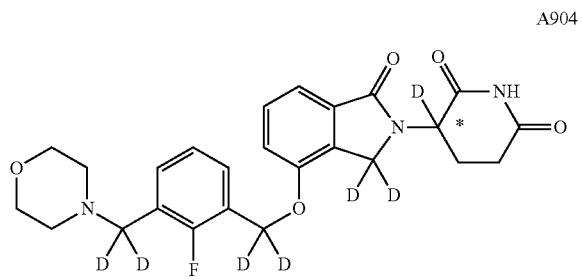
A905
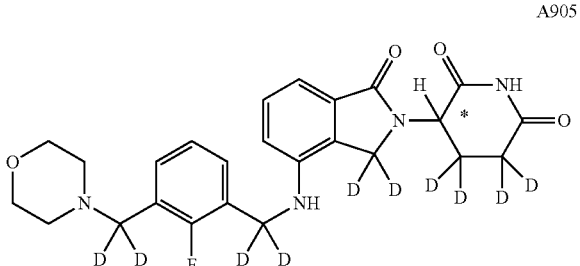
A906
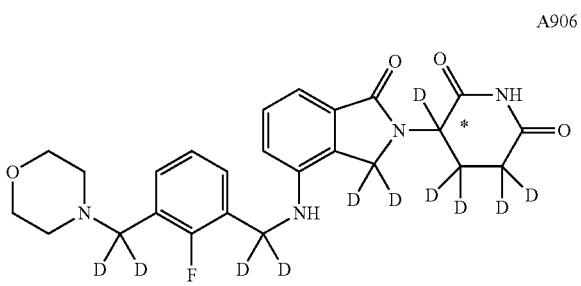
A907
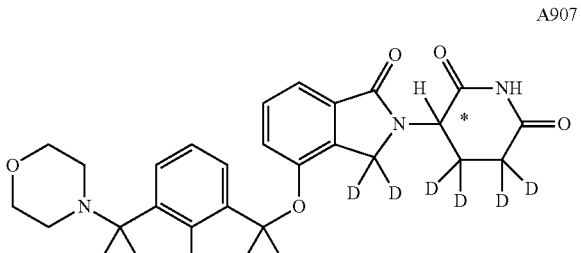
A908
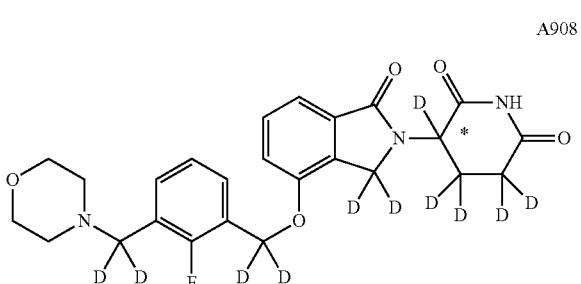
-continued
A909
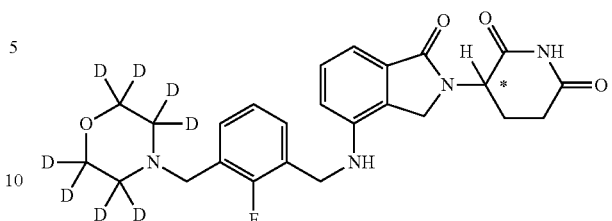
A910
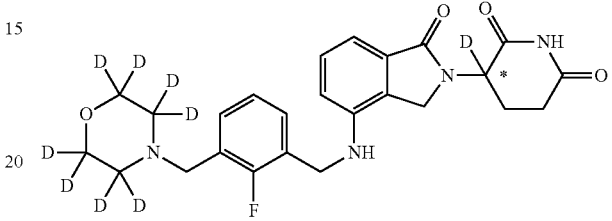
A911
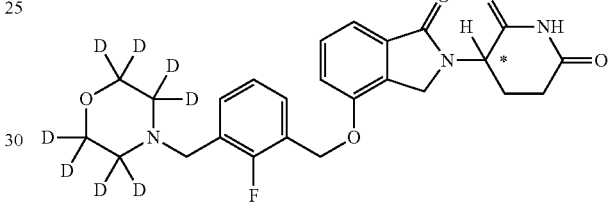
A912
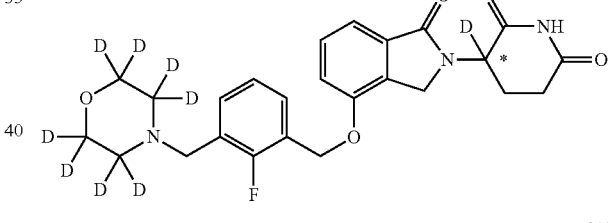
A913
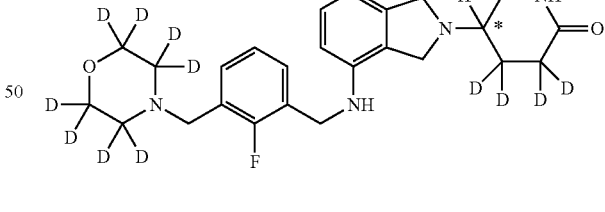
A914
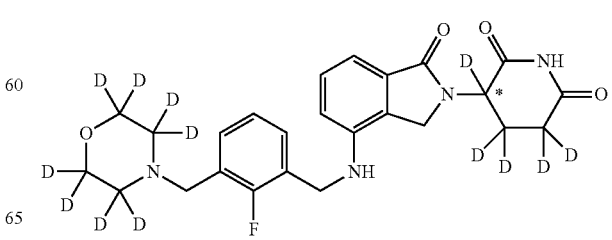

A915
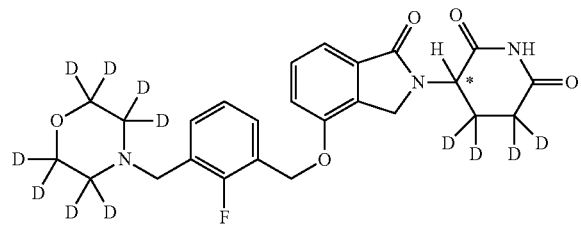
A916
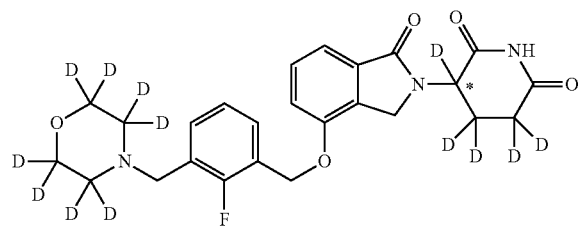
A917
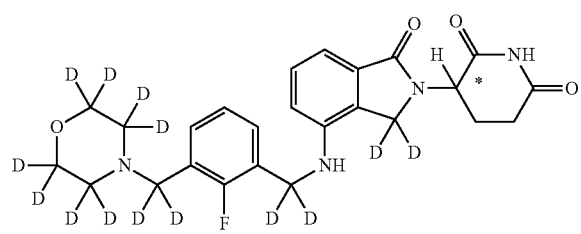
A918
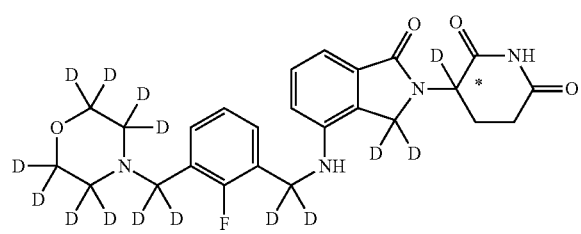
A919
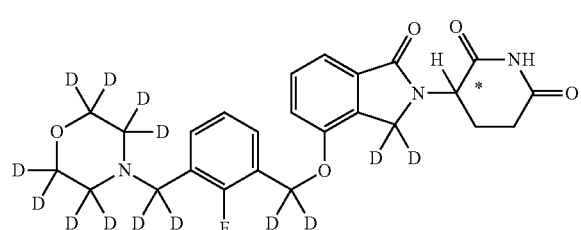
A920
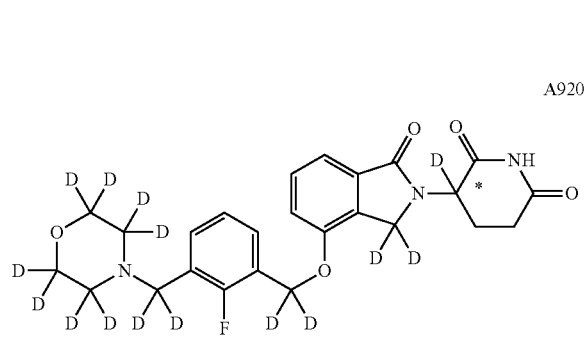
A921
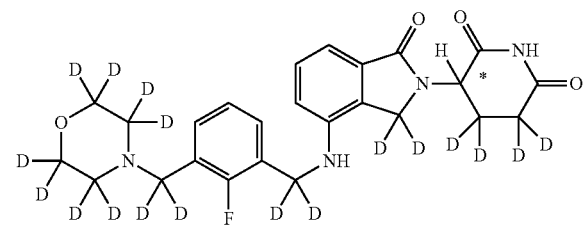
A922
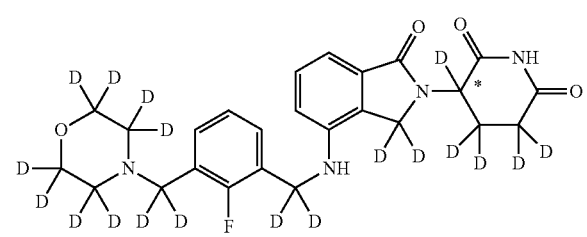
A923
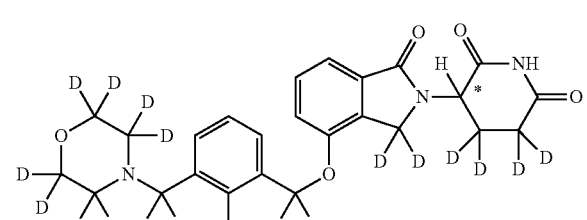
A924
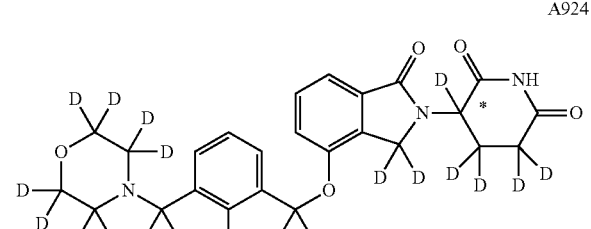
A925
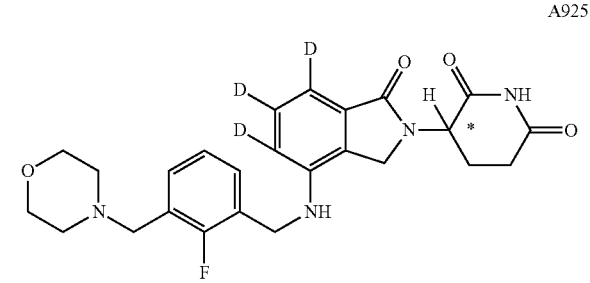
A926
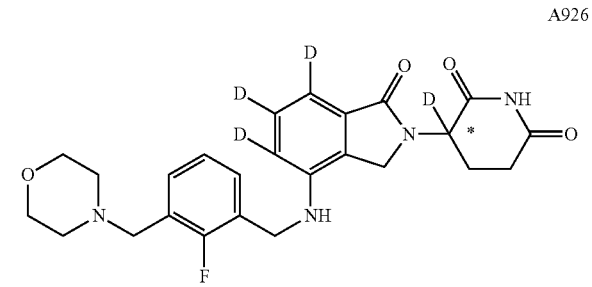

-continued

A927

A928

A929

A930

A931

A932

A933

A934

A935

A936

A937

A938

A939
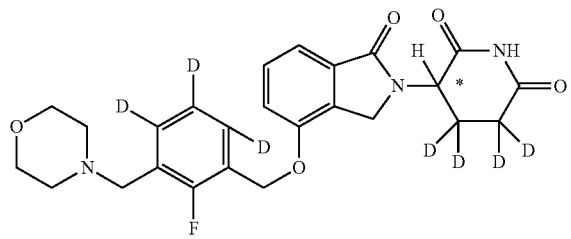
A940
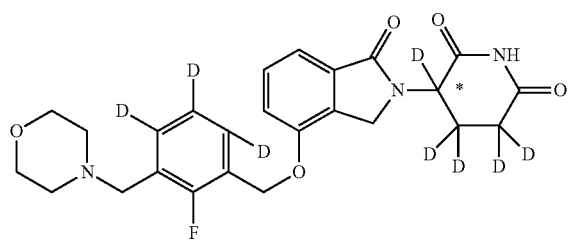
A941
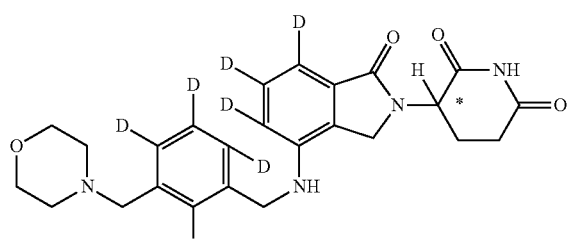
A942
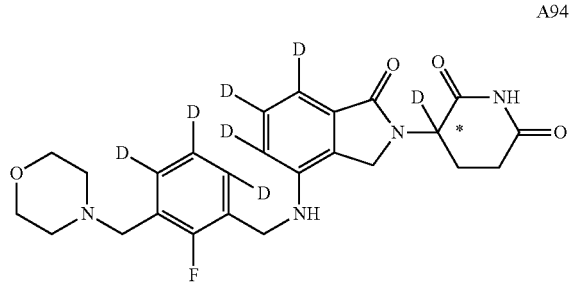
A943
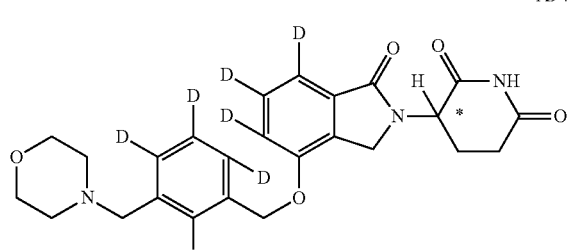
A944
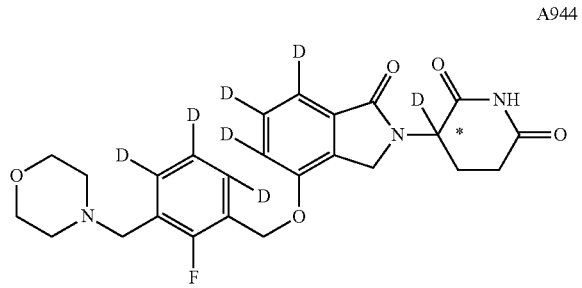
A945
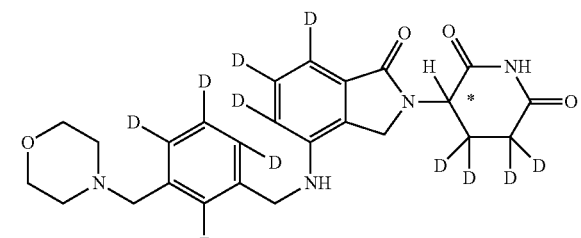
A946
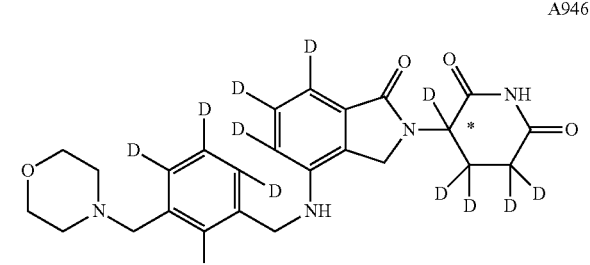
A947
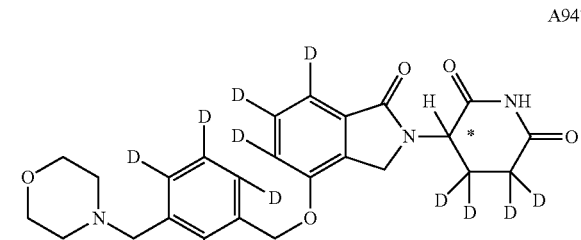
A948
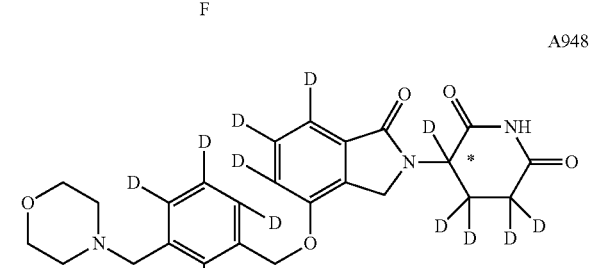
A949
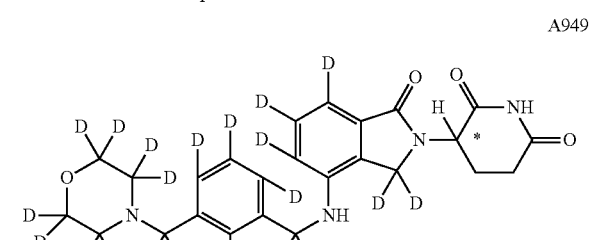
A950
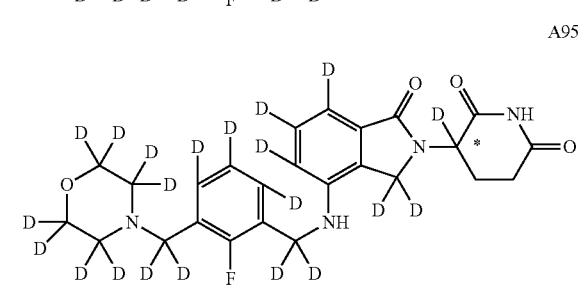

A951
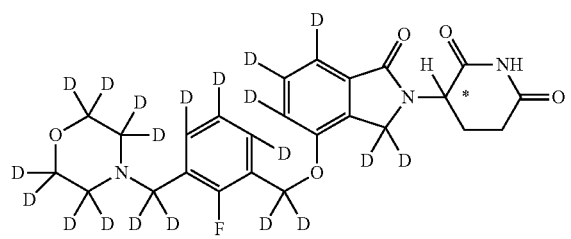
A382
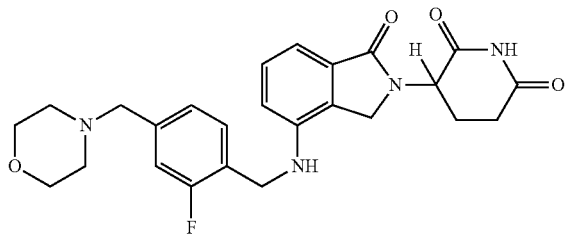
A952
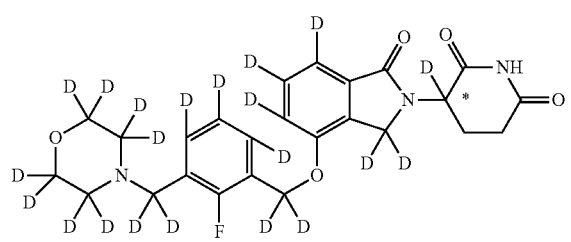
A957
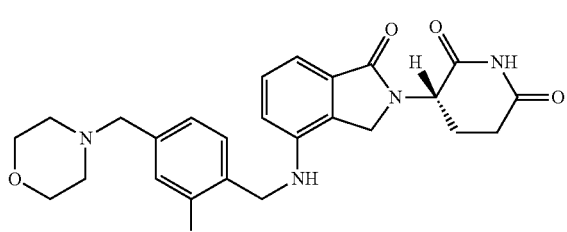
A953
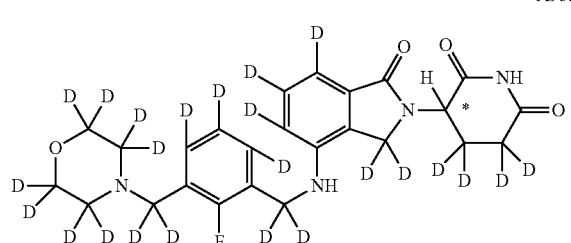
A958
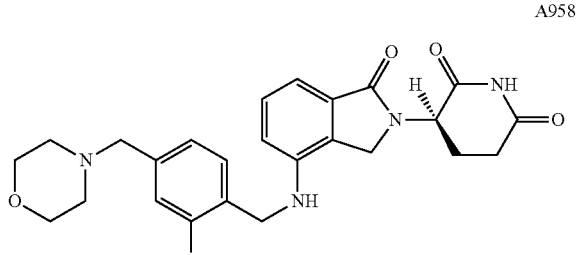
A954
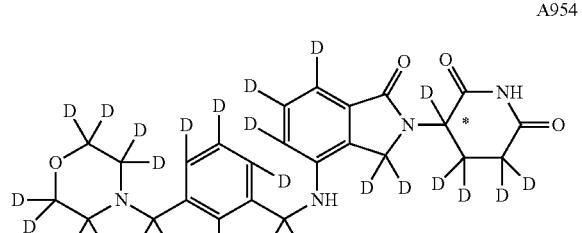
A426
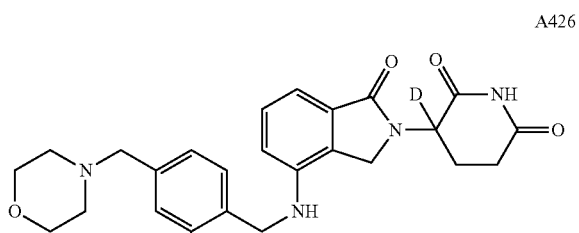
A955
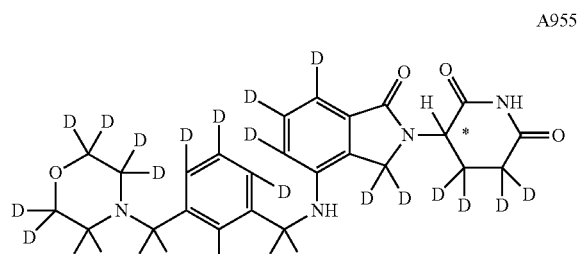
A402
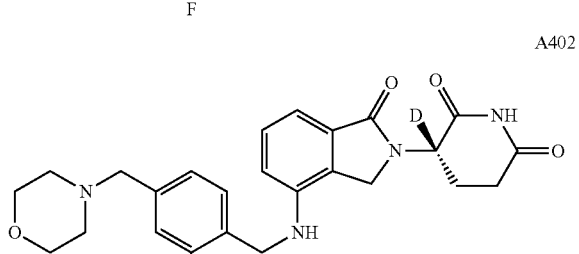
A956
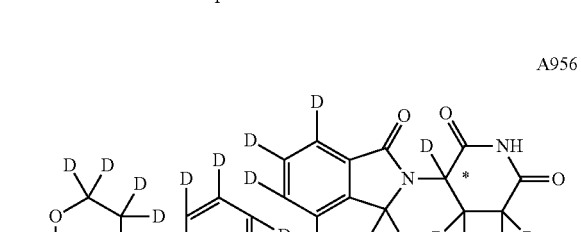
A959
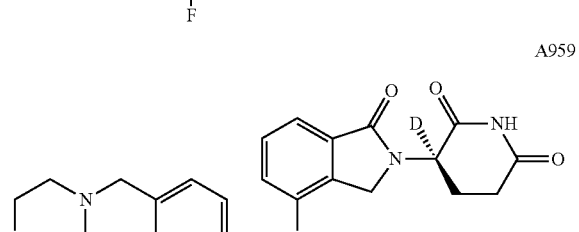

A386
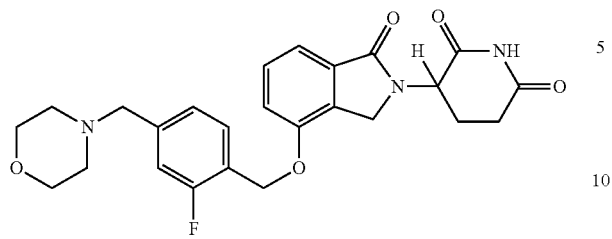
A960
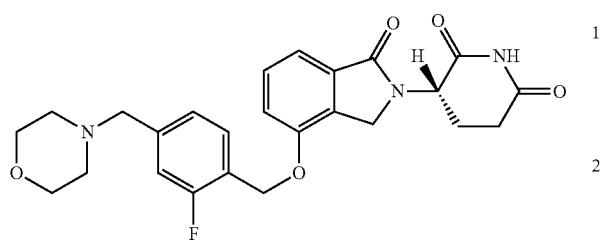
A961
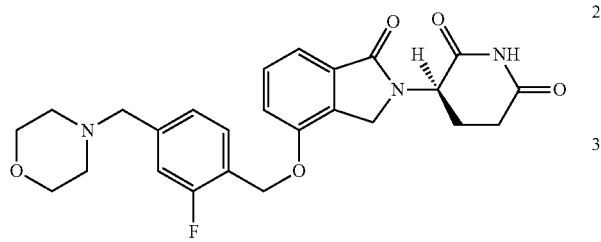
A425
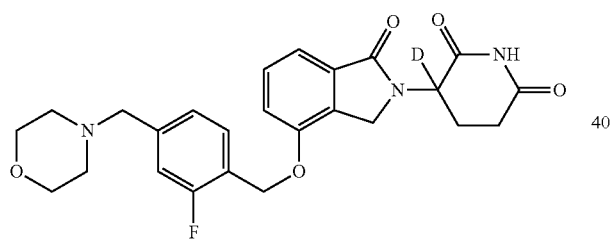
A406
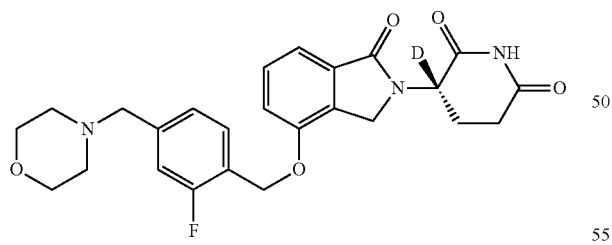
A962
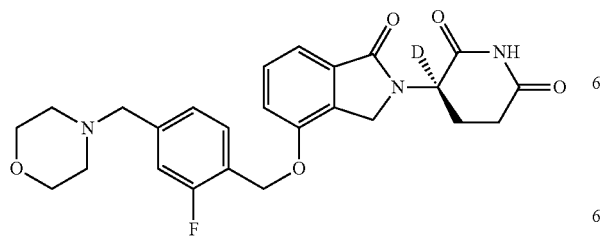
A963
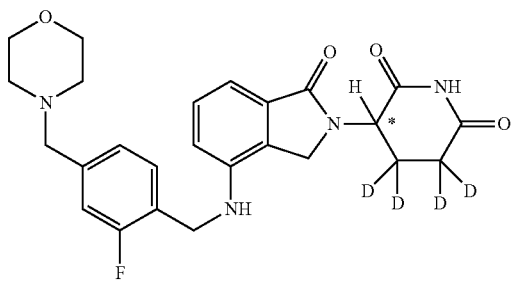
A964
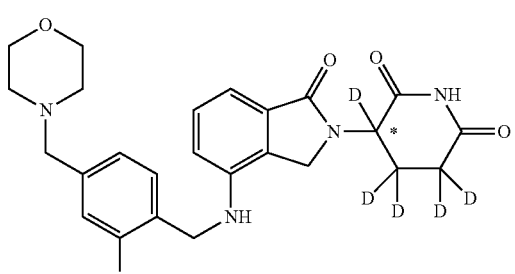
A965
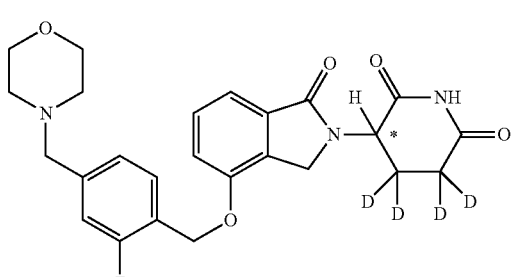
A966
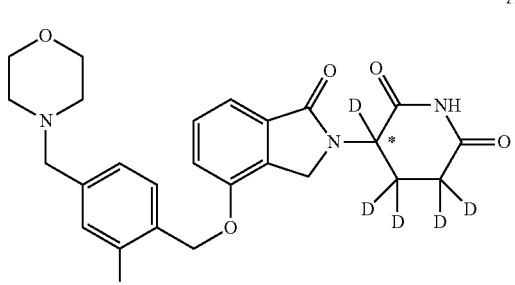
A967
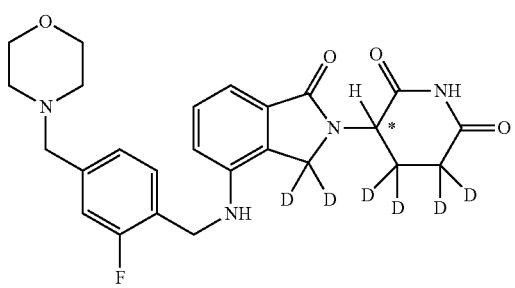

439
-continued
A968
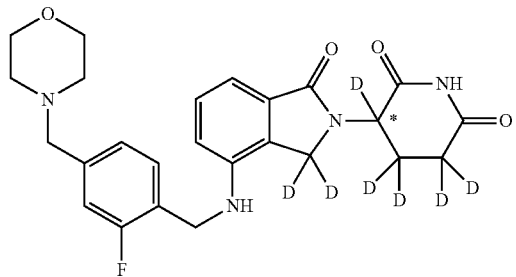
A969
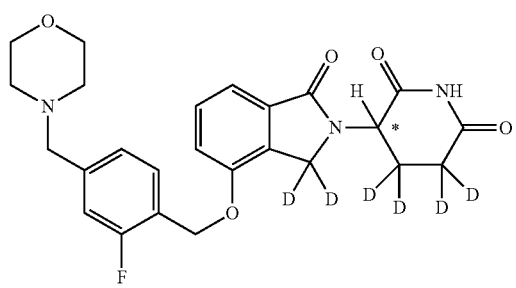
A970
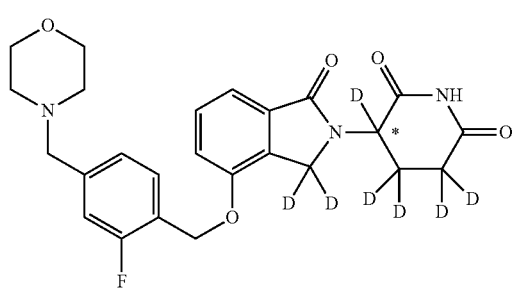
A971
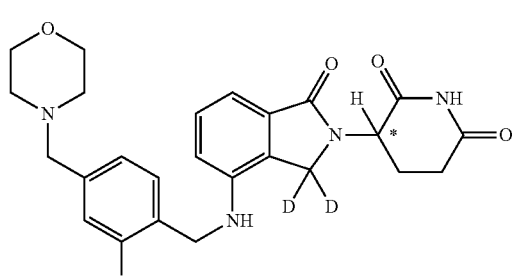
A972
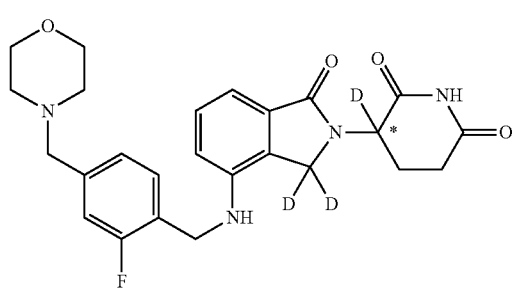
440
-continued
A973
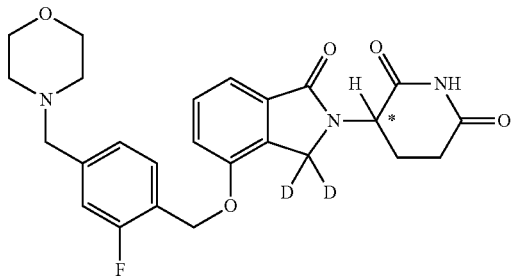
A974
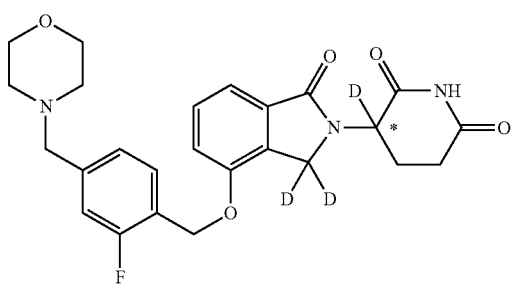
A975
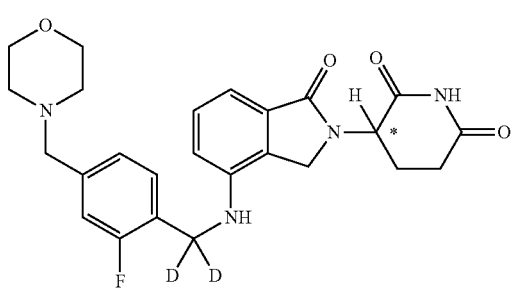
A976
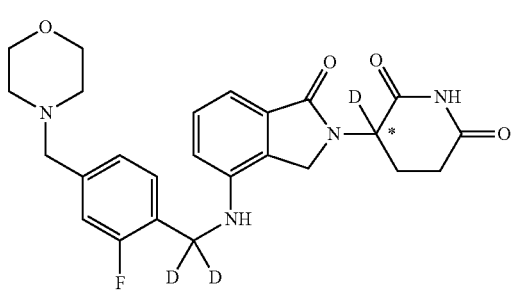
A977
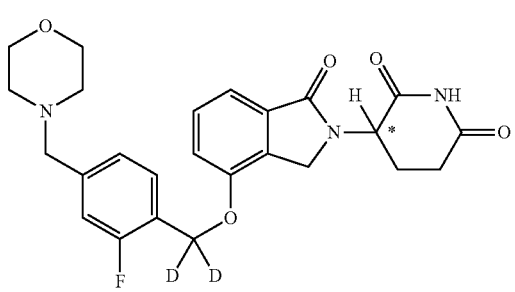

A978 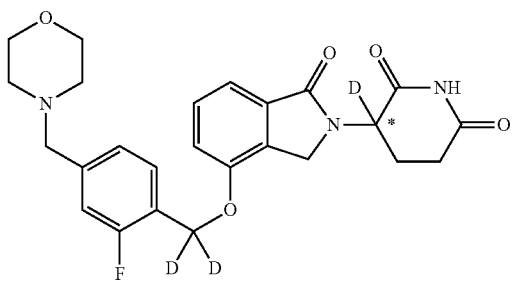
A983 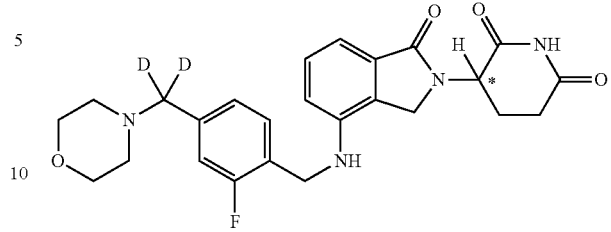
A979 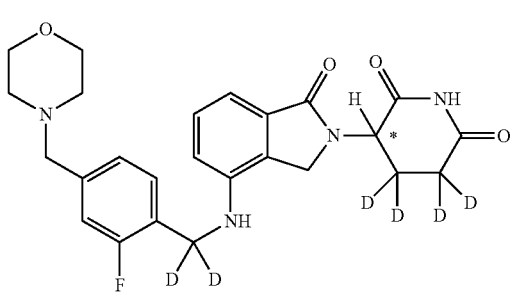
A984 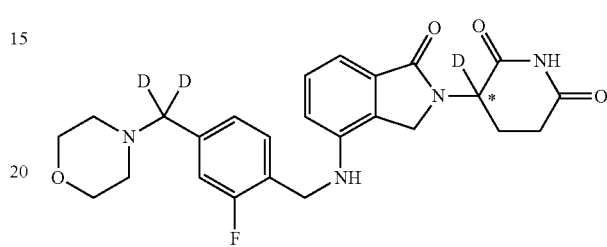
A980 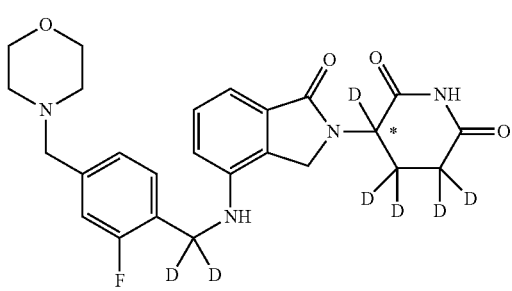
A985 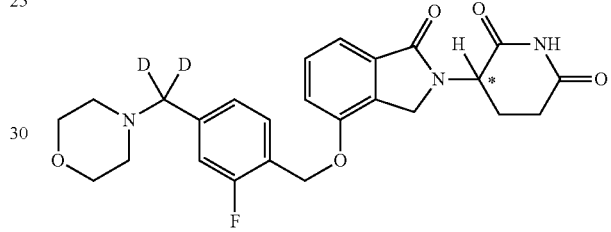
A981 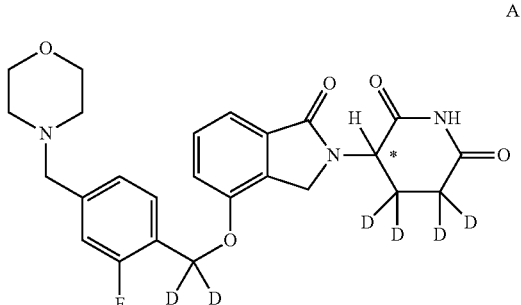
A986 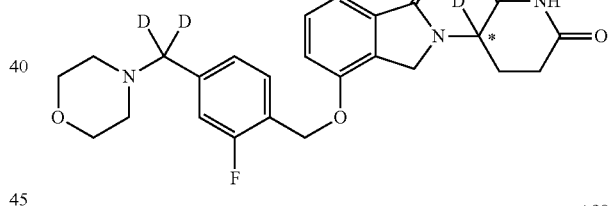
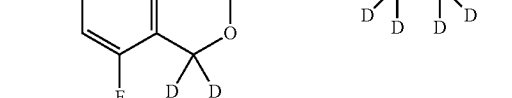
A987 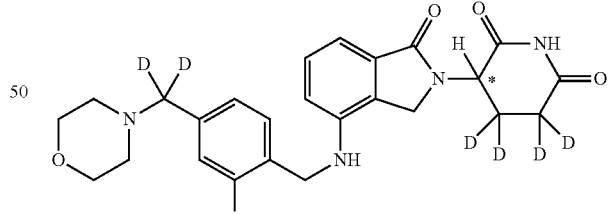
A982 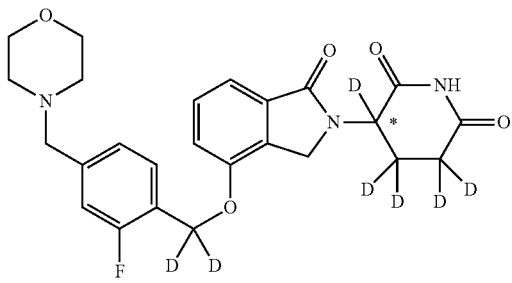
A988 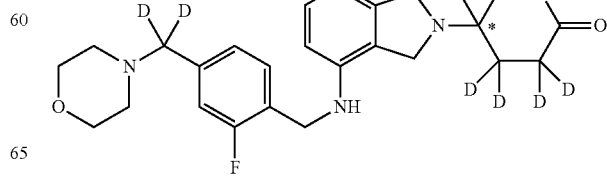

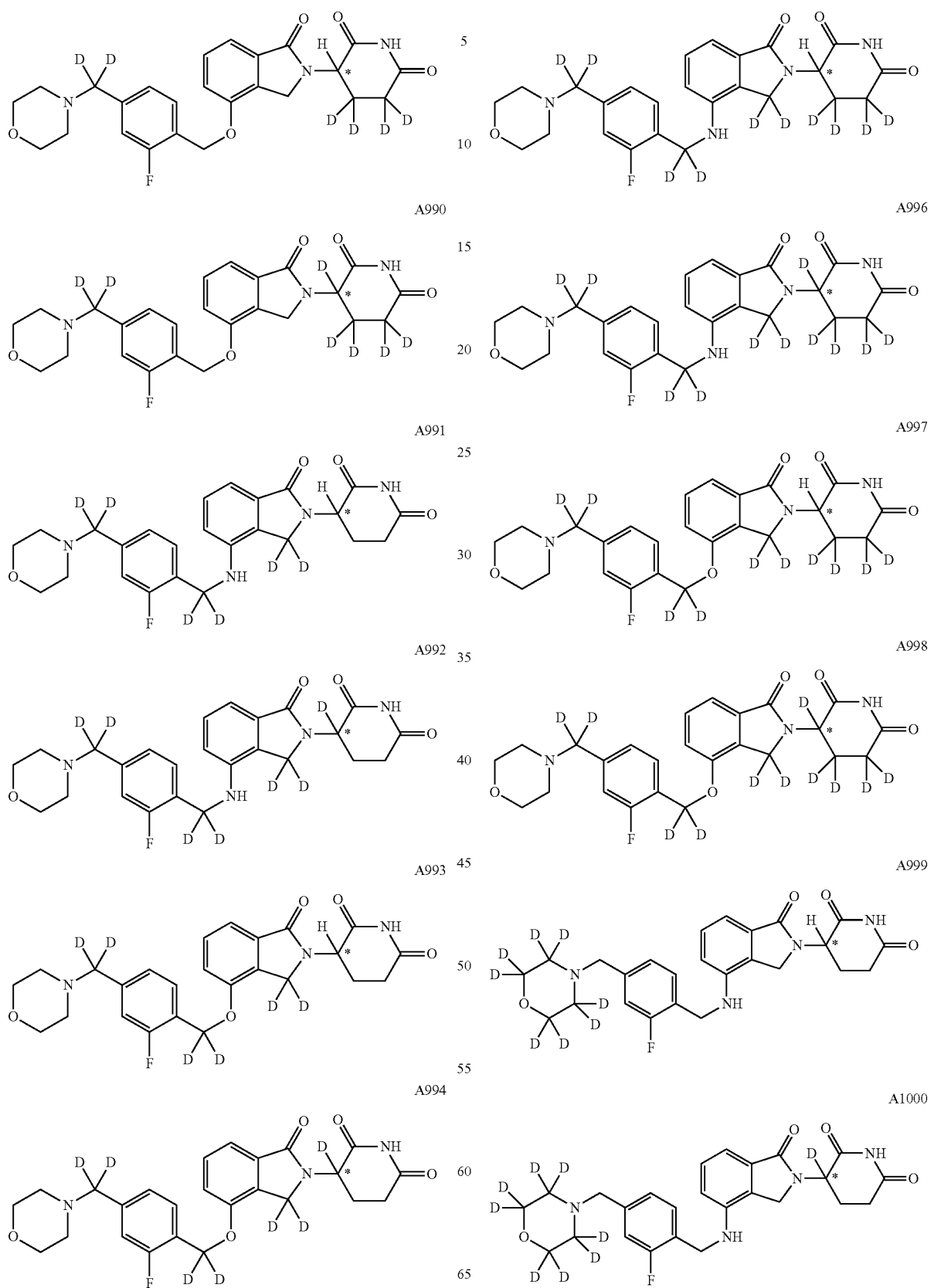

A1001
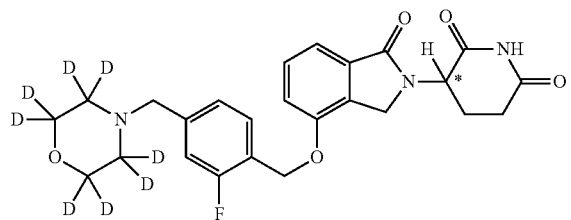
A1002
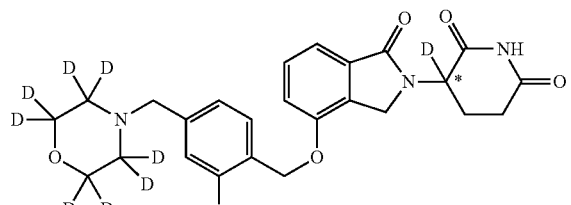
A1003
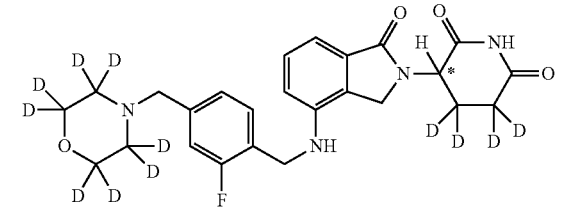
A1004
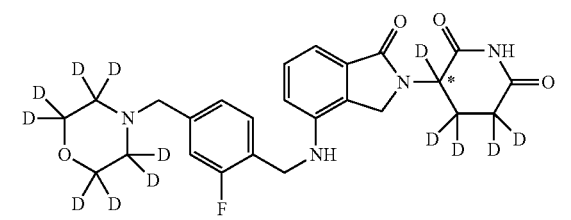
A1005
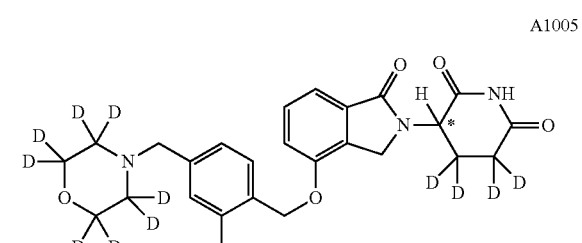
A1006
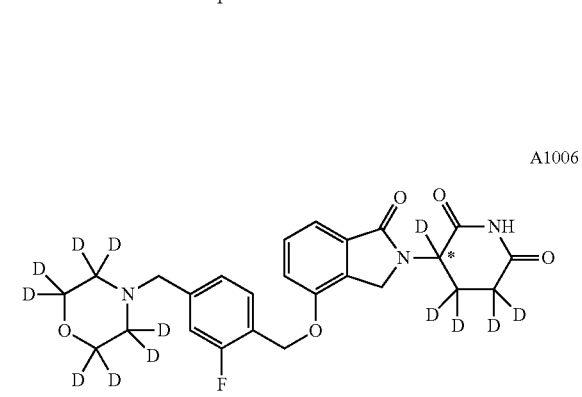
A1007
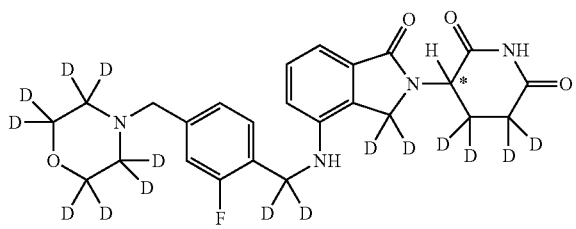
A1008
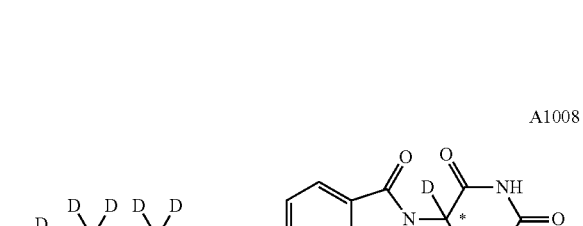
A1009
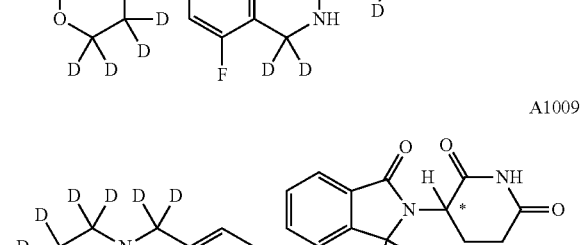
A1100
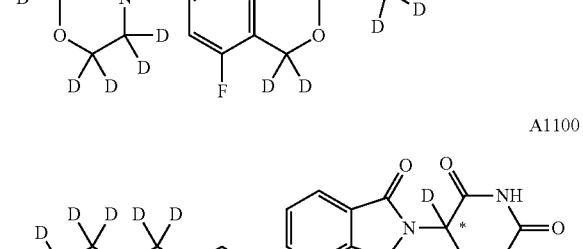
A1101
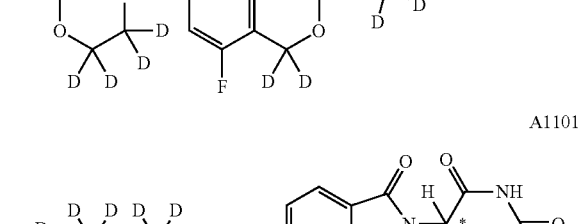
A1102
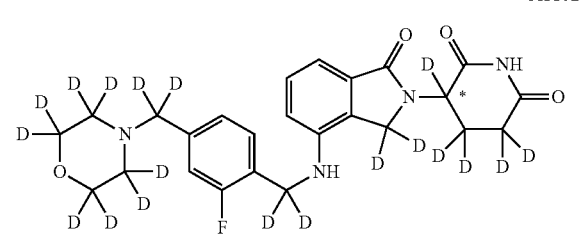

A1103
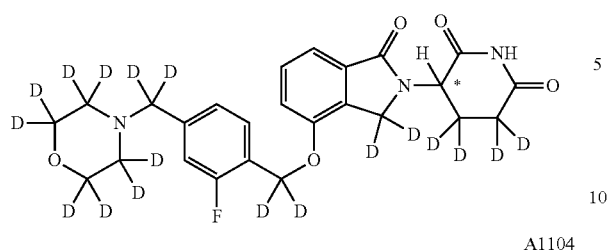
A1104
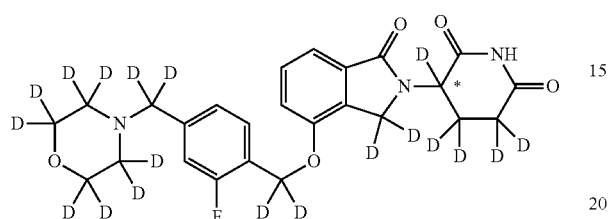
A1105
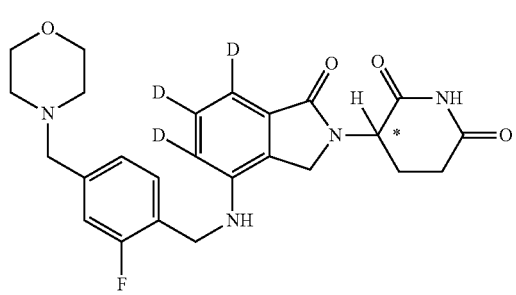
A1106
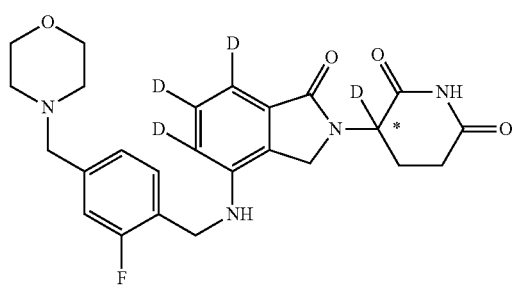
A1107
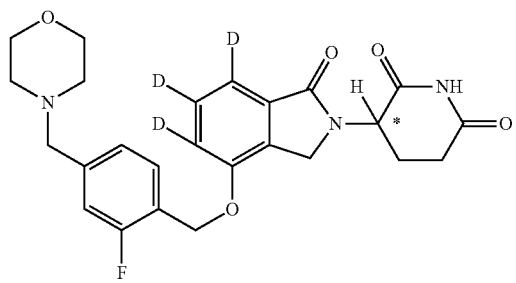
A1108
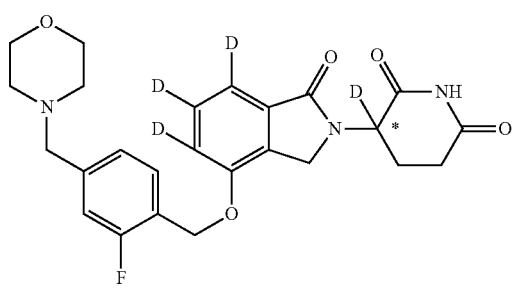
A1109
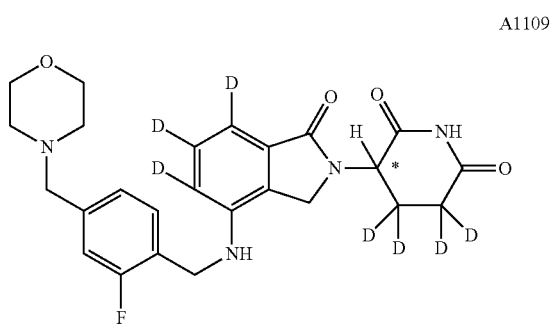
A1110
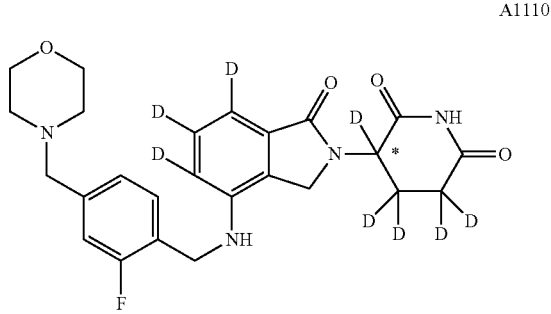
A1111
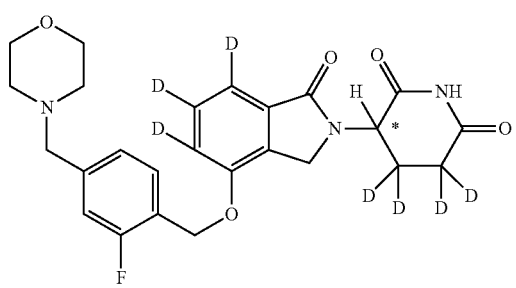
A1112
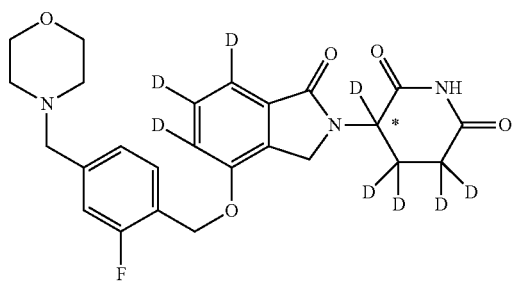

449
-continued
A1113
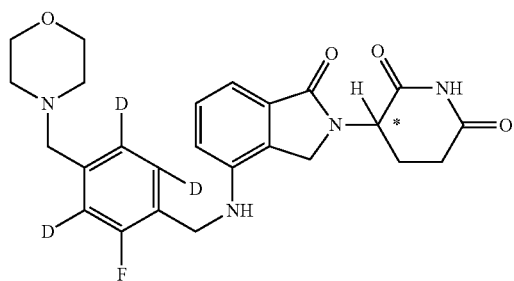
A1114
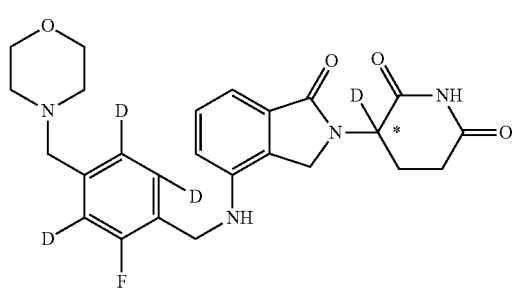
A1115
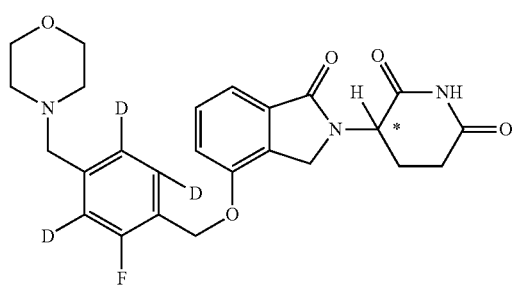
A1116
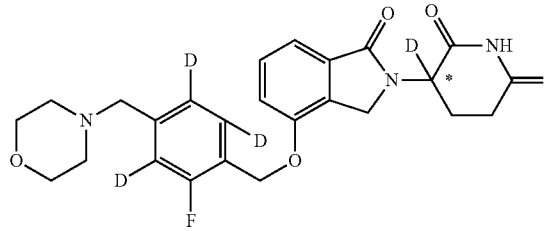
A1117
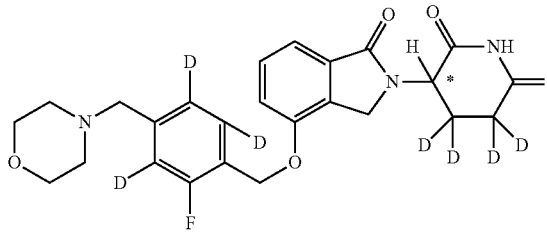
450
-continued
A1118
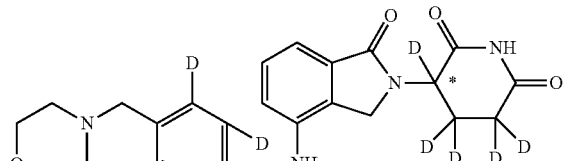
A1119
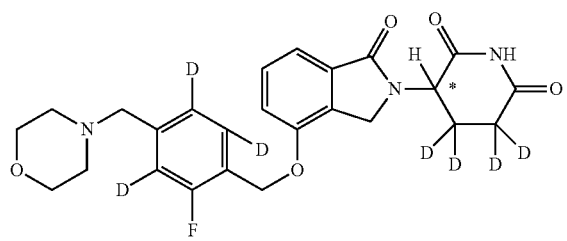
A1120
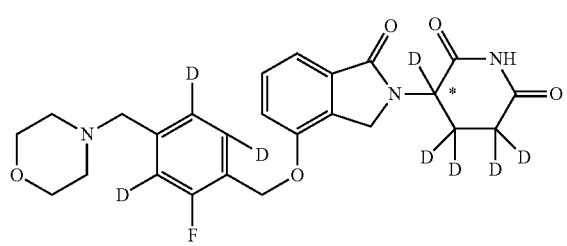
A1121
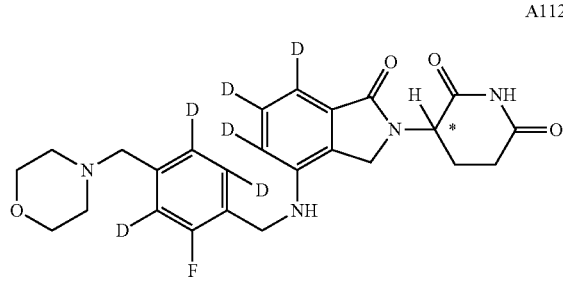
A1122
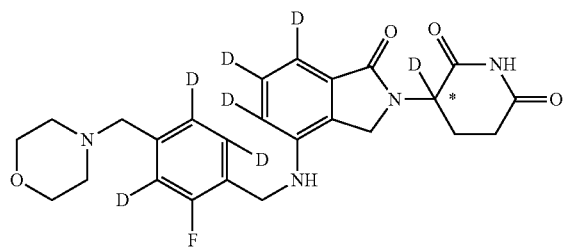
A1123
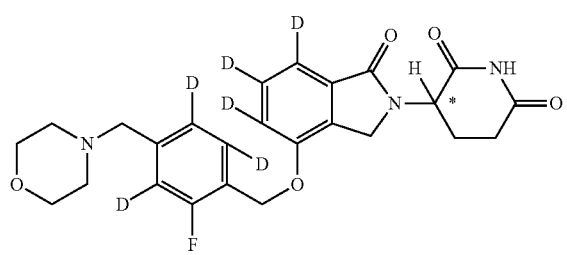

A1124
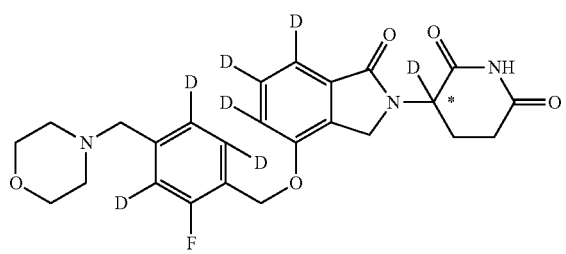
A1130
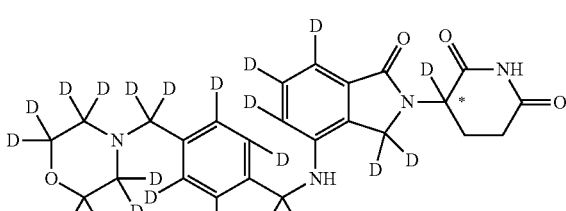
A1125
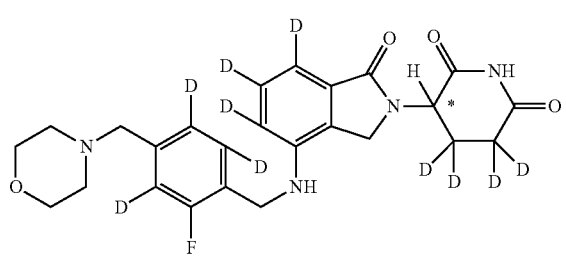
A1131
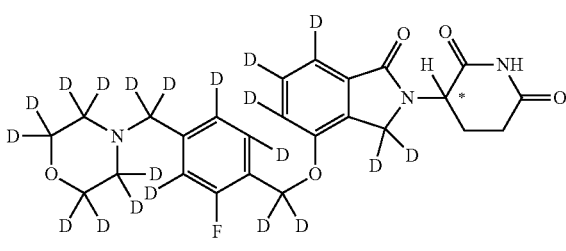
A1126
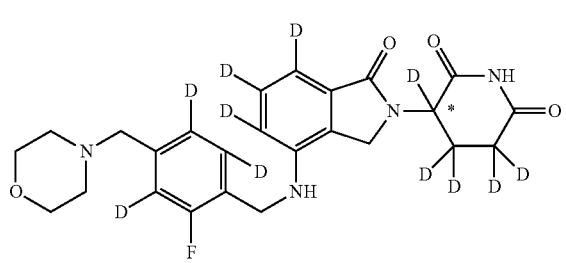
A1132
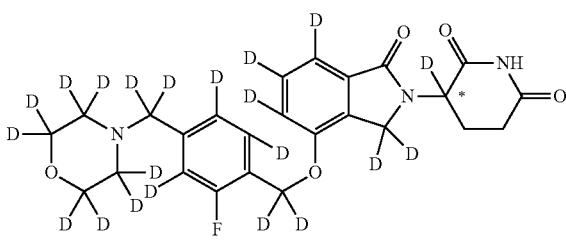
A1127
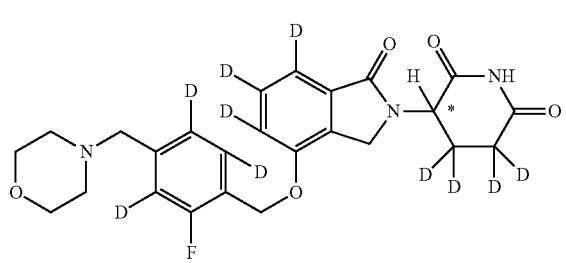
A1133
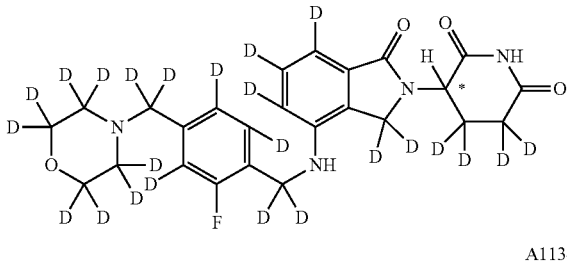
A1128
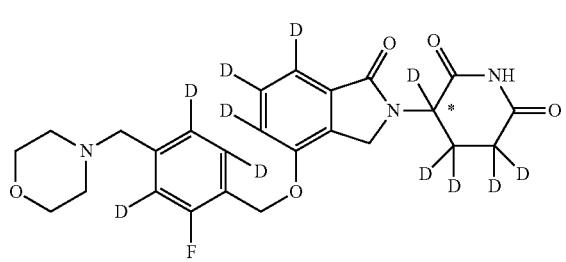
A1134
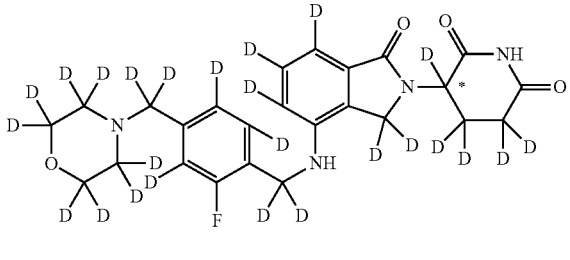
A1129
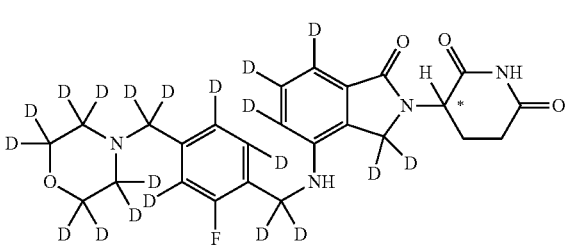
A1135
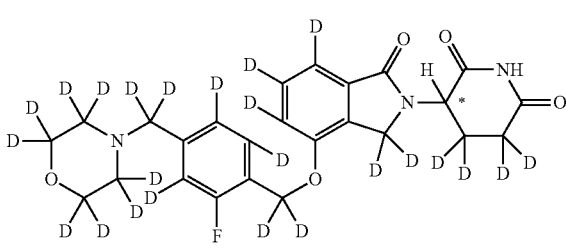

453
-continued
A1136
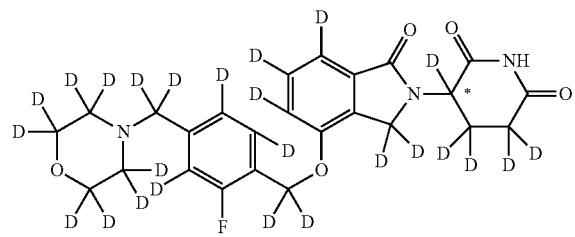
A383
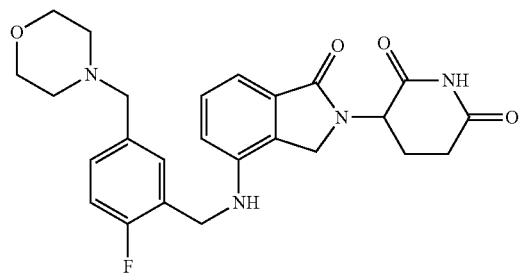
A1137
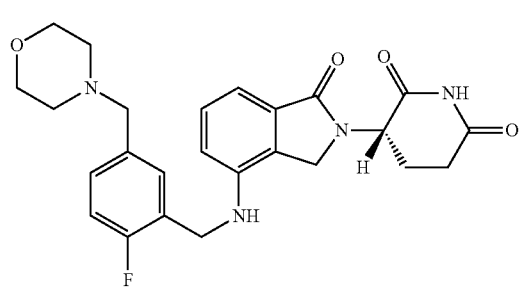
A1138
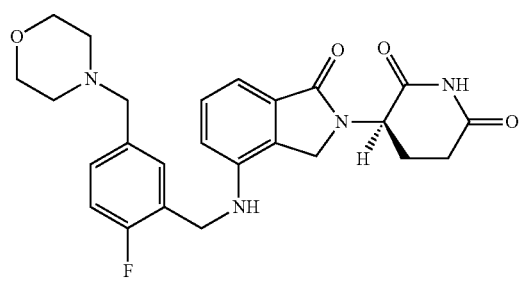
A1139
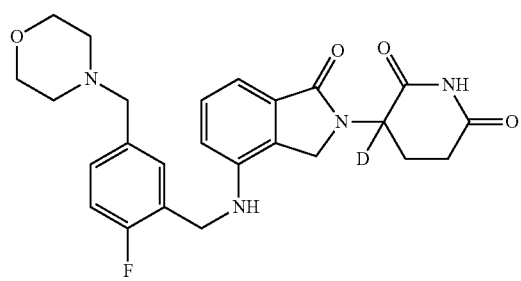
454
-continued
A401
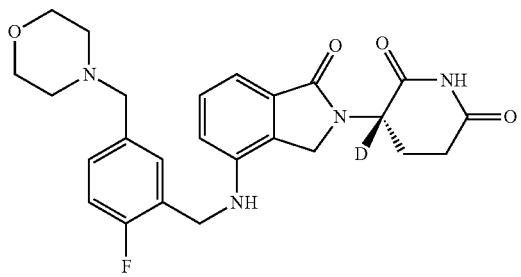
A1140
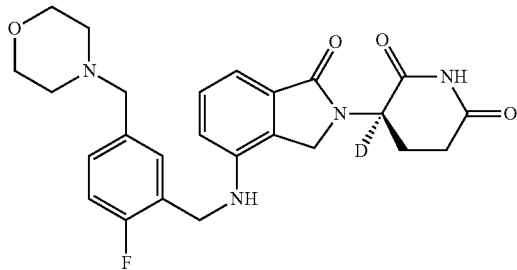
A398
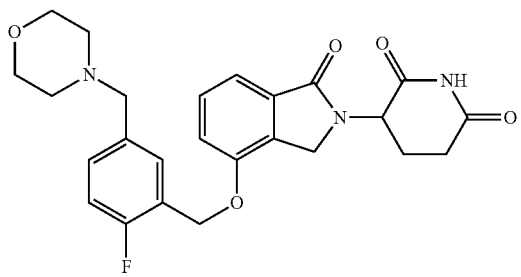
A1141
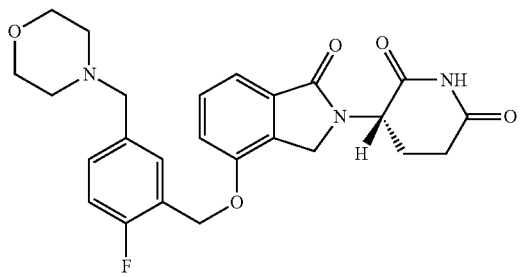
A1142
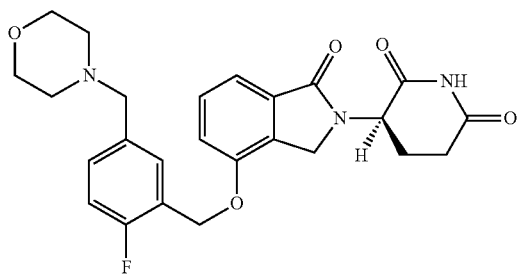

A1143
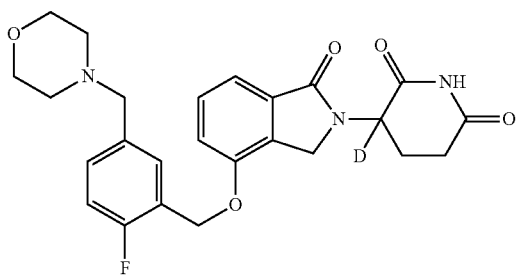
A403
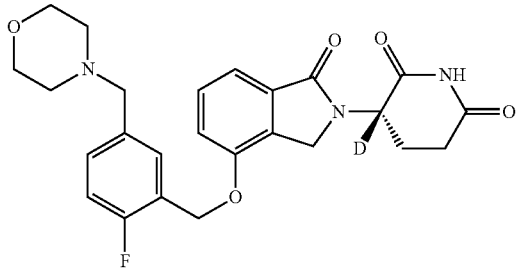
A1144
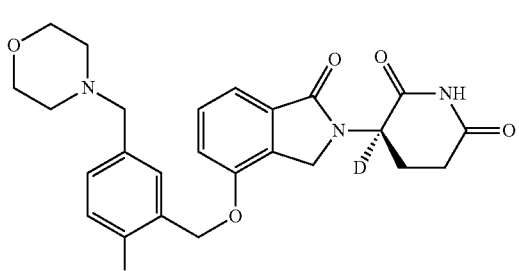
A1145
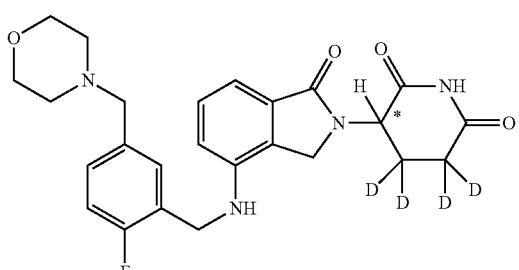
A1146
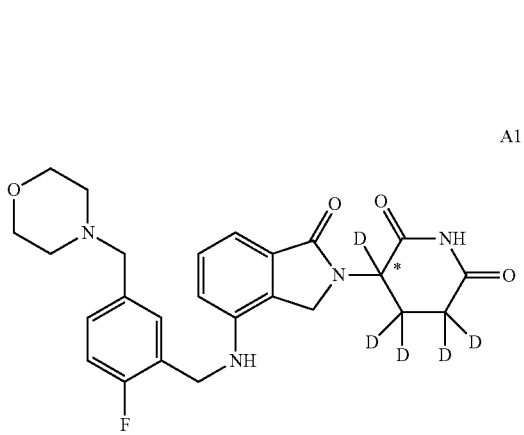
A1147
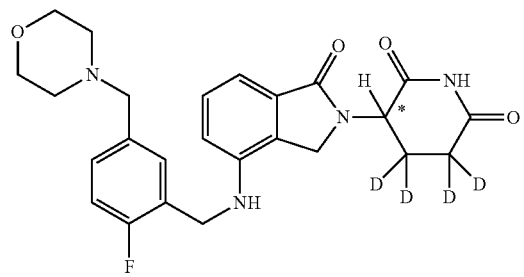
A1148
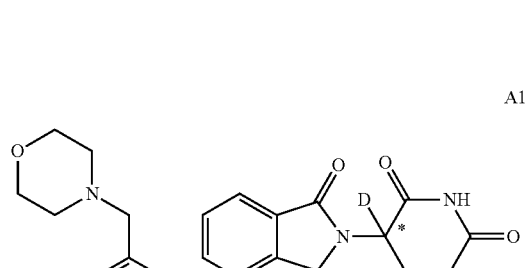
A1149
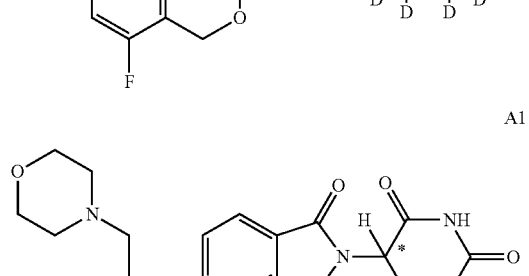
A1150
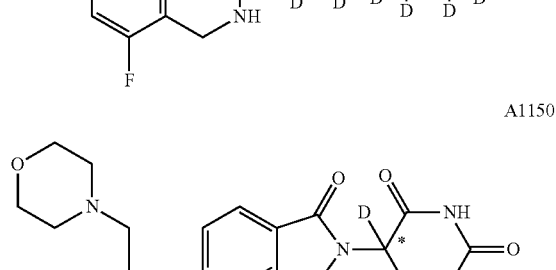
A1151
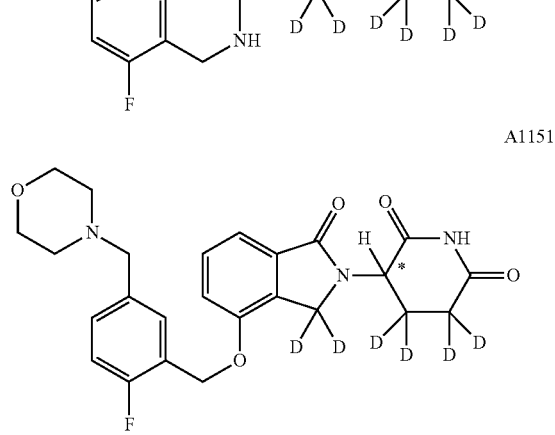

457
-continued
A1152
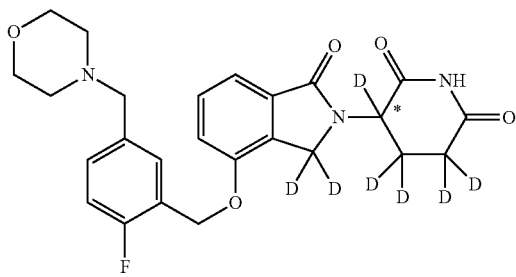
A1153
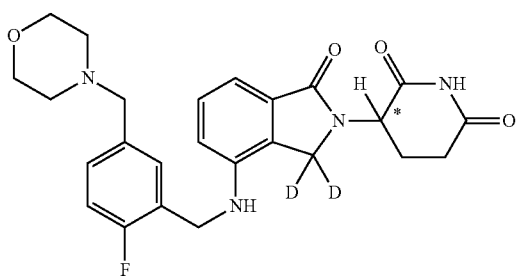
A1154
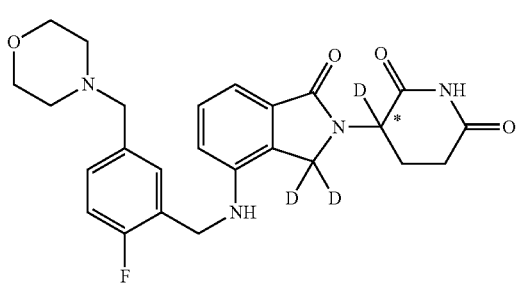
A1155
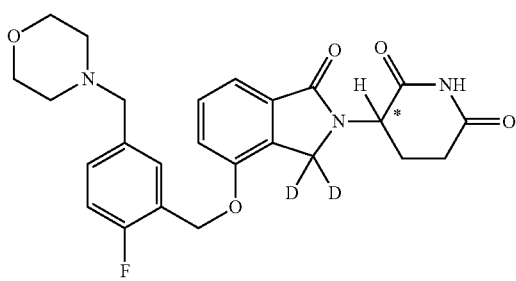
A1156
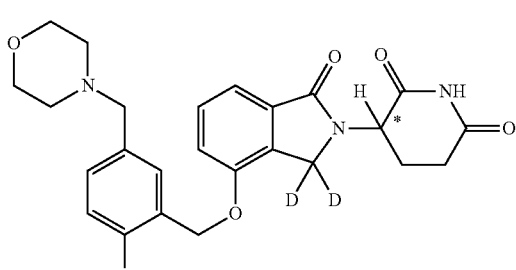
458
-continued
A1157
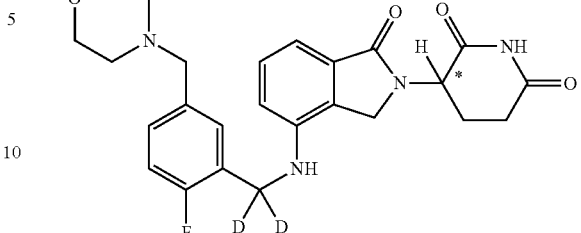
A1158
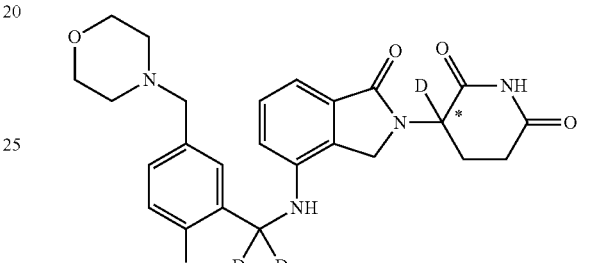
A1159
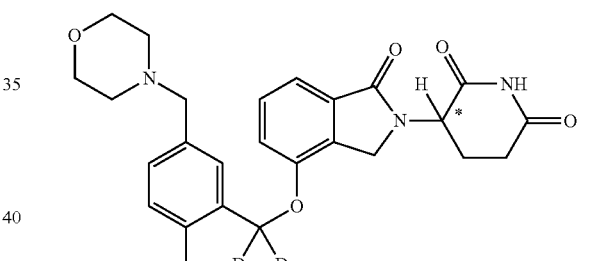
A1160
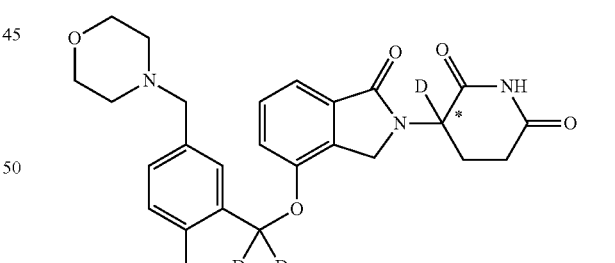
A1161
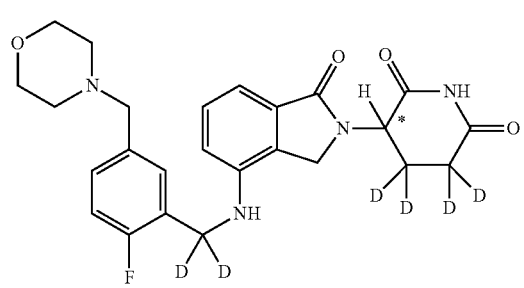

-continued
A1162
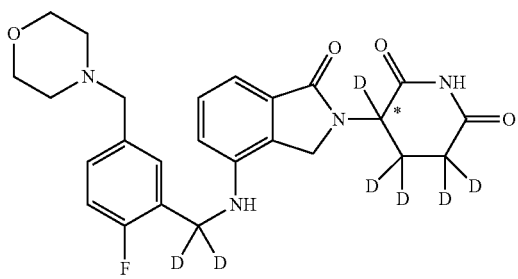
A1163
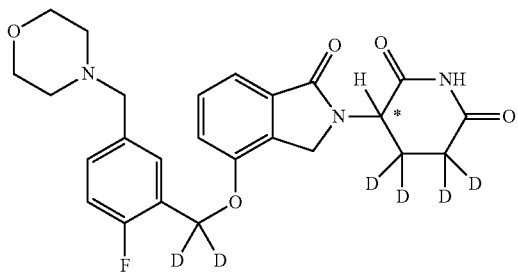
A1164
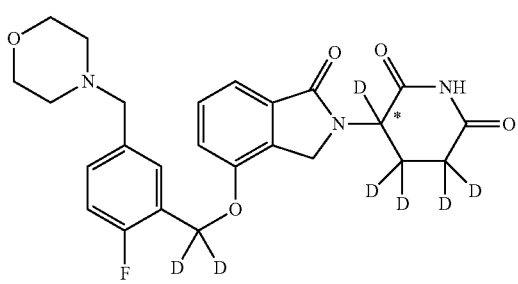
A1165
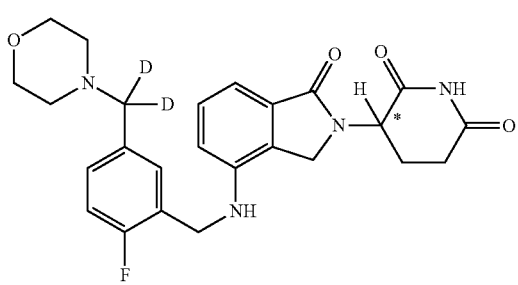
A1166
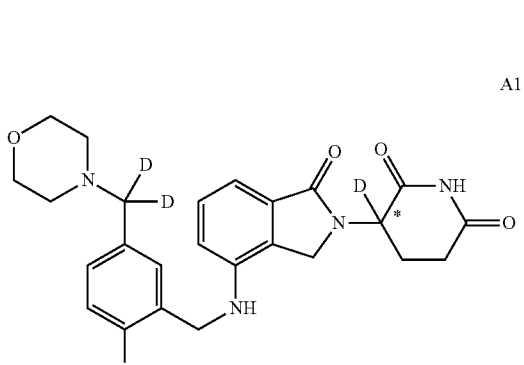
-continued
A1167
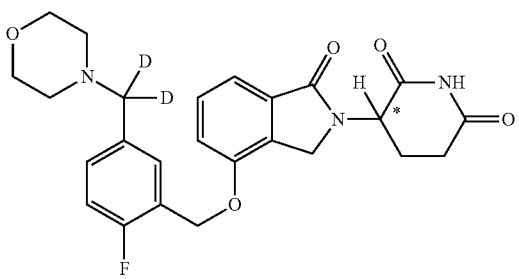
A1168
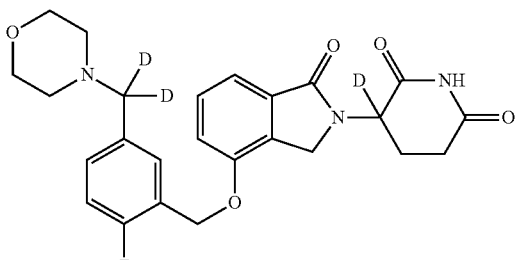
A1169
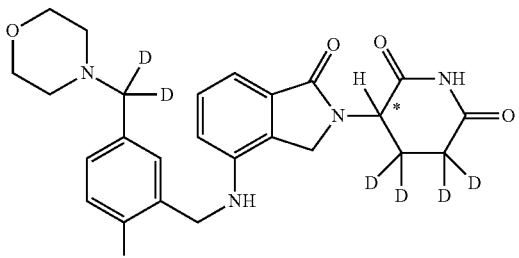
A1170
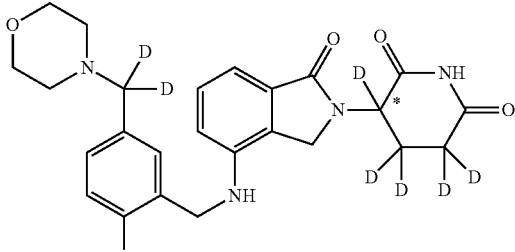
A1171
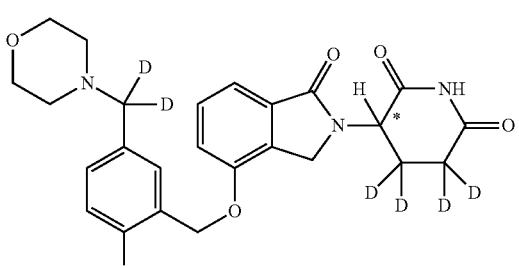

A1172
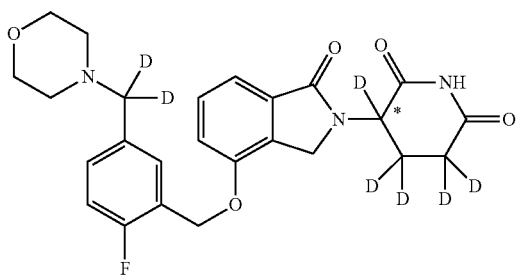
A1173
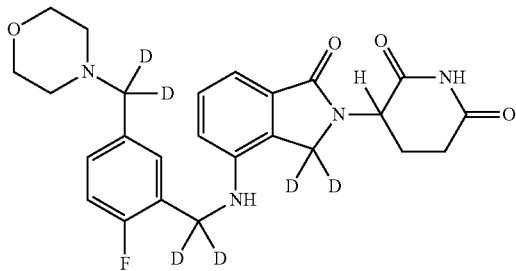
A1174
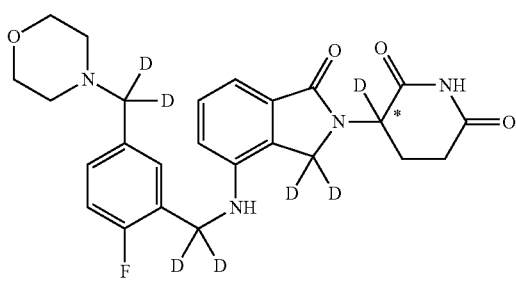
A1175
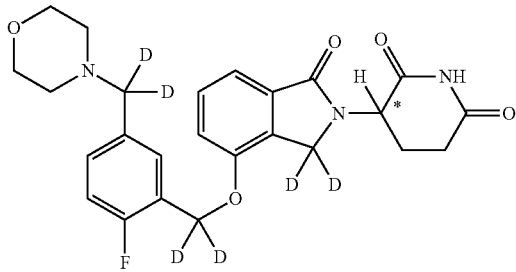
A1176
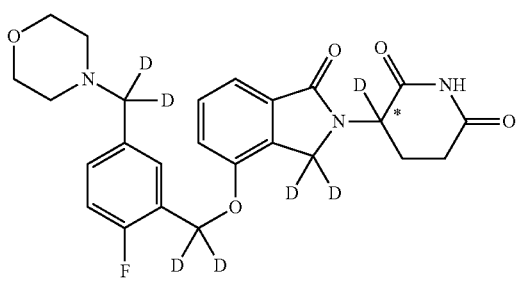
A1177
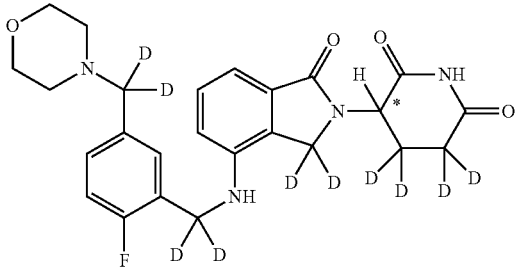
A1178
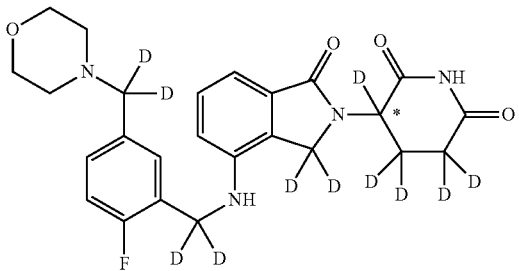
A1179
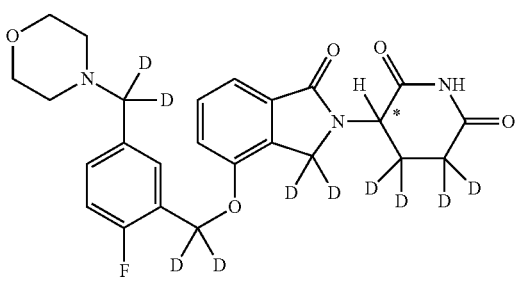
A1180
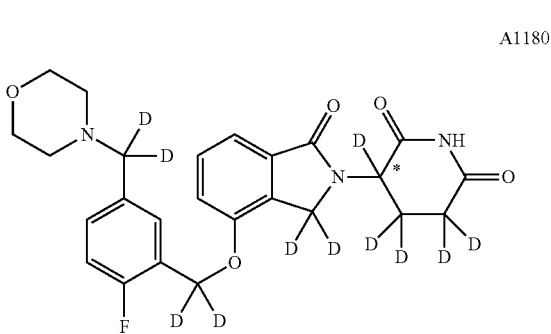
A1181
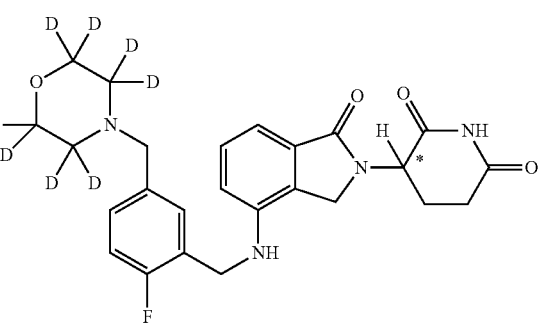

A1182 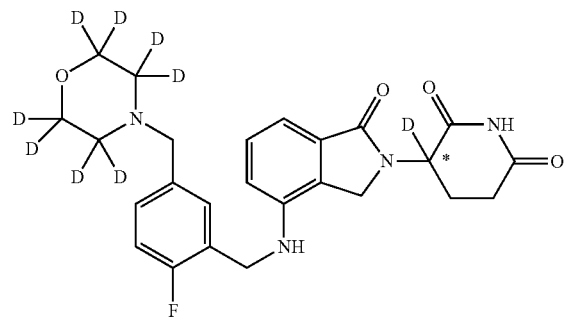
A1186 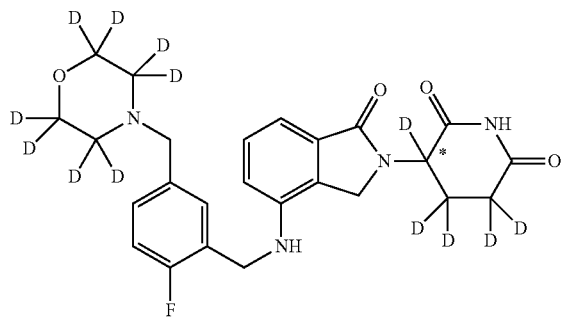
A1183 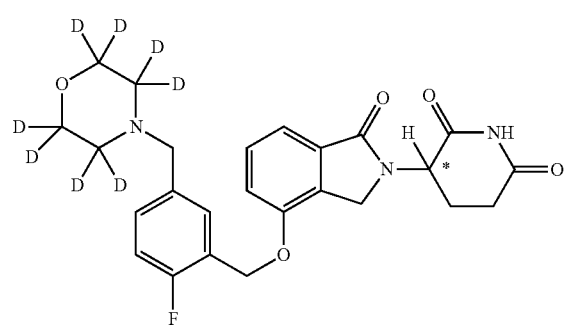
A1187 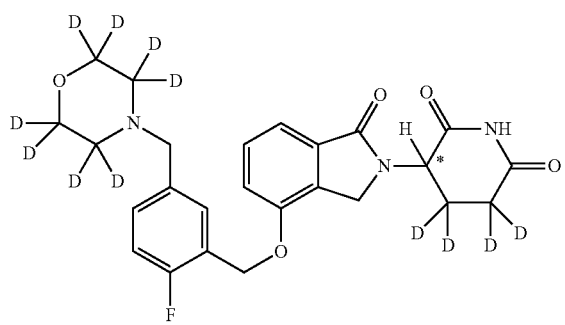
A1184 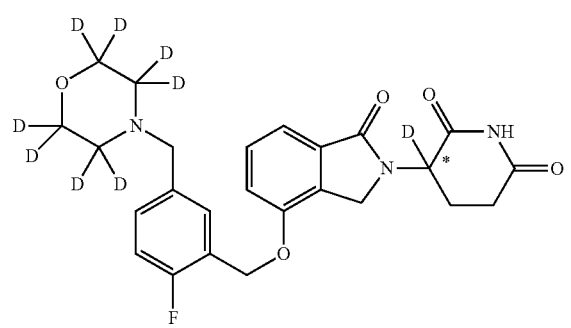
A1188 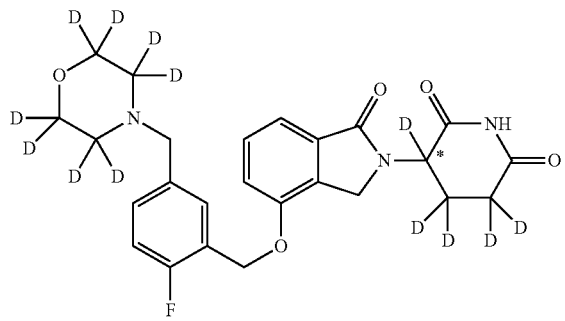
A1185 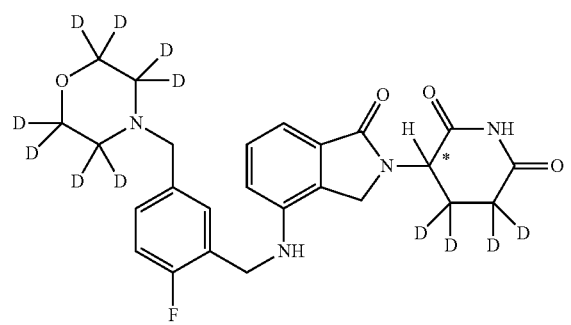
A1189 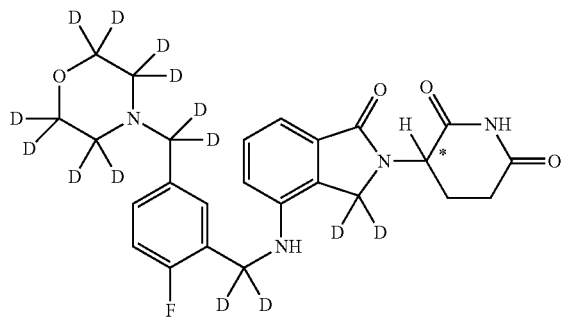

A1190
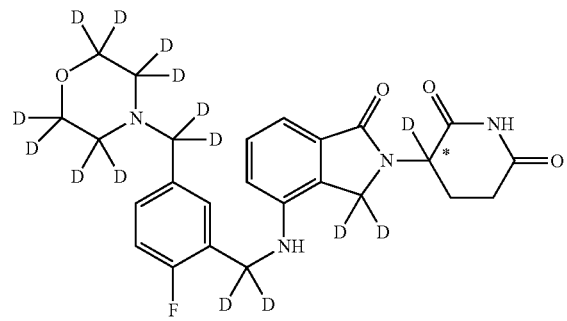
A1191
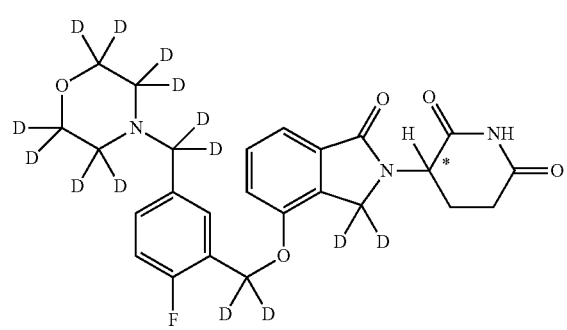
A1192
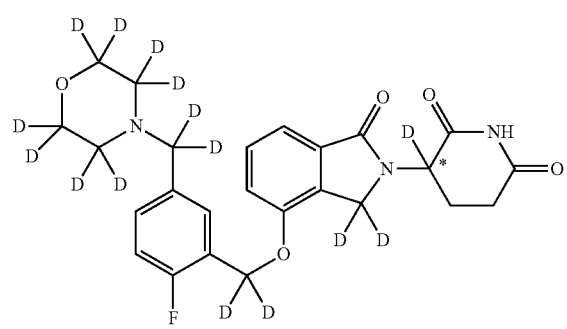
A1193
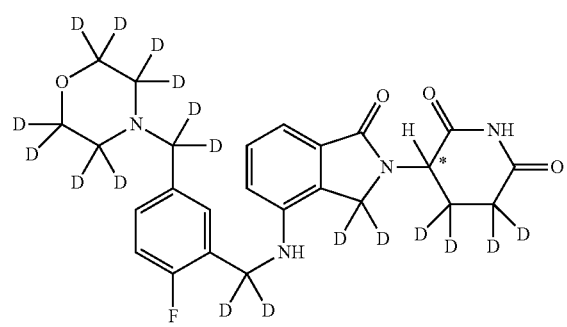
A1194
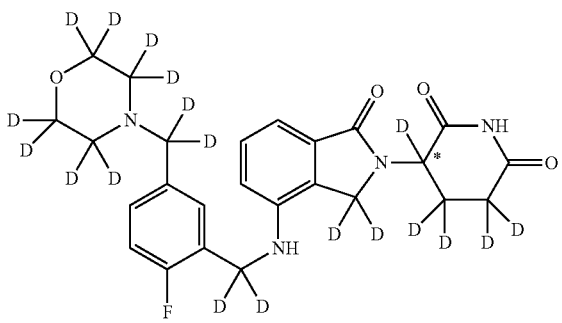
A1195
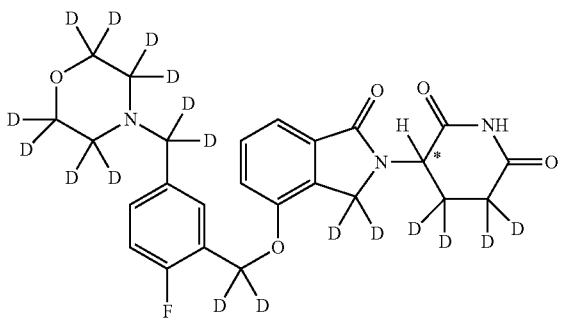
A1196
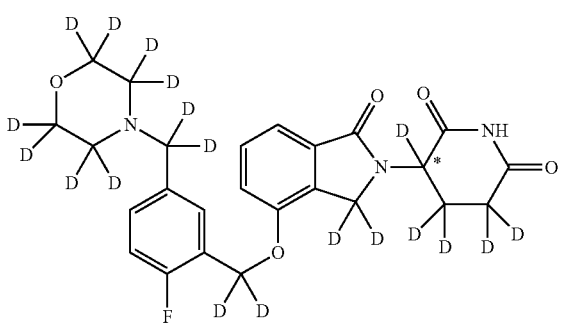
A1197
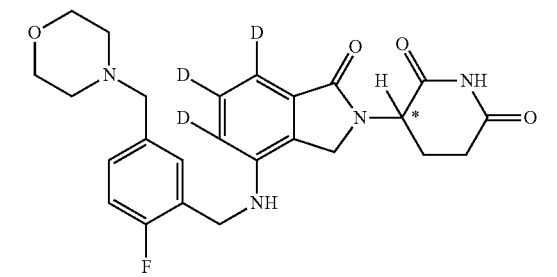
A1198
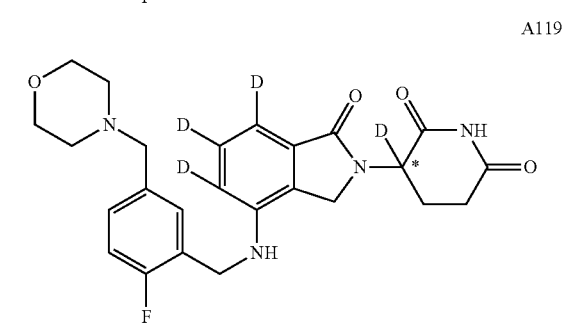

A1199
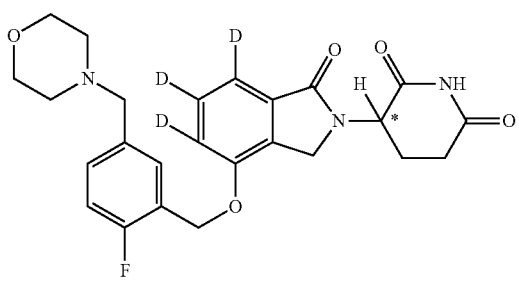
A1200
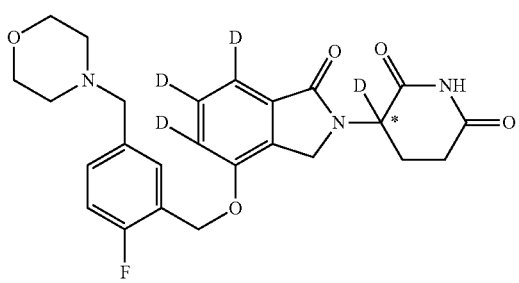
A1201
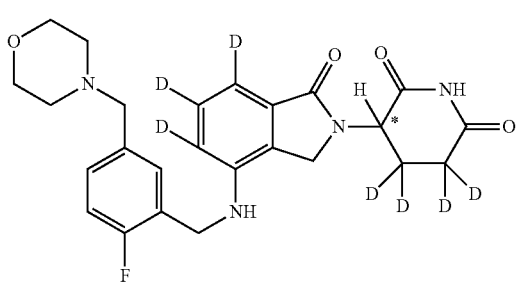
A1202
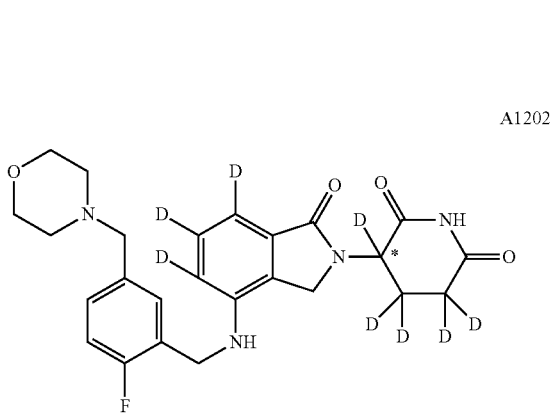
A1203
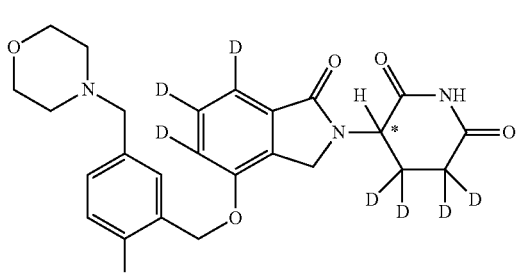
A1204
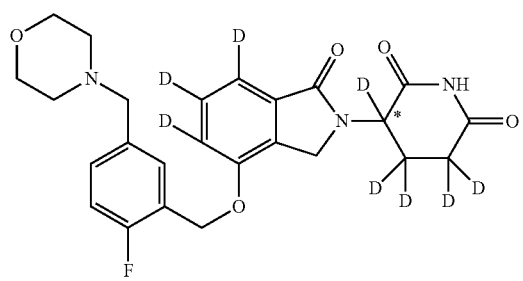
A1205
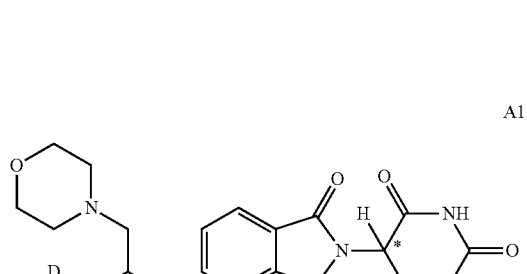
A1206
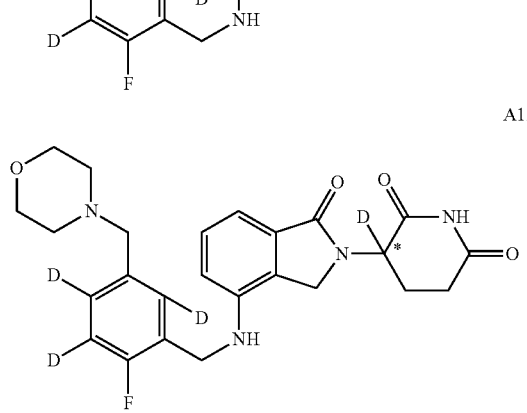
A1207
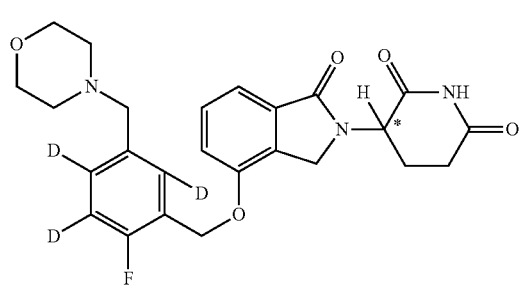
A1208
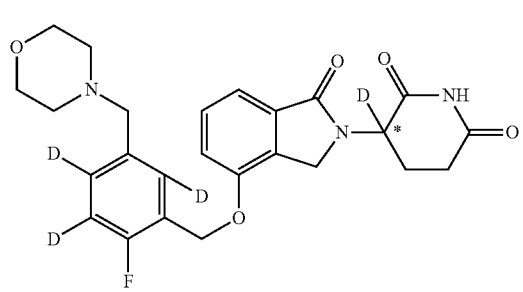

A1209
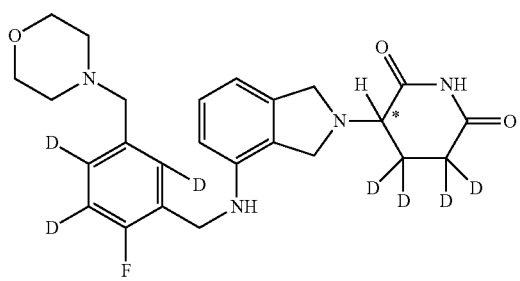
A1210
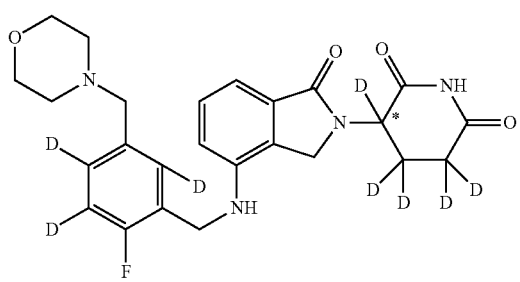
A1211
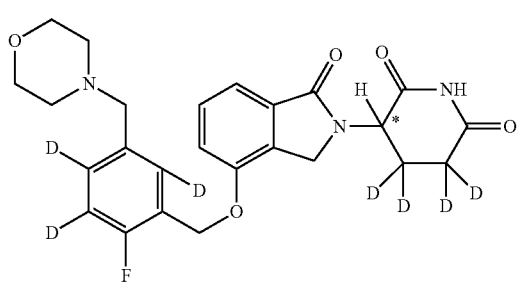
A1212
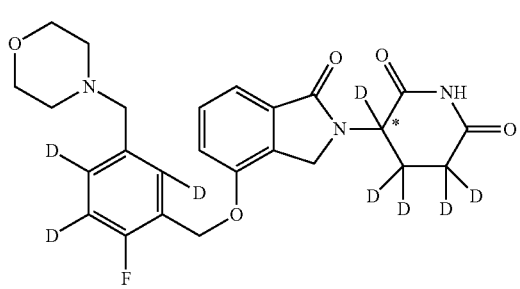
A1213
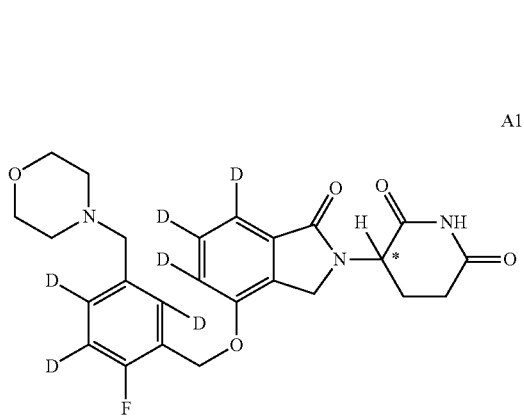
A1214
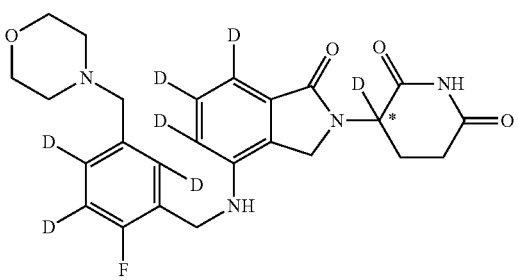
A1215
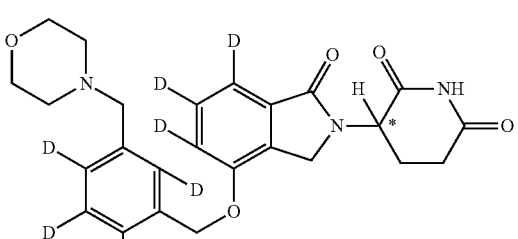
A1216
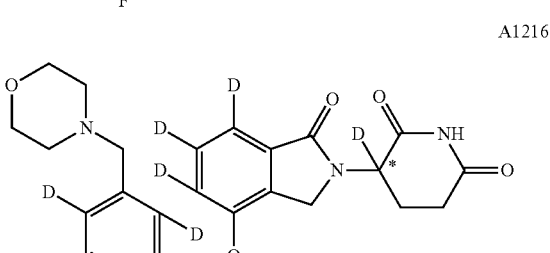
A1217
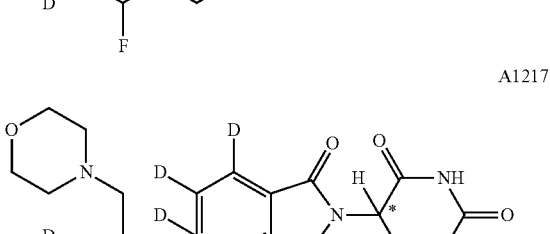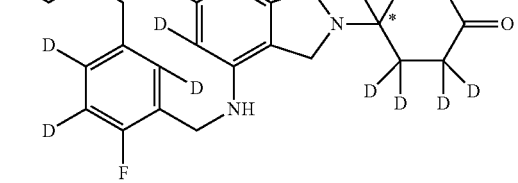
A1218
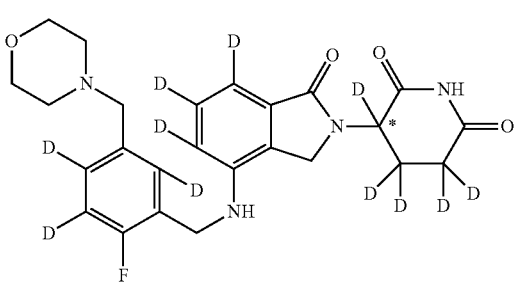

A1219
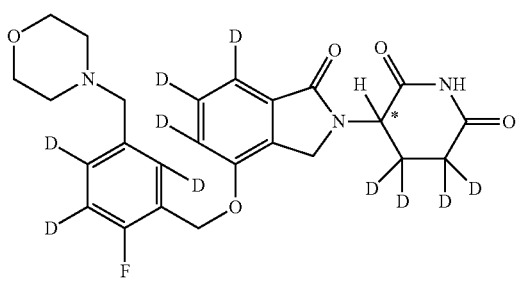
A1220
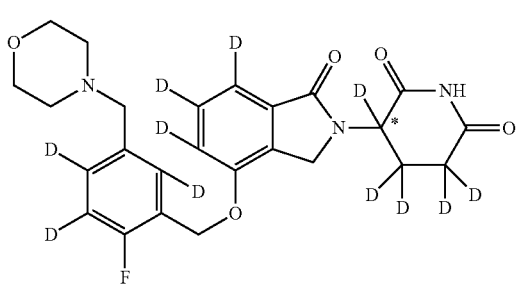
A1221
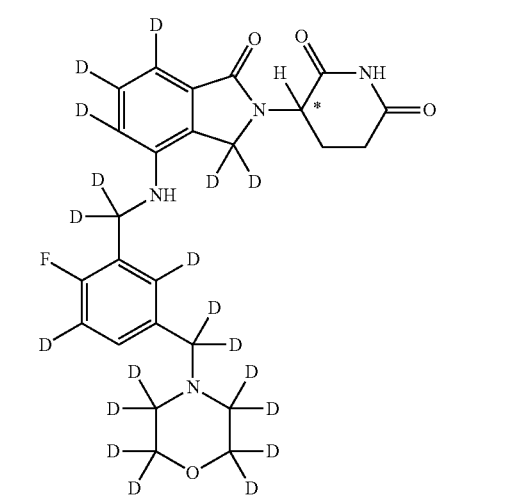
A1222
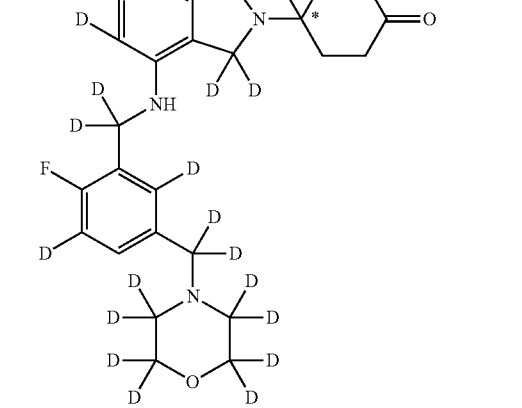
A1223
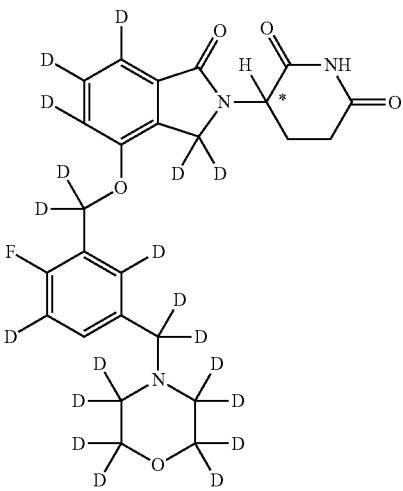
A1224
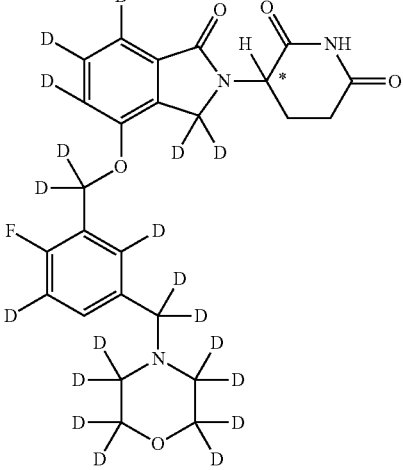
A1225
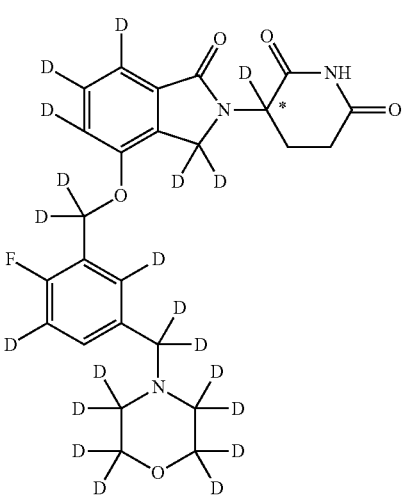

473
-continued
A1226
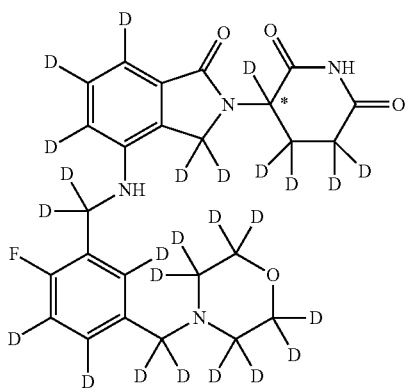
A1227
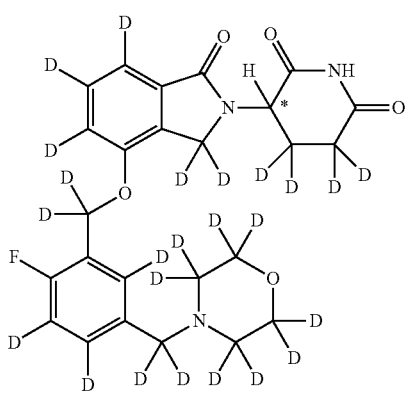
A1228
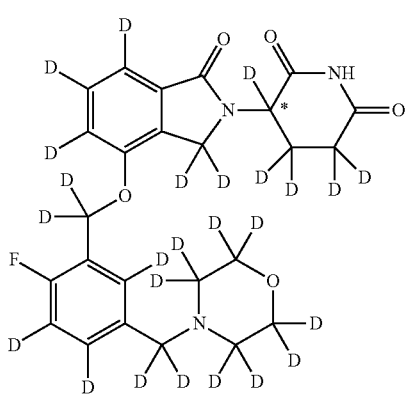
A1278
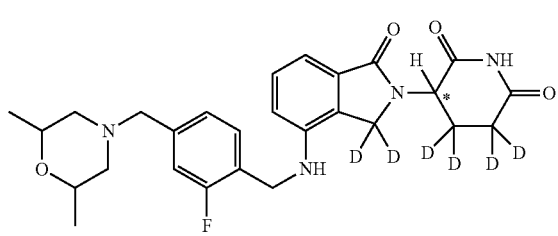
474
-continued
A1279
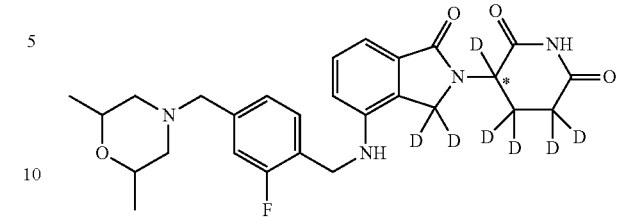
A1280
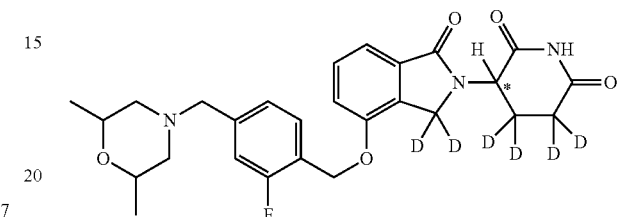
A1281
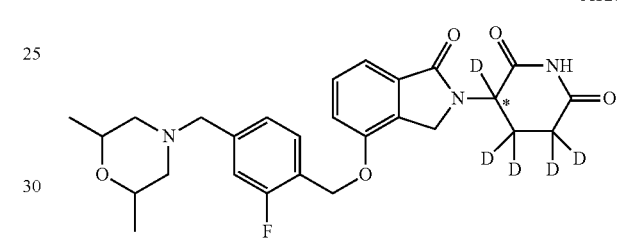
A1282
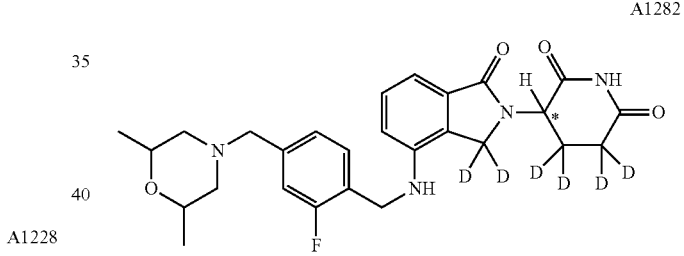
A1283
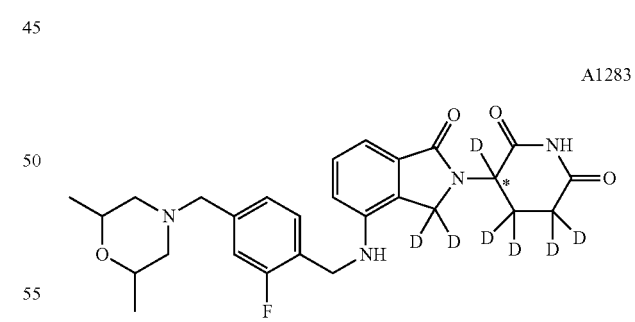
A1284
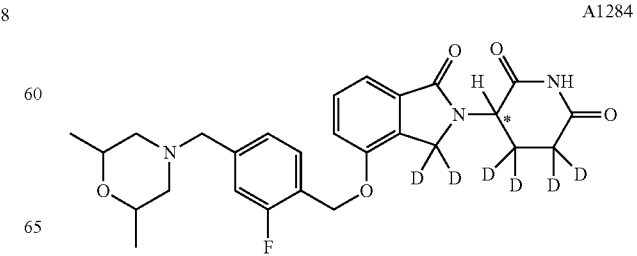

A1285
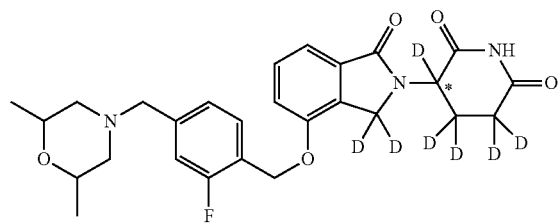
A1291
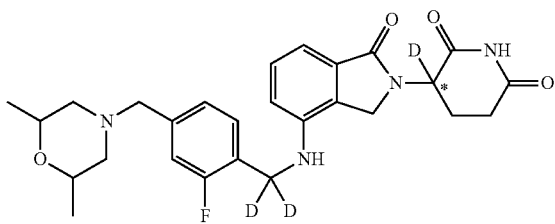
A1286
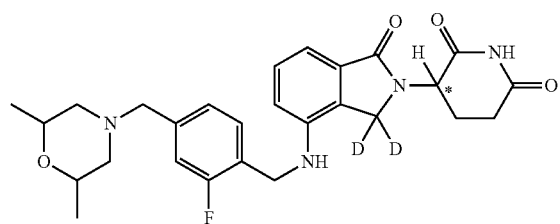
A1292
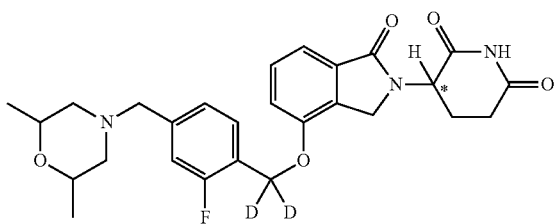
A1287
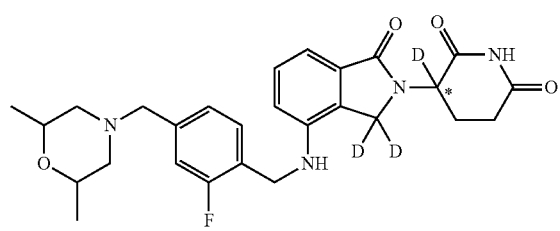
A1293
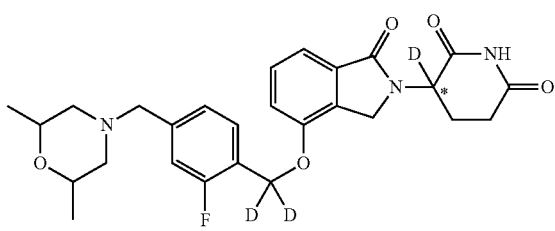
A1288
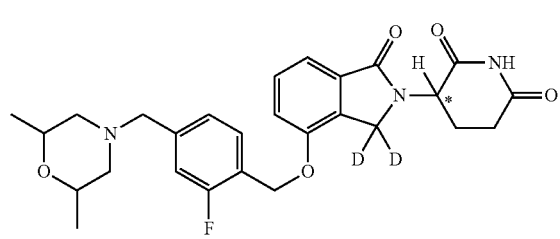
A1294
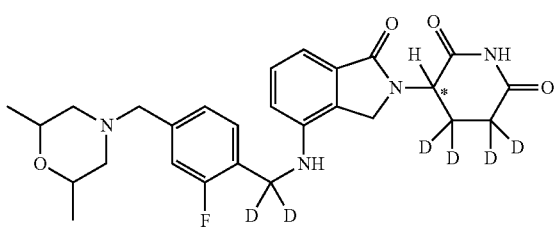
A1289
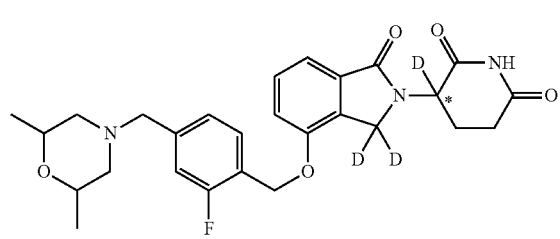
A1295
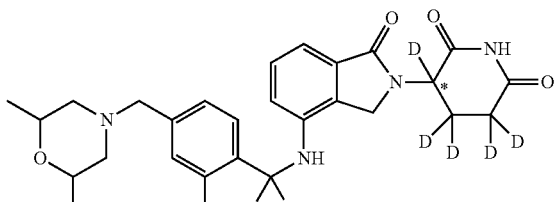
A1290
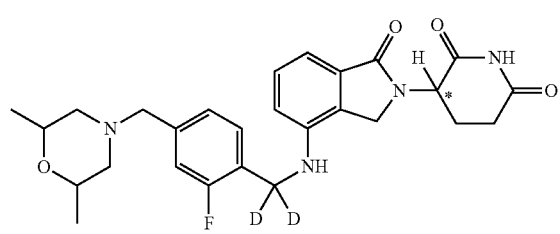
A1296

-continued
A1297
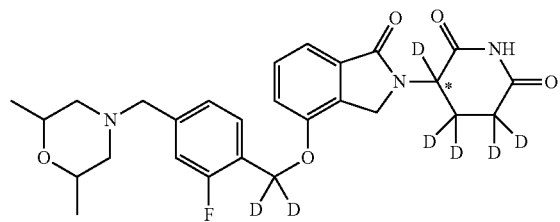
A1298
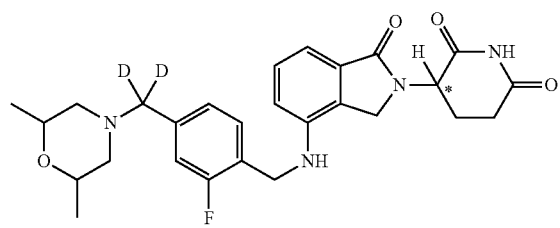
A1299
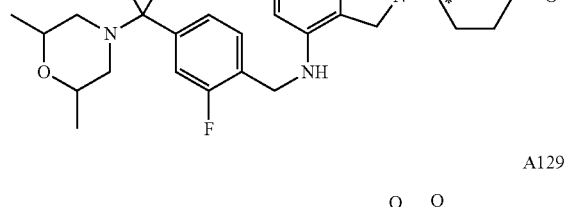
A1300
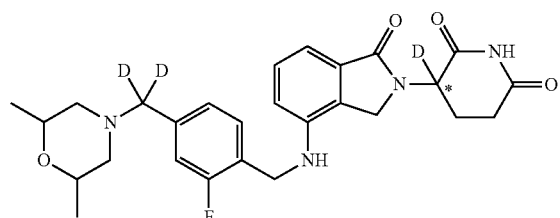
A1301
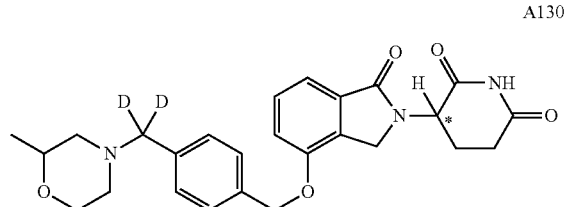
A1302
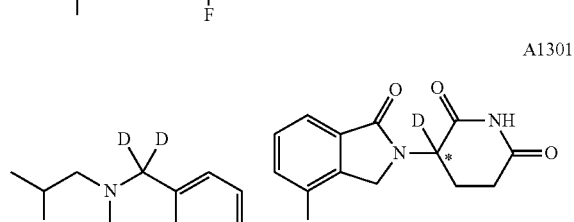
-continued
A1303
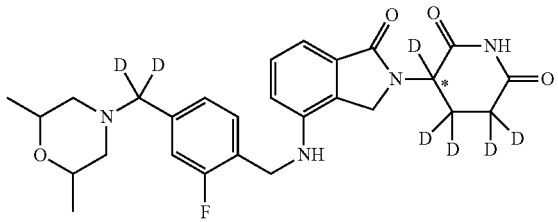
A1304
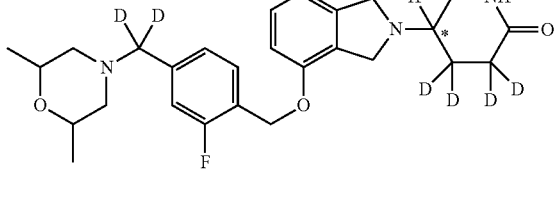
A1305
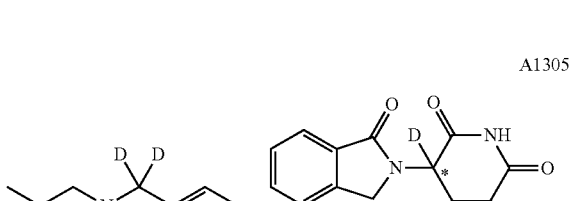
A1306
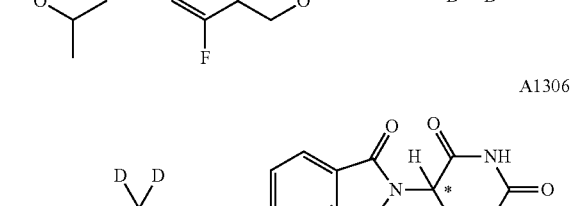
A1307
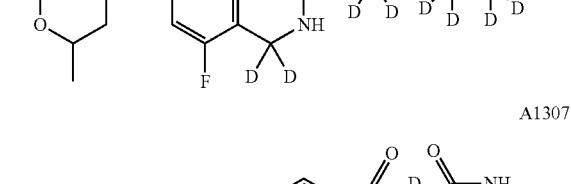
A1308
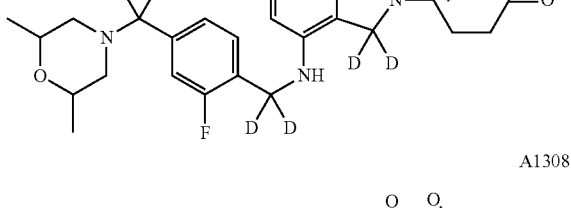

479
-continued
A1309
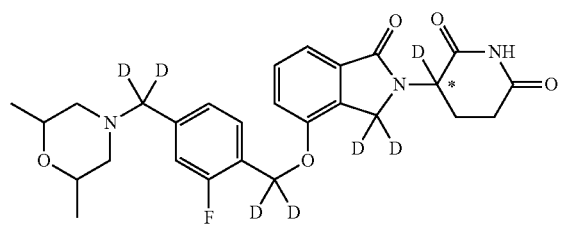
A1310
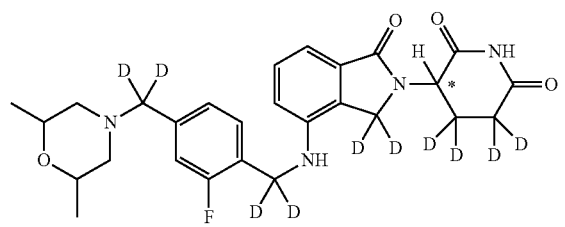
A1311
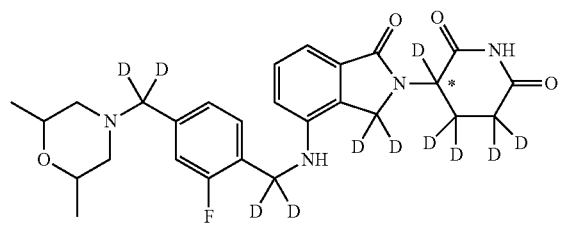
A1312
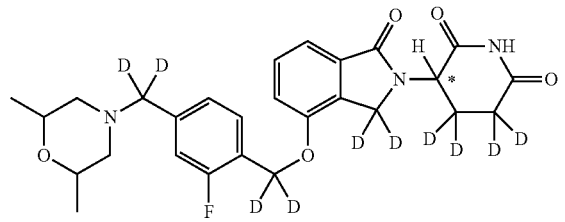
A1313
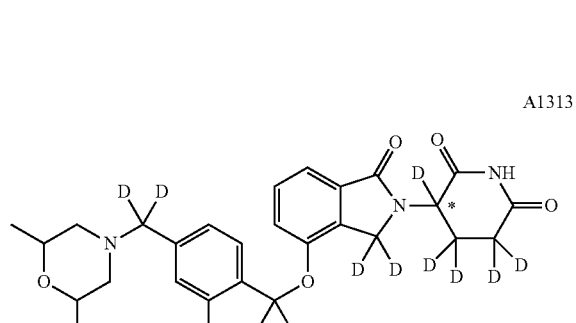
A1314
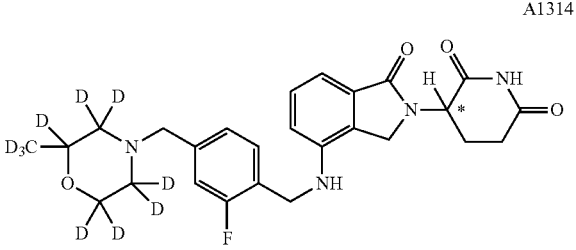
480
-continued
A1315
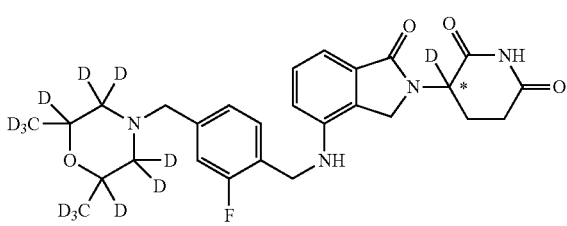
A1316
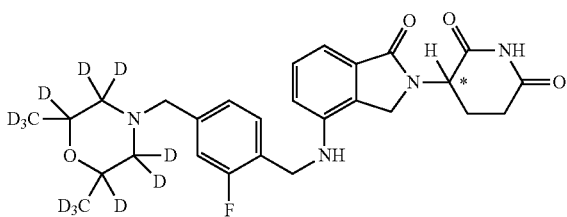
A1317
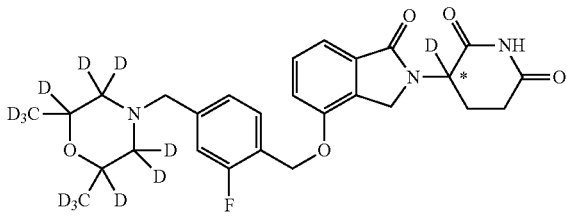
A1318
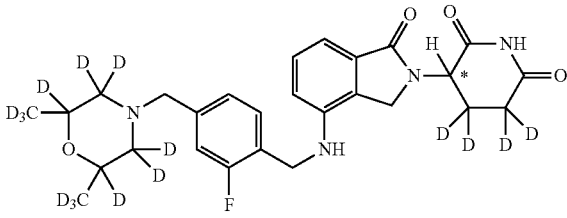
A1319
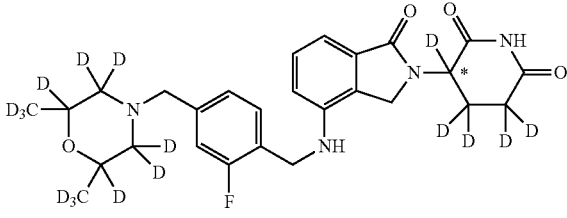
A1320
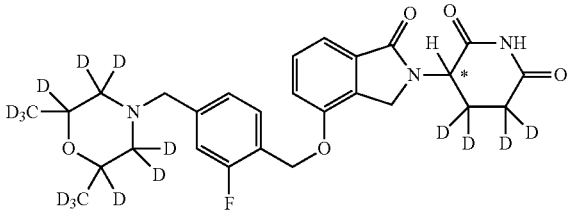

A1321
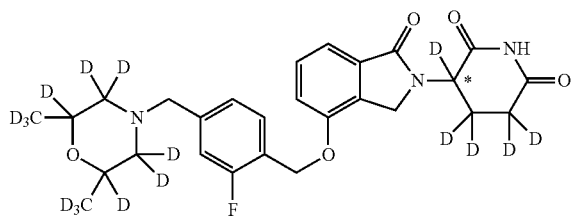
A1327
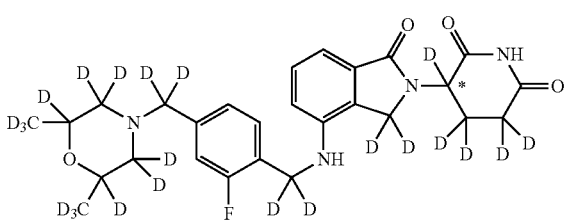
A1322
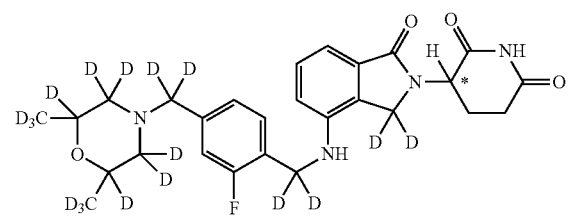
A1328
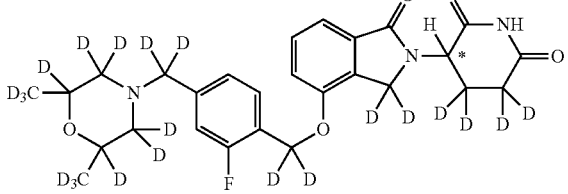
A1323
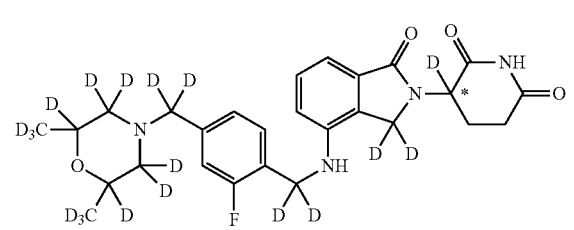
A1329
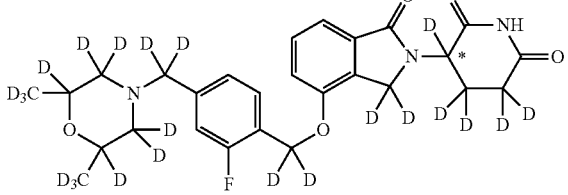
A1324
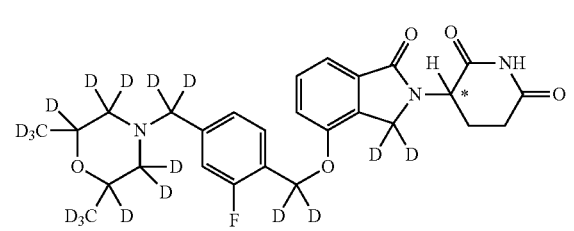
A1381
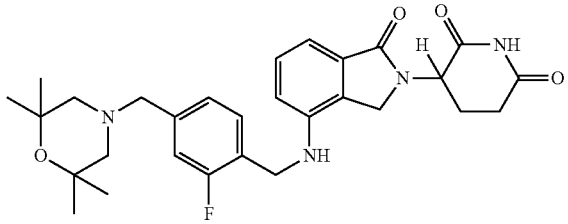
A1325
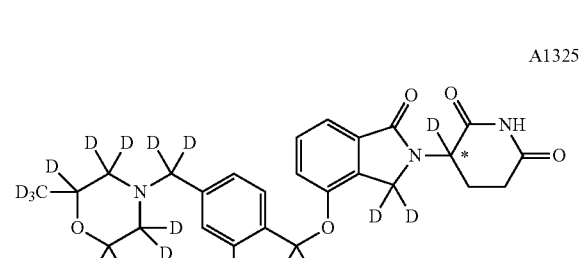
A1382
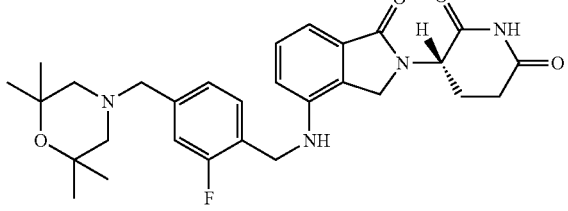
A1326
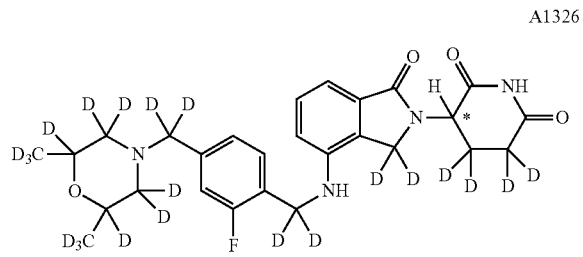
A1383
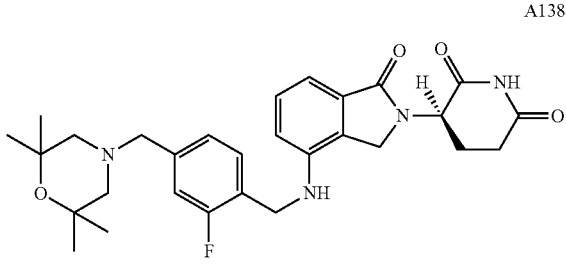

483
-continued
A1384
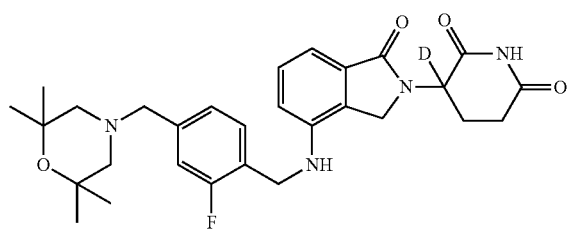
A1385
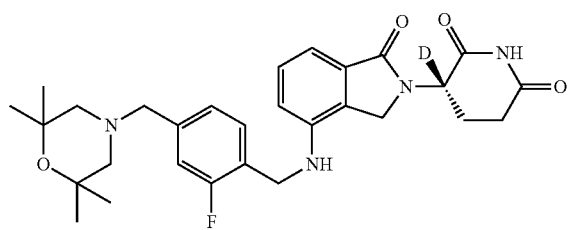
A1386
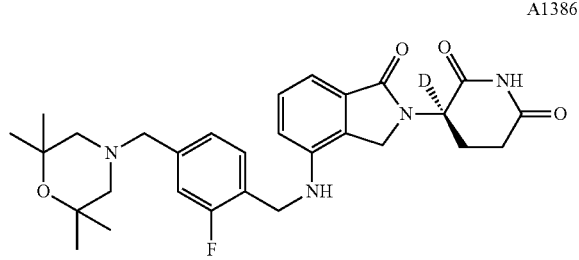
A1387
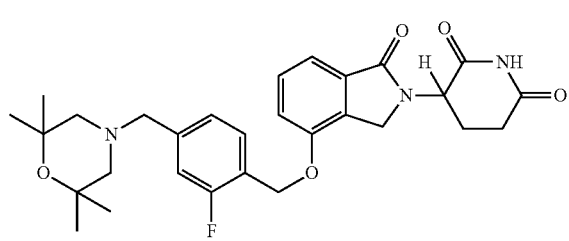
A1388
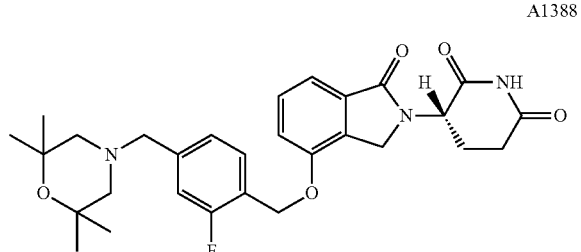
A1389
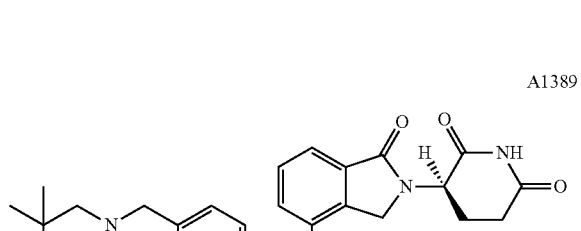
484
-continued
A1390
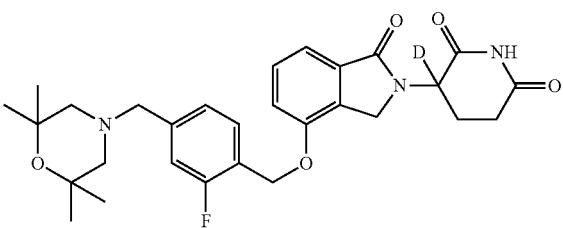
A1391
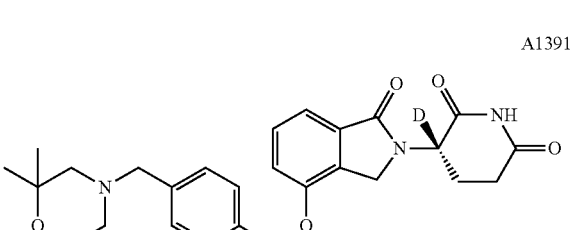
A1392
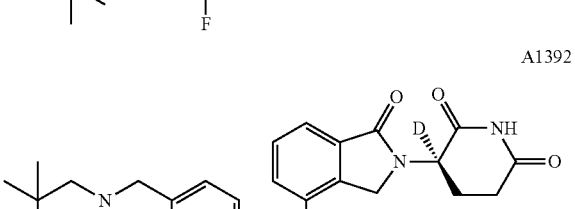
A1393
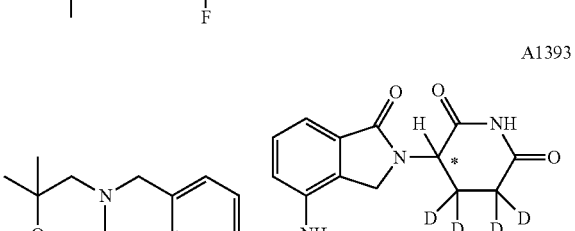
A1394
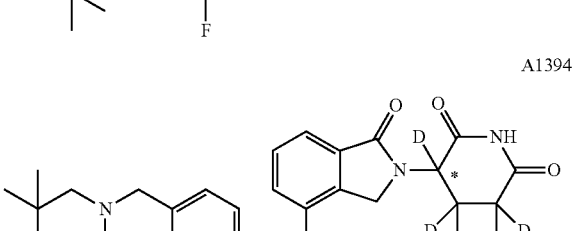
A1395
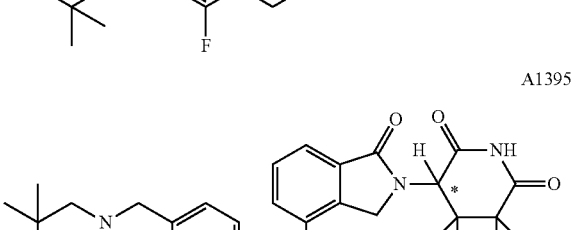

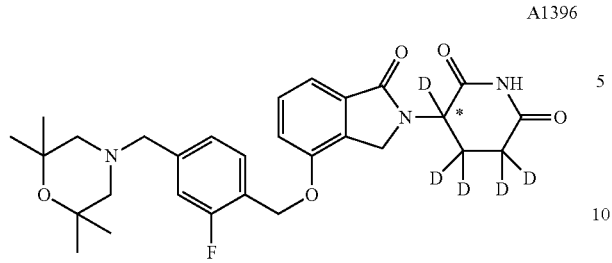
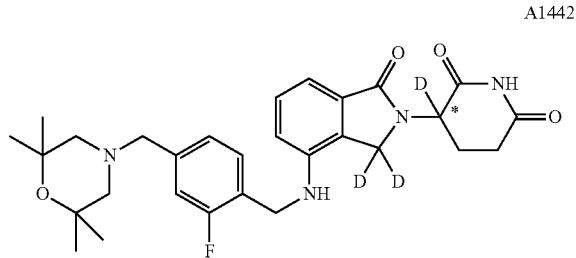

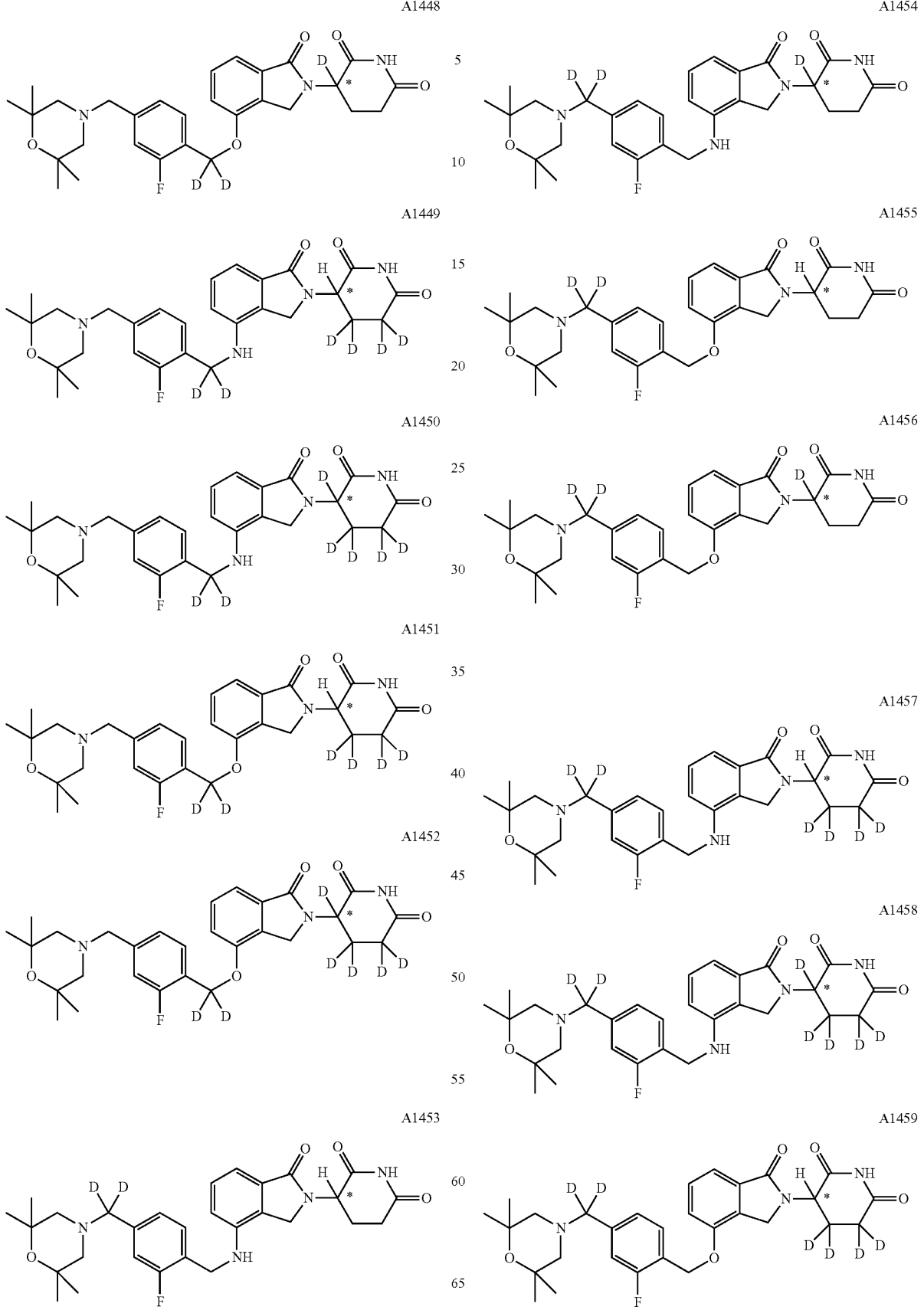

489
-continued
A1460
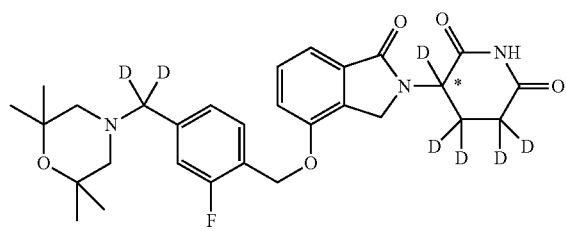
A1461
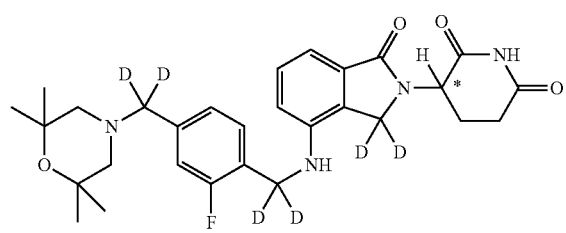
A1462
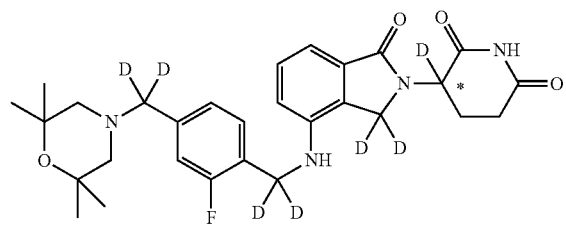
A1463
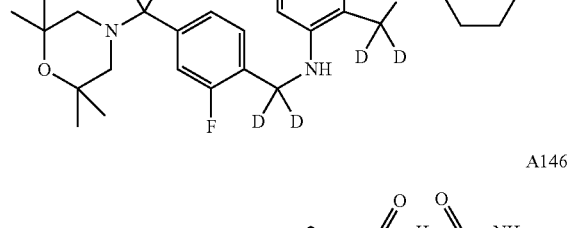
A1464
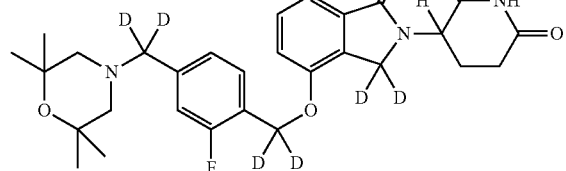
A1465
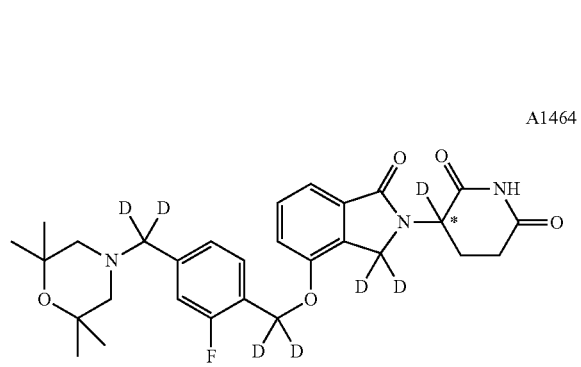
490
-continued
A1466
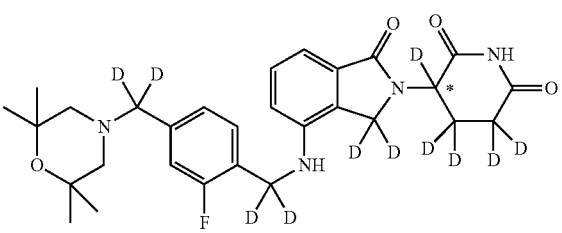
A1467
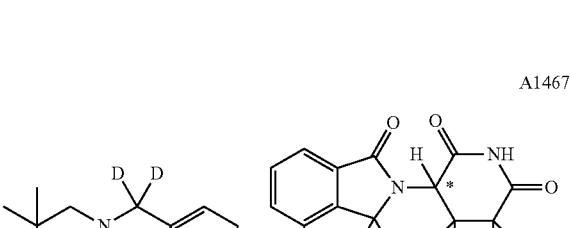
A1468
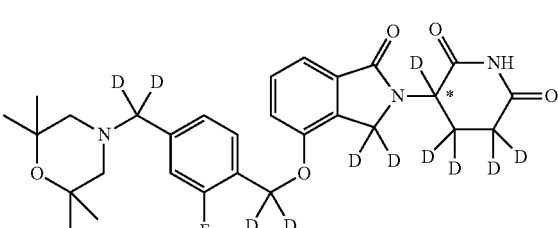
A1469
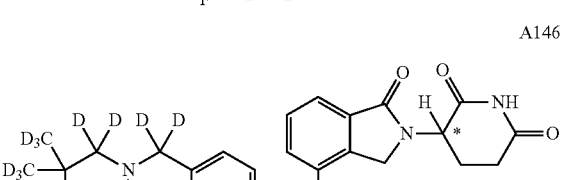
A1470
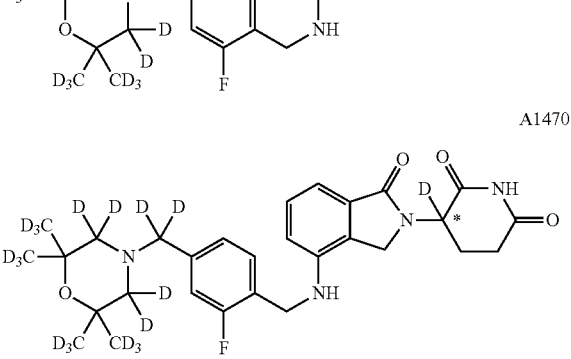
A1471
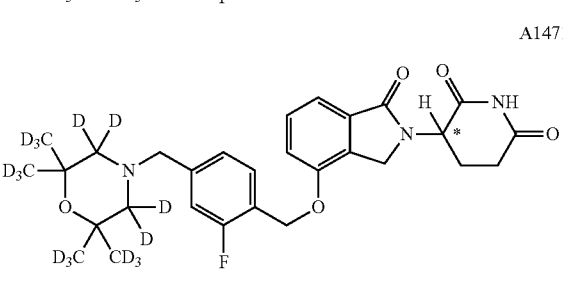

491
-continued
A1472
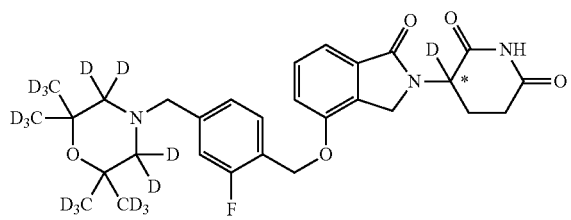
A1473
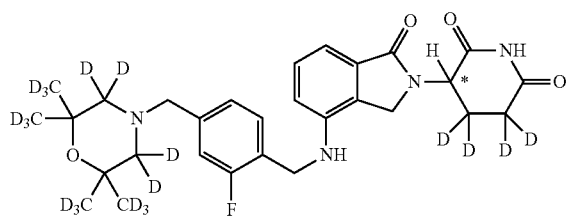
A1474
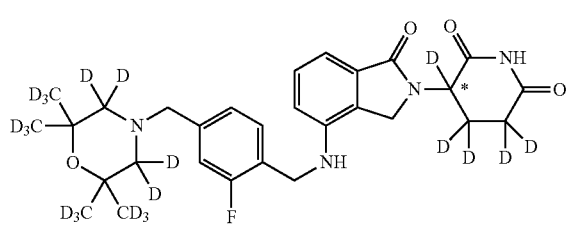
A1475
A1476
A1477
492
-continued
A1478
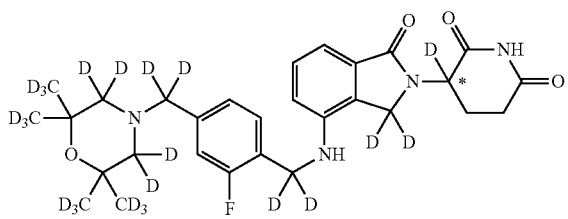
A1479
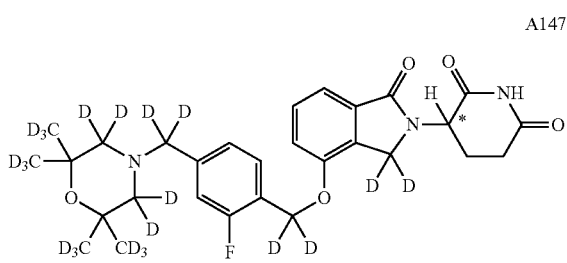
A1480
A1481
A1482
A1483

A1484
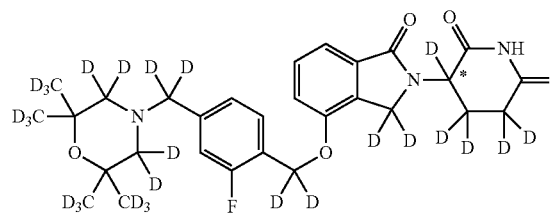
A1536
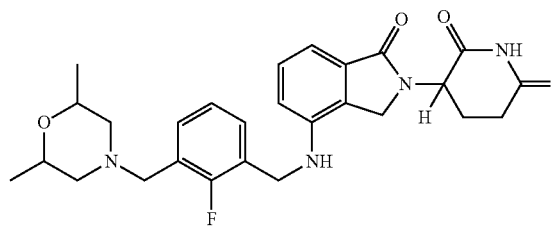
A1537
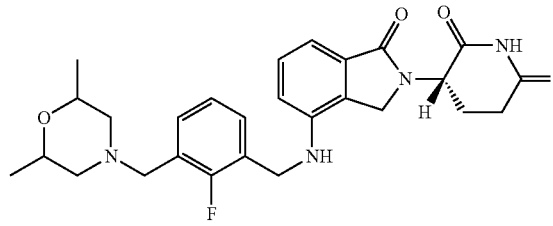
A1538
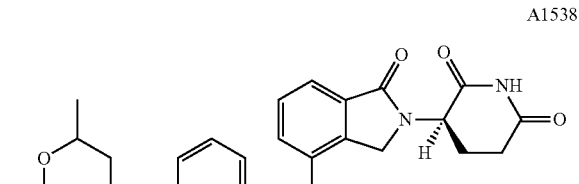
A1539
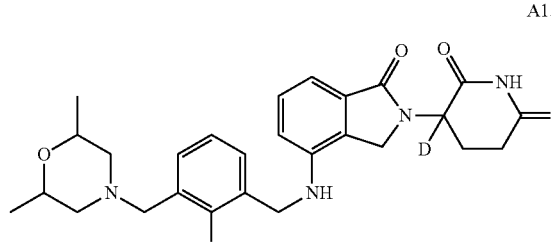
A1540
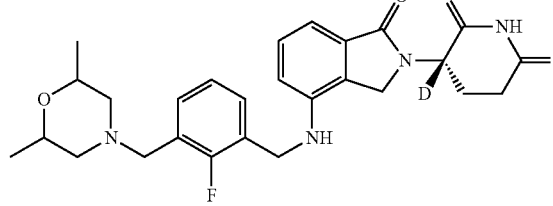
A1541
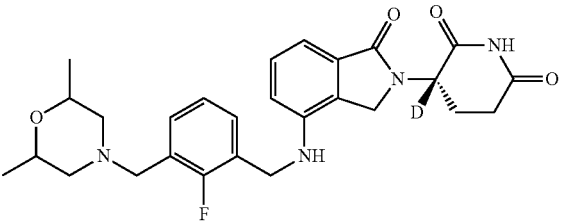
A1542
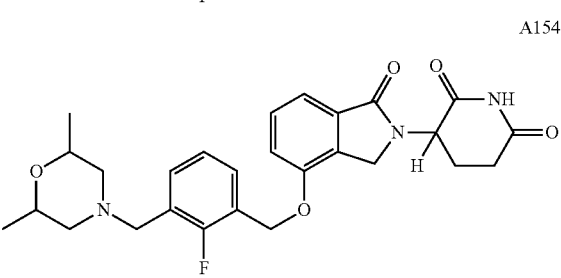
A1543
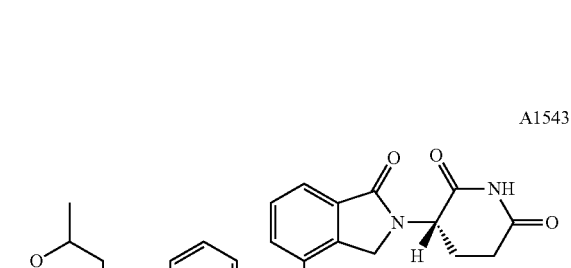
A1544
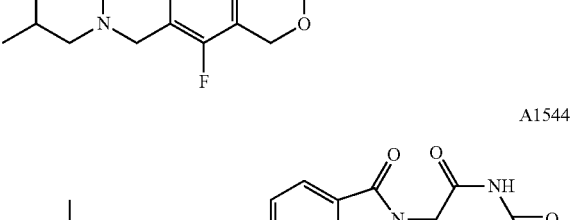
A1545
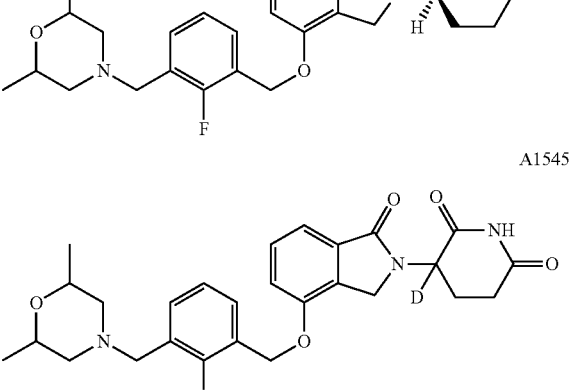
A1546
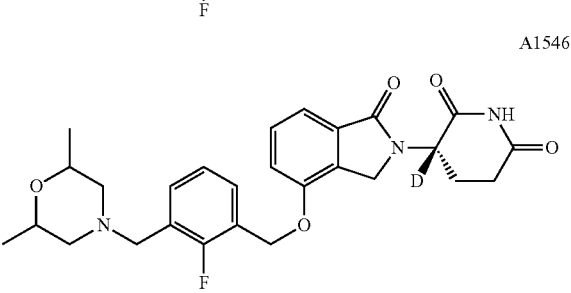

-continued
A1547
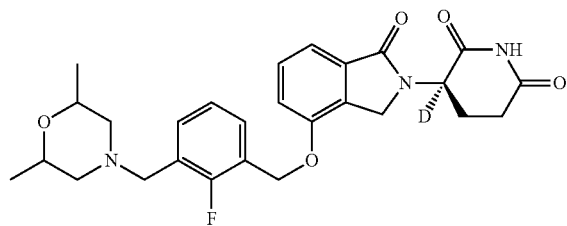
A1548
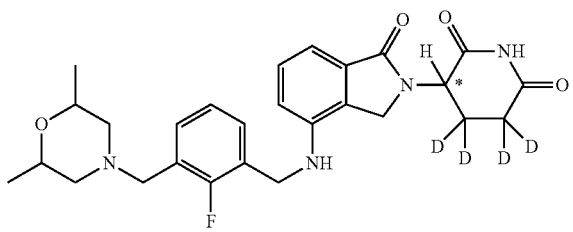
A1549
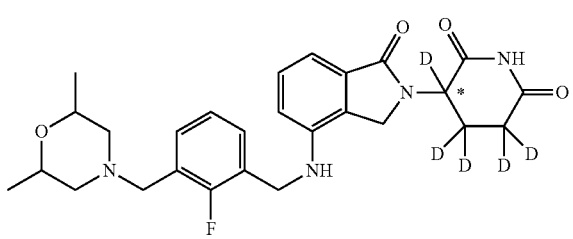
A1550
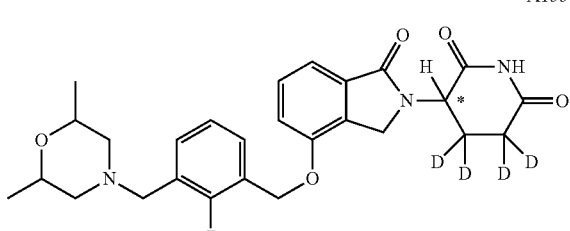
A1551
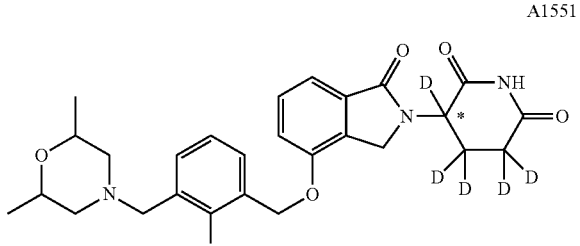
A1552
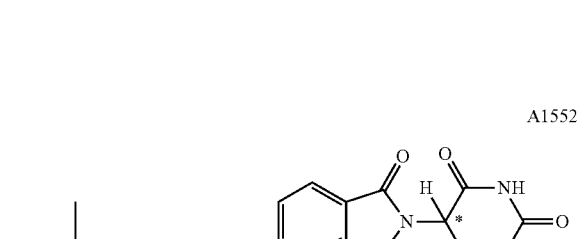
-continued
A1553
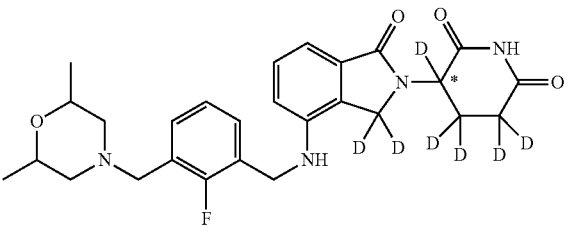
A1554
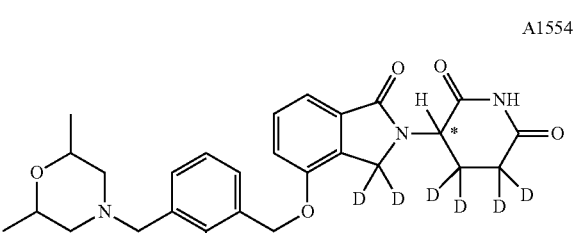
A1555
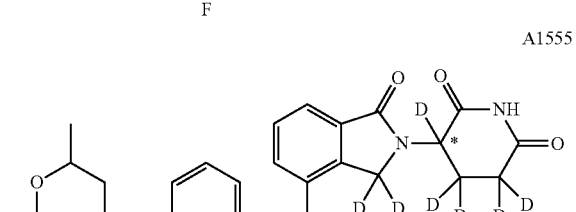
A1556
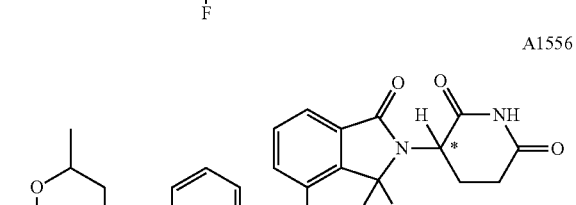
A1557
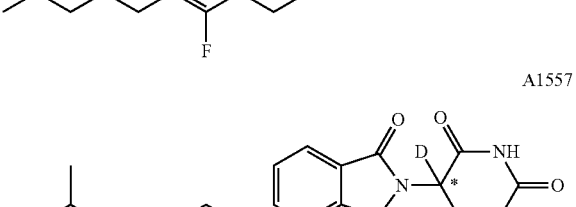
A1558
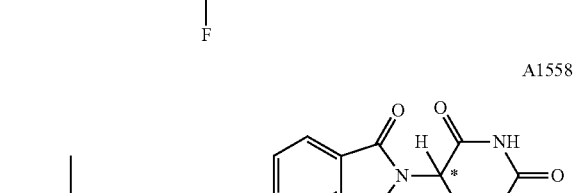

A1559
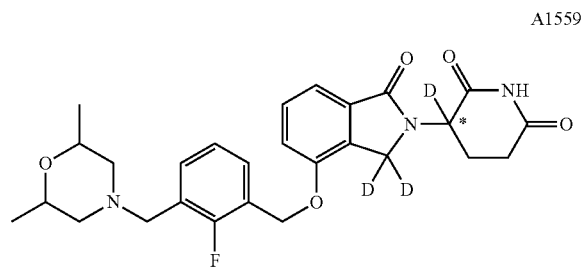
A1560
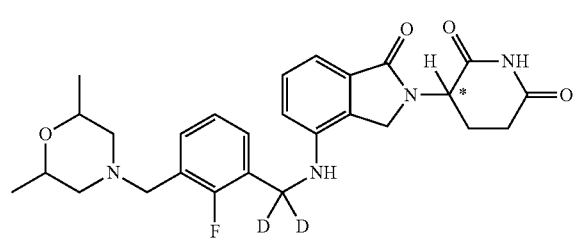
A1561
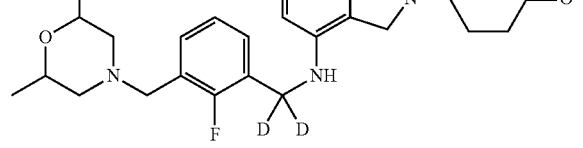
A1562
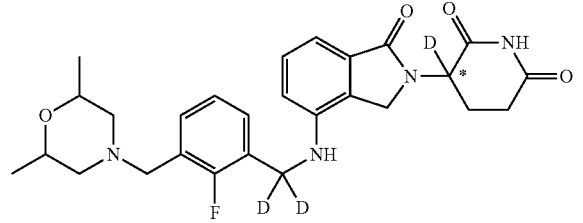
A1563
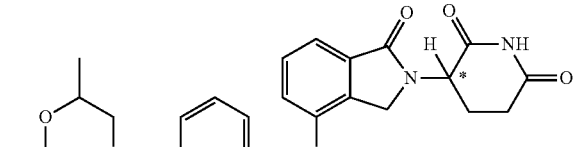
A1564
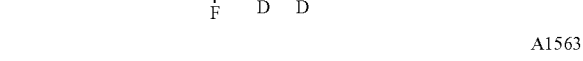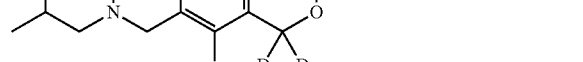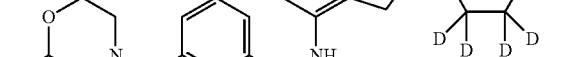
A1565
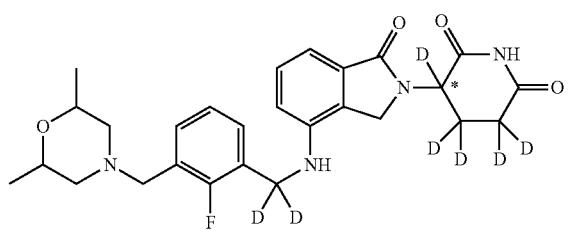
A1566
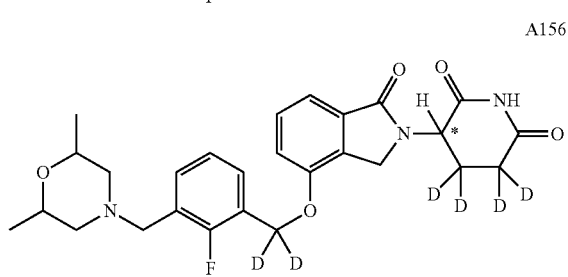
A1567
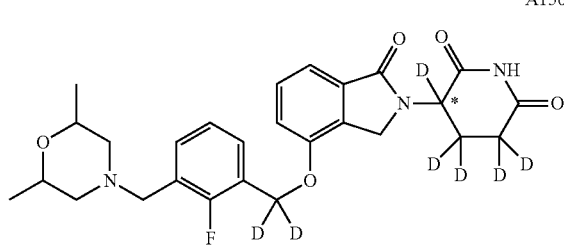
A1568
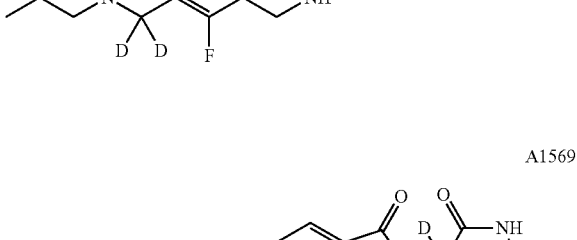
A1569
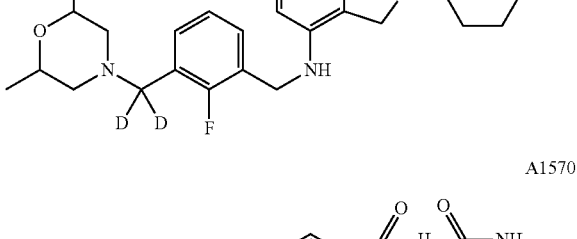
A1570
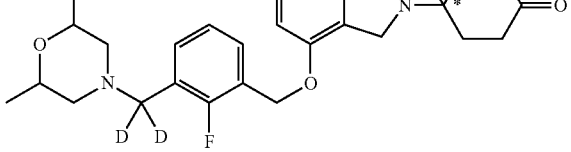

499
-continued
A1571
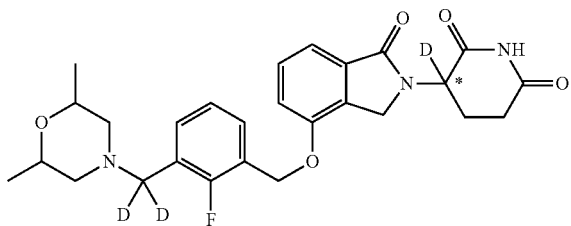
A1572
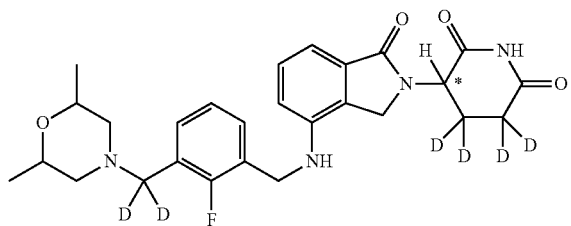
A1573
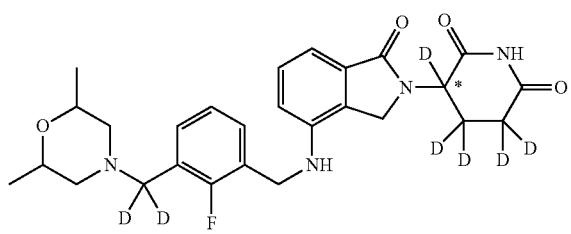
A1574
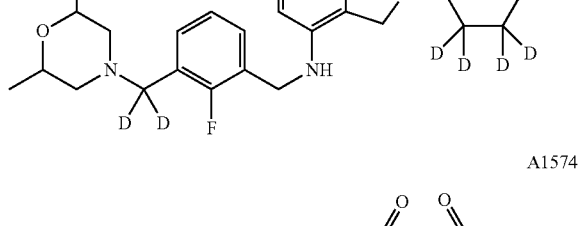
A1575
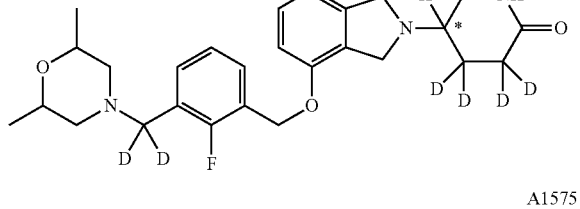
A1576
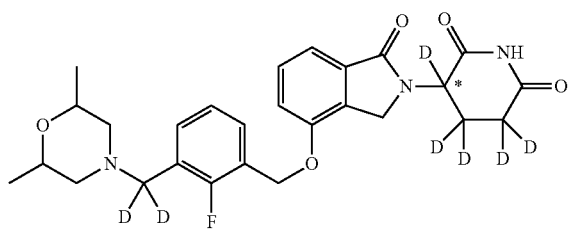
500
-continued
A1577
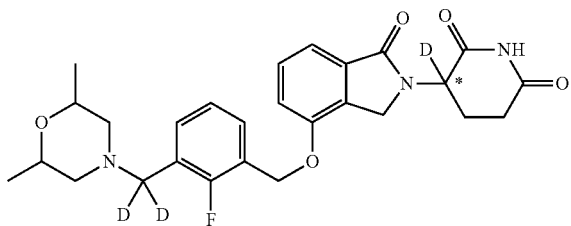
A1578
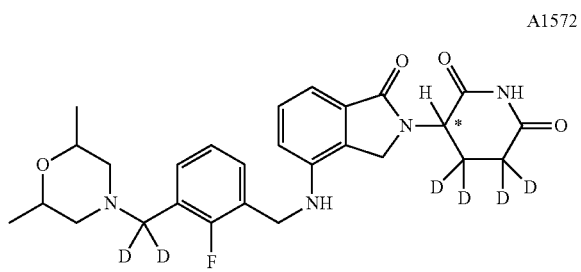
A1579
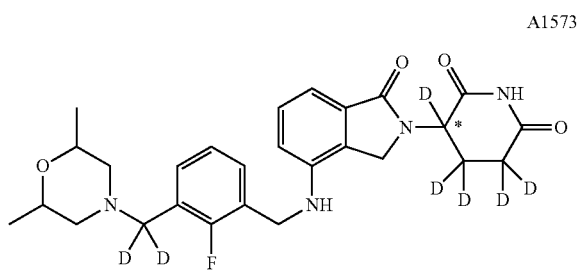
A1580
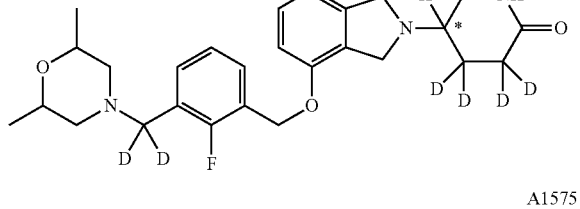
A1581
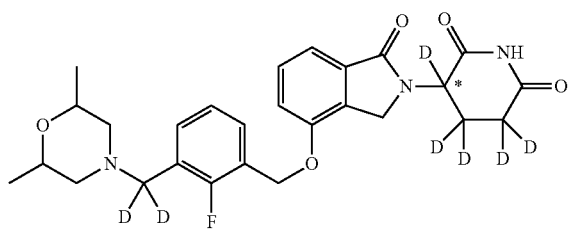
A1582
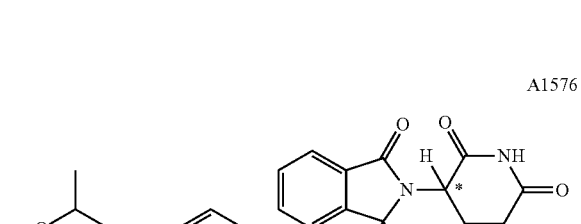

501
-continued
A1583
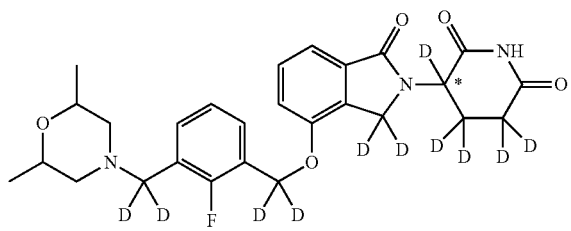
A1584
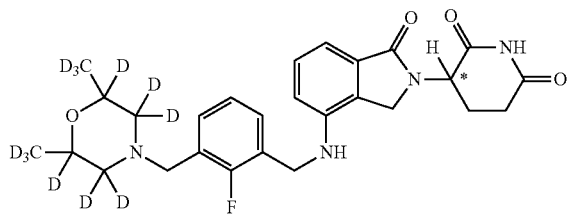
A1585
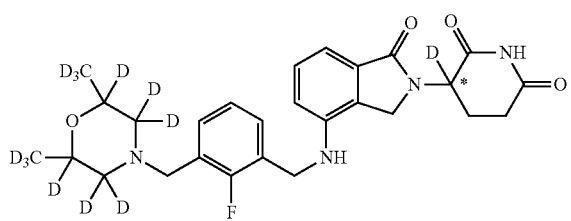
A1586
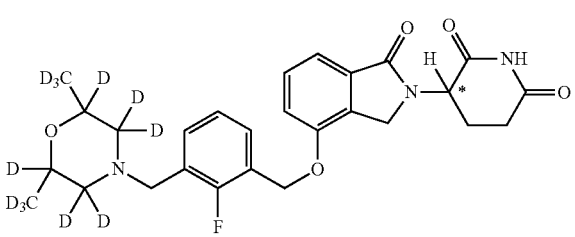
A1587
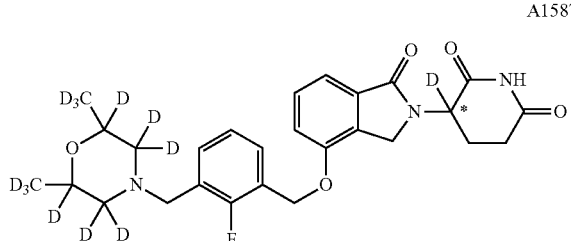
A1588
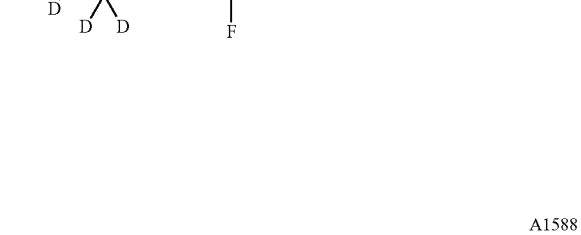
502
-continued
A1589
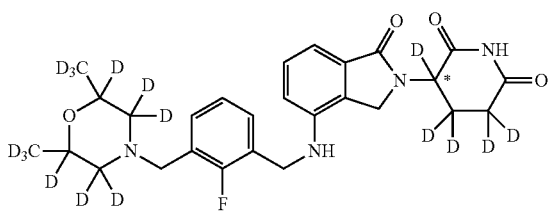
A1590
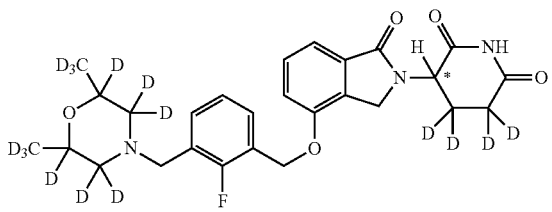
A1591
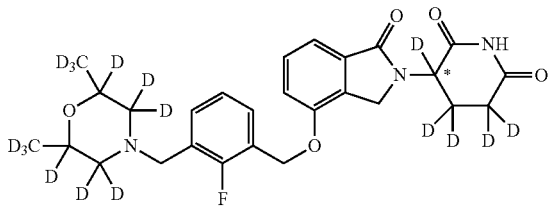
A1592
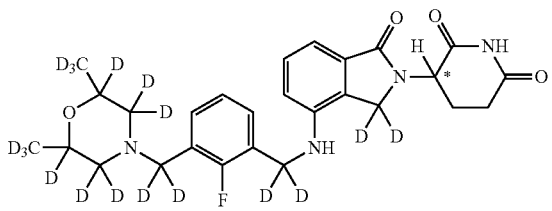
A1593
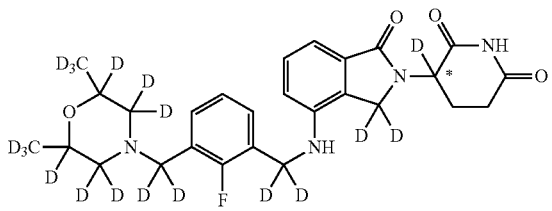
A1594
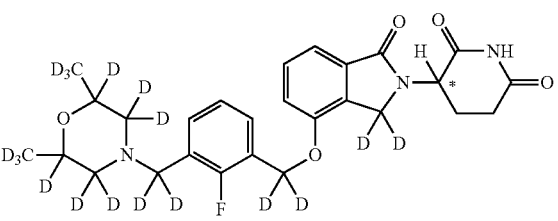

503
-continued
A1595
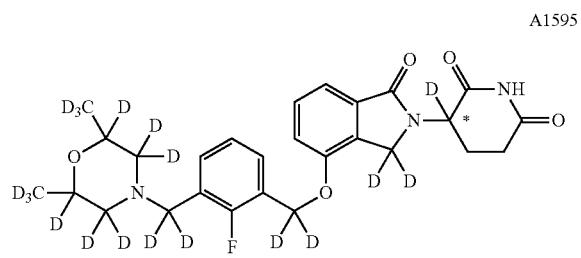
A1596
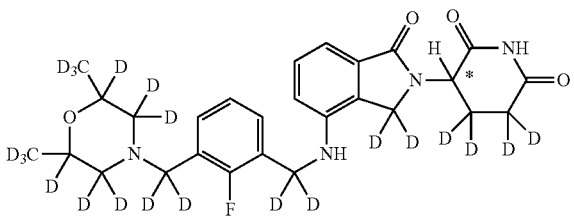
A1597
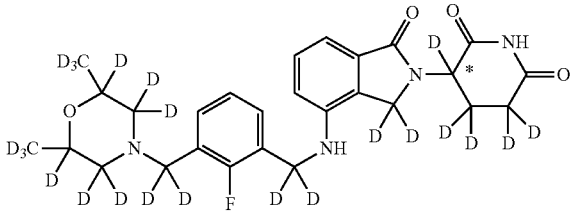
A1598
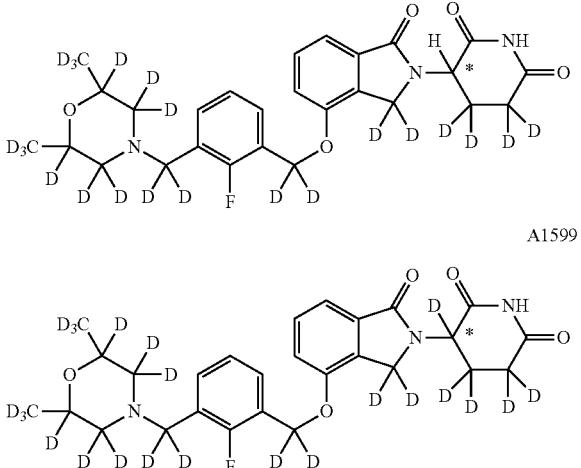
A1599
A1651
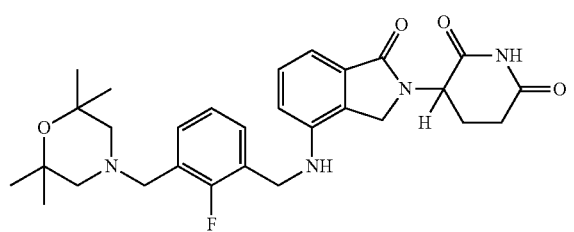
504
-continued
A1652
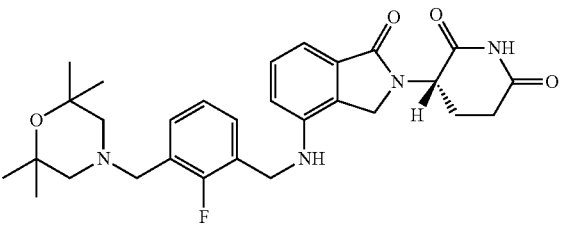
A1653
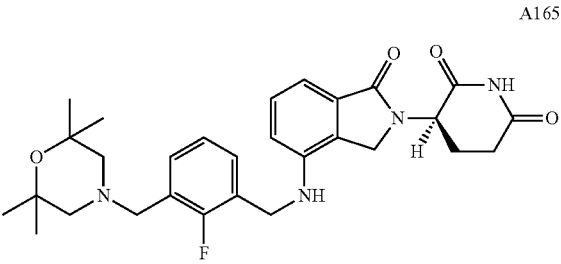
A1654
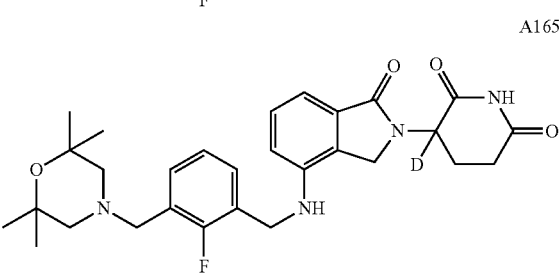
A1655
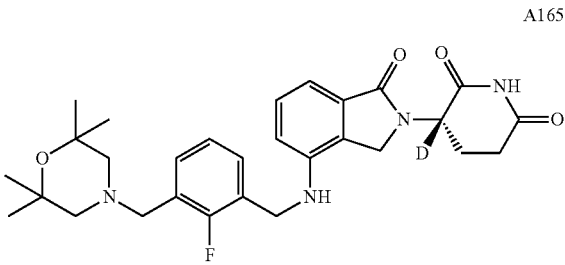
A1656
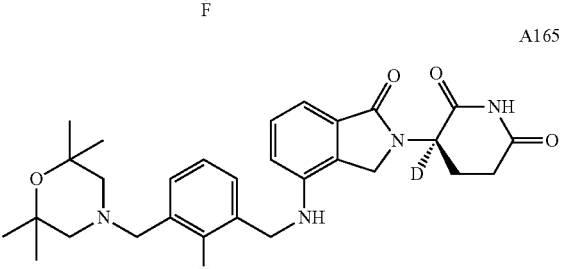
A1657
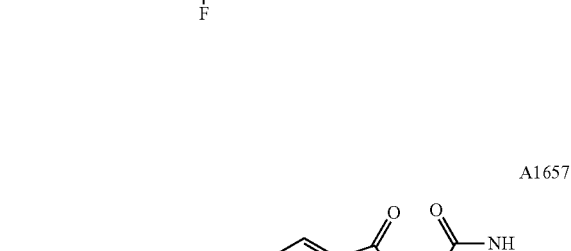
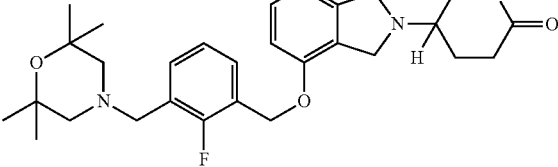

A1658
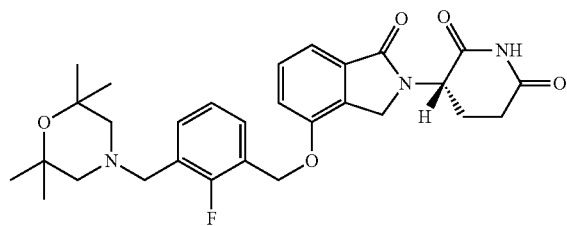
A1659
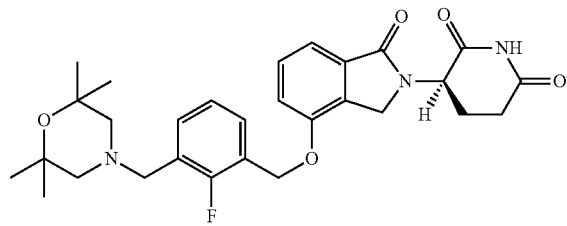
A1660
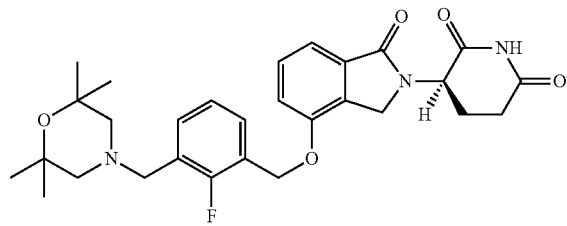
A1661
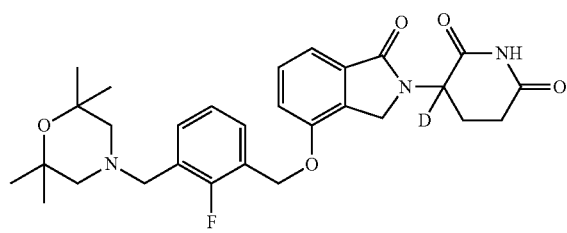
A1662
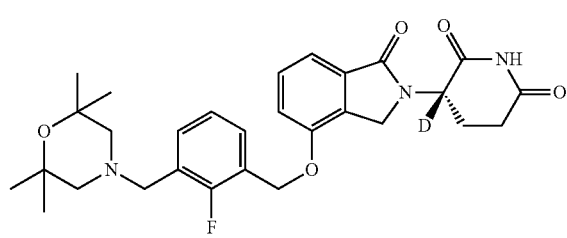
A1663
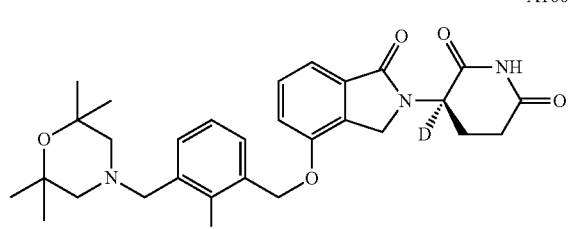
A1664
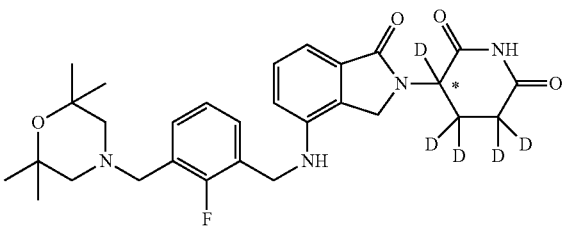
A1665
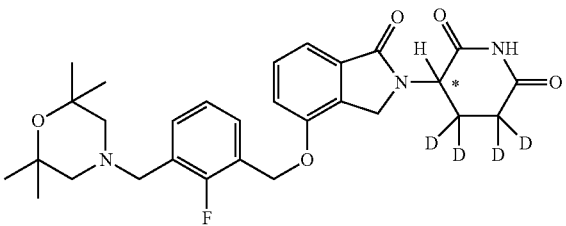
A1666
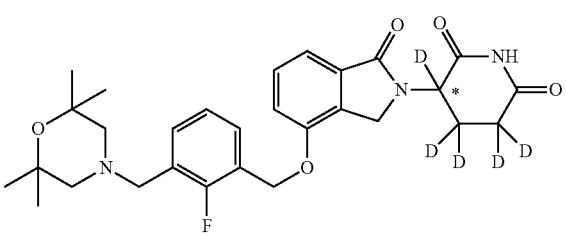
A1667
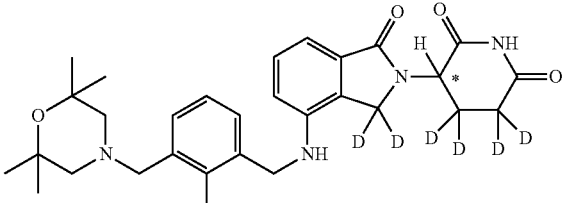
A1668
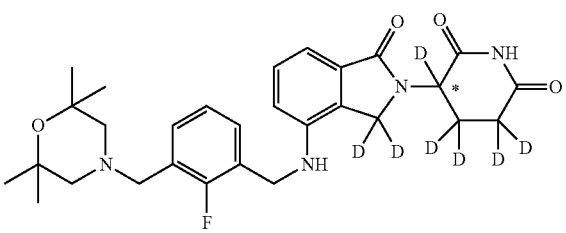
A1669
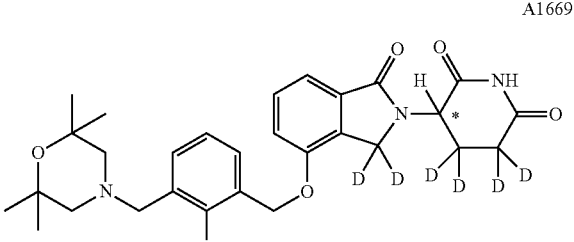

507
-continued
A1670
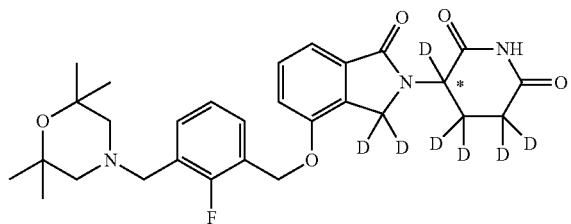
A1671
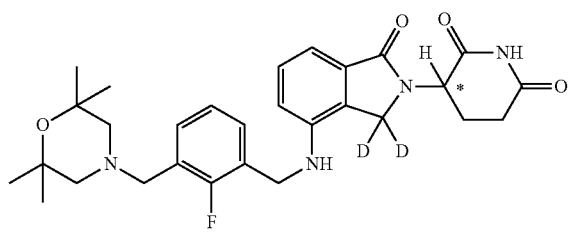
A1672
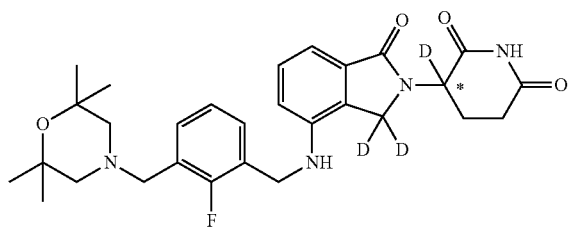
A1673
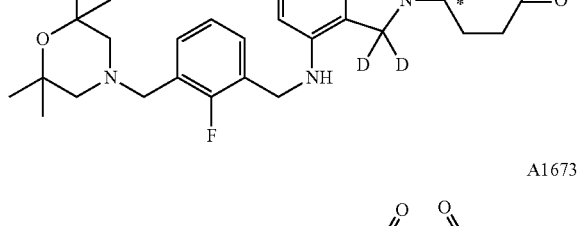
A1674
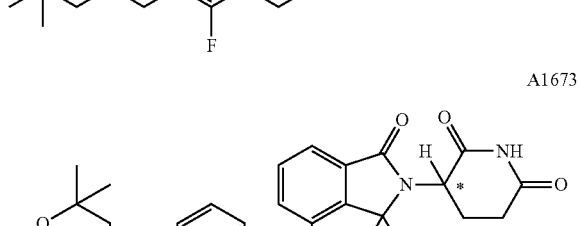
A1675
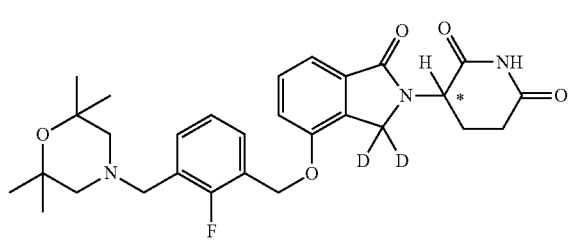
508
-continued
A1676
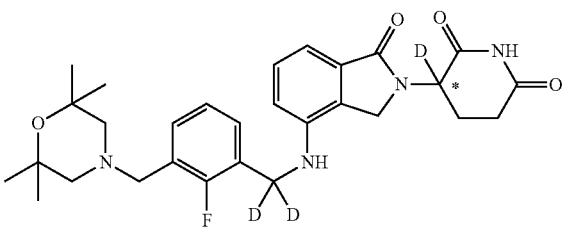
A1677
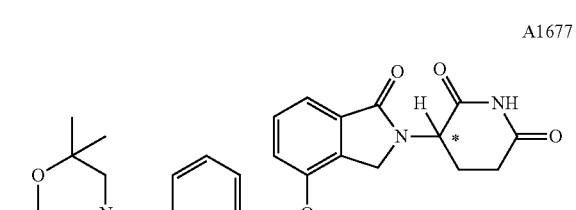
A1678
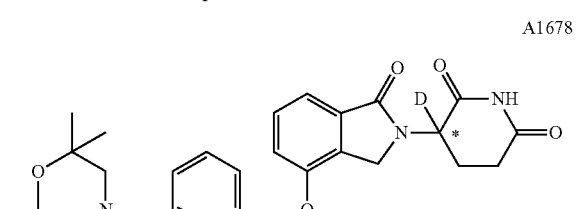
A1679
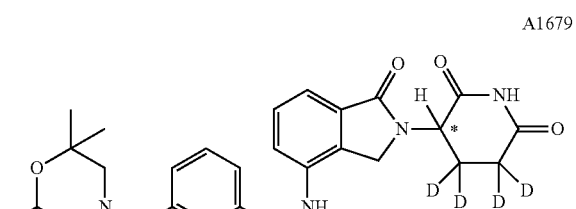
A1680
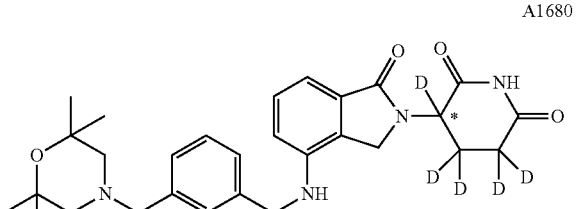
A1681
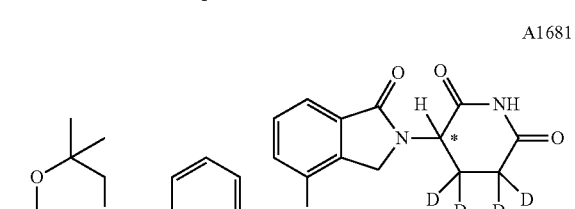

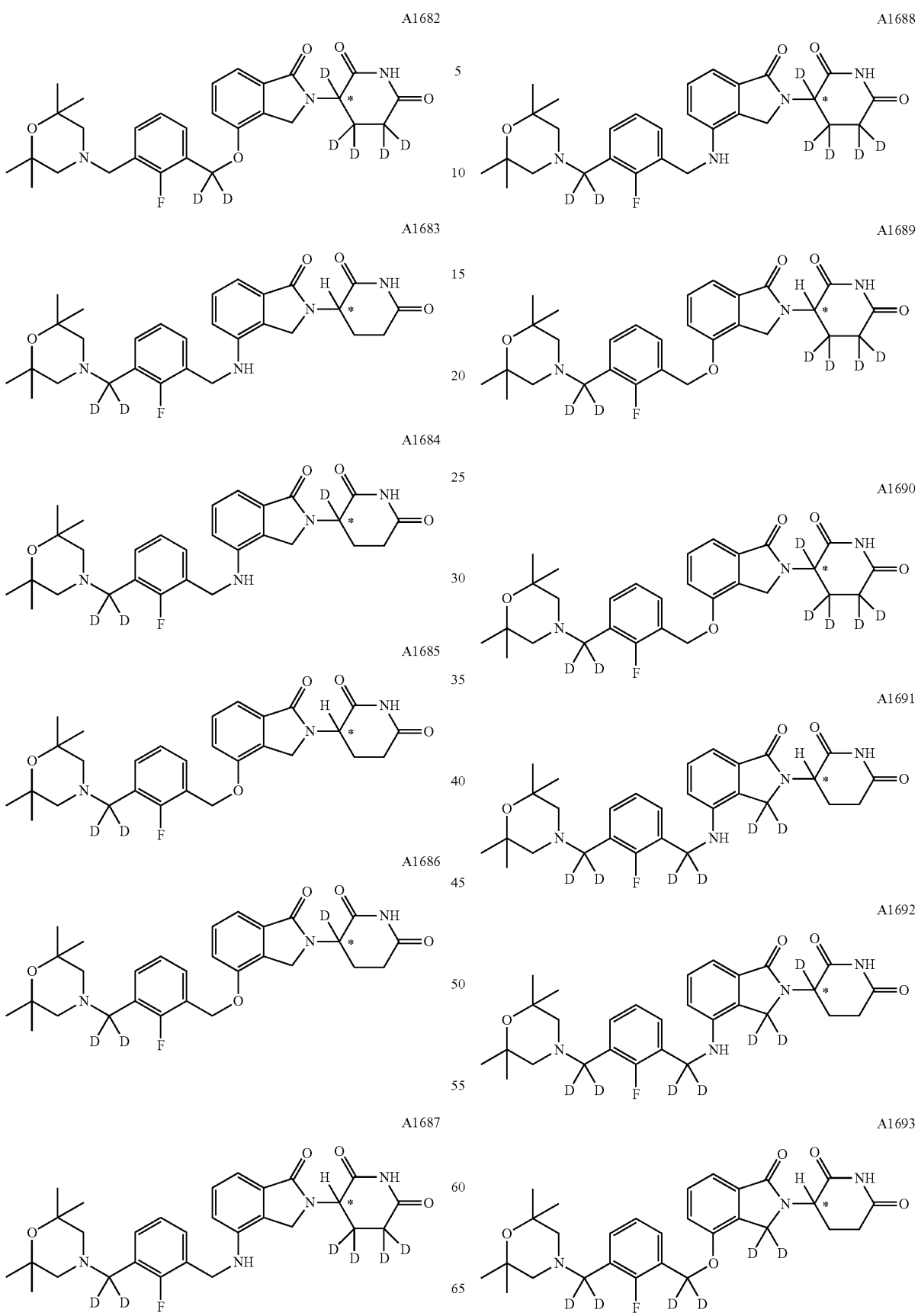

A1694
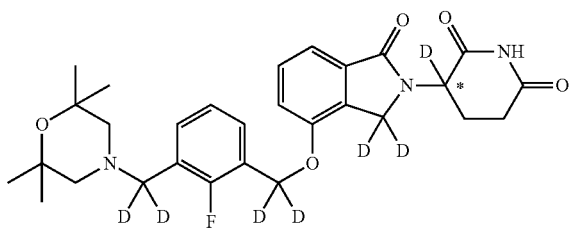
A1695
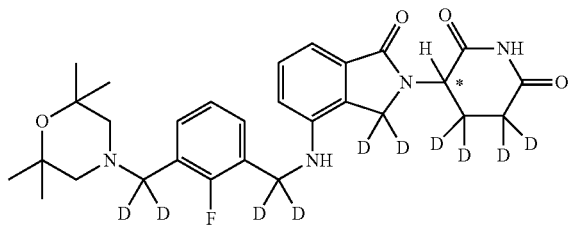
A1696
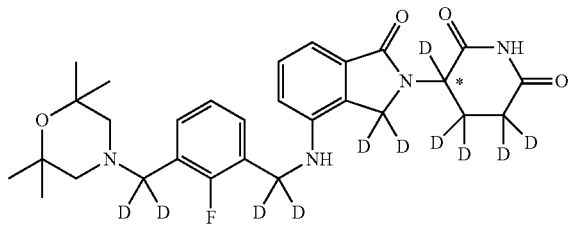
A1697
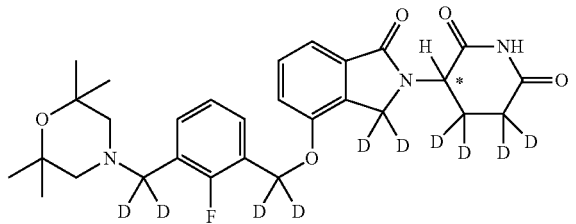
A1698
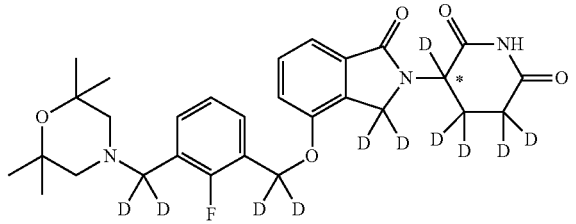
A1699
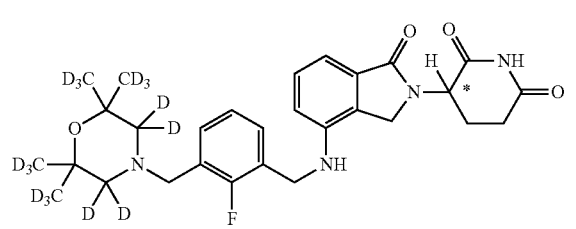
A1700
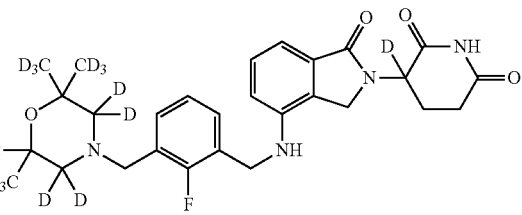
A1701
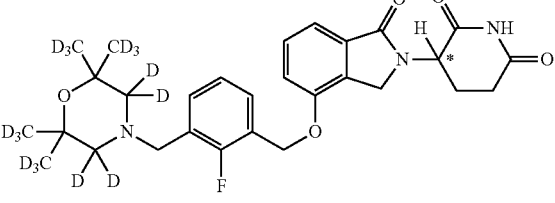
A1702
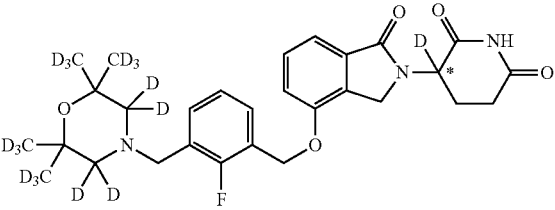
A1703
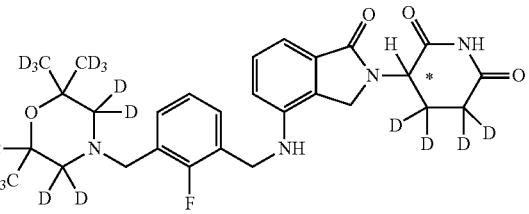
A1704
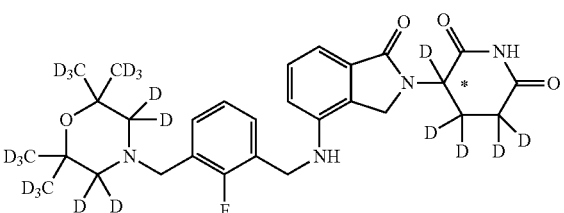
A1705
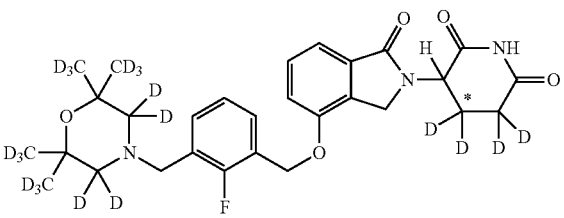

-continued
A1706
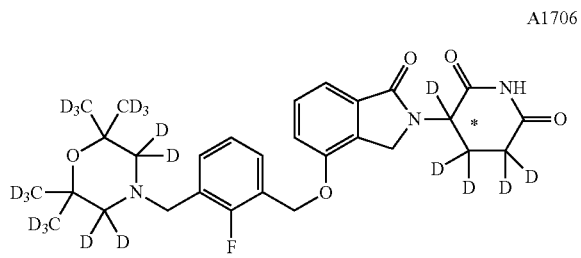
A1707
A1708
A1709
A1710
A1711
-continued
A1712
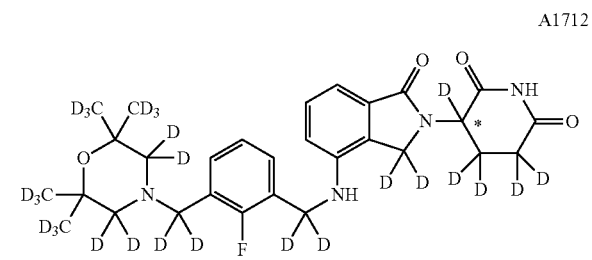
A1713
A1714
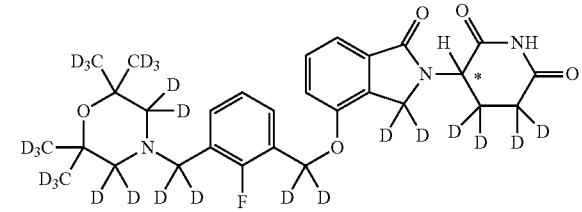
A1766
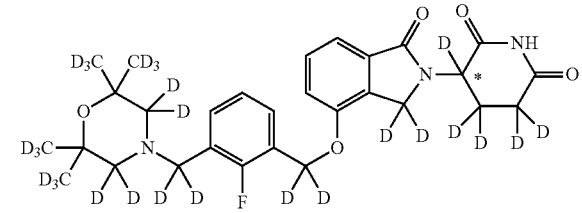
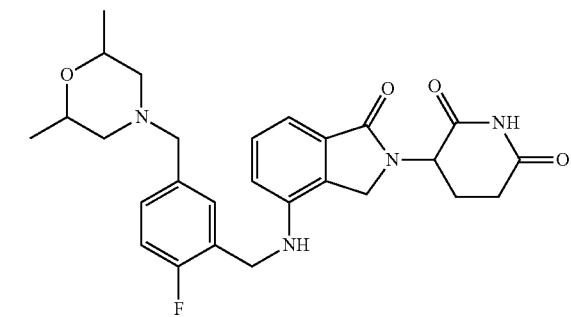
A1767
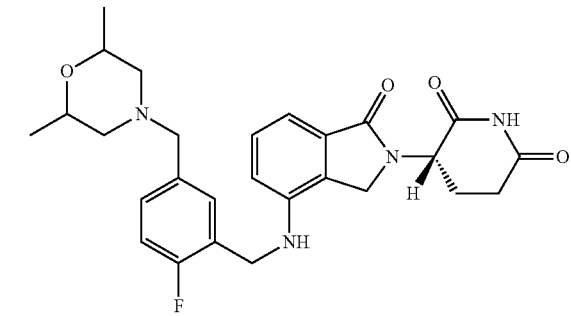

A1768
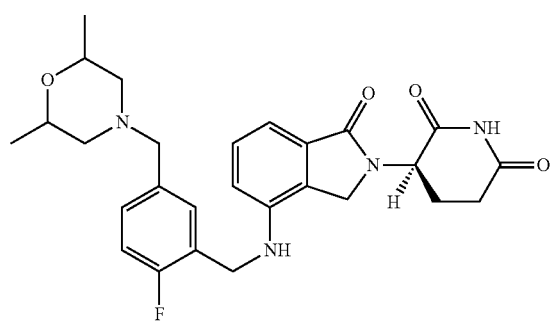
A1769
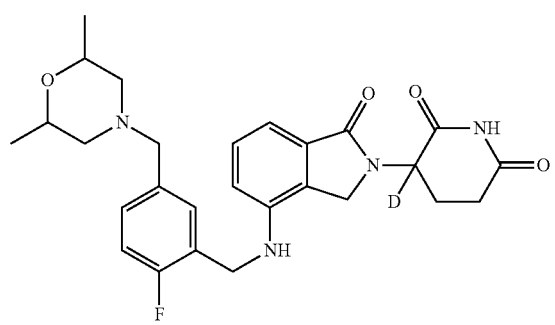
A1770
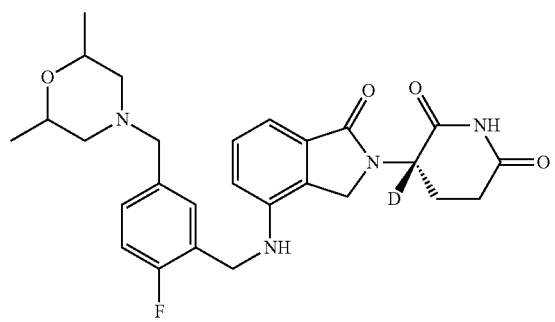
A1771
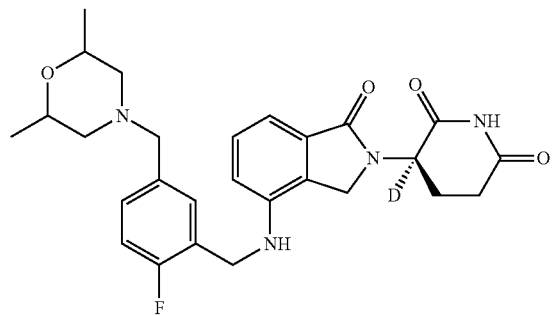
A1772
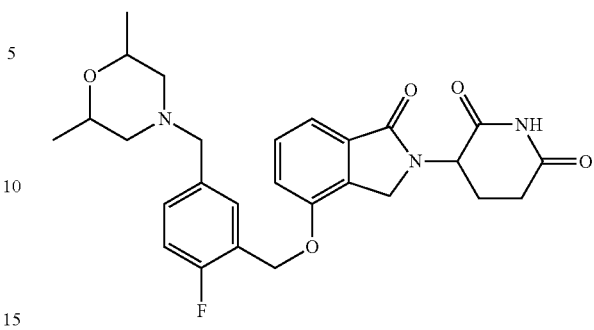
A1773
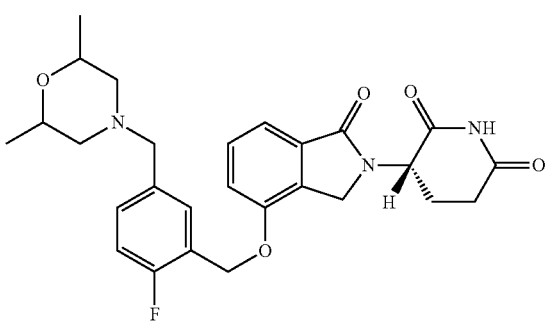
A1774
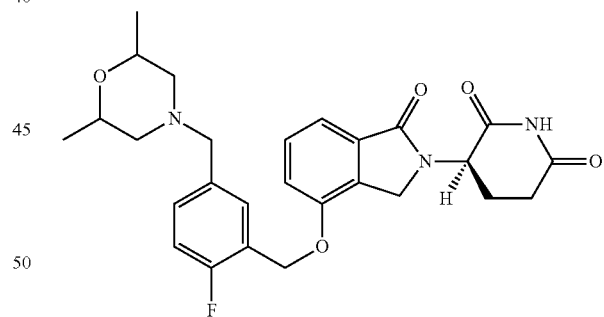
A1775
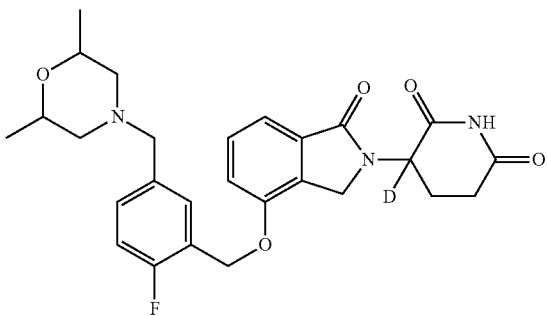

A1776
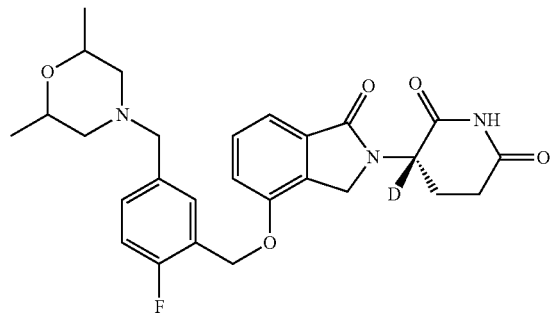
A1777
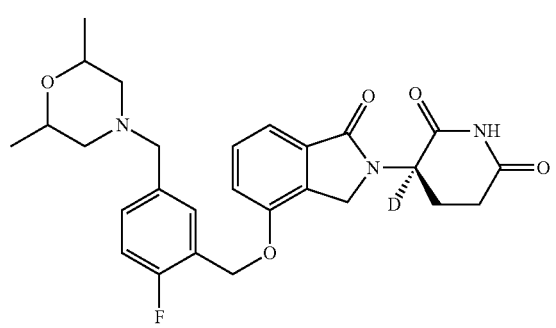
A1778
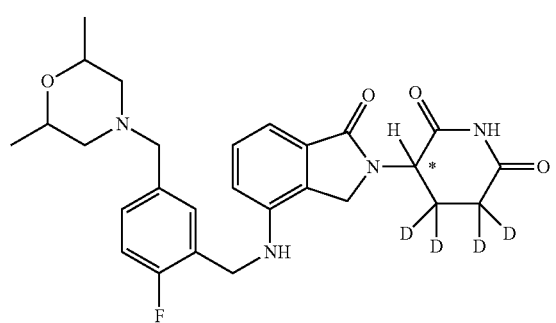
A1779
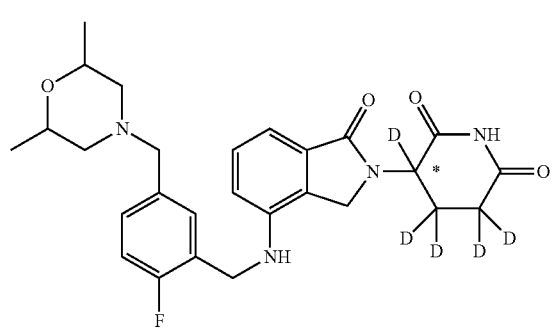
A1780
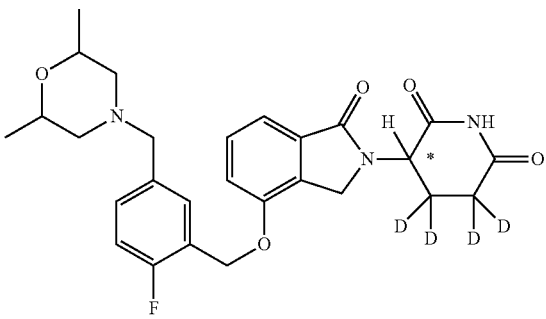
A1781
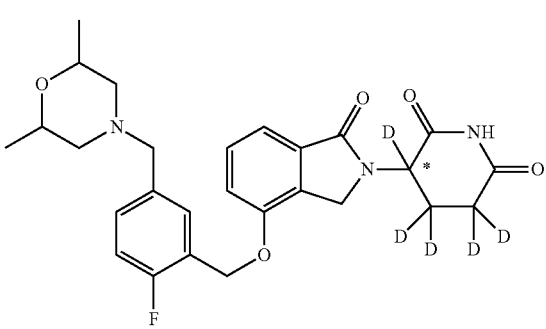
A1782
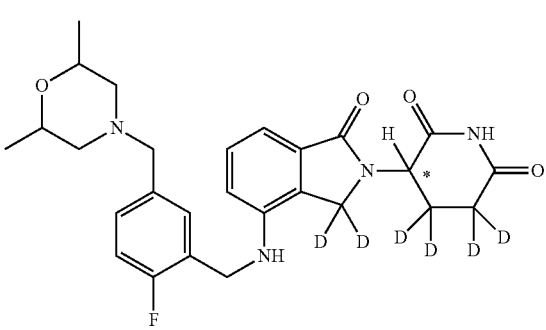
A1783
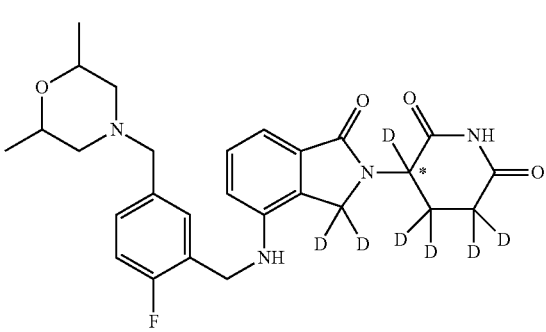

A1784
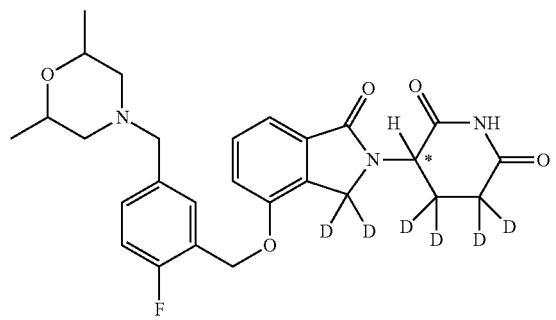
A1785
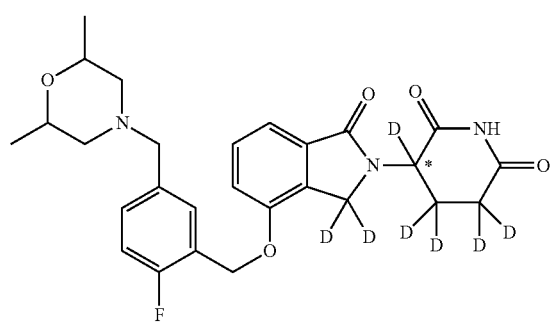
A1786
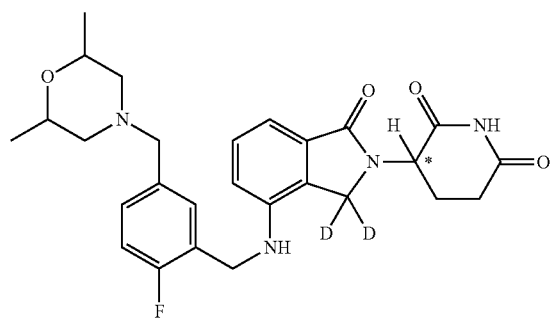
A1787
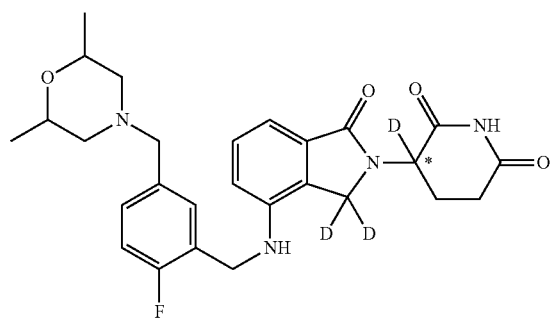
A1788
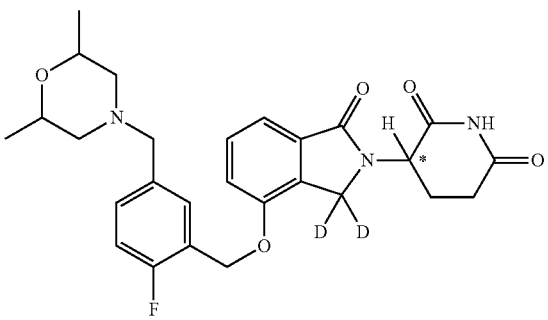
A1789
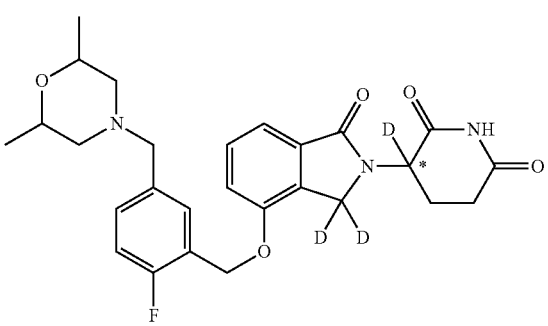
A1790
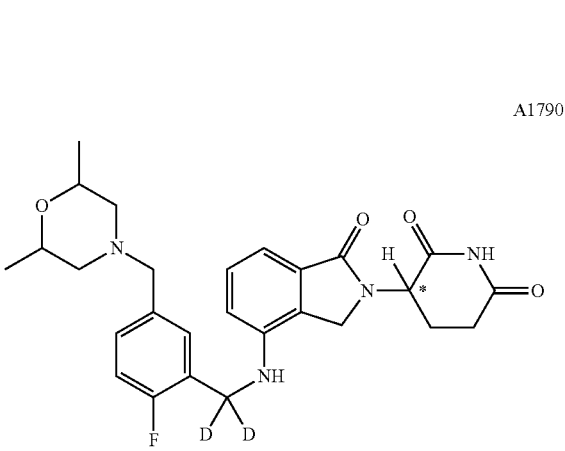
A1791
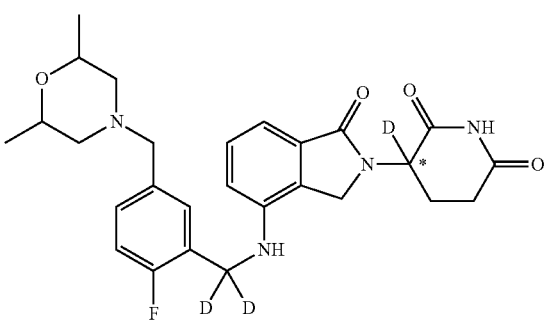

A1792
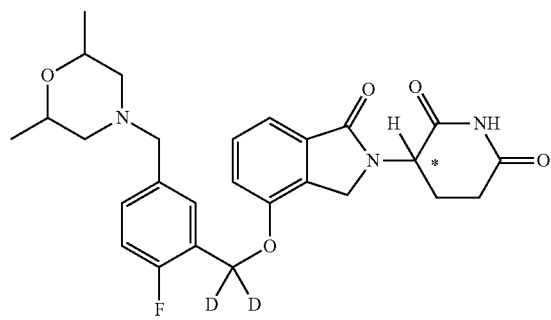
A1796
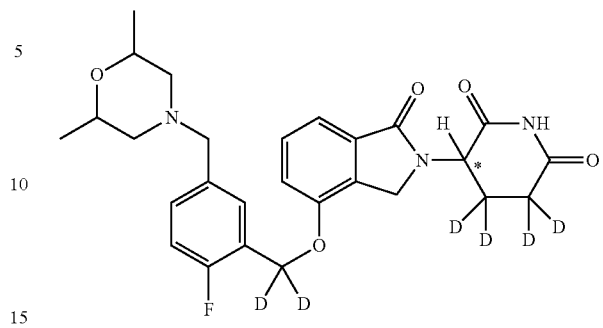
A1793
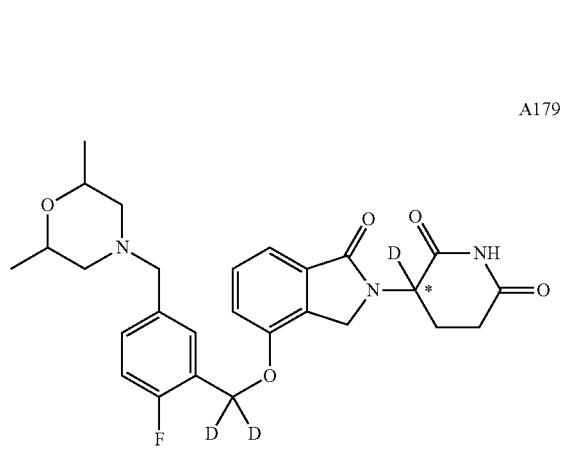
A1798
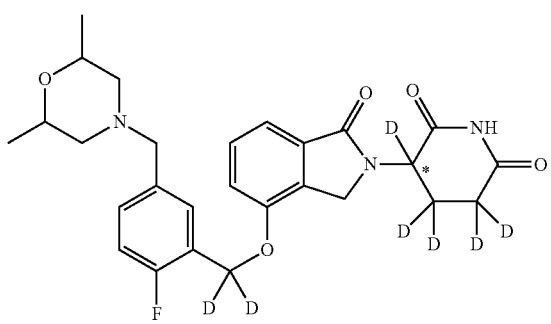
A1794
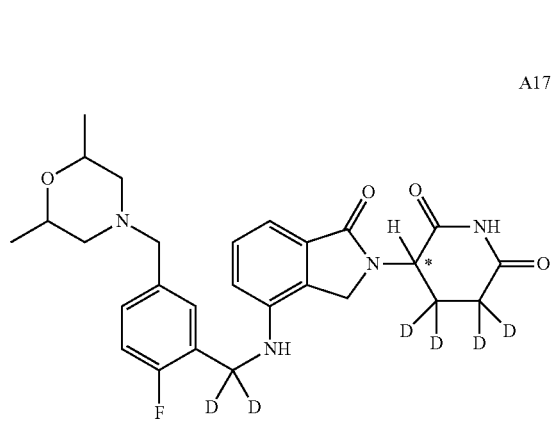
A1799
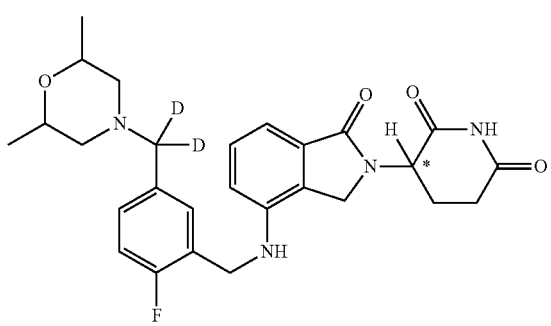
A1795
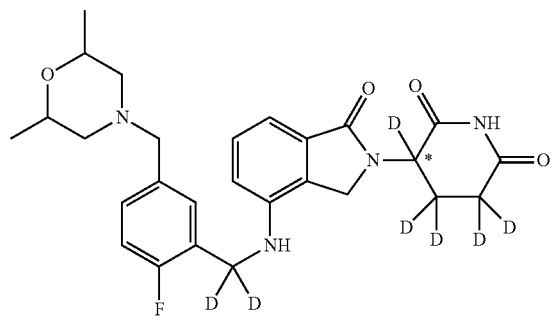
A1800
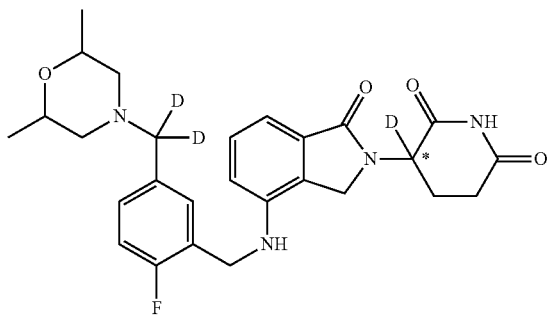

A1801
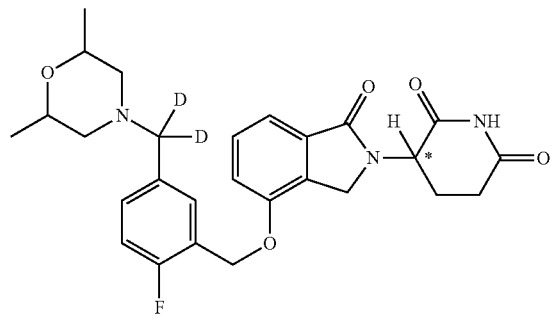
A1805
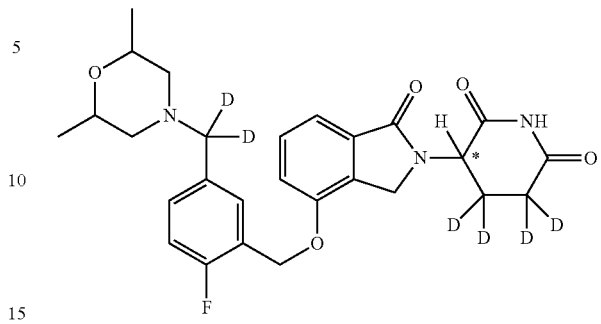
A1802
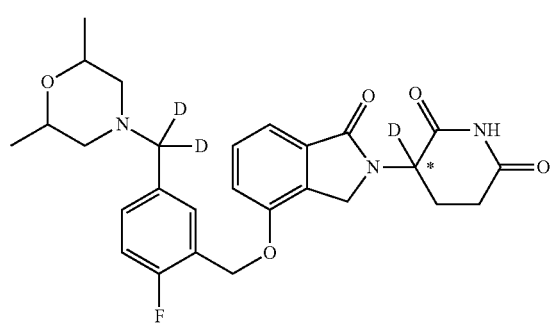
A1806
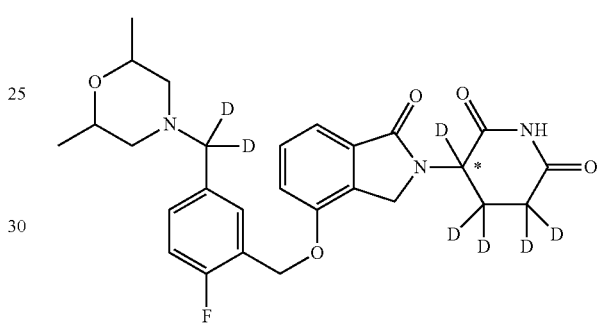
A1803
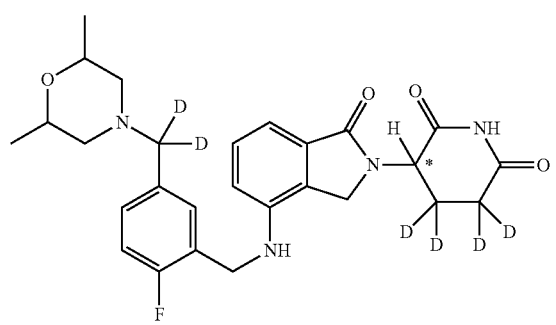
A1807
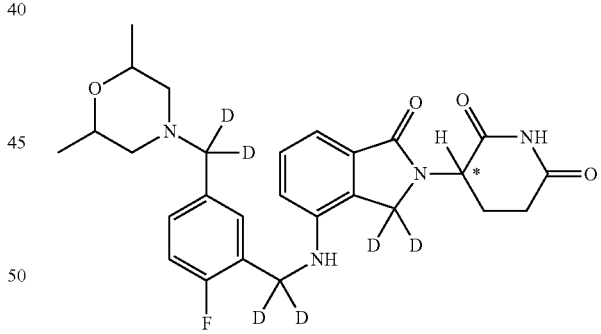
A1804
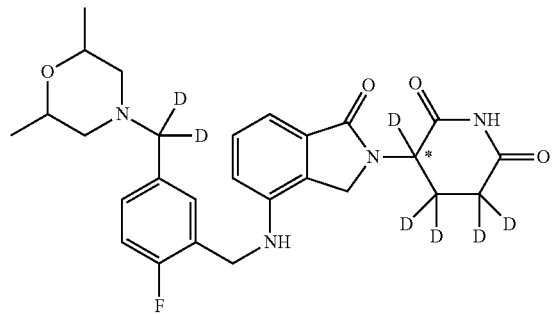
A1808
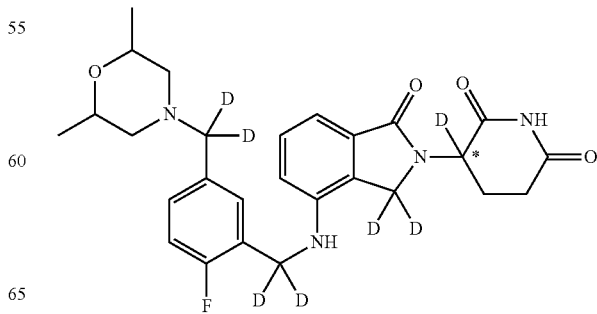

A1809
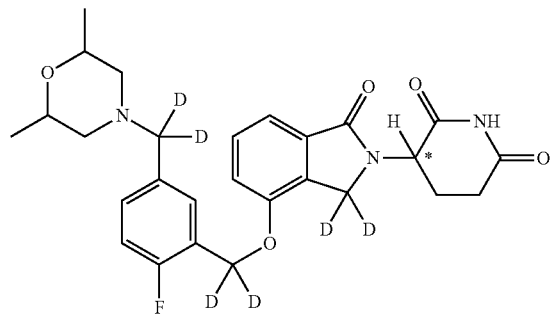
A1810
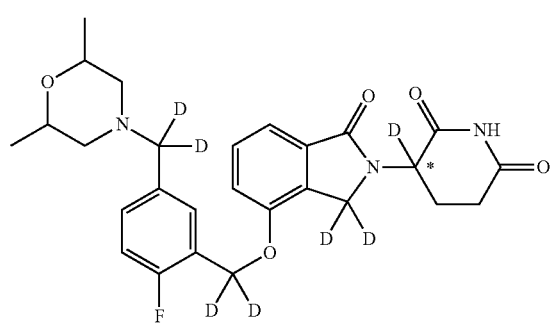
A1811
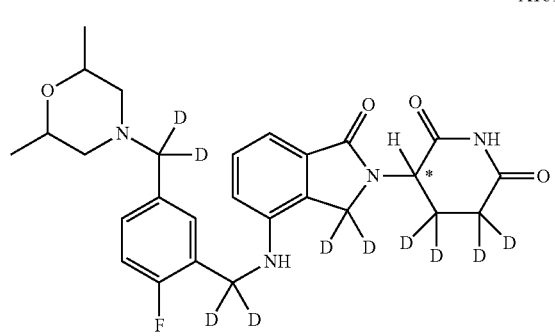
A1812
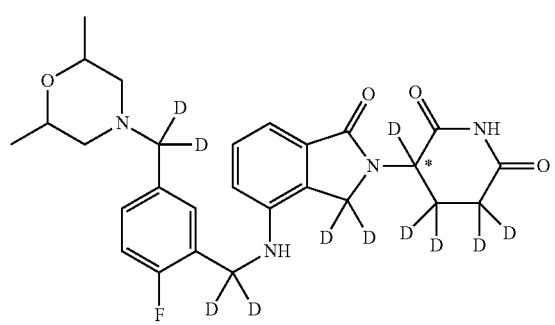
A1813
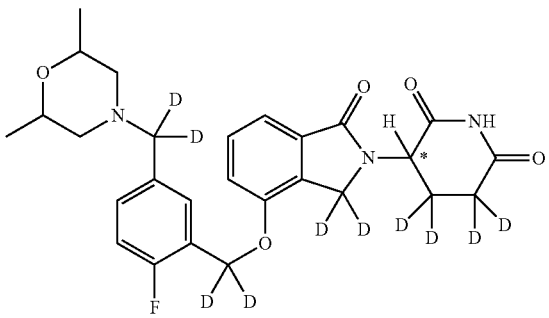
A1814
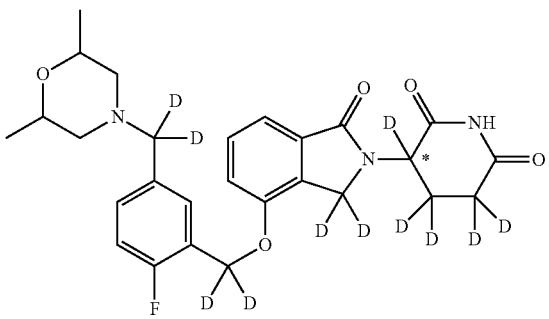
A1815
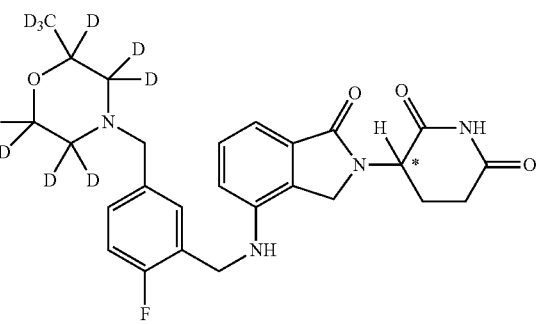
A1816
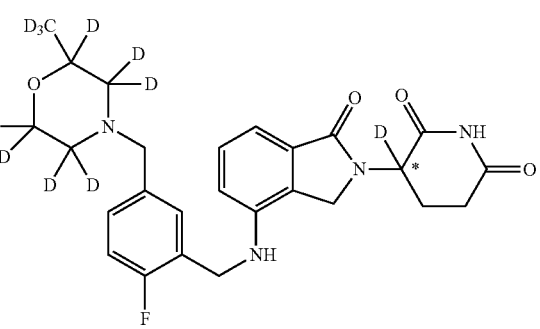

527
-continued
A1817
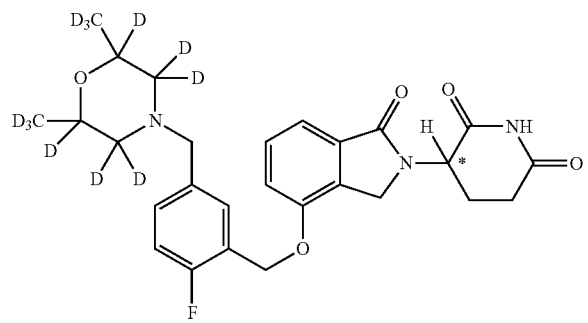
A1818
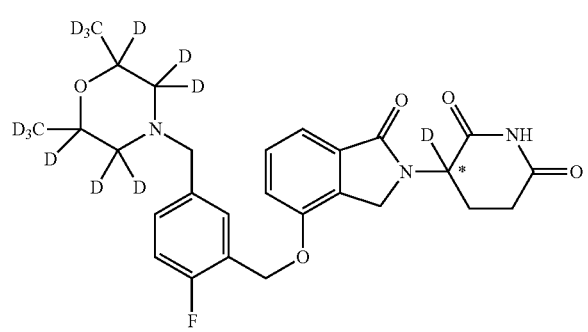
A1819
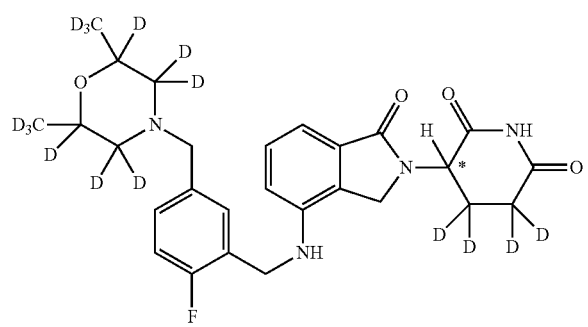
A1820
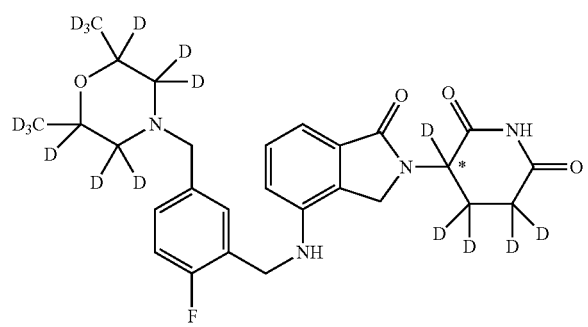
528
-continued
A1821
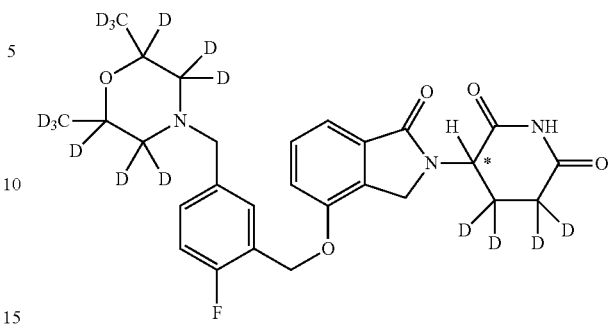
A1822
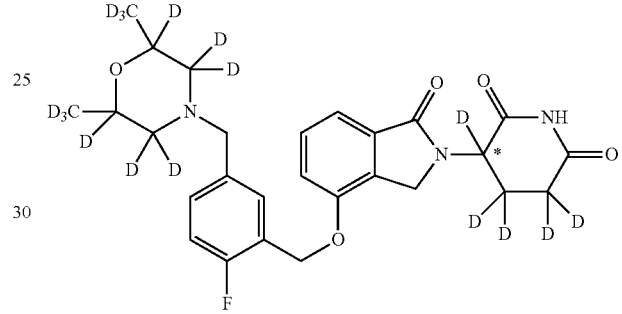
A1823
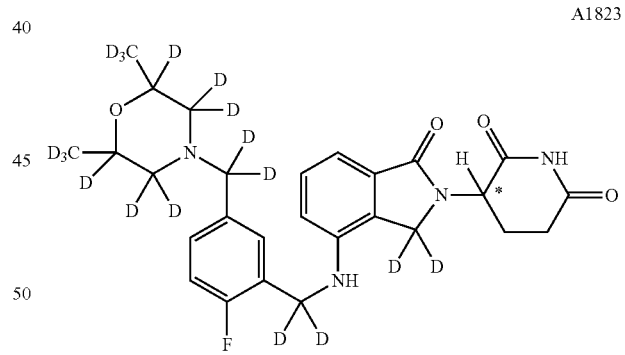
A1824

529
-continued
A1825
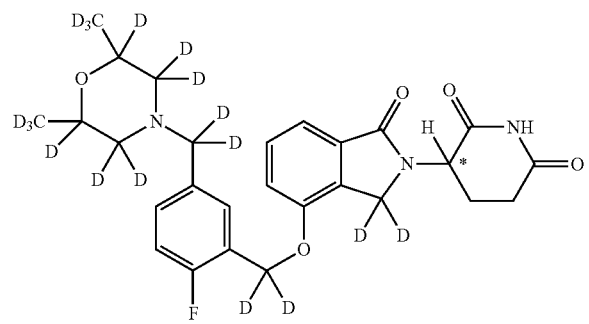
A1826
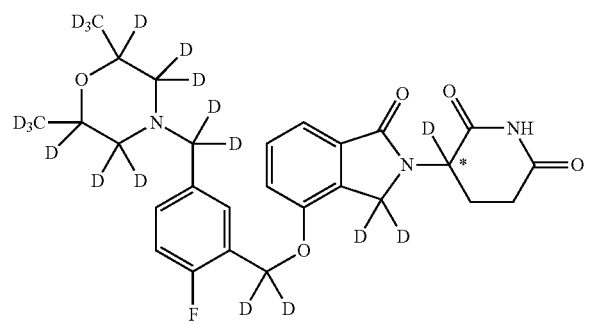
A1827
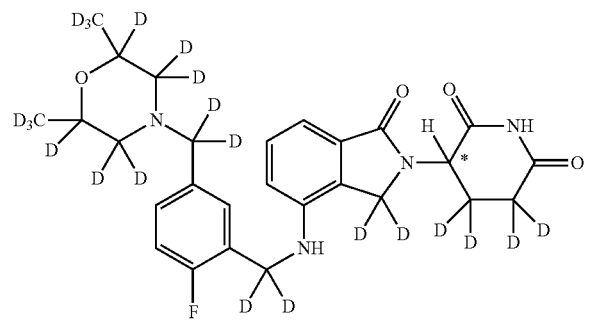
A1828
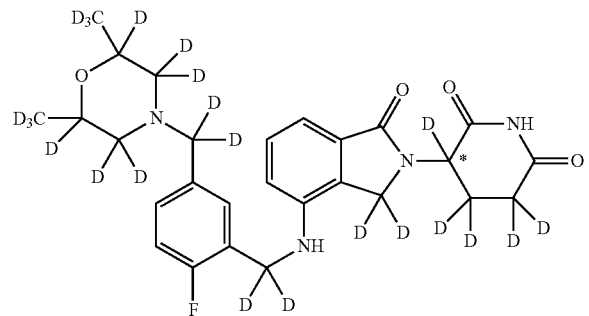
530
-continued
A1829
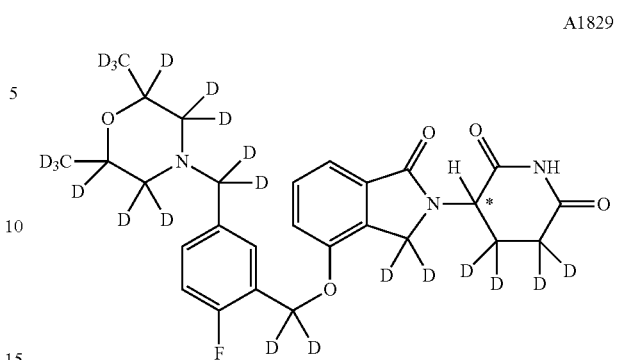
A1830
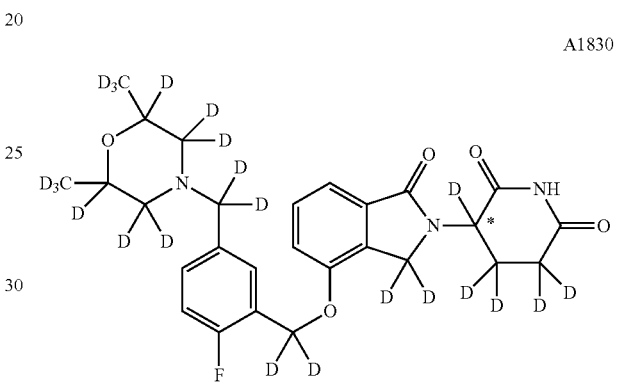
A1882
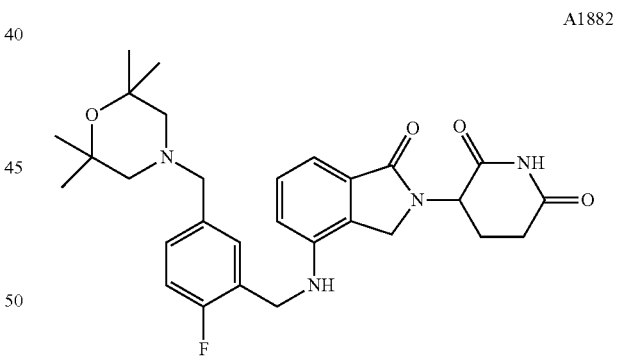
A1883
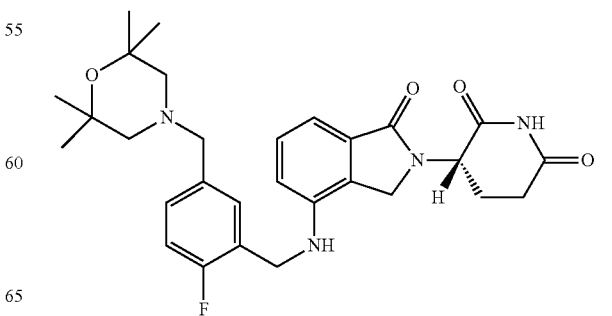

A1884
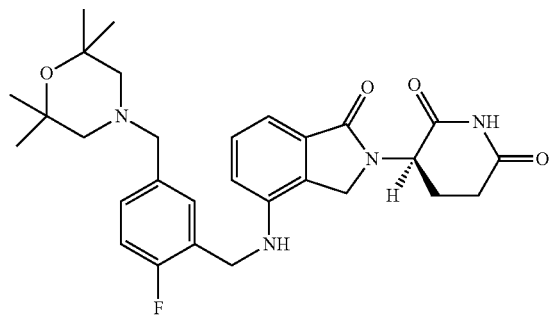
A1885
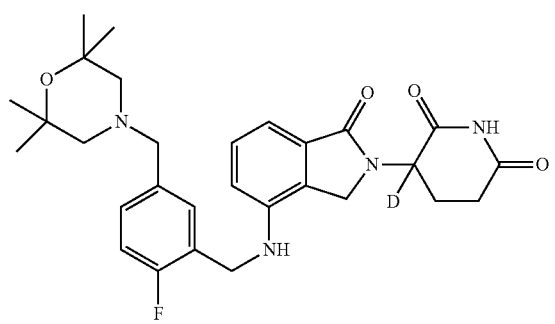
A1886
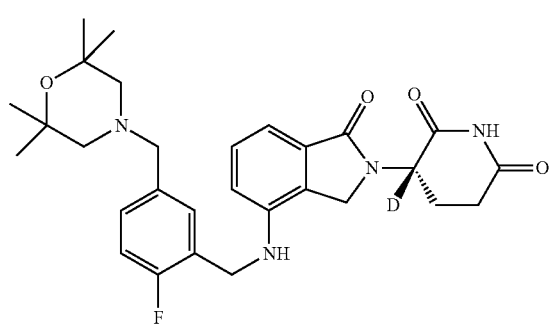
A1887
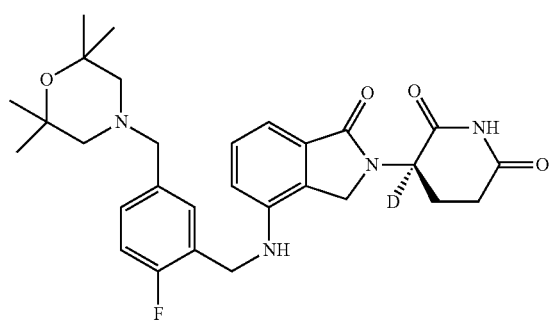
A1888
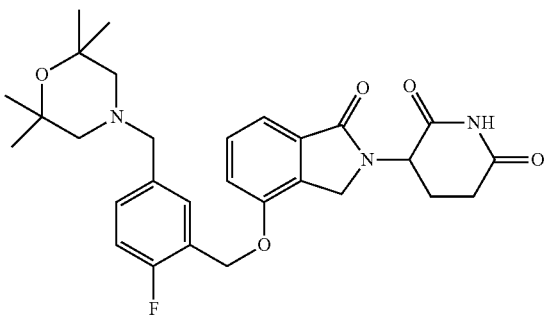
A1889
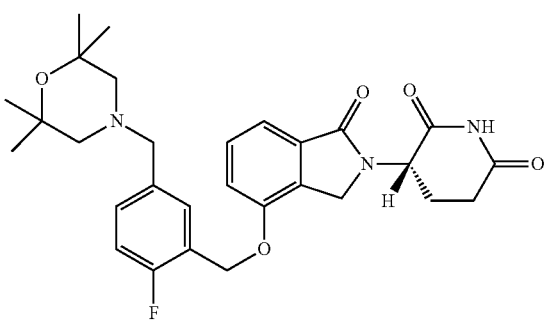
A1890
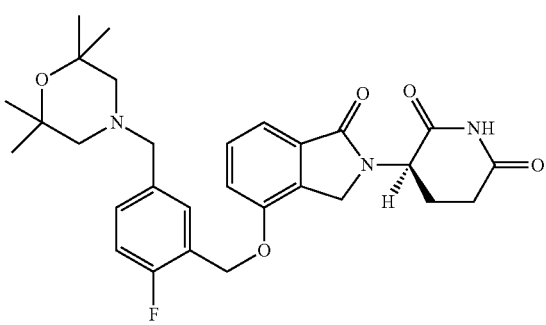
A1891
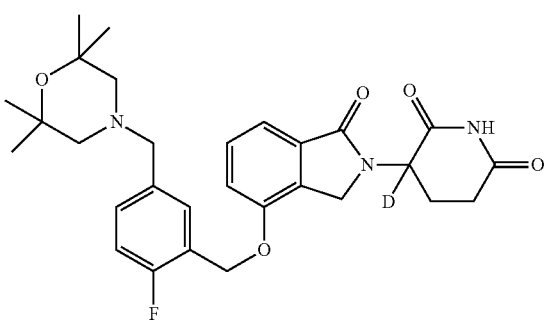

A1892
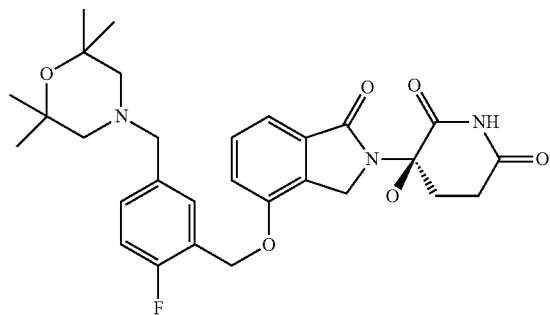
A1893
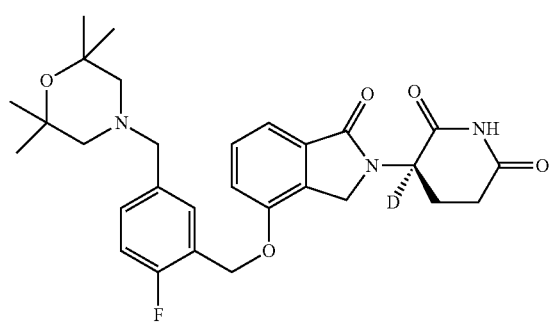
A1894
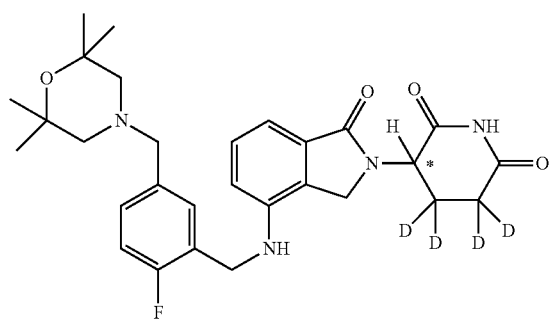
A1895
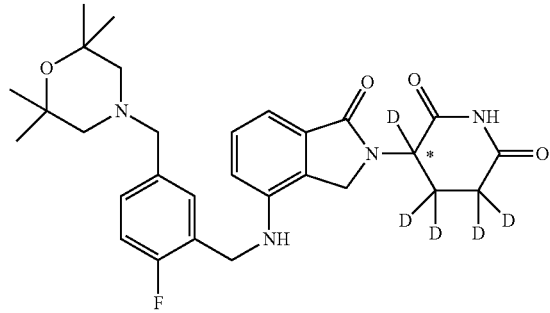
A1896
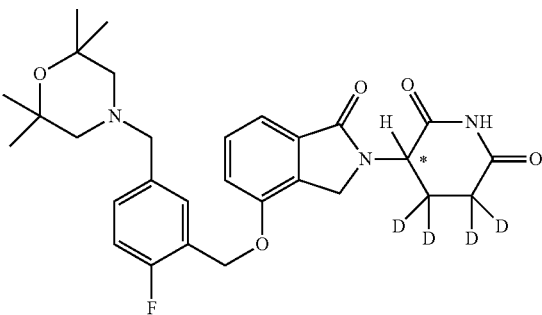
A1897
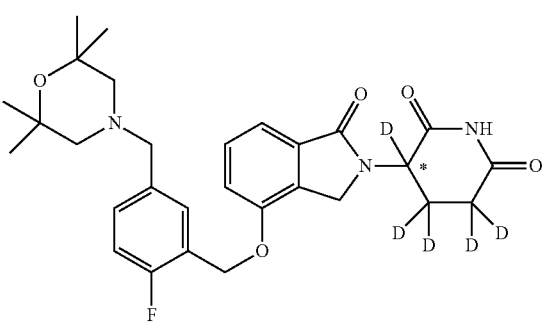
A1898
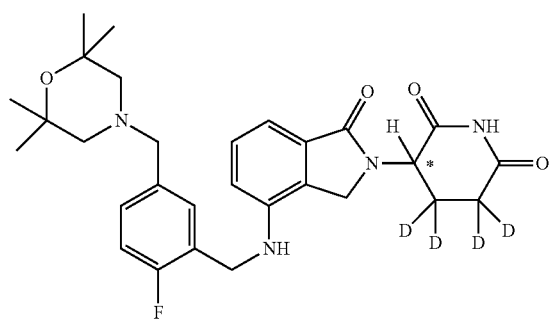
A1899
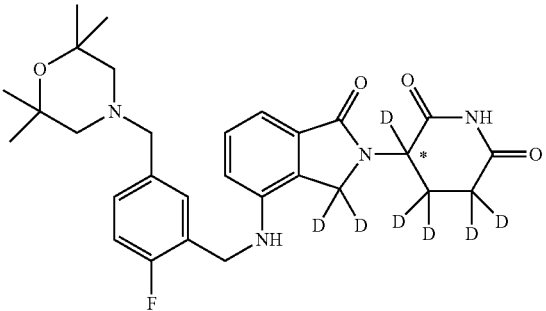

535
-continued
A1900
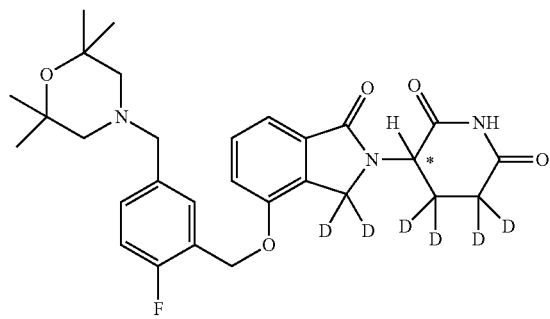
A1901
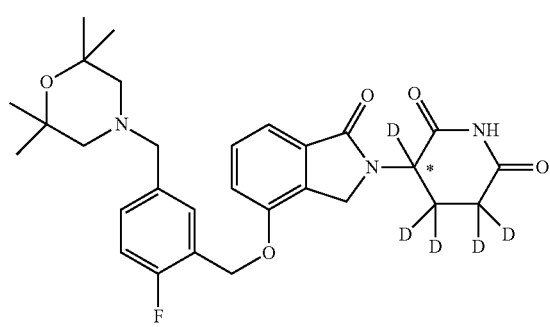
A1902
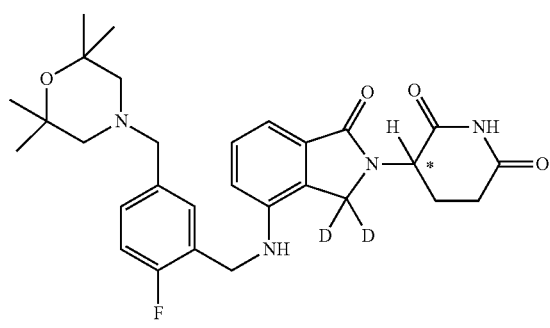
A1903
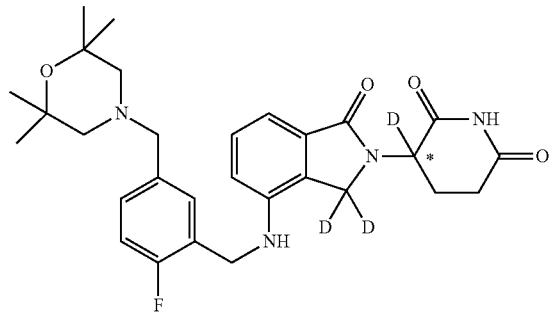
536
-continued
A1904
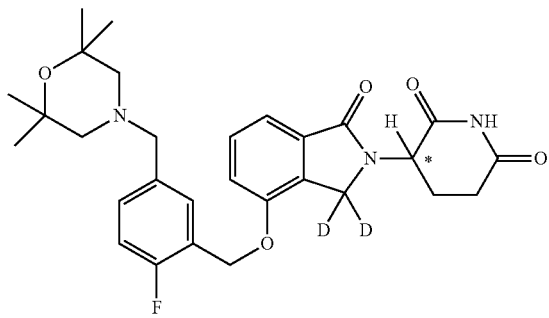
A1905
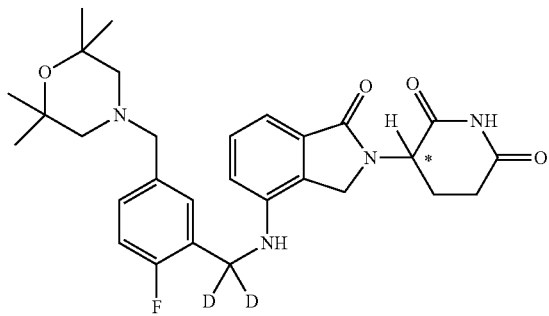
A1906
A1907
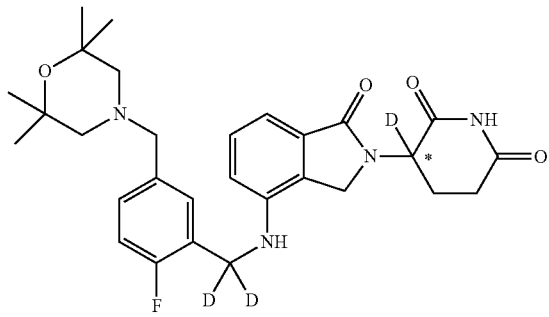

A1908
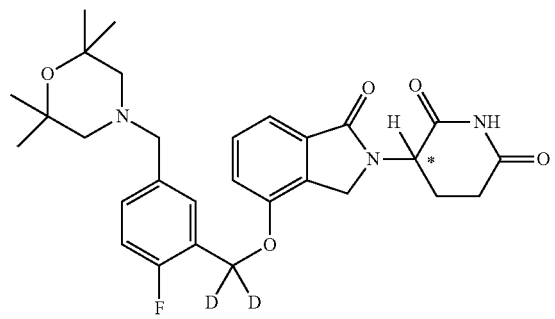
A1912
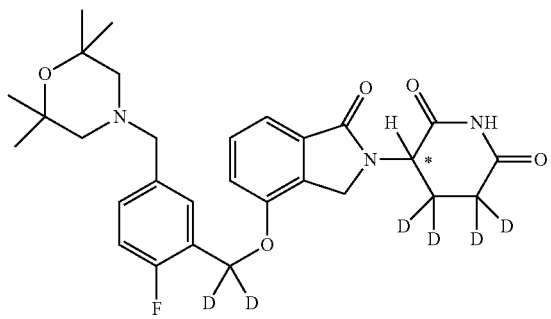
A1909
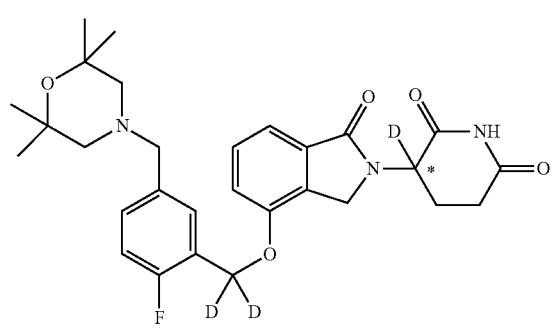
A1913
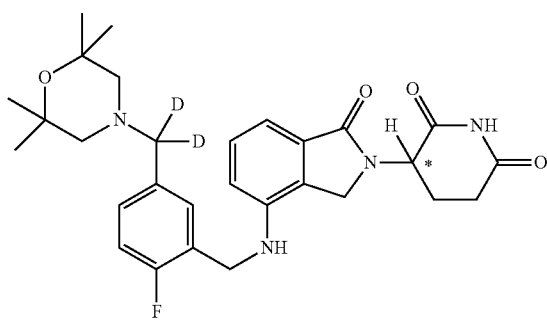
A1910
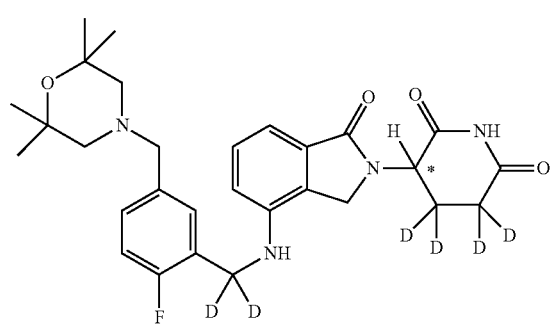
A1914
A1911
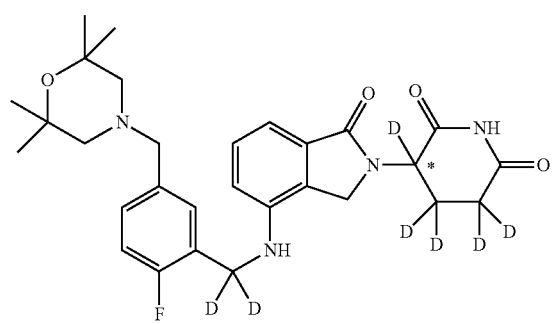
A1915
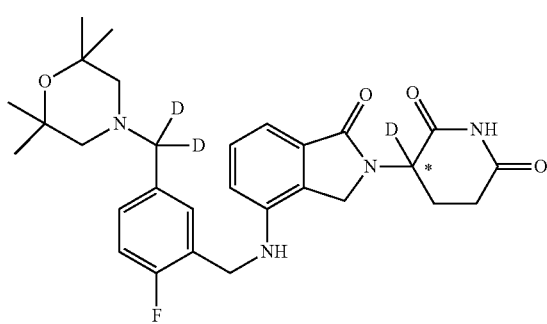

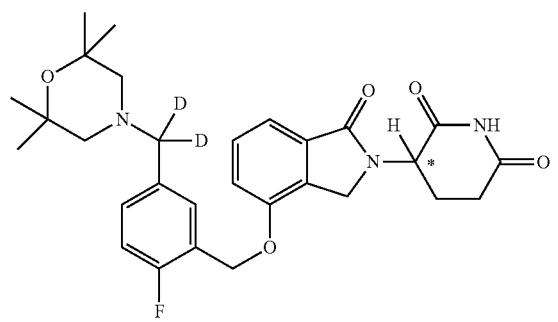
A1916
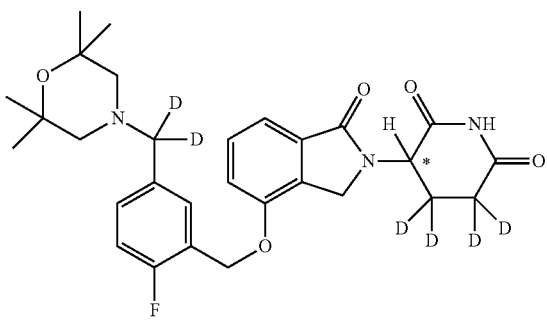
A1920
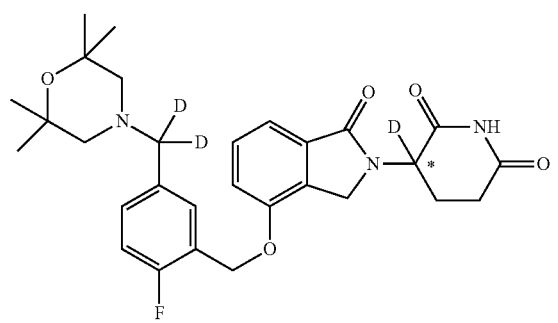
A1917
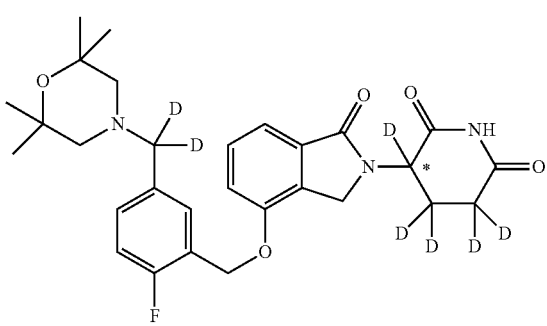
A1921
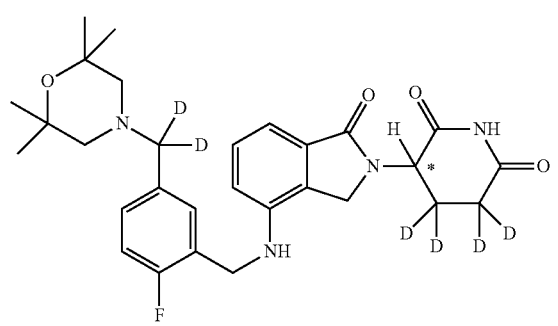
A1918
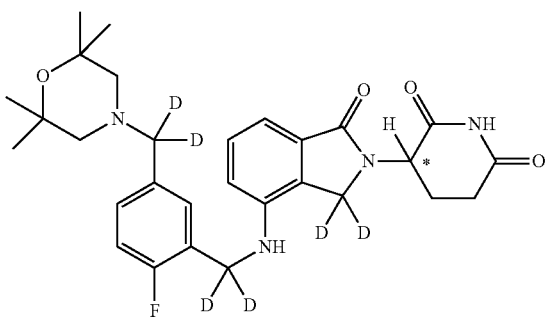
A1922
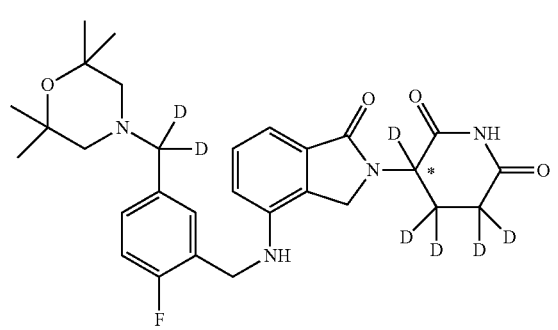
A1919
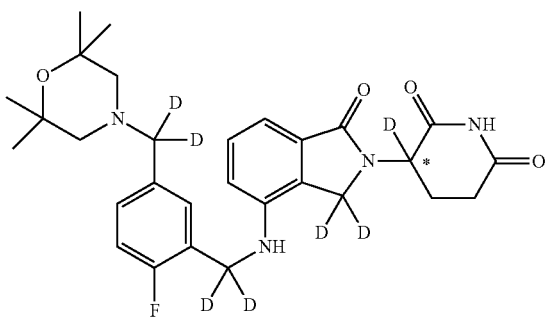
A1923

A1924
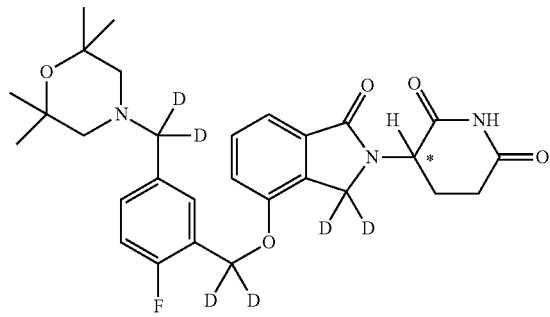
A1925
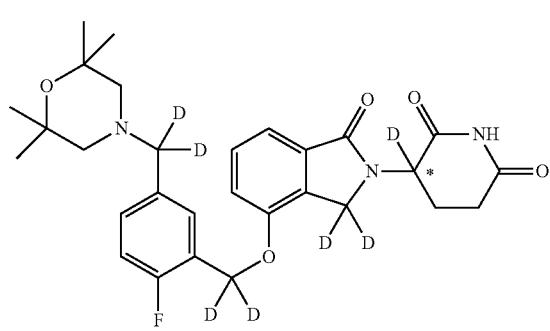
A1926
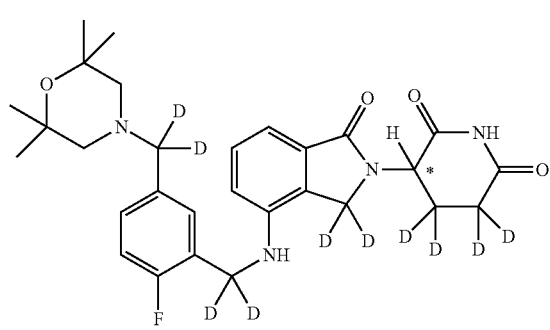
A1927
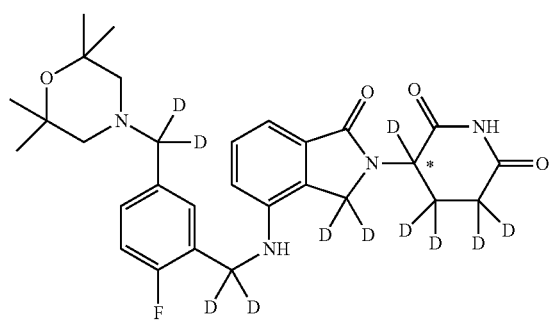
A1928
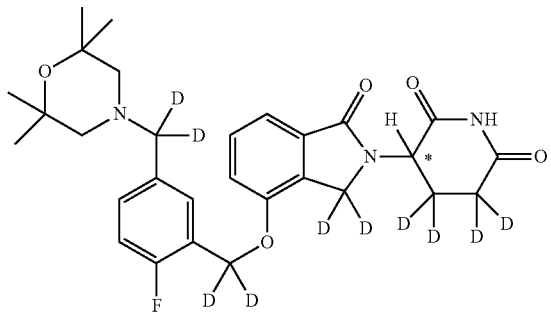
A1929
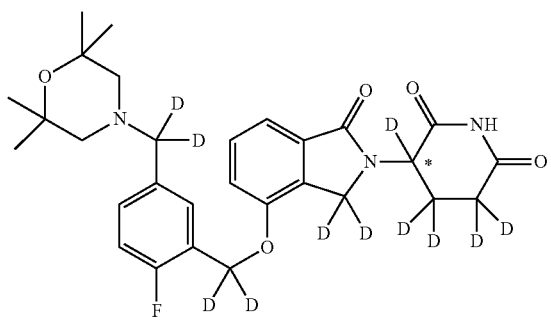
A1930
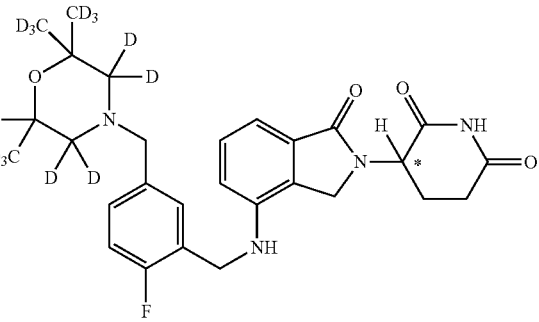
A1931
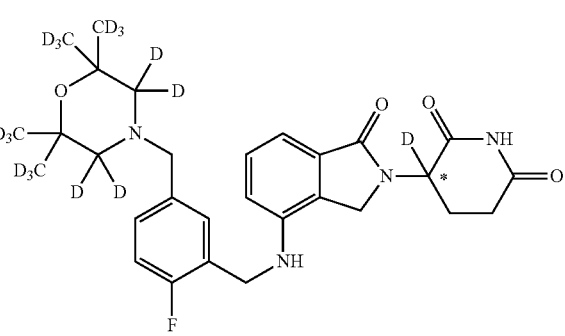

543
-continued
A1932
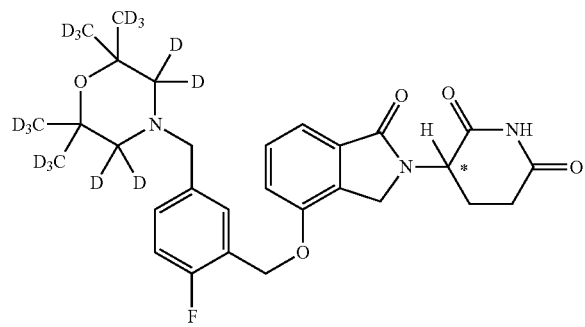
A1933
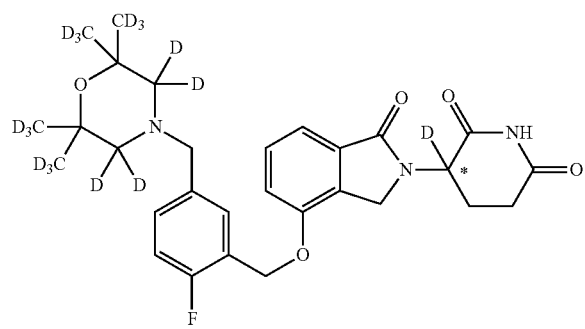
A1934
A1935
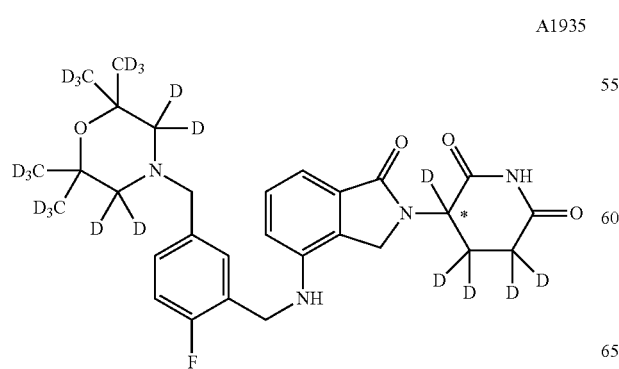
544
-continued
A1936
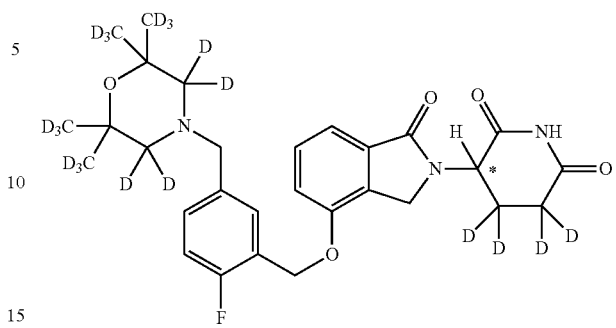
A1937
A1942
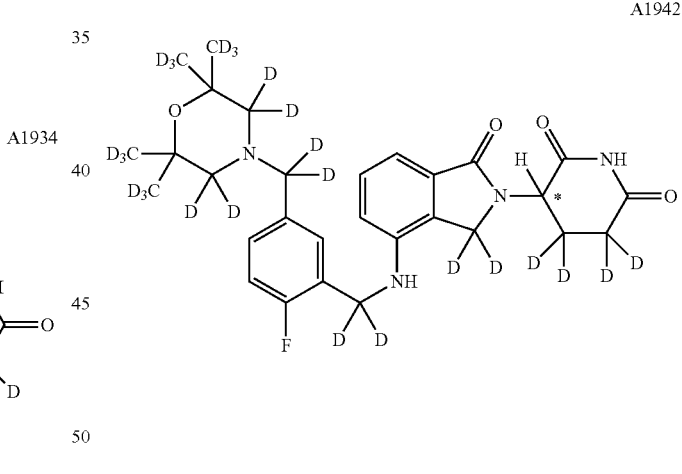
A1943
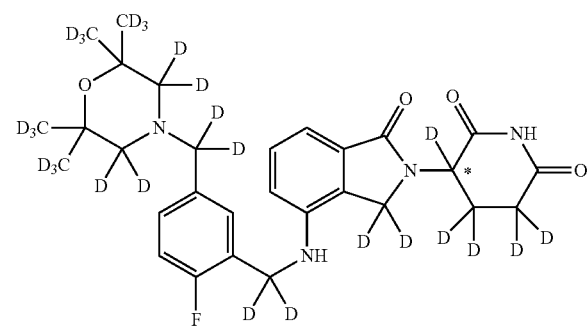

A1944
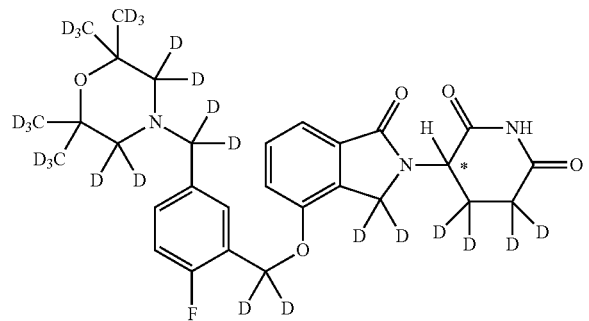
A1944
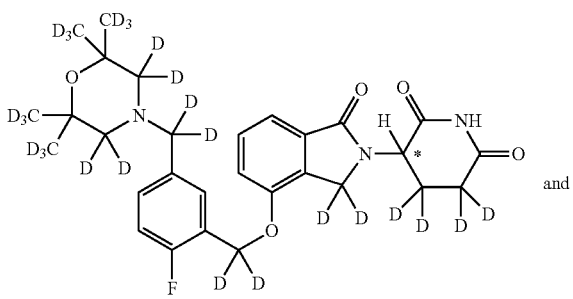
and
A1945
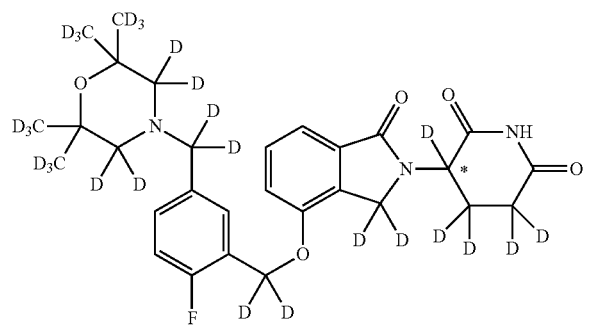
A1945
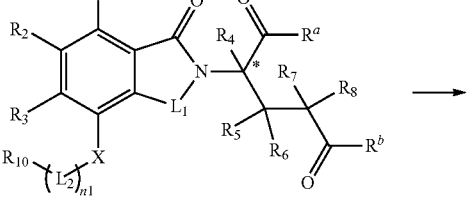
.
9. A process for preparing the isoindoline derivative having a structure of general formula (I) according to claim 1, comprising:
conducting a deprotection reaction with compound A-06 (1) to give compound A-06(a1) and thereafter an amidation reaction with compound A-06(a1) to give the compound of general formula (I);
A1942
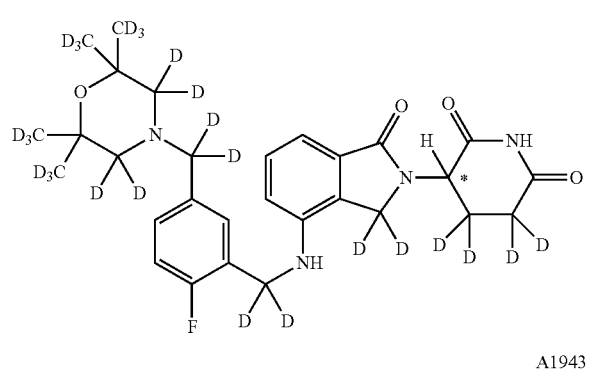
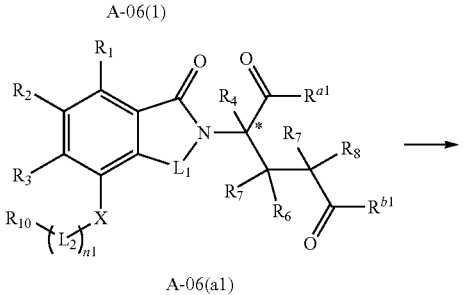
A-06(1)
A-06(a1)
A1943

-continued

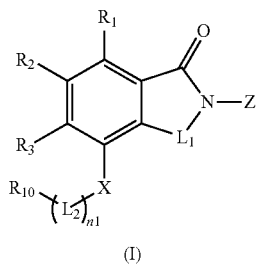
(I)

wherein in compound A-06(1), compound A-06(a1) or the general formula (I), $L_1$, $L_2$, X, Z, *, $R_1$-$R_{10}$ and n1 are as defined in claim 1; one of $R^a$ and $R^b$ is

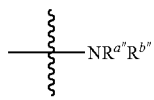

and the other is

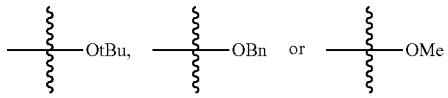

and one of $R^{a1}$ and $R^{b1}$ is

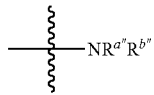

and the other is

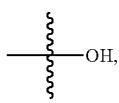

wherein in

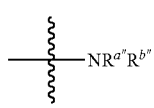

each of $R^{a''}$ and $R^{b''}$ is independently H or D.

10. A process for preparing an isoindoline derivative having a structure of general formula (I) according to claim 1 where n1 is 0, comprising:

conducting a reduction reaction with compound I-RS to give the compound of general formula (I);

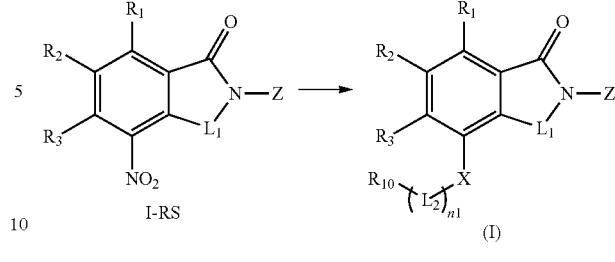

wherein in compound I-RS or the general formula (I), $R_2$ is halogen, n1 is 0, X is NH or ND, $R_{10}$ is H or D, and $L_1$, Z, $R_1$ and $R_3$ are as defined in claim 1.

11. A process for preparing an isoindoline derivative having a structure of general formula (I) according to claim 1 where n1 is 1 and X is NH or HD, comprising:

conducting a reductive amination reaction with compound P-01 and

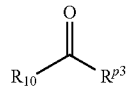

to give the compound of general formula (I);

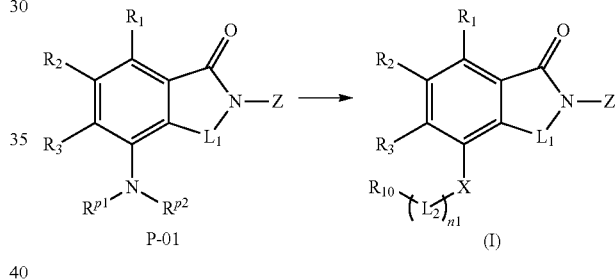

wherein in

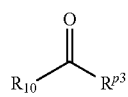

$R^{p3}$ is independently H or D and $R_{10}$ is

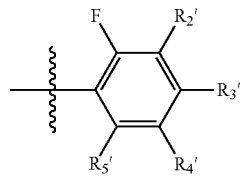

where $R_2'$, $R_3'$, $R_4'$ and $R_5'$ are as defined in claim 1, in the compound P-01 each of $R^{p1}$ and $R^{p2}$ is independently H or D and $L_1$, Z, $R_1$, $R_2$ and $R_3$ are as defined in claim 1, and in the general formula (I) X is NH or ND, n1 is 0, and $L_1$, $L_2$, Z, $R_1$, $R_2$ and $R_3$ are as defined in claim 1.

12. The process according to claim 9, further comprising conducting a reduction reaction with compound A-05(1) to give the compound A-06(1);

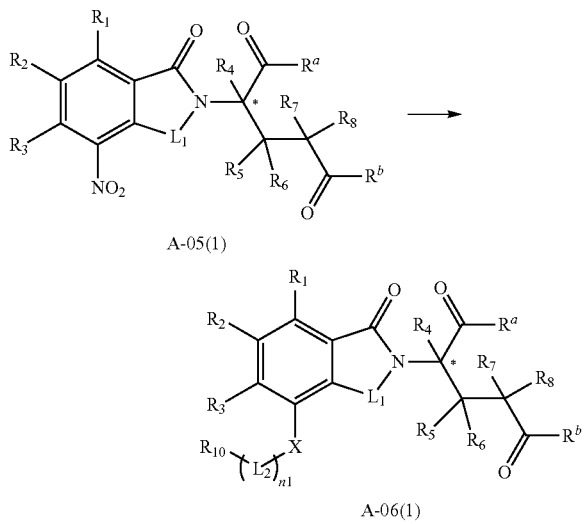

A-05(1)

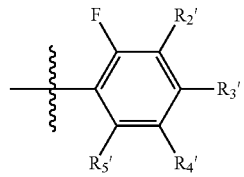

A-06(1)

wherein in compound A-05(1) L$_1$, R$_1$-R$_8$, and R$^a$ and R$^b$ are as defined in claim 9 and in compound A-06(1) L$_1$, L$_2$, R$_1$-R$_8$, R$^a$ and R$^b$ are as defined in claim 9, X is NH or ND, n1 is 0, and R$_{10}$ is H or D.

13. The process of claim 9, further comprising conducting a reductive amination reaction with compound A-05(2) and

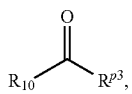

to give compound A-06(1);

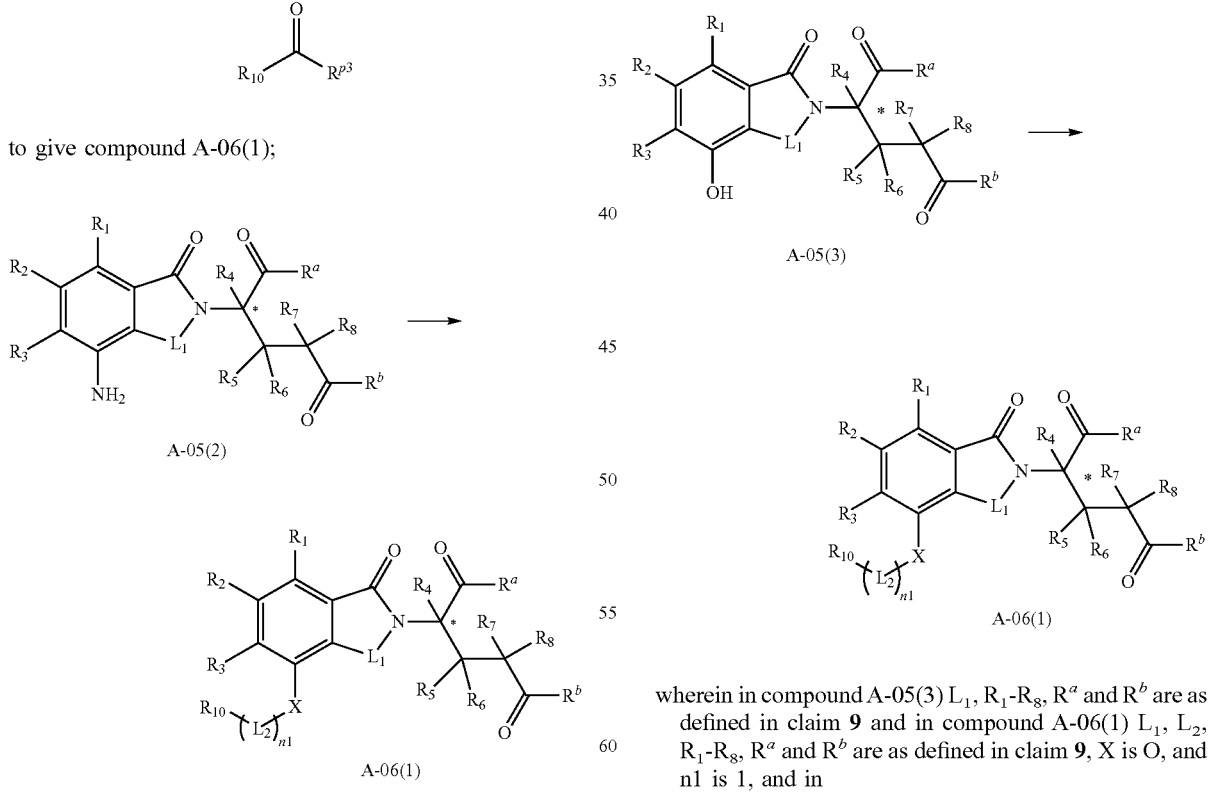

wherein in compound A-05(2) L$_1$, R$_1$-R$_9$, R$^a$ and R$^b$ are as defined in claim 9 and in compound A-06(1) L$_1$, L$_2$, R$_1$-R$_9$, R$^a$ and R$^b$ are as defined in claim 9, X is NH or ND and n1 is 1, and in $$R_{10}\overset{O}{\underset{}{\|}}R^{p3},$$

R$^{p3}$ is H or D and R$_{10}$ is

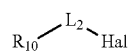

wherein R$_2$', R$_3$', R$_4$' and R$_5$' are as defined in claim 1.

14. The process of claim 9, further comprising conducting a nucleophilic substitution reaction with compound A-05(3) and R$_{10}$—L$_2$—Hal to give compound A-06(1);

A-05(3)

A-06(1)

wherein in compound A-05(3) L$_1$, R$_1$-R$_8$, R$^a$ and R$^b$ are as defined in claim 9 and in compound A-06(1) L$_1$, L$_2$, R$_1$-R$_8$, R$^a$ and R$^b$ are as defined in claim 9, X is O, and n1 is 1, and in R$_{10}$—L$_2$—Hal, $R_{10}$ is

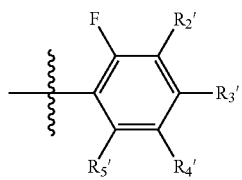

where $R_2'$, $R_3'$, $R_4'$ and $R_5'$ are as defined in claim 1.

15. The process of claim 10, further comprising conducting a coupling reaction with compound A-03 and compound A-04(2) or salt thereof to give compound I-RS;

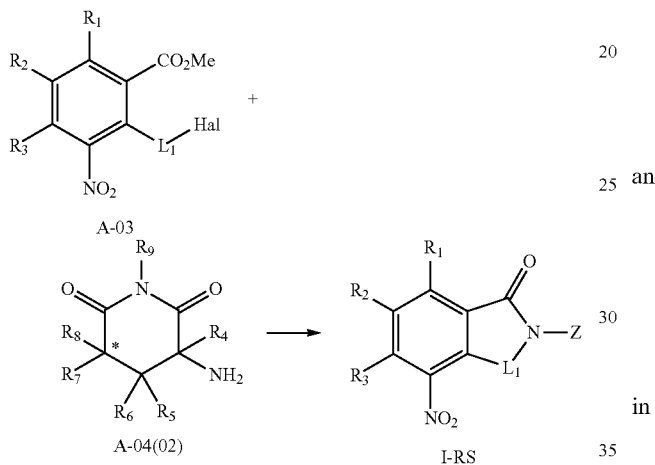

wherein in compound A-03 $L_1$ and $R_1$-$R_3$ are as defined in claim 9 and Hal is a halogen, in compound A-04(2) * and $R_4$-$R_9$ are as defined in claim 9, and in compound I-RS $L_1$, Z, *, and $R_1$-$R_3$ are as defined in claim 9.

16. The process of claim 10, further comprising conducting a deprotection and an amidation reaction sequentially with compound A-05(1) to give compound I-RS;

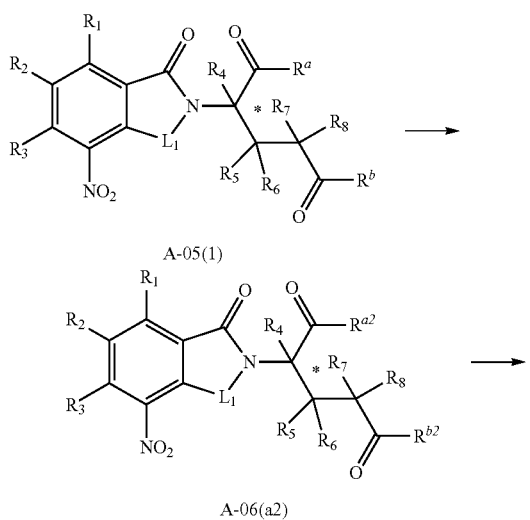

wherein in compound A-05(1) $L_1$, *, $R_1$-$R_8$, $R^a$ and $R^b$ are as defined in claim 9, in compound A-06(a2) $L_1$ and $R_1$-$R_8$ are as defined in claim 9 and one of $R^{a2}$ and $R^{b2}$ is

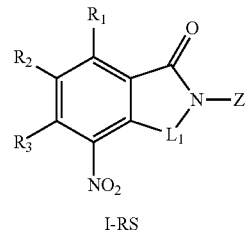

and the other is

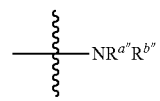

—OH;

in

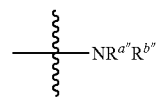

where each of $R^{a''}$ and $R^{b''}$ is independently H or D, and in compound I-RS $L_1$, Z, and $R_1$-$R_3$ are as defined in claim 9.

17. The process of claim 11, further comprising conducting a reduction reaction with compound I-RS to give compound P-01;

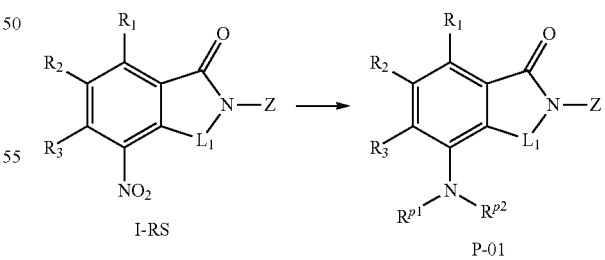

wherein in compound I-RS $R_2$ is H, D or a halogen and $L_1$, Z, $R_1$ and $R_3$ are as defined in claim 11 and in P-01, $R_2$ is H, D or a halogen, each of $R^{p1}$ and $R^{p2}$ is independently H or D, and $L_1$, Z, $R_1$ and $R_3$ are as defined in claim 11.

18. An intermediate compound A-06(1) or A-06(a1):

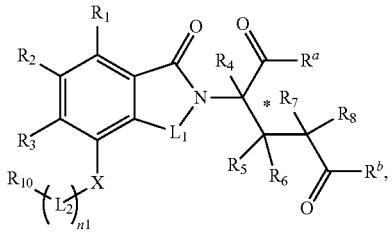

A-06(1)

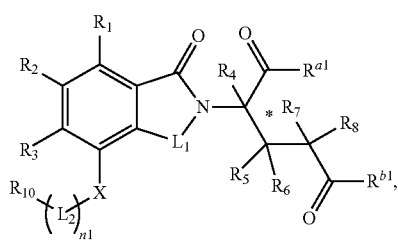

A-06(a1)

wherein in compound A-06(1) or A-06(a1), the definitions of $L_1$, $L_2$, X, n1, Z, $R_1$-$R_{10}$ refer to those in claim 1; in compound A-06(1), one of $R^a$ and $R^b$ is

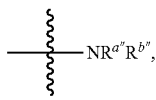

the other is

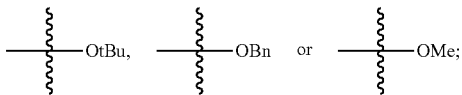

in compound A-06(a1), one of $R^{a1}$ and $R^{b1}$ is

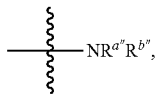

the other is

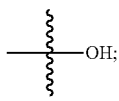 [SMILES: *O]

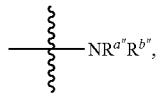

each of $R^{a''}$ and $R^{b''}$ is independently H or D.

19. A pharmaceutical composition, which comprises a therapeutically effective and/or prophylactically effective amount of the substance selected from the group consisting of the isoindoline derivatives having a structure of general formula (I), the pharmaceutically acceptable salt, the polymorph, the stereoisomer, the isotopic compound, and the metabolite thereof according to claim 1.

20. The pharmaceutical composition according to claim 19, wherein the composition comprises other therapeutic agent(s), the other therapeutic agent(s) is selected from the group consisting of elotuzumab, palbociclib, nivolumab, pembrolizumab, panobinostat, PD-1 inhibitor, PD-L1 inhibitor, pemetrexed, topotecan, doxorubicin, bortezomib, gemcitabine, dacarbazine, dexamethasone, biaxin, vincristine, azacitidine, rituximab, trastuzumab, prednisone, docetaxel, clofarabine injection, Ublituximab, romidepsin, HDAC inhibitor, androgen receptor inhibitor, androgen biosynthesis inhibitor, BTK inhibitor, erythropoietin, eltrombopag, minocycline and melphalan.

21. A method of treating a disease, symptom or disorder caused by TNF-α or associated with abnormal regulation of TNF-α activity, wherein the method comprises administering to a subject a therapeutically or prophylactically effective amount of a substance selected from the group consisting of the isoindoline derivative having a structure of general formula (I), the pharmaceutically acceptable salt, the polymorph, the stereoisomer, the isotopic compound, and the metabolite thereof according to claim 1.

22. The method of claim 21, wherein the disease, symptom or disorder includes myelodysplastic syndrome, multiple myeloma, mantle cell lymphoma, non Hodgkin's lymphoma, papillary and follicular thyroid carcinoma, breast cancer, prostate cancer, chronic lymphocytic leukemia, amyloidosis, type I complex regional pain syndrome, malignant melanoma, radiculopathy, myelofibrosis, glioblastoma, glioma sarcomatosum, malignant glioma, refractory plasma cell tumor, chronic myelomonocytic leukemia, follicular lymphoma, ciliary and chronic melanoma, iris melanoma, recurrent ocular melanoma, extraocular extension melanoma, solid tumor, T-cell lymphoma, erythroid lymphoma, monoblastic and monocytic leukemia; myeloid leukemia, central nervous system lymphoma, brain tumors, meningiomas, spinal tumor, thyroid cancer, non-small cell lung cancer, ovarian cancer, skin cancer, renal cell carcinoma, myelofibrosis, Burkitt's lymphoma, Hodgkin's lymphoma, large cell lymphoma, diffuse large B cell lymphoma, astrocytoma, hepatocellular carcinoma, or primary macroglobulinemia.

23. A method of treating a disease, symptom or disorder caused by TNF-α or associated with abnormal regulation of TNF-α activity, wherein the method comprises administering to a subject a therapeutically or prophylactically effective amount of the pharmaceutical composition according to claim 19.

* * * * *

UNITED STATES PATENT AND TRADEMARK OFFICE
CERTIFICATE OF CORRECTION

PATENT NO. : 10,017,492 B2
APPLICATION NO. : 15/523651
DATED : July 10, 2018
INVENTOR(S) : Chuansheng Ge et al.

It is certified that error appears in the above-identified patent and that said Letters Patent is hereby corrected as shown below:

On the Title Page

(30) Foreign Application Priority Data:
Oct. 30, 2014 (CN)........2014 1 0605148, should read as --2014 1 0605148.8--.
Nov. 11, 2014 (CN).......2014 1 0632870, should read as --2014 1 0632870.0--.

In the Claims

Claim 5, Column 357, Line 54, "of $R_3$'," should read as --of $R_2$', $R_3$',--.

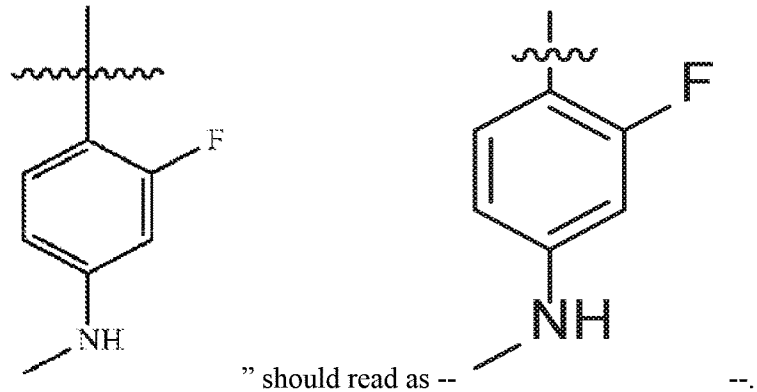

Claim 7, Column 362, Lines 5-10, " [structure] " should read as -- [structure] --.

Signed and Sealed this
Twenty-fifth Day of December, 2018

Andrei Iancu
*Director of the United States Patent and Trademark Office*

CERTIFICATE OF CORRECTION (continued)
U.S. Pat. No. 10,017,492 B2

Page 2 of 5

Claim 8, Column 403, Figure A652, " 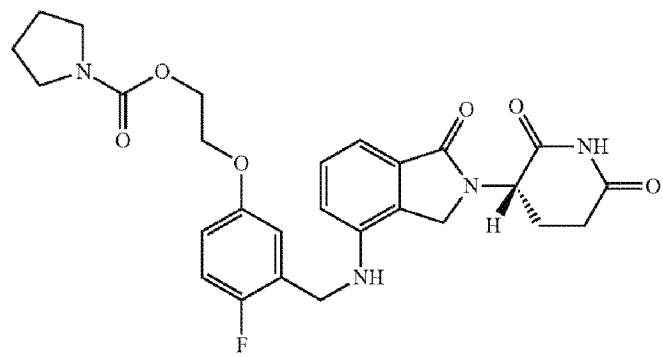 "

should read as -- 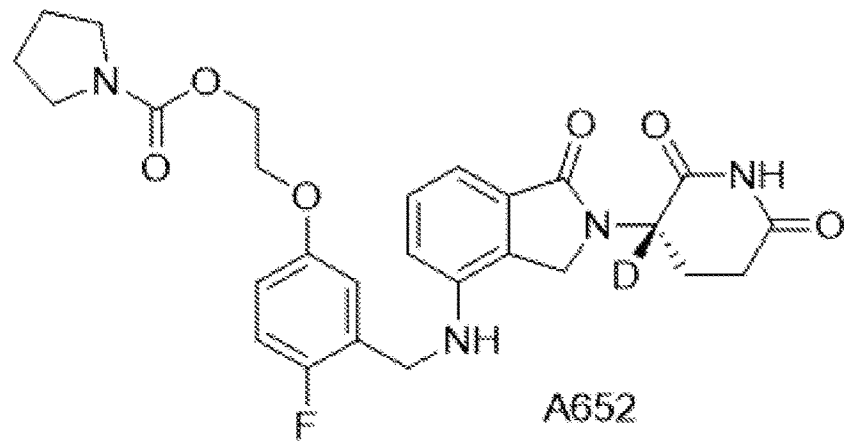 --.

Claim 8, Column 456, Figure A1147, " 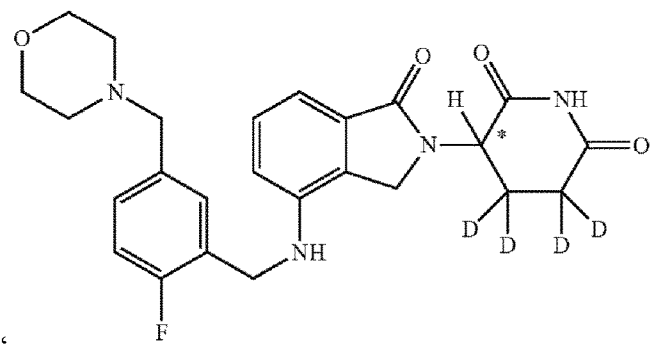 "

CERTIFICATE OF CORRECTION (continued)
U.S. Pat. No. 10,017,492 B2 should read as --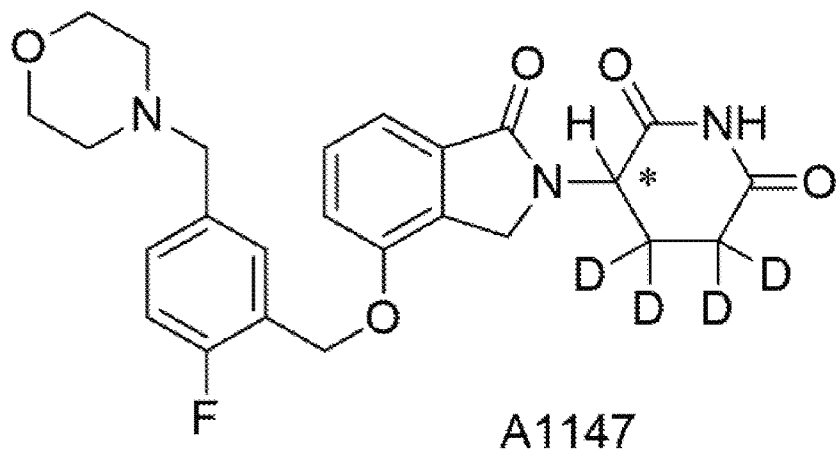--.

Claim 8, Column 469, Figure A1209, "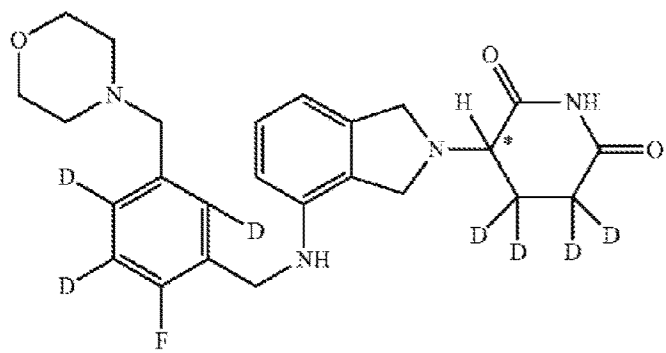"

should read as --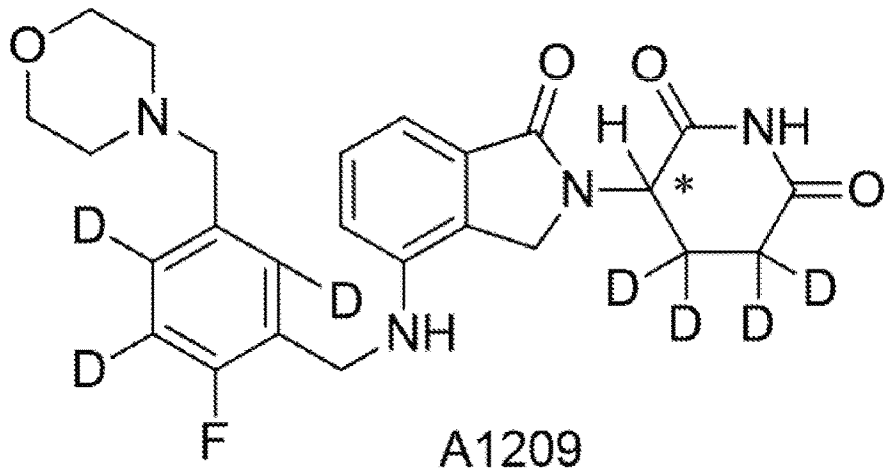--.

CERTIFICATE OF CORRECTION (continued)
U.S. Pat. No. 10,017,492 B2

Claim 8, Column 469, Figure A1213, " 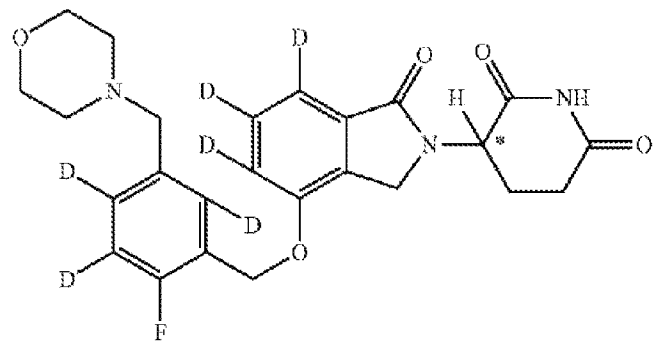 "

should read as -- 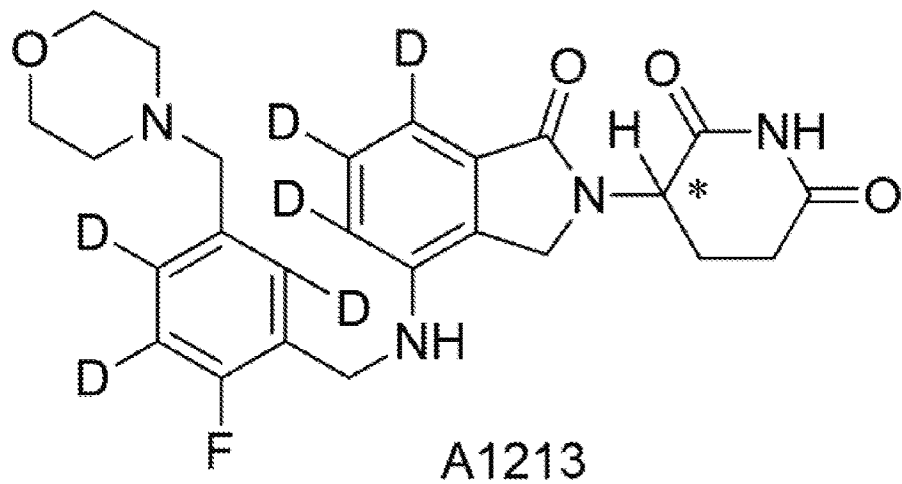 --.

Claim 8, Column 492, Figure A1483, " 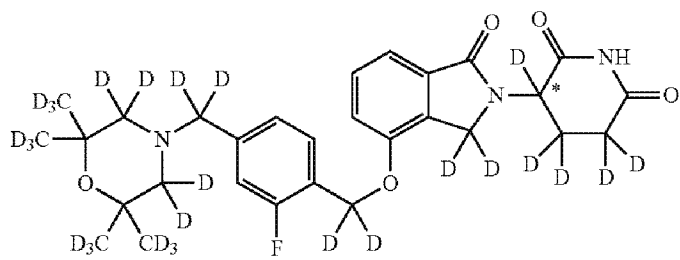 "

should read as -- 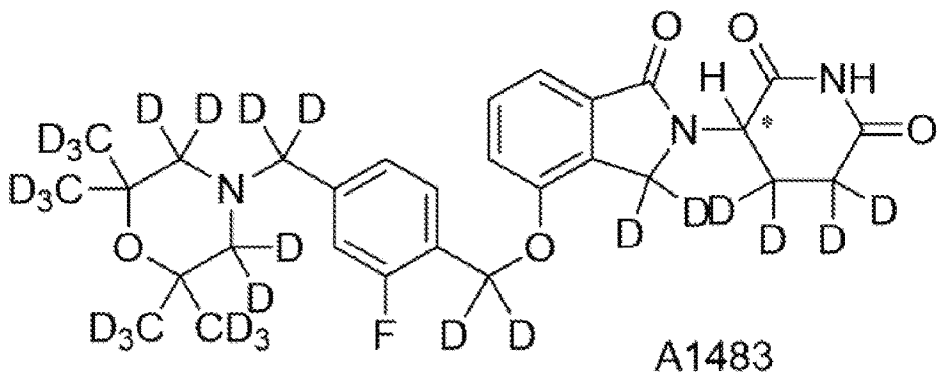 --.

CERTIFICATE OF CORRECTION (continued)
U.S. Pat. No. 10,017,492 B2

Claim 8, Column 533, A1892, " 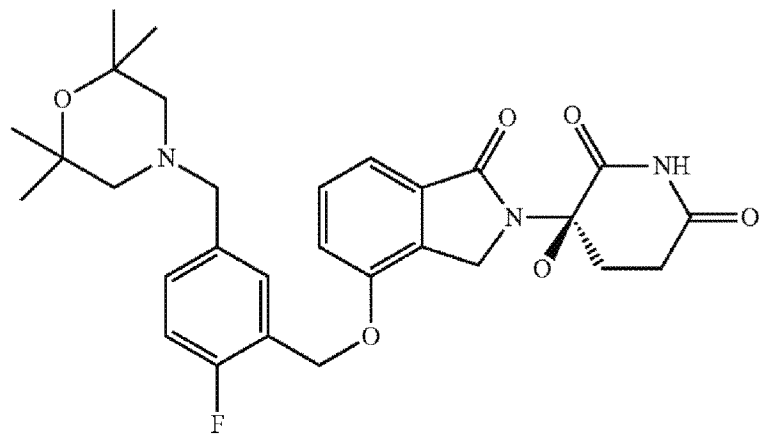 "

should read as -- 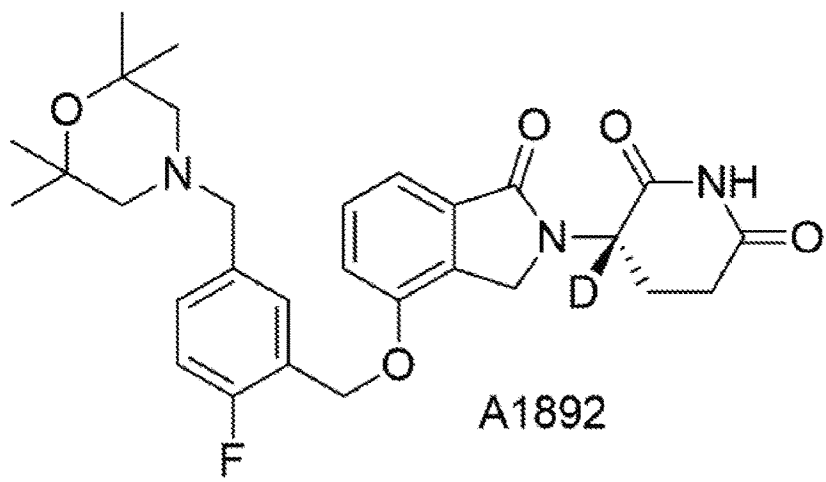 --.

Claim 18, Column 553, Line 26, "Z," should read as --Z, *,--.